United States Patent
Kumaran et al.

(10) Patent No.: US 11,807,890 B2
(45) Date of Patent: *Nov. 7, 2023

(54) METHODS FOR PRODUCTION OF OXYGENATED TERPENES

(71) Applicants: GIVAUDAN SA, Vernier (CH); MANUS BIO INC., Cambridge, MA (US)

(72) Inventors: Ajikumar Parayil Kumaran, Cambridge, SC (US); Chin Giaw Lim, Allston, MA (US); Liwei Li, Arlington, MA (US); Souvik Ghosh, Cambridge, MA (US); Christopher Pirie, Cambridge, MA (US); Anthony Qualley, Beavercreek, OH (US); Geoff Marshall-Hill, Buckinghamshire (GB); Martin Preininger, Neuss (DE)

(73) Assignees: GIVAUDAN SA, Vernier (CH); MANUS BIO INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/456,126

(22) Filed: Nov. 22, 2021

(65) Prior Publication Data

US 2022/0073955 A1 Mar. 10, 2022

Related U.S. Application Data

(60) Continuation of application No. 16/669,051, filed on Oct. 30, 2019, now Pat. No. 11,180,782, which is a division of application No. 15/505,022, filed as application No. PCT/US2015/046421 on Aug. 21, 2015, now Pat. No. 10,501,760.

(60) Provisional application No. 62/040,284, filed on Aug. 21, 2014.

(51) Int. Cl.
| | |
|---|---|
| *C12P 7/26* | (2006.01) |
| *C12N 9/02* | (2006.01) |
| *A01N 27/00* | (2006.01) |
| *C12P 5/00* | (2006.01) |
| *A23L 27/12* | (2016.01) |

(52) U.S. Cl.
CPC ............... *C12P 7/26* (2013.01); *A01N 27/00* (2013.01); *A23L 27/13* (2016.08); *C12N 9/0073* (2013.01); *C12P 5/002* (2013.01); *C12Y 114/13078* (2013.01); *A23V 2002/00* (2013.01); *C07K 2319/03* (2013.01)

(58) Field of Classification Search
None
See application file for complete search history.

(56) References Cited

U.S. PATENT DOCUMENTS

| | | |
|---|---|---|
| 5,847,226 A | 12/1998 | Muller et al. |
| 6,200,786 B1 | 3/2001 | Huang et al. |
| 6,890,960 B1 | 5/2005 | Henderson et al. |
| 7,211,420 B1 | 5/2007 | Wong et al. |
| 7,273,735 B2 | 9/2007 | Schalk et al. |
| 8,097,442 B2 | 1/2012 | Hitchman et al. |
| 8,415,136 B1 | 4/2013 | Gardner et al. |
| 8,512,988 B2 | 8/2013 | Ajikumar et al. |
| 8,927,241 B2 | 1/2015 | Ajikumar et al. |
| 9,284,570 B2 | 3/2016 | Stephanopoulos et al. |
| 9,359,624 B2 | 6/2016 | Ajikumar et al. |
| 9,494,130 B2 | 8/2016 | Ajikumar et al. |
| 9,796,980 B2 | 10/2017 | Ajikumar et al. |
| 9,957,527 B2 | 5/2018 | Ajikumar et al. |
| 10,501,760 B2 * | 12/2019 | Kumaran ............... A01N 27/00 |
| 10,774,314 B2 | 9/2020 | Donald et al. |
| 2011/0189717 A1 | 8/2011 | Ajikumar et al. |
| 2012/0107893 A1 | 5/2012 | Ajikumar et al. |
| 2012/0164678 A1 | 6/2012 | Stephanopoulos et al. |
| 2012/0246767 A1 | 9/2012 | Amick et al. |
| 2017/0002366 A1 | 1/2017 | Ajikumar et al. |
| 2017/0002382 A1 | 1/2017 | Ajikumar et al. |
| 2017/0332673 A1 | 11/2017 | Philippe et al. |
| 2018/0135081 A1 | 5/2018 | Kumaran et al. |
| 2018/0251738 A1 | 9/2018 | Donald et al. |
| 2018/0327789 A1 | 11/2018 | Kumaran et al. |
| 2020/0224224 A1 | 7/2020 | Kumaran |

FOREIGN PATENT DOCUMENTS

| | | |
|---|---|---|
| JP | 2004067723 | 3/2004 |
| WO | 2006079020 | 7/2006 |
| WO | 2011060057 | 5/2011 |
| WO | 2016029187 | 2/2016 |

OTHER PUBLICATIONS

Database WPI Week 200423, Thomson Scientific, London, GB: AN 2004-244290, XP002752397, & JP 2004 067723 (Hasegawa Co. Ltd.) Mar. 4, 2004.
International Search Report and Written Opinion dated Dec. 14, 2015 for international application PCT/US2015/046369.
International Search Report and Written Opinion dated Mar. 22, 2016 for international application PCT/US2015/046421.
International Search Report and Written Opinion for International application PCT/US2016/047692.
"Beta-Nootkaton", Product information from Pubchem, downloaded from pubchem.ncbi.nim.nih.gov/compound/Nootkatol (Year: 2018).
"Predicted: en-kaurene oxidase, chloroplastic-like [Malus domestica]", Database Genpept XP002752377, Jun. 20, 2014.
Ajikumar , et al., "Isoprenoid Pathway Optimization for Taxol Precursor Overproduction in *Escherichia coli*", Science, 2010, vol. 1, No. 330 (6000), pp. 1-11.

(Continued)

*Primary Examiner* — Anand U Desai

(74) *Attorney, Agent, or Firm* — Curatolo Sidoti & Trillis Co., LPA; Salvatore A. Sidoti; Floyd Trillis, III

(57) ABSTRACT

The present disclosure relates to methods for producing oxygenated terpenoids, and preparation of compositions and formulations thereof. Polynucleotides, derivative enzymes, and host cells for use in such methods are also provided.

16 Claims, 76 Drawing Sheets

Specification includes a Sequence Listing.

(56) References Cited

OTHER PUBLICATIONS

Chang, et al., "Engineering *Escherichia coli* for Production of Functionalized Terpenoids Using Plant P450s", Nature, 2007, Chemical Biology, vol. 3, No. 5, pp. 274-277.

Drew, et al., "Transcritome Analysis of Thapsia laciniata Rouy Provides Insights into Terpenoid Biosynthesis and Diversity in Apiaceae", 2013 International Journal of Molecular Sciences, 2013, vol. 14, pp. 9080-9098.

Hotze, et al., "Cinnamate 4-hydroxylase from Catharanthus Roseuseand and Strategy for the Functional Expression of Plant Cytochrome p. 450 Proteins as Translational Fusions with P450 Reductase in *Escherichia coli*", FEBS Letters, 1995, vol. 374, pp. 345-350.

Humphrey, et al., "Spatial organization of four enzymes from Stevia rebaudiana that are involved in steviol glycoside synthesis", Plant Molecular Biology (2006) 61:47-62.

Humphrey, et al., "Subname: full-ent-kaurene oxidase CYP701A5", Uniprot Database, Feb. 19, 2014.

Humphrey, et al., "Subname: Full-kaurene oxidase", Uniprot Database, Jul. 9, 2014.

King, "Production of Bioactive Diterpenoids in the Euphorbiaceae Depends on Evolutionary Conserved Gene Clusters", The Plant Cell, 2014, vol. 26, pp. 3286-3298.

Kumaran, et al., Notice of Allowance dated Apr. 4, 2019 for U.S. Appl. No. 15/505,022.

Kumaran, et al., Notice of Allowance dated Aug. 5, 2021 for U.S. Appl. No. 16/669,051.

Kumaran, et al., Office Action dated Mar. 19, 2019 for U.S. Appl. No. 15/505,503.

Kumaran, et al., Office Action dated Mar. 3, 2021 for U.S. Appl. No. 16/669,051.

Kumaran, et al., Office Action dated Nov. 23, 2018 for U.S. Appl. No. 15/505,022.

Kumaran, et al., Restriction Requirement dated Dec. 20, 2018 for U.S. Appl. No. 15/505,503.

Kumaran, et al., Restriction Requirement dated Oct. 9, 2018 for U.S. Appl. No. 15/505,022.

Lange, et al., "Isoprenoid Biosynthesis: The Evolution of Two Ancient and Distinct Pathways Across Genomes", PNAS 97:13172-13177, 2000 (Year 2000).

Leonard, et al., "Functional Expression of a P450 Flavonoid Hydroxy Lase for the Biosynthesis of Plant-Specific Hydroxlated Flavonols in *Escherichia coli*", Metabolic Engineering, 2007, vol. 8, pp. 172-181.

Schuckel, et al., "A gene-fusion approach to enabling plant cytochromes P450 for Biocatalysis", Chembiochem, vol. 13, No. 18, Nov. 5, 2012, pp. 2758-2763.

Seifert, et al., "Rational design of a minimal and highly enriched CYP102A1 mutant library with improved regio-, stereo, and chemoselectivity", Chembiochem, vol. 10, No. 5, Mar. 23, 2009.

Singh, "Chemistry of Terpenoids and Carotenoids", Discovery Publishing House, New Delhi, 2007, pp. 3 and 4 (Year: 2007).

Wriessnegger, et al., "Production of the sesquiterpenoid (+)-nootkalone by metabolic engineering of Pichia pastoris", Metabolic Engineering, vol. 24, Apr. 16, 2014, pp. 18-29.

\* cited by examiner

>VvVS [Vitis vinifera]
MSTQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIAMTSILDDIHDAYGTPEELKLFIEAIERWDINSINQLPEYMKLCY
VALLDVYKEIEEEMEKEGNQYRVHYAKEVMKNQVRAYFAEAKWLHEEHVPAFEEYMRV
ALASSGYCLLATTSFVGMGEIATKEAFDWVTSDPKIMSSSNFITRLMDDIKSHKFEQK
RGHVTSAVECYMKQYGVSEEQVYSEFQKQIENAWLDINQECLKPTAVSMPLLARLLNF
TRTMDVIYKEQDSYTHVGKVMRDNIASVFINAVI (SEQ ID NO: 1)

ATGGCTACGCAGGTCTCAGCCTCGTCACTGGCACAAATCCCGCAGCCGAAAAATCGTC
CGGTGGCGAACTTCCATCCGAATATCTGGGGTGACCAGTTTATCACGTATACCCCGGA
AGATAAAGTGACCCGTGCGTGCAAGGAAGAACAAATTGAAGACCTGAAAAAGGAAGTC
AAACGCAAGCTGACCGCAGCAGCAGTGGCAAACCCGTCTCAGCTGCTGAATTTTATCG
ATGCGGTTCAACGTCTGGGCGTCGCCTATCATTTCGAACAGGAAATTGAAGAAGCACT
GCAACATATCTGCAACAGCTTTCACGATTGTAATGATATGGACGGCGATCTGTATAAC
ATTGCTCTGGGTTTCCGTCTGCTGCGCCAGCAAGGCTACACGATTTCCTGTGACATCT
TTAATAAATTCACCGATGAACGTGGTCGCTTTAAGGAAGCGCTGATCTCAGACGTTCG
TGGCATGCTGGGTCTGTATGAAGCTGCGCATCTGCGCGTCCACGGCGAAGATATTCTG
GCCAAAGCACTGGCTTTCACCACGACCCACCTGAAGGCGATGGTCGAATCTCTGGGTT
ACCATCTGGCAGAACAGGTGGCACACGCCCTGAACCGTCCGATCCGCAAAGGCCTGGA
ACGTCTGGAAGCGCGCTGGTATATTAGTGTGTACCAGGACGAAGCATTTCATGATAAA
ACCCTGCTGGAACTGGCTAAGCTGGATTTCAACCTGGTTCAATCTCTGCACAAAGAAG
AACTGAGTAATCTGGCCCGTTGGTGGAAAGAACTGGACTTTGCGACCAAGCTGCCGTT
CGCCCGTGATCGCCTGGTTGAAGGCTATTTTTGGATGCATGGTGTCTATTTCGAACCG
CAGTACCTGCGCGGTCGTCGCATTCTGACGAAAGTGATCGCAATGACCTCGATTCTGG
ATGACATCCACGACGCTTACGGCACCCCGGAAGAACTGAAACTGTTTATTGAAGCGAT
CGAACGTTGGGATATTAACAGCATCAATCAGCTGCCGGAATATATGAAACTGTGCTAC
GTGGCCCTGCTGGATGTTTACAAGGAAATCGAAGAAGAAATGGAAAAGGAAGGTAACC
AGTATCGTGTTCATTACGCGAAAGAAGTCATGAAGAATCAAGTGCGCGCCTACTTTGC
AGAAGCTAAATGGCTGCATGAAGAACACGTGCCGGCGTTCGAAGAATATATGCGCGTT
GCGCTGGCCAGCTCTGGCTACTGTCTGCTGGCCACGACCTCTTTTGTGGGCATGGGTG
AAATTGCAACGAAAGAAGCGTTTGACTGGGTTACCAGTGATCCGAAGATTATGAGTTC
CTCAAACTTTATCACCCGTCTGATGGATGACATTAAATCCCATAAGTTCGAACAGAAA
CGCGGTCACGTCACCTCAGCCGTGGAATGCTATATGAAACAGTACGGCGTTTCGGAAG
AACAAGTCTATAGCGAATTTCAGAAACAAATCGAAACGCATGGCTGGATATTAATCA
GGAATGTCTGAAACCGACGGCAGTCTCCATGCCGCTGCTGGCTCGTCTGCTGAATTTT
ACGCGCACGATGGATGTGATCTATAAGAACAGGATTCGTACACCCATGTGGGCAAGG
TTATGCGCGATAACATTGCAAGCGTGTTCATTAATGCTGTTATCTAA (SEQ ID
NO: 2)

FIG. 3A

\>Vv1M1 | engineered valencene synthase
MATQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIAMTSILDDIHDAYGSPEELKLFIEAIEKWDESSINQLPEYMKLCF
VALIDVYNEIEEEMEKEGNQYRIHYLKEVMKNQVRAYFAEAKWLHDEHVPAFEEYMRV
ALASSGYCLLAVTSFVGMGEIVTKEAFDWVTSDPKLMSSSNFITRLMDDIKSHKFEQK
RGHVTSAVECYMKQYGVTEEQVYSEFKKQIENAWLDINQECLKPTAVPMPLLARLLNF
TRTMDVIYKEQDSYTHVGKVMRDNIASVFINPVI (SEQ ID NO: 3)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCTGCAAAGAGGAGCAGATCGAGGACCTGAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGCACGGCGTTTACTTCGAGCCG
CAATACCTGCGTGGCCGCCGCATCCTGACGAAGGTGATCGCCATGACCAGCATTCTGG
ACGACATCCACGATGCGTACGGGAGCCCTGAGGAGTTAAAGCTGTTCATCGAGGCAAT
CGAGAAGTGGGATGAGAGTAGCATCAACCAACTGCCGGAGTATATGAAACTGTGCTTC
GTGGCCCTGATTGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGAAGCTGATGAGCAG
CAGCAACTTCATCACCCGTCTGATGGACGACATCAAGAGCCACAAGTTCGAGCAGAAA
CGCGGTCACGTTACCAGCGCCGTGGAGTGCTACATGAAGCAGTACGGCGTGACAGAGG
AGCAAGTGTACAGCGAGTTCAAGAAACAAATCGAGAACGCCTGGCTGGACATCAACCA
GAGTGCCTGAAACCGACCGCAGTGCCGATGCCTCTGTTAGCCCGTCTGCTGAATTTC
ACACGCACGATGGACGTTATCTACAAGGAGCAGGATAGCTACACCCACGTTGGTAAGG
TGATGCGCGACAACATCGCCAGTGTGTTCATCAACCCGGTGATCTAA (SEQ ID
NO: 4)

FIG. 3A (Cont'd)

>Vv2M1 | engineered valencene synthase
MATQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWTSDPRIMSSSNFITRLMDDIKSHKFEQK
RGHVTSAVECYMKQYAVTEEQVYSEFKKQIENAWLDINQECLKPTAVPMPLLARLLNF
TRTMDVIYKEQDSYTHVGKTMRDNIASVFINPVI (SEQ ID NO: 5)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCTGCAAAGAGGAGCAGATCGAGGACCTGAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGCACGGCGTTTACTTCGAGCCG
CAATACCTGCGTGGCCGCCGCATCCTGACGAAGGTGATCGCCCTGACCAGCATTCTGG
ACGACATCCACGATGCGTACGGGACCCCTGAGGAGTTAAAGCTGTTCATCGAGGCAAT
CGAGAAGTGGGATGAGAGTAGCATCAACCAACTGCCGGAGTATATGAAACTGTGCTAT
GTGGCCCTGCTGGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGCGTATTATGAGCAG
CAGCAACTTCATCACCCGTCTGATGGACGACATCAAGAGCCACAAGTTCGAGCAGAAA
CGCGGTCACGTTACCAGCGCCGTGGAGTGCTACATGAAGCAGTACGCAGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGCAGGATAGCTACACCCACGTTGGTAAGA
CCATGCGCGACAACATCGCCAGTGTGTTCATCAACCCGGTGATCTAA (SEQ ID
NO: 6)

FIG. 3A (Cont'd)

>VvlM5 | engineered valencene synthase
MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIAMTSILDDIHDAYGSPEELKLFIEAIEKWDESSINQLPEYMKLCF
VALIDVYNEIEEEMEKEGNQYRIHYLKEVMKNQVRAYFAEAKWLHDEHVPAFEEYMRV
ALASSGYCLLAVTSFVGMGEIVTKEAFDWVTSDPKLMSSSNTITRLMDDIKSHKFEQK
RGHVTSAVECYMKQYGVTEEQVYSEFKKQIENAWLDINQECLKPTAVPMPLLARLLNF
TRTMDVIYKEEDSYTHVGKVMRDNIASVFINPVI (SEQ ID NO: 7)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCAAAAAGAGGAGCAGATCGAGGACCTGAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGATGGGCGTTTACTTCGAGCCG
CAATACCTGCGTGGCCGCCGCATCCTGACGAAGGTGATCGCCATGACCAGCATTCTGG
ACGACATCCACGATGCGTACGGGAGCCCTGAGGAGTTAAAGCTGTTCATCGAGGCAAT
CGAGAAGTGGGATGAGAGTAGCATCAACCAACTGCCGGAGTATATGAAACTGTGCTTC
GTGGCCCTGATTGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGAAGCTGATGAGCAG
CAGCAACACCATCACCCGTCTGATGGACGACATCAAGAGCCACAAGTTCGAGCAGAAA
CGCGGTCACGTTACCAGCGCCGTGGAGTGCTACATGAAGCAGTACGGCGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGGAAGATAGCTACACCCACGTTGGTAAGG
TGATGCGCGACAACATCGCCAGTGTGTTCATCAACCCGGTGATCTAA (SEQ ID
NO: 8)

FIG. 3A (Cont'd)

>Vv2M5 | engineered valencene synthase
```
MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWVTSDPRIMSSSNTITRLMDDIKSHKFEQK
RGHVTSAVECYMKQYAVTEEQVYSEFKKQIENAWLDINQECLKPTAVPMPLLARLLNF
TRTMDVIYKEEDSYTHVGKTMRDNIASVFINPVI (SEQ ID NO: 9)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCAAAAAGAGGAGCAGATCGAGGACCTGAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGATGGGCGTTTACTTCGAGCCG
CAATACCTGCGTGGCCGCCGCATCCTGACGAAGGTGATCGCCCTGACCAGCATTCTGG
ACGACATCCACGATGCGTACGGGACCCCTGAGGAGTTAAAGCTGTTCATCGAGGCAAT
CGAGAAGTGGGATGAGAGTAGCATCAACCAACTGCCGGAGTATATGAAACTGTGCTAT
GTGGCCCTGCTGGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGCGTATTATGAGCAG
CAGCAACACCATCACCCGTCTGATGGACGACATCAAGAGCCACAAGTTCGAGCAGAAA
CGCGGTCACGTTACCAGCGCCGTGGAGTGCTACATGAAGCAGTACGCAGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGGAAGATAGCTACACCCACGTTGGTAAGA
CCATGCGCGACAACATCGCCAGTGTGTTCATCAACCCGGTGATCTAA (SEQ ID
NO: 10)
```

FIG. 3A (Cont'd)

>VS2 | engineered valencene synthase
MATQVSASSLAQIPQPKNRPVANFHPNIWGDQFITYTPEDKVTRAKKEEQIEDLKKEVK
RKLTAAAVANPSQLLNFIDAVQRLGVAYHFEQEIEEALQHICNSFHDCNDMDGDLYNIA
LGFRLLRQQGYTISCDIFNKFTDERGRFKEALISDVRGMLGLYEAAHLRVHGEDILAKA
LAFTTTHLKAMVESLGYHLAEQVAHALNRPIRKGLERLEARWYISVYQDEAFHDKTLLE
LAKLDFNLVQSLHKEELSNLARWWKELDFATKLPFARDRLVEGYFWMMGVYFEPQYLRG
RRILTKVIALTSILDDIHDAYGTPEELKLFIEAIEKWDESSINQLPEYMKLCYVALLDV
YNEIEEEMEKEGNQYRIHYLKEVMKNQVRAYFAEAKWLHDEHVPAFEEYMRVALASSGY
CLLAVTSFVGMGEIVTKEAFDWVTSDPRIMSSSNTITRLMDDIKSHKFEQKRGHVTSAV
ECYMKQYAVTEEQVYSEFKKQIENAWLDINQECLKPTAVPMPLLARLLNFTRTMDVIYK
EEDSYTHVGKTMRDNIASVFINPVI (SEQ ID NO: 11)

ATGGCAACCCAGGTGAGCGCCAGTAGCCTGGCACAAATCCCGCAGCCTAAAAACCGCC
CTGTTGCCAATTTCCATCCGAACATCTGGGGCGACCACTTTATCACCTACACCCCGGA
AGACAAAGTGACCCGCGCCAAAAAGAAGAGAGGATTGAAGATCTGAAGGAAGAAGTG
AAACGCAAACTGACCGCAGCCGCCGTGGCCAATCCGAGTCAACTGCTGAACTTCATTG
ATGCAGTTCAGCGCCTGGGCGTTGCCTATCACTTTGAGCAGGAGATCGAGGAGGCATT
ACAGCATATTTGTAATAGCTTTCACGACTGCAATGATATGGATGGCGACCTGTATAAT
ATCGCCCTGCTATTTCGTCTGCTGCGCCAACAGGGTTACACAATCAGTTGCGACATCT
TTAACAAGTTCACCGATGAAGAGGGCCGCTTTAAGAAGCCCTGATTAGCGACGTGCG
CGGTATGTTAGGCCTGTATGAAGCAGCCCACCTGCGCGTTCACGGCGAAGACATCCTG
GCAGAGGCACTGGCCTTTACAACCACCCACCTGAAAGCAATGGTTGAATCGCTGGGCT
ACCATCTGGCCGAGCAAGTGAGGCACGCCTTAAACCGTCCGATCCGTAAAGGCATGGA
ACGTCTGGAAGCACGTTGGTACATCAGCATATACCAGGATGAGGCCTTTCATGACAAA
ACCCTGCTGGAGCTGGCCAAACTGGACTTCAACCTGGTGCAGAGCCTGCACAAAGAAG
AGCTGAGCAATCTGGCACGCTGGTGGAAGGAGCTGGATTTTGCCACCAAACTGCCTTT
TGCCCGCGACCGTTTAGTTGAAGGCTACTTTTGGATGATGGGTGTGTATTTTGAGCCG
CAGTATCTGCGTGGCCGTCGCATCCTGACAAAGGTGATCGCCCTGACCAGCATCATTG
ACGACATCCACGATGCCTATGGCACCCCGGAGGAACTGAAACTGTTTATCGAGGCCAT
CGAAAAATGGGACGAGAGCAGCATCAACCAACTGCCTGAGTACATGAAGCTGTGCTAT
GTGGCCCTGCTGGACGTGTATAATGAAATCGAAGAGGAGATGGAAAAGGAGGGCAACC
AATACCGTATCCACTACCTGAAGGAGGTTATGAAAAACCAGGTGCGTGCCTACTTTGC
AGAGGCAAAATGGCTGCACGATGAGCATGTGCCGGCCTTTGAAGAATACATGCGCGTT
GCCCTGGCCAGCAGTGGTTATTGTCTGCTGGCCGTTACAAGTTTTGTGGGCATGGGCG
AGATCGTGACAAAGGAAGCCTTTGACTGGGTTACAAGCGACCCGCGCATCATAAGCAG
CAGCAACACAATTACACGCCTGATGGACGACATTAAAAGCCATAAATTTGAACAGAAA
CGCGGTCATGTGACCAGCGCCGTGGAATGCTACATGAAACAGTACGCCGTGACCGAAG
AGCAGGTTTACGAGGAATTTAAAAAACAGATTGAAACGCATGGCTGGACATTAATCA
GGAGTGTCTGAAGCCGACCGCAGTGCCGATGCCGCTGTTAGCACGCCTGCTGAATTTC
ACCCGCACAATGGATGTGATTTATAAAGAAGAAGACAGCTATACCCATGTGGGCAAGA
CCATGCGCGACAACATCGCCAGCGTGTTTATCAACCCTGTGATCTAA (SEQ ID NO: 120)

FIG. 3A (Cont'd)

>CsVS | Citrus sinensis valencene synthase
MASGETFRPTADFHPSLWRNHFLKGASDFKTVDHTATQERHEALKEEVRRMITDAEDKP
VQKLRLIDEVQRLGVAYHFEKEIGDAIQKLCPIYIDSNRADLHTVSLHFRLLRQQGIKI
SCDVFEKFKDDEGRFKSSLINDVQGMLSLYEAAYMAVRGEHILDEAIAFTTTHLKSLVA
QDHVTPKLAEQINHALYRPLRKTLPRLEARYFMSMINSTSDHLCNKTLLNFAKLDFNIL
LELHKEELNELTKWWKDLDFTTKLPYARDRLVELYFWDLGTYFEPQYAFGRKIMTQLNY
ILSIIDDTYDAYGTLEELSLFTEAVQRWNIEAVDMLPEYMKLIYRTLLDAFNEIEEDMA
KQGRSHCVRYAKEENQKVIGAYSVQAKWFSEGYVPTIEEYMPIALTSCAYTFVITNSFL
GMGDFATKEVFEWISNNPKVVKAASVICRLMDDMQGHEFEQKRGHVASAIECYTKQHGV
SKEEAIKMFEEEVANAWKDINEELMMKPTVVARPLLGTILNLARAIDFIYKEDDGYTHS
YLIKDQIASVLGDHVPF (SEQ ID NO: 12)

ATGGCCTCCGGCGAAACCTTCCGTCCGACCGCAGACTTCCATCCGTCACTGTGGCGTA
ATCACTTCCTGAAAGGCGCAAGCGACTTCAAAACGGTGGATCATACGGCAACCCAGGA
ACGTCACGAAGCTCTGAAGGAAGAAGTCCGTCGCATGATTACCGATGCCGAAGACAAA
CCGGTGCAGAAGCTGCGTCTGATCGATGAAGTTCAACGCCTGGGCGTCGCGTATCATT
TTGAAAAGAAATTGGTGACGCCATCCAGAAGCTGTGCCCGATTTACATCGATAGCAA
CCGCGCAGACCTGCATACCGTGTCTCTGCACTTTCGTCTGCTGCGCCAGCAAGGCATC
AAGATCAGCTGTGATGTTTTCGAAAAGTTCAAGGATGACGAAGGCCGTTTCAAAAGCT
CTCTGATTAATGATGTTCAGGGTATGCTGTCTCTGTATGAAGCGGCCTACATGGCGGT
CCGCGGTGAACATATTCTGGATGAAGCGATCGCCTTTACCACGACCCATCTGAAAAGC
CTGGTGGCCCAGGACCACGTTACGCCGAAGCTGGCGGAACAAATTAACCACGCCCTGT
ATCGTCCGCTGCGCAAAACCCTGCCGCGTCTGGAAGCACGCTACTTCATGAGCATGAT
TAATAGTACGTCCGATCATCTGTGCAACAAAACCCTGCTGAATTTTGCTAAGCTGGAC
TTCAACATCCTGCTGGAACTGCACAAAGAAGAACTGAATGAACTGACCAAATGGTGGA
AGGATCTGGACTTTACGACCAAACTGCCGTATGCACGTGATCGCCTGGTTGAACTGTA
CTTCTGGGACCTGGGCACGTATTTTGAACCGCAGTACGCTTTCGGTCGTAAAATTATG
ACCCAACTGAACTATATCCTGTCAATTATCGATGACACGTATGATGCGTACGGCACCC
TGGAAGAACTGTCGCTGTTTACGGAAGCGGTGCAGCGTTGGAATATTGAAGCCGTTGA
TATGCTGCCGGAATATATGAAACTGATTTACCGCACCCTGCTGGATGCATTCAACGAA
ATCGAAGAAGACATGGCTAAACAAGGTCGTAGTCATTGCGTGCGCTATGCGAAAGAAG
AAAATCAGAAGGTTATTGGCGCGTACTCAGTCCAAGCCAAATGGTTTTCGGAAGGTTA
TGTTCCGACGATTGAAGAATACATGCCGATCGCACTGACCTCATGTGCTTATACGTTT
GTGATCACCAACTCGTTCCTGGGCATGGGTGATTTTGCCACCAAAGAAGTTTTCGAAT
GGATTAGCAACAATCCGAAAGTGGTTAAGGCAGCTTCTGTCATCTGCCGTCTGATGGA
TGACATGCAGGGCCATGAATTTGAACAAAAACGCGGTCACGTTGCAAGTGCTATTGAA
TGTTATACCAAGCAGCACGGCGTCTCCAAAGAAGAAGCAATTAAGATGTTCGAAGAAG
AAGTGGCGAACGCCTGGAAAGATATCAATGAAGAACTGATGATGAAGCCGACGGTCGT
GGCACGTCCGCTGCTGGGCACCATCCTGAATCTGGCACGCGCTATCGATTTCATCTAC
AAAGAAGATGACGGCTACACCCATAGTTACCTGATTAAGGATCAGATCGCCTCCGTCC
TGGGTGACCACGTGCCGTTCTAA (SEQ ID NO: 119)

FIG. 3A (Cont'd)

```
Vv2M5    MATQVSASSLAQIPQPKNRPVANFHPNIWGDQFITYTPEDK-VTRAKKEEQIEDLKKEVK  59
VS2      MATQVSASSLAQIPQPKNRPVANFHPNIWGDQFITYTPEDK-VTRAKKEEQIEDLKKEVK  59
VvVS     MSTQVSASSLAQIPQPKNRPVANFHPNIWGDQFITYTPEDK-VTRACKEEQIEDLKKEVK  59
CsVS     MASGETF-------------RPTADFHPSLWRNHFLKGASDFKTVDHTATQERHEALKEEVR  49
         *::    :              **.*:***.:* ::*:. ..: * *  ::  .:*: * **:**:

Vv2M5    RKLTAAAVANPSQLLNFIDAVQRLGVAYHFEQEIEEALQHICNSFHDCNDMDGDLYNIAL  119
VS2      RKLTAAAVANPSQLLNFIDAVQRLGVAYHFEQEIEEALQHICNSFHDCNDMDGDLYNIAL  119
VvVS     RKLTAAAVANPSQLLNFIDAVQRLGVAYHFEQEIEEALQHICNSFHDCNDMDGDLYNIAL  119
CsVS     RMITDAEDK-PVQKLRLIDEVQRLGVAYHFEKEIGDAIQKLCPIYIDSNRAD--LHTVSL  106
         * :* *    :  * * *:** ***********:** :*:*:: *   : *.*  *  *:.::*

Vv2M5    GFRLLRQQGYTISCDIFNKFTDERGRFKEALISDVRGMLGLYEAAHLRVHGEDILAKALA  179
VS2      GFRLLRQQGYTISCDIFNKFTDERGRFKEALISDVRGMLGLYEAAHLRVHGEDILAKALA  179
VvVS     GFRLLRQQGYTISCDIFNKFTDERGRFKEALISDVRGMLGLYEAAHLRVHGEDILAKALA  179
CsVS     HFRLLRQQGIKISCDVFEKFKDDEGRFKSSLINDVQGMLSLYEAAYMAVRGEHILDEAIA  166
         ********  .:****:*:**:.*:****.:**.*:****:*****::.*:**.** :*:*

Vv2M5    FTTTHLKAMVES--LGYHLAEQVAHALNRPIRKGLERLEARWYISVY--QDEAFHDKTLL  235
VS2      FTTTHLKAMVES--LGYHLAEQVAHALNRPIRKGLERLEARWYISVY--QDEAFHDKTLL  235
VvVS     FTTTHLKAMVES--LGYHLAEQVAHALNRPIRKGLERLEARWYISVY--QDEAFHDKTLL  235
CsVS     FTTTHLKSLVAQDHVTPKLAEQINHALYRPLRKTLPRLEARYFMSMINSTSDHLCNKTLL  226
         *******::*   .  :  :**** : *** **:** * *****:::* :   .: : :****

Vv2M5    ELAKLDFNLVQSLHKEELSNLARWWKELDFATKLPFARDRLVEGYFWMMGVYFEPQYLRG  295
VS2      ELAKLDFNLVQSLHKEELSNLARWWKELDFATKLPFARDRLVEGYFWMMGVYFEPQYLRG  295
VvVS     ELAKLDFNLVQSLHKEELSNLARWWKELDFATKLPFARDRLVEGYFWMHGVYFEPQYLRG  295
CsVS     NFAKLDFNILLELHKEELNELTKWWKDLDFTTKLPYARDRLVELYFWDLGTYFEPQYAFG  286
         :.******:: ..******.:*.:**:**:****:*****: *** ***  *.******   *

Vv2M5    RRILTKVIALTSILDDIHDAYGTPEELKLFIEAIEKWDESSINQLPEYMKLCYVALLDVY  355
VS2      RRILTKVIALTSILDDIHDAYGTPEELKLFIEAIEKWDESSINQLPEYMKLCYVALLDVY  355
VvVS     RRILTKVIAMTSILDDIHDAYGTPEELKLFIEAIERWDINSINQLPEYMKLCYVALLDVY  355
CsVS     RKIMTQLNYILSIIDDTYDAYGTLEELSLFTEAVQRWNIEAVDMLPEYMKLIYRTLLDAF  346
         *:*:*::   : **:** :*****  ***.** **:::*:  .::: *******  * .:***.:

Vv2M5    NEIEEEMEKEGNQYRIHYLKEVMKNQVRAYFAEAKWLHDEHVPAFEEYMRVALASSGYCL  415
VS2      NEIEEEMEKEGNQYRIHYLKEVMKNQVRAYFAEAKWLHDEHVPAFEEYMRVALASSGYCL  415
VvVS     KEIEEEMEKEGNQYRVHYAKEVMKNQVRAYFAEAKWLHEEHVPAFEEYMRVALASSGYCL  415
CsVS     NEIEEDMAKQGRSHCVRYAKEENQKVIGAYSVQAKWFSEGYVPTIEEYMPIALTSCAYTF  406
         :****:*  *:*.::: ::* **  :: : ** .:***: : :**:****  :**:*..* :

Vv2M5    LAVTSFVGMGEIVTKEAFDWVTSDPRIMSSSNTITRLMDDIKSHKFEQKRGHVTSAVECY  475
VS2      LAVTSFVGMGEIVTKEAFDWVTSDPRIMSSSNTITRLMDDIKSHKFEQKRGHVTSAVECY  475
VvVS     LATTSFVGMGEIATKEAFDWVTSDPKIMSSSNFITRLMDDIKSHKFEQKRGHVTSAVECY  475
CsVS     VITNSFLGMGDFATKEVFEWISNNPKVVKAASVICRLMDDMQGHEFEQKRGHVASAIECY  466
         : ..:**:***::,***.*.*:*::.  ** ..:.  * *****::.:****** ***.**:***

Vv2M5    MKQYAVTEEQVYSEFKKQIENAWLDINQEC-LKPTAVPMPLLARLLNFTRTMDVIYKEED  534
VS2      MKQYAVTEEQVYSEFKKQIENAWLDINQEC-LKPTAVPMPLLARLLNFTRTMDVIYKEED  534
VvVS     MKQYGVSEEQVYSEFQKQIENAWLDINQEC-LKPTAVSMPLLARLLNFTRTMDVIYKEQD  534
CsVS     TKQHGVSKEEAIKMFEEEVANAWKDINEELMMKPTVVARPLLGTILNLARAIDFIYKEDD  526
         ::*: *:::*::.  . ::::    *** *** **:*.* .***. :*::*:::*.*****

Vv2M5    SYTHVGKTMRDNIASVFINPVI-  556
VS2      SYTHVGKTMRDNIASVFINPVI-  556
VvVS     SYTHVGKVMRDNIASVFINAVI-  556
CsVS     GYTHS-YLIKDQIASVLGDHVPF  548
         .***      ::*:*****: :  *
```

FIG. 3B

>ZzHO [Zingiber zerumbet]
MEAISLFSPFFFITLFLGFFITLLIKRSSRSSVHKQQVLLASLPPSPPRLPLIGNIHQLVGG
NPHRILLQLARTHGPLICLRLGQVDQVVASSVEAVEEIIKRHDLKFADRPRDLTFSRIFFYD
GNAVVMTPYGGEWKQMRKIYAMELLNSRRVKSFAAIREDVARKLTGEIAHKAFAQTPVINLS
EMVMSMINAIVIRVAFGDKCKQQAYFLHLVKEAMSYVSSFSVADMYPSLKFLDTLTGLKSKL
EGVHGKLDKVFDEIIAQRQAALAAEQAEEDLIIDVLLKLKDEGNQEFPITYTSVKAIVMEIF
LAGTETSSSVIDWVMSELIKNPKAMEKVQKEMREAMQGKTKLEESDIPKFSYLNLVIKETLR
LHPPGPLLFPRECRETCEVMGYRVPAGARLLINAFALSRDEKYWGSDAESFKPERFEGISVD
FKGSNFEFMPFGAGRRICPGMTFGISSVEVALAHLLFHFDWQLPQGMKIEDLDMMEVSGMSA
TRRSPLLVLAKLIIPLP (SEQ ID No: 13 | Wild Type)

MALLLAVFFFFITLFLGFFITLLIKRS*SRS*SVHKQQVLLASLPPSPPRLPLIGNIHQLVGGN
PHRILLQLARTHGPLICLRLGQVDQVVASSVEAVEEIIKRHDLKFADRPRDLTF*SR*IFFYDG
NAVVMTPYGGEWKQMRKIYAMELLN*SRR*VKSFAAIREDVARKLTGEIAHKAFAQTPVINLSE
MVMSMINAIVIRVAFGDKCKQQAYFLHLVKEAMSYVSSFSVADMYPSLKFLDTLTGLKSKLE
GVHGKLDKVFDEIIAQRQAALAAEQAEEDLIIDVLLKLKDEGNQEFPITYTSVKAIVMEIFL
AGTETSSSVIDWVMSELIKNPKAMEKVQKEMREAMQGKTKLEESDIPKFSYLNLVIKETLRL
HPPGPLLFPRECRETCEVMGYRVPAGARLLINAFAL*SR*DEKYWGSDAESFKPERFEGISVDF
KGSNFEFMPFGAGRRICPGMTFGISSVEVALAHLLFHFDWQLPQGMKIEDLDMMEVSGMSAT
RRSPLLVLAKLIIPLP (SEQ ID NO: 14)

ATGGCTCTGTTATTAGCAGTGTTCTTCTTTTTCATTACGCTGTTTCTGGGTTTCTTTATTAC
GCTGCTGATTAAACGCTCGTCCCGTAGCTCTGTCCATAAACAGCAAGTGCTGCTGGCCTCTC
TGCCGCCGAGTCCGCCGCGCCTGCCGCTGATTGGCAACATCCATCAACTGGTGGGCGGCAAC
CCGCATCGTATTCTGCTGCAACTGGCGCGTACCCACGGCCCGCTGATCTGCCTGCGTCTGGG
TCAGGTTGATCAAGTGGTTGCAAGTTCCGTGGAAGCTGTTGAAGAAATTATCAAACGTCACG
ACCTGAAATTTGCAGATCGTCCGCGCGACCTGACCTTTAGCCGTATTTTCTTTTATGATGGT
AACGCTGTCGTGATGACGCCGTACGGCGGTGAATGGAAACAGATGCGTAAAATCTATGCAAT
GGAACTGCTGAACAGCCGTCGTGTGAAATCTTTTGCGGCCATTCGTGAAGACGTTGCACGCA
AACTGACCGGCGAAATCGCTCACAAAGCATTCGCTCAGACGCCGGTCATTAACCTGTCTGAA
ATGGTGATGAGTATGATCAATGCGATTGTCATCCGCGTGGCCTTTGGTGATAAATGTAAACA
GCAAGCATACTTCCTGCATCTGGTGAAGAAGCTATGTCCTATGTTTCATCGTTTTCAGTCG
CGGATATGTACCCGTCCCTGAAATTCCTGGACACCCTGACGGGCCTGAAAAGCAAACTGGAA
GGCGTTCACGGTAAACTGGATAAAGTCTTCGACGAAATCATCGCACAGCGTCAAGCAGCGCT
GGCGGCGGAACAGGCTGAAGAAGATCTGATTATCGACGTGCTGCTGAAACTGAAAGATGAAG
GCAACCAGGAATTTCCGATTACCTATACGTCAGTTAAAGCGATTGTCATGGAAATCTTCCTG
GCCGGCACCGAAACCAGCAGCAGCGTGATTGACTGGGTTATGAGTGAACTGATCAAAAACCC
GAAAGCGATGGAAAAAGTGCAGAAAGAAATGCGTGAAGCCATGCAAGGCAAAACCAAACTGG
AAGAATCGGATATTCCGAAATTTAGCTACCTGAATCTGGTTATCAAAGAAACCCTGCGTCTG
CATCCGCCGGGTCCGCTGCTGTTCCCGCGTGAATGCCGCGAAACCTGCGAAGTGATGGGCTA
TCGTGTTCCGGCGGGTGCCCGCCTGCTGATTAACGCATTTGCTCTGTCTCGTGATGAAAAAT
ACTGGGGTTCCGACGCCGAATCATTTAAACCGGAACGCTTTGAAGGCATCTCTGTGGATTTC
AAAGGTAGTAATTTTGAATTTATGCCGTTCGGCGCGGGCCGTCGTATTTGTCCGGGCATGAC
CTTTGGTATCTCCTCAGTTGAAGTCGCGCTGGCCCATCTGCTGTTTCACTTCGATTGGCAAC
TGCCGCAAGGCATGAAAATTGAAGATCTGGACATGATGGAAGTCTCGGGTATGAGCGCAACC
CGTCGTAGCCCGCTGCTGGTTCTGGCCAAACTGATTATCCCGCTGCCG (SEQ ID NO: 15)

FIG. 4A

>BsGAO [Barnadesia spinosa]

```
MELTLTTSLGLAVFVFILFKLLTGSKSTKNSLPEAWRLPIIGHMHHLVGTLPHRGVTDMARK
YGSLMHLQLGEVSTIVVSSPRWAKEVLTTYDITFANRPETLTGEIVAYHNTDIVLSPYGEYW
RQLRKLCTLELLSAKKVKSFQSLREEECWNLVKEVRSSGSGSPVDLSESIFKLIATILSRAA
FGKGIKDQREFTEIVKEILRLTGGFDVADIFPSKKILHHLSGKRAKLTNIHNKLDSLINNIV
SEHPGSRTSSSQESLLDVLLRLKDSAELPLTSDNVKAVILDMFGAGTDTSSATIEWAISELI
RCPRAMEKVQTELRQALNGKERIQEEDIQELSYLKLVIKETLRLHPPLPLVMPRECREPCVL
AGYEIPTKTKLIVNVFAINRDPEYWKDAETFMPERFENSPINIMGSEYEYLPFGAGRRMCPG
AALGLANVELPLAHILYYFNWKLPNGARLDELDMSECFGATVQRKSELLLVPTAYKTANNSA
(SEQ ID No: 16 | Wild Type)
```

```
MALLLAVFLGLAVFVFILFKLLTGSKSTKNSLPEAWRLPIIGHMHHLVGTLPHRGVTDMARK
YGSLMHLQLGEVSTIVVSSPRWAKEVLTTYDITFANRPETLTGEIVAYHNTDIVLSPYGEYW
RQLRKLCTLELLSAKKVKSFQSLREEECWNLVKEVRSSGSGSPVDLSESIFKLIATIL*SRA*A
FGKGIKDQREFTEIVKEILRLTGGFDVADIFPSKKILHHLSGKRAKLTNIHNKLDSLINNIV
SEHPG*SRT*SSSQESLLDVLLRLKDSAELPLTSDNVKAVILDMFGAGTDTSSATIEWAISELI
RCPRAMEKVQTELRQALNGKERIQEEDIQELSYLKLVIKETLRLHPPLPLVMPRECREPCVL
AGYEIPTKTKLIVNVFAINRDPEYWKDAETFMPERFENSPINIMGSEYEYLPFGAGRRMCPG
AALGLANVELPLAHILYYFNWKLPNGARLDELDMSECFGATVQRKSELLLVPTAYKTANNSA
(SEQ ID NO: 17)
```

```
ATGGCTCTGTTATTAGCAGTTTTCCTGGGCCTGGCTGTCTTCGTCTTTATCCTGTTCAAACT
GCTGACCGGCTCAAAATCAACCAAAAATTCACTGCCGGAAGCATGGCGTCTGCCGATCATTG
GCCACATGCATCACCTGGTTGGCACGCTGCCGCATCGCGGTGTGACCGACATGGCGCGTAAA
TACGGCAGCCTGATGCATCTGCAACTGGGCGAAGTGAGCACCATTGTCGTCTCATCGCCGCG
TTGGGCAAAAGAAGTGCTGACGACGTATGATATTACCTTTGCGAATCGCCCGGAAACCCTGA
CCGGCGAAATTGTTGCGTACCACAACACGGATATTGTGCTGTCACCGTATGGCGAATACTGG
CGCCAACTGCGTAAACTGTGCACGCTGGAACTGCTGAGCGCCAAAAAAGTGAAAAGTTTTCA
GTCGCTGCGTGAAGAAGAATGCTGGAATCTGGTGAAAGAAGTGCGTTCGAGCGGCTCAGGTT
CCCCGGTCGATCTGTCGGAATCCATCTTTAAACTGATTGCAACCATTCTGAGCCGCGCAGCG
TTTGGCAAAGGTATCAAAGATCAGCGTGAATTTACCGAAATTGTGAAAGAAATCCTGCGCCT
GACGGGCGGTTTTGATGTGGCGGATATTTTCCCGTCCAAAAAGATCCTGCACCACCTGAGCG
GCAAACGTGCGAAACTGACCAACATCCACAACAAACTGGATTCCCTGATTAATAACATTGTT
TCTGAACATCCGGGTTCGCGTACCTCGTCGAGCCAGGAAAGCCTGCTGGATGTGCTGCTGCG
CCTGAAAGATTCCGCGGAACTGCCGCTGACCTCGGACAATGTTAAAGCCGTGATCCTGGATA
TGTTCGGTGCGGGCACGGATACGTCGAGCGCCACGATTGAATGGGCGATCAGCGAACTGATC
CGCTGCCCGCGTGCAATGGAAAAGTGCAAACGGAACTGCGTCAAGCGCTGAATGGTAAAGA
ACGCATTCAGGAAGAAGATATTCAGGAACTGTCCTATCTGAAACTGGTCATTAAAGAAACCC
TGCGCCTGCATCCGCCGCTGCCGCTGGTGATGCCGCGTGAATGTCGTGAACCGTGTGTCCTG
GCGGGTTACGAAATCCCGACCAAAACGAAACTGATTGTGAATGTCTTTGCCATCAATCGTGA
CCCGGAATACTGGAAAGATGCAGAAACCTTCATGCCGGAACGCTTTGAAAACAGCCCGATTA
ACATCATGGGTAGTGAATATGAATACCTGCCGTTTGGCGCAGGCCGCCGTATGTGTCCGGGT
GCAGCTCTGGGTCTGGCGAATGTGGAACTGCCGCTGGCGCACATCCTGTATTATTTTAACTG
GAAACTGCCGAATGGCGCTCGCCTGGATGAACTGGATATGTCGGAATGCTTTGGCGCGACGG
TCCAACGCAAAAGCGAACTGCTGCTGGTCCCGACGGCATACAAAACGGCAAACAACTCCGCA
(SEQ ID NO: 18)
```

FIG. 4A (Cont'd)

>HmPO [Hyoscyamus muticus]

MQFFSLVSIFLFLSFLFLLRKWKNSNSQSKKLPPGPWKLPLLGSMLHMVGGLPHHVLRDLAK
KYGPLMHLQLGEVSAVVVTSPDMAKEVLKTHDIAFASRPKLLAPEIVCYNRSDIAFCPYGDY
WRQMRKICVLEVLSAKNVRSFSSIRRDEVLRLVNFVRSSTSEPVNFTERLFLFTSSMTCRSA
FGKVFKEQETFIQLIKEVIGLAGGFDVADIFPSLKFLHVLTGMEGKIMKAHHKVDAIVEDVI
NEHKKNLAMGKTNGALGGEDLIDVLLRLMNDGGLQFPITNDNIKAIIFDMFAAGTETSSSTL
VWAMVQMMRNPTILAKAQAEVREAFKGKETFDENDVEELKYLKLVIKETLRLHPPVPLLVPR
ECREETEINGYTIPVKTKVMVNVWALGRDPKYWDDADNFKPERFEQCSVDFIGNNFEYLPFG
GGRRICPGISFGLANVYLPLAQLLYHFDWKLPTGMEPKDLDLTELVGVTAARKSDLMLVATP
YQPSRE (SEQ ID NO: 19 | Wild Type)

MALLLAVFFFSLVSIFLFLSFLFLLRKWKNSNSQSKKLPPGPWKLPLLGSMLHMVGGLPHHV
LRDLAKKYGPLMHLQLGEVSAVVVTSPDMAKEVLKTHDIAFASRPKLLAPEIVCYNRSDIAF
CPYGDYWRQMRKICVLEVLSAKNVRSFSSIRRDEVLRLVNFVRSSTSEPVNFTERLFLFTSS
MTCRSAFGKVFKEQETFIQLIKEVIGLAGGFDVADIFPSLKFLHVLTGMEGKIMKAHHKVDA
IVEDVINEHKKNLAMGKTNGALGGEDLIDVLLRLMNDGGLQFPITNDNIKAIIFDMFAAGTE
TSSSTLVWAMVQMMRNPTILAKAQAEVREAFKGKETFDENDVEELKYLKLVIKETLRLHPPV
PLLVPRECREETEINGYTIPVKTKVMVNVWALGRDPKYWDDADNFKPERFEQCSVDFIGNNF
EYLPFGGGRRICPGISFGLANVYLPLAQLLYHFDWKLPTGMEPKDLDLTELVGVTAARKSDL
MLVATPYQPSRE (SEQ ID NO: 20)

ATGGCTCTGTTATTAGCAGTTTTCTTCTTCTCCCTGGTCTCAATCTTTCTGTTCCTGTCCTT
TCTGTTCCTGCTGCGTAAATGGAAAAACTCAAACTCCCAATCGAAAAAACTGCCGCCGGGTC
CGTGGAAACTGCCGCTGCTGGGCTCTATGCTGCACATGGTTGGCGGCCTGCCGCATCACGTT
CTGCGTGATCTGGCGAAAAAATATGGTCCGCTGATGCATCTGCAACTGGGCGAAGTCTCCGC
CGTGGTTGTCACCTCACCGGATATGGCAAAAGAAGTGCTGAAAACGCATGACATTGCGTTCG
CCTCCCGTCCGAAACTGCTGGCCCCGGAAATTGTGTGCTACAACCGCTCAGATATTGCATTT
TGTCCGTATGGTGACTACTGGCGTCAAATGCGCAAAATTTGCGTCCTGGAAGTGCTGTCGGC
CAAAAATGTGCGCAGCTTTAGCTCTATTCGTCGTGATGAAGTTCTGCGTCTGGTTAACTTCG
TCCGCAGTTCCACCTCGGAGCCGGTGAATTTTACGGAACGTCTGTTTCTGTTCACCTCATCG
ATGACCTGCCGTAGCGCATTTGGTAAAGTTTTCAAAGAACAGGAAACCTTCATTCAACTGAT
CAAAGAAGTCATTGGCCTGGCCGGCGGTTTTGATGTGGCAGACATCTTTCCGAGTCTGAAAT
TCCTGCATGTTCTGACCGGCATGGAAGGCAAAATTATGAAAGCTCATCACAAAGTCGATGCG
ATTGTGGAAGACGTTATCAACGAACACAAGAAAAACCTGGCGATGGGCAAAACGAACGGCGC
ACTGGGCGGTGAAGATCTGATCGACGTTCTGCTGCGTCTGATGAATGATGGCGGCCTGCAAT
TCCGATCACCAACGATAATATCAAAGCTATTATCTTTGATATGTTTGCGGCGGGCACCGAA
ACCAGCAGCAGCACCCTGGTGTGGGCGATGGTGCAGATGATGCGTAACCCGACGATTCTGGC
AAAAGCTCAAGCGGAAGTGCGCGAAGCCTTCAAAGGCAAAGAAACCTTTGATGAAAATGACG
TTGAAGAACTGAAATATCTGAAACTGGTCATCAAAGAAACGCTGCGTCTGCATCCGCCGGTT
CCGCTGCTGGTCCCGCGTGAATGCCGCGAAGAAACCGAAATTAACGGTTATACCATCCCGGT
TAAAACGAAAGTGATGGTTAATGTCTGGGCTCTGGGCCGTGATCCGAAATACTGGGATGACG
CGGACAACTTTAAACCGGAACGCTTTGAACAGTGCTCTGTGGATTTCATCGGCAACAACTTT
GAATATCTGCCGTTTGGCGGTGGCCGTCGCATTTGTCCGGGTATCAGCTTCGGCCTGGCTAA
TGTTTATCTGCCGCTGGCGCAACTGCTGTACCACTTTGATTGGAAACTGCCGACCGGCATGG
AACCGAAAGATCTGGACCTGACCGAACTGGTGGGCGTTACGGCAGCTCGTAAATCTGATCTG
ATGCTGGTTGCGACCCCGTACCAGCCGAGCCGTGAA (SEQ ID NO: 21)

*FIG. 4A (Cont'd)*

>LsGAO [Lactuca sativa]
MELSITTSIALATIVFFLYKLATRPKSTKKQLPEASRLPIIGHMHHLIGTMPHRGVMDLARK
HGSLMHLQLGEVSTIVVSSPKWAKEILTTYDITFANRPETLTGEIIAYHNTDIVLAPYGEYW
RQLRKLCTLELLSVKKVKSFQSIREEECWNLVKEVKESGSGKPINLSESIFTMIATILSRAA
FGKGIKDQREFTEIVKEILRQTGGFDVADIFPSKKFLHHLSGKRARLTSIHKKLDNLINNIV
AEHHVSTSSKANETLLDVLLRLKDSAEFPLTADNVKAIILDMFGAGTDTSSATVEWAISELI
RCPRAMEKVQAELRQALNGKEKIQEEDIQDLAYLNLVIRETLRLHPPLPLVMPRECREPVNL
AGYEIANKTKLIVNVFAINRDPEYWKDAEAFIPERFENNPNNIMGADYEYLPFGAGRRMCPG
AALGLANVQLPLANILYHFNWKLPNGASHDQLDMTESFGATVQRKTELLLVPSF (SEQ ID
NO: 22 | Wild Type)

MALLLAVFIALATIVFFLYKLATRPKSTKKQLPEA*SRLP*IIGHMHHLIGTMPHRGVMDLARK
HGSLMHLQLGEVSTIVVSSPKWAKEILTTYDITFANRPETLTGEIIAYHNTDIVLAPYGEYW
RQLRKLCTLELLSVKKVKSFQSIREEECWNLVKEVKESGSGKPINLSESIFTMIATIL*SRAA*
FGKGIKDQREFTEIVKEILRQTGGFDVADIFPSKKFLHHLSGKRARLTSIHKKLDNLINNIV
AEHHVSTSSKANETLLDVLLRLKDSAEFPLTADNVKAIILDMFGAGTDTSSATVEWAISELI
RCPRAMEKVQAELRQALNGKEKIQEEDIQDLAYLNLVIRETLRLHPPLPLVMPRECREPVNL
AGYEIANKTKLIVNVFAINRDPEYWKDAEAFIPERFENNPNNIMGADYEYLPFGAGRRMCPG
AALGLANVQLPLANILYHFNWKLPNGASHDQLDMTESFGATVQRKTELLLVPSF (SEQ ID
NO: 23)

ATGGCTCTGTTATTAGCAGTTTTCATCGCACTGGCTACCATCGTCTTCTTCCTGTATAAACT
GGCAACGCGCCCGAAATCTACCAAAAAACAACTGCCGGAAGCGAGCCGTCTGCCGATTATCG
GCCACATGCATCACCTGATTGGCACCATGCCGCACCGTGGTGTCATGGATCTGGCCCGCAAA
CATGGCTCGCTGATGCATCTGCAACTGGGCGAAGTGAGCACCATTGTGGTTAGCTCTCCGAA
ATGGGCAAAAGAAATTCTGACCACCTATGATATTACCTTTGCTAACCGCCCGGAAACCCTGA
CGGGCGAAATTATCGCGTACCATAATACGGACATTGTGCTGGCCCCGTATGGTGAATACTGG
CGTCAACTGCGTAAACTGTGCACCCTGGAACTGCTGTCCGTTAAAAAAGTCAAATCATTTCA
ATCGATTCGTGAAGAAGAATGTTGGAACCTGGTGAAAGAAGTTAAAGAAAGCGGCTCTGGTA
AACCGATTAATCTGAGTGAATCCATCTTCACCATGATTGCGACGATCCTGAGTCGTGCGGCC
TTTGGCAAAGGTATTAAAGATCAGCGCGAATTTACCGAAATTGTCAAAGAAATCCTGCGTCA
AACGGGCGGTTTCGATGTGGCAGACATTTTTCCGAGCAAAAAATTCCTGCATCACCTGTCTG
GCAAACGTGCTCGCCTGACCAGTATCCATAAAAAACTGGATAACCTGATCAACAATATCGTC
GCGGAACATCATGTGAGCACCAGCAGCAAAGCGAATGAAACGCTGCTGGATGTTCTGCTGCG
CCTGAAAGACAGTGCCGAATTCCGCTGACCGCAGACAACGTCAAAGCTATTATCCTGGATA
TGTTCGGTGCAGGCACCGATACCAGCAGCGCAACGGTGGAATGGGCCATTAGCGAACTGATC
CGTTGCCCGCGCGCAATGGAAAAAGTTCAGGCAGAACTGCGTCAAGCTCTGAACGGTAAAGA
AAAAATCCAGGAAGAAGATATTCAAGACCTGGCCTATCTGAATCTGGTGATTCGTGAAACCC
TGCGTCTGCACCCGCCGCTGCCGCTGGTTATGCCGCGTGAATGCCGTGAGCCGGTGAACCTG
GCGGGCTATGAAATCGCCAATAAAACCAAACTGATCGTCAATGTGTTTGCGATTAACCGTGA
CCCGGAATACTGGAAAGACGCGGAAGCCTTTATCCCGGAACGTTTTGAAAACAATCCGAACA
ATATCATGGGTGCAGATTATGAATACCTGCCGTTTGGCGCTGGTCGTCGCATGTGTCCGGGC
GCAGCTCTGGGTCTGGCAAACGTTCAACTGCCGCTGGCGAACATTCTGTACCATTTCAACTG
GAAACTGCCGAATGGCGCGTCCCACGATCAACTGGACATGACCGAATCATTTGGTGCCACCG
TGCAACGTAAAACGGAACTGCTGCTGGTTCCGAGCTTC (SEQ ID NO: 24)

FIG. 4A (Cont'd)

>NtEAO [Nicotiani tabacum]
MQFFSLVSIFLFLSFLFLLRKWKNSNSQSKKLPPGPWKIPILGSMLHMIGGEPHHVLRDLAK
KYGPLMHLQLGEISAVVVTSRDMAKEVLKTHDVVFASRPKIVAMDIICYNQSDIAFSPYGDH
WRQMRKICVMELLNAKNVRSFSSIRRDEVVRLIDSIRSDSSSGELVNFTQRIIWFASSMTCR
SAFGQVLKGQDIFAKKIREVIGLAEGFDVVDIFPTYKFLHVLSGMKRKLLNAHLKVDAIVED
VINEHKKNLAAGKSNGALGGEDLIDVLLRLMNDTSLQFPITNDNIKAVIVDMFAAGTETSST
TTVWAMAEMMKNPSVFTKAQAEVREAFRDKVSFDENDVEELKYLKLVIKETLRLHPPSPLLV
PRECREDTDINGYTIPAKTKVMVNVWALGRDPKYWDDAESFKPERFEQCSVDFFGNNFEFLP
FGGGRRICPGMSFGLANLYLPLAQLLYHFDWKLPTGIMPRDLDLTELSGITIARKGGLYLNA
TPYQPSRE (SEQ ID NO: 25 | Wild Type)

MALLAVFFFSLVSIFLFLSFLFLLRKWKNSNSQSKKLPPGPWKIPILGSMLHMIGGEPHHV
LRDLAKKYGPLMHLQLGEISAVVVT*SRDMAKEVLKTHDVVFA*SRPKIVAMDIICYNQSDIAF
SPYGDHWRQMRKICVMELLNAKNVRSFSSIRRDEVVRLIDSIRSDSSSGELVNFTQRIIWFA
SSMTCRSAFGQVLKGQDIFAKKIREVIGLAEGFDVVDIFPTYKFLHVLSGMKRKLLNAHLKV
DAIVEDVINEHKKNLAAGKSNGALGGEDLIDVLLRLMNDTSLQFPITNDNIKAVIVDMFAAG
TETSSTTTVWAMAEMMKNPSVFTKAQAEVREAFRDKVSFDENDVEELKYLKLVIKETLRLHP
PSPLLVPRECREDTDINGYTIPAKTKVMVNVWALGRDPKYWDDAESFKPERFEQCSVDFFGN
NFEFLPFGGGRRICPGMSFGLANLYLPLAQLLYHFDWKLPTGIMPRDLDLTELSGITIARKG
GLYLNATPYQPSRE (SEQ ID NO: 26)

ATGGCTCTGTTATTAGCAGTTTTCTTCTTCTCCCTGGTCTCAATCTTCCTGTTCCTGTCCTT
TCTGTTCCTGCTGCGTAAATGGAAAAACTCTAATAGCCAATCCAAAAAACTGCCGCCGGGTC
CGTGGAAAATTCCGATCCTGGGCTCTATGCTGCACATGATTGGCGGTGAACCGCATCATGTG
CTGCGTGATCTGGCGAAAAAATATGGTCCGCTGATGCATCTGCAACTGGGCGAAATCTCTGC
GGTGGTTGTCACGAGTCGTGACATGGCCAAAGAAGTGCTGAAAACCCATGATGTGGTTTTTG
CATCTCGCCCGAAAATCGTTGCTATGGATATTATCTGCTATAACCAGTCGGACATCGCGTTC
AGCCCGTACGGTGATCACTGGCGTCAAATGCGCAAAATTTGTGTCATGGAACTGCTGAACGC
CAAAAATGTGCGCAGTTTTAGCTCTATTCGTCGTGATGAAGTCGTGCGTCTGATTGATTCCA
TCCGCTCAGACAGTTCCTCAGGCGAACTGGTGAATTTTACGCAGCGTATTATCTGGTTCGCA
TCGAGCATGACCTGCCGCTCGGCTTTTGGTCAGGTTCTGAAAGGCCAAGATATTTTGCGAA
GAAAATTCGTGAAGTGATCGGTCTGGCCGAAGGCTTCGATGTTGTGGATATTTTTCCGACCT
ATAAATTCCTGCATGTCCTGAGCGGTATGAAACGCAAACTGCTGAACGCGCACCTGAAAGTT
GATGCCATTGTCGAAGACGTGATCAACGAACATAAGAAAAACCTGGCGGCGGGTAAATCCAA
CGGCGCACTGGGCGGTGAAGATCTGATTGACGTGCTGCTGCGTCTGATGAATGATACCAGCC
TGCAATTTCCGATCACCAACGACAACATTAAAGCGGTGATCGTTGATATGTTCGCGGCGGGC
ACCGAAACCTCTAGTACCACGACCGTTTGGGCGATGGCCGAAATGATGAAAAACCCGTCGGT
GTTTACCAAAGCACAAGCGGAAGTGCGTGAAGCGTTTCGTGATAAAGTTAGCTTCGATGAAA
ATGATGTGGAAGAACTGAAATACCTGAAACTGGTGATTAAAGAAACGCTGCGTCTGCATCCG
CCGAGCCCGCTGCTGGTTCCGCGTGAATGCCGTGAAGATACCGACATTAACGGTTATACGAT
CCCGGCAAAAACCAAAGTCATGGTGAATGTTTGGGCTCTGGGCCGTGACCCGAAATACTGGG
ATGACGCAGAATCCTTTAAACCGGAACGCTTTGAACAGTGCTCAGTGGATTTCTTTGGTAAC
AACTTTGAATTTCTGCCGTTTGGCGGTGGCCGTCGCATTTGTCCGGGTATGTCCTTCGGCCT
GGCGAACCTGTATCTGCCGCTGGCCCAACTGCTGTACCACTTTGATTGGAAACTGCCGACGG
GTATTATGCCGCGTGATCTGGACCTGACGGAACTGTCTGGCATTACCATCGCACGCAAAGGT
GGCCTGTATCTGAATGCTACCCCGTACCAGCCGAGTCGTGAA (SEQ ID NO: 27)

FIG. 4A (Cont'd)

>CpVO [Citrus x paradisi]
MELPLKSIALTIVIVTVLTWAWRVLNWVWLRPKKLEKFLRQQGLKGNSYRLLFGDLKENSIE
LKEAKARPLSLDDDIAIRVNPFLHKLVNDYGKNSFMWFGPTPRVNIMNPDQIKAIFTKINDF
QKVNSIPLARLLIVGLATLEGEKWAKHRKLINPAFHQEKLKLMLPAFYLSCIEIITKWEKQM
SVEGSSELDVWPYLANLTSDVISRTAFGSSYEEGRRIFQLQAELAELTMQVFRSVHIPGWRF
LPTKRNRRMKEIDKEIRASLMGIIKNREKAMRAGEAANNDLLGILMETSFREIEEHGNNKNV
GFSMNDVIEECKLFYFAGQETTSVLLNWTMVLLSKHQDWQERARQEVLQVFGNNKPDYDGLN
HLKIVQMILYEVLRLYPPVTVLSRAVFKETKLGNLTLPAGVQIGLPMILVHQDPELWGDDAV
EFKPERFAEGISKAAKNQVSYFPFALGPRICVGQNFALVEAKMATAMILQNYSFELSPSYVH
APTAVPTLHPELGTQLILRKLWCKNN (SEQ ID NO: 28 | Wild Type)

MALLLAVFIALTIVIVTVLTWAWRVLNWVWLRPKKLEKFLRQQGLKGNSYRLLFGDLKENSI
ELKEAKARPLSLDDDIAIRVNPFLHKLVNDYGKNSFMWFGPTPRVNIMNPDQIKAIFTKIND
FQKVNSIPLARLLIVGLATLEGEKWAKHRKLINPAFHQEKLKLMLPAFYLSCIEIITKWEKQ
MSVEGSSELDVWPYLANLTSDVI*SRT*AFGSSYEEGRRIFQLQAELAELTMQVFRSVHIPGWR
FLPTKRNRRMKEIDKEIRASLMGIIKNREKAMRAGEAANNDLLGILMETSFREIEEHGNNKN
VGFSMNDVIEECKLFYFAGQETTSVLLNWTMVLLSKHQDWQERARQEVLQVFGNNKPDYDGL
NHLKIVQMILYEVLRLYPPVTVLSRAVFKETKLGNLTLPAGVQIGLPMILVHQDPELWGDDA
VEFKPERFAEGISKAAKNQVSYFPFALGPRICVGQNFALVEAKMATAMILQNYSFELSPSYV
HAPTAVPTLHPELGTQLILRKLWCKNN (SEQ ID NO: 29)

```
ATGGCTCTGTTATTAGCAGTTTTCATTGCTCTGACGATTGTTATTGTTACGGTGCTGACCTG
GGCGTGGCGTGTGCTGAACTGGGTTTGGCTGCGTCCGAAAAAACTGGAAAATTTCTGCGCC
AGCAAGGCCTGAAGGGTAACAGCTATCGTCTGCTGTTCGGCGATCTGAAAGAAAATTCTATT
GAACTGAAAGAAGCGAAAGCCCGTCCGCTGAGTCTGGATGACGATATTGCAATCCGCGTTAA
CCCGTTTCTGCATAAACTGGTCAACGATTACGGCAAAAATTCTTTTATGTGGTTCGGTCCGA
CCCCGCGCGTGAACATTATGAACCCGGATCAGATTAAAGCGATCTTTACGAAAATCAACGAT
TTCCAAAAAGTTAATAGCATTCCGCTGGCGCGTCTGCTGATCGTCGGCCTGGCCACCCTGGA
AGGTGAAAAATGGGCAAAACATCGCAAACTGATTAACCCGGCTTTTCACCAAGAAAAACTGA
AACTGATGCTGCCGGCGTTCTATCTGTCCTGCATCGAAATTATCACGAAATGGGAAAAACAG
ATGTCAGTGGAAGGTAGCTCTGAACTGGACGTTTGGCCGTATCTGGCCAATCTGACCAGCGA
TGTTATTTCTCGTACGGCATTTGGCAGTTCCTACGAAGAAGGTCGTCGCATCTTCCAGTTAC
AGGCGGAACTGGCCGAACTGACCATGCAGGTTTTTCGTTCTGTCCATATTCCGGGCTGGCGT
TTCCTGCCGACGAAACGCAACCGTCGCATGAAAGAAATTGACAAAGAAATCCGCGCCAGTCT
GATGGGTATTATCAAAAATCGTGAAAAGCAATGCGCGCTGGCGAAGCGGCCAACAATGATC
TGCTGGGTATTCTGATGGAAACCAGCTTTCGTGAAATCGAAGAACACGGCAACAATAAAAAC
GTCGGTTTCAGCATGAATGACGTGATCGAAGAATGTAAACTGTTTTATTTCGCTGGCCAGGA
AACCACGTCAGTTCTGCTGAACTGGACGATGGTGCTGCTGTCGAAACATCAGGATTGGCAAG
AACGTGCCCGCCAGGAAGTCCTGCAAGTGTTTGGCAACAATAAACCGGACTACGATGGTCTG
AACCACCTGAAAATTGTGCAGATGATCCTGTATGAAGTTCTGCGTCTGTATCCGCCGGTGAC
GGTGCTGAGCCGTGCGGTGTTTAAAGAAACCAAACTGGGTAATCTGACGCTGCCGGCAGGCG
TCCAGATTGGTCTGCCGATGATCCTGGTGCACCAGGACCCGGAACTGTGGGGCGACGATGCT
GTGGAATTTAAACCGGAACGTTTCGCGGAAGGTATTAGTAAAGCAGCTAAAAATCAGGTTTC
CTATTTTCCGTTCGCGCTGGGTCCGCGTATTTGCGTCGGTCAAAACTTTGCACTGGTGGAAG
CTAAAATGGCAACCGCTATGATCCTGCAAAATTATAGCTTTGAACTGTCACCGAGCTATGTT
CATGCGCCGACCGCCGTTCCGACGCTGCACCCGGAACTGGGCACGCAACTGATTCTGCGTAA
ACTGTGGTGTAAAAACAAT (SEQ ID NO: 30)
```

FIG. 4A (Cont'd)

>AaAO [Artemesia annua]
MKSILKAMALSLTTSIALATILLFVYKFATRSKSTKKSLPEPWRLPIIGHMHHLIGTTPHRG
VRDLARKYGSLMHLQLGEVPTIVVSSPKWAKEILTTYDITFANRPETLTGEIVLYHNTDVVL
APYGEYWRQLRKICTLELLSVKKVKSFQSLREEECWNLVQEIKASGSGRPVNLSENVFKLIA
TILSRAAFGKGIKDQKELTEIVKEILRQTGGFDVADIFPSKKFLHHLSGKRARLTSLRKKID
NLIDNLVAEHTVNTSSKTNETLLDVLLRLKDSAEFPLTSDNIKAIILDMFGAGTDTSSSTIE
WAISELIKCPKAMEKVQAELRKALNGKEKIHEEDIQELSYLNMVIKETLRLHPPLPLVLPRE
CRQPVNLAGYNIPNKTKLIVNVFAINRDPEYWKDAEAFIPERFENSSATVMGAEYEYLPFGA
GRRMCPGAALGLANVQLPLANILYHFNWKLPNGVSYDQIDMTESSGATMQRKTELLLVPSF
(SEQ ID NO: 31 | Wild Type)

MALLLAVFIALATILLFVYKFATRSKSTKKSLPEPWRLPIIGHMHHLIGTTPHRGVRDLARK
YGSLMHLQLGEVPTIVVSSPKWAKEILTTYDITFANRPETLTGEIVLYHNTDVVLAPYGEYW
RQLRKICTLELLSVKKVKSFQSLREEECWNLVQEIKASGSGRPVNLSENVFKLIATILSRAA
FGKGIKDQKELTEIVKEILRQTGGFDVADIFPSKKFLHHLSGKRARLTSLRKKIDNLIDNLV
AEHTVNTSSKTNETLLDVLLRLKDSAEFPLTSDNIKAIILDMFGAGTDTSSSTIEWAISELI
KCPKAMEKVQAELRKALNGKEKIHEEDIQELSYLNMVIKETLRLHPPLPLVLPRECRQPVNL
AGYNIPNKTKLIVNVFAINRDPEYWKDAEAFIPERFENSSATVMGAEYEYLPFGAGRRMCPG
AALGLANVQLPLANILYHFNWKLPNGVSYDQIDMTESSGATMQRKTELLLVPSF (SEQ ID
NO: 32)

ATGGCTCTGTTATTAGCAGTTTTCATCGCACTGGCAACCATTCTGCTGTTTGTGTATAAATT
CGCTACCCGTTCCAAATCAACGAAAAAATCACTGCCGGAACCGTGGCGCCTGCCGATTATCG
GTCACATGCATCACCTGATCGGCACCACCCGCATCGTGGCGTGCGTGATCTGGCACGCAAA
TATGGCTCGCTGATGCATCTGCAACTGGGTGAAGTCCCGACCATTGTGGTTAGCTCTCCGAA
ATGGGCGAAAGAAATCCTGACCACCTATGATATTACCTTTGCCAACCGCCCGGAAACCCTGA
CGGGCGAAATCGTGCTGTACCACAATACGGATGTGGTGCTGGCGCCGTATGGTGAATACTGG
CGTCAACTGCGTAAAATTTGCACCCTGGAACTGCTGAGTGTGAAAAAGTTAAATCTTTCCA
GAGCCTGCGTGAAGAAGAATGTTGGAACCTGGTTCAAGAAATTAAAGCATCGGGCAGCGGTC
GCCCGGTTAACCTGAGTGAAAATGTCTTTAAACTGATTGCTACCATCCTGTCCCGTGCGGCC
TTCGGCAAAGGTATCAAAGATCAGAAAGAACTGACCGAAATTGTCAAAGAAATCCTGCGCCA
AACGGGCGGTTTTGATGTGGCGGACATTTTTCCGTCGAAAAAATTCCTGCATCACCTGAGCG
GTAAACGTGCCCGCCTGACCAGCCTGCGTAAGAAAATTGATAACCTGATCGACAATCTGGTC
GCGGAACATACCGTGAACACGAGTTCCAAAACCAATGAAACGCTGCTGGATGTGCTGCTGCG
CCTGAAAGACTCCGCCGAATTTCCGCTGACCTCAGATAATATCAAAGCGATTATCCTGGATA
TGTTCGGTGCAGGCACCGATACCAGCAGCAGCACCATTGAATGGGCAATCTCAGAACTGATT
AAATGCCCGAAAGCTATGGAAAAAGTCCAGGCAGAACTGCGCAAAGCTCTGAACGGCAAAGA
AAAAATCCATGAAGAAGATATTCAAGAACTGTCTTACCTGAACATGGTTATCAAAGAAACCC
TGCGTCTGCACCCGCCGCTGCCGCTGGTGCTGCCGCGTGAATGTCGCCAGCCGGTTAACCTG
GCAGGCTATAACATCCCGAATAAAACGAAACTGATCGTTAACGTCTTTGCTATTAACCGTGA
CCCGGAATACTGGAAAGACGCGGAAGCCTTTATCCCGGAACGCTTTGAAAACAGCAGCGCGA
CCGTGATGGGTGCCGAATATGAATACCTGCCGTTTGGCGCGGGTCGTCGCATGTGTCCGGGC
GCAGCTCTGGGTCTGGCAAACGTGCAACTGCCGCTGGCTAATATCCTGTATCACTTCAACTG
GAAACTGCCGAATGGCGTTAGCTACGATCAAATTGACATGACCGAAAGCTCAGGTGCCACGA
TGCAACGCAAAACCGAACTGCTGCTGGTGCCGTCCTTC (SEQ ID NO: 33)

FIG. 4A (Cont'd)

>AtKO [Arabidopsis thaliana]
MAFFSMISILLGFVISSFIFIFFFKKLLSFSRKNMSEVSTLPSVPVVPGFPVIGNLLQLKEK
KPHKTFTRWSEIYGPIYSIKMGSSSLIVLNSTETAKEAMVTRFSSISTRKLSNALTVLTCDK
SMVATSDYDDFHKLVKRCLLNGLLGANAQKRKRHYRDALIENVSSKLHAHARDHPQEPVNFR
AIFEHELFGVALKQAFGKDVESIYVKELGVTLSKDEIFKVLVHDMMEGAIDVDWRDFFPYLK
WIPNKSFEARIQQKHKRRLAVMNALIQDRLKQNGSESDDDCYLNFLMSEAKTLTKEQIAILV
WETIIETADTTLVTTEWAIYELAKHPSVQDRLCKEIQNVCGGEKFKEEQLSQVPYLNGVFHE
TLRKYSPAPLVPIRYAHEDTQIGGYHVPAGSEIAINIYGCNMDKKRWERPEDWWPERFLDDG
KYETSDLHKTMAFGAGKRVCAGALQASLMAGIAIGRLVQEFEWKLRDGEEENVDTYGLTSQK
LYPLMAIINPRRS (SEQ ID NO: 34 | Wild Type)

MALLLAVFSMISILLGFVISSFIFIFFFKKLLSF*SRKNMSEVSTLPSVPVVPGFPVIGNLL
QLKEKKPHKTFTRWSEIYGPIYSIKMGSSSLIVLNSTETAKEAMVTRFSSISTRKLSNALT
VLTCDKSMVATSDYDDFHKLVKRCLLNGLLGANAQKRKRHYRDALIENVSSKLHAHARDHP
QEPVNFRAIFEHELFGVALKQAFGKDVESIYVKELGVTLSKDEIFKVLVHDMMEGAIDVDW
RDFFPYLKWIPNKSFEARIQQKHKRRLAVMNALIQDRLKQNGSESDDDCYLNFLMSEAKTL
TKEQIAILVWETIIETADTTLVTTEWAIYELAKHPSVQDRLCKEIQNVCGGEKFKEEQLSQ
VPYLNGVFHETLRKYSPAPLVPIRYAHEDTQIGGYHVPAGSEIAINIYGCNMDKKRWERPE
DWWPERFLDDGKYETSDLHKTMAFGAGKRVCAGALQASLMAGIAIGRLVQEFEWKLRDGEE
ENVDTYGLTSQKLYPLMAIINPRRS (SEQ ID NO: 35)

ATGGCTCTGTTATTAGCAGTTTTTTCGATGATTTCTATCCTGCTGGGCTTTGTTATCTCGTC
CTTTATCTTTATCTTCTTCTTCAAAAAACTGCTGTCGTTTTCTCGTAAAAACATGTCCGAAG
TTTCAACCCTGCCGAGTGTCCCGGTGGTTCCGGGTTTTCCGGTTATCGGTAATCTGCTGCAG
CTGAAAGAAAAGAAACCGCATAAGACCTTCACGCGCTGGTCCGAAATCTATGGCCCGATCTA
CTCAATTAAAATGGGTAGCTCAGTCTGATTGTGCTGAACTCTACCGAAACGGCAAAAGAAG
CTATGGTTACCCGTTTTTCCTCAATTTCGACGCGCAAGCTGAGCAATGCGCTGACCGTCCTG
ACGTGCGACAAATCTATGGTGGCCACCAGTGATTACGATGACTTCCATAAACTGGTTAAGCG
TTGTCTGCTGAACGGCCTGCTGGGTGCGAATGCCCAGAAGCGTAAGCGCCACTATCGCGACG
CCCTGATTGAAAACGTGTCGAGCAAACTGCATGCACACGCTCGTGATCATCCGCAGGAACCG
GTCAATTTTCGCGCAATCTTCGAACACGAACTGTTTGGCGTGGCGCTGAAACAAGCCTTCGG
CAAGGATGTTGAATCGATTTACGTCAAGAACTGGGCGTGACCCTGAGCAAAGACGAAATCT
TTAAGGTCCTGGTGCATGATATGATGGAAGGTGCAATTGACGTTGATTGGCGTGATTTCTTT
CCGTATCTGAAATGGATTCCGAACAAGTCATTCGAAGCTCGCATTCAGCAAAAACACAAGCG
TCGCCTGGCAGTGATGAACGCTCTGATTCAGGATCGTCTGAAACAAAATGGCTCTGAAAGTG
ATGACGATTGCTATCTGAATTTTCTGATGTCCGAAGCAAAAACCCTGACGAAGGAACAGATT
GCTATCCTGGTTTGGGAAACCATTATCGAAACGGCGGACACCACGCTGGTCACCACGGAATG
GGCGATCTACGAACTGGCCAAGCATCCGAGCGTTCAGGATCGCCTGTGCAAAGAAATTCAAA
ACGTCTGTGGCGGTGAAAAATTTAAGGAAGAACAGCTGTCGCAAGTGCCGTATCTGAATGGT
GTTTTCCACGAAACCCTGCGTAAATATAGCCCGGCACCGCTGGTCCCGATCCGTTACGCCCA
TGAAGATACCCAGATTGGCGGTTATCACGTGCCGGCAGGCAGTGAAATTGCTATCAACATTT
ACGGTTGCAATATGGACAAAAGCGTTGGGAACGCCCGGAAGATTGGTGGCCGGAACGTTTT
CTGGACGATGGCAAATATGAAACCTCTGATCTGCATAAGACGATGGCGTTCGGTGCAGGTAA
ACGTGTGTGTGCAGGTGCACTGCAAGCAAGTCTGATGGCAGGCATCGCTATTGGTCGTCTGG
TGCAAGAATTTGAATGGAAACTGCGCGACGGCGAAGAAGAAACGTTGATACCTATGGTCTG
ACGTCCCAGAAACTGTACCCGCTGATGGCCATTATCAATCCGCGTCGCTCA (SEQ ID
NO: 36)

FIG. 4A (Cont'd)

>SrKO [Stevia rebaudiana]
MDAVTGLLTVPATAITIGGTAVALAVALIFWYLKSYTSARRSQSNHLPRVPEVPGVPLLGNL
LQLKEKKPYMTFTRWAATYGPIYSIKTGATSMVVVSSNEIAKEALVTRFQSISTRNLSKALK
VLTADKTMVAMSDYDDYHKTVKRHILTAVLGPNAQKKHRIHRDIMMDNISTQLHEFVKNNPE
QEEVDLRKIFQSELFGLAMRQALGKDVESLYVEDLKITMNRDEIFQVLVVDPMMGAIDVDWR
DFFPYLKWVPNKKFENTIQQMYIRREAVMKSLIKEHKKRIASGEKLNSYIDYLLSEAQTLTD
QQLLMSLWEPIIESSDTTMVTTEWAMYELAKNPKLQDRLYRDIKSVCGSEKITEEHLSQLPY
ITAIFHETLRRHSPVPIIPLRHVHEDTVLGGYHVPAGTELAVNIYGCNMDKNVWENPEEWNP
ERFMKENETIDFQKTMAFGGGKRVCAGSLQALLTASIGIGRMVQEFEWKLKDMTQEEVNTIG
LTTQMLRPLRAIIKPRI (SEQ ID NO: 37 | Wild Type)

MALLLAVFAVALAVALIFWYLKSYTSARRSQSNHLPRVPEVPGVPLLGNLLQLKEKKPYMT
FTRWAATYGPIYSIKTGATSMVVVSSNEIAKEALVTRFQSISTRNLSKALKVLTADKTMVA
MSDYDDYHKTVKRHILTAVLGPNAQKKHRIHRDIMMDNISTQLHEFVKNNPEQEEVDLRKI
FQSELFGLAMRQALGKDVESLYVEDLKITMNRDEIFQVLVVDPMMGAIDVDWRDFFPYLKW
VPNKKFENTIQQMYIRREAVMKSLIKEHKKRIASGEKLNSYIDYLLSEAQTLTDQQLLMSL
WEPIIESSDTTMVTTEWAMYELAKNPKLQDRLYRDIKSVCGSEKITEEHLSQLPYITAIFH
ETLRRHSPVPIIPLRHVHEDTVLGGYHVPAGTELAVNIYGCNMDKNVWENPEEWNPERFMK
ENETIDFQKTMAFGGGKRVCAGSLQALLTASIGIGRMVQEFEWKLKDMTQEEVNTIGLTTQ
MLRPLRAIIKPRI (SEQ ID NO: 38)

ATGGCTCTGTTATTAGCAGTTTTTGCCGTCGCTCTGGCGGTAGCACTGATCTTCTGGTATCT
GAAATCTTACACTAGCGCGCGCCGCTCTCAGTCCAACCACCTGCCGCGTGTGCCGGAAGTTC
CGGGTGTGCCACTGCTGGGCAACCTGCTGCAACTGAAAGAAAAGAAACCGTACATGACCTTT
ACCCGCTGGGCAGCGACTTATGGTCCTATCTACAGCATTAAAACCGGCGCTACGTCTATGGT
TGTGGTTTCTTCCAACGAAATCGCGAAAGAAGCCCTGGTGACTCGTTTCCAGTCCATTAGCA
CCCGCAACCTGTCCAAAGCGCTGAAGGTTCTGACGGCTGACAAGACTATGGTGGCTATGAGC
GACTATGATGACTACCACAAAACCGTTAAACGTCACATCCTGACCGCAGTACTGGGTCCGAA
CGCACAGAAAAAACATCGCATCCACCGCGACATTATGATGGATAACATCTCCACGCAGCTGC
ATGAGTTCGTTAAGAACAATCCAGAACAGGAAGAGGTAGATCTGCGTAAAATTTTTCAGTCC
GAACTGTTCGGTCTGGCTATGCGTCAGGCGCTGGGCAAAGACGTTGAAAGCCTGTATGTCGA
AGACCTGAAAATTACCATGAACCGTGATGAGATCTTCCAGGTTCTGGTTGTAGATCCGATGA
TGGGCGCCATCGACGTGGATTGGCGTGACTTCTTTCCGTACCTGAAATGGGTCCCGAACAAG
AAGTTCGAAAACACCATCCAGCAAATGTACATCCGTCGTGAAGCGGTGATGAAAAGCCTGAT
CAAAGAACACAAAAAGCGTATTGCTTCTGGTGAGAAACTGAACTCCTACATCGATTATCTGC
TGTCCGAAGCGCAGACCCTGACCGACCAACAGCTGCTGATGTCTCTGTGGGAACCGATTATC
GAAAGCAGCGACACCACTATGGTCACTACCGAATGGGCAATGTATGAGCTGGCCAAAAACCC
GAAACTGCAGGATCGTCTGTACCGTGACATCAAAAGCGTTTGCGGCTCCGAGAAAATCACTG
AAGAACACCTGTCTCAGCTGCCGTACATCACTGCTATTTTCCACGAAACCCTGCGTCGCCAT
TCTCCGGTTCCGATCATTCCGCTGCGTCACGTTCACGAAGATACTGTGCTGGGTGGTTACCA
TGTACCGGCAGGCACTGAACTGGCTGTCAACATCTACGGCTGTAACATGGATAAAAACGTTT
GGGAGAATCCTGAAGAATGGAACCCGGAACGCTTCATGAAAGAGAACGAAACCATCGACTTC
CAGAAAACGATGGCTTTCGGCGGTGGTAAACGTGTGTGCGCAGGTTCTCTGCAGGCGCTGCT
GACGGCGTCCATTGGTATCGGTCGCATGGTACAGGAATTTGAATGGAAGCTGAAAGACATGA
CCCAAGAAGAGGTGAATACCATTGGTCTGACTACCCAGATGCTGCGTCCACTGCGTGCAATC
ATCAAACCTCGTATT (SEQ ID NO: 39)

*FIG. 4A (Cont'd)*

>PpKO [Physcomitrella patens]
MAKHLATQLLQQWNEALKTMPPGFRTAGKILVWEELASNKVLITIALAWVLLFVARTCLRN
KKRLPPAIPGGLPVLGNLLQLTEKKPHRTFTAWSKEHGPIFTIKVGSVPQAVVNNSEIAKE
VLVTKFASISKRQMPMALRVLTRDKTMVAMSDYGEEHRMLKKLVMTNLLGPTTQNKRSLR
DDALIGMIEGVLAELKASPTSPKVVNRDYVQRSLFPFALQQVFGYIPDQVEVLELGTCVS
TWDMFDALVVAPLSAVINVDWRDFFPALRWIPNRSVEDLVRTVDFKRNSIMKALIRAQRMR
LANLKEPPRCYADIALTEATHLTEKQLEMSLWEPIIESADTTLVTSEWAMYEIAKNPDCQD
RLYREIVSVAGTERMVTEDDLPNMPYLGAIIKETLRKYTPVPLIP*SRF*VEEDITLGGYDIP
KGYQILVNLFAIANDPAVWSNPEKWDPERMLANKKVDMGFRDFSLMPFGAGKRMCAGITQA
MFIIPMNVAALVQHCEWRLSPQEISNINNKIEDVVYLTTHKLSPLSCEATPRISHRLP
(SEQ ID NO: 40 | Wild Type)

MALLLAVFTQLLQQWNEALKTMPPGFRTAGKILVWEELASNKVLITIALAWVLLFVARTCL
RNKKRLPPAIPGGLPVLGNLLQLTEKKPHRTFTAWSKEHGPIFTIKVGSVPQAVVNNSEIA
KEVLVTKFASISKRQMPMALRVLTRDKTMVAMSDYGEEHRMLKKLVMTNLLGPTTQNKRS
LRDDALIGMIEGVLAELKASPTSPKVVNRDYVQRSLFPFALQQVFGYIPDQVEVLELGTC
VSTWDMFDALVVAPLSAVINVDWRDFFPALRWIPNRSVEDLVRTVDFKRNSIMKALIRAQR
MRLANLKEPPRCYADIALTEATHLTEKQLEMSLWEPIIESADTTLVTSEWAMYEIAKNPDC
QDRLYREIVSVAGTERMVTEDDLPNMPYLGAIIKETLRKYTPVPLIP*SRF*VEEDITLGGYD
IPKGYQILVNLFAIANDPAVWSNPEKWDPERMLANKKVDMGFRDFSLMPFGAGKRMCAGIT
QAMFIIPMNVAALVQHCEWRLSPQEISNINNKIEDVVYLTTHKLSPLSCEATPRISHRLP
(SEQ ID NO: 41)

ATGGCTCTGTTATTAGCAGTTTTTACGCAACTGCTGCAACAATGGAATGAAGCTCTGAAGAC
GATGCCGCCGGGTTTTCGCACCGCTGGCAAAATTCTGGTGTGGGAAGAACTGGCAAGCAATA
AAGTTCTGATTACGATCGCACTGGCTTGGGTCCTGCTGTTTGTGGCTCGTACCTGCCTGCGC
AATAAAAAGCGTCTGCCGCCGGCAATCCCGGGCGGTCTGCCGGTGCTGGGCAACCTGCTGCA
GCTGACGGAAAAGAAACCGCATCGTACCTTTACGGCGTGGAGCAAGGAACACGGCCCGATTT
TCACCATCAAAGTCGGTTCGGTGCCGCAGGCTGTGGTTAACAATAGCGAAATTGCGAAAGAA
GTCCTGGTGACCAAGTTCGCCAGCATCTCTAAACGTCAAATGCCGATGGCACTGCGCGTCCT
GACGCGTGATAAAACGATGGTGGCTATGTCTGACTATGGCGAAGAACATCGCATGCTGAAAA
AGCTGGTGATGACGAATCTGCTGGGTCCGACCACGCAGAACAAAAATCGTAGTCTGCGCGAT
GACGCACTGATTGGCATGATCGAAGGTGTTCTGGCGGAACTGAAGGCCAGTCCGACCTCCCC
GAAAGTCGTGAACGTTCGCGATTATGTCCAGCGTTCTCTGTTTCCGTTCGCGCTGCAGCAAG
TGTTTGGCTACATTCCGGATCAAGTTGAAGTCCTGGAACTGGGCACGTGTGTTTCTACCTGG
GATATGTTCGACGCACTGGTTGTCGCTCCGCTGAGTGCGGTTATTAACGTCGATTGGCGTGA
CTTTTTCCCGGCCCTGCGCTGGATTCCGAATCGTTCCGTGGAAGATCTGGTGCGCACCGTTG
ACTTTAAGCGTAACTCAATTATGAAAGCCCTGATCCGTGCACAGCGTATGCGCCTGGCTAAC
CTGAAGGAACCGCCGCGCTGCTACGCAGATATTGCTCTGACCGAAGCGACGCACCTGACCGA
AAAACAACTGGAAATGAGTCTGTGGGAACCGATTATCGAATCCGCCGATACCACGCTGGTGA
CCTCAGAATGGGCTATGTATGAAATTGCGAAAAATCCGGATTGTCAGGACCGTCTGTACCGC
GAAATCGTGTCCGTTGCCGGCACGGAACGCATGGTTACCGAAGATGACCTGCCGAACATGCC
GTATCTGGGTGCAATTATCAAAGAAACGCTGCGCAAGTACACCCCGGTTCCGCTGATTCCGA
GTCGTTTTGTCGAAGAAGATATCACCCTGGGCGGTTATGACATTCCGAAAGGTTACCAGATC
CTGGTCAACCTGTTCGCGATTGCCAATGATCCGGCCGTTGGTCGAACCCGGAAAAATGGGA
CCCGGAACGCATGCTGGCAAATAAAAAGGTGGATATGGGCTTTCGTGACTTCAGCCTGATGC
CGTTTGGCGCCGGTAAACGCATGTGCGCCGGTATCACCCAAGCAATGTTCATTATCCCGATG
AATGTGGCGGCCCTGGTTCAGCATTGTGAATGGCGCCTGAGCCCGCAAGAAATCTCTAACAT
CAACAACAAGATCGAAGATGTGGTTTACCTGACCACGCATAAACTGTCACCGCTGTCGTGCG
AAGCAACCCCGCGTATCAGCCACCGTCTGCCG (SEQ ID NO: 42)

FIG. 4A (Cont'd)

>BmVO [Bacillus megaterium]

MTIKEMPQPKTFGELKNLPLLNTDKPVQALMKIADELGEIFKFEAPGRVTRYLSSQRLIKEA
CDE*SR*FDKNLSQALKFVRDFAGDGLATSWTHEKNWKKAHNILLPSFSQQAMKGYHAMMVDIA
VQLVQKWERLNADEHIEVPEDMTRLTLDTIGLCGFNYRFNSFYRDQPHPFITSMVRALDEAM
NKLQRANPDDPAYDENKRQFQEDIKVMNDLVDKIIADRKASGEQSDDLLTHMLNGKDPETGE
PLDDENIRYQIITFLIAGHETTSGLLSFALYFLVKNPHVLQKAAEEAARVLVDPVPSYKQVK
QLKYVGMVLNEALRLWPTIPAFSLYAKEDTVLGGEYPLEKGDELMVLIPQLHRDKTIWGDDV
EEFRPERFENPSAIPQHAFKPFGNGQRACIGQQFALHEATLVLGMMLKHFDFEDHTNYELDI
KETLTLKPEGFVVKAKSKKIPLGGIPSPSTEQSAKKVRKKAENAHNTPLLVLYGSNMGTAEG
TARDLADIAMSKGFAPQVATLDSHAGNLPREGAVLIVTASYNGHPPDNAKQFVDWLDQASAD
EVKGVRYSVFGCGDKNWATTYQKVPAFIDETLAAKGAENIADRGEADASDDFEGTYEEWREH
MWSDVAAYFNLDIENSEDNKSTLSLQFVDSAADMPLAKMHGAFSTNVVASKELQQPGSARST
RHLEIELPKEASYQEGDHLGVIPRNYEGIVNRVTARFGLDASQQIRLEAEEEKLAHLPLAKT
VSVEELLQYVELQDPVTRTQLRAMAAKTVCPPHKVELEALLEKQAYKEQVLAKRLTMLELLE
KYPACEMKFSEFIALLPSIRPRYYSISSSPRVDEKQASITVSVVSGEAWSGYGEYKGIASNY
LAELQEGDTITCFISTPQSEFTLPKDPETPLIMVGPGTGVAPFRGFVQARKQLKEQGQSLGE
AHLYFGCRSPHEDYLYQEELENAQSEGIITLHTAF*SR*MPNQPKTYVQHVMEQDGKKLIELLD
QGAHFYICGDGSQMAPAVEATLMKSYADVHQVSEADARLWLQQLEEKGRYAKDVWAG (SEQ
ID NO: 43)

FIG. 4A (Cont'd)

```
ATGACGATTAAAGAAATGCCGCAACCGAAGACGTTTGGCGAACTGAAGAACCTGCCGCTGCT
GAACACGGATAAGCCGGTGCAAGCCCTGATGAAGATTGCTGATGAACTGGGCGAAATCTTTA
AATTCGAAGCGCCGGGTCGTGTGACCCGTTATCTGAGCAGCCAGCGTCTGATTAAAGAAGCC
TGCGATGAATCGCGCTTTGACAAGAACCTGAGCCAGGCACTGAAATTTGTTCGTGATTTCGC
AGGTGACGGTCTGGCCACCAGCTGGACGCATGAAAAGAACTGGAAAAGGCCCACAATATTC
TGCTGCCGTCGTTCAGCCAGCAAGCAATGAAAGGCTACCATGCTATGATGGTCGATATCGCG
GTTCAGCTGGTCCAAAAATGGGAACGTCTGAATGCGGACGAACACATTGAAGTGCCGGAAGA
TATGACCCGCCTGACGCTGGACACCATCGGTCTGTGTGGCTTTAACTATCGTTTTAATTCGT
TCTACCGCGATCAGCCGCATCCGTTCATTACCAGCATGGTGCGTGCGCTGGACGAAGCCATG
AACAAACTGCAGCGTGCAAACCCGGATGACCCGGCGTATGATGAAAACAAGCGTCAGTTTCA
AGAAGACATCAAAGTGATGAATGATCTGGTTGACAAGATTATCGCAGATCGCAAAGCGAGCG
GCGAACAGTCAGATGACCTGCTGACGCACATGCTGAACGGCAAGACCCGGAAACCGGTGAA
CCGCTGGATGACGAAAACATCCGTTATCAGATCATCACCTTTCTGATCGCAGGCCATGAAAC
CACGTCGGGTCTGCTGAGCTTTGCGCTGTACTTCCTGGTCAAGAACCCGCACGTGCTGCAGA
AAGCGGCCGAAGAAGCAGCTCGTGTGCTGGTTGATCCGGTTCCGTCGTATAAACAGGTCAAG
CAACTGAAATACGTGGGTATGGTTCTGAATGAAGCGCTGCGCCTGTGGCCGACGATTCCGGC
ATTTAGCCTGTATGCTAAGGAAGATACCGTTCTGGGCGGTGAATACCCGCTGGAAAAAGGCG
ATGAACTGATGGTCCTGATTCCGCAGCTGCATCGCGACAAAACCATCTGGGGTGATGACGTG
GAAGAATTTCGCCCGGAACGCTTCGAAAACCCGAGCGCGATTCCGCAGCATGCCTTTAAACC
GTTCGGCAATGGTCAACGTGCGTGCATCGGCCAGCAATTTGCGCTGCACGAAGCCACGCTGG
TTCTGGGTATGATGCTGAAACATTTTGATTTCGAAGACCACACCAACTATGAACTGGATATT
AAGGAAACCCTGACGCTGAAACCGGAAGGCTTCGTGGTTAAAGCGAAGTCTAAAAAGATTCC
GCTGGGCGGTATCCCGTCTCCGAGTACGGAACAGAGTGCCAAAAAGGTCCGTAAAAAGGCGG
AAAACGCCCATAATACCCCGCTGCTGGTGCTGTATGGTTCTAACATGGGCACGGCAGAAGGC
ACCGCTCGCGATCTGGCAGACATTGCTATGTCTAAAGGTTTTGCGCCGCAGGTGGCCACGCT
GGATAGTCATGCAGGCAATCTGCCGCGTGAAGGTGCTGTCCTGATCGTGACCGCAAGCTACA
ACGGTCACCCGCCGGATAATGCGAAGCAGTTCGTTGATTGGCTGGACCAAGCGTCGGCCGAT
GAAGTTAAAGGTGTCCGCTATAGCGTGTTTGGCTGTGGTGACAAGAACTGGGCTACCACGTA
CCAGAAAGTTCCGGCGTTCATTGATGAAACGCTGGCGGCCAAAGGCGCAGAAAATATCGCTG
ATCGTGGTGAAGCAGACGCTTCCGATGACTTTGAAGGCACCTATGAAGAATGGCGCGAACAC
ATGTGGTCGGATGTGGCAGCTTACTTCAACCTGGATATTGAAAACAGCGAAGACAATAAATC
CACCCTGTCACTGCAGTTTGTTGATAGTGCGGCCGACATGCCGCTGGCAAAGATGCACGGCG
CTTTCTCCACGAATGTCGTGGCTTCAAAAGAACTGCAGCAACCGGGTTCGGCACGTAGCACC
CGCCATCTGGAAATTGAACTGCCGAAAGAAGCCAGCTATCAGGAAGGCGATCACCTGGGTGT
GATTCCGCGTAACTACGAAGGCATCGTGAATCGTGTTACGGCCCGCTTTGGTCTGGATGCAT
CCCAGCAAATCCGCCTGGAAGCGGAAGAAGAAAAGCTGGCGCATCTGCCGCTGGCCAAAACC
GTCTCAGTGGAAGAACTGCTGCAGTATGTGGAACTGCAAGATCCGGTTACCCGTACGCAGCT
GCGTGCGATGGCGGCTAAGACCGTCTGCCCGCCGCACAAAGTGGAACTGGAAGCTCTGCTGG
AAAAGCAGGCGTATAAAGAACAAGTGCTGGCGAAACGCCTGACCATGCTGGAACTGCTGGAA
AAGTACCCGGCCTGTGAAATGAAGTTCTCTGAATTTATCGCACTGCTGCCGTCTATCCGTCC
GCGTTATTACAGTATTAGTTCCTCACCGCGTGTGGATGAAAAACAGGCCAGTATCACCGTTT
CTGTTGTCAGTGGCGAAGCATGGTCTGGCTATGGTGAATACAAGGGTATCGCAAGTAACTAC
CTGGCTGAACTGCAGGAAGGCGATACCATTACGTGCTTTATCTCTACGCCGCAAAGTGAATT
TACCCTGCCGAAAGACCCGGAAACGCCGCTGATCATGGTTGGCCCGGGCACCGGTGTCGCAC
CGTTTCGTGGTTTCGTGCAGGCACGCAAGCAACTGAAAGAACAGGGCCAATCCCTGGGTGAA
GCGCATCTGTATTTTGGCTGTCGCTCACCGCACGAAGATTATCTGTACCAGGAAGAACTGGA
AAACGCGCAATCCGAAGGTATTATCACGCTGCATACCGCCTTCTCACGTATGCCGAATCAGC
CGAAAACCTACGTCCAGCACGTGATGGAACAAGATGGCAAAAAGCTGATTGAACTGCTGGAC
CAGGGTGCGCATTTTTATATCTGCGGTGATGGCAGCCAAATGGCACCGGCAGTGGAAGCAAC
CCTGATGAAATCCTACGCAGATGTTCACCAGGTCTCAGAAGCAGACGCTCGTCTGTGGCTGC
AGCAACTGGAAGAAAAGGGCCGCTATGCGAAAGATGTTTGGGCCGGTTAA (SEQ ID NO:
44)
```

FIG. 4A (Cont'd)

>PsVO [Pleurotus sapidus]
MRYGCAAVALFYLTAMGKLHPLAIIPDYKGSMAASVTIFNKRTNPLDISVNQANDWPWRYAKT
CVLSSDWALHEMIIHLNNTHLVEEAVIVAAQRKLSPSHIVFRLLEPHWVVTLSLNALARSVLI
PEVIVPIAGFSAPHIFQFIRESFTNFDWKSLYVPADLE*SRG*FPVDQLNSPKFHNYAYARDIND
MWTTLKKFVSSVLQDAQYYPDDASVAGDTQIQAWCDEMRSGMGAGMTNFPESITTVDDLVNMV
TMCIHIAAPQHTAVNYLQQYYQTFVSNKPSALFSPLPTSIAQLQKYTESDLMAALPLNAKRQW
LLMAQIPYLLSMQVQEDENIVTYAANASTDKDPIIASAGRQLAADLKKLAAVFLVNSAQLDDQ
NTPYDVLAPEQLANAIVI (SEQ ID NO: 45)
ATGCGTTATGGCTGTGCTGCTGTGGCTCTGTTCTATCTGACCGCTATGGGCAAACTGCACCCG
CTGGCTATTATCCCGGACTACAAGGGTAGCATGGCGGCCTCTGTCACCATTTTTAACAAACGT
ACGAATCCGCTGGATATCAGCGTTAACCAGGCAAATGACTGGCCGTGGCGCTATGCTAAGACG
TGCGTGCTGAGCAGCGATTGGGCGCTGCATGAAATGATTATCCACCTGAACAATACCCATCTG
GTGGAAGAAGCCGTCATTGTGGCAGCTCAGCGTAAACTGTCACCGTCGCACATCGTTTTTCGC
CTGCTGGAACCGCATTGGGTGGTTACCCTGTCGCTGAACGCACTGGCTCGTAGCGTGCTGATC
CCGGAAGTTATTGTCCCGATCGCGGGTTTCTCTGCCCCGCACATTTTTCAGTTCATCCGCGAA
TCTTTTACCAATTTCGATTGGAAAAGTCTGTACGTCCCGGCGGACCTGGAATCGCGTGGCTTT
CCGGTGGATCAGCTGAACAGCCCGAAGTTCCATAATTATGCGTACGCCCGCGATATCAACGAC
ATGTGGACCACGCTGAAAAAGTTTGTGAGTTCCGTTCTGCAGGATGCCCAATATTACCCGGAT
GACGCAAGTGTGGCTGGTGATACGCAGATTCAAGCATGGTGCGACGAAATGCGTTCCGGCATG
GGTGCGGGCATGACCAACTTCCCGGAATCAATCACCACGGTTGATGACCTGGTCAATATGGTG
ACCATGTGTATTCACATCGCGGCCCCGCAGCATACGGCGGTTAACTATCTGCAGCAATACTAC
CAAACCTTCGTCAGTAACAAGCCGTCCGCACTGTTCTCACCGCTGCCGACCTCTATTGCTCAG
CTGCAAAAATACACGGAAAGTGATCTGATGGCAGCTCTGCCGCTGAACGCGAAGCGTCAGTGG
CTGCTGATGGCCCAAATTCCGTATCTGCTGTCGATGCAGGTGCAAGAAGATGAAAACATCGTT
ACCTACGCGGCCAATGCGTCCACGGATAAAGACCCGATTATCGCATCAGCTGGCCGCCAGCTG
GCAGCTGACCTGAAAAAGCTGGCGGCCGTTTTTCTGGTCAACTCAGCCCAGCTGGATGACCAA
AATACCCCGTATGATGTGCTGGCACCGGAACAGCTGGCGAATGCCATTGTTATCTAA (SEQ
ID NO: 46)

FIG. 4A (Cont'd)

>PoLO [Pleurotus ostreatus]
MAPTMSLSRSALKNVHLPYMVQHPEPTDCSTAMKHAAEGYDRARQMIAFLFDILDYESSVPQK
FTPEEKKEKYTWSHSDKFPPHLAIIPEDIDVPAYIIFSIVRLVQTLSIMSGIQCNERLAPGPE
QNTMEKLTKWNAERHKNQGWVKDMFNEPNIGLRNDWYTDAVFAQQFFTGPNPTTITLASDTWM
KAFTEEAASQGKRDLISLFRSAPPNSFYVQDFSDFRARMGAKPDEELCATSDGGVTRYGCAAV
ALFYLPPTGELHPLAIVPDYKGSMAASITLFNKRVDPSDASVDQANDWPWRYAKTCVLSADWV
LHEMIIHLNNTHLVQEAVIVAVQRTLPDSHIVFRLLKPHWVVTLSLNAQARSVLIPEVIVPIA
GFSELRIFQFVGHAFTNFDWKALYVPTDLEFRGFPLDRLDDDKFHNYAYAKDIKDMWMALRKF
VSSVLKDGKYYPDDSAVAADAQIQDWCDEMRSEKGAGMKKFPESISTLDDLIDMVTMCIHIAA
PQHTAVNYLQQYYQTFVPNKPSALFSPLPTLLSQLESYTESDLMAALPLGAKQEWLLMAQVPY
LLSKEVEQDGNIVTYAGTASNNEDPIIAAAGKELSADLVILAGVFLKNSEKLDDQNTAYNVLA
PDQLANAIVI (SEQ ID NO: 47)
ATGGCCCCGACGATGTCACTGTCTCGCTCCGCACTGAAGAATGTCCACCTGCCGTATATGGTC
CAACACCCGGAACCGACCGATTGCAGCACCGCGATGAAACACGCGGCCGAAGGTTATGATCGT
GCTCGCCAGATGATTGCGTTTCTGTTCGACATCCTGGATTACGAAAGCTCTGTTCCGCAAAAA
TTTACCCCGGAAGAAAAGAAAGAAAAATATACGTGGTCACACTCGGATAAGTTCCCGCCGCAT
CTGGCCATTATCCCGGAAGACATTGATGTGCCGGCATACATTATCTTTAGCATCGTTCGTCTG
GTCCAGACCCTGAGTATTATGTCCGGCATCCAATGCAACGAACGTCTGGCACCGGGGCCGGAA
CAGAATACGATGGAAAAACTGACGAAGTGGAACGCGGAACGTCATAAAAATCAAGGCTGGGTC
AAGGATATGTTTAACGAACCGAATATTGGTCTGCGCAACGACTGGTATACCGATGCTGTGTTC
GCGCAGCAATTTTTCACGGGTCCGAATCCGACCACGATTACCCTGGCCTCTGATACGTGGATG
AAAGCATTTACCGAAGAAGCAGCTAGTCAGGGCAAGCGTGACCTGATCAGCCTGTTTCGCTCT
GCCCCGCCGAACTCCTTCTACGTTCAGGACTTTTCAGATTTCCGTGCTCGCATGGGCGCGAAA
CCGGACGAAGAACTGTGCGCGACCTCTGATGGCGGTGTTACCCGTTATGGCTGTGCAGCAGTC
GCACTGTTTTACCTGCCGCCGACCGGTGAACTGCATCCGCTGGCCATTGTGCCGGATTATAAA
GGCAGTATGGCAGCTTCCATCACGCTGTTCAACAAGCGTGTGGACCCGTCAGATGCCTCGGTT
GACCAGGCAAATGATTGGCCGTGGCGCTACGCTAAAACCTGTGTTCTGTCCGCGGATTGGGTC
CTGCATGAAATGATTATCCACCTGAACAATACCCATCTGGTGCAGGAAGCCGTCATTGTGGCA
GTTCAACGTACGCTGCCGGATTCACACATCGTTTTTCGCCTGCTGAAACCGCATTGGGTGGTT
ACCCTGTCGCTGAATGCCCAGGCACGTAGCGTTCTGATCCCGGAAGTCATTGTGCCGATCGCG
GGCTTCAGTGAACTGCGCATCTTTCAGTTCGTTGGTCACGCCTTTACCAACTTCGACTGGAAA
GCACTGTATGTCCCGACGGATCTGGAATTTCGTGGTTTCCCGCTGGACCGCCTGGATGACGAT
AAGTTCCATAACTATGCTTACGCGAAGGACATTAAGGATATGTGGATGGCCCTGCGTAAGTTC
GTGAGTTCCGTTCTGAAAGATGGCAAGTATTACCCGGACGATTCGGCTGTTGCAGCAGACGCG
CAGATTCAAGACTGGTGCGATGAAATGCGCAGCGAAAAGGCGCGGGTATGAAAAAGTTCCCG
GAAAGCATTTCTACCCTGGACGATCTGATCGATATGGTGACGATGTGTATTCACATCGCAGCT
CCGCAGCATACCGCCGTGAACTATCTGCAGCAATATTACCAAACGTTTGTTCCGAATAAACCG
TCAGCACTGTTCTCGCCGCTGCCGACCCTGCTGAGCCAGCTGGAATCTTACACGGAAAGTGAT
CTGATGGCGGCCCTGCCGCTGGGTGCTAAACAGGAATGGCTGCTGATGGCGCAAGTGCCGTAT
CTGCTGTCTAAGGAAGTCGAACAGGATGGCAACATTGTGACCTACGCCGGTACGGCAAGTAAC
AATGAAGATCCGATTATCGCAGCTGCGGGCAAAGAACTGTCCGCTGACCTGGTCATCCTGGCG
GGTGTGTTTCTGAAAAACTCAGAAAAGCTGGACGATCAGAACACCGCCTATAATGTCCTGGCA
CCGGATCAACTGGCCAATGCAATTGTGATCTAA (SEQ ID NO: 48)

FIG. 4A (Cont'd)

>CiVO [Cichorium intybus]
MEISIPTTLGLAVIIFIIFKLLTRTTSKKNLLPEPWRLPIIGHMHHLIGTMPHRGVMELARK
HGSLMHLQLGEVSTIVVSSPRWAKEVLTTYDITFANRPETLTGEIVAYHNTDIVLAPYGEYW
RQLRKLCTLELLSNKKVKSFQSLREEECWNLVKDIRSTGQGSPINLSENIFKMIATILSRAA
FGKGIKDQMKFTELVKEILRLTGGFDVADIFPSKKLLHHLSGKRAKLTNIHNKLDNLINNII
AEHPGNRTSSSQETLLDVLLRLKESAEFPLTADNVKAVILDMFGAGTDTSSATIEWAISELI
RCPRAMEKVQTELRQALNGKERIQEEDLQELNYLKLVIKETLRLHPPLPLVMPRECREPCVL
GGYDIPSKTKLIVNVFAINRDPEYWKDAETFMPERFENSPITVMGSEYEYLPFGAGRRMCPG
AALGLANVELPLAHILYFNWKLPNGKTFEDLDMTESFGATVQRKTELLLVPTDFQTLTAST
(SEQ ID NO: 49 | Wild Type)

MALLLAVFLAVIIFIIFKLLTRTTSKKNLLPEPWRLPIIGHMHHLIGTMPHRGVMELARKHG
SLMHLQLGEVSTIVVSSPRWAKEVLTTYDITFANRPETLTGEIVAYHNTDIVLAPYGEYWRQ
LRKLCTLELLSNKKVKSFQSLREEECWNLVKDIRSTGQGSPINLSENIFKMIATILSRAAFG
KGIKDQMKFTELVKEILRLTGGFDVADIFPSKKLLHHLSGKRAKLTNIHNKLDNLINNIIAE
HPGNRTSSSQETLLDVLLRLKESAEFPLTADNVKAVILDMFGAGTDTSSATIEWAISELIRC
PRAMEKVQTELRQALNGKERIQEEDLQELNYLKLVIKETLRLHPPLPLVMPRECREPCVLGG
YDIPSKTKLIVNVFAINRDPEYWKDAETFMPERFENSPITVMGSEYEYLPFGAGRRMCPGAA
LGLANVELPLAHILYFNWKLPNGKTFEDLDMTESFGATVQRKTELLLVPTDFQTLTAST
(SEQ ID NO: 50)

ATGGCTCTGTTATTAGCAGTTTTTCTGGCTGTCATTATCTTTATCATCTTCAAACTGCTGAC
CCGCACCACCTCGAAGAAAAACCTGCTGCCGGAACCGTGGCGTCTGCCGATTATCGGCCACA
TGCATCACCTGATTGGCACCATGCCGCACCGTGGTGTGATGGAACTGGCGCGCAAACATGGC
TCACTGATGCACCTGCAGCTGGGTGAAGTGAGCACCATCGTGGTTAGCTCTCCGCGTTGGGC
GAAAGAAGTTCTGACCACGTATGATATTACCTTTGCCAACCGCCCGGAAACCCTGACGGGCG
AAATCGTGGCATACCATAATACGGACATTGTTCTGGCTCCGTATGGTGAATACTGGCGTCAG
CTGCGCAAACTGTGCACCCTGGAACTGCTGAGTAACAAAAAGTCAAATCTTTTCAAAGTCT
GCGTGAAGAAGAATGTTGGAATCTGGTGAAAGATATCCGCTCCACCGGCCAGGGTTCACCGA
TCAACCTGTCGGAAAACATCTTCAAAATGATCGCGACGATCCTGTCTCGTGCGGCCTTTGGC
AAAGGTATTAAAGACCAAATGAAATTCACCGAACTGGTTAAAGAAATCCTGCGCCTGACGGG
CGGTTTTGATGTCGCAGACATTTTCCCGAGTAAAAAACTGCTGCATCACCTGTCCGGCAAAC
GTGCTAAACTGACCAACATCCATAACAAACTGGATAACCTGATCAACAACATTATCGCCGAA
CACCCGGGTAATCGTACCAGTTCCTCACAGGAAACGCTGCTGGATGTTCTGCTGCGCCTGAA
AGAAAGCGCAGAATTTCCGCTGACCGCGGACAATGTTAAAGCCGTCATTCTGGATATGTTCG
GTGCAGGCACCGACACGTCGAGCGCAACCATTGAATGGGCTATCTCTGAACTGATTCGTTGC
CCGCGCGCGATGGAAAAAGTGCAGACGGAACTGCGTCAAGCCCTGAACGGCAAAGAACGCAT
CCAGGAAGAAGATCTGCAAGAACTGAACTACCTGAAACTGGTTATCAAAGAAACCCTGCGCC
TGCATCCGCCGCTGCCGCTGGTCATGCCGCGTGAATGCCGCGAACCGTGTGTGCTGGGCGGT
TATGATATCCCGAGCAAAACCAAACTGATCGTCAACGTGTTTGCAATTAATCGTGACCCGGA
ATACTGGAAAGACGCTGAAACCTTTATGCCGGAACGCTTCGAAAACAGCCCGATTACGGTTA
TGGGTTCTGAATATGAATACCTGCCGTTTGGTGCAGGTCGTCGCATGTGTCCGGGTGCAGCT
CTGGGTCTGGCGAATGTCGAACTGCCGCTGGCCCACATCCTGTATTACTTCAACTGGAAACT
GCCGAATGGCAAAACCTTTGAAGATCTGGACATGACCGAATCCTTCGGTGCAACGGTGCAAC
GCAAAACCGAACTGCTGCTGGTGCCGACGGATTTCCAAACGCTGACCGCATCAACG (SEQ
ID NO: 51)

FIG. 4A (Cont'd)

>HaGAO [Helianthus annuus]
MEVSLTTSIALATIVFFLYKLLTRPTSSKNRLPEPWRLPIIGHMHHLIGTMPHRGVMDLARKY
GSLMHLQLGEVSAIVVSSPKWAKEILTTYDIPFANRPETLTGEIIAYHNTDIVLAPYGEYWRQ
LRKLCTLELLSVKKVKSFQSLREEECWNLVQEIKASGSGTPFNLSEGIFKVIATVLSRAAFGK
GIKDQKQFTEIVKEILRETGGFDVADIFPSKKFLHHLSGKRGRLTSIHNKLDSLINNLVAEHT
VSKSSKVNETLLDVLLRLKNSEEFPLTADNVKAIILDMFGAGTDTSSATVEWAISELIRCPRA
MEKVQAELRQALNGKERIKEEEIQDLPYLNLVIRETLRLHPPLPLVMPRECRQAMNLAGYDVA
NKTKLIVNVFAINRDPEYWKDAESFNPERFENSNTTIMGADYEYLPFGAGRRMCPGSALGLAN
VQLPLANILYYFKWKLPNGASHDQLDMTESFGATVQRKTELMLVPSF (SEQ ID NO: 52
| Wild Type)

MALLLAVFIALATIVFFLYKLLTRPTSSKNRLPEPWRLPIIGHMHHLIGTMPHRGVMDLARKY
GSLMHLQLGEVSAIVVSSPKWAKEILTTYDIPFANRPETLTGEIIAYHNTDIVLAPYGEYWRQ
LRKLCTLELLSVKKVKSFQSLREEECWNLVQEIKASGSGTPFNLSEGIFKVIATVLSRAAFGK
GIKDQKQFTEIVKEILRETGGFDVADIFPSKKFLHHLSGKRGRLTSIHNKLDSLINNLVAEHT
VSKSSKVNETLLDVLLRLKNSEEFPLTADNVKAIILDMFGAGTDTSSATVEWAISELIRCPRA
MEKVQAELRQALNGKERIKEEEIQDLPYLNLVIRETLRLHPPLPLVMPRECRQAMNLAGYDVA
NKTKLIVNVFAINRDPEYWKDAESFNPERFENSNTTIMGADYEYLPFGAGRRMCPGSALGLAN
VQLPLANILYYFKWKLPNGASHDQLDMTESFGATVQRKTELMLVPSF (SEQ ID NO: 53)

ATGGCTCTGTTATTAGCAGTTTTCATCGCCCTGGCAACCATTGTCTTTTTCCTGTATAAACTG
CTGACCCGTCCGACCTCATCTAAAAACCGTCTGCCGGAACCGTGGCGCCTGCCGATTATCGGC
CACATGCATCACCTGATTGGCACCATGCCGCACCGTGGTGTCATGGATCTGGCACGCAAATAT
GGCAGCCTGATGCATCTGCAACTGGGTGAAGTTTCTGCGATTGTGGTTAGCTCTCCGAAATGG
GCCAAAGAAATTCTGACCACCTATGATATTCCGTTTGCGAACCGCCCGGAAACCCTGACGGGC
GAAATTATCGCATACCACAATACCGACATTGTGCTGGCTCCGTATGGTGAATACTGGCGTCAA
CTGCGTAAACTGTGCACGCTGGAACTGCTGAGTGTTAAAAAAGTCAAAAGTTTCCAGAGCCTG
CGTGAAGAAGAATGTTGGAACCTGGTTCAAGAAATTAAAGCGAGCGGCAGCGGCACCCCGTTT
AATCTGAGTGAAGGTATTTTCAAAGTGATTGCGACCGTGCTGAGCCGTGCGGCATTTGGTAAA
GGTATCAAAGATCAGAAACAATTCACCGAAATTGTCAAAGAAATCCTGCGCGAAACGGGCGGT
TTTGATGTGGCGGACATCTTTCCGAGCAAAAAATTCCTGCATCACCTGTCTGGCAAACGTGGT
CGCCTGACCTCAATTCATAACAAACTGGATTCGCTGATCAACAATCTGGTCGCCGAACATACC
GTGAGCAAAAGCAGCAAAGTGAATGAAACGCTGCTGGATGTCCTGCTGCGTCTGAAAAACTCG
GAAGAATTTCCGCTGACCGCAGACAATGTGAAAGCTATTATCCTGGATATGTTCGGTGCAGGC
ACCGATACCAGCAGCGCAACGGTGGAATGGGCCATTAGCGAACTGATCCGTTGCCCGCGCGCA
ATGGAAAAAGTTCAGGCAGAACTGCGTCAAGCTCTGAACGGCAAAGAACGCATTAAAGAAGAA
GAAATCCAGGATCTGCCGTATCTGAATCTGGTTATTCGTGAAACCCTGCGTCTGCATCCGCCG
CTGCCGCTGGTCATGCCGCGTGAATGTCGCCAAGCAATGAACCTGGCTGGCTATGACGTGGCA
AATAAAACCAAACTGATCGTCAATGTGTTTGCGATTAACCGTGACCCGGAATACTGGAAAGAC
GCGGAAAGTTTTAACCCGGAACGCTTTGAAAACAGCAACACCACGATTATGGGTGCGGATTAT
GAATACCTGCCGTTTGGCGCCGGTCGTCGCATGTGTCCGGGCAGCGCGCTGGGTCTGGCCAAC
GTTCAACTGCCGCTGGCCAATATCCTGTATTACTTCAAATGGAAACTGCCGAATGGCGCCTCA
CACGATCAACTGGACATGACCGAATCGTTTGGTGCAACCGTGCAACGCAAAACGGAACTGATG
CTGGTTCCGTCTTTC (SEQ ID NO: 54)

FIG. 4A (Cont'd)

>n20yhcB-t29SrKO
MAWEYALIGLVVGIIIGAVAAWYLKSYTSARRSQSNHLPRVPEVPGVPLLGNLLQLKEKKPYM
TFTRWAATYGPIYSIKTGATSMVVVSSNEIAKEALVTRFQSISTRNLSKALKVLTADKTMVAM
SDYDDYHKTVKRHILTAVLGPNAQKKHRIHRDIMMDNISTQLHEFVKNNPEQEEVDLRKIFQS
ELFGLAMRQALGKDVESLYVEDLKITMNRDEIFQVLVVDPMMGAIDVDWRDFFPYLKWVPNKK
FENTIQQMYIRREAVMKSLIKEHKKRIASGEKLNSYIDYLLSEAQTLTDQQLLMSLWEPIIES
SDTTMVTTEWAMYELAKNPKLQDRLYRDIKSVCGSEKITEEHLSQLPYITAIFHETLRRHSPV
PIIPLRHVHEDTVLGGYHVPAGTELAVNIYGCNMDKNVWENPEEWNPERFMKENETIDFQKTM
AFGGGKRVCAGSLQALLTASIGIGRMVQEFEWKLKDMTQEEVNTIGLTTQMLRPLRAIIKPRI
(SEQ ID NO: 55)

>n22yhcB-t30VO1c9
MAWEYALIGLVVGIIIGAVAMRWYLKSYTSARRSQSNHLPRVPEVPGVPLLGNLLQLKEKKPY
MTFTRWAATYGPIYSIKTGATSVVVSSNEIAKEAMVTRFQSISTRNLSKALKVLTADKTMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 56)

>n22yhcB-t30VO1c12
MAWEYALIGLVVGIIIGAVAMRWYLKSYTSARRSQSNHLPRVPEVPGVPLLGNLLQLKEKKPY
MTFTKWAATYGPIYSIKTGATSMVVVSSNEIAKEAMVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 57)

>n22yhcB-t30VO1b4
MAWEYALIGLVVGIIIGAVAMRWYLKSYTSARRSQSNHLPRVPEVPGVPLLGNLLQLKEKKPY
MTFTRWAATYGPIYSIKTGATSVVVSSNEIAKEAMVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 58)

*FIG. 4B*

>n20yhcB-t29VO1c11
MAWEYALIGLVVGIIIGAVAAWYLKSYTSARRSQSNHLPRVPEVPGVPLLGNLLQLKEKKPYM
TFTKWAATYGPIYSIKTGATSMVVVSSNEIAKEAMVTRFQSISTRNLSKALKVLTADKQMVAM
SDYDDYHKTVKRHILTAVLGPNAQKKHRIHRDIMMDNISTQLHEFVKNNPEQEEVDLRKIFQS
ELFGLAMRQALGKDVESLYVEDLKITMNRDEILQVLVVDPMMGAIDVDWRDFFPYLKWVPNKK
FENTIQQMYIRREAVMKSLIKEHKKRIASGEKLNSYIDYLLSEAQTLTDQQLLMSLWEPIIES
SDTTMVTTEWAMYELAKNPKLQDRLYRDIKSVCGSEKITEEHLSQLPYITAIFHETLRKHSPV
PILPLRHVHEDTVLGGYHVPAGTELAVNIYGCNMDKNVWENPEEWNPERFMKENETIDFQKTM
AFGGGKRVCAGSLQALLIASIGIGRMVQEFEWKLKDMTQEEVNTIGLTNQMLRPLRAIIKPRI
(SEQ ID NO: 59)

>n22yhcB-t30VO1b6
MAWEYALIGLVVGIIIGAVAMRWYLKSYTSARRSQSNHLPRVPEVPGVPLLGNLLQLKEKKPY
MTFTKWAATYGPIYSIKTGATSVVVVSSNEIAKEAMVTRFQSISTRNLSKALKVLTADKTMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPIIPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 60)

>n22yhcB-t30VO1c6 (VO2)

MAWEYALIGLVVGIIIGAVAMRWYLKSYTSARRSQSNHLPRVPEVPGVPLLGNLLQLKEKKPY
MTFTKWAATYGPIYSIKTGATSVVVVSSNEIAKEALVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEQKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 61)

FIG. 4B (Cont'd)

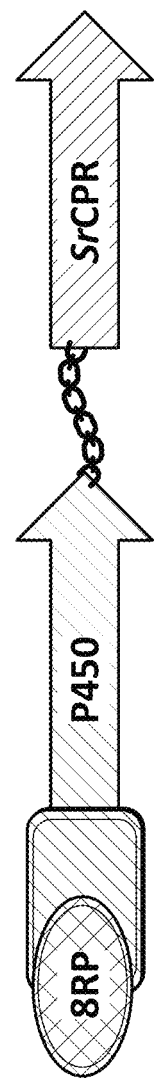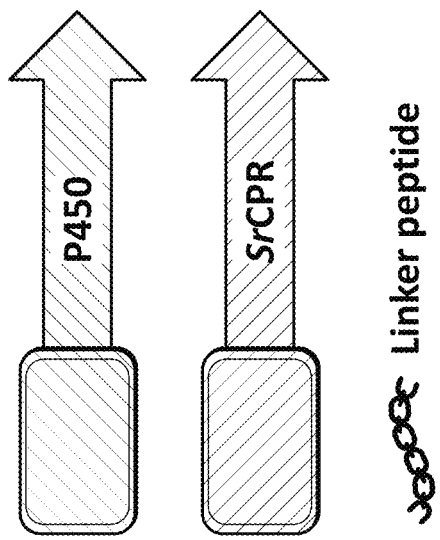
FIG. 5B

>SrCPR [Stevia rebaudiana]
MQSDSVKVSPFDLVSAAMNGKAMEKLNASESEDPTTLPALKMLVENRELLTLFTTSFAVLIGC
LVFLMWRRSSSKKLVQDPVPQVIVVKKKEKESEVDDGKKKVSIFYGTQTGTAEGFAKALVEEA
KVRYEKTSFKVIDLDDYAADDDEYEEKLKKESLAFFFLATYGDGEPTDNAANFYKWFTEGDDK
GEWLKKLQYGVFGLGNRQYEHFNKIAIVVDDKLTEMGAKRLVPVGLGDDDQCIEDDFTAWKEL
VWPELDQLLRDEDDTSVTTPYTAAVLEYRVVYHDKPADSYAEDQTHTNGHVVHDAQHP*SRSNV*
*AFKKELHTSQSDRSCTHLEFDISHTGLSYETGDHVGVYSENLSEVVDEALKLLGLSPDTYFSV*
*HADKEDGTPIGGASLPPPFPPCTLRDALTRYADVLSSPKKVALLALAAHASDPSEADRLKFLA*
*SPAGKDEYAQWIVANQRSLLEVMQSFPSAKPPLGVFFAAVAPRLQPRYYSISSSPKMSPNRIH*
*VTCALVYETTPAGRIHRGLCSTWMKNAVPLTESPDCSQASIFVRTSNFRLPVDPKVPVIMIGP*
*GTGLAPFRGFLQERLALKESGTELGSSIFFFGCRNRKVDFIYEDELNNFVETGALSELIVAFS*
*REGTAKEYVQHKMSQKASDIWKLLSEGAYLYVCGDAKGMAKDVHRTLHTIVQEQGSLDSSKAE*
*LYVKNLQMSGRYLRDVW* (SEQ ID NO: 62)

ATGCAGAGCGATTCTGTTAAAGTATCCCCGTTCGACCTGGTCTCTGCGGCTATGAACGGCAAA
GCAATGGAGAAACTGAACGCGAGCGAATCTGAAGATCCAACCACCCTGCCGGCACTGAAAATG
CTGGTAGAAAACCGTGAACTGCTGACTCTGTTCACCACCTCCTTCGCCGTTCTGATTGGTTGC
CTGGTCTTCCTGATGTGGCGCCGTTCCTCTTCCAAGAAGCTGGTACAGGACCCGGTTCCTCAG
GTGATCGTCGTTAAAAAGAAAGAGAAGGAAAGCGAAGTCGATGACGGCAAAAAGAAGGTTTCC
ATTTTCTACGGTACTCAGACCGGCACCGCTGAGGGTTTTGCCAAAGCACTGGTTGAAGAGGCA
AAAGTGCGTTACGAAAAACTTCCTTCAAAGTGATTGACCTGGACGACTATGCTGCGGATGAT
GATGAATACGAGGAAAAACTGAAAAAGAAAGCCTGGCCTTCTTCTTCCTGGCAACCTATGGC
GATGGTGAACCGACCGACAACGCGGCGAACTTCTACAAATGGTTTACCGAAGGCGACGACAAA
GGTGAATGGCTGAAGAAACTGCAGTATGGTGTTTTCGGTCTGGGCAATCGCCAGTACGAACAT
TTTAACAAAATCGCAATCGTTGTTGATGACAAACTGACTGAAATGGGTGCGAAACGTCTGGTG
CCGGTTGGCCTGGGTGACGATGATCAATGCATCGAAGATGACTTCACCGCATGGAAAGAACTG
GTTTGGCCGGAACTGGATCAGCTGCTGCGCGACGAAGACGACACTTCCGTGACCACCCCGTAT
ACCGCTGCAGTGCTGGAGTACCGTGTTGTTTACCACGATAAACCGGCGGACTCTTACGCCGAA
GATCAGACTCACACTAACGGTCACGTCGTACATGACGCACAGCACCCGTCTCGTAGCAATGTT
GCGTTTAAGAAAGAGCTGCACACGAGCCAGTCCGACCGCTCTTGTACGCACCTGGAGTTCGAT
ATCTCCCACACCGGTCTGTCCTATGAAACCGGTGACCATGTTGGCGTTTACAGCGAAAACCTG
AGCGAGGTAGTTGATGAAGCGCTGAAACTGCTGGGCCTGTCTCCAGACACCTACTTTAGCGTG
CATGCTGACAAGGAAGATGGTACTCCGATTGGCGGCGCTTCCCTGCCGCCACCGTTTCCACCT
TGCACTCTGCGTGATGCTCTGACTCGTTACGCTGATGTTCTGTCTAGCCCGAAAAAGGTTGCG
CTGCTGGCGCTGGCCGCACATGCTTCTGACCCGTCTGAAGCTGACCGTCTGAAATTCCTGGCG
TCTCCGGCCGGCAAAGACGAATACGCGCAGTGGATTGTCGCTAACCAGCGCTCTCTGCTGGAA
GTGATGCAGTCCTTCCCGTCTGCCAAACCGCCACTGGGCGTGTTTTTCGCAGCTGTGGCTCCG
CGCCTGCAGCCGCGCTACTATTCTATCTCTAGCTCCCCGAAAATGAGCCCGAACCGCATCCAC
GTTACTTGTGCTCTGGTTTACGAAACCACCCCTGCGGGCCGTATCCACCGTGGTCTGTGCTCT
ACGTGGATGAAAAATGCCGTGCCGCTGACCGAATCCCCGGACTGCTCTCAGGCGTCCATCTTC
GTGCGTACCTCTAACTTCCGTCTGCCGGTGGACCCGAAAGTTCCTGTTATCATGATCGGTCCT
GGCACGGGTCTGGCCCCGTTTCGTGGTTTTCTGCAGGAGCGTCTGGCTCTGAAAGAATCCGGT
ACTGAGCTGGGCTCTTCCATCTTTTTCTTCGGTTGTCGTAACCGCAAAGTCGATTTCATCTAT
GAAGACGAACTGAACAACTTCGTAGAGACTGGTGCACTGTCCGAACTGATTGTGGCATTCTCT
CGTGAAGGCACGGCGAAAGAATACGTTCAACACAAAATGTCTCAGAAAGCGAGCGATATCTGG
AAACTGCTGTCCGAGGGTGCGTATCTGTATGTTTGTGGCGACGCGAAAGGCATGGCTAAAGAT
GTACACCGCACCCTGCACACCATTGTACAAGAACAAGGCTCTCTGGATAGCTCCAAGGCAGAA
CTGTACGTGAAAAACCTGCAGATGTCTGGCCGTTACCTGCGTGATGTATGGTAA (SEQ ID
NO: 63)

FIG. 6A

>AtCPR [Arabidopsis thaliana]
MTSALYASDLFKQLKSIMGTDSLSDDVVLVIATTSLALVAGFVVLLWKKTTADRSGELKPLMI
PKSLMAKDEDDDLDLGSGKTRVSIFFGTQTGTAEGFAKALSEEIKARYEKAAVKVIDLDDYAA
DDDQYEEKLKKETLAFFCVATYGDGEPTDNAARFSKWFTEENERDIKLQQLAYGVFALGNRQY
EHFNKIGIVLDEELCKKGAKRLIEVGLGDDDQSIEDDFNAWKESLWSELDKLLKDEDDKSVAT
PYTAVIPEYRVVTHDPRFTTQKSMESNVANGNTTIDIHHPCRVDVAVQKELHTHESDRSCIHL
EFDI*SRT*GITYETGDHVGVYAENHVEIVEEAGKLLGHSLDLVFSIHADKEDGSPLESAVPPPF
PGPCTLGTGLARYADLLNPPRKSALVALAAYATEPSEAEKLKHLTSPDGKDEYSQWIVASQRS
LLEVMAAFPSAKPPLGVFFAAIAPRLQPRYYSISSCQDWAP*SRV*HVTSALVYGPTPTGRIHKG
VCSTWMKNAVPAEKSHECSGAPIFIRASNFKLPSNPSTPIVMVGPGTGLAPFRGFLQERMALK
EDGEELGSSLLFFGCRNRQMDFIYEDELNNFVDQGVISELIMAF*SRE*GAQKEYVQHKMMEKAA
QVWDLIKEEGYLYVCGDAKGMARDVHRTLHTIVQEQEGVSSSEAEAIVKKLQTEGRYLRDVW
(SEQ ID NO: 64)

ATGACCAGCGCACTGTACGCAAGCGACCTGTTTAAGCAACTGAAGAGCATTATGGGCACCGAT
AGCCTGAGCGATGATGTTGTCCTGGTCATTGCGACCACGAGCCTGGCACTGGTGGCTGGTTTT
GTGGTTCTGCTGTGGAAAAAGACCACGGCCGATCGTTCTGGCGAACTGAAACCGCTGATGATT
CCGAAAAGTCTGATGGCAAAGGACGAAGATGACGATCTGGATCTGGGCTCCGGTAAAACCCGT
GTGTCAATCTTTTTCGGTACCCAGACGGGCACCGCAGAAGGTTTCGCAAAAGCTCTGTCTGAA
GAAATTAAGGCGCGCTATGAAAAGCGGCCGTTAAGGTCATCGATCTGGACGATTATGCAGCT
GACGATGACCAGTACGAAGAAAAACTGAAAAAGGAAACCCTGGCGTTTTTCTGCGTTGCCACC
TACGGCGACGGTGAACCGACGGATAACGCGGCCCGTTTTAGTAAATGGTTCACCGAAGAAAAT
GAACGCGACATTAAGCTGCAGCAACTGGCGTATGGCGTGTTTGCTCTGGGTAACCGTCAGTAC
GAACATTTCAACAAGATCGGTATCGTCCTGGATGAAGAACTGTGTAAAAAGGGCGCGAAGCGC
CTGATTGAAGTGGGCCTGGGTGATGACGATCAATCCATCGAAGACGATTTTAACGCCTGGAAA
GAATCTCTGTGGAGTGAACTGGACAAACTGCTGAAGGATGAAGACGATAAGAGCGTGGCGACG
CCGTATACCGCCGTTATTCCGGAATACCGTGTCGTGACCCATGATCCGCGCTTCACCACGCAG
AAAAGCATGGAATCAAATGTTGCGAACGGTAATACCACGATTGACATCCATCACCCGTGCCGT
GTGGATGTTGCCGTCCAAAAAGAACTGCATACCCACGAATCGGACCGTAGCTGTATCCACCTG
GAATTTGATATTAGCCGCACGGGCATCACCTATGAAACGGGCGACCATGTGGGTGTTTACGCA
GAAAACCACGTGGAAATTGTTGAAGAAGCTGGCAAACTGCTGGGTCATTCGCTGGATCTGGTT
TTTAGCATCCACGCGGACAAGGAAGATGGTTCGCCGCTGGAAAGCGCAGTGCCGCCGCCGTTC
CCGGGTCCGTGCACCCTGGGTACGGGTCTGGCACGTTATGCAGATCTGCTGAATCCGCCGCGC
AAATCCGCACTGGTGGCTCTGGCAGCTTACGCAACCGAACCGTCAGAAGCTGAAAAACTGAAG
CATCTGACGTCGCCGGACGGTAAAGATGAATATAGCCAGTGGATTGTTGCGTCTCAACGCAGT
CTGCTGGAAGTCATGGCAGCATTTCCGTCGGCAAAACCGCCGCTGGGCGTGTTTTTCGCAGCT
ATTGCACCGCGTCTGCAGCCGCGCTATTACAGCATCAGCTCTTGTCAAGATTGGGCGCCGTCT
CGTGTCCATGTGACCAGTGCACTGGTGTATGGTCCGACGCCGACCGGTCGCATTCACAAAGGC
GTGTGCTCTACCTGGATGAAAAACGCGGTTCCGGCCGAAAAGTCTCACGAATGTAGTGGTGCG
CCGATTTTTATCCGTGCCAGTAACTTCAAACTGCCGTCCAATCCGTCAACCCCGATCGTTATG
GTCGGTCCGGGTACGGGTCTGGCACCGTTTCGTGGTTTCCTGCAGGAACGCATGGCTCTGAAA
GAAGATGGCGAAGAACTGGGTAGTTCCCTGCTGTTTTTCGGCTGCCGTAATCGCCAGATGGAC
TTCATCTACGAAGATGAACTGAACAACTTCGTCGATCAAGGTGTGATTTCCGAACTGATCATG
GCATTTTCACGCGAAGGCGCTCAGAAAGAATACGTCCAACATAAAATGATGGAAAAGGCGGCC
CAAGTGTGGGATCTGATCAAGAAGAAGGCTATCTGTACGTTTGTGGCGACGCAAAGGGTATG
GCTCGTGATGTCCATCGCACCCTGCACACGATTGTTCAGGAACAAGAAGGTGTCTCATCGAGC
GAAGCGGAAGCCATCGTGAAAAAGCTGCAGACCGAAGGCCGTTATCTGCGCGATGTTTGGTAA
(SEQ ID NO: 65)

*FIG. 6A (Cont'd)*

>TcCPR [Taxus cuspidata]

MQANSNTVEGASQGKSLLDI*SR*LDHIFALLLNGKGGDLGAMTGSALILTENSQNLMILTTALA
VLVACVFFFVWRRGGSDTQKPAVRPTPLVKEEDEEEDDSAKKKVTIFFGTQTGTAEGFAKAL
AEEEAKARYEKAVFKVVDLDNYAADDEQYEEKLKKEKLAFFMLATYGDGEPTDNAARFYKWFLE
GKEREPWLSDLTYGVFGLGNRQYEHFNKVAKAVDEVLIEQGAKRLVPVGLGDDDQCIEDDFTA
WREQVWPELDQLLRDEDDEPTSATPYTAAIPEYRVEIYDSVVSVYEETHALKQNGQAVYDIHH
PCRSNVAVRRELHTPLSDRSCIHLEFDISDTGLIYETGDHVGVHTENSIETVEEAAKLLGYQL
DTIFSVHGDKEDGTPLGGSSLPPPFPGPCTLRTALARYADLLNPPRKAAFLALAAHASDPAEA
ERLKFLSSPAGKDEYSQWVTASQRSLLEIMAEFPSAKPPLGVFFAAIAPRLQPRYYSISSSPR
FAP*SR*IHVTCALVYGPSPTGRIHKGVCSNWMKNSLPSEETHDCSWAPVFVRQSNFKLPADSTT
PIVMVGPGTGFAPFRGFLQERAKLQEAGEKLGPAVLFFGCRNRQMDYIYEDELKGYVEKGILT
NLIVAF*SR*EGATKEYVQHKMLEKASDTWSLIAQGGYLYVCGDAKGMARDVHRTLHTIVQEQES
VDSSKAEFLVKKLQMDGRYLRDIW (SEQ ID NO: 66)

ATGCAGGCTAATTCCAACACGGTGGAAGGTGCCTCCCAGGGGAAGAGCCTGCTGGACATATCT
CGGCTGGACCATATTTTTGCGCTGCTGTTGAACGGCAAGGGAGGAGATCTGGGAGCCATGACC
GGCTCGGCTTTGATTTTGACAGAGAATTCGCAGAATTTGATGATTTTGACCACGGCTTTGGCT
GTTTTGGTCGCGTGTGTTTTCTTCTTCGTTTGGAGGAGGGGAGGATCGGATACGCAGAAGCCG
GCGGTGAGACCGACGCCTCTGGTGAAGGAGGAAGATGAGGAGGAAGAAGACGATTCTGCAAAG
AAGAAAGTCACGATTTTCTTTGGGACACAGACTGGGACGGCCGAGGGATTTGCCAAGGCTCTA
GCAGAAGAGGCAAAGGCAAGATATGAGAAAGCTGTGTTTAAAGTCGTAGATTTGGACAACTAT
GCAGCAGATGATGAGCAGTATGAAGAAAAATTGAAAAGGAAAAATTAGCATTTTTTATGCTA
GCAACGTATGGAGATGGGGAGCCCACTGACAATGCAGCAAGATTTTATAAGTGGTTTCTTGAG
GGCAAGGAGAGGGAGCCATGGCTTTCTGATCTCACTTATGGGGTGTTTGGATTAGGCAACAGA
CAATATGAACATTTTAATAAGGTGGCTAAAGCAGTAGATGAAGTCTTAATTGAACAAGGTGCA
AAGCGACTTGTTCCAGTGGGCCTTGGTGATGATGACCAATGCATTGAAGATGACTTTACTGCT
TGGCGAGAGCAGGTTTGGCCTGAACTGGATCAGTTACTCCGGGATGAAGATGATGAGCCCACA
AGTGCTACACCTTATACAGCTGCCATACCTGAGTATAGGGTTGAAATTTATGATTCCGTGGTT
TCAGTGTACGAGGAAACTCATGCTCTCAAGCAAAATGGCCAAGCTGTTTATGATATCCATCAC
CCCTGCAGATCTAATGTGGCAGTGAGAAGAGAGCTTCATACACCTTTGTCTGACCGCTCTTGC
ATCCATTTGGAATTTGATATATCAGACACTGGCCTTATATATGAGACAGGAGATCATGTTGGT
GTCCATACAGAAAACAGCATTGAAACTGTGGAGGAAGCAGCAAAGCTACTAGGCTACCAATTG
GACACTATATTCTCAGTCCACGGTGACAAAGAAGATGGCACGCCACTTGGAGGGTCTTCTTTG
CCACCACCTTTCCCTGGTCCATGCACCCTACGAACTGCTCTTGCTCGTTATGCTGATTTGCTG
AATCCTCCTCGGAAGGCCGCCTTTCTTGCATTGGCAGCTCATGCATCTGATCCAGCAGAGGCA
GAGCGGTTGAAGTTCCTCTCATCACCAGCTGGAAAGGATGAATATTCTCAATGGGTCACTGCA
AGTCAGAGAAGTCTTTTAGAAATAATGGCAGAATTTCCATCAGCAAAACCACCCCTTGGTGTT
TTCTTTGCAGCAATAGCCCCTCGTCTGCAACCCCGATATTATTCTATTTCTTCCTCTCCCAGG
TTTGCACCCTCAAGAATACATGTGACATGTGCTCTTGTTTACGGGCCCAGTCCAACCGGTAGA
ATTCACAAAGGTGTTTGTTCTAACTGGATGAAGAATTCGCTACCCTCAGAAGAAACCCATGAC
TGTAGCTGGGCTCCAGTCTTTGTCAGGCAATCAAATTTTAAATTGCCAGCAGATTCTACTACT
CCTATTGTCATGGTGGGTCCTGGAACTGGTTTTGCACCTTTTAGAGGTTTTTTGCAGGAAAGA
GCAAAACTTCAAGAAGCTGGTGAGAAGCTCGGTCCGGCTGTTTTATTTTTTGGGTGCAGGAAT
CGCCAAATGGACTACATTTATGAAGATGAGCTGAAGGGCTATGTGGAGAAAGGAATACTGACC
AATCTCATTGTTGCTTTCTCTCGTGAAGGAGCAACCAAAGAGTATGTCCAGCACAAGATGCTG
GAAAAGGCATCCGATACCTGGAGTCTCATTGCTCAGGGTGGGTATCTTTATGTATGTGGTGAT
GCCAAGGGTATGGCTAGGGATGTACACAGGACACTGCACACTATTGTCCAAGAGCAGGAATCT
GTGGATAGCAGCAAAGCAGAGTTTCTAGTGAAGAAATTACAGATGGATGGAAGATACTTACGA
GATATATGGTGA (SEQ ID NO: 67)

FIG. 6A (Cont'd)

>AaCPR [Artemisia annua]
MAQSTTSVKLSPFDLMTALLNGKVSFDTSNTSDTNIPLAVFMENRELLMILTTSVAVLIGCVV
VLVWRRSSSAAKKAAESPVIVVPKKVTEDEVDDGRKKVTVFFGTQTGTAEGFAKALVEEAKAR
YEKAVFKVIDLDDYAAEDDEYEEKLKKESLAFFFLATYGDGEPTDNAARFYKWFTEGEEKGEW
LDKLQYAVFGLGNRQYEHFNKIAKVVDEKLVEQGAKRLVPVGMGDDDQCIEDDFTAWKELVWP
ELDQLLRDEDDTSVATPYTAAVAEYRVVFHDKPETYDQDQLTNGHAVHDAQHPCRSNVAVKKE
LHSPLSDRSCTHLEFDISNTGLSYETGDHVGVYVENLSEVVDEAEKLIGLPPHTYFSVHADNE
DGTPLGGASLPPPFPPCTLRKALASYADVLSSPKKSALLALAAHATDSTEADRLKFLASPAGK
DEYAQWIVASHRSLLEVMEAFPSAKPPLGVFFASVAPRLQPRYYSISSSPRFAPNRIHVTCAL
VYEQTPSGRVHKGVCSTWMKNAVPMTESQDCSWAPIYVRTSNFRLPSDPKVPVIMIGPGTGLA
PFRGFLQERLAQKEAGTELGTAILFFGCRNRKVDFIYEDELNNFVETGALSELVTAFSREGAT
KEYVQHKMTQKASDIWNLLSEGAYLYVCGDAKGMAKDVHRTLHTIVQEQGSLDSSKAELYVKN
LQMAGRYLRDVW (SEQ ID NO: 68)

ATGGCGCAGTCTACCACCAGCGTGAAATTGTCCCCTTTTGATCTCATGACCGCTCTGCTGAAT
GGGAAAGTCTCATTCGATACAAGCAACACAAGTGATACCAACATCCCTTTGGCGGTTTTTATG
GAGAATAGAGAGTTACTCATGATTTTAACGACTTCCGTGGCCGTGCTCATTGGGTGCGTCGTC
GTACTTGTCTGGCGCCGGTCAAGTAGCGCAGCAAAGAAGGCGGCGGAGTCCCCGGTTATCGTC
GTCCCAAAGAAGGTTACAGAGGACGAGGTGGACGACGGACGCAAAAAGTGACGGTATTCTTT
GGTACACAGACCGGAACCGCGGAAGGATTTGCTAAAGCGCTGGTGGAAGAAGCTAAAGCCCGT
TACGAAAAAGCGGTATTCAAAGTGATAGACCTGGATGACTATGCGGCAGAGGACGACGAGTAC
GAGGAAAAATTGAAAAAGAATCTCTTGCGTTCTTTTTTCTCGCCACTTACGGCGATGGAGAA
CCTACTGATAATGCGGCTCGGTTTTATAAGTGGTTCACTGAGGGTGAAGAAAAGGTGAATGG
CTGGACAAATTGCAGTACGCAGTATTTGGACTCGGGAATCGTCAATATGAACATTTTAACAAA
ATTGCTAAGGTCGTCGATGAAAAACTGGTTGAGCAGGGTGCGAAACGTCTGGTCCCGGTTGGA
ATGGGCGATGACGACCAGTGCATTGAAGACGACTTTACAGCATGGAAGGAACTGGTGTGGCCG
GAACTGGACCAACTTTTGCGTGACGAGGATGACACATCTGTAGCTACGCCGTACACTGCTGCG
GTAGCCGAGTATAGGGTCGTTTTTCACGATAAACCGGAAACCTACGACCAAGACCAGCTCACA
AATGGTCATGCAGTACATGATGCGCAACATCCTTGCAGGTCAAATGTGGCGGTGAAGAAAGAG
CTGCACAGTCCTCTGTCAGATCGTTCTTGCACCCACCTGGAATTTGACATATCCAATACGGGC
CTTTCGTATGAAACCGGAGATCACGTTGGTGTCTATGTTGAAAATCTGTCGGAAGTGGTTGAT
GAGGCGGAAAAACTTATCGGTCTGCCGCCTCATACGTACTTTTCAGTCCACGCTGATAATGAA
GACGGAACCCCGCTGGGTGGCGCATCGTTACCCCCACCCTTTCCACCATGCACTCTGCGTAAG
GCGCTTGCCAGTTATGCTGATGTTTTGTCTAGTCCCAAAAAGAGTGCACTTCTCGCACTGGCG
GCCCATGCCACTGATAGTACAGAGGCCGACAGGCTGAAATTTCTGGCGTCACCAGCGGGAAAA
GACGAATACGCCCAATGGATCGTTGCCAGTCATCGGTCTTTACTGGAAGTGATGGAAGCGTTC
CCTTCCGCTAAGCCACCTCTGGGGGTCTTTTTCGCTAGTGTGGCACCCCGTCTACAGCCCCGG
TATTACTCAATATCTAGCTCACCCAGATTTGCTCCAATAGAATACACGTAACATGCGCGCTG
GTCTATGAGCAGACCCCAAGTGGACGGGTGCATAAGGGGTTTGTTCTACCTGGATGAAGAAC
GCCGTCCCAATGACCGAGTCTCAGGATTGTTCCTGGGCACCTATATATGTTAGAACATCAAAC
TTTCGACTGCCAAGTGACCCGAAAGTTCCGGTAATTATGATAGGTCCAGGAACAGGGCTGGCT
CCCTTTCGCGGGTTCCTCCAGGAACGTCTGGCGCAGAAGGAGGCGGGAACTGAACTGGGGACG
GCGATTTATTTTTCGGGTGTAGAAATCGTAAAGTCGATTTATATATGAAGATGAGTTGAAC
AATTTCGTGGAAACCGGGGCATTATCGGAATTAGTTACGGCTTTTAGCAGGGAGGGGCGACT
AAAGAGTATGTCCAGCACAAGATGACTCAGAAAGCCTCAGATATATGGAACCTGCTGTCGGAG
GGAGCCTATCTTTATGTTTGCGGTGATGCAAAAGGAATGGCCAAAGATGTCCACCGGACCCTC
CACACTATTGTGCAGGAACAGGGTTCATTAGACTCAAGTAAAGCCGAACTTTACGTAAAAAAT
CTACAGATGGCGGGCCGTTACCTCCGTGACGTTTGGTAA (SEQ ID NO: 69)

FIG. 6A (Cont'd)

>AtCPR1 [Arabidopsis thaliana]
MATSALYASDLFKQLKSIMGTDSLSDDVVLVIATTSLALVAGFVVLLWKKTTADRSGELKPLM
IPKSLMAKDEDDDLDLGSGKTRVSIFFGTQTGTAEGFAKALSEEIKARYEKAAVKVIDLDDYA
ADDDQYEEKLKKETLAFFCVATYGDGEPTDNAARFYKWFTEENERDIKLQQLAYGVFALGNRQ
YEHFNKIGIVLDEELCKKGAKRLIEVGLGDDDQSIEDDFNAWKESLWSELDKLLKDEDDKSVA
TPYTAVIPEYRVVTHDPRFTTQKSMESNVANGNTTIDIHHPCRVDVAVQKELHTHESDRSCIH
LEFDISRTGITYETGDHVGVYAENHVEIVEEAGKLLGHSLDVFSIHADKEDGSPLESAVPPP
FPGPCTLGTGLARYADLLNPPRKSALVALAAYATEPSEAEKLKHLTSPDGKDEYSQWIVASQR
SLLEVMAAFPSAKPPLGVFFAAIAPRLQPRYYSISSSPRLAPSRVHVTSALVYGPTPTGRIHK
GVCSTWMKNAVPAEKSHECSGAPIFIRASNFKLPSNPSTPIVMVGPGTGLAPFRGFLQERMAL
KEDGEELGSSLLFFGCRNRQMDFIYEDELNNFVDQGVISELIMAFSREGAQKEYVQHKMMEKA
AQVWDLIKEEGYLYVCGDAKGMARDVHRTLHTIVQEQEGVSSSEAEAIVKKLQTEGRYLRDVW
(SEQ ID NO: 70)

ATGGCGACCAGCGCTCTGTATGCTAGTGACCTTTTTAAACAGCTCAAAAGCATCATGGGCACT
GATAGCCTGTCCGACGATGTTGTCCTGGTAATCGCAACCACTTCCCTTGCGCTTGTTGCGGGC
TTTGTGGTGTTACTGTGGAAGAAGACTACCGCAGATAGGAGTGGTGAATTGAAACCGCTGATG
ATCCCAAAAAGTCTGATGGCCAAAGATGAGGATGATGATCTGGATCTTGGATCAGGGAAGACG
CGAGTCAGTATTTTTTTCGGGACCCAGACGGGCACCGCGGAGGGCTTCGCCAAAGCTCTGTCC
GAGGAAATAAAGGCCAGATACGAGAAAGCCGCCGTAAAGGTTATAGACCTAGATGATTACGCC
GCTGATGACGATCAGTATGAGGAGAAACTTAAAAAGGAGACTCTGGCGTTTTTTTGCGTGGCA
ACTTACGGAGACGGCGAGCCCACCGATAATGCAGCTAGGTTTTACAAGTGGTTTACCGAGGAG
AACGAACGAGATATAAAGTTACAGCAGTTGGCCTATGGCGTGTTTGCCCTGGGTAATCGGCAA
TATGAGCATTTCAACAAAATTGGCATCGTTCTGGATGAGGAATTGTGCAAAAAGGGTGCAAAA
CGGCTGATAGAGGTGGGTCTAGGTGACGATGATCAATCTATAGAAGACGATTTTAATGCGTGG
AAAGAGAGCTTATGGAGTGAACTGGATAAGCTCTTGAAAGATGAAGACGACAAGTCAGTGGCG
ACCCCTTATACCGCGGTAATCCCGGAATACCGCGTCGTGACACACGATCCGAGGTTTACAACC
CAAAAATCTATGGAGTCTAATGTCGCCAATGGCAACACAACGATTGATATTCACCACCCTGT
CGTGTTGACGTGGCTGTTCAAAAGAACTTCATACACGAAAGTGACCGAAGTTGCATACAC
TTGGAATTTGACATTAGTCGCACCGGAATTACGTATGAAACTGGTGATCACGTGGGTGTATAC
GCAGAAAATCATGTCGAAATAGTAGAAGAAGCTGGCAAACTGCTGGGACATTCACTCGATCTA
GTGTTTAGTATACATGCCGATAAAGAGGATGGCAGCCCATTGGAAAGTGCCGTCCCTCCGCCG
TTTCCTGGACCGTGTACTCTGGGGACGGGACTCGCCCGCTATGCTGACCTGTTAAACCCCCCT
CGTAAAGCGCCCTTGTGGCCCTGGCGGCATACGCAACTGAACCGAGCGAAGCGGAGAAGCTG
AAACATCTGACATCACCGGATGGCAAAGACGAGTATAGTCAGTGGATAGTAGCCTCTCAGCGC
TCTCTGCTGGAAGTGATGGCCGCATTTCCGTCCGCCAAACCACCTTTGGGAGTATTTTTCGCT
GCTATCGCACCTCGGCTCCAGCCGCGCTATTACAGCATATCTTCAAGTCCCCGCTTAGCACCG
TCTCGTGTCCATGTCACTTCTGCGTTGGTTTATGGTCCGACTCCAACAGGTCGCATCCACAAA
GGTGTCTGTTCAACCTGGATGAAAAACGCGGTGCCCGCGGAGAAATCTCATGAGTGCAGTGGT
GCACCTATTTTTATCCGCGCAAGTAACTTCAAACTCCCTTCTAATCCGAGCACGCCCATTGTG
ATGGTTGGCCCAGGCACTGGCCTTGCTCCGTTTCGCGGTTTTCTACAGGAGCGGATGGCCCTT
AAGAAGATGGGGAAGAATTGGGATCATCGTTGCTCTTTTTTGGCTGCCGAAATCGCCAGATG
GATTTTATCTACGAAGACGAGTTGAATAACTTTGTCGATCAAGGAGTAATTTCGGAGTTGATT
ATGGCATTTTCACGCGAAGGGCTCAGAAAGAGTATGTCCAACACAAGATGATGGAAAAAGCG
GCACAAGTGTGGGATCTTATTAAGAAGAAGGCTATCTTTATGTATGTGGGGATGCGAAAGGT
ATGGCCCGTGATGTCCATCGCACCCTGCACACGATTGTACAGGAACAGGAAGGTGTGTCCTCG
TCCGAAGCAGAAGCAATCGTTAAAAAACTGCAAACAGAGGGTCGTTACCTTCGCGACGTGTGG
TAA (SEQ ID NO: 71)

FIG. 6A (Cont'd)

>AtCPR2 [Arabidopsis thaliana]
MASSSSSSSTSMIDLMAAIIKGEPVIVSDPANASAYESVAAELSSMLIENRQFAMIVTTSIAV
LIGCIVMLVWRRSGSGNSKRVEPLKPLVIKPREEEIDDGRKKVTIFFGTQTGTAEGFAKALGE
EAKARYEKTRFKIVDLDDYAADDDEYEEKLKKEDVAFFFLATYGDGEPTDNAARFYKWFTEGN
DRGEWLKNLKYGVFGLGNRQYEHFNKVAKVVDDILVEQGAQRLVQVGLGDDDQCIEDDFTAWR
EALWPELDTILREEGDTAVATPYTAAVLEYRVSIHDSEDAKFNDINMANGNGYTVFDAQHPYK
ANVAVKRELHTPESDRSCIHLEFDIAGSGLTYETGDHVGVLCDNLSETVDEALRLLDMSPDTY
FSLHAEKEDGTPISSSLPPPFPPCNLRTALTRYACLLSSPKKSALVALAAHASDPTEAERLKH
LASPAGKDEYSKWVVESQRSLLEVMAEFPSAKPPLGVFFAGVAPRLQPRFYSISSSPKIAETR
IHVTCALVYEKMPTGRIHKGVCSTWMKNAVPYEKSENCSSAPIFVRQSNFKLPSDSKVPIIMI
GPGTGLAPFRGFLQERLALVESGVELGPSVLFFGCRNRRMDFIYEEELQRFVESGALAELSVA
FSREGPTKEYVQHKMMDKASDIWNMISQGAYLYVCGDAKGMARDVHRSLHTIAQEQGSMDSTK
AEGFVKNLQTSGRYLRDVW (SEQ ID NO: 72)

ATGGCGTCCAGCAGTTCATCGAGTTCTACAAGCATGATCGATCTGATGGCCGCTATTATCAAA
GGGGAACCCGTAATTGTCTCTGATCCAGCAAATGCCTCGGCATACGAGTCGGTGGCTGCCGAA
TTATCATCTATGTTAATTGAAAATAGACAATTTGCCATGATTGTGACAACTTCTATTGCTGTG
CTGATAGGTTGCATCGTCATGCTCGTGTGGCGCCGTAGCGGATCAGGCAACTCAAAGCGCGTC
GAGCCTTTGAAACCCCTGGTTATCAAACCGCGAGAGGAGGAAATCGATGATGGCAGAAAAAG
GTTACTATCTTTTTTGGCACACAGACGGGGACAGCGGAAGGTTTCGCGAAAGCACTCGGAGAG
GAAGCGAAAGCCCGATACGAGAAAACACGGTTCAAAATTGTGGATCTGGATGACTATGCGGCT
GATGATGATGAGTATGAAGAAAAACTGAAAAAGAAGATGTGGCGTTTTTTTTTCTTGCCACT
TATGGCGACGGAGAGCCCACCGATAATGCAGCGCGGTTTTACAAGTGGTTCACCGAAGGAAAT
GATCGGGGAGAATGGTTAAAAAATCTGAAATACGGTGTGTTCGGTCTTGGCAATCGCCAATAT
GAGCATTTTAATAAAGTCGCGAAAGTGGTCGATGATATATTGGTAGAACAGGGCGCTCAGCGC
CTCGTCCAGGTGGGGCTTGGCGACGATGATCAGTGCATAGAAGATGATTTTACTGCATGGCGT
GAAGCGCTGTGGCCGGAGCTGGACACCATTTTACGTGAAGAGGCGATACAGCAGTGGCAACC
CCGTACACGGCTGCCGTCTTAGAGTATCGTGTGTCCATTCATGATAGCGAGGATGCCAAATTC
AATGACATCAATATGGCGAATGGAAATGGGTACACCGTGTTTGACGCGCAGCACCCGTATAAG
GCAAACGTTGCAGTCAAGAGGGAACTGCATACTCCTGAAAGTGATCGCAGTTGCATCCACCTG
GAGTTCGATATTGCGGGATCAGGTTTAACGTACGAAACGGGCGACCACGTAGGTGTGCTGTGC
GACAATCTTTCAGAGACAGTGGACGAAGCTCTGCGCCTGCTGGATATGAGCCCGGATACCTAT
TTTAGCTTGCACGCTGAGAAGAAGATGGGACTCCAATTAGCAGTAGCTTACCTCCACCCTTT
CCGCCGTGTAATTTGCGTACCGCCCTTACGCGCTATGCGTGTCTGCTGAGTTCGCCAAAGAAG
TCGGCCCTTGTGGCACTGGCGGCACATGCAAGTGACCCGACCGAGGCGGAGAGGCTGAAACAT
CTGGCTTCTCCAGCGGGCAAAGATGAATACAGCAAATGGGTGGTAGAATCACAGCGTTCCCTA
CTAGAAGTAATGGCCGAATTTCCCTCAGCTAAACCACCGCTGGGAGTGTTCTTTGCGGGCGTT
GCTCCCCGCTTGCAACCACGCTTTTATTCAATTAGCTCAAGTCCTAAGATAGCGGAAACACGG
ATACATGTAACTTGCGCATTGGTTTATGAAAAAATGCCAACCGGGAGGATACATAAAGGCGTA
TGTTCAACCTGGATGAAAAATGCTGTGCCATACGAAAGTCGGAGAATTGCTCCTCTGCCCCA
ATTTTCGTGCGTCAAAGCAACTTTAAACTGCCGAGTGATTCAAAGGTGCCTATTATTATGATA
GGCCCTGGTACAGGACTCGCCCCGTTTCGTGGTTTTCTTCAAGAAAGACTGGCTCTGGTCGAA
TCAGGCGTGGAATTAGGACCCTCCGTGTTATTTTTTGGCTGCCGCAACCGTCGAATGGACTTC
ATCTATGAAGAAGAATTGCAACGTTTTGTGGAGTCAGGCGCTCTGGCGGAACTATCCGTCGCC
TTTAGTAGAGAAGGCCCAACCAAAGAATACGTACAGCATAAGATGATGGATAAAGCGAGCGAC
ATTTGGAATATGATCTCACAAGGGGCGTACCTGTACGTATGTGGAGATGCCAAAGGAATGGCA
CGAGACGTACATAGATCGTTGCATACTATTGCTCAAGAACAGGGAAGCATGGATTCGACTAAA
GCAGAAGGCTTTGTTAAAAATCTACAGACATCTGGTCGCTATCTGCGTGACGTGTGGTAA
(SEQ ID NO: 73)

FIG. 6A (Cont'd)

>ATR2 [Arabidopsis thaliana]
MASSSSSSSTSMIDLMAAIIKGEPVIVSDPANASAYESVAAELSSMLIENRQFAMIVTTSIAV
LIGCIVMLVWRRSGSGNSKRVEPLKPLVIKPREEEIDDGRKKVTIFFGTQTGTAEGFAKALGE
EAKARYEKTRFKIVDLDDYAADDDEYEEKLKKEDVAFFFLATYGDGEPTDNAARFYKWFTEGN
DRGEWLKNLKYGVFGLGNRQYEHFNKVAKVVDDILVEQGAQRLVQVGLGDDDQCIEDDFTAWR
EALWPELDTILREEGDTAVATPYTAAVLEYRVSIHDSEDAKFNDITLANGNGYTVFDAQHPYK
ANVAVKRELHTPESDRSCIHLEFDIAGSGLTMKLGDHVGVLCDNLSETVDEALRLLDMSPDTY
FSLHAEKEDGTPISSSLPPPFPPCNLRTALTRYACLLSSPKKSALVALAAHASDPTEAERLKH
LASPAGKDEYSKWVVESQRSLLEVMAEFPSAKPPLGVFFAGVAPRLQPRFYSISSSPKIAETR
IHVTCALVYEKMPTGRIHKGVCSTWMKNAVPYEKSEKLFLGRPIFVRQSNFKLPSDSKVPIIM
IGPGTGLAPFRGFLQERLALVESGVELGPSVLFFGCRNRRMDFIYEEELQRFVESGALAELSV
AFSREGPTKEYVQHKMMDKASDIWNMISQGAYLYVCGDAKGMARDVHRSLHTIAQEQGSMDST
KAEGFVKNLQTSGRYLRDVW (SEQ ID NO: 74)

ATGGCGAGCAGTTCGTCCTCCTCTTCTACCAGTATGATCGATCTGATGGCCGCTATTATAAAA
GGAGAACCAGTCATTGTGTCTGATCCTGCAAACGCATCAGCCTACGAATCTGTGGCTGCTGAA
CTGTCCTCGATGCTGATCGAAAATCGCCAATTTGCAATGATTGTTACAACCAGCATCGCTGTT
CTTATCGGGTGTATTGTCATGCTGGTTTGGCGGCGGAGTGGCAGCGGCAATTCTAAAAGAGTG
GAGCCACTGAAGCCTCTGGTAATCAAACCCCGCGAAGAAGAAATCGATGATGGACGTAAGAAA
GTTACAATTTTTTTTGGTACACAGACAGGTACAGCAGAGGGCTTTGCCAAAGCTCTTGGAGAA
GAAGCAAAAGCTCGATATGAGAAAACACGCTTCAAGATCGTCGATCTGGATGACTACGCGGCA
GACGACGATGAGTACGAAGAAAAACTCAAAAAGAGGATGTGGCTTTTTTTTTCCTGGCAACT
TATGGGGACGGCGAGCCTACCGACAATGCAGCGCGGTTTTACAAATGGTTTACCGAAGGCAAT
GATAGAGGGGAGTGGCTCAAAAATCTCAAATACGGAGTTTTCGGATTGGGGAATAGACAATAC
GAACACTTTAATAAGGTTGCGAAAGTGGTAGATGATATTCTGGTCGAGCAGGGCGCGCAACGT
TTAGTACAGGTCGGCCTGGGTGATGACGACCAGTGCATCGAAGATGACTTTACGGCCTGGCGA
GAAGCGCTCTGGCCGGAATTAGATACAATCCTTCGGGAAGAGGGGGACACTGCTGTCGCTACC
CCGTACACTGCCGCAGTGCTGGAATATCGTGTTTCAATACATGATTCGGAAGATGCCAAGTTT
AATGACATCACCCTGGCAAACGGCAACGGATATACCGTATTTGACGCTCAACATCCGTATAAG
GCCAATGTAGCAGTAAAGCGGGAACTCCATACTCCCGAAAGTGACAGAAGTTGCATCCATCTG
GAGTTCGATATAGCGGGAAGCGGACTGACTATGAAACTGGGAGATCATGTAGGGGTCCTGTGC
GATAATTTGAGCGAAACCGTTGACGAAGCGCTCCGGCTTTTAGATATGTCCCCTGATACTTAT
TTCTCTTTGCACGCCGAGAAGGAAGATGGTACACCTATATCCTCCTCGCTGCCGCCGCCTTTT
CCACCATGTAATCTGCGTACGGCCTTGACTAGGTATGCATGTCTTCTTAGCTCCCCGAAAAAG
TCCGCACTGGTAGCGTTGGCAGCTCATGCCAGCGATCCCACGGAGGCAGAGCGTTTAAAACAC
CTGGCGAGTCCTGCTGGCAAAGATGAATACAGCAAATGGGTGGTTGAGTCGCAGAGGTCCCTG
CTGGAAGTCATGGCTGAATTTCCGTCTGCGAAACCGCCTCTGGGAGTTTTCTTCGCAGGAGTA
GCCCCACGTTTACAACCGCGTTTCTATTCTATTTCTTCCTCCCCAAGATCGCGGAAACTCGA
ATACACGTAACGTGCGCATTGGTGTATGAAAGATGCCAACTGGTCGTATCCACAAGGGAGTG
TGCTCAACCTGGATGAAAAACGCCGTTCCGTATGAAAAATCGGAAAAATTGTTTTGGGTAGA
CCCATATTCGTTCGGCAGTCAAACTTTAAACTACCTTCTGATAGCAAGGTTCCGATTATTATG
ATTGGACCGGGTACTGGCCTGGCGCCGTTCCGTGGTTTCCTGCAAGAACGGTTGGCGCTGGTG
GAATCCGGCGTGGAACTTGGGCCATCGGTTTTGTTTTCGGGTGCCGCAATCGTCGCATGGAC
TTCATCTACGAGGAAGAACTCCAGCGTTTTGTCGAAAGCGGTGCCCTTGCTGAATTGTCCGTT
GCATTCAGCCGCGAAGGTCCAACTAAGGAGTATGTGCAGCACAAAATGATGGACAAAGCGAGC
GATATTTGGAATATGATTAGCCAGGGCGCATACCTTTATGTGTGCGGTGATGCTAAGGGAATG
GCGCGCGATGTCCATAGATCTTTACATACCATTGCACAGGAGCAGGGCTCTATGGATTCAACA
AAAGCTGAAGGTTTTGTGAAAAACCTTCAGACCAGCGGGCGGTATCTTCGCGATGTTTGGTAA
(SEQ ID NO: 75)

FIG. 6A (Cont'd)

>SrCPR1 [Stevia rebaudiana]
MAQSDSVKVSPFDLVSAAMNGKAMEKLNASESEDPTTLPALKMLVENRELLTLFTTSFAVLIG
CLVFLMWRRSSSKKLVQDPVPQVIVVKKKEKESEVDDGKKKVSIFYGTQTGTAEGFAKALVEE
AKVRYEKTSFKVIDLDDYAADDDEYEEKLKKESLAFFFLATYGDGEPTDNAANFYKWFTEGDD
KGELLKKLQYGVFGLGNRQYEHFNKIAIVVDDKLTEMGAKRLVPVGLGDDDQCIEDDFTAWKE
LVWPELDQLLRDEDDTSVTTPYTAAVLEYRVVYHDKPADSYAEDQTHTNGHVVHDAQHPSRSN
VAFKKELHTSQSDRSCTHLEFDISHTGLSYETGDHVGVYSENLSEVVDEALKLLGLSPDTYFS
VHADKEDGTPIGGASLPPPFPPCTLRDALTRYADVLSSPKKVALLALAAHASDPSEADRLKFL
ASPAGKDEYAQWIVANQRSLLEVMQSFPSAKPPLGVFFAAVAPRLQPRYYSISSSPKMSPNRI
HVTCALVYETTPAGRIHRGLCSTWMKNAVPLTESPDCSQASIFVRTSNFRLPVDPKVPVIMIG
PGTGLAPFRGFLQERLALKESGTELGSSIFFFGCRNRKVDFIYEDELNNFVETGALSELIVAF
SREGTAKEYVQHKMSQKASDIWKLLSEGAYLYVCGDAKGMAKDVHRTLHTIVQEQGSLDSSKA
ELYVKNLQMSGRYLRDVW (SEQ ID NO: 76)

ATGGCTCAGAGCGATTCTGTTAAAGTATCCCCGTTCGACCTGGTCTCTGCGGCTATGAACGGC
AAAGCAATGGAGAAACTGAACGCGAGCGAATCTGAAGATCCAACCACCCTGCCGGCACTGAAA
ATGCTGGTAGAAAACCGTGAACTGCTGACTCTGTTCACCACCTCCTTCGCCGTTCTGATTGGT
TGCCTGGTCTTCCTGATGTGGCGCCGTTCCTCTTCCAAGAAGCTGGTACAGGACCCGGTTCCT
CAGGTGATCGTCGTTAAAAAGAAAGAGAAGGAAAGCGAAGTCGATGACGGCAAAAAGAAGGTT
TCCATTTTCTACGGTACTCAGACCGGCACCGCTGAGGGTTTTGCCAAAGCACTGGTTGAAGAG
GCAAAAGTGCGTTACGAAAAAACTTCCTTCAAAGTGATTGACCTGGACGACTATGCTGCGGAT
GATGATGAATACGAGGAAAAACTGAAAAAGAAAGCCTGGCCTTCTTCTTCCTGGCAACCTAT
GGCGATGGTGAACCGACCGACAACGCGGCGAACTTCTACAAATGGTTTACCGAAGGCGACGAC
AAAGGTGAATTGCTGAAGAAACTGCAGTATGGTGTTTTCGGTCTGGGCAATCGCCAGTACGAA
CATTTTAACAAAATCGCAATCGTTGTTGATGACAAACTGACTGAAATGGGTGCGAAACGTCTG
GTGCCGGTTGGCCTGGGTGACGATGATCAATGCATCGAAGATGACTTCACCGCATGGAAAGAA
CTGGTTTGGCCGGAACTGGATCAGCTGCTGCGCGACGAAGACGACACTTCCGTGACCACCCCG
TATACCGCTGCAGTGCTGGAGTACCGTGTTGTTTACCACGATAAACCGGCGGACTCTTACGCC
GAAGATCAGACTCACACTAACGGTCACGTCGTACATGACGCACAGCACCCGTCTCGTAGCAAT
GTTGCGTTTAAGAAAGAGCTGCACACGAGCCAGTCCGACCGCTCTTGTACGCACCTGGAGTTC
GATATCTCCCACACCGGTCTGTCCTATGAAACCGGTGACCATGTTGGCGTTTACAGCGAAAAC
CTGAGCGAGGTAGTTGATGAAGCGCTGAAACTGCTGGGCCTGTCTCCAGACACCTACTTTAGC
GTGCATGCTGACAAGGAAGATGGTACTCCGATTGGCGGCGCTTCCTGCCGCCACCGTTTCCA
CCTTGCACTCTGCGTGATGCTCTGACTCGTTACGCTGATGTTCTGTCTAGCCCGAAAAAGGTT
GCGCTGCTGGCGCTGGCCGCACATGCTTCTGACCCGTCTGAAGCTGACCGTCTGAAATTCCTG
GCGTCTCCGGCCGGCAAAGACGAATACGCGCAGTGGATTGTCGCTAACCAGCGCTCTCTGCTG
GAAGTGATGCAGTCCTTCCCGTCTGCCAAACCGCCACTGGGCGTGTTTTTCGCAGCTGTGGCT
CCGCGCCTGCAGCCGCGCTACTATTCTATCTCAGCTCCCCGAAAATGAGCCCGAACCGCATC
CACGTTACTTGTGCTCTGGTTTACGAAACCACCCCTGCGGGCCGTATCCACCGTGGTCTGTGC
TCTACGTGGATGAAAAATGCCGTGCCGCTGACCGAATCCCCGGACTGCTCTCAGGCGTCCATC
TTCGTGCGTACCTCTAACTTCCGTCTGCCGGTGGACCCGAAAGTTCCTGTTATCATGATCGGT
CCTGGCACGGGTCTGGCCCCGTTTCGTGGTTTTCTGCAGGAGCGTCTGGCTCTGAAAGAATCC
GGTACTGAGCTGGGCTCTTCCATCTTTTTCTTCGGTTGTCGTAACCGCAAAGTCGATTTCATC
TATGAAGACGAACTGAACAACTTCGTAGAGACTGGTGCACTGTCCGAACTGATTGTGGCATTC
TCTCGTGAAGGCACGGCGAAAGAATACGTTCAACACAAAATGTCTCAGAAAGCGAGCGATATC
TGGAAACTGCTGTCCGAGGGTGCGTATCTGTATGTTTGTGGCGACGCGAAAGGCATGGCTAAA
GATGTACACCGCACCCTGCACACCATTGTACAAGAACAAGGCTCTCTGGATAGCTCCAAGGCA
GAACTGTACGTGAAAAACCTGCAGATGTCTGGCCGTTACCTGCGTGATGTATGGTAA (SEQ
ID NO: 77)

FIG. 6A (Cont'd)

>SrCPR2 [Stevia rebaudiana]

MAQSESVEASTIDLMTAVLKDTVIDTANASDNGDSKMPPALAMMFEIRDLLLILTTSVAVLVG
CFVVLVWKRSSGKKSGKELEPPKIVVPKRRLEQEVDDGKKKVTIFFGTQTGTAEGFAKALFEE
AKARYEKAAFKVIDLDDYAADLDEYAEKLKKETYAFFFLATYGDGEPTDNAAKFYKWFTEGDE
KGVWLQKLQYGVFGLGNRQYEHFNKIGIVVDDGLTEQGAKRIVPVGLGDDDQSIEDDFSAWKE
LVWPELDLLLRDEDDKAAATPYTAAIPEYRVVFHDKPDAFSDDHTQTNGHAVHDAQHPCRSNV
AVKKELHTPESDRSCTHLEFDISHTGLSYETGDHVGVYCENLIEVVEEAGKLLGLSTDTYFSL
HIDNEDGSPLGGPSLQPPFPPCTLRKALTNYADLLSSPKKSTLLALAAHASDPTEADRLRFLA
SREGKDEYAEWVVANQRSLLEVMEAFPSARPPLGVFFAAVAPRLQPRYYSISSSPKMEPNRIH
VTCALVYEKTPAGRIHKGICSTWMKNAVPLTESQDCSWAPIFVRTSNFRLPIDPKVPVIMIGP
GTGLAPFRGFLQERLALKESGTELGSSILFFGCRNRKVDYIYENELNNFVENGALSELDVAFS
RDGPTKEYVQHKMTQKASEIWNMLSEGAYLYVCGDAKGMAKDVHRTLHTIVQEQGSLDSSKAE
LYVKNLQMSGRYLRDVW (SEQ ID NO: 78)

ATGGCGCAATCTGAAAGTGTTGAGGCCAGTACCATCGACCTTATGACGGCAGTGTTGAAGGAT
ACAGTTATTGACACTGCAAATGCTTCAGATAACGGCGATTCTAAAATGCCTCCTGCGCTTGCG
ATGATGTTCGAGATCCGCGATCTTCTGCTGATCCTTACCACATCAGTAGCGGTGCTGGTGGGA
TGCTTTGTGGTACTCGTGTGGAAACGTTCGTCGGGCAAAAAATCAGGTAAGGAGCTGGAACCG
CCTAAGATTGTCGTACCGAAACGCCGACTGGAACAAGAAGTTGATGATGGCAAAAAAAAGTG
ACTATATTTTTGGGACACAGACAGGCACAGCGGAGGGATTTGCGAAAGCCTTATTCGAGGAG
GCGAAGGCACGTTACGAGAAAGCAGCTTTTAAAGTCATTGATCTGGATGACTATGCAGCAGAC
CTAGATGAATACGCAGAGAAACTGAAAAAGAAACTTATGCGTTTTTCTTCCTGGCCACATAC
GGAGACGGTGAACCGACGGACAATGCCGCCAAGTTTTATAAGTGGTTCACTGAAGGGATGAG
AAAGGTGTATGGCTTCAGAAATTGCAATACGGAGTGTTCGGACTAGGAAATCGGCAATATGAG
CACTTTAATAAAATAGGCATAGTAGTAGACGATGGGCTAACCGAGCAGGGGGCCAAACGGATT
GTACCCGTGGGCCTGGGGGACGATGATCAGTCTATTGAGGATGATTTTAGTGCTTGGAAAGAG
CTTGTTTGGCCTGAACTGGACTTACTCCTGCGTGATGAAGACGATAAAGCGGCAGCGACTCCA
TACACGGCAGCAATCCCCGAGTATAGAGTCGTATTCCATGATAAACCGGATGCTTTCTCTGAT
GACCATACCCAAACTAATGGTCATGCGGTCCATGATGCACAACATCCCTGCCGCAGCAATGTA
GCGGTGAAAAAGGAGCTGCATACGCCTGAAAGTGATCGCTCATGTACGCATCTGGAGTTTGAT
ATTTCACACAGGTCTTAGCTACGAGACTGGAGATCACGTCGGAGTCTATTGCGAAAATCTG
ATCGAAGTGGTTGAAGAGGCCGGGAAACTGTTGGGACTAAGTACAGATACTTATTTTTCTTTA
CATATAGATAACGAGGATGGTTCCCCACTTGGCGGTCCATCTCTTCAGCCTCCATTCCCACCA
TGTACCTTACGCAAAGCGCTGACTAACTACGCAGATCTGCTGTCTAGCCCAAAGAAATCAACG
CTTCTGGCGTTGGCTGCTCATGCCTCAGATCCGACCGAAGCTGATCGCCTTCGTTTTCTGGCA
TCCCGAGAAGGTAAAGATGAATATGCAGAATGGGTGGTAGCGAATCAGCGTTCTTTGCTGGAA
GTCATGGAGGCATTCCCCAGCGCGCGCCCTCCGCTGGGTGTTTTCTTCGCAGCGGTGGCCCCG
CGGCTCCAGCCGCGTTATTATTCAATTAGCAGTTCTCCTAAGATGGAACCTAATCGAATCCAT
GTAACATGTGCATTGGTCTATGAGAAAACGCCGGCTGGCCGCATCCATAAAGGTATATGTAGC
ACATGGATGAAAAATGCAGTACCCCTCACGGAGTCCCAGGATTGTAGTTGGGCGCCGATATTT
GTTCGGACGAGCAATTTTAGACTTCCTATAGACCCAAAGGTTCCAGTTATTATGATTGGTCCT
GGCACCGGACTTGCGCCATTCCGGGGGTTTCTGCAAGAAAGACTGGCTCTGAAAGAAAGCGGT
ACAGAACTCGGCTCCAGTATATTGTTTTCGGCTGTCGCAACCGGAAAGTAGATTATATATAT
GAAAACGAGCTGAATAACTTCGTTGAAATGGTGCCCTGTCTGAACTCGATGTCGCTTTTTCG
CGAGATGGCCCGACAAAAGAATACGTGCAGCATAAAATGACCCAGAAAGCAAGTGAAATCTGG
AATATGCTGTCAGAAGGGGCATATCTGTATGTGTGCGGAGATGCAAAGGGCATGGCCAAAGAC
GTTCACAGAACCTTGCATACCATAGTACAAGAGCAGGGCTCTCTGGATAGCTCAAAAGCCGAG
CTGTACGTGAAAAATCTCCAGATGAGTGGACGCTACCTGAGGGATGTTTGGTAA (SEQ ID NO: 79)

>SrCPR3 [Stevia rebaudiana]

MAQSNSVKISPLDLVTALFSGKVLDTSNASESGESAMLPTIAMIMENRELLMILTTSVAVLI
GCVVVLVWRRSSTKKSALEPPVIVVPKRVQEEEVDDGKKKVTVFFGTQTGTAEGFAKALVEE
AKARYEKAVFKVIDLDDYAADDDEYEEKLKKESLAFFFLATYGDGEPTDNAARFYKWFTEGD
AKGEWLNKLQYGVFGLGNRQYEHFNKIAKVVDDGLVEQGAKRLVPVGLGDDDQCIEDDFTAW
KELVWPELDQLLRDEDDTTVATPYTAAVAEYRVVFHEKPDALSEDYSYTNGHAVHDAQHPCR
SNVAVKKELHSPESDRSCTHLEFDISNTGLSYETGDHVGVYCENLSEVVNDAERLVGLPPDT
YFSIHTDSEDGSPLGGASLPPPFPPCTLRKALTCYADVLSSPKKSALLALAAHATDPSEADR
LKFLASPAGKDEYSQWIVASQRSLLEVMEAFPSAKPSLGVFFASVAPRLQPRYYSISSSPKM
APDRIHVTCALVYEKTPAGRIHKGVCSTWMKNAVPMTESQDCSWAPIYVRTSNFRLPSDPKV
PVIMIGPGTGLAPFRGFLQERLALKEAGTDLGLSILFFGCRNRKVDFIYENELNNFVETGAL
SELIVAFSREGPTKEYVQHKMSEKASDIWNLLSEGAYLYVCGDAKGMAKDVHRTLHTIVQEQ
GSLDSSKAELYVKNLQMSGRYLRDVW (SEQ ID NO: 80)

ATGGCGCAATCTAATTCTGTGAAAATCTCTCCATTGGATCTGGTTACAGCACTCTTTAGCGG
GAAGGTACTGGATACAAGTAACGCCAGTGAAAGCGGGGAATCCGCGATGCTGCCAACAATCG
CGATGATCATGGAAAATCGGGAACTGCTAATGATTCTGACAACGTCTGTAGCAGTTTTAATC
GGTTGCGTTGTGGTTCTGGTGTGGCGTCGATCATCCACGAAAAGAGCGCATTAGAACCGCC
TGTTATCGTAGTACCAAAAAGAGTTCAGGAGGAAGAGGTGGATGATGGGAAAAAAAAGTCA
CCGTTTTCTTCGGGACCCAAACTGGTACGGCAGAAGGTTTTGCGAAAGCACTGGTCGAAGAG
GCGAAAGCCCGCTATGAGAAGGCGGTTTTTAAGGTTATTGACCTTGATGACTATGCGGCGGA
CGATGATGAATACGAAGAAAAATTAAAGAAAGAATCACTTGCCTTTTTTTTTGGCAACAT
ACGGTGATGGCGAGCCGACTGATAACGCGGCACGGTTTTACAAATGGTTTACCGAAGGCGAC
GCGAAGGGGGAGTGGTTGAACAAGTTACAGTACGGTGTGTTCGGCTTGGGGAACCGCCAGTA
CGAGCACTTTAACAAGATAGCTAAAGTTGTCGATGATGGTCTGGTAGAACAGGGAGCGAAGC
GTCTCGTGCCAGTAGGGCTGGGCGATGATGATCAGTGTATAGAAGATGATTTTACGGCTTGG
AAGGAGTTAGTTTGGCCGGAACTGGACCAACTGCTGCGCGATGAGGATGATACAACTGTCGC
TACCCCGTATACAGCAGCGGTAGCTGAATACAGGGTGGTTTTTCACGAGAAACCTGATGCGC
TGAGTGAGGACTATTCGTATACTAACGGCCATGCCGTTCACGATGCACAGCACCCGTGCCGT
TCTAATGTCGCCGTAAAAAAGGAACTGCATAGCCCGGAGTCGGACCGCAGTTGTACCCATCT
GGAGTTTGATATTTCAAATACCGGGCTGAGTTACGAAACGGGCGATCACGTTGGCGTGTACT
GTGAGAATCTAAGCGAGGTTGTTAACGATGCAGAACGACTGGTCGGTTTGCCTCCAGATACT
TATTTCTCGATCCACACTGATAGCGAAGATGGCTCTCCACTCGGGGGGCGAGTCTGCCGCC
CCCGTTTCCCCCGTGTACGCTGAGAAAGGCCCTTACATGTTATGCAGATGTACTCTCTTCCC
CCAAAAAAAGTGCCTTGCTCGCATTAGCAGCCCACGCTACCGATCCCTCGGAAGCAGATCGT
CTGAAATTCTTGGCATCGCCGGCGGGCAAAGATGAATACAGCCAATGGATAGTTGCAAGTCA
GCGCAGTCTCTTAGAAGTGATGGAAGCGTTTCCGTCCGCAAAGCCGTCCTTAGGTGTGTTTT
TCGCGTCCGTGGCACCGCGTCTTCAGCCTAGATATTACAGCATTAGTTCCTCTCCAAAAATG
GCCCCGGACCGTATTCACGTGACTTGTGCTCTTGTATATGAGAAAACCCCGGCAGGTCGTAT
TCACAAAGGCGTGTGCAGCACCTGGATGAAGAATGCAGTGCCGATGACCGAAAGCCAGGATT
GTTCATGGGCGCCAATCTATGTCAGGACAAGTAATTTCAGACTTCCGTCTGATCCTAAAGTT
CCAGTCATAATGATTGGCCCCGGCACGGGACTGGCTCCTTTTCGTGGTTTCCTGCAAGAGCG
CTTGGCACTGAAAGAAGCAGGCACTGACCTGGGACTGTCCATCCTGTTCTTTGGGTGCCGTA
ATCGTAAGGTCGATTTTATATATGAAAATGAATTGAACAACTTTGTAGAAACAGGCGCATTA
TCCGAACTGATCGTAGCTTTTAGTAGAGAGGGGCCGACGAAAGAATATGTACAACACAAGAT
GTCTGAGAAGGCTTCGGATATATGGAACCTGCTCTCTGAGGGTGCCTATCTGTACGTTTGCG
GTGATGCCAAAGGAATGGCCAAAGATGTGCACCGCACTTTACATACAATCGTCCAAGAGCAG
GGTAGCTTGGACTCATCTAAAGCTGAACTGTATGTGAAGAACTTACAGATGAGCGGGCGCTA
TTTGCGAGATGTTTGGTAA (SEQ ID NO: 81)

FIG. 6A (Cont'd)

\>PgCPR [Pelargonium graveolens]

MAQSSSGSMSPFDFMTAIIKGKMEPSNASLGAAGEVTAMILDNRELVMILTTSIAVLIGCVV
VFIWRRSSSQTPTAVQPLKPLLAKETESEVDDGKQKVTIFFGTQTGTAEGFAKALADEAKAR
YDKVTFKVVDLDDYAADDEEYEEKLKKETLAFFFLATYGDGEPTDNAARFYKWFLEGKERGE
WLQNLKFGVFGLGNRQYEHFNKIAIVVDEILAEQGGKRLISVLGDDDQCIEDDFTAWRESL
WPELDQLLRDEDDTTVSTPYTAAVLEYRVVFHDPADAPTLEKSYSNANGHSVVDAQHPLRAN
VAVRRELHTPASDRSCTHLEFDISGTGIAYETGDHVGVYCENLAETVEEALELLGLSPDTYF
SVHADKEDGTPLSGSSLPPPFPPCTLRTALTLHADLLSSPKKSALLALAAHASDPTEADRLR
HLASPAGKDEYAQWIVASQRSLLEVMAEFPSAKPPLGVFFASVAPRLQPRYYSISSSPRIAP
SRIHVTCALVYEKTPTGRVHKGVCSTWMKNSVPSEKSDECSWAPIFVRQSNFKLPADAKVPI
IMIGPGTGLAPFRGFLQERLALKEAGTELGPSILFFGCRNSKMDYIYEDELDNFVQNGALSE
LVLAFSREGPTKEYVQHKMMEKASDIWNLISQGAYLYVCGDAKGMARDVHRTLHTIAQEQGS
LDSSKAESMVKNLQMSGRYLRDVW (SEQ ID NO: 82)

ATGGCGCAGTCAAGCAGTGGATCAATGAGCCCTTTCGATTTTATGACCGCTATAATAAAAGG
TAAAATGGAGCCAAGTAATGCGTCTTTAGGAGCGGCAGGTGAAGTCACAGCAATGATACTTG
ATAATAGGGAGCTGGTTATGATTCTGACGACCAGCATTGCAGTGCTGATCGGTTGCGTTGTA
GTGTTCATTTGGCGTCGTTCATCATCCCAGACCCCTACCGCGGTGCAGCCATTAAAACCACT
TTTAGCGAAGGAAACAGAGAGCGAAGTAGACGATGGCAAACAGAAAGTAACTATCTTTTTTG
GTACTCAAACTGGAACCGCTGAAGGTTTCGCGAAAGCGCTCGCAGACGAGGCCAAAGCACGG
TATGATAAAGTCACTTTTAAAGTGGTTGATCTGGACGATTATGCCGCAGATGACGAAGAATA
TGAAGAAAAGCTGAAGAAGGAAACGTTAGCATTCTTTTTTCTTGCGACGTATGGAGATGGTG
AACCTACTGACAATGCTGCAAGGTTTTATAAGTGGTTTCTGGAAGGTAAAGAACGCGGAGAA
TGGCTTCAGAATCTAAAATTTGGTGTGTTTGGTTTAGGCAACCGTCAGTATGAGCATTTCAA
TAAAATTGCCATTGTGGTTGATGAAATCCTTGCAGAACAAGGTGGTAAGCGTCTCATTTCAG
TTGGCCTGGGCGATGATGATCAGTGTATTGAGGATGACTTTACTGCCTGGAGGGAATCGCTG
TGGCCGGAGCTAGATCAGTTATTACGCGATGAGGATGATACTACGGTTTCTACGCCGTATAC
CGCCGCGGTGCTGGAATACAGAGTCGTTTTTCATGATCCGGCAGATGCCCCAACTCTCGAAA
AAAGCTACAGCAACGCTAACGGGCATAGCGTGGTTGATGCGCAACATCCGTTACGGGCAAAT
GTTGCCGTCAGACGGGAGTTGCATACTCCTGCGTCTGACCGCTCATGTACCCATCTGGAATT
TGATATATCTGGTACTGGCATCGCATACGAGACGGGTGATCATGTTGGCGTGTATTGCGAGA
ATCTTGCAGAGACGGTAGAAGAAGCGTTGGAACTTTTAGGTCTTTCCCCGGATACATACTTC
TCCGTACACGCAGATAAAGAGGACGGTACGCCTCTCTCAGGCTCATCTCTCCCGCCGCCATT
TCCACCGTGCACTTTACGTACAGCCCTGACGTTACATGCTGACTTACTGTCTTCCCCAAAGA
AATCTGCATTGCTCGCGCTTGCAGCTCATGCATCAGACCCCACTGAAGCTGATCGATTGCGG
CACCTAGCAAGCCCTGCGGGCAAGGACGAATACGCTCAGTGGATAGTTGCTAGTCAGCGTTC
CTTGCTGGAAGTGATGGCGGAGTTCCCCAGTGCCAAGCCCCGCTGGGAGTATTCTTCGCAT
CGGTTGCTCCAAGATTGCAGCCCCGGTACTACTCTATTTCTTCTTCCCCAAGAATAGCGCCG
TCTCGCATACACGTGACCTGCGCGTTAGTTTACGAGAAAACACCTACGGGCAGAGTACACAA
AGGAGTTTGCTCCACTTGGATGAAAAACTCAGTGCCCTCTGAAAAGAGTGATGAATGTTCAT
GGGCACCAATTTTCGTACGACAGAGCAACTTTAAACTGCCCGCCGATGCGAAAGTACCCATA
ATTATGATTGGTCCAGGAACGGGTCTGGCACCATTTCGCGGCTTCCTCCAGGAGCGGCTTGC
ATTGAAAGAAGCAGGGACAGAACTGGGACCTTCCATATTATTTTTTGGGTGCCGCAACAGCA
AAATGGACTATATATACGAGGATGAACTGGATAATTTTGTACAGAATGGGGCACTCTCTGAA
CTCGTGTTGGCGTTCTCACGTGAAGGTCCTACCAAAGAGTATGTGCAACATAAGATGATGGA
GAAAGCCTCAGATATATGGAACCTTATTTCACAGGGAGCTTATTTGTATGTGTGCGGGGACG
CAAAAGGCATGGCGCGTGATGTGCACCGCACGTTACATACCATCGCTCAGGAGCAGGGGTCA
TTAGATAGCTCAAAAGCAGAGAGTATGGTGAAGAATCTTCAGATGTCAGGCAGATACCTGCG
CGATGTCTGGTAA (SEQ ID NO: 83)

FIG. 6A (Cont'd)

```
AtCPR2   MASSSSSSSTSMIDLMAAIIKGE-PVIVSDPANASAYESVAAELSSMLIENRQFAMIVTT    59
ATR2     MASSSSSSSTSMIDLMAAIIKGE-PVIVSDPANASAYESVAAELSSMLIENRQFAMIVTT    59
AaCPR    MAQSTTSVKLSPFDLMTALLNG---KVSFDTSNTSDTN----IPLAVFMENRELLMILTT    53
AtCPR    ---MTSALYASDLFKQLKSIMGTDS---------------------LSDDVLVIATT      34
AtCPR1   --MATSALYASDLFKQLKSIMGTDS---------------------LSDDVLVIATT      35
          :: :  : *                                      :: *   *

AtCPR2   SIAVLIGCIVMLVWRRSGSGNSKRVE-PLKPLVIKPREEE----IDDGRKKVTIFFGTQT   114
ATR2     SIAVLIGCIVMLVWRRSGSGNSKRVE-PLKPLVIKPREEE----IDDGRKKVTIFFGTQT   114
AaCPR    SVAVLIGCVVVLVWRRSSSAAKKAAES PVIVVPKKVTEDE----VDDGRKKVTVFFGTQT   109
AtCPR    SLALVAG-FVVLLWKKTTADRSGELKPLMIPKSLMAKDEDDDLGSGKTRVSIFFGTQT     93
AtCPR1   SLALVAG-FVVLLWKKTTADRSGELKPLMIPKSLMAKDEDDDLGSGKTRVSIFFGTQT     94
         * :: *  .: : : :: :                            :     ******

AtCPR2   GTAEGFAKALGEEEAKARYEKTRFKIVDLDDYAADDDEYEEKLKKEDVAFFFLATYGDGEP   174
ATR2     GTAEGFAKALGEEEAKARYEKTRFKIVDLDDYAADDDRYEEKLKKEDVAFFFLATYGDGEP   174
AaCPR    GTAEGFAKALVEEAKARYEKAVFEKVIDLDDYAAEDDEYEEKLKKESLAFFFLATYGDGEP   169
AtCPR    GTAEGFAKALSEEIKARYEKAAVKVIDLDDYAADDQYEEKLKKETLAFFCVATYGDGEP    153
AtCPR1   GTAEGFAKALSEEIKARYEKAAVKVIDLDDYAADDQYEEKLKKETLAFFCVATYGDGEP    154
         ******** ..**:****** . :.**.***** :**:**** **** .:*******

AtCPR2   TDNAARFYKWFTEGNDRGEWLKNLKYGVFGLGNRQYEHFNKVAKVVDDILVEQGAQRLVQ   234
ATR2     TDNAARFYKWFTEGNDRGEWLKNLKYGVFGLGNRQYEHFNKVAKVVDDILVEQGAQRLVQ   234
AaCPR    TDNAARFYKWFTEGEEKGEWLDKLQYAVFGLGNRQYEHFNKIAKVVDEKLVEQGAKRLVP   229
AtCPR    TDNAARFSKWFTEENERDIKLQQLAYGVFALGNRQYEHFNKIGIVLDEELCKKGAKRLIE   213
AtCPR1   TDNAARFSKWFTEENERDIKLQQLAYGVFALGNRQYEHFNKIGIVLDEELCKKGAKRLIE   214
         ******* *****.: : *   : * *:*********:   :: : : * *.:**::

AtCPR2   VGLGDDDQCIEDDFTAWREALMPELDTILREEGDTAVATPYTAAVLEYRVSIHDSEDAKF   294
ATR2     VGLGDDDQCIEDDFTAWREALMPELDTILREEGDTAVATPYTAAVLEYRVSIHDSEDAKF   294
AaCPR    VGMGDDDQCIEDDFTAWKELVWPELDQLLRDEDDTSVATPYTAAVAEYRVVFHD--KPETY   288
AtCPR    VGLGDDDQSIEDDFNAWKESLWSELDKLLKDEDDKSLKDEDDKSVATPYTAVIPEYRVTHDPRFTTQ   273
AtCPR1   VGLGDDDQSIEDDFNAWKESLWSELDKLLKDEDDKSVATPYTAVIPEYRVTHDPRFTTQ   274
         **:*****.*****.**:: : ***.:::: : :  .:*****.: ***.  . :

AtCPR2   NDINMANGNGYTVFDAQHPYKANVAVKRELHTPESDRSCIHLEFDIAGSGLTYETGDHVG   354
ATR2     NDITLANGNGYTVFDAQHPYKANVAVKRELHTPESDRSCIHLEFDIAGSGLTMKLGDHVG   354
AaCPR    DQDQLTNG--HAVHDAQHPCRSNVAVKKELHSPLSDRSCCHLEFDISNTGLSYETGDHVG   346
AtCPR    KSMESNVANGNTTIDIHHPCRVDVAVQKELHTHESDRSCIHLEFDISRTGITYETGDHVG   333
AtCPR1   KSMESNVANGNTTIDIHHPCRVDVAVQKELHTHESDRSCIHLEFDISRTGITYETGDHVG   334
         :  :  *   . :* :** : :***::***: ****** *****: **    *****
```

FIG. 6B

```
AtCPR2  VLCDNLSETVDEALRLRLLDMSPDTYFSLHAEKEDGTPIS-SSLPPPFP-PCNLRTALTRYA  412
ATR2    VLCDNLSETVDEALRLRLLDMSPDTYFSLHAEKEDGTPIS-SSLPPPFP-PCNLRTALTRYA  412
AaCPR   VYVENLSEVVDEAEKLIGLPPHTYFSVHADNEDGTPLGGASLPPPFP-PCTLRKALASYA   405
AtCPR   VYAENHVEIVEEAGKLLGHSLDLVFSIHADKEDGSPLE-SAVPPPFPGPCTLGTGLARYA   392
AtCPR1  VYAENHVEIVEEAGKLLGHSLDLVFSIHADKEDGSPLE-SAVPPPFPGPCTLGTGLARYA   393
         *  :*.*  :**.     *:::.**.*::.*****  . ..**  ..** ** * **.*

AtCPR2  CLLSSPKKSALVALAAHASDFTEAERLKHLASPAGKDEYSKWVVESQRSLLEVMAEFPSA   472
ATR2    CLLSSPKKSALVALAAHASDPTEAERLKHLASPAGKDEYSKWVVESQRSLLEVMAEFPSA   472
AaCPR   DVLSSPKKSALLALAAHATDSTEADRLKFLASPAGKDEYAQWIVASHRSLLEVMAFFPSA   465
AtCPR   DLLNPPRKSALVALAAYATEPSEAEKLKHLTSPDGKDEYSQWIVASQRSLLEVMAAFPSA   452
AtCPR1  DLLNPPRKSALVALAAYATEPSEAEKLKHLTSPDGKDEYSQWIVASQRSLLEVMAAFPSA   453
         . *.*:****:*****::: .**:**:*:**.****::*:**.:***** *:***

AtCPR2  KPPLGVFFAGVAPRLQPRFYSISSSPKIAETRIHVTCALVYEKMPTGRIHKGVCSTWMKN   532
ATR2    KPPLGVFFAGVAPRLQPRFYSISSSPKIAETRIHVTCALVYEKMPTGRIHKGVCSTWMKN   532
AaCPR   KPPLGVFFASVAPRLQPRYYSISSSPRFAPNRIHVTCALVYEQTPSGRVHKGVCSTWMKN   525
AtCPR   KPPLGVFFAAIAPRLQPRYYSISSSCQDWAPSRVHVTSALVYGPTPTGRIHKGVCSTWMKN   512
AtCPR1  KPPLGVFFAAIAPRLQPRYYSISSSPRLAPSRVHVTSALVYGFTPTGRIHKGVCSTWMKN   513
        *********.:******:*****.   . .*:****.*** .   ** *********

AtCPR2  AVPYEKSENCCSS-APIFVRQSNFKLPSDSKVPIIMIGPGTGLAPFRGFLQERLALVESGV   591
ATR2    AVPYEKSEKLFLGRPIFVRQSNFKLPSDSKVPIIMIGPGTGLAPFRGFLQERLALVESGV   592
AaCPR   AVPMTESQDCSW-APIYVRTSNFRLPSDPKVPVIMIGPGTGLAPFRGFLQERLAQKEAGT   584
AtCPR   AVPAEKSHECSG-APIFIRASNFKLPSNPSTPIVMVGPGTGLAPFRGFLQERMALKEDGE   571
AtCPR1  AVPAEKSHECSG-APIFIRASNFKLPSNPSTPIVMVGPGTGLAPFRGFLQERMALKEDGE   572
        ***  .:. .    ** :* ***:**. . *::*:*****************:** .

AtCPR2  ELGPSVLFFGCRNRRMDFIYEEELQRFVESGALAELSVAFSREGPTKEYVQHKMMDKASD   651
ATR2    ELGPSVLFFGCRNRRMDFIYEEELQRFVESGALAELSVAFSREGPTKEYVQHKMMDKASD   652
AaCPR   ELGTAILFFGCRNRKVDFIYEDELNNFVETGALSELVTAFSREGATKEYVQHKMTQKASD   644
AtCPR   ELGSSLLFFGCRNRQMDFIYEDELNNFVDQGVISELIMAFSREGAQKEYVQHKMMEKAAQ   631
AtCPR1  ELGSSLLFFGCRNRQMDFIYEDELNNFVDQGVISELIMAFSREGAQKEYVQHKMMEKAAQ   632
        ***: :********::*****:***:.**: *.*:: ******. *******  **::

AtCPR2  IWNMISQGAYLYVCGDAKGMARDVHRSLHTIAQEQGSMDSTKAEGFVKNLQTSGRYLRDVW   712
ATR2    IWNMISQGAYLYVCGDAKGMARDVHRSLHTIAQEQGSMDSTKAEGFVKNLQTSGRYLRDVW   713
AaCPR   IWNLLSEGAYLYVCGDAKGMARDVHRTLHTIVQEQGSLDSSKAELYVKNLQMAGRYLRDVW   705
AtCPR   VWDLIKEEGYLYVCGDAKGMARDVHRTLHTIVQEQEGVSSSEEAEAIVKKLQTEGRYLRDVW   692
AtCPR1  VWDLIKEEGYLYVCGDAKGMARDVHRTLHTIVQEQEGVSSSEEAEAIVKKLQTEGRYLRDVW   693
        :*::: : *.******************:***.***:. ... **  **:** :*******
```

FIG. 6B (Cont'd)

```
SrCPR2    MAQSESVEASTIDLMTAVLKDTVIDTANASDNGDSKMPPALAMFEIRDLILILTTSVAV      60
SrCPR3    MAQSNSVKISPLDIVTALFSGKVLDTSNASESGESAMLPTIAMIMENRELLMILTTSVAV      60
SrCPR     -MQSDSVKVSPFDLVSAAMNGKAMEKLNASESEDPTTLPALKMLVENRELLTLFTTSFAV      59
SrCPR1    MAQSDSVKVSPFDLVSAAMNGKAMEKLNASESEDPTTLPALKMLVENRELLTLFTTSFAV      60
                 :*.*   ::.  . *       :       *  *: **  *:   *:::**:**

SrCPR2    LIVGCFVVLVWKRSSGKKSGKELEPPKIVVPKRRLEQEVDDGKKKVTIFFGTQTGTAEGFA    120
SrCPR3    LIGCVVVLVWRRSSTKKS--ALEPPVIVVPKRVQEEEVDDGKKKVTVFFGTQTGTAEGFA    118
SrCPR     LIGCLVFLMWRRSSSKKLVQDPVFQVIVVKKEKESEVDDGKKKVSIFYGTQTGTAEGFA     119
SrCPR1    LIGCLVFLMWRRSSSKKLVQDPVFQVIVVKKEKESEVDDGKKKVSIFYGTQTGTAEGFA     120
          ** . * *:*:**  *      **:**:: ::  ***********:*::***********

SrCPR2    KALFEEAKARYEKAAFKVIDLDDYAADLDEYAEKLKKETYAFFFLATYGDGEPTDNAAKF    180
SrCPR3    KALVEEAKARYEKAVFKVIDLDDYAADDDEYEEKLKKESLAFFFLATYGDGEPTDNAARF    178
SrCPR     KALVEEAKVRYEKTSFKVIDLDDYAADDDEYEEKLKKESLAFFFLATYGDGEPTDNAANF    179
SrCPR1    KALVEEAKVRYEKTSFKVIDLDDYAADDDEYEEKLKKESLAFFFLATYGDGEPTDNAANF    180
          ***:****.****::***********:**:*******: *************** .*

SrCPR2    YKWFTEGDEKGVWLQKLQYGVFGLGNRQYEHFNKIGIVVDDGLTEQGAKRIVPVGLGDDD    240
SrCPR3    YKWFTEGDAKGEWLNKLQYGVFGLGNRQYEHFNKIAKVVDDGLVEQGAKRLVPVGLGDDD    238
SrCPR     YKWFTEGDDKGEWLKKLQYGVFGLGNRQYEHFNKIAIVVDDKLTEMGAKRLVPVGLGDDD    239
SrCPR1    YKWFTEGDDKGELLKKLQYGVFGLGNRQYEHFNKIAIVVDDKLTEMGAKRLVPVGLGDDD    240
          ********.** :*:************** ***  ****.* *  ****:*********

SrCPR2    QSIEDDFSAWKELVWPELDLLLREDDKAAATPYTAAIPEYRVVFHDKP-DAFSDDHTQT    299
SrCPR3    QCIEDDFTAWKELVWPELDQLLREDDTTVATPYTAAVAEYRVVFHEKP-DALSEDYSYT    297
SrCPR     QCIEDDFTAWKELVWPELDQLLREDDTSVTTPYTAAVLEYRVVYHDKPADSYAEDQTHT    299
SrCPR1    QCIEDDFTAWKELVWPELDQLLREDDTSVTTPYTAAVLEYRVVYHDKPADSYAEDQTHT    300
          * *****:*********** *:****.  :****** ****::*:*  *: :.*: .*

SrCPR2    NGHAVHDAQHPCRSNVAVKKELHTPESDRSCTHLEFDISHTGLSYETGDHVGVYCENLIE    359
SrCPR3    NGHAVHDAQHPCRSNVAVKKELHSPESDRSCTHLEFDISNTGLSYETGDHVGVYCENLSE    357
SrCPR     NGHVVHDAQHPSRSNVAFKKELHTSQSDRSCTHLEFDISHTGLSYETGDHVGVYSENLSE    359
SrCPR1    NGHVVHDAQHPSRSNVAFKKELHTSQSDRSCTHLEFDISHTGLSYETGDHVGVYSENLSE    360
          ***.*******.*****.*****:.:*************.*************.***.*

SrCPR2    VVEEAGKLLGLSTDTYFSLHIDNEDGSPLGGPSLQPFPPCTLRKALTNYADLLSSPKKS    419
SrCPR3    VVNDAERLVGLPPDTYFSIHTDSEDGSPLGGASLPPFPPCTLRKALTCYADVLSSPKKS    417
SrCPR     VVDEALKLLGLSPDTYFSVHADKEDGTPIGGASLPPFPPCTLRDALTRYADVLSSPKKV    419
SrCPR1    VVDEALKLLGLSPDTYFSVHADKEDGTPIGGASLPPFPPCTLRDALTRYADVLSSPKKV    420
          **::* :*:**. *****:*.* ***:*:**.**.********.*** ***:******
```

FIG. 6C

```
SrCPR2  TLLALALAAHASDPTEADRLRFLASREGKDEYAEWVVANQRSLLEVMEAFPSARPPLGVFFA  479
SrCPR3  ALLALAAHATDPSEADRLKFLASPAGKDEYSQWIVASQRSLLEVMEAFPSAKPSLGVFFA    477
SrCPR   ALLALAAHASDPSEADRLKFLASPAGKDEYAQWIVANQRSLLEVMQSFPSAKPPLGVFFA    479
SrCPR1  ALLALAAHASDPSEADRLKFLASPAGKDEYAQWIVANQRSLLEVMQSFPSAKPPLGVFFA    480
        :*******:*.********:***** *****:*:**.*******:*:  *** *******

SrCPR2  AVAPRLQPRYYSISSSPKMEPNRIHVTCALVYEKTPAGRIHKGICSTWMKNAVPLTESQD    539
SrCPR3  SVAPRLQPRYYSISSSPKMAPDRIHVTCALVYEKTPAGRIHKGVCSTWMKNAVPMTESQD    537
SrCPR   AVAPRLQPRYYSISSSPKMSPNRIHVTCALVYETTPAGRIHRGLCSTWMKNAVPLTESPD    539
SrCPR1  AVAPRLQPRYYSISSSPKMSPNRIHVTCALVYETTPAGRIHRGLCSTWMKNAVPLTESPD    540
        :**********.******. *:***********:.******:*:**********:***

SrCPR2  CSWAPIFVRTSNFRLPIDPKVPVIMIGPGTGLAPFRGFLQERLALKESGTELGSSILFFG    599
SrCPR3  CSWAPIYVRTSNFRLPSDPKVPVIMIGPGTGLAPFRGFLQERLALKEAGTDLGLSILFFG    597
SrCPR   CSQASIFVRTSNFRLPVDPKVPVIMIGPGTGLAPFRGFLQERLALKESGTELGSSIFFFG    599
SrCPR1  CSQASIFVRTSNFRLPVDPKVPVIMIGPGTGLAPFRGFLQERLALKESGTELGSSIFFFG    600
        ** *.*:********* *****************************:**:**.**:***

SrCPR2  CRNRKVDYIYENELNNFVENGALSELDVAFSRDGPTKEYVQHKMTQKASEIWNMLSEGAY   659
SrCPR3  CRNRKVDFIYENELNNFVETGALSELIVAFSREGPTKEYVQHKMSEKASDIWNLLSEGAY   657
SrCPR   CRNRKVDFIYEDELNNFVETGALSELIVAFSREGTAKEYVQHKMSQKASDIWKLLSEGAY   659
SrCPR1  CRNRKVDFIYEDELNNFVETGALSELIVAFSREGTAKEYVQHKMSQKASDIWKLLSEGAY   660
        *******:***:*******.******:*****:*..*********::***:**::******

SrCPR2  LYVCGDAKGMAKDVHRTLHTIVQEQGSLDSSKAELYVKNLQMSGRYLRDVW   710
SrCPR3  LYVCGDAKGMAKDVHRTLHTIVQEQGSLDSSKAELYVKNLQMSGRYLRDVW   708
SrCPR   LYVCGDAKGMAKDVHRTLHTIVQEQGSLDSSKAELYVKNLQMSGRYLRDVW   710
SrCPR1  LYVCGDAKGMAKDVHRTLHTIVQEQGSLDSSKAELYVKNLQMSGRYLRDVW   711
        ***************************************************
```

FIG. 6C
(Cont'd)

```
ATR2     MASSSSSSSTSMIDLMAAIIKGEPVIVSDPANASAYESVAAELSSMLIENRQFAMIVTTS  60
AtCPR2   MASSSSSSSTSMIDLMAAIIKGEPVIVSDPANASAYESVAAELSSMLIENRQFAMIVTTS  60
PgCPR    MAQSSSGS-MSPFDFMTAIIKG----KMEPSNAS--LGAAGEVTAMILDNRELVMLTTS   53
AaCPR    MAQSTTSVKLSPFDLMTALLNGKVS-FDTSNTSDTN----IP-LAVFMENRELLMILTTS  54
SrCPR3   MAQSN-SVKISPLDLVTALFSGKV--LDTSNASESGESAMLPTIAMIMENRELLMILTTS  57
SrCPR    MAQSD-SVKVSPFDLVSAAMNGKA--MEKLNASESEDPTTLPALKMLVENRELLTLFTTS  57
SrCPR2   MAQSE-SVEASTIDLMTAVLKDTV---IDTANASDNGDSKMPPALAMMFEIRDLLLILTTS 57
AtCPR1   MATSALYASDLFKQLKSIMGTDS-------------------------LSDDVVLVIATTS 36
         ** *            ::  :    ..                       ..    .  : ***

ATR2     IAVLIGCIVMLVWRRSGSGNSKRVEPLKP--LVIKPR----EEEIDDGRKKVTIFFGTQTG 115
AtCPR2   IAVLIGCIVMLVWRRSGSGNSKRVEPLKP--LVIKPR----EEEIDDGRKKVTIFFGTQTG 115
PgCPR    IAVLIGCVVVFIWRRSSSQTPTAVQPLKP--LLAKET---ESEVDDGKQKVTIFFGTQTG 108
AaCPR    VAVLIGCVVVLVWRRSSSAAKKAAESP------VIVVPKKVTEDEVDDGRKKVTVFFGTQTG 110
SrCPR3   VAVLIGCVVVLVWRRSS-TKKSALEPP----VIVVPKRVQEEEVDDGKKKVTVFFGTQTG 112
SrCPR    FAVLIGCLVFLMWRPSS-SKKLVQDPVPQ--VIVVKKKEKESEVDDGKKKVSIFYGTQTG 114
SrCPR2   VAVLVGCFVVLVWKRSS-GKKSGKELEPP--KIVVPKRRLEQEVDDGRKKVTIFFGTQTG 114
AtCPR1   LALVAG-FVVLLWKKTEADRSGELKPLMIPKSLMAKDEDDDLDLGSGKTRVSIFFGTQTG  95
         .*::  *  .*.:*:::                      :   ::..*: :*:**:*****

ATR2     TAEGFAKALGEEAKARYEKTRFKIVDLDDYAADDDEYEEKLKKEDVAFFFLATYGDGEPT 175
AtCPR2   TAEGFAKALGEEAKARYEKTRFKIVDLDDYAADDDEYEEKLKKEDVAFFFLATYGDGEPT 175
PgCPR    TAEGFAKALADEAKARYDKVTFKVVDLDDYAADDEEYEEKLKKETLAFFFLATYGDGEPT 168
AaCPR    TAEGFAKALVEEAKARYEKAVFKVIDLDDYAAEDDEYEEKLKKESLAFFFLATYGDGEPT 170
SrCPR3   TAEGFAKALVEEAKARYEKAVFKVIDLDDYAADDDEYEEKLKKESLAFFFLATYGDGEPT 172
SrCPR    TAEGFAKALVEEAKVRYEKTSFKVIDLDDYAADDDEYEEKLKKESLAFFFLATYGDGEPT 174
SrCPR2   TAEGFAKALFEEAKARYEKAAFKVIDLDDYAADLDEYAEKLKKETYAFFFLATYGDGEPT 174
AtCPR1   TAEGFAKALSEEIKARYEKAAVKVIDLDDYAADDDQYEEKLKKETLAFFCVATYGDGEPT 155
         ********* :*  *.**:*.  .*::*******:  ::*  ******    *** :*********

ATR2     DNAARFYKWFTEGNDRGEWLKNLKYGVFGLGNRQYEHFNKVAKVVDDILVEQGAQRLVQV 235
AtCPR2   DNAARFYKWFTEGNDRGEWLKNLKYGVFGLGNRQYEHFNKVAKVVDDILVEQGAQRLVQV 235
PgCPR    DNAARFYKWFLEGKEPGEWLQNLKFGVFGLGNRQYEHFNKIAIVVDEILAEQGGKRLISV 228
AaCPR    DNAARFYKWFTEGEEKGEWLDKLQYAVFGLGNRQYEHFNKIAKVVDEKLVEQGAKRLVPV 230
SrCPR3   DNAARFYKWFTEGDAKGEWLNKLQYGVFGLGNRQYEHFNKIAKVVDDGLVEQGAKRLVPV 232
SrCPR    DNAANFYKWFTEGDDKGELLKKLQYGVFGLGNRQYEHFNKIAIVVDDKLTEMGAKPLVPV 234
SrCPR2   DNAAKFYKWFTEGDEKGVWLQKLQYGVFGLGNRQYEHFNKIGIVVDDGLTEQGAKRIVPV 234
AtCPR1   DNAARFYKWFTEENERDIKLQQLAYGVFALGNRQYEHFNKIGIVLDEELCKKGAKRLIEV 215
         ****.***** *  .. ::.  *.:* :.**.***********:.  *:*: * : *.:*:: *

ATR2     GLGDDDQCIEDDFTAWREALWPELDTILREEGDTAVATPYTAAVLEYRVSIHDSE--DAK 293
AtCPR2   GLGDDDQCIEDDFTAWREALWPELDTILREEGDTAVATPYTAAVLEYRVSIHDSE--DAK 293
PgCPR    GLGDDDQCIEDDFTAWRESLWPELDQLLRDEDDTTVSTPYTAAVLEYRVFHDPA--DAP 286
AaCPR    GMGDDDQCIEDDFTAWKELVWPELDQLLRDEDDTSVATPYTAAVAEYRVVHDKP--ETY 288
SrCPR3   GLGDDDQCIEDDFTAWKELVWPELDQLLRDEDDTTVATPYTAAVAEYRVVHEKP--DAL 290
SrCPR    GLGDDDQCIEDDFTAWKELVWPELDQLLRDEDDTSVTTPYTAAVLEYRVVYHDKPA-DSY 293
SrCPR2   GLGDDDQSIEDDFSAWKELVWPELDLLLRDEDDKAAATPYTAAIPEYRVVFHDKP--DAF 292
AtCPR1   GLGDDDQSIEDDFNAWKESLWSELDKLLKDEDDKSVATPYTAVIPEYRVTHDPRFTTQK 275
         *:*****.*****.**:* *.:**  :: *.*.::*******.:  ****  *:

ATR2     FNDITLANGNGYTVFDAQHPYKANVAVKRELHTPESDRSCIHLEFDIAGSGLTMKLGDHV 353
AtCPR2   FNDINMANGNGYTVFDAQHPYKANVAVKRELHTPESDRSCIHLEFDIAGSGLTYETGDHV 353
PgCPR    TLEKSYSNANGHSVVDAQHPLKANVAVRRELHTPASDRSCTHLEFDISGTGIAYETGDRV 346
AaCPR    DQDQ-LTN---GHAVHDAQHPCRSNVAVKKELHSPLSDRSCTHLEFDISNTGLSYETGDHV 345
SrCPR3   SEDYSYTN--GHAVHDAQHPCRSNVAVKKELHSPESDRSCTHLEFDISNTGLSYETGDHV 348
SrCPR    AEDQTHTN--GHVVHDAQHPSRSNVAFKKELHTSQSDRSCTHLEFDISHTGLSYETGDHV 351
SrCPR2   SDDRTQTN--GHAVHDAQHPCRSNVAVKKELHTPESDRSCTHLEFDISHTGLSYETGDHV 350
AtCPR1   SMESNVAN--GNTTIDIHHPCRVDVAVQKELHTHESDRSCIHLEFDISRTGITYETGDHV 333
         :    : *    *  .:*   :**  : :**:.:***  ***** *****:  *:;: ***
```

FIG. 6D

```
ATR2     GVLCDNLSETVDEALRLLDMSPDTYFSLHAEKEDGTPIS-SSLPPPFP--PCNLRTALTRY  411
AtCPR2   GVLCDNLSETVDEALRLLDMSPDTYFSLHAEKEDGTPIS-SSLPPPFP--PCNLRTALTRY  411
PgCPR    GVYCENLAETVEEALELLGLSPDTYFSVHADKEDGTPLSGSSLPPPFP--PCTLRTALTLR  405
AaCPR    GVYVENLSEVVDEAEKLIGLPPHTYFSVHADNEDGTPLGGASLPPPFP--PCTLRKALASY  404
SrCPR3   GVYCENLSEVVNDAERLVGLPPDTYFSIHTDSEDGSPLGGASLPPPFP--PCTLRKALTCY  407
SrCPR    GVYSENLSEVVDEALKLLGLSPDTYFSVHADKEDGTPIGGASLPPPFP--PCTLRDALTRY  410
SrCPR2   GVYCENLIEVVEEAGKLLGLSTDTYFSLHIDNEDGSPLGGPSLQPPFP--PCTLRKALTNY  409
AtCPR1   GVYAENHVEIVEEAGKLLGHSLDLVFSIHADKEDGSPLE-SAVPPPFPGPCTLGTGLARY   392
         **  :*   * *:;*  . *:.  . .  **:*  :***:*:    .:: **** **.*  .*; :

ATR2     ACLLSSPKKSALVALAAHASDPTEAERLKHLASPAGKDEYSKWVVESQRSLLEVMAEFPS  471
AtCPR2   ACLLSSPKKSALVALAAHASDPTEAERLKHLASPAGKDEYSKWVVESQRSLLEVMAEFPS  471
PgCPR    ADLLSSPKKSALLALAAHASDPTEADRLRHLASPAGKDEYAQWIVASQRSLLEVMAEFPS  465
AaCPR    ADVLSSPKKSALLALAAHATDSTEADRLKFLASPAGKDEYAQWIVASHRSLLEVMEAFPS  464
SrCPR3   ADVLSSPKKSALLALAAHATDSPEADRLKFLASPAGKDEYAQWIVASQRSLLEVMEAFPS  467
SrCPR    ADVLSSPKKVALLALAAHASDPSEADRLKFLASPAGKDEYAQWIVANQRSLLEVMQSFPS  470
SrCPR2   ADLLSSPKKSTLLALAAHASDPTEADRLRFLASREGKDEYAEWVVANQRSLLEVMEAFPS  469
AtCPR1   ADLLNPPPKSALVALAAYATEPSEAEKLKHLTSPDGKDEYSQWIVASQRSLLEVMAAFPS  452
         * : *..:** :*;****:*;;.:**;;;*;*     ***** **;*   .;******* ***

ATR2     AKPPLGVFFAGVAPRLQPRFYSISSSPKIAETRIHVTCALVYEKMPTGRIHKGVCSTWMK  531
AtCPR2   AKPPLGVFFAGVAPRLQPRFYSISSSPKIAETRIHVTCALVYEKMPTGRIHKGVCSTWMK  531
PgCPR    AKPPLGVFFASVAPRLQPRYYSISSSPRIAPSRIHVTCALVYEKTPTGRVHKGVCSTWMK  525
AaCPR    AKPPLGVFFASVAPRLQPRYYSISSSPRFAPNRIHVTCALVYEQTPSGRVHKGVCSTWMK  524
SrCPR3   AKPSLGVFFASVAPRLQPRYYSISSSPKMAPDRIHVTCALVYEKTPAGRIHKGVCSTWMK  527
SrCPR    AKPPLGVFFAAVAPRLQPRYYSISSSPKMSPNRIHVTCALVYETTPAGRIHRGLCSTWMK  530
SrCPR2   ARPPLGVFFAAVAPRLQPRYYSISSSPKMEPNRIHVTCALVYEKTPAGRIHKGICSTWMK  529
AtCPR1   AKPPLGVFFAAIAPRLQPRYYSISSSPRLAPSRVHVTSALVYGPTPTGRIHKGVCSTWMK  512
         *;*.******.;*******;*******;:   *;***.****   *;**;*;*;******

ATR2     NAVPYEKSEKLFLGRPIFVRQSNFKLPSDSKVPIIMIGPGTGLAPFRGFLQERLALVESG  591
AtCPR2   NAVPYEKSENCSS-APIFVRQSNFKLPSDSKVPIIMIGPGTGLAPFRGFLQERLALVESG  590
PgCPR    NSVPSEKSDECSW-APIFVRQSNFKLPADAKVPIIMIGPGTGLAPFRGFLQERLALKEAG  584
AaCPR    NAVPMTESQDCSW-APIYVRTSNFRLPSDPKVPVIMIGPGTGLAPFRGFLQERLAQKEAG  583
SrCPR3   NAVPMTESQDCSW-APIYVRTSNFRLPSDPKVPVIMIGPGTGLAPFRGFLQERLALKEAG  586
SrCPR    NAVPLTESPDCSQ-ASIFVRTSNFRLPVDPKVPVIMIGPGTGLAPFRGFLQERLALKESG  589
SrCPR2   NAVPLTESQDCSW-APIFVRTSNFRLPIDPKVPVIMIGPGTGLAPFRGFLQERLALKESG  588
AtCPR1   NAVPAEKSHECSG-APIFIRASNFKLPSNPSTPIVMVGPGTGLAPFRGFLQERMALKEDG  571
         *;**   :*  .       .*::*  ***:**  ...*::*;*****************;* * *

ATR2     VELGPSVLFFGCRNRRMDFIYEEELQRFVESGALAELSVAFSREGPTKEYVQHKMMDKAS  651
AtCPR2   VELGPSVLFFGCRNRRMDFIYEEELQRFVESGALAELSVAFSREGPTKEYVQHKMMDKAS  650
PgCPR    TELGPILFFGCRPNSKMDYIYEDELDNFVQNGALSELVLAFSREGPTKEYVQHKMMEKAS  644
AaCPR    TELGTAILFFGCRNRKVDFIYENELNNFVETGALSELVTAFSREGATKEYVQHKMTQKAS  643
SrCPR3   TDLGLSILFFGCRNRKVDFIYENELNNFVETGALSELIVAFSREGPTKEYVQHKMSEKAS  646
SrCPR    TELGSSIFFFGCRNRKVDFIYEDELNNFVETGALSELIVAFSREGTAKEYVQHKMSQKAS  649
SrCPR2   TELGSSILFFGCRNRKVDYIYENELNNFVENGALSELDVAFSRDGPTKEYVQHKMTQKAS  648
AtCPR1   EELGSSLLFFGCRNRQMDFIYEDELNNFVDQGVISELIMAFSREGAQKEYVQHKMMEKAA  631
         :**   :::;******  :;:;***;**;.**; *.::;** ****;*. *******  ;**;

ATR2     DIWNMISQGAYLYVCGDAKGMARDVHRSLHTIAQEQGSMDSTKAEGFVKNLQTSGRYLRDVW  713
AtCPR2   DIWNMISQGAYLYVCGDAKGMARDVHRSLHTIAQEQGSMDSTKAEGFVKNLQTSGRYLRDVW  712
PgCPR    DIWNLISQGAYLYVCGDAKGMARDVHRTLHTIAQEQGSLDSSKAESMVKNLQMSGRYLRDVW  706
AaCPR    DIWNLLSEGAYLYVCGDAKGMAKDVHRTLHTIVQEQGSLDSSKAELYVKNLQMAGRYLRDVW  705
SrCPR3   DIWNLLSEGAYLYVCGDAKGMAKDVHRTLHTIVQEQGSLDSSKAELYVKNLQMSGRYLRDVW  708
SrCPR    DIWKLLSEGAYLYVCGDAKGMAKDVHRTLHTIVQEQGSLDSSKAELYVKNLQMSGRYLRDVW  711
SrCPR2   EIWNMLSEGAYLYVCGDAKGMAKDVHRTLHTIVQEQGSLDSSKAELYVKNLQMSGRYLRDVW  710
AtCPR1   QVWDLIKEEGYLYVCGDAKGMARDVHRTLHTIVQEQEGVSSSEAEAIVKKLQTEGRYLRDVW  693
         ::*.::..: .***********;****;****.***  .;;:;**   **;** *******
```

FIG. 6D (Cont'd)

>ReCDH [Rhodococcus erythropolis]

MARVEGQVALITGAARGQGRSHAIKLAEEGADVILVDVPNDVVDIGYPLGTADELDQTAKDVENLG
RKAIVIHADVRDLESLTAEVDRAVSTLGRLDIVSANAGIASVPFLSHDIPDNTWRQMIDINLTGVW
HTAKVAVPHILAGERGGSIVLTSSAAGLKGYAQISHYSAAKHGVVGLMRSLALELAPHRVRVNSLH
PTQVNTPMIQNEGTYRIFSPDLENPTREDFEIASTTTNALPIPWVESVDVSNALLFLVSEDARYIT
GAAIPVDAGTTLK (SEQ ID NO: 84)

ATGGCCCGTGTGGAAGGTCAAGTGGCTCTGATTACCGGCGCTGCTCGTGGTCAAGGTCGTAGTCAT
GCGATTAAACTGGCGGAAGAAGGCGCGGATGTGATTCTGGTTGACGTCCCGAATGATGTGGTTGAC
ATCGGCTATCCGCTGGGTACGGCAGATGAACTGGACCAGACCGCTAAAGATGTTGAAAACCTGGGT
CGTAAGGCGATTGTCATCCATGCCGATGTGCGCGACCTGGAATCACTGACGGCAGAAGTGGATCGT
GCTGTTAGTACCCTGGGCCGCCTGGACATTGTTTCCGCAAATGCTGGTATCGCCAGCGTCCCGTTT
CTGTCTCACGATATTCCGGACAACACCTGGCGTCAGATGATTGATATCAATCTGACGGGCGTCTGG
CATACCGCGAAAGTGGCCGTTCCGCACATTCTGGCCGGTGAACGCGGCGGTTCCATCGTTCTGACC
AGCTCTGCGGCCGGCCTGAAAGGTTATGCACAAATTAGTCATTACTCCGCAGCTAAGCACGGCGTC
GTGGGTCTGATGCGTTCACTGGCACTGGAACTGGCTCCGCATCGTGTCCGCGTGAACTCGCTGCAC
CCGACGCAGGTGAACACCCCGATGATTCAAAATGAAGGCACGTATCGTATCTTTAGCCCGGATCTG
GAAAACCCGACCCGCGAAGACTTCGAAATTGCGTCTACCACGACCAATGCCCTGCCGATCCCGTGG
GTGGAATCAGTTGATGTCTCGAACGCACTGCTGTTCCTGGTTAGCGAAGACGCACGTTACATTACC
GGTGCAGCAATCCCGGTGGATGCCGGTACGACCCTGAAGTAA (SEQ ID NO: 85)

>CsDH [Citrus sinensis]

MATPPISSLISQRLLGKVALVTGGASGIGEGIVRLFHRHGAKVCFVDVQDELGYRLQESLVGDKDS
NIFYSHCDVTVEDDVRRAVDLTVTKFGTLDIMVNNAGISGTPSSDIRNVDVSEFEKVFDINVKGVF
MGMKYAASVMIPRKQGSIISLGSVGSVIGGIGPHHYISSKHAVVGLTRSIAAELGQHGIRVNCVSP
YAVPTNLAVAHLPEDERTEDMFTGFREFAKKNANLQGVELTVEDVANAVLFLASEDARYISGDNLI
VDGGFTRVNHSFRVFR (SEQ ID NO: 86)

ATGGCAACGCCGCCGATTTCATCCCTGATTTCACAACGCCTGCTGGGTAAAGTCGCCCTGGTCACG
GGTGGTGCTTCTGGTATTGGTGAAGGCATCGTGCGTCTGTTTCACCGTCATGGCGCGAAAGTGTGC
TTTGTTGATGTGCAGGATGAACTGGGCTACCGTCTGCAAGAATCTCTGGTGGGCGACAAAGATTCA
AACATCTTTTATAGCCACTGTGATGTCACCGTGGAAGACGATGTGCGCCGCGCTGTGGATCTGACC
GTGACGAAATTCGGTACGCTGGATATTATGGTCAATAACGCGGGTATTAGTGGCACCCCGTCCAGC
GATATTCGTAATGTTGATGTGAGCGAATTTGAAAAAGTGTTTGATATTAACGTCAAAGGCGTGTTT
ATGGGCATGAAATATGCCGCGAGCGTGATGATCCCGCGCAAACAGGGTAGCATCATCTCCCTGGGT
TCTGTTGGCAGCGTGATCGGTGGCATTGGCCCGCACCATTATATCAGCTCGAAACATGCGGTTGTG
GGCCTGACCCGCAGCATTGCAGCGGAACTGGGTCAGCATGGCATTCGTGTGAACTGTGTGTCTCCG
TATGCGGTTCCGACCAATCTGGCGGTTGCACACCTGCCGGAAGATGAACGTACCGAAGATATGTTT
ACGGGCTTCCGTGAATTTGCGAAAAAGAATGCCAACCTGCAAGGTGTTGAACTGACCGTCGAAGAT
GTGGCCAATGCGGTGCTGTTTCTGGCCAGCGAAGATGCACGCTACATTAGCGGTGATAATCTGATC
GTTGATGGCGGCTTTACCCGTGTGAACCACTCATTTCGTGTTTTCCGTTAA (SEQ ID NO: 87)

*FIG. 22A*

>CsDH1 [Citrus sinensis]

MSKPRLQGKVAIIMGAASGIGEATAKLFAEHGAFVIIADIQDELGNQVVSSIGPEKASYRHCDVRD
EKQVEETVAYAIEKYGSLDIMYSNAGVAGPVGTILDLDMAQFDRTIATNLAGSVMAVKYAARVMVA
NKIRGSIICTTSTASTVGGSGPHAYTISKHGLLGLVRSAASELGKHGIRVNCVSPFGVATPFSAGT
INDVEGFVCKVANLKGIVLKAKHVAEAALFLASDESAYVSGHDLVVDGGFTAVTNVMSMLEGHG
(SEQ ID NO: 88)

ATGTCAAAACCGCGTCTGCAAGGCAAAGTGGCTATTATTATGGGTGCTGCGTCTGGCATCGGTGAA
GCTACGGCTAAACTGTTCGCTGAACATGGCGCATTTGTGATTATCGCTGATATTCAGGACGAACTG
GGCAACCAGGTGGTTAGCTCTATCGGCCCGGAAAAAGCGTCTTATCGTCACTGCGATGTGCGTGAT
GAAAAACAGGTTGAAGAAACCGTCGCGTATGCGATTGAAAAATACGGCAGCCTGGATATTATGTAC
TCCAATGCGGGCGTGGCCGGTCCGGTTGGCACGATTCTGGATCTGGACATGGCCCAATTCGACCGT
ACCATCGCAACGAACCTGGCTGGTAGTGTTATGGCAGTCAAATATGCGGCCCGTGTCATGGTGGCG
AATAAAATTCGCGGTAGCATTATCTGTACCACGAGTACCGCCTCCACGGTGGGCGGCAGCGGCCCG
CACGCCTATACCATTAGCAAACACGGTCTGCTGGGCCTGGTTCGTTCAGCAGCTTCGGAACTGGGT
AAACATGGCATCCGCGTGAACTGCGTTAGCCCGTTTGGTGTTGCGACCCCGTTCTCTGCCGGTACG
ATTAACGATGTCGAAGGCTTTGTCTGTAAAGTGGCGAATCTGAAAGGCATCGTCCTGAAAGCGAAG
CATGTGGCCGAAGCGGCCCTGTTCCTGGCAAGCGATGAATCTGCTTATGTGAGCGGTCACGACCTG
GTGGTGGATGGTGGCTTTACGGCAGTTACGAATGTCATGTCAATGCTGGAAGGTCACGGCTAA
(SEQ ID NO: 89)

>CsDH2 [Citrus sinensis]

MSNPRMEGKVALITGAASGIGEAAVRLFAEHGAFVVAADVQDELGHQVAASVGTDQVCYHHCDVRD
EKQVEETVRYTLEKYGKLDVLFSNAGIMGPLTGILELDLTGFGNTMATNVCGVAATIKHAARAMVD
KNIRGSIICTTSVASSLGGTAPHAYTTSKHALVGLVRTACSELGAYGIRVNCISPFGVATPLSCTA
YNLRPDEVEANSCALANLKGIVLKAKHIAEAALFLASDESAYISGHNLAVDGGFTVVNHSSSSAT
(SEQ ID NO: 90)

ATGTCAAACCCGCGTATGGAAGGCAAAGTCGCACTGATTACGGGCGCAGCATCTGGTATCGGTGAA
GCAGCAGTCCGTCTGTTCGCTGAACATGGTGCGTTTGTCGTGGCGGCAGATGTGCAAGACGAACTG
GGTCATCAGGTGGCGGCATCTGTGGGTACGGACCAGGTGTGCTACCATCACTGCGATGTGCGCGAT
GAAAAACAAGTGGAAGAAACCGTGCGTTATACCCTGGAAAAATACGGCAAACTGGATGTCCTGTTT
TCAAACGCGGGCATCATGGGTCCGCTGACCGGCATTCTGGAACTGGATCTGACCGGCTTCGGTAAC
ACGATGGCAACCAATGTGTGCGGTGTTGCCGCGACCATTAAACACGCGGCACGCGCAATGGTGGAC
AAAAACATTCGCGGTAGCATTATCTGCACCACCAGCGTGGCTTCATCGCTGGGTGGCACCGCGCCG
CACGCATACACCACGAGCAAACACGCACTGGTGGGCCTGGTTCGTACGGCATGTTCGGAACTGGGT
GCGTATGGCATTCGTGTGAACTGTATCAGCCCGTTTGGTGTTGCAACGCCGCTGTCTTGCACGGCC
TATAACCTGCGCCCGGATGAAGTGGAAGCAAACTCATGCGCACTGGCGAACCTGAAAGGTATTGTG
CTGAAAGCGAAACACATTGCGGAAGCAGCGCTGTTCCTGGCGAGCGATGAAAGCGCGTATATTAGC
GGTCATAATCTGGCGGTGGATGGTGGTTTCACGGTGGTTAATCATTCAAGTTCGTCGGCGACGTAA
(SEQ ID NO: 91)

*FIG. 22A (Cont'd)*

>CsDH3 [Citrus sinensis]

MTTAGSRDSPLVAQRLLGKVALVTGGATGIGESIVRLFHKHGAKVCVVDINDDLGQHLCQTLGPTT
RFIHGDVAIEDDVSRAVDFTVANFGTLDIMVNNAGMGGPPCPDIREFPISTFEKVFDINTKGTFIG
MKHAARVMIPSKKGSIVSISSVTSAIGGAGPHAYTASKHAVLGLTKSVAAELGQHGIRVNCVSPYA
ILTNLALAHLHEDERTDDARAGFRAFIGKNANLQGVDLVEDDVANAVLFLASDDARYISGDNLFVD
GGFTCTNHSLRVFR (SEQ ID NO: 92)

ATGACGACGGCTGGTTCGCGTGACAGTCCGCTGGTCGCTCAACGCCTGCTGGGCAAAGTGGCCCTG
GTTACGGGTGGTGCTACCGGCATTGGTGAAAGTATCGTGCGTCTGTTTCATAAACACGGCGCGAAA
GTTTGCGTGGTTGATATTAACGATGACCTGGGCCAGCATCTGTGTCAAACCCTGGGTCCGACCACC
CGTTTCATTCACGGCGATGTTGCAATCGAAGATGATGTGAGCCGTGCGGTTGATTTACCGTCGCC
AACTTCGGTACGCTGGACATTATGGTGAACAATGCCGGTATGGGCGGTCCGCCGTGCCCGGATATT
CGTGAATTTCCGATCTCGACCTTTGAAAAAGTCTTCGACATTAACACCAAAGGCACGTTCATCGGT
ATGAAACATGCGGCCCGCGTGATGATTCCGAGTAAAAAGGTAGTATTGTCAGCATTAGCAGCGTG
ACCAGCGCGATTGGCGGCGCGGGTCCGCACGCCTATACCGCGAGCAAACATGCGGTGCTGGGCCTG
ACGAAATCTGTCGCGGCGGAACTGGGCCAGCACGGTATTCGTGTCAACTGTGTGTCTCCGTACGCC
ATCCTGACCAATCTGGCGCTGGCCCATCTGCACGAAGATGAACGTACGGATGACGCGCGTGCGGGT
TTTCGTGCATTCATTGGTAAAAACGCTAATCTGCAAGGTGTTGATCTGGTCGAAGATGACGTGGCG
AATGCCGTTCTGTTTCTGGCATCAGATGACGCTCGCTATATCTCGGGCGATAACCTGTTCGTGGAT
GGCGGCTTCACCTGTACCAATCACTCCCTGCGTGTGTTCCGTTAA (SEQ ID NO: 93)

>VvDH [Vitis vinifera]

MAATSIDNSPLPSQRLLGKVALVTGGATGIGESIVRLFLKQGAKVCIVDVQDDLGQKLCDTLGGDP
NVSFFHCDVTIEDDVCHAVDFTVTKFGTLDIMVNNAGMAGPPCSDIRNVEVSMFEKVFDVNVKGVF
LGMKHAARIMIPLKKGTIISLCSVSSAIAGVGPHAYTGSKCAVAGLTQSVAAEMGGHGIRVNCISP
YAIATGLALAHLPEDERTEDAMAGFRAFVGKNANLQGVELTVDDVAHAAVFLASDEARYISGLNLM
LDGGFSCTNHSLRVFR (SEQ ID NO: 94)

ATGGCCGCAACGAGCATTGATAATTCTCCGCTGCCGAGTCAACGTCTGCTGGGTAAAGTCGCACTG
GTCACGGGTGGCGCTACGGGTATTGGCGAAAGCATCGTGCGTCTGTTTCTGAAACAGGGTGCTAAA
GTGTGCATTGTGGACGTGCAAGATGACCTGGGCCAGAAACTGTGCGATACCCTGGGTGGCGATCCG
AACGTTAGCTTTTTCCATTGCGATGTGACCATCGAAGATGATGTGTGCCATGCAGTTGATTTTACC
GTCACGAAATTCGGCACCCTGGATATTATGGTGAACAATGCGGGTATGGCAGGTCCGCCGTGCTCG
GACATCCGCAACGTGGAAGTCAGCATGTTTGAAAAAGTGTTTGATGTGAATGTGAAAGGTGTTTTC
CTGGGCATGAAACATGCAGCCCGCATTATGATTCCGCTGAAAAAAGGCACCATTATCAGCCTGTGT
TCAGTTTCCAGCGCTATCGCGGGCGTTGGTCCGCACGCATATACGGGTAGCAAATGCGCAGTGGCG
GGTCTGACGCAATCGGTCGCAGCAGAAATGGGTGGTCATGGCATTCGCGTGAACTGTATCAGCCCG
TATGCAATCGCAACGGGTCTGGCGCTGGCACATCTGCCGGAAGATGAACGCACGGAAGATGCAATG
GCGGGTTTCCGTGCGTTTGTGGGTAAAAATGCGAATCTGCAAGGTGTTGAACTGACCGTGGATGAT
GTGGCGCACGCAGCGGTGTTTCTGGCAAGCGATGAAGCACGTTACATCTCTGGTCTGAATCTGATG
CTGGACGGCGGCTTTTCGTGTACCAACCACTCGCTGCGTGTCTTTCGCTAA (SEQ ID NO: 95)

FIG. 22A (Cont'd)

>VvDH1 [Vitis vinifera]

MSTASSGDVSLLSQRLVGKVALITGGATGIGESIARLFYRHGAKVCIVDIQDNPGQNLCRELGTDD
ACFFHCDVSIEIDVIRAVDFVVNRFGKLDIMVNNAGIADPPCPDIRNTDLSIFEKVFDVNVKGTFQ
CMKHAARVMVPQKKGSIISLTSVASVIGGAGPHAYTGSKHAVLGLTKSVAAELGLHGIRVNCVSPY
AVPTGMPLAHLPESEKTEDAMMGMRAFVGRNANLQGIELTVDDVANSVVFLASDEARYVSGLNLML
DGGFSCVNHSLRVFR (SEQ ID NO: 96)

ATGTCAACGGCTTCCTCGGGTGATGTGTCGCTGCTGTCGCAACGCCTGGTCGGTAAAGTCGCTCTG
ATTACGGGTGGTGCAACGGGCATTGGTGAATCGATTGCGCGTCTGTTTTACCGTCATGGTGCGAAA
GTGTGCATCGTTGACATTCAGGATAATCCGGGTCAAAACCTGTGCCGTGAACTGGGCACCGACGAT
GCGTGCTTCTTTCACTGCGATGTGAGCATTGAAATCGATGTGATTCGTGCTGTTGACTTTGTGGTT
AACCGCTTTGGTAAACTGGACATTATGGTTAATAACGCGGGCATCGCAGATCCGCCGTGCCCGGAT
ATTCGCAACACCGATCTGAGCATTTTTGAAAAAGTGTTCGATGTGAACGTGAAAGGCACCTTTCAG
TGTATGAAACACGCAGCGCGTTATGGTGCCGCAGAAAAAGGTAGCATTATCAGCCTGACCTCG
GTGGCGAGCGTGATTGGTGGCGCGGGTCCGCACGCCTATACGGGTAGCAAACACGCGGTTCTGGGT
CTGACGAAAAGCGTTGCGGCAGAACTGGGTCTGCATGGTATTCGCGTGAACTGTGTGAGTCCGTAT
GCAGTTCCGACGGGTATGCCGCTGGCACATCTGCCGGAATCGGAAAAAACCGAAGATGCGATGATG
GGTATGCGTGCATTTGTGGGTCGTAATGCCAACCTGCAAGGTATTGAACTGACCGTGGACGATGTC
GCAAATAGCGTCGTGTTTCTGGCGTCGGATGAAGCGCGTTATGTTAGCGGTCTGAACCTGATGCTG
GACGGCGGCTTCTCGTGTGTCAACCACTCGCTGCGTGTGTTTCGCTAA (SEQ ID NO: 97)

>CsABA2 [Citrus sinensis]

MSNSNSTDSSPAVQRLVGRVALITGGATGIGESTVRLFHKHGAKVCIADVQDNLGQQVCQSLGGEP
DTFFCHCDVTKEEDVCSAVDLTVEKFGTLDIMVNNAGISGAPCPDIREADLSEFEKVFDINVKGVF
HGMKHAARIMIPQTKGTIISICSVAGAIGGLGPHAYTGSKHAVLGLNKNVAAELGKYGIRVNCVSP
YAVATGLALAHLPEEERTEDAMVGFRNFVARNANMQGTELTANDVANAVLFLASDEARYISGTNLM
VDGGFTSVNHSLRVFR (SEQ ID NO: 98)

ATGTCCAATAGCAACTCTACGGATTCGTCGCCGGCAGTCCAACGCCTGGTCGGTCGTGTCGCCCTG
ATTACGGGTGGTGCAACGGGTATTGGCGAAAGCACGGTGCGCCTGTTTCATAAACATGGCGCGAAA
GTGTGTATTGCCGACGTTCAGGATAACCTGGGTCAGCAAGTGTGTCAGAGTCTGGGTGGCGAACCG
GATACCTTTTTCTGCCATTGTGATGTGACGAAAGAAGAAGATGTGTGTAGCGCAGTTGATCTGACC
GTGGAAAAATTTGGCACCCTGGACATTATGGTGAACAATGCGGGTATTAGCGGCGCACCGTGCCCG
GACATTCGTGAAGCCGATCTGAGCGAATTTGAAAAGTTTTCGACATCAACGTGAAAGGCGTGTTT
CACGGCATGAAACATGCAGCGCGTATTATGATCCCGCAAACCAAAGGCACCATTATCAGCATTTGC
TCCGTGGCTGGTGCGATTGGTGGCCTGGGTCCGCACGCATATACCGGCTCCAAACATGCAGTCCTG
GGCCTGAACAAAAACGTGGCCGCGGAACTGGGCAAATACGGTATCCGTGTGAATTGCGTCAGCCCG
TATGCTGTTGCCACCGGCCTGGCTCTGGCACACCTGCCGGAAGAAGAACGTACCGAAGATGCAATG
GTGGGCTTTCGTAATTTTGTGGCACGCAACGCGAATATGCAAGGCACCGAACTGACGGCGAATGAT
GTGGCAAACGCGGTCCTGTTTCTGGCCTCTGATGAAGCCCGTTATATCAGCGGCACGAATCTGATG
GTGGATGGCGGTTTTACCTCGGTCAATCACTCGCTGCGTGTCTTCCGTTAA (SEQ ID NO: 99)

FIG. 22A (Cont'd)

>BdDH [Brachypodium distachyon]

MSAAAAVSSSSSPRLEGKVALVTGGASGIGEAIVRLFRQHGAKVCIADVQDEAGQQVRDSLGDDAG
TDVLFVHCDVTVEEDVSRAVDAAAEKFGTLDIMVNNAGITGDKVTDIRNLDFAEVRKVFDINVHGM
LLGMKHAARVMIPGKKGSIVSLASVASVMGGMGPHAYTASKHAVVGLTKSVALELGKHGIRVNCVS
PYAVPTALSMPHLPQGEHKGDAVRDFLAFVGGEANLKGVDLLPKDVAQAVLYLASDEARYISALNL
VVDGGFTSVNPNLKAFED (SEQ ID NO: 100)

ATGTCCGCTGCTGCCGCCGTGTCCTCCTCATCGTCGCCGCGTCTGGAAGGCAAAGTCGCTCTGGTT
ACGGGTGGTGCGTCAGGTATCGGCGAAGCCATTGTGCGCCTGTTCCGTCAACATGGTGCCAAAGTG
TGTATCGCGGATGTCCAAGACGAAGCGGGCCAACAGGTCCGTGATAGCCTGGGTGACGATGCCGGT
ACGGATGTGCTGTTTGTGCATTGCGACGTTACCGTGGAAGAAGATGTGTCACGCGCGGTGGATGCC
GCTGCGGAAAAATTCGGCACCCTGGACATTATGGTGAACAACGCAGGTATTACGGGCGACAAAGTG
ACGGACATTCGCAACCTGGATTTCGCTGAAGTCCGTAAAGTGTTCGACATCAATGTGCACGGTATG
CTGCTGGGCATGAAACATGCGGCCCGCGTGATGATTCCGGGTAAAAAGGCTCGATTGTGAGCCTG
GCATCGGTCGCAAGCGTTATGGGTGGTATGGGTCCGCACGCATATACCGCAAGCAAACACGCGGTT
GTGGGTCTGACGAAAGCGTTGCACTGGAACTGGGCAAACATGGTATTCGTGTCAACTGTGTGAGC
CCGTATGCAGTTCCGACCGCACTGTCAATGCCGCACCTGCCGCAGGGCGAACATAAAGGTGATGCG
GTGCGTGATTTCCTGGCGTTTGTTGGCGGTGAAGCGAATCTGAAAGGTGTCGATCTGCTGCCGAAA
GATGTTGCACAGGCGGTTCTGTATCTGGCAAGCGACGAAGCGCGCTATATTTCTGCGCTGAATCTG
GTGGTTGATGGCGGTTTTACGAGCGTGAATCCGAATCTGAAAGCATTTGAAGACTAA (SEQ ID
NO: 101)

>ZzSDR [Zingiber zerumbet]

MRLEGKVALVTGGASGIGESIARLFIEHGAKICIVDVQDELGQQVSQRLGGDPHACYFHCDVTVED
DVRRAVDFTAEKYGTIDIMVNNAGITGDKVIDIRDADFNEFKKVFDINVNGVFLGMKHAARIMIPK
MKGSIVSLASVSSVIAGAGPHGYTGAKHAVVGLTKSVAAELGRHGIRVNCVSPYAVPTRLSMPYLP
ESEMQEDALRGFLTFVRSNANLKGVDLMPNDVAEAVLYLATEESKYVSGLNLVIDGGFSIANHTLQ
VFE (SEQ ID NO: 102)

ATGCGTCTGGAAGGCAAAGTGGCTCTGGTCACGGGCGGTGCGTCGGGTATTGGCGAATCTATTGCT
CGTCTGTTTATTGAACACGGTGCAAAAATTTGCATCGTGGATGTCCAGGATGAACTGGGTCAACAG
GTCTCTCAGCGTCTGGGTGGCGATCCGCACGCCTGTTATTTCCACTGTGATGTGACCGTGGAAGAT
GACGTTCGTCGCGCGGTGGATTTTACGGCGGAAAAATATGGCACCATTGACATTATGGTTAACAAT
GCGGGCATTACGGGCGATAAAGTGATCGATATTCGTGATGCGGATTTCAACGAATTTAAAAAAGTG
TTCGACATTAACGTGAATGGTGTCTTTCTGGGCATGAAACACGCAGCGCGTATTATGATCCCGAAA
ATGAAAGGCTCCATCGTTTCGCTGGCGTCCGTTAGCTCGGTGATTGCTGGTGCAGGTCCGCATGGC
TATACCGGCGCAAAACATGCGGTTGTGGGTCTGACCAAAAGCGTTGCAGCCGAACTGGGTCGTCAT
GGTATTCGCGTGAACTGCGTTTCGCCGTATGCGGTGCCGACGCGCCTGTCAATGCCGTATCTGCCG
GAATCGGAAATGCAGGAAGATGCACTGCGCGGCTTTCTGACCTTTGTGCGTAGCAATGCGAACCTG
AAAGGCGTTGATCTGATGCCGAATGATGTGGCGGAAGCTGTTCTGTATCTGGCGACCGAAGAAAGC
AAATATGTTTCAGGTCTGAATCTGGTTATTGACGGCGGCTTCTCCATCGCTAATCATACCCTGCAA
GTGTTTGAATAA (SEQ ID NO: 103)

FIG. 22A (Cont'd)

```
CsDH3    MTTAGSRDSPIVAQRLLGKVALVTGGATGIGESIVRLFHKHGAKVCVVDIN------------ 51
VvDH     MAATSIDNSPLPSQRLLGKVALVTGGATGIGESIVRLFLKHGAKVCIVDVQ------------ 51
VvDH1    MSTASSGDVSLLSQRLVGKVALITGGATGIGESIARLFYRHGAKVCIVDIQ------------ 51
CsABA2   MSNSNSTDSSPAVQRLVGRVALITGGATGIGESTVRLFHKHGAKVCFVDVQ------------ 51
CsDH     MATPPIS--SLISQRLLGKVALVTGGASGIGEGIVRLFHRHGAKVCFVDVQ------------ 49
BdDH     -MSAAAAVSSSSSPRLEGKVALVTGGASGIGEAIVRLFRQHGAKVCIADVQ------------ 50
ZzSDR    ------------MRLEGKVALVTGGASGIGESIARLFIEHGAKICIVDVQ------------ 38
CsDH1    ---------MSKPRLQGKVAIIMGAASGIGEATAKLFAEHGAFVIIADIQ------------ 41
CsDH2    ---------MSNPRMEGKVALITGAASGIGEAAVRLFAEHGAFVVAADVQ------------ 41
ReCDH    ------MARVEGQVALITGAARGQGRSHAIKLAEEGADVILVDVPNDVVDIGYP 48
                  *::: ****:*  .* ..*. ***..* :..  *    *

CsDH3    -----DDLGQHLCQTLG-----PTTRFIHGDVAIEDDVSRAVDFTVANFGTLDIMVNNAGMG 103
VvDH     -----DDLGQKLCDTLGG----DPNVSFFHCDVTIEDDVCHAVDFTVTKFGTLDIMVNNAGMA 105
VvDH1    -----DNPGQNLCRELG-----TDDACFFHCDVSIEIDVIRAVDFVVNREGKLDIMVNNAGIA 104
CsABA2   -----DNLGQQVCQSLGG----EPDTEFCHCDVTKEEDVCSAVDLTVEKFGTLDIMVNNAGIS 105
CsDH     -----DELGYRLQESLVGDKDSNIFYSHCDVTVEDDVRRAVDLTVTKFGTLDIMVNNAGIS 105
BdDH     -----DEAGQQVRDSLGDDAGTDVLFVHCDVTVEEDVSRAVDAAAEKFGTLDIMVNNAGIT 106
ZzSDR    -----DELGQQVSQRLGGDP---HACYFHCDVTVEDDVRRAVDFTAEKYGTIDIMVNNAGIT 92
CsDH1    -----DELGNQVVSSIGP-----EKASYRHCDVRDEKQVEETVAYAIEKYGSLDIMYSNAGVA 94
CsDH2    -----DELGHQVAASVGT-----DQVCYHHCDVRDEKQVEETVRYTLEKYGKLDVLFSNAGIM 94
ReCDH    LGTADELDQTAKDVENLG-----RKAIVIHADVRDLESLTAEVDRAVSTLGRLDIVSANAGIA 106
             *:        .         *  :  .*       . :  :.: *** :  .**:

CsDH3    GPPCPDIREEFPISTFEKVFDINTKGTEFIGMKHAARVMIPS-KKGSIVSISSVTSAIGGAG 162
VvDH     GPPCCSDIRNVEVSMFEKVFDVNVKGVFLGMKHAARIMIPL-KKGTIISLCSVSSAIAGVG 164
VvDH1    DPPCPDIRNTDLSIFEKVFDVNVKGTFQCMKHAARVMVPQ-KKGSIISLTSVASVIGGAG 163
CsABA2   GAPCPDIREADLSEFEKVFDINVKGVFHGMKHAARIMIPQ-TKGTIISICSVAGAIGGLG 164
CsDH     GTPSSDIRNVDVSEFEKVFDINVKGVFMGMKYAASVMIPR-KQGSIISLGSVGSVIGIGIG 164
BdDH     GDKVTDIRNLDFAEVRKVFDINVHGMLLGMKHAARVMIPG-KKGSIVSLASVASVMGGMG 165
ZzSDR    GDKVIDIRDADFNEFKKVFDINVNGVFLGMKHAARIMIPK-MKGSIVSLASVSSVIAGAG 151
CsDH1    G-PVGTILDLDMAQFDRTIATNLAGSVMAVKYAARVMVANKIRGSTICTTSTASTVGGSG 153
CsDH2    G-PLTGILELDLTGFGNTMATNVCGVAATIKHAARAMVDKNIRGSTICTTSVASSLGGTA 153
ReCDH    SVPFLSH-DIPDNTWRQMIDINLTGVWHTAKVAVPHILAGERGGSIVLTSSAAGLKGYAQ 165
                         :  . :* .      :         *  :.::*..

FIG. 22B
```

```
CsDH3    PHAYTASKHAVLGLTKSVAAELGQHGIRVNCVSPYAILTNLA----LAHLHEDERTDDAR 218
VvDH     PHAYTGSKCAVAGLTQSVAAEMGGHGIRVNCISPYATATGLA----LAHLPEDERTEDAM 220
VvDH1    PHAYTGSKHAVLGLTKSVAAELGLHGIRVNCVSPYAVPTGMP----LAHLPESEKTEDAM 219
CsABA2   PHAYTGSKHAVLGLNKNVAAELGKYGIRVNCVSPYAVATGLA----LAHLPEEERTEDAM 220
CsDH     PHHYISSKHAVVGLTRSIAAELGQHGIRVNCVSPYAVPTNLA----VAHLPEDERTEDMF 220
BdDH     PHAYTASKHAVVGLTKSVALELGKHGIRVNCVSPYAVPTALS----MPHLPQGEHKGDAV 221
ZzSDR    PHGYTGAKHAVVGLTKSVAAELGRHGIRVNCVSPYAVPTRLS----MPYLPESEMQEDAL 207
CsDH1    PHAYTISKHGLLGLVRSAAASELGKHGIRVNCVSPFGVATPFS----AGTIN-------- 200
CsDH2    PHAYTTSKHALVGLVRTACSELGAYGIRVNCISPFGVATPLS----CTAYNLRP------ 203
ReCDH    ISHYSAAKHGVVGLMRSLALELAPHRVRVNSLHPTQVNTPMIQNEGTYRIFSPDLENPTR 225
         *   :  .:  ** . ::**:**.*:       :

CsDH3    AGFRAFIGKNANLQGVDLVEDDVANAVLFLASDDARYISGDNLFVDGGFTCTNHSLRVFR---- 278
VvDH     AGFRAFVGKNANLQGVELTVDDVAHAAVFLASDEARYISGLNLMLDGGFSCTNHSLRVFR---- 280
VvDH1    MGMRAFVGRNANLQGIELTVDDVANSVVFLASDEARYVSGLNLMLDGGFSCVNHSLRVFR---- 279
CsABA2   VGFRNFVARNANMQGTELTANDVANAVLFLASDEARYISGTNLMVDGGFTSVNHSLRVFR---- 280
CsDH     TGFREFAKKNANLQGVELTVEDVANAVLFLASEDARYISGDNLIVDGGFTRVNHSFRVFR---- 280
BdDH     RDFLAFVGGEANLKGVDLLPKDVAQAVLYLASDEARYISALNLVVDGGFTSVNPNLKAFED--- 282
ZzSDR    RGFLTFVRSNANLKGVDLMPNDVAEAVLYLATEESKYVSGLNLVIDGGFSIANHTLQVFE---- 267
CsDH1    -DVEGFVCKVANLKGIVLKGIVLKAKHVAEAALFLASDESAYVSGHDLVVDGGFTAVTNVMSMLEGHG 262
CsDH2    DEVEANSCALANLKGIVLKAKHIAEAALFLASDESAYISGHNLAVDGGFTVVNHSSSSAT--- 263
ReCDH    EDFEIASTTTNALPIPWVESVDVSNALLFLVSEDARYITGAAIPVDAGTTLK---------- 277
                   .:  : ::: . . ::* *    :*         
```

*FIG. 22B (Cont'd)*

```
8rp-t20srKO      ------MALLLAVFAVALAVALIFWYLKSYTSARRSQSNHLPRVPEVPGVPLLGNLLQLKEK
8rp-t20v00       ------MALLLAVFAVALAVALIFWYLKSYTSARRSQSNHLPRVPEVPGVPLLGNLLQLKEK
n22yhcB-t30v00   MAWEYALIGLVVGIIIGAVAMRWYLKSYTSARRSQSNRLPRVPEVPGVPLLGNLLQLKEK
n22yhcB-t30v01   MAWEYALIGLVVGIIIGAVAMRWYLKSYTSARRSQSNRLPRVPEVPGVPLLGNLLQLKEK
n22yhcB-t30v02   MAWEYALIGLVVGIIIGAVAMRWYLKSYTSARRSQSNRLPRVPEVPGVPLLGNLLQLKEK
                       *:.     :  :...::*************:****************

8rp-t20srKO      KPYMTFTRWAATYGPIYSIKTGATSMVVSSNEIAKEALVTRFQSISTRNLSKALKVLTA
8rp-t20v00       KPYMTFTRWAATYGPIYSIKTGATSMVVSSNEIAKEALVTRFQSISTRNLSKALKVLTA
n22yhcB-t30v00   KPYMTFTRWAATYGPIYSIKTGATSMVVSSNEIAKEALVTRFQSISTRNLSKALKVLTA
n22yhcB-t30v01   KPYMTFTRWAATYGPIYSIKTGATSVVVSSNEIAKEALVTRFQSISTRNLSKALKVLTA
n22yhcB-t30v02   KPYMTFTRWAATYGPIYSIKTGATSVVVSSNEIAKEALVTRFQSISTRNLSKALKVLTA
                 *************************:*******************************

8rp-t20srKO      DKTMVAMSDYDDYHKTVKRHILTAVLGPNAQKKHRIHRDIMMDNISTQLHEFVKNNPEQE
8rp-t20v00       DKTMVAMSDYDDYHKTVKRHILTAVLGPNAQKKHRIHRDIMMDNISTQLHEFVKNNPEQE
n22yhcB-t30v00   DKTMVAMSDYDDYHKTVKRHILTAVLGPNAQKKHRIHRDIMMDNISTQLHEFVKNNPEQE
n22yhcB-t30v01   DKTMVAMSDYDDYHKTVKRHILTAVLGPNAQKKHRIHRDIMMDNISTQLHEFVKNNPEQE
n22yhcB-t30v02   DKQMVAMSDYDDYHKTVKRHILTAVLGPNAQKKHRIHRDIMMDNISTQLHEFVKNNPEQE
                 ** *******************************************************

8rp-t20srKO      EVDLRKIFQSELFGLAMRQALGKDVESLYVEDLKITMNRDEIFQVLVVDPMMGAIDVDWR
8rp-t20v00       EVDLRKIFQSELFGLAMRQALGKDVESLYVEDLKITMNRDEIFQVLVVDPMMGAIDVDWR
n22yhcB-t30v00   EVDLRKIFQSELFGLAMRQALGKDVESLYVEDLKITMNRDEIFQVLVVDPMMGAIDVDWR
n22yhcB-t30v01   EVDLRKIFQSELFGLAMRQALGKDVESLYVEDLKITMNRDEILQVLVVDPMMGAIDVDWR
n22yhcB-t30v02   EVDLRKIFQSELFGLAMRQALGKDVESLYVEDLKITMNRDEILQVLVVDPMMGAIDVDWR
                 ******************************************:****************

8rp-t20srKO      DFFPYLKWVPNKKFENTTQQMYIRREAVMKSLIKEHKKRIASGEKLNSYIDYLLSEAQTL
8rp-t20v00       DFFPYLKWVPNKKFENTTQQMYIRREAVMKSLIKEHKKRIASGEKLNSYIDYLLSEAQTL
n22yhcB-t30v00   DFFPYLKWVPNKKFENTTQQMYIRREAVMKSLIKEQKKRIASGEKLNSYIDYLLSEAQTL
n22yhcB-t30v01   DFFPYLKWVPNKKFENTTQQMYIRREAVMKSLIKEQKKRIASGEKLNSYIDYLLSEAQTL
n22yhcB-t30v02   DFFPYLKWVPNKKFENTTQQMYIRREAVMKSLIKEQKKRIASGEKLNSYIDYLLSEAQTL
                 ************************************:**********************

8rp-t20srKO      TDQQLLMSLWEPIIESSDTTMVTTEWAMYELAKNPKLQDRLYRDIKSVCGSEKITEEHLS
8rp-t20v00       TDQQLLMSLWEPIIESSDTTMVTTEWAMYELAKNPKLQDRLYRDIKSVCGSEKITEEHLS
n22yhcB-t30v00   TDQQLLMSLWEPIIESSDTTMVTTEWAMYELAKNPKLQDRLYRDIKSVCGSEKITEEHLS
n22yhcB-t30v01   TDQQLLMSLWEPIIESSDTTMVTTEWAMYELAKNPKLQDRLYRDIKSVCGSEKITEEHLS
n22yhcB-t30v02   TDQQLLMSLWEPIIESSDTTMVTTEWAMYELAKNPKLQDRLYRDIKSVCGSEKITEEHLS
                 ************************************************************
```

FIG. 23A

```
8rp-t20srKO     QLPYITAIFHETLRRHSPVPIIPLRHVHEDTVLGGYHVPAGTELAVNIYGCNMDKNVWEN
8rp-t20v00      QLPYITAIFHETLRRHSPVPIIPLRHVHEDTVLGGYHVPAGTELAVNIYGCNMDKNVWEN
n22yhcB-t30v01  QLPYITAIFHETLRKHSPVPIIPLRHVHEDTQLGGYHVPAGTELAVNIYGCNMDKNVWEN
n22yhcB-t30v02  QLPYITAIFHETLRKHSPVPILPLRHVHEDTVLGGYHVPAGTELAVNIYGCNMDKNVWEN
                ************** :***** :*******  ****************************

8rp-t20srKO     PEEWNPERFMKENETIDFQKTMAFGGGKRVCAGSLQALLTASIGIGRMVQEFEWKLKDMT
8rp-t20v00      PEEWNPERFMKENETIDFQKTMAFGGGKRVCAGSLQALLTASIGIGRMVQEFEWKLKDMT
n22yhcB-t30v01  PEEWNPERFMKENETADFQKTMAFGGGKRVCAGSLQALLTASIGIGRMVQEFEWKLKDMD
n22yhcB-t30v02  PEEWNPERFMKENETIDFQKTMAFGGGKRVCAGSLQALLTASIGIGRMVQEFEWKLKDMT
                *************** ********************************************

8rp-t20srKO     QEEVNTIGLTTQMLRPLRAIIKPRI  (SEQ ID NO: 106)
8rp-t20v00      QEEVNTIGLTNQMLRPLRAIIKPRI  (SEQ ID NO: 107)
n22yhcB-t30v01  QEEVNTIGLTNQMLRPLRAIIKPRI  (SEQ ID NO: 104)
n22yhcB-t30v02  QEEVNTIGLTNQMLRPLRAIIKPRI  (SEQ ID NO: 105)
                ********** *************.
```

*FIG. 23A (Cont'd)*

```
VO2    MDAVTGLLTVPATAITIGGTAVALAVALIFWYLKSYTSARRSQSNHLPRVPEVPGVPLLG
VO1    MDAVTGLLTVPATAITIGGTAVALAVALIFWYLKSYTSARRSQSNRLPRVPEVPGVPLLG
SrKO   MDAVTGLLTVPATAITIGGTAVALAVALIFWYLKSYTSARRSQSNHLPRVPEVPGVPLLG
VOO    MDAVTGLLTVPATAITIGGTAVALAVALIFWYLKSYTSARRSQSNHLPRVPEVPGVPLLG
       ********************************* ************************

VO2    NLLQLKEKKPYMTFTKWAATYGPIYSIKTGATSVVVVSSNEIAKEALVTRFQSISTRNLS
VO1    NLLQLKEKKPYMTFTRWAATYGPIYSIKTGATSVVVVSSNEIAKEALVTRFQSISTRNLS
SrKO   NLLQLKEKKPYMTFTRWAATYGPIYSIKTGATSMVVVSSNEIAKEALVTRFQSISTRNLS
VOO    NLLQLKEKKPYMTFTRWAATYGPIYSIKTGATSMVVVSSNEIAKEALVTRFQSISTRNLS
       *************** **************** ***************************

VO2    KALKVLTADKQMVAMSDYDDYHKTVKRHILTAVLGPNAQKKHRIHRDIMMDNISTQLHEF
VO1    KALKVLTADKTMVAMSDYDDYHKTVKRHILTAVLGPNAQKKHRIHRDIMMDNISTQLHEF
SrKO   KALKVLTADKTMVAMSDYDDYHKTVKRHILTAVLGPNAQKKHRIHRDIMMDNISTQLHEF
VOO    KALKVLTADKTMVAMSDYDDYHKTVKRHILTAVLGPNAQKKHRIHRDIMMDNISTQLHEF
       ********** *************************************************

VO2    VKNNPEQEEVDLRKIFQSELFGLAMRQALGKDVESLYVEDLKITMNRDEILQVLVVDPMM
VO1    VKNNPEQEEVDLRKIFQSELFGLAMRQALGKDVESLYVEDLKITMNRDEILQVLVVDPMM
SrKO   VKNNPEQEEVDLRKIFQSELFGLAMRQALGKDVESLYVEDLKITMNRDEIFQVLVVDPMM
VOO    VKNNPEQEEVDLRKIFQSELFGLAMRQALGKDVESLYVEDLKITMNRDEIFQVLVVDPMM
       ***************************************************:********

VO2    GAIDVDWRDFFPYLKWVPNKKFENTIQQMYIRREAVMKSLIKEQKKRIASGEKLNSYIDY
VO1    GAIDVDWRDFFPYLKWVPNKKFENTIQQMYIRREAVMKSLIKEQKKRIASGEKLNSYIDY
SrKO   GAIDVDWRDFFPYLKWVPNKKFENTIQQMYIRREAVMKSLIKEHKKRIASGEKLNSYIDY
VOO    GAIDVDWRDFFPYLKWVPNKKFENTIQQMYIRREAVMKSLIKEHKKRIASGEKLNSYIDY
       ******************************************* ***************
```

*FIG. 23B*

```
VO2   LLSEAQTLTDQQLLMSLWEPIIESSDTTMVTTEWAMYELAKNPKLQDRLYRDIKSVCGSE
VO1   LLSEAQTLTDQQLLMSLWEPIIESSDTTMVTTEWAMYELAKNPKLQDRLYRDIKSVCGSE
SrKO  LLSEAQTLTDQQLLMSLWEPIIESSDTTMVTTEWAMYELAKNPKLQDRLYRDIKSVCGSE
VO0   LLSEAQTLTDQQLLMSLWEPIIESSDTTMVTTEWAMYELAKNPKLQDRLYRDIKSVCGSE
      ************************************************************

VO2   KITEEHLSQLPYITAIFHETLRKHSPVPIIPLRHVHEDTVLGGYHVPAGTELAVNIYGCN
VO1   KITEEHLSQLPYITAIFHETLRKHSPVPIIPLRHVHEDTVLGGYHVPAGTELAVNIYGCN
SrKO  KITEEHLSQLPYITAIFHETLRRHSPVPIIPLRHVHEDTQLGGYHVPAGTELAVNIYGCN
VO0   KITEEHLSQLPYITAIFHETLRRHSPVPIIPLRHVHEDTVLGGYHVPAGTELAVNIYGCN
      **********************:**************  *********************

VO2   MDKNVWENPEEWNPERFMKENETIDFQKTMAFGGGKRVCAGSLQALLIASIGIGRMVQEF
VO1   MDKNVWENPEEWNPERFMKENETADFQKTMAFGGGKRVCAGSLQALLTASIGIGRMVQEF
SrKO  MDKNVWENPEEWNPERFMKENETIDFQKTMAFGGGKRVCAGSLQALLTASIGIGRMVQEF
VO0   MDKNVWENPEEWNPERFMKENETIDFQKTMAFGGGKRVCAGSLQALLTASIGIGRMVQEF
      ***********************:***********************:************

VO2   EWKLKDMTQEEVNTIGLTNQMLRPLRAIIKPRI  (SEQ ID NO: 111)
VO1   EWKLKDMDQEEVNTIGLTNQMLRPLRAIIKPRI  (SEQ ID NO: 110)
SrKO  EWKLKDMTQEEVNTIGLTTQMLRPLRAIIKPRI  (SEQ ID NO: 108)
VO0   EWKLKDMTQEEVNTIGLTNQMLRPLRAIIKPRI  (SEQ ID NO: 109)
      *******. *********.*************
```

FIG. 23B (Cont'd)

SEQUENCE LISTING

```
<160> NUMBER OF SEQ ID NOS: 132

<210> SEQ ID NO 1
<211> LENGTH: 556
<212> TYPE: PRT
<213> ORGANISM: Vitis vinifera

<400> SEQUENCE: 1

Met Ser Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
```

Tyr Glu Ala Ala His Leu Arg Val His Gly Glu Asp Ile Leu Ala Lys
145                 150                 155                 160

Ala Leu Ala Phe Thr Thr Thr His Leu Lys Ala Met Val Glu Ser Leu
            165                 170                 175

Gly Tyr His Leu Ala Glu Gln Val Ala His Ala Leu Asn Arg Pro Ile
        180                 185                 190

Arg Lys Gly Leu Glu Arg Leu Glu Ala Arg Trp Tyr Ile Ser Val Tyr
    195                 200                 205

Gln Asp Glu Ala Phe His Asp Lys Thr Leu Leu Glu Leu Ala Lys Leu
210                 215                 220

Asp Phe Asn Leu Val Gln Ser Leu His Lys Glu Leu Ser Asn Leu
225                 230                 235                 240

Ala Arg Trp Trp Lys Glu Leu Asp Phe Ala Thr Lys Leu Pro Phe Ala
        245                 250                 255

Arg Asp Arg Leu Val Glu Gly Tyr Phe Trp Met His Gly Val Tyr Phe
    260                 265                 270

Glu Pro Gln Tyr Leu Arg Gly Arg Ile Leu Thr Lys Val Ile Ala
        275                 280                 285

Met Thr Ser Ile Leu Asp Asp Ile His Asp Ala Tyr Gly Thr Pro Glu
290                 295                 300

Glu Leu Lys Leu Phe Ile Glu Ala Ile Glu Arg Trp Asp Ile Asn Ser
305                 310                 315                 320

Ile Asn Gln Leu Pro Glu Tyr Met Lys Leu Cys Tyr Val Ala Leu Leu
        325                 330                 335

Asp Val Tyr Lys Glu Ile Glu Glu Met Glu Lys Glu Gly Asn Gln
    340                 345                 350

Tyr Arg Val His Tyr Ala Lys Glu Val Met Lys Asn Gln Val Arg Ala
355                 360                 365

Tyr Phe Ala Glu Ala Lys Trp Leu His Glu His Val Pro Ala Phe
370                 375                 380

Glu Glu Tyr Met Arg Val Ala Leu Ala Ser Ser Gly Tyr Cys Leu Leu
385                 390                 395                 400

Ala Thr Thr Ser Phe Val Gly Met Gly Glu Ile Ala Thr Lys Glu Ala
        405                 410                 415

Phe Asp Trp Val Thr Ser Asp Pro Lys Ile Met Ser Ser Ser Asn Phe
    420                 425                 430

Ile Thr Arg Leu Met Asp Asp Ile Lys Ser His Lys Phe Glu Gln Lys
        435                 440                 445

Arg Gly His Val Thr Ser Ala Val Glu Cys Tyr Met Lys Gln Tyr Gly
450                 455                 460

Val Ser Glu Glu Gln Val Tyr Ser Glu Phe Gln Lys Gln Ile Glu Asn
465                 470                 475                 480

Ala Trp Leu Asp Ile Asn Gln Glu Cys Leu Lys Pro Thr Ala Val Ser
        485                 490                 495

Met Pro Leu Leu Ala Arg Leu Leu Asn Phe Thr Arg Thr Met Asp Val
    500                 505                 510

Ile Tyr Lys Glu Gln Asp Ser Tyr Thr His Val Gly Lys Val Met Arg
        515                 520                 525

Asp Asn Ile Ala Ser Val Phe Ile Asn Ala Val Ile
530                 535                 540

545                 550                 555

<210> SEQ ID NO 2

<211> LENGTH: 1671
<212> TYPE: DNA
<213> ORGANISM: Vitis vinifera

<400> SEQUENCE: 2

| | | | | | |
|---|---|---|---|---|---|
| atggctacgc | aggtctcagc | ctcgtcactg | gcacaaatcc | cgcagccgaa | aaatcgtccg | 60 |
| gtggcgaact | tccatccgaa | tatctggggt | gaccagttta | tcacgtatac | cccggaagat | 120 |
| aaagtgaccc | gtgcgtgcaa | ggaagaacaa | attgaagacc | tgaaaaagga | agtcaaacgc | 180 |
| aagctgaccg | cagcagcagt | ggcaaacccg | tctcagctgc | tgaattttat | cgatgcggtt | 240 |
| caacgtctgg | gcgtcgccta | tcatttcgaa | caggaaattg | aagaagcact | gcaacatatc | 300 |
| tgcaacagct | ttcacgattg | taatgatatg | gacggcgatc | tgtataacat | tgctctgggt | 360 |
| ttccgtctgc | tgcgccagca | aggctacacg | atttcctgtg | acatctttaa | taaattcacc | 420 |
| gatgaacgtg | gtcgctttaa | ggaagcgctg | atctcagacg | ttcgtggcat | gctgggtctg | 480 |
| tatgaagctg | cgcatctgcg | cgtccacggc | gaagatattc | tggccaaagc | actggctttc | 540 |
| accacgaccc | acctgaaggc | gatggtcgaa | tctctgggtt | accatctggc | agaacaggtg | 600 |
| gcacacgccc | tgaaccgtcc | gatccgcaaa | ggcctggaac | gtctggaagc | gcgctggtat | 660 |
| attagtgtgt | accaggacga | agcatttcat | gataaaaccc | tgctggaact | ggctaagctg | 720 |
| gatttcaacc | tggttcaatc | tctgcacaaa | gaagaactga | gtaatctggc | ccgttggtgg | 780 |
| aaagaactgg | actttgcgac | caagctgccg | ttcgcccgtg | atcgcctggt | tgaaggctat | 840 |
| ttttggatgc | atggtgtcta | tttcgaaccg | cagtacctgc | gcggtcgtcg | cattctgacg | 900 |
| aaagtgatcg | caatgaccctc | gattctggat | gacatccacg | acgcttacgg | cacccccggaa | 960 |
| gaactgaaac | tgtttattga | agcgatcgaa | cgttgggata | ttaacagcat | caatcagctg | 1020 |
| ccggaatata | tgaaactgtg | ctacgtggcc | ctgctggatg | tttacaagga | aatcgaagaa | 1080 |
| gaaatggaaa | aggaaggtaa | ccagtatcgt | gttcattacg | cgaaagaagt | catgaagaat | 1140 |
| caagtgcgcg | cctactttgc | agaagctaaa | tggctgcatg | aagaacacgt | gccggcgttc | 1200 |
| gaagaatata | tgcgcgttgc | gctggccagc | tctggctact | gtctgctggc | cacgacctct | 1260 |
| tttgtgggca | tgggtgaaat | tgcaacgaaa | gaagcgtttg | actgggttac | cagtgatccg | 1320 |
| aagattatga | gttcctcaaa | ctttatcacc | cgtctgatgg | atgacattaa | atcccataag | 1380 |
| ttcgaacaga | aacgcggtca | cgtcacctca | gccgtggaat | gctatatgaa | acagtacggc | 1440 |
| gtttcggaag | aacaagtcta | tagcgaattt | cagaaacaaa | tcgaaaacgc | atggctggat | 1500 |
| attaatcagg | aatgtctgaa | accgacggca | gtctccatgc | cgctgctggc | tcgtctgctg | 1560 |
| aattttacgc | gcacgatgga | tgtgatctat | aaagaacagg | attcgtacac | ccatgtgggc | 1620 |
| aaggttatgc | gcgataacat | tgcaagcgtg | ttcattaatg | ctgttatcta | a | 1671 |

<210> SEQ ID NO 3
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 3

Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu

```
                35                  40                  45
Glu Gln Ile Glu Asp Leu Lys Lys Glu Val Lys Arg Lys Leu Thr Ala
 50                  55                  60
Ala Ala Val Ala Asn Pro Ser Gln Leu Leu Asn Phe Ile Asp Ala Val
 65                  70                  75                  80
Gln Arg Leu Gly Val Ala Tyr His Phe Glu Gln Glu Ile Glu Glu Ala
                 85                  90                  95
Leu Gln His Ile Cys Asn Ser Phe His Asp Cys Asn Asp Met Asp Gly
                100                 105                 110
Asp Leu Tyr Asn Ile Ala Leu Gly Phe Arg Leu Leu Arg Gln Gln Gly
                115                 120                 125
Tyr Thr Ile Ser Cys Asp Ile Phe Asn Lys Phe Thr Asp Glu Arg Gly
                130                 135                 140
Arg Phe Lys Glu Ala Leu Ile Ser Asp Val Arg Gly Met Leu Gly Leu
145                 150                 155                 160
Tyr Glu Ala Ala His Leu Arg Val His Gly Glu Asp Ile Leu Ala Lys
                165                 170                 175
Ala Leu Ala Phe Thr Thr Thr His Leu Lys Ala Met Val Glu Ser Leu
                180                 185                 190
Gly Tyr His Leu Ala Glu Gln Val Ala His Ala Leu Asn Arg Pro Ile
                195                 200                 205
Arg Lys Gly Leu Glu Arg Leu Glu Ala Arg Trp Tyr Ile Ser Val Tyr
210                 215                 220
Gln Asp Glu Ala Phe His Asp Lys Thr Leu Leu Glu Leu Ala Lys Leu
225                 230                 235                 240
Asp Phe Asn Leu Val Gln Ser Leu His Lys Glu Leu Ser Asn Leu
                245                 250                 255
Ala Arg Trp Trp Lys Glu Leu Asp Phe Ala Thr Lys Leu Pro Phe Ala
                260                 265                 270
Arg Asp Arg Leu Val Glu Gly Tyr Phe Trp Met His Gly Val Tyr Phe
                275                 280                 285
Glu Pro Gln Tyr Leu Arg Gly Arg Ile Leu Thr Lys Val Ile Ala
                290                 295                 300
Met Thr Ser Ile Leu Asp Asp Ile His Asp Ala Tyr Gly Ser Pro Glu
305                 310                 315                 320
Glu Leu Lys Leu Phe Ile Glu Ala Ile Glu Lys Trp Asp Glu Ser Ser
                325                 330                 335
Ile Asn Gln Leu Pro Glu Tyr Met Lys Leu Cys Phe Val Ala Leu Ile
                340                 345                 350
Asp Val Tyr Asn Glu Ile Glu Glu Met Glu Lys Glu Gly Asn Gln
                355                 360                 365
Tyr Arg Ile His Tyr Leu Lys Glu Val Met Lys Asn Gln Val Arg Ala
                370                 375                 380
Tyr Phe Ala Glu Ala Lys Trp Leu His Asp Glu His Val Pro Ala Phe
385                 390                 395                 400
Glu Glu Tyr Met Arg Val Ala Leu Ala Ser Ser Gly Tyr Cys Leu Leu
                405                 410                 415
Ala Val Thr Ser Phe Val Gly Met Gly Glu Ile Val Thr Lys Glu Ala
                420                 425                 430
Phe Asp Trp Val Thr Ser Asp Pro Lys Leu Met Ser Ser Ser Asn Phe
                435                 440                 445
Ile Thr Arg Leu Met Asp Asp Ile Lys Ser His Lys Phe Glu Gln Lys
                450                 455                 460
```

```
Arg Gly His Val Thr Ser Ala Val Glu Cys Tyr Met Lys Gln Tyr Gly
465                 470                 475                 480

Val Thr Glu Glu Gln Val Tyr Ser Glu Phe Lys Lys Gln Ile Glu Asn
            485                 490                 495

Ala Trp Leu Asp Ile Asn Gln Glu Cys Leu Lys Pro Thr Ala Val Pro
                500                 505                 510

Met Pro Leu Leu Ala Arg Leu Leu Asn Phe Thr Arg Thr Met Asp Val
            515                 520                 525

Ile Tyr Lys Glu Gln Asp Ser Tyr Thr His Val Gly Lys Val Met Arg
530                 535                 540

Asp Asn Ile Ala Ser Val Phe Ile Asn Pro Val Ile
545                 550                 555
```

<210> SEQ ID NO 4
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 4

```
atggcaaccc aggtgagtgc aagcagcctg gcccaaatcc ctcagccgaa aaaccgcccg      60
gttgcaaact tccaccctaa tatctggggc gatcagttca tcacctatac cccggaagat     120
aaagtgacaa gggcctgcaa agaggagcag atcgaggacc tgaaaaaaga ggtgaagcgc     180
aagctgaccg cagccgcagt ggcaaacccg agccaactgt taaacttcat cgatgccgtg     240
cagcgcctgg gcgttgccta tcacttcgag caggaaatcg aagaagccct acagcacatc     300
tgtaacagct tccacgattg taacgacatg gatggcgact tatacaacat agcattaggt     360
ttccgcttac tgcgtcagca gggctacacc ataagctgcg acatctttaa caagtttacc     420
gacgagcgcg tcgttttaa agaggcgctg attagcgacg ttcgcggcat gttaggtctg     480
tacgaagccg cacatctgcg cgtgcacggc gaagacattc tggcgaaggc gctggcattc     540
acaaccacac acctgaaggc aatggtggaa agtctgggct accacttagc cgagcaggtt     600
gcccatgcac tgaatcgccc gattcgtaag ggcctggaac cctggaagc ccgctggtac     660
atcagtgttt atcaggatga agcctttcat gataagaccc tgctggagct ggcaaagctg     720
gatttcaacc tggttcagag cctgcataag aagagctga gcaacctggc ccgttggtgg     780
aaggagctgg atttcgcaac caagctgccg ttcgccaggg acaggttagt gaaggctac     840
ttctggatgc acgcgtttta cttcgagccg caatacctgc gtggccgccg catcctgacg     900
aaggtgatcg ccatgaccag cattctggac gacatccacg atgcgtacgg gagccctgag     960
gagttaaagc tgttcatcga ggcaatcgag aagtgggatg agagtagcat caaccaactg    1020
ccggagtata tgaaactgtg cttcgtggcc ctgattgatg tttacaatga gattgaagag    1080
gagatggaga agagggggaa ccagtaccgc atccactacc tgaaagaggt gatgaagaat    1140
caggtgcgcg catacttcgc agaggccaaa tggctgcatg atgagcatgt tcctgccttc    1200
gaggagtaca tgcgcgtggc attagccagc agtggttact gtctgttagc cgttacgagc    1260
ttcgtgggta tgggcgagat cgtgaccaaa gaggcattcg actgggtgac gagcgacccg    1320
aagctgatga gcagcagcaa cttcatcacc cgtctgatgg acgacatcaa gagccacaag    1380
ttcgagcaga aacgcggtca cgttaccagc gccgtggagt gctacatgaa gcagtacggc    1440
gtgacagagg agcaagtgta cagcgagttc aagaaacaaa tcgagaacgc ctggctggac    1500
```

```
atcaaccaag agtgcctgaa accgaccgca gtgccgatgc ctctgttagc ccgtctgctg    1560
aatttcacac gcacgatgga cgttatctac aaggagcagg atagctacac ccacgttggt    1620
aaggtgatgc gcgacaacat cgccagtgtg ttcatcaacc cggtgatcta a             1671
```

<210> SEQ ID NO 5
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 5

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
    290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335
```

```
Ile Asn Gln Leu Pro Glu Tyr Met Lys Leu Cys Tyr Val Ala Leu Leu
                340                 345                 350

Asp Val Tyr Asn Glu Ile Glu Glu Met Glu Lys Glu Gly Asn Gln
            355                 360                 365

Tyr Arg Ile His Tyr Leu Lys Glu Val Met Lys Asn Gln Val Arg Ala
370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Met Ser Ser Asn Phe
        435                 440                 445

Ile Thr Arg Leu Met Asp Asp Ile Lys Ser His Lys Phe Glu Gln Lys
            450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Thr Met Arg
            530                 535                 540

Asp Asn Ile Ala Ser Val Phe Ile Asn Pro Val Ile
545                 550                 555

<210> SEQ ID NO 6
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 6
atggcaaccc aggtgagtgc aagcagcctg gcccaaatcc ctcagccgaa aaaccgcccg      60 gttgcaaaact tccaccctaa tatctggggc gatcagttca tcacctatac cccggaagat    120
aaagtgacaa gggcctgcaa agaggagcag atcgaggacc tgaaaaaaga ggtgaagcgc     180
aagctgaccg cagccgcagt ggcaaaccccg agccaactgt taaacttcat cgatgccgtg    240
cagcgcctgg gcgttgccta tcacttcgag caggaaatcg aagaagccct acagcacatc     300
tgtaacagct ccacgattg taacgacatg gatggcgact tatacaacat agcattaggt      360
ttccgcttac tgcgtcagca gggctacacc ataagctgcg acatctttaa caagtttacc     420
gacgagcgcg tcgttttaa agaggcgctg attagcgacg ttcgcggcat gttaggtctg      480
tacgaagccg cacatctgcg cgtgcacggc gaagacattc tggcgaaggc gctggcattc    540
acaaccacac acctgaaggc aatggtggaa agtctgggct accacttagc cgagcaggtt     600
gcccatgcac tgaatcgccc gattcgtaag ggcctggaac gcctggaagc cgctggtac     660 atcagtgttt atcaggatga agcctttcat gataagaccc tgctggagct ggcaaagctg    720
gatttcaacc tggttcagag cctgcataag gaagagctga gcaacctggc ccgttggtgg    780
aaggagctgg atttcgcaac caagctgccg ttcgccaggg acaggttagt tgaaggctac    840
```

-continued

```
ttctggatgc acggcgttta cttcgagccg caatacctgc gtggccgccg catcctgacg      900
aaggtgatcg ccctgaccag cattctggac gacatccacg atgcgtacgg accccctgag      960
gagttaaagc tgttcatcga ggcaatcgag aagtgggatg agagtagcat caaccaactg     1020
ccggagtata tgaaactgtg ctatgtggcc ctgctggatg tttacaatga gattgaagag     1080
gagatggaga agagggggaa ccagtaccgc atccactacc tgaaagaggt gatgaagaat     1140
caggtgcgcg catacttcgc agaggccaaa tggctgcatg atgagcatgt tcctgccttc     1200
gaggagtaca tgcgcgtggc attagccagc agtggttact gtctgttagc cgttacgagc     1260
ttcgtgggta tgggcgagat cgtgaccaaa gaggcattcg actgggtgac gagcgacccg     1320
cgtattatga gcagcagcaa cttcatcacc cgtctgatgg acgacatcaa gagccacaag     1380
ttcgagcaga aacgcggtca cgttaccagc gccgtggagt gctacatgaa gcagtacgca     1440
gtgacagagg agcaagtgta cagcgagttc aagaaacaaa tcgagaacgc ctggctggac     1500
atcaaccaag agtgcctgaa accgaccgca gtgccgatgc ctctgttagc ccgtctgctg     1560
aatttcacac gcacgatgga cgttatctac aaggagcagg atagctacac ccacgttggt     1620
aagaccatgc gcgacaacat cgccagtgtg ttcatcaacc cggtgatcta a              1671
```

<210> SEQ ID NO 7
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 7

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Ile Glu Glu Ala
            85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
```

```
                210                 215                 220
Gln Asp Glu Ala Phe His Asp Lys Thr Leu Leu Glu Leu Ala Lys Leu
225                 230                 235                 240

Asp Phe Asn Leu Val Gln Ser Leu His Lys Glu Leu Ser Asn Leu
                245                 250                 255

Ala Arg Trp Trp Lys Glu Leu Asp Phe Ala Thr Lys Leu Pro Phe Ala
                260                 265                 270

Arg Asp Arg Leu Val Glu Gly Tyr Phe Trp Met Met Gly Val Tyr Phe
                275                 280                 285

Glu Pro Gln Tyr Leu Arg Gly Arg Ile Leu Thr Lys Val Ile Ala
                290                 295                 300

Met Thr Ser Ile Leu Asp Asp Ile His Asp Ala Tyr Gly Ser Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Phe Val Ala Leu Ile
                340                 345                 350

Asp Val Tyr Asn Glu Ile Glu Glu Met Glu Lys Glu Gly Asn Gln
                355                 360                 365

Tyr Arg Ile His Tyr Leu Lys Glu Val Met Lys Asn Gln Val Arg Ala
                370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
                420                 425                 430

Phe Asp Trp Val Thr Ser Asp Pro Lys Leu Met Ser Ser Ser Asn Thr
                435                 440                 445

Ile Thr Arg Leu Met Asp Asp Ile Lys Ser His Lys Phe Glu Gln Lys
450                 455                 460

Arg Gly His Val Thr Ser Ala Val Glu Cys Tyr Met Lys Gln Tyr Gly
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Gly Cys Leu Lys Pro Thr Ala Val Pro
                500                 505                 510

Met Pro Leu Leu Ala Arg Leu Leu Asn Phe Thr Arg Thr Met Asp Val
                515                 520                 525

Ile Tyr Lys Glu Glu Asp Ser Tyr Thr His Val Gly Lys Val Met Arg
530                 535                 540

Asp Asn Ile Ala Ser Val Phe Ile Asn Pro Val Ile
545                 550                 555

<210> SEQ ID NO 8
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 8
atggcaaccc aggtgagtgc aagcagcctg gcccaaatcc ctcagccgaa aaaccgcccg      60
gttgcaaact tccaccctaa tatctggggc gatcagttca tcacctatac cccggaagat     120
```

-continued

| | |
|---|---|
| aaagtgacaa gggccaaaaa agaggagcag atcgaggacc tgaaaaaaga ggtgaagcgc | 180 |
| aagctgaccg cagccgcagt ggcaaacccg agccaactgt taaacttcat cgatgccgtg | 240 |
| cagcgcctgg gcgttgccta tcacttcgag caggaaatcg aagaagccct acagcacatc | 300 |
| tgtaacagct tccacgattg taacgacatg gatggcgact atacaacat agcattaggt | 360 |
| ttccgcttac tgcgtcagca gggctacacc ataagctgcg acatctttaa caagtttacc | 420 |
| gacgagcgcg tcgttttaa agaggcgctg attagcgacg ttcgcggcat gttaggtctg | 480 |
| tacgaagccg cacatctgcg cgtgcacggc gaagacattc tggcgaaggc gctggcattc | 540 |
| acaaccacac acctgaaggc aatggtggaa agtctgggct accacttagc cgagcaggtt | 600 |
| gcccatgcac tgaatcgccc gattcgtaag ggcctggaac gcctggaagc ccgctggtac | 660 |
| atcagtgttt atcaggatga agcctttcat gataagaccc tgctggagct ggcaaagctg | 720 |
| gatttcaacc tggttcagag cctgcataag gaagagctga gcaacctggc ccgttggtgg | 780 |
| aaggagctgg atttcgcaac caagctgccg ttcgccaggg acaggttagt tgaaggctac | 840 |
| ttctggatga tgggcgttta cttcgagccg caatacctgc gtggccgccg catcctgacg | 900 |
| aaggtgatcg ccatgaccag cattctggac gacatccacg atgcgtacgg gagccctgag | 960 |
| gagttaaagc tgttcatcga ggcaatcgag aagtgggatg agagtagcat caaccaactg | 1020 |
| ccggagtata tgaaactgtg cttcgtggcc ctgattgatg tttacaatga gattgaagag | 1080 |
| gagatggaga agaggggaa ccagtaccgc atccactacc tgaaagaggt gatgaagaat | 1140 |
| caggtgcgcg catacttcgc agaggccaaa tggctgcatg atgagcatgt tcctgccttc | 1200 |
| gaggagtaca tgcgcgtggc attagccagc agtggttact gtctgttagc cgttacgagc | 1260 |
| ttcgtgggta tgggcgagat cgtgaccaaa gaggcattcg actgggtgac gagcgacccg | 1320 |
| aagctgatga cagcagcaa caccatcacc cgtctgatgg acgacatcaa gagccacaag | 1380 |
| ttcgagcaga aacgcggtca cgttaccagc gccgtggagt gctacatgaa gcagtacggc | 1440 |
| gtgacagagg agcaagtgta cagcgagttc aagaaacaaa tcgagaacgc ctggctggac | 1500 |
| atcaaccaag agtgcctgaa accgaccgca gtgccgatgc ctctgttagc ccgtctgctg | 1560 |
| aatttcacac gcacgatgga cgttatctac aaggaggaag atagctacac ccacgttggt | 1620 |
| aaggtgatgc gcgacaacat cgccagtgtg ttcatcaacc cggtgatcta a | 1671 |

<210> SEQ ID NO 9
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 9

Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

```
Leu Gln His Ile Cys Asn Ser Phe His Asp Cys Asn Asp Met Asp Gly
                100                 105                 110

Asp Leu Tyr Asn Ile Ala Leu Gly Phe Arg Leu Leu Arg Gln Gln Gly
                115                 120                 125

Tyr Thr Ile Ser Cys Asp Ile Phe Asn Lys Phe Thr Asp Glu Arg Gly
            130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
                180                 185                 190

Gly Tyr His Leu Ala Glu Gln Val Ala His Ala Leu Asn Arg Pro Ile
                195                 200                 205

Arg Lys Gly Leu Glu Arg Leu Glu Ala Arg Trp Tyr Ile Ser Val Tyr
            210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
                260                 265                 270

Arg Asp Arg Leu Val Glu Gly Tyr Phe Trp Met Met Gly Val Tyr Phe
            275                 280                 285

Glu Pro Gln Tyr Leu Arg Gly Arg Arg Ile Leu Thr Lys Val Ile Ala
                290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Val Ala Leu Leu
            340                 345                 350

Asp Val Tyr Asn Glu Ile Glu Glu Met Glu Lys Glu Gly Asn Gln
                355                 360                 365

Tyr Arg Ile His Tyr Leu Lys Glu Val Met Lys Asn Gln Val Arg Ala
            370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Gly Tyr Cys Leu Leu
                405                 410                 415

Ala Val Thr Ser Phe Val Gly Met Gly Glu Ile Val Thr Lys Glu Ala
                420                 425                 430

Phe Asp Trp Val Thr Ser Asp Pro Arg Ile Met Ser Ser Asn Thr
            435                 440                 445

Ile Thr Arg Leu Met Asp Asp Ile Lys Ser His Lys Phe Glu Gln Lys
            450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
                500                 505                 510
```

Met Pro Leu Leu Ala Arg Leu Leu Asn Phe Thr Arg Thr Met Asp Val
            515                 520                 525

Ile Tyr Lys Glu Glu Asp Ser Tyr Thr His Val Gly Lys Thr Met Arg
    530                 535                 540

Asp Asn Ile Ala Ser Val Phe Ile Asn Pro Val Ile
545                 550                 555

<210> SEQ ID NO 10
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 10

| | | | |
|---|---|---|---|
| atggcaaccc aggtgagtgc aagcagcctg gcccaaatcc ctcagccgaa aaaccgcccg | | | 60 |
| gttgcaaaact tccaccctaa tatctggggc gatcagttca tcacctatac cccggaagat | | | 120 |
| aaagtgacaa gggccaaaaa agaggagcag atcgaggacc tgaaaaaaga ggtgaagcgc | | | 180 |
| aagctgaccg cagccgcagt ggcaaacccg agccaactgt taaacttcat cgatgccgtg | | | 240 |
| cagcgcctgg gcgttgccta tcacttcgag caggaaatcg aagaagccct acagcacatc | | | 300 |
| tgtaacagct ccacgattg taacgacatg gatggcgact tatacaacat agcattaggt | | | 360 |
| ttccgcttac tgcgtcagca gggctacacc ataagctgcg acatctttaa caagtttacc | | | 420 |
| gacgagcgcg gtcgttttaa agaggcgctg attagcgacg ttcgcggcat gttaggtctg | | | 480 |
| tacgaagccg cacatctgcg cgtgcacggc gaagacattc tggcgaaggc gctggcattc | | | 540 |
| acaaccacac acctgaaggc aatggtggaa agtctgggct accacttagc cgagcaggtt | | | 600 |
| gcccatgcac tgaatcgccc gattcgtaag ggcctggaac gcctggaagc ccgctggtac | | | 660 |
| atcagtgttt atcaggatga agccttcat gataagaccc tgctggagct ggcaaagctg | | | 720 |
| gatttcaacc tggttcagag cctgcataag gaagagctga gcaacctggc ccgttggtgg | | | 780 |
| aaggagctgg atttcgcaac caagctgccg ttcgccaggg acaggttagt tgaaggctac | | | 840 |
| ttctggatga tgggcgttta cttcgagccg caataccctgc gtggccgccg catcctgacg | | | 900 |
| aaggtgatcg ccctgaccag cattctggac gacatccacg atgcgtacgg accccctgag | | | 960 |
| gagttaaagc tgttcatcga ggcaatcgag aagtgggatg agagtagcat caaccaactg | | | 1020 |
| ccggagtata tgaaactgtg ctatgtggcc ctgctggatg tttacaatga gattgaagag | | | 1080 |
| gagatggaga aagaggggaa ccagtaccgc atccactacc tgaaagaggt gatgaagaat | | | 1140 |
| caggtgcgcg catacttcgc agaggccaaa tggctgcatg atgagcatgt tcctgccttc | | | 1200 |
| gaggagtaca tgcgcgtggc attagccagc agtggttact gtctgttagc cgttacgagc | | | 1260 |
| ttcgtgggta tgggcgagat cgtgaccaaa gaggcattcg actgggtgac gagcgacccg | | | 1320 |
| cgtattatga gcagcagcaa caccatcacc cgtctgatgg acgacatcaa gagccacaag | | | 1380 |
| ttcgagcaga aacgcggtca cgttaccagc gccgtggagt gctacatgaa gcagtacgca | | | 1440 |
| gtgacagagg agcaagtgta cagcgagttc aagaaacaaa tcgagaacgc ctggctggac | | | 1500 |
| atcaaccaag agtgcctgaa accgaccgca gtgccgatgc ctctgttagc ccgtctgctg | | | 1560 |
| aatttcacac gcacgatgga cgttatctac aaggaggaag atagctacac ccacgttggt | | | 1620 |
| aagaccatgc gcgacaacat cgccagtgtg ttcatcaacc cggtgatcta a | | | 1671 |

<210> SEQ ID NO 11
<211> LENGTH: 556
<212> TYPE: PRT

<213> ORGANISM: Artificial Sequence
<220> FEATURE:
<223> OTHER INFORMATION: Synthetic - Engineered valencene synthase

<400> SEQUENCE: 11

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
        275                 280                 285

Glu Pro Gln Tyr Leu Arg Gly Arg Ile Leu Thr Lys Val Ile Ala
    290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Val Ala Leu Leu
            340                 345                 350

Asp Val Tyr Asn Glu Ile Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
```

```
            385                 390                 395                 400
   Glu Glu Tyr Met Arg Val Ala Leu Ala Ser Ser Gly Tyr Cys Leu Leu
                       405                 410                 415

Ala Val Thr Ser Phe Val Gly Met Gly Glu Ile Val Thr Lys Glu Ala
                       420                 425                 430

Phe Asp Trp Val Thr Ser Asp Pro Arg Ile Met Ser Ser Asn Thr
                   435                 440                 445

Ile Thr Arg Leu Met Asp Asp Ile Lys Ser His Lys Phe Glu Gln Lys
                   450                 455                 460

Arg Gly His Val Thr Ser Ala Val Glu Cys Tyr Met Lys Gln Tyr Ala
   465                 470                 475                 480

Val Thr Glu Glu Gln Val Tyr Ser Glu Phe Lys Lys Gln Ile Glu Asn
                       485                 490                 495

Ala Trp Leu Asp Ile Asn Gln Glu Cys Leu Lys Pro Thr Ala Val Pro
                   500                 505                 510

Met Pro Leu Leu Ala Arg Leu Leu Asn Phe Thr Arg Thr Met Asp Val
                   515                 520                 525

Ile Tyr Lys Glu Glu Asp Ser Tyr Thr His Val Gly Lys Thr Met Arg
                   530                 535                 540

Asp Asn Ile Ala Ser Val Phe Ile Asn Pro Val Ile
   545                 550                 555

<210> SEQ ID NO 12
<211> LENGTH: 548
<212> TYPE: PRT
<213> ORGANISM: Citrus sinensis

<400> SEQUENCE: 12

Met Ala Ser Gly Glu Thr Phe Arg Pro Thr Ala Asp Phe His Pro Ser
   1               5                   10                  15

Leu Trp Arg Asn His Phe Leu Lys Gly Ala Ser Asp Phe Lys Thr Val
                   20                  25                  30

Asp His Thr Ala Thr Gln Glu Arg His Glu Ala Leu Lys Glu Glu Val
                   35                  40                  45

Arg Arg Met Ile Thr Asp Ala Glu Asp Lys Pro Val Gln Lys Leu Arg
       50                  55                  60

Leu Ile Asp Glu Val Gln Arg Leu Gly Val Ala Tyr His Phe Glu Lys
   65                  70                  75                  80

Glu Ile Gly Asp Ala Ile Gln Lys Leu Cys Pro Ile Tyr Ile Asp Ser
                       85                  90                  95

Asn Arg Ala Asp Leu His Thr Val Ser Leu His Phe Arg Leu Leu Arg
                   100                 105                 110

Gln Gln Gly Ile Lys Ile Ser Cys Asp Val Phe Glu Lys Phe Lys Asp
               115                 120                 125

Asp Glu Gly Arg Phe Lys Ser Ser Leu Ile Asn Asp Val Gln Gly Met
           130                 135                 140

Leu Ser Leu Tyr Glu Ala Ala Tyr Met Ala Val Arg Gly Glu His Ile
   145                 150                 155                 160

Leu Asp Glu Ala Ile Ala Phe Thr Thr Thr His Leu Lys Ser Leu Val
                       165                 170                 175

Ala Gln Asp His Val Thr Pro Lys Leu Ala Glu Gln Ile Asn His Ala
                   180                 185                 190

Leu Tyr Arg Pro Leu Arg Lys Thr Leu Pro Arg Leu Glu Ala Arg Tyr
               195                 200                 205
```

Phe Met Ser Met Ile Asn Ser Thr Ser Asp His Leu Cys Asn Lys Thr
    210                 215                 220

Leu Leu Asn Phe Ala Lys Leu Asp Phe Asn Ile Leu Glu Leu His
225                 230                 235                 240

Lys Glu Glu Leu Asn Glu Leu Thr Lys Trp Trp Lys Asp Leu Asp Phe
                    245                 250                 255

Thr Thr Lys Leu Pro Tyr Ala Arg Asp Arg Leu Val Glu Leu Tyr Phe
                260                 265                 270

Trp Asp Leu Gly Thr Tyr Phe Glu Pro Gln Tyr Ala Phe Gly Arg Lys
            275                 280                 285

Ile Met Thr Gln Leu Asn Tyr Ile Leu Ser Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
                340                 345                 350

Met Ala Lys Gln Gly Arg Ser His Cys Val Arg Tyr Ala Lys Glu Glu
            355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
                420                 425                 430

Val Val Lys Ala Ala Ser Val Ile Cys Arg Leu Met Asp Asp Met Gln
            435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
                500                 505                 510

Asn Leu Ala Arg Ala Ile Asp Phe Ile Tyr Lys Glu Asp Asp Gly Tyr
            515                 520                 525

Thr His Ser Tyr Leu Ile Lys Asp Gln Ile Ala Ser Val Leu Gly Asp
    530                 535                 540

His Val Pro Phe
545

<210> SEQ ID NO 13
<211> LENGTH: 513
<212> TYPE: PRT
<213> ORGANISM: Zingiber zerumbet

<400> SEQUENCE: 13

Met Glu Ala Ile Ser Leu Phe Ser Pro Phe Phe Ile Thr Leu Phe
1               5                   10                  15

Leu Gly Phe Phe Ile Thr Leu Leu Ile Lys Arg Ser Ser Arg Ser Ser
                20                  25                  30

```
Val His Lys Gln Gln Val Leu Leu Ala Ser Leu Pro Pro Ser Pro Pro
         35                  40                  45

Arg Leu Pro Leu Ile Gly Asn Ile His Gln Leu Val Gly Gly Asn Pro
     50                  55                  60

His Arg Ile Leu Leu Gln Leu Ala Arg Thr His Gly Pro Leu Ile Cys
 65                  70                  75                  80

Leu Arg Leu Gly Gln Val Asp Gln Val Val Ala Ser Ser Val Glu Ala
                 85                  90                  95

Val Glu Glu Ile Ile Lys Arg His Asp Leu Lys Phe Ala Asp Arg Pro
                100                 105                 110

Arg Asp Leu Thr Phe Ser Arg Ile Phe Phe Tyr Asp Gly Asn Ala Val
            115                 120                 125

Val Met Thr Pro Tyr Gly Gly Glu Trp Lys Gln Met Arg Lys Ile Tyr
        130                 135                 140

Ala Met Glu Leu Leu Asn Ser Arg Arg Val Lys Ser Phe Ala Ala Ile
145                 150                 155                 160

Arg Glu Asp Val Ala Arg Lys Leu Thr Gly Glu Ile Ala His Lys Ala
                165                 170                 175

Phe Ala Gln Thr Pro Val Ile Asn Leu Ser Glu Met Val Met Ser Met
            180                 185                 190

Ile Asn Ala Ile Val Ile Arg Val Ala Phe Gly Asp Lys Cys Lys Gln
        195                 200                 205

Gln Ala Tyr Phe Leu His Leu Val Lys Glu Ala Met Ser Tyr Val Ser
    210                 215                 220

Ser Phe Ser Val Ala Asp Met Tyr Pro Ser Leu Lys Phe Leu Asp Thr
225                 230                 235                 240

Leu Thr Gly Leu Lys Ser Lys Leu Glu Gly Val His Gly Lys Leu Asp
                245                 250                 255

Lys Val Phe Asp Glu Ile Ile Ala Gln Arg Gln Ala Ala Leu Ala Ala
            260                 265                 270

Glu Gln Ala Glu Glu Asp Leu Ile Ile Asp Val Leu Leu Lys Leu Lys
        275                 280                 285

Asp Glu Gly Asn Gln Glu Phe Pro Ile Thr Tyr Thr Ser Val Lys Ala
    290                 295                 300

Ile Val Met Glu Ile Phe Leu Ala Gly Thr Glu Thr Ser Ser Ser Val
305                 310                 315                 320

Ile Asp Trp Val Met Ser Glu Leu Ile Lys Asn Pro Lys Ala Met Glu
                325                 330                 335

Lys Val Gln Lys Glu Met Arg Glu Ala Met Gln Gly Lys Thr Lys Leu
            340                 345                 350

Glu Glu Ser Asp Ile Pro Lys Phe Ser Tyr Leu Asn Leu Val Ile Lys
        355                 360                 365

Glu Thr Leu Arg Leu His Pro Pro Gly Pro Leu Leu Phe Pro Arg Glu
    370                 375                 380

Cys Arg Glu Thr Cys Glu Val Met Gly Tyr Arg Val Pro Ala Gly Ala
385                 390                 395                 400

Arg Leu Leu Ile Asn Ala Phe Ala Leu Ser Arg Asp Glu Lys Tyr Trp
                405                 410                 415

Gly Ser Asp Ala Glu Ser Phe Lys Pro Glu Arg Phe Glu Gly Ile Ser
            420                 425                 430

Val Asp Phe Lys Gly Ser Asn Phe Glu Phe Met Pro Phe Gly Ala Gly
        435                 440                 445
```

```
Arg Arg Ile Cys Pro Gly Met Thr Phe Gly Ile Ser Ser Val Glu Val
    450                 455                 460

Ala Leu Ala His Leu Leu Phe His Phe Asp Trp Gln Leu Pro Gln Gly
465                 470                 475                 480

Met Lys Ile Glu Asp Leu Asp Met Met Glu Val Ser Gly Met Ser Ala
                485                 490                 495

Thr Arg Arg Ser Pro Leu Leu Val Leu Ala Lys Leu Ile Ile Pro Leu
                500                 505                 510

Pro

<210> SEQ ID NO 14
<211> LENGTH: 512
<212> TYPE: PRT
<213> ORGANISM: Zingiber zerumbet

<400> SEQUENCE: 14

Met Ala Leu Leu Leu Ala Val Phe Phe Phe Ile Thr Leu Phe Leu
1               5                   10                  15

Gly Phe Phe Ile Thr Leu Leu Ile Lys Arg Ser Ser Arg Ser Ser Val
                20                  25                  30

His Lys Gln Gln Val Leu Leu Ala Ser Leu Pro Pro Ser Pro Pro Arg
            35                  40                  45

Leu Pro Leu Ile Gly Asn Ile His Gln Leu Val Gly Gly Asn Pro His
    50                  55                  60

Arg Ile Leu Leu Gln Leu Ala Arg Thr His Gly Pro Leu Ile Cys Leu
65                  70                  75                  80

Arg Leu Gly Gln Val Asp Gln Val Val Ala Ser Ser Val Glu Ala Val
                85                  90                  95

Glu Glu Ile Ile Lys Arg His Asp Leu Lys Phe Ala Asp Arg Pro Arg
            100                 105                 110

Asp Leu Thr Phe Ser Arg Ile Phe Phe Tyr Asp Gly Asn Ala Val Val
        115                 120                 125

Met Thr Pro Tyr Gly Gly Glu Trp Lys Gln Met Arg Lys Ile Tyr Ala
    130                 135                 140

Met Glu Leu Leu Asn Ser Arg Arg Val Lys Ser Phe Ala Ala Ile Arg
145                 150                 155                 160

Glu Asp Val Ala Arg Lys Leu Thr Gly Glu Ile Ala His Lys Ala Phe
                165                 170                 175

Ala Gln Thr Pro Val Ile Asn Leu Ser Glu Met Val Met Ser Met Ile
            180                 185                 190

Asn Ala Ile Val Ile Arg Val Ala Phe Gly Asp Lys Cys Lys Gln Gln
        195                 200                 205

Ala Tyr Phe Leu His Leu Val Lys Glu Ala Met Ser Tyr Val Ser Ser
    210                 215                 220

Phe Ser Val Ala Asp Met Tyr Pro Ser Leu Lys Phe Leu Asp Thr Leu
225                 230                 235                 240

Thr Gly Leu Lys Ser Lys Leu Glu Gly Val His Gly Lys Leu Asp Lys
                245                 250                 255

Val Phe Asp Glu Ile Ile Ala Gln Arg Gln Ala Ala Leu Ala Ala Glu
            260                 265                 270

Gln Ala Glu Glu Asp Leu Ile Ile Asp Val Leu Leu Lys Leu Lys Asp
        275                 280                 285

Glu Gly Asn Gln Glu Phe Pro Ile Thr Tyr Thr Ser Val Lys Ala Ile
    290                 295                 300
```

Val Met Glu Ile Phe Leu Ala Gly Thr Glu Ser Ser Val Ile
305             310             315             320

Asp Trp Val Met Ser Glu Leu Ile Lys Asn Pro Lys Ala Met Glu Lys
            325             330             335

Val Gln Lys Glu Met Arg Glu Ala Met Gln Gly Lys Thr Lys Leu Glu
        340             345             350

Glu Ser Asp Ile Pro Lys Phe Ser Tyr Leu Asn Leu Val Ile Lys Glu
    355             360             365

Thr Leu Arg Leu His Pro Pro Gly Pro Leu Leu Phe Pro Arg Glu Cys
370             375             380

Arg Glu Thr Cys Glu Val Met Gly Tyr Arg Val Pro Ala Gly Ala Arg
385             390             395             400

Leu Leu Ile Asn Ala Phe Ala Leu Ser Arg Asp Glu Lys Tyr Trp Gly
            405             410             415

Ser Asp Ala Glu Ser Phe Lys Pro Glu Arg Phe Glu Gly Ile Ser Val
        420             425             430

Asp Phe Lys Gly Ser Asn Phe Glu Phe Met Pro Phe Gly Ala Gly Arg
    435             440             445

Arg Ile Cys Pro Gly Met Thr Phe Gly Ile Ser Ser Val Glu Val Ala
450             455             460

Leu Ala His Leu Leu Phe His Phe Asp Trp Gln Leu Pro Gln Gly Met
465             470             475             480

Lys Ile Glu Asp Leu Asp Met Met Glu Val Ser Gly Met Ser Ala Thr
            485             490             495

Arg Arg Ser Pro Leu Leu Val Leu Ala Lys Leu Ile Ile Pro Leu Pro
        500             505             510

<210> SEQ ID NO 15
<211> LENGTH: 1536
<212> TYPE: DNA
<213> ORGANISM: Zingiber zerumbet

<400> SEQUENCE: 15

| | | |
|---|---|---|
| atggctctgt tattagcagt gttcttcttt tcattacgc tgtttctggg tttctttatt | 60 |
| acgctgctga ttaaacgctc gtcccgtagc tctgtccata acagcaagt gctgctggcc | 120 |
| tctctgccgc cgagtccgcc gcgcctgccg ctgattggca acatccatca actggtgggc | 180 |
| ggcaacccgc atcgtattct gctgcaactg gcgcgtaccc acggcccgct gatctgcctg | 240 |
| cgtctgggtc aggttgatca agtggttgca agttccgtgg aagctgttga agaaattatc | 300 |
| aaacgtcacg acctgaaatt tgcagatcgt ccgcgcgacc tgacctttag ccgtattttc | 360 |
| ttttatgatg gtaacgctgt cgtgatgacg ccgtacggcg tgaatggaa acagatgcgt | 420 |
| aaaatctatg caatggaact gctgaacagc cgtcgtgtga atctttttgc ggccattcgt | 480 |
| gaagacgttg cacgcaaact gaccggcgaa atcgctcaca agcattcgc tcagacgccg | 540 |
| gtcattaacc tgtctgaaat ggtgatgagt atgatcaatg cgattgtcat ccgcgtggcc | 600 |
| tttggtgata atgtaaaca gcaagcatac ttcctgcatc tggtgaaaga agctatgtcc | 660 |
| tatgtttcat cgttttcagt cgcggatatg tacccgtccc tgaaattcct ggacaccctg | 720 |
| acgggcctga aaagcaaact ggaaggcgtt acggtaaac tggataaagt cttcgacgaa | 780 |
| atcatcgcac agcgtcaagc agcgctggcg gcggaacagg ctgaagaaga tctgattatc | 840 |
| gacgtgctgc tgaaactgaa agatgaaggc aaccaggaat ttccgattac ctatacgtca | 900 |
| gttaaagcga ttgtcatgga aatcttcctg gccggcaccg aaaccagcag cagcgtgatt | 960 |

```
gactgggtta tgagtgaact gatcaaaaac ccgaaagcga tggaaaaagt gcagaaagaa  1020
atgcgtgaag ccatgcaagg caaaaccaaa ctggaagaat cggatattcc gaaatttagc  1080
tacctgaatc tggttatcaa agaaaccctg cgtctgcatc cgccgggtcc gctgctgttc  1140
ccgcgtgaat gccgcgaaac ctgcgaagtg atgggctatc gtgttccggc gggtgcccgc  1200
ctgctgatta acgcatttgc tctgtctcgt gatgaaaaat actggggttc cgacgccgaa  1260
tcatttaaac cggaacgctt tgaaggcatc tctgtggatt caaaggtag taattttgaa   1320 tttatgccgt tcggcgcggg ccgtcgtatt tgtccgggca tgacctttgg tatctcctca  1380
gttgaagtcg cgctggccca tctgctgttt cacttcgatt ggcaactgcc gcaaggcatg  1440
aaaattgaag atctggacat gatggaagtc tcgggtatga gcgcaacccg tcgtagcccg  1500
ctgctggttc tggccaaact gattatcccg ctgccg                            1536
```

<210> SEQ ID NO 16
<211> LENGTH: 496
<212> TYPE: PRT
<213> ORGANISM: Barnadesia spinosa

<400> SEQUENCE: 16

```
Met Glu Leu Thr Leu Thr Thr Ser Leu Gly Leu Ala Val Phe Val Phe
1               5                   10                  15

Ile Leu Phe Lys Leu Leu Thr Gly Ser Lys Thr Lys Asn Ser Leu
                20                  25                  30

Pro Glu Ala Trp Arg Leu Pro Ile Ile Gly His Met His His Leu Val
                35                  40                  45

Gly Thr Leu Pro His Arg Gly Val Thr Asp Met Ala Arg Lys Tyr Gly
        50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
                100                 105                 110

Thr Asp Ile Val Leu Ser Pro Tyr Gly Glu Tyr Trp Arg Gln Leu Arg
            115                 120                 125

Lys Leu Cys Thr Leu Glu Leu Leu Ser Ala Lys Lys Val Lys Ser Phe
        130                 135                 140

Gln Ser Leu Arg Glu Glu Glu Cys Trp Asn Leu Val Lys Glu Val Arg
145                 150                 155                 160

Ser Ser Gly Ser Gly Ser Pro Val Asp Leu Ser Glu Ser Ile Phe Lys
                165                 170                 175

Leu Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Leu Thr
        195                 200                 205

Gly Gly Phe Asp Val Ala Asp Ile Phe Pro Ser Lys Lys Ile Leu His
    210                 215                 220

His Leu Ser Gly Lys Arg Ala Lys Leu Thr Asn Ile His Asn Lys Leu
225                 230                 235                 240

Asp Ser Leu Ile Asn Asn Ile Val Ser Glu His Pro Gly Ser Arg Thr
                245                 250                 255

Ser Ser Ser Gln Glu Ser Leu Leu Asp Val Leu Leu Arg Leu Lys Asp
            260                 265                 270
```

```
Ser Ala Glu Leu Pro Leu Thr Ser Asp Asn Val Lys Ala Val Ile Leu
            275                 280                 285

Asp Met Phe Gly Ala Gly Thr Asp Thr Ser Ser Ala Thr Ile Glu Trp
290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
    450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495

<210> SEQ ID NO 17
<211> LENGTH: 496
<212> TYPE: PRT
<213> ORGANISM: Barnadesia spinosa

<400> SEQUENCE: 17

Met Ala Leu Leu Leu Ala Val Phe Leu Gly Leu Ala Val Phe Val Phe
1               5                   10                  15

Ile Leu Phe Lys Leu Leu Thr Gly Ser Lys Ser Thr Lys Asn Ser Leu
            20                  25                  30

Pro Glu Ala Trp Arg Leu Pro Ile Ile Gly His Met His His Leu Val
        35                  40                  45

Gly Thr Leu Pro His Arg Gly Val Thr Asp Met Ala Arg Lys Tyr Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ser Pro Tyr Gly Glu Tyr Trp Arg Gln Leu Arg
        115                 120                 125

Lys Leu Cys Thr Leu Glu Leu Leu Ser Ala Lys Lys Val Lys Ser Phe
    130                 135                 140

Gln Ser Leu Arg Glu Glu Glu Cys Trp Asn Leu Val Lys Glu Val Arg
145                 150                 155                 160
```

Ser Ser Gly Ser Gly Ser Pro Val Asp Leu Ser Glu Ser Ile Phe Lys
            165                 170                 175

Leu Ile Ala Thr Ile Leu Ser Arg Ala Ala Phe Gly Lys Gly Ile Lys
        180                 185                 190

Asp Gln Arg Glu Phe Thr Glu Ile Val Lys Glu Ile Leu Arg Leu Thr
    195                 200                 205

Gly Gly Phe Asp Val Ala Asp Ile Phe Pro Ser Lys Lys Ile Leu His
210                 215                 220

His Leu Ser Gly Lys Arg Ala Lys Leu Thr Asn Ile His Asn Lys Leu
225                 230                 235                 240

Asp Ser Leu Ile Asn Asn Ile Val Ser Glu His Pro Gly Ser Arg Thr
                245                 250                 255

Ser Ser Ser Gln Glu Ser Leu Leu Asp Val Leu Leu Arg Leu Lys Asp
            260                 265                 270

Ser Ala Glu Leu Pro Leu Thr Ser Asp Asn Val Lys Ala Val Ile Leu
        275                 280                 285

Asp Met Phe Gly Ala Gly Thr Asp Thr Ser Ser Ala Thr Ile Glu Trp
    290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
    450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495

<210> SEQ ID NO 18
<211> LENGTH: 1488
<212> TYPE: DNA
<213> ORGANISM: Barnadesia spinosa

<400> SEQUENCE: 18
atggctctgt tattagcagt tttcctgggc ctggctgtct tcgtctttat cctgttcaaa      60
ctgctgaccg gctcaaaatc aaccaaaaat tcactgccgg aagcatggcg tctgccgatc     120
attggccaca tgcatcacct ggttggcacg ctgccgcatc gcggtgtgac cgacatggcg     180
cgtaaatacg gcagcctgat gcatctgcaa ctgggcgaag tgagcaccat tgtcgtctca     240

```
tcgccgcgtt gggcaaaaga agtgctgacg acgtatgata ttacctttgc gaatcgcccg    300
gaaaccctga ccggcgaaat tgttgcgtac cacaacacgg atattgtgct gtcaccgtat    360
ggcgaatact ggcgccaact gcgtaaactg tgcacgctgg aactgctgag cgccaaaaaa    420
gtgaaaagtt ttcagtcgct gcgtgaagaa gaatgctgga atctggtgaa agaagtgcgt    480
tcgagcggct caggttcccc ggtcgatctg tcggaatcca tctttaaact gattgcaacc    540
attctgagcc gcgcagcgtt tggcaaaggt atcaaagatc agcgtgaatt taccgaaatt    600
gtgaaagaaa tcctgcgcct gacgggcggt tttgatgtgg cggatatttt cccgtccaaa    660
aagatcctgc accacctgag cggcaaacgt gcgaaactga ccaacatcca caacaaactg    720
gattccctga ttaataacat tgtttctgaa catccgggtt cgcgtacctc gtcgagccag    780
gaaagcctgc tggatgtgct gctgcgcctg aaagattccg cggaactgcc gctgacctcg    840
gacaatgtta aagccgtgat cctggatatg ttcggtgcgg cacggatac gtcgagcgcc    900 acgattgaat gggcgatcag cgaactgatc cgctgcccgc gtgcaatgga aaaagtgcaa    960
acggaactgc gtcaagcgct gaatggtaaa gaacgcattc aggaagaaga tattcaggaa   1020
ctgtcctatc tgaaactggt cattaaagaa accctgcgcc tgcatccgcc gctgccgctg   1080
gtgatgccgc gtgaatgtcg tgaaccgtgt gtcctggcgg gttacgaaat cccgaccaaa   1140
acgaaactga ttgtgaatgt cttttgccatc aatcgtgacc cggaatactg aaagatgca   1200 gaaaccttca tgccggaacg ctttgaaaac agcccgatta acatcatggg tagtgaatat   1260 gaataccctgc cgtttggcgc aggccgccgt atgtgtccgg tgcagctct gggtctggcg   1320 aatgtggaac tgccgctggc gcacatcctg tattatttta actggaaact gccgaatggc   1380
gctcgcctgg atgaactgga tatgtcggaa tgctttggcg cgacggtcca acgcaaaagc   1440
gaactgctgc tggtcccgac ggcatacaaa acggcaaaca actccgca               1488
```

<210> SEQ ID NO 19
<211> LENGTH: 502
<212> TYPE: PRT
<213> ORGANISM: Hyoscyamus muticus

<400> SEQUENCE: 19

```
Met Gln Phe Phe Ser Leu Val Ser Ile Phe Leu Phe Leu Ser Phe Leu
1               5                   10                  15

Phe Leu Leu Arg Lys Trp Lys Asn Ser Asn Ser Gln Ser Lys Lys Leu
                20                  25                  30

Pro Pro Gly Pro Trp Lys Leu Pro Leu Leu Gly Ser Met Leu His Met
            35                  40                  45

Val Gly Gly Leu Pro His His Val Leu Arg Asp Leu Ala Lys Lys Tyr
        50                  55                  60

Gly Pro Leu Met His Leu Gln Leu Gly Glu Val Ser Ala Val Val Val
65                  70                  75                  80

Thr Ser Pro Asp Met Ala Lys Glu Val Leu Lys Thr His Asp Ile Ala
                85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Val Leu Ser Ala Lys Asn Val Arg Ser
    130                 135                 140

Phe Ser Ser Ile Arg Arg Asp Glu Val Leu Arg Leu Val Asn Phe Val
```

```
            145                 150                 155                 160
Arg Ser Ser Thr Ser Glu Pro Val Asn Phe Thr Glu Arg Leu Phe Leu
                165                 170                 175

Phe Thr Ser Ser Met Thr Cys Arg Ser Ala Phe Gly Lys Val Phe Lys
                180                 185                 190

Glu Gln Glu Thr Phe Ile Gln Leu Ile Lys Glu Val Ile Gly Leu Ala
                195                 200                 205

Gly Gly Phe Asp Val Ala Asp Ile Phe Pro Ser Leu Lys Phe Leu His
    210                 215                 220

Val Leu Thr Gly Met Glu Gly Lys Ile Met Lys Ala His His Lys Val
225                 230                 235                 240

Asp Ala Ile Val Glu Asp Val Ile Asn Glu His Lys Lys Asn Leu Ala
                245                 250                 255

Met Gly Lys Thr Asn Gly Ala Leu Gly Gly Asp Leu Ile Asp Val
                260                 265                 270

Leu Leu Arg Leu Met Asn Asp Gly Gly Leu Gln Phe Pro Ile Thr Asn
                275                 280                 285

Asp Asn Ile Lys Ala Ile Ile Phe Asp Met Phe Ala Ala Gly Thr Glu
    290                 295                 300

Thr Ser Ser Ser Thr Leu Val Trp Ala Met Val Gln Met Met Arg Asn
305                 310                 315                 320

Pro Thr Ile Leu Ala Lys Ala Gln Ala Glu Val Arg Glu Ala Phe Lys
                325                 330                 335

Gly Lys Glu Thr Phe Asp Glu Asn Asp Val Glu Glu Leu Lys Tyr Leu
                340                 345                 350

Lys Leu Val Ile Lys Glu Thr Leu Arg Leu His Pro Pro Val Pro Leu
                355                 360                 365

Leu Val Pro Arg Glu Cys Arg Glu Glu Thr Glu Ile Asn Gly Tyr Thr
    370                 375                 380

Ile Pro Val Lys Thr Lys Val Met Val Asn Val Trp Ala Leu Gly Arg
385                 390                 395                 400

Asp Pro Lys Tyr Trp Asp Asp Ala Asp Asn Phe Lys Pro Glu Arg Phe
                405                 410                 415

Glu Gln Cys Ser Val Asp Phe Ile Gly Asn Asn Phe Glu Tyr Leu Pro
                420                 425                 430

Phe Gly Gly Gly Arg Arg Ile Cys Pro Gly Ile Ser Phe Gly Leu Ala
                435                 440                 445

Asn Val Tyr Leu Pro Leu Ala Gln Leu Leu Tyr His Phe Asp Trp Lys
    450                 455                 460

Leu Pro Thr Gly Met Glu Pro Lys Asp Leu Asp Leu Thr Glu Leu Val
465                 470                 475                 480

Gly Val Thr Ala Ala Arg Lys Ser Asp Leu Met Leu Val Ala Thr Pro
                485                 490                 495

Tyr Gln Pro Ser Arg Glu
                500

<210> SEQ ID NO 20
<211> LENGTH: 508
<212> TYPE: PRT
<213> ORGANISM: Hyoscyamus muticus

<400> SEQUENCE: 20

Met Ala Leu Leu Leu Ala Val Phe Phe Phe Ser Leu Val Ser Ile Phe
1               5                   10                  15
```

```
Leu Phe Leu Ser Phe Leu Phe Leu Leu Arg Lys Trp Lys Asn Ser Asn
             20                  25                  30

Ser Gln Ser Lys Lys Leu Pro Pro Gly Pro Trp Lys Leu Pro Leu Leu
         35                  40                  45

Gly Ser Met Leu His Met Val Gly Leu Pro His His Val Leu Arg
     50                  55                  60

Asp Leu Ala Lys Lys Tyr Gly Pro Leu Met His Leu Gln Leu Gly Glu
65                  70                  75                  80

Val Ser Ala Val Val Thr Ser Pro Asp Met Ala Lys Glu Val Leu
             85                  90                  95

Lys Thr His Asp Ile Ala Phe Ala Ser Arg Pro Lys Leu Leu Ala Pro
                100                 105                 110

Glu Ile Val Cys Tyr Asn Arg Ser Asp Ile Ala Phe Cys Pro Tyr Gly
             115                 120                 125

Asp Tyr Trp Arg Gln Met Arg Lys Ile Cys Val Leu Glu Val Leu Ser
        130                 135                 140

Ala Lys Asn Val Arg Ser Phe Ser Ser Ile Arg Arg Asp Glu Val Leu
145                 150                 155                 160

Arg Leu Val Asn Phe Val Arg Ser Ser Thr Ser Glu Pro Val Asn Phe
                165                 170                 175

Thr Glu Arg Leu Phe Leu Phe Thr Ser Ser Met Thr Cys Arg Ser Ala
            180                 185                 190

Phe Gly Lys Val Phe Lys Glu Gln Glu Thr Phe Ile Gln Leu Ile Lys
            195                 200                 205

Glu Val Ile Gly Leu Ala Gly Gly Phe Asp Val Ala Asp Ile Phe Pro
    210                 215                 220

Ser Leu Lys Phe Leu His Val Leu Thr Gly Met Glu Gly Lys Ile Met
225                 230                 235                 240

Lys Ala His His Lys Val Asp Ala Ile Val Glu Asp Val Ile Asn Glu
                245                 250                 255

His Lys Lys Asn Leu Ala Met Gly Lys Thr Asn Gly Ala Leu Gly Gly
                260                 265                 270

Glu Asp Leu Ile Asp Val Leu Leu Arg Leu Met Asn Asp Gly Gly Leu
        275                 280                 285

Gln Phe Pro Ile Thr Asn Asp Asn Ile Lys Ala Ile Ile Phe Asp Met
    290                 295                 300

Phe Ala Ala Gly Thr Glu Thr Ser Ser Ser Thr Leu Val Trp Ala Met
305                 310                 315                 320

Val Gln Met Met Arg Asn Pro Thr Ile Leu Ala Lys Ala Gln Ala Glu
                325                 330                 335

Val Arg Glu Ala Phe Lys Gly Lys Glu Thr Phe Asp Glu Asn Asp Val
            340                 345                 350

Glu Glu Leu Lys Tyr Leu Lys Leu Val Ile Lys Glu Thr Leu Arg Leu
        355                 360                 365

His Pro Pro Val Pro Leu Leu Val Pro Arg Glu Cys Arg Glu Glu Thr
    370                 375                 380

Glu Ile Asn Gly Tyr Thr Ile Pro Val Lys Thr Lys Val Met Val Asn
385                 390                 395                 400

Val Trp Ala Leu Gly Arg Asp Pro Lys Tyr Trp Asp Asp Ala Asp Asn
                405                 410                 415

Phe Lys Pro Glu Arg Phe Glu Gln Cys Ser Val Asp Phe Ile Gly Asn
            420                 425                 430

Asn Phe Glu Tyr Leu Pro Phe Gly Gly Gly Arg Arg Ile Cys Pro Gly
```

```
                435                 440                 445
Ile Ser Phe Gly Leu Ala Asn Val Tyr Leu Pro Leu Ala Gln Leu Leu
    450                 455                 460

Tyr His Phe Asp Trp Lys Leu Pro Thr Gly Met Glu Pro Lys Asp Leu
465                 470                 475                 480

Asp Leu Thr Glu Leu Val Gly Val Thr Ala Ala Arg Lys Ser Asp Leu
                485                 490                 495

Met Leu Val Ala Thr Pro Tyr Gln Pro Ser Arg Glu
            500                 505
```

<210> SEQ ID NO 21
<211> LENGTH: 1524
<212> TYPE: DNA
<213> ORGANISM: Hyoscyamus muticus

<400> SEQUENCE: 21

```
atggctctgt tattagcagt tttcttcttc tccctggtct caatctttct gttcctgtcc    60
tttctgttcc tgctgcgtaa atggaaaaac tcaaactccc aatcgaaaaa actgccgccg   120
ggtccgtgga aactgccgct gctgggctct atgctgcaca tggttggcgg cctgccgcat   180
cacgttctgc gtgatctggc gaaaaaatat ggtccgctga tgcatctgca actgggcgaa   240
gtctccgccg tggttgtcac ctcaccggat atggcaaaag aagtgctgaa acgcatgac    300
attgcgttcg cctcccgtcc gaaactgctg ccccgaaaa ttgtgtgcta caaccgctca   360
gatattgcat tttgtccgta tggtgactac tggcgtcaaa tgcgcaaaat ttgcgtcctg   420
gaagtgctgt cggccaaaaa tgtgcgcagc tttagctcta ttcgtcgtga tgaagttctg   480
cgtctggtta acttcgtccg cagttccacc tcggagccgg tgaatttac ggaacgtctg    540
tttctgttca cctcatcgat gacctgccgt agcgcatttg gtaaagtttt caagaacag    600
gaaaccttca ttcaactgat caagaagtc attggcctgg ccggcggttt tgatgtggca   660
gacatctttc cgagtctgaa attcctgcat gttctgaccg gcatggaagg caaaattatg   720
aaagctcatc acaaagtcga tgcgattgtg aagacgtta tcaacgaaca caagaaaaac    780
ctggcgatgg gcaaaacgaa cggcgcactg gcggtgaag atctgatcga cgttctgctg    840
cgtctgatga atgatggcgg cctgcaattt ccgatcacca acgataatat caaagctatt   900
atctttgata tgtttgcggc gggcaccgaa accagcagca gcaccctggt gtgggcgatg   960
gtgcagatga tgcgtaaccc gacgattctg gcaaaagctc aagcggaagt gcgcgaagcc  1020
ttcaaaggca agaaaccctt tgatgaaaat gacgttgaag aactgaaata tctgaaactg  1080
gtcatcaaag aaacgctgcg tctgcatccg ccggttccgc tgctggtccc gcgtgaatgc  1140
cgcgaagaaa ccgaaattaa cggttatacc atcccggtta aaacgaaagt gatggttaat  1200
gtctgggctc tgggccgtga tccgaaatac tgggatgacg cggacaactt taaaccggaa  1260
cgctttgaac agtgctctgt ggatttcatc ggcaacaact ttgaatatct gccgtttggc  1320
ggtggccgtc gcatttgtcc gggtatcagc ttcggcctgg ctaatgttta tctgccgctg  1380
gcgcaactgc tgtaccactt tgattggaaa ctgccgaccg gcatggaacc gaaagatctg  1440
gacctgaccg aactggtggg cgttacggca gctcgtaaat ctgatctgat gctggttgcg  1500
accccgtacc agccgagccg tgaa                                         1524
```

<210> SEQ ID NO 22
<211> LENGTH: 488
<212> TYPE: PRT
<213> ORGANISM: Lactuca sativa

```
<400> SEQUENCE: 22

Met Glu Leu Ser Ile Thr Thr Ser Ile Ala Leu Ala Thr Ile Val Phe
1               5                   10                  15

Phe Leu Tyr Lys Leu Ala Thr Arg Pro Lys Ser Thr Lys Lys Gln Leu
            20                  25                  30

Pro Glu Ala Ser Arg Leu Pro Ile Ile Gly His Met His His Leu Ile
        35                  40                  45

Gly Thr Met Pro His Arg Gly Val Met Asp Leu Ala Arg Lys His Gly
    50                  55                  60

Ser Leu Met His Leu Gln Leu Gly Glu Val Ser Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
130                 135                 140

Gln Ser Ile Arg Glu Glu Cys Trp Asn Leu Val Lys Glu Val Lys
145                 150                 155                 160

Glu Ser Gly Ser Gly Lys Pro Ile Asn Leu Ser Glu Ser Ile Phe Thr
                165                 170                 175

Met Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Gln Thr
        195                 200                 205

Gly Gly Phe Asp Val Ala Asp Ile Phe Pro Ser Lys Lys Phe Leu His
    210                 215                 220

His Leu Ser Gly Lys Arg Ala Arg Leu Thr Ser Ile His Lys Lys Leu
225                 230                 235                 240

Asp Asn Leu Ile Asn Asn Ile Val Ala Glu His His Val Ser Thr Ser
                245                 250                 255

Ser Lys Ala Asn Glu Thr Leu Leu Asp Val Leu Leu Arg Leu Lys Asp
            260                 265                 270

Ser Ala Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
    290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Lys Ile Gln Glu Glu
                325                 330                 335

Asp Ile Gln Asp Leu Ala Tyr Leu Asn Leu Val Ile Arg Glu Thr Leu
            340                 345                 350

Arg Leu His Pro Pro Leu Pro Leu Val Met Pro Arg Glu Cys Arg Glu
        355                 360                 365

Pro Val Asn Leu Ala Gly Tyr Glu Ile Ala Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
```

-continued

```
                405                 410                 415
Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser His Asp
    450                 455                 460

Gln Leu Asp Met Thr Glu Ser Phe Gly Ala Thr Val Gln Arg Lys Thr
465                 470                 475                 480

Glu Leu Leu Leu Val Pro Ser Phe
                485

<210> SEQ ID NO 23
<211> LENGTH: 488
<212> TYPE: PRT
<213> ORGANISM: Lactuca sativa

<400> SEQUENCE: 23

Met Ala Leu Leu Leu Ala Val Phe Ile Ala Leu Ala Thr Ile Val Phe
1               5                   10                  15

Phe Leu Tyr Lys Leu Ala Thr Arg Pro Lys Ser Thr Lys Lys Gln Leu
            20                  25                  30

Pro Glu Ala Ser Arg Leu Pro Ile Ile Gly His Met His His Leu Ile
        35                  40                  45

Gly Thr Met Pro His Arg Gly Val Met Asp Leu Ala Arg Lys His Gly
    50                  55                  60

Ser Leu Met His Leu Gln Leu Gly Glu Val Ser Thr Ile Val Val Ser
65                  70                  75                  80

Ser Pro Lys Trp Ala Lys Glu Ile Leu Thr Thr Tyr Asp Ile Thr Phe
            85                  90                  95

Ala Asn Arg Pro Glu Thr Leu Thr Gly Glu Ile Ile Ala Tyr His Asn
        100                 105                 110

Thr Asp Ile Val Leu Ala Pro Tyr Gly Glu Tyr Trp Arg Gln Leu Arg
    115                 120                 125

Lys Leu Cys Thr Leu Glu Leu Leu Ser Val Lys Val Lys Ser Phe
130                 135                 140

Gln Ser Ile Arg Glu Glu Glu Cys Trp Asn Leu Val Lys Glu Val Lys
145                 150                 155                 160

Glu Ser Gly Ser Gly Lys Pro Ile Asn Leu Ser Glu Ser Ile Phe Thr
            165                 170                 175

Met Ile Ala Thr Ile Leu Ser Arg Ala Ala Phe Gly Lys Gly Ile Lys
        180                 185                 190

Asp Gln Arg Glu Phe Thr Glu Ile Val Lys Glu Ile Leu Arg Gln Thr
    195                 200                 205

Gly Gly Phe Asp Val Ala Asp Ile Phe Pro Ser Lys Lys Phe Leu His
210                 215                 220

His Leu Ser Gly Lys Arg Ala Arg Leu Thr Ser Ile His Lys Lys Leu
225                 230                 235                 240

Asp Asn Leu Ile Asn Asn Ile Val Ala Glu His His Val Ser Thr Ser
            245                 250                 255

Ser Lys Ala Asn Glu Thr Leu Leu Asp Val Leu Leu Arg Leu Lys Asp
        260                 265                 270

Ser Ala Glu Phe Pro Leu Thr Ala Asp Asn Val Lys Ala Ile Ile Leu
    275                 280                 285
```

```
Asp Met Phe Gly Ala Gly Thr Asp Thr Ser Ser Ala Thr Val Glu Trp
        290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Lys Ile Gln Glu Glu
                325                 330                 335

Asp Ile Gln Asp Leu Ala Tyr Leu Asn Leu Val Ile Arg Glu Thr Leu
            340                 345                 350

Arg Leu His Pro Pro Leu Pro Leu Val Met Pro Arg Glu Cys Arg Glu
        355                 360                 365

Pro Val Asn Leu Ala Gly Tyr Glu Ile Ala Asn Lys Thr Lys Leu Ile
370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
                405                 410                 415

Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser His Asp
450                 455                 460

Gln Leu Asp Met Thr Glu Ser Phe Gly Ala Thr Val Gln Arg Lys Thr
465                 470                 475                 480

Glu Leu Leu Leu Val Pro Ser Phe
                485
```

<210> SEQ ID NO 24
<211> LENGTH: 1464
<212> TYPE: DNA
<213> ORGANISM: Lactuca sativa

<400> SEQUENCE: 24

```
atggctctgt tattagcagt tttcatcgca ctggctacca tcgtcttctt cctgtataaa     60
ctggcaacgc gcccgaaatc taccaaaaaa caactgccgg aagcgagccg tctgccgatt    120
atcggccaca tgcatcacct gattggcacc atgccgcacc gtggtgtcat ggatctggcc    180
cgcaaacatg gctcgctgat gcatctgcaa ctgggcgaag tgagccacat gtggttagc    240
tctccgaaat gggcaaaaga aattctgacc acctatgata ttacctttgc taaccgcccg    300
gaaaccctga cgggcgaaat tatcgcgtac cataatacgg acattgtgct ggccccgtat    360
ggtgaatact ggcgtcaact gcgtaaactg tgcaccctgg aactgctgtc cgttaaaaaa    420
gtcaaatcat ttcaatcgat tcgtgaagaa gaatgttgga acctggtgaa agaagttaaa    480
gaaagcggct ctggtaaacc gattaatctg agtgaatcca tcttcaccat gattgcgacg    540
atcctgagtc gtgcggcctt tggcaaaggt attaagatca gcgcgaatt taccgaaatt    600
gtcaaagaaa tcctgcgtca acgggcggt ttcgatgtgg cagacatttt tccgagcaaa    660
aaattcctgc atcacctgtc tggcaaacgt gctcgcctga ccagtatcca taaaaaactg    720
gataacctga tcaacaatat cgtcgcggaa catcatgtga gcaccagcag caaagcgaat    780
gaaacgctgc tggatgttct gctgcgcctg aaagacagtg ccgaatttcc gctgaccgca    840
gacaacgtca agctattat cctggatatg ttcggtgcag gcaccgatac cagcagcgca    900
acggtggaat gggccattag cgaactgatc cgttgcccgc gcgcaatgga aaaagttcag    960
```

-continued

```
gcagaactgc gtcaagctct gaacggtaaa gaaaaaatcc aggaagaaga tattcaagac    1020
ctggcctatc tgaatctggt gattcgtgaa accctgcgtc tgcacccgcc gctgccgctg    1080
gttatgccgc gtgaatgccg tgagccggtg aacctggcgg ctatgaaat cgccaataaa     1140 accaaactga tcgtcaatgt gtttgcgatt aaccgtgacc cggaatactg gaaagacgcg    1200
gaagccttta tcccggaacg ttttgaaaac aatccgaaca atatcatggg tgcagattat    1260
gaatacctgc cgtttggcgc tggtcgtcgc atgtgtccgg cgcagctct gggtctggca     1320 aacgttcaac tgccgctggc gaacattctg taccatttca actggaaact gccgaatggc    1380
gcgtcccacg atcaactgga catgaccgaa tcatttggtg ccaccgtgca acgtaaaacg    1440
gaactgctgc tggttccgag cttc                                           1464
```

<210> SEQ ID NO 25
<211> LENGTH: 504
<212> TYPE: PRT
<213> ORGANISM: Nicotiani tabacum

<400> SEQUENCE: 25

```
Met Gln Phe Phe Ser Leu Val Ser Ile Phe Leu Phe Ser Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Ile Pro Ile Leu Gly Ser Met Leu His Met
        35                  40                  45

Ile Gly Gly Glu Pro His His Val Leu Arg Asp Leu Ala Lys Lys Tyr
    50                  55                  60

Gly Pro Leu Met His Leu Gln Leu Gly Glu Ile Ser Ala Val Val Val
65                  70                  75                  80

Thr Ser Arg Asp Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140

Phe Ser Ser Ile Arg Arg Asp Glu Val Val Arg Leu Ile Asp Ser Ile
145                 150                 155                 160

Arg Ser Asp Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Ile Phe Ala Lys Lys Ile Arg Glu Val Ile Gly
        195                 200                 205

Leu Ala Glu Gly Phe Asp Val Val Asp Ile Phe Pro Thr Tyr Lys Phe
    210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
                245                 250                 255

Leu Ala Ala Gly Lys Ser Asn Gly Ala Leu Gly Gly Glu Asp Leu Ile
            260                 265                 270

Asp Val Leu Leu Arg Leu Met Asn Asp Thr Ser Leu Gln Phe Pro Ile
        275                 280                 285
```

```
Thr Asn Asp Asn Ile Lys Ala Val Ile Val Asp Met Phe Ala Ala Gly
    290                 295                 300

Thr Glu Thr Ser Ser Thr Thr Thr Val Trp Ala Met Ala Glu Met Met
305                 310                 315                 320

Lys Asn Pro Ser Val Phe Thr Lys Ala Gln Ala Glu Val Arg Glu Ala
                325                 330                 335

Phe Arg Asp Lys Val Ser Phe Asp Glu Asn Asp Val Glu Glu Leu Lys
            340                 345                 350

Tyr Leu Lys Leu Val Ile Lys Glu Thr Leu Arg Leu His Pro Pro Ser
        355                 360                 365

Pro Leu Leu Val Pro Arg Glu Cys Arg Glu Asp Thr Asp Ile Asn Gly
    370                 375                 380

Tyr Thr Ile Pro Ala Lys Thr Lys Val Met Val Asn Val Trp Ala Leu
385                 390                 395                 400

Gly Arg Asp Pro Lys Tyr Trp Asp Asp Ala Glu Ser Phe Lys Pro Glu
                405                 410                 415

Arg Phe Glu Gln Cys Ser Val Asp Phe Phe Gly Asn Asn Phe Glu Phe
            420                 425                 430

Leu Pro Phe Gly Gly Gly Arg Arg Ile Cys Pro Gly Met Ser Phe Gly
        435                 440                 445

Leu Ala Asn Leu Tyr Leu Pro Leu Ala Gln Leu Leu Tyr His Phe Asp
    450                 455                 460

Trp Lys Leu Pro Thr Gly Ile Met Pro Arg Asp Leu Asp Leu Thr Glu
465                 470                 475                 480

Leu Ser Gly Ile Thr Ile Ala Arg Lys Gly Leu Tyr Leu Asn Ala
                485                 490                 495

Thr Pro Tyr Gln Pro Ser Arg Glu
            500

<210> SEQ ID NO 26
<211> LENGTH: 510
<212> TYPE: PRT
<213> ORGANISM: Nicotiani tabacum

<400> SEQUENCE: 26

Met Ala Leu Leu Leu Ala Val Phe Phe Phe Ser Leu Val Ser Ile Phe
1               5                   10                  15

Leu Phe Leu Ser Phe Leu Phe Leu Leu Arg Lys Trp Lys Asn Ser Asn
                20                  25                  30

Ser Gln Ser Lys Lys Leu Pro Pro Gly Pro Trp Lys Ile Pro Ile Leu
            35                  40                  45

Gly Ser Met Leu His Met Ile Gly Gly Glu Pro His His Val Leu Arg
        50                  55                  60

Asp Leu Ala Lys Lys Tyr Gly Pro Leu Met His Leu Gln Leu Gly Glu
65                  70                  75                  80

Ile Ser Ala Val Val Thr Ser Arg Asp Met Ala Lys Glu Val Leu
                85                  90                  95

Lys Thr His Asp Val Val Phe Ala Ser Arg Pro Lys Ile Val Ala Met
                100                 105                 110

Asp Ile Ile Cys Tyr Asn Gln Ser Asp Ile Ala Phe Ser Pro Tyr Gly
            115                 120                 125

Asp His Trp Arg Gln Met Arg Lys Ile Cys Val Met Glu Leu Leu Asn
        130                 135                 140

Ala Lys Asn Val Arg Ser Phe Ser Ser Ile Arg Arg Asp Glu Val Val
```

```
                145                 150                 155                 160
Arg Leu Ile Asp Ser Ile Arg Ser Asp Ser Ser Gly Glu Leu Val
                165                 170                 175

Asn Phe Thr Gln Arg Ile Ile Trp Phe Ala Ser Ser Met Thr Cys Arg
                180                 185                 190

Ser Ala Phe Gly Gln Val Leu Lys Gly Gln Asp Ile Phe Ala Lys Lys
                195                 200                 205

Ile Arg Glu Val Ile Gly Leu Ala Glu Gly Phe Asp Val Val Asp Ile
210                 215                 220

Phe Pro Thr Tyr Lys Phe Leu His Val Leu Ser Gly Met Lys Arg Lys
225                 230                 235                 240

Leu Leu Asn Ala His Leu Lys Val Asp Ala Ile Val Glu Asp Val Ile
                245                 250                 255

Asn Glu His Lys Lys Asn Leu Ala Ala Gly Lys Ser Asn Gly Ala Leu
                260                 265                 270

Gly Gly Glu Asp Leu Ile Asp Val Leu Leu Arg Leu Met Asn Asp Thr
                275                 280                 285

Ser Leu Gln Phe Pro Ile Thr Asn Asp Asn Ile Lys Ala Val Ile Val
                290                 295                 300

Asp Met Phe Ala Ala Gly Thr Glu Thr Ser Ser Thr Thr Thr Val Trp
305                 310                 315                 320

Ala Met Ala Glu Met Met Lys Asn Pro Ser Val Phe Thr Lys Ala Gln
                325                 330                 335

Ala Glu Val Arg Glu Ala Phe Arg Asp Lys Val Ser Phe Asp Glu Asn
                340                 345                 350

Asp Val Glu Glu Leu Lys Tyr Leu Lys Leu Val Ile Lys Glu Thr Leu
                355                 360                 365

Arg Leu His Pro Pro Ser Pro Leu Leu Val Pro Arg Glu Cys Arg Glu
                370                 375                 380

Asp Thr Asp Ile Asn Gly Tyr Thr Ile Pro Ala Lys Thr Lys Val Met
385                 390                 395                 400

Val Asn Val Trp Ala Leu Gly Arg Asp Pro Lys Tyr Trp Asp Asp Ala
                405                 410                 415

Glu Ser Phe Lys Pro Glu Arg Phe Glu Gln Cys Ser Val Asp Phe Phe
                420                 425                 430

Gly Asn Asn Phe Glu Phe Leu Pro Phe Gly Gly Gly Arg Arg Ile Cys
                435                 440                 445

Pro Gly Met Ser Phe Gly Leu Ala Asn Leu Tyr Leu Pro Leu Ala Gln
                450                 455                 460

Leu Leu Tyr His Phe Asp Trp Lys Leu Pro Thr Gly Ile Met Pro Arg
465                 470                 475                 480

Asp Leu Asp Leu Thr Glu Leu Ser Gly Ile Thr Ile Ala Arg Lys Gly
                485                 490                 495

Gly Leu Tyr Leu Asn Ala Thr Pro Tyr Gln Pro Ser Arg Glu
                500                 505                 510
```

<210> SEQ ID NO 27
<211> LENGTH: 1530
<212> TYPE: DNA
<213> ORGANISM: Nicotiani tabacum

<400> SEQUENCE: 27

```
atggctctgt tattagcagt tttcttcttc tccctggtct caatcttcct gttcctgtcc    60
tttctgttcc tgctgcgtaa atggaaaaac tctaatagcc aatccaaaaa actgccgccg   120
```

```
ggtccgtgga aaattccgat cctgggctct atgctgcaca tgattggcgg tgaaccgcat      180
catgtgctgc gtgatctggc gaaaaaatat ggtccgctga tgcatctgca actgggcgaa      240
atctctgcgg tggttgtcac gagtcgtgac atggccaaag aagtgctgaa aacccatgat      300 gtggttttg catctcgccc gaaaatcgtt gctatggata ttatctgcta taaccagtcg       360
gacatcgcgt tcagcccgta cggtgatcac tggcgtcaaa tgcgcaaaat tgtgtcatg      420 gaactgctga acgccaaaaa tgtgcgcagt tttagctcta ttcgtcgtga tgaagtcgtg      480
cgtctgattg attccatccg ctcagacagt tcctcaggcg aactggtgaa ttttacgcag      540
cgtattatct ggttcgcatc gagcatgacc tgccgctcgg cttttggtca ggttctgaaa      600
ggccaagata tttttgcgaa gaaaattcgt gaagtgatcg gtctggccga aggcttcgat      660
gttgtggata tttttccgac ctataaattc ctgcatgtcc tgagcggtat gaaacgcaaa      720
ctgctgaacg cgcacctgaa agttgatgcc attgtcgaag acgtgatcaa cgaacataag      780
aaaaacctgg cggcgggtaa atccaacggc gcactgggcg gtgaagatct gattgacgtg      840
ctgctgcgtc tgatgaatga taccagcctg caatttccga tcaccaacga caacattaaa      900
gcggtgatcg ttgatatgtt cgcggcgggc accgaaaacct ctagtaccac gaccgtttgg     960
gcgatggccg aaatgatgaa aaacccgtcg gtgtttacca agcacaagc ggaagtgcgt      1020 gaagcgtttc gtgataaagt tagcttcgat gaaaatgatg tggaagaact gaaatacctg      1080
aaactggtga ttaaagaaac gctgcgtctg catccgccga gcccgctgct ggttccgcgt      1140
gaatgccgtg aagataccga cattaacggt tatcgatcc cggcaaaaac caaagtcatg      1200
gtgaatgttt gggctctggg ccgtgacccg aaatactggg atgacgcaga atcctttaaa      1260
ccggaacgct ttgaacagtg ctcagtggat ttctttggta caactttga atttctgccg      1320 tttggcggtg gccgtcgcat ttgtccgggt atgtccttcg gcctggcgaa cctgtatctg      1380
ccgctggccc aactgctgta ccactttgat tggaaactgc cgacgggtat tatgccgcgt      1440
gatctggacc tgacggaact gtctggcatt accatcgcac gcaaaggtgg cctgtatctg      1500
aatgctaccc cgtaccagcc gagtcgtgaa                                       1530
```

<210> SEQ ID NO 28
<211> LENGTH: 522
<212> TYPE: PRT
<213> ORGANISM: Citrus x paradisi

<400> SEQUENCE: 28

Met Glu Leu Pro Leu Lys Ser Ile Ala Leu Thr Ile Val Ile Val Thr
1               5                   10                  15

Val Leu Thr Trp Ala Trp Arg Val Leu Asn Trp Val Trp Leu Arg Pro
            20                  25                  30

Lys Lys Leu Glu Lys Phe Leu Arg Gln Gln Gly Leu Lys Gly Asn Ser
        35                  40                  45

Tyr Arg Leu Leu Phe Gly Asp Leu Lys Glu Asn Ser Ile Glu Leu Lys
    50                  55                  60

Glu Ala Lys Ala Arg Pro Leu Ser Leu Asp Asp Ile Ala Ile Arg
65                  70                  75                  80

Val Asn Pro Phe Leu His Lys Leu Val Asn Asp Tyr Gly Lys Asn Ser
                85                  90                  95

Phe Met Trp Phe Gly Pro Thr Pro Arg Val Asn Ile Met Asn Pro Asp
            100                 105                 110

Gln Ile Lys Ala Ile Phe Thr Lys Ile Asn Asp Phe Gln Lys Val Asn

```
            115                 120                 125
Ser Ile Pro Leu Ala Arg Leu Leu Ile Val Gly Leu Ala Thr Leu Glu
    130                 135                 140
Gly Glu Lys Trp Ala Lys His Arg Lys Leu Ile Asn Pro Ala Phe His
145                 150                 155                 160
Gln Glu Lys Leu Lys Leu Met Leu Pro Ala Phe Tyr Leu Ser Cys Ile
                165                 170                 175
Glu Ile Ile Thr Lys Trp Glu Lys Gln Met Ser Val Glu Gly Ser Ser
            180                 185                 190
Glu Leu Asp Val Trp Pro Tyr Leu Ala Asn Leu Thr Ser Asp Val Ile
        195                 200                 205
Ser Arg Thr Ala Phe Gly Ser Ser Tyr Glu Glu Gly Arg Arg Ile Phe
    210                 215                 220
Gln Leu Gln Ala Glu Leu Ala Glu Leu Thr Met Gln Val Phe Arg Ser
225                 230                 235                 240
Val His Ile Pro Gly Trp Arg Phe Leu Pro Thr Lys Arg Asn Arg Arg
                245                 250                 255
Met Lys Glu Ile Asp Lys Glu Ile Arg Ala Ser Leu Met Gly Ile Ile
            260                 265                 270
Lys Asn Arg Glu Lys Ala Met Arg Ala Gly Glu Ala Ala Asn Asn Asp
        275                 280                 285
Leu Leu Gly Ile Leu Met Glu Thr Ser Phe Arg Glu Ile Glu Glu His
    290                 295                 300
Gly Asn Asn Lys Asn Val Gly Phe Ser Met Asn Asp Val Ile Glu Glu
305                 310                 315                 320
Cys Lys Leu Phe Tyr Phe Ala Gly Gln Glu Thr Thr Ser Val Leu Leu
                325                 330                 335
Asn Trp Thr Met Val Leu Leu Ser Lys His Gln Asp Trp Gln Glu Arg
            340                 345                 350
Ala Arg Gln Glu Val Leu Gln Val Phe Gly Asn Asn Lys Pro Asp Tyr
        355                 360                 365
Asp Gly Leu Asn His Leu Lys Ile Val Gln Met Ile Leu Tyr Glu Val
    370                 375                 380
Leu Arg Leu Tyr Pro Pro Val Thr Val Leu Ser Arg Ala Val Phe Lys
385                 390                 395                 400
Glu Thr Lys Leu Gly Asn Leu Thr Leu Pro Ala Gly Val Gln Ile Gly
                405                 410                 415
Leu Pro Met Ile Leu Val His Gln Asp Pro Glu Leu Trp Gly Asp Asp
            420                 425                 430
Ala Val Glu Phe Lys Pro Glu Arg Phe Ala Glu Gly Ile Ser Lys Ala
        435                 440                 445
Ala Lys Asn Gln Val Ser Tyr Phe Pro Phe Ala Leu Gly Pro Arg Ile
    450                 455                 460
Cys Val Gly Gln Asn Phe Ala Leu Val Glu Ala Lys Met Ala Thr Ala
465                 470                 475                 480
Met Ile Leu Gln Asn Tyr Ser Phe Glu Leu Ser Pro Ser Tyr Val His
                485                 490                 495
Ala Pro Thr Ala Val Pro Thr Leu His Pro Glu Leu Gly Thr Gln Leu
            500                 505                 510
Ile Leu Arg Lys Leu Trp Cys Lys Asn Asn
        515                 520
```

<210> SEQ ID NO 29

<211> LENGTH: 523
<212> TYPE: PRT
<213> ORGANISM: Citrus x paradisi

<400> SEQUENCE: 29

```
Met Ala Leu Leu Leu Ala Val Phe Ile Ala Leu Thr Ile Val Ile Val
1               5                   10                  15

Thr Val Leu Thr Trp Ala Trp Arg Val Leu Asn Trp Val Trp Leu Arg
                20                  25                  30

Pro Lys Lys Leu Glu Lys Phe Leu Arg Gln Gln Gly Leu Lys Gly Asn
            35                  40                  45

Ser Tyr Arg Leu Leu Phe Gly Asp Leu Lys Glu Asn Ser Ile Glu Leu
        50                  55                  60

Lys Glu Ala Lys Ala Arg Pro Leu Ser Leu Asp Asp Ile Ala Ile
65                  70                  75                  80

Arg Val Asn Pro Phe Leu His Lys Leu Val Asn Asp Tyr Gly Lys Asn
                85                  90                  95

Ser Phe Met Trp Phe Gly Pro Thr Pro Arg Val Asn Ile Met Asn Pro
            100                 105                 110

Asp Gln Ile Lys Ala Ile Phe Thr Lys Ile Asn Asp Phe Gln Lys Val
        115                 120                 125

Asn Ser Ile Pro Leu Ala Arg Leu Leu Ile Val Gly Leu Ala Thr Leu
    130                 135                 140

Glu Gly Glu Lys Trp Ala Lys His Arg Lys Leu Ile Asn Pro Ala Phe
145                 150                 155                 160

His Gln Glu Lys Leu Lys Leu Met Leu Pro Ala Phe Tyr Leu Ser Cys
                165                 170                 175

Ile Glu Ile Ile Thr Lys Trp Glu Lys Gln Met Ser Val Glu Gly Ser
            180                 185                 190

Ser Glu Leu Asp Val Trp Pro Tyr Leu Ala Asn Leu Thr Ser Asp Val
        195                 200                 205

Ile Ser Arg Thr Ala Phe Gly Ser Ser Tyr Glu Glu Gly Arg Arg Ile
    210                 215                 220

Phe Gln Leu Gln Ala Glu Leu Ala Glu Leu Thr Met Gln Val Phe Arg
225                 230                 235                 240

Ser Val His Ile Pro Gly Trp Arg Phe Leu Pro Thr Lys Arg Asn Arg
                245                 250                 255

Arg Met Lys Glu Ile Asp Lys Glu Ile Arg Ala Ser Leu Met Gly Ile
            260                 265                 270

Ile Lys Asn Arg Glu Lys Ala Met Arg Ala Gly Glu Ala Ala Asn Asn
        275                 280                 285

Asp Leu Leu Gly Ile Leu Met Glu Thr Ser Phe Arg Glu Ile Glu Glu
    290                 295                 300

His Gly Asn Asn Lys Asn Val Gly Phe Ser Met Asn Asp Val Ile Glu
305                 310                 315                 320

Glu Cys Lys Leu Phe Tyr Phe Ala Gly Gln Gly Thr Thr Ser Val Leu
                325                 330                 335

Leu Asn Trp Thr Met Val Leu Leu Ser Lys His Gln Asp Trp Gln Glu
            340                 345                 350

Arg Ala Arg Gln Glu Val Leu Gln Val Phe Gly Asn Asn Lys Pro Asp
        355                 360                 365

Tyr Asp Gly Leu Asn His Leu Lys Ile Val Gln Met Ile Leu Tyr Glu
    370                 375                 380

Val Leu Arg Leu Tyr Pro Pro Val Thr Val Leu Ser Arg Ala Val Phe
```

```
                385                 390                 395                 400
Lys Glu Thr Lys Leu Gly Asn Leu Thr Leu Pro Ala Gly Val Gln Ile
                405                 410                 415

Gly Leu Pro Met Ile Leu Val His Gln Asp Pro Glu Leu Trp Gly Asp
            420                 425                 430

Asp Ala Val Glu Phe Lys Pro Glu Arg Phe Ala Glu Gly Ile Ser Lys
        435                 440                 445

Ala Ala Lys Asn Gln Val Ser Tyr Phe Pro Phe Ala Leu Gly Pro Arg
    450                 455                 460

Ile Cys Val Gly Gln Asn Phe Ala Leu Val Glu Ala Lys Met Ala Thr
465                 470                 475                 480

Ala Met Ile Leu Gln Asn Tyr Ser Phe Glu Leu Ser Pro Ser Tyr Val
                485                 490                 495

His Ala Pro Thr Ala Val Pro Thr Leu His Pro Glu Leu Gly Thr Gln
            500                 505                 510

Leu Ile Leu Arg Lys Leu Trp Cys Lys Asn Asn
            515                 520
```

<210> SEQ ID NO 30
<211> LENGTH: 1569
<212> TYPE: DNA
<213> ORGANISM: Citrus x paradisi

<400> SEQUENCE: 30

```
atggctctgt tattagcagt tttcattgct ctgacgattg ttattgttac ggtgctgacc     60
tgggcgtggc gtgtgctgaa ctgggtttgg ctgcgtccga aaaaactgga aaaatttctg    120
cgccagcaag gcctgaaggg taacagctat cgtctgctgt tcggcgatct gaaagaaaat    180
tctattgaac tgaaagaagc gaaagcccgt ccgctgagtc tggatgacga tattgcaatc    240
cgcgttaacc cgtttctgca taaactggtc aacgattacg gcaaaaattc ttttatgtgg    300
ttcggtccga ccccgcgcgt gaacattatg aacccggatc agattaaagc gatctttacg    360
aaaatcaacg atttccaaaa agttaatagc attccgctgg cgcgtctgct gatcgtcggc    420
ctggccaccc tggaaggtga aaatgggca aacatcgca aactgattaa cccggctttt    480
caccaagaaa aactgaaact gatgctgccg gcgttctatc tgtcctgcat cgaaattatc    540
acgaaatggg aaaaacagat gtcagtggaa ggtagctctg aactggacgt ttggccgtat    600
ctggccaatc tgaccagcga tgttattct cgtacggcat ttggcagttc ctacgaagaa    660
ggtcgtcgca tcttccagtt acaggcgaa ctggccgaac tgaccatgca ggttttcgt    720
tctgtcccata ttccgggctg cgtttcctg ccgacgaaac gcaaccgtcg catgaaagaa    780
attgacaaag aaatccgcgc cagtctgatg ggtattatca aaaatcgtga aaagcaatg    840
cgcgctggcg aagcggccaa caatgatctg ctgggtattc tgatggaaac cagctttcgt    900
gaaatcgaag aacacggcaa caataaaaac gtcggtttca gcatgaatga cgtgatcgaa    960
gaatgtaaac tgttttattt cgctggccag gaaaccacgt cagttctgct gaactggacg   1020
atggtgctgc tgtcgaaaca tcaggattgg caagaacgtg cccgccagga agtcctgcaa   1080
gtgtttggca acaataaacc ggactacgat ggtctgaacc acctgaaaat tgtgcagatg   1140
atcctgtatg aagttctgcg tctgtatccg ccggtgacgg tgctgagccg tgcggtgttt   1200
aaagaaacca aactgggtaa tctgacgctc ccggcaggcg tccagattgg tctgccgatg   1260
atcctggtgc accaggaccc ggaactgtgg ggcgacgatg ctgtggaatt taaaccggaa   1320
cgtttcgcgg aaggtattag taaagcagct aaaaatcagg tttcctattt tccgttcgcg   1380
```

```
ctgggtccgc gtatttgcgt cggtcaaaac tttgcactgg tggaagctaa aatggcaacc   1440
gctatgatcc tgcaaaatta tagctttgaa ctgtcaccga gctatgttca tgcgccgacc   1500
gccgttccga cgctgcaccc ggaactgggc acgcaactga ttctgcgtaa actgtggtgt   1560
aaaaacaat                                                            1569
```

<210> SEQ ID NO 31
<211> LENGTH: 495
<212> TYPE: PRT
<213> ORGANISM: Artemesia annua

<400> SEQUENCE: 31

```
Met Lys Ser Ile Leu Lys Ala Met Ala Leu Ser Leu Thr Thr Ser Ile
1               5                   10                  15

Ala Leu Ala Thr Ile Leu Leu Phe Val Tyr Lys Phe Ala Thr Arg Ser
            20                  25                  30

Lys Ser Thr Lys Lys Ser Leu Pro Glu Pro Trp Arg Leu Pro Ile Ile
        35                  40                  45

Gly His Met His His Leu Ile Gly Thr Thr Pro His Arg Gly Val Arg
    50                  55                  60

Asp Leu Ala Arg Lys Tyr Gly Ser Leu Met His Leu Gln Leu Gly Glu
65                  70                  75                  80

Val Pro Thr Ile Val Ser Ser Pro Lys Trp Ala Lys Glu Ile Leu
                85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
    210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
            260                 265                 270

Val Leu Leu Arg Leu Lys Asp Ser Ala Glu Phe Pro Leu Thr Ser Asp
        275                 280                 285

Asn Ile Lys Ala Ile Ile Leu Asp Met Phe Gly Ala Gly Thr Asp Thr
    290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                325                 330                 335
```

```
Lys Glu Lys Ile His Glu Asp Ile Gln Glu Leu Ser Tyr Leu Asn
            340                 345                 350

Met Val Ile Lys Glu Thr Leu Arg Leu His Pro Pro Leu Pro Leu Val
        355                 360                 365

Leu Pro Arg Glu Cys Arg Gln Pro Val Asn Leu Ala Gly Tyr Asn Ile
370                 375                 380

Pro Asn Lys Thr Lys Leu Ile Val Asn Val Phe Ala Ile Asn Arg Asp
385                 390                 395                 400

Pro Glu Tyr Trp Lys Asp Ala Glu Ala Phe Ile Pro Glu Arg Phe Glu
                405                 410                 415

Asn Ser Ser Ala Thr Val Met Gly Ala Glu Tyr Glu Tyr Leu Pro Phe
            420                 425                 430

Gly Ala Gly Arg Arg Met Cys Pro Gly Ala Ala Leu Gly Leu Ala Asn
        435                 440                 445

Val Gln Leu Pro Leu Ala Asn Ile Leu Tyr His Phe Asn Trp Lys Leu
    450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Leu Val Pro Ser Phe
                485                 490                 495

<210> SEQ ID NO 32
<211> LENGTH: 488
<212> TYPE: PRT
<213> ORGANISM: Artemesia annua

<400> SEQUENCE: 32

Met Ala Leu Leu Leu Ala Val Phe Ile Ala Leu Ala Thr Ile Leu Leu
1               5                   10                  15

Phe Val Tyr Lys Phe Ala Thr Arg Ser Lys Ser Thr Lys Lys Ser Leu
                20                  25                  30

Pro Glu Pro Trp Arg Leu Pro Ile Ile Gly His Met His His Leu Ile
            35                  40                  45

Gly Thr Thr Pro His Arg Gly Val Arg Asp Leu Ala Arg Lys Tyr Gly
        50                  55                  60

Ser Leu Met His Leu Gln Leu Gly Glu Val Pro Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Val Leu Tyr His Asn
            100                 105                 110

Thr Asp Val Val Leu Ala Pro Tyr Gly Glu Tyr Trp Arg Gln Leu Arg
        115                 120                 125

Lys Ile Cys Thr Leu Glu Leu Leu Ser Val Lys Lys Val Lys Ser Phe
130                 135                 140

Gln Ser Leu Arg Glu Glu Glu Cys Trp Asn Leu Val Gln Glu Ile Lys
145                 150                 155                 160

Ala Ser Gly Ser Gly Arg Pro Val Asn Leu Ser Glu Asn Val Phe Lys
                165                 170                 175

Leu Ile Ala Thr Ile Leu Ser Arg Ala Ala Phe Gly Lys Gly Ile Lys
            180                 185                 190

Asp Gln Lys Glu Leu Thr Glu Ile Val Lys Glu Ile Leu Arg Gln Thr
        195                 200                 205

Gly Gly Phe Asp Val Ala Asp Ile Phe Pro Ser Lys Lys Phe Leu His
```

His Leu Ser Gly Lys Arg Ala Arg Leu Thr Ser Leu Arg Lys Lys Ile
225                 230                 235                 240

Asp Asn Leu Ile Asp Asn Leu Val Ala Glu His Thr Val Asn Thr Ser
            245                 250                 255

Ser Lys Thr Asn Glu Thr Leu Leu Asp Val Leu Leu Arg Leu Lys Asp
        260                 265                 270

Ser Ala Glu Phe Pro Leu Thr Ser Asp Asn Ile Lys Ala Ile Ile Leu
    275                 280                 285

Asp Met Phe Gly Ala Gly Thr Asp Thr Ser Ser Thr Ile Glu Trp
290                 295                 300

Ala Ile Ser Glu Leu Ile Lys Cys Pro Lys Ala Met Glu Lys Val Gln
305                 310                 315                 320

Ala Glu Leu Arg Lys Ala Leu Asn Gly Lys Glu Lys Ile His Glu Glu
                325                 330                 335

Asp Ile Gln Glu Leu Ser Tyr Leu Asn Met Val Ile Lys Glu Thr Leu
            340                 345                 350

Arg Leu His Pro Pro Leu Pro Leu Val Leu Pro Arg Glu Cys Arg Gln
        355                 360                 365

Pro Val Asn Leu Ala Gly Tyr Asn Ile Pro Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Ser Ser Ala Thr Val Met
                405                 410                 415

Gly Ala Glu Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Val Ser Tyr Asp
    450                 455                 460

Gln Ile Asp Met Thr Glu Ser Ser Gly Ala Thr Met Gln Arg Lys Thr
465                 470                 475                 480

Glu Leu Leu Leu Val Pro Ser Phe
                485

<210> SEQ ID NO 33
<211> LENGTH: 1464
<212> TYPE: DNA
<213> ORGANISM: Artemesia annua

<400> SEQUENCE: 33
atggctctgt tattagcagt tttcatcgca ctggcaacca ttctgctgtt tgtgtataaa      60
ttcgctaccc gttccaaatc aacgaaaaaa tcactgccgg aaccgtggcg cctgccgatt     120
atcggtcaca tgcatcacct gatcggcacc acccgcatc gtggcgtgcg tgatctggca     180
cgcaaatatg gctcgctgat gcatctgcaa ctgggtgaag tcccgaccat tgtggttagc     240
tctccgaaat gggcgaaaga atcctgacc acctatgata ttacctttgc caaccgcccg     300
gaaaccctga cggcgaaat cgtgctgtac cacaatacgg atgtggtgct ggcgccgtat     360
ggtgaatact ggcgtcaact gcgtaaaatt tgcaccctgg aactgctgag tgtgaaaaaa     420
gttaaatctt tccagagcct gcgtgaagaa gaatgttgga acctggttca agaaattaaa     480
gcatcgggca gcggtcgccc ggttaacctg agtgaaaatg tctttaaact gattgctacc     540

```
atcctgtccc gtgcggcctt cggcaaaggt atcaaagatc agaaagaact gaccgaaatt    600
gtcaaagaaa tcctgcgcca acgggcggt tttgatgtgg cggacatttt tccgtcgaaa    660
aaattcctgc atcacctgag cggtaaacgt gcccgcctga ccagcctgcg taagaaaatt    720
gataacctga tcgacaatct ggtcgcggaa cataccgtga acacgagttc caaaaccaat    780
gaaacgctgc tggatgtgct gctgcgcctg aaagactccg ccgaatttcc gctgacctca    840
gataatatca aagcgattat cctggatatg ttcggtgcag caccgatac cagcagcagc    900 accattgaat gggcaatctc agaactgatt aaatgcccga agctatgga aaaagtccag    960 gcagaactgc gcaaagctct gaacggcaaa gaaaaaatcc atgaagaaga tattcaagaa    1020
ctgtcttacc tgaacatggt tatcaaagaa accctgcgtc tgcacccgcc gctgccgctg    1080
gtgctgccgc gtgaatgtcg ccagccggtt aacctggcag ctataacat cccgaataaa    1140 acgaaactga tcgttaacgt ctttgctatt aaccgtgacc cggaatactg gaaagacgcg    1200
gaagccttta tcccggaacg ctttgaaaac agcagcgcga ccgtgatggg tgccgaatat    1260
gaatacctgc cgtttggcgc gggtcgtcgc atgtgtccgg gcgcagctct gggtctggca    1320
aacgtgcaac tgccgctggc taatatcctg tatcacttca actggaaact gccgaatggc    1380
gttagctacg atcaaattga catgaccgaa agctcaggtg ccacgatgca acgcaaaacc    1440
gaactgctgc tggtgccgtc cttc                                          1464
```

```
<210> SEQ ID NO 34
<211> LENGTH: 509
<212> TYPE: PRT
<213> ORGANISM: Arabidopsis thaliana

<400> SEQUENCE: 34

Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
            20                  25                  30

Lys Asn Met Ser Glu Val Ser Thr Leu Pro Ser Val Pro Val Pro
        35                  40                  45

Gly Phe Pro Val Ile Gly Asn Leu Leu Gln Leu Lys Glu Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205
```

```
Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505

<210> SEQ ID NO 35
<211> LENGTH: 513
<212> TYPE: PRT
<213> ORGANISM: Arabidopsis thaliana

<400> SEQUENCE: 35

Met Ala Leu Leu Leu Ala Val Phe Ser Met Ile Ser Ile Leu Leu Gly
1               5                   10                  15

Phe Val Ile Ser Ser Phe Ile Phe Ile Phe Phe Lys Lys Leu Leu
                20                  25                  30

Ser Phe Ser Arg Lys Asn Met Ser Glu Val Ser Thr Leu Pro Ser Val
            35                  40                  45

Pro Val Val Pro Gly Phe Pro Val Ile Gly Asn Leu Leu Gln Leu Lys
        50                  55                  60

Glu Lys Lys Pro His Lys Thr Phe Thr Arg Trp Ser Glu Ile Tyr Gly
65                  70                  75                  80
```

```
Pro Ile Tyr Ser Ile Lys Met Gly Ser Ser Leu Ile Val Leu Asn
                 85                  90                  95

Ser Thr Glu Thr Ala Lys Glu Ala Met Val Thr Arg Phe Ser Ser Ile
                100                 105                 110

Ser Thr Arg Lys Leu Ser Asn Ala Leu Thr Val Leu Thr Cys Asp Lys
                115                 120                 125

Ser Met Val Ala Thr Ser Asp Tyr Asp Phe His Lys Leu Val Lys
130                 135                 140

Arg Cys Leu Leu Asn Gly Leu Leu Gly Ala Asn Ala Gln Lys Arg Lys
145                 150                 155                 160

Arg His Tyr Arg Asp Ala Leu Ile Glu Asn Val Ser Ser Lys Leu His
                165                 170                 175

Ala His Ala Arg Asp His Pro Gln Glu Pro Val Asn Phe Arg Ala Ile
                180                 185                 190

Phe Glu His Glu Leu Phe Gly Val Ala Leu Lys Gln Ala Phe Gly Lys
                195                 200                 205

Asp Val Glu Ser Ile Tyr Val Lys Glu Leu Gly Val Thr Leu Ser Lys
                210                 215                 220

Asp Glu Ile Phe Lys Val Leu Val His Asp Met Met Glu Gly Ala Ile
225                 230                 235                 240

Asp Val Asp Trp Arg Asp Phe Phe Pro Tyr Leu Lys Trp Ile Pro Asn
                245                 250                 255

Lys Ser Phe Glu Ala Arg Ile Gln Gln Lys His Lys Arg Arg Leu Ala
                260                 265                 270

Val Met Asn Ala Leu Ile Gln Asp Arg Leu Lys Gln Asn Gly Ser Glu
                275                 280                 285

Ser Asp Asp Asp Cys Tyr Leu Asn Phe Leu Met Ser Glu Ala Lys Thr
290                 295                 300

Leu Thr Lys Glu Gln Ile Ala Ile Leu Val Trp Glu Thr Ile Ile Glu
305                 310                 315                 320

Thr Ala Asp Thr Thr Leu Val Thr Thr Glu Trp Ala Ile Tyr Glu Leu
                325                 330                 335

Ala Lys His Pro Ser Val Gln Asp Arg Leu Cys Lys Glu Ile Gln Asn
                340                 345                 350

Val Cys Gly Gly Glu Lys Phe Lys Glu Glu Gln Leu Ser Gln Val Pro
                355                 360                 365

Tyr Leu Asn Gly Val Phe His Glu Thr Leu Arg Lys Tyr Ser Pro Ala
                370                 375                 380

Pro Leu Val Pro Ile Arg Tyr Ala His Glu Asp Thr Gln Ile Gly Gly
385                 390                 395                 400

Tyr His Val Pro Ala Gly Ser Glu Ile Ala Ile Asn Ile Tyr Gly Cys
                405                 410                 415

Asn Met Asp Lys Lys Arg Trp Glu Arg Pro Glu Asp Trp Trp Pro Glu
                420                 425                 430

Arg Phe Leu Asp Asp Gly Lys Tyr Glu Thr Ser Asp Leu His Lys Thr
                435                 440                 445

Met Ala Phe Gly Ala Gly Lys Arg Val Cys Ala Gly Ala Leu Gln Ala
                450                 455                 460

Ser Leu Met Ala Gly Ile Ala Ile Gly Arg Leu Val Gln Glu Phe Glu
465                 470                 475                 480

Trp Lys Leu Arg Asp Gly Glu Glu Glu Asn Val Asp Thr Tyr Gly Leu
                485                 490                 495
```

Thr Ser Gln Lys Leu Tyr Pro Leu Met Ala Ile Ile Asn Pro Arg Arg
        500                 505                 510

Ser

<210> SEQ ID NO 36
<211> LENGTH: 1539
<212> TYPE: DNA
<213> ORGANISM: Arabidopsis thaliana

<400> SEQUENCE: 36

| | | | | | | |
|---|---|---|---|---|---|---|
| atggctctgt | tattagcagt | tttttcgatg | atttctatcc | tgctgggctt | tgttatctcg | 60 |
| tcctttatct | ttatcttctt | cttcaaaaaa | ctgctgtcgt | tttctcgtaa | aaacatgtcc | 120 |
| gaagtttcaa | ccctgccgag | tgtcccggtg | gttccgggtt | ttccggttat | cggtaatctg | 180 |
| ctgcagctga | agaaaagaa | accgcataag | accttcacgc | gctggtccga | aatctatggc | 240 |
| ccgatctact | caattaaaat | gggtagctct | agtctgattg | tgctgaactc | taccgaaacg | 300 |
| gcaaaagaag | ctatggttac | ccgttttttcc | tcaatttcga | cgcgcaagct | gagcaatgcg | 360 |
| ctgaccgtcc | tgacgtgcga | caaatctatg | gtggccacca | gtgattacga | tgacttccat | 420 |
| aaactggtta | gcgttgtct | gctgaacggc | ctgctgggtg | cgaatgccca | gaagcgtaag | 480 |
| cgccactatc | gcgacgccct | gattgaaaac | gtgtcgagca | aactgcatgc | acacgctcgt | 540 |
| gatcatccgc | aggaaccggt | caattttcgc | gcaatcttcg | aacacgaact | gtttggcgtg | 600 |
| gcgctgaaac | aagccttcgg | caaggatgtt | gaatcgattt | acgtcaaaga | actgggcgtg | 660 |
| accctgagca | agacgaaat | ctttaaggtc | ctggtgcatg | atatgatgga | aggtgcaatt | 720 |
| gacgttgatt | ggcgtgattt | ctttccgtat | ctgaaatgga | ttccgaacaa | gtcattcgaa | 780 |
| gctcgcattc | agcaaaaaca | caagcgtcgc | ctggcagtga | tgaacgctct | gattcaggat | 840 |
| cgtctgaaac | aaaatggctc | tgaaagtgat | gacgattgct | atctgaattt | tctgatgtcc | 900 |
| gaagcaaaaa | ccctgacgaa | ggaacagatt | gctatcctgg | tttgggaaac | cattatcgaa | 960 |
| acggcggaca | ccacgctggt | caccacggaa | tgggcgatct | acgaactggc | caagcatccg | 1020 |
| agcgttcagg | atcgcctgtg | caaagaaatt | caaaacgtct | gtggcggtga | aaaatttaag | 1080 |
| gaagaacagc | tgtcgcaagt | gccgtatctg | aatggtgttt | ccacgaaaac | cctgcgtaaa | 1140 |
| tatagcccgg | caccgctggt | cccgatccgt | tacgcccatg | aagatacccca | gattggcggt | 1200 |
| tatcacgtgc | cggcaggcag | tgaaattgct | atcaacattt | acggttgcaa | tatggacaaa | 1260 |
| aagcgttggg | aacgcccgga | agattggtgg | ccggaacgtt | ttctggacga | tggcaaatat | 1320 |
| gaaacctctg | atctgcataa | gacgatgcg | ttcggtgcag | gtaaacgtgt | gtgtgcaggt | 1380 |
| gcactgcaag | caagtctgat | ggcaggcatc | gctattggtc | gtctggtgca | agaatttgaa | 1440 |
| tggaaactgc | gcgacggcga | agaagaaaac | gttgatacct | atggtctgac | gtcccagaaa | 1500 |
| ctgtacccgc | tgatggccat | tatcaatccg | cgtcgctca | | | 1539 |

<210> SEQ ID NO 37
<211> LENGTH: 513
<212> TYPE: PRT
<213> ORGANISM: Stevia rebaudiana

<400> SEQUENCE: 37

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

```
Leu Lys Ser Tyr Thr Ser Ala Arg Ser Gln Ser Asn His Leu Pro
        35                  40                  45

Arg Val Pro Glu Val Pro Gly Val Pro Leu Leu Gly Asn Leu Leu Gln
50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
        210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
        370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
```

```
                    450                 455                 460
Ala Leu Leu Thr Ala Ser Ile Gly Ile Gly Arg Met Val Gln Glu Phe
465                 470                 475                 480

Glu Trp Lys Leu Lys Asp Met Thr Gln Glu Val Asn Thr Ile Gly
                    485                 490                 495

Leu Thr Thr Gln Met Leu Arg Pro Leu Arg Ala Ile Ile Lys Pro Arg
                500                 505                 510

Ile

<210> SEQ ID NO 38
<211> LENGTH: 501
<212> TYPE: PRT
<213> ORGANISM: Stevia rebaudiana

<400> SEQUENCE: 38

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
                20                  25                  30

Asn His Leu Pro Arg Val Pro Glu Val Pro Gly Val Pro Leu Leu Gly
            35                  40                  45

Asn Leu Leu Gln Leu Lys Glu Lys Lys Pro Tyr Met Thr Phe Thr Arg
50                  55                  60

Trp Ala Ala Thr Tyr Gly Pro Ile Tyr Ser Ile Lys Thr Gly Ala Thr
65                  70                  75                  80

Ser Met Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
                100                 105                 110

Val Leu Thr Ala Asp Lys Thr Met Val Ala Met Ser Asp Tyr Asp Asp
            115                 120                 125

Tyr His Lys Thr Val Lys Arg His Ile Leu Thr Ala Val Leu Gly Pro
            130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
            195                 200                 205

Leu Lys Ile Thr Met Asn Arg Asp Glu Ile Phe Gln Val Leu Val Val
210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
            275                 280                 285

Leu Leu Ser Glu Ala Gln Thr Leu Thr Asp Gln Gln Leu Leu Met Ser
290                 295                 300

Leu Trp Glu Pro Ile Ile Glu Ser Ser Asp Thr Thr Met Val Thr Thr
```

Glu Trp Ala Met Tyr Glu Leu Ala Lys Asn Pro Lys Leu Gln Asp Arg
305                 310                 315                 320

Leu Tyr Arg Asp Ile Lys Ser Val Cys Gly Ser Glu Lys Ile Thr Glu
        325                 330                 335

Glu His Leu Ser Gln Leu Pro Tyr Ile Thr Ala Ile Phe His Glu Thr
                340                 345                 350

Leu Arg Arg His Ser Pro Val Pro Ile Ile Pro Leu Arg His Val His
            355                 360                 365

Glu Asp Thr Val Leu Gly Gly Tyr His Val Pro Ala Gly Thr Glu Leu
370                 375                 380

Ala Val Asn Ile Tyr Gly Cys Asn Met Asp Lys Asn Val Trp Glu Asn
        385                 390                 395                 400

Pro Glu Glu Trp Asn Pro Glu Arg Phe Met Lys Glu Asn Glu Thr Ile
                405                 410                 415

Asp Phe Gln Lys Thr Met Ala Phe Gly Gly Gly Lys Arg Val Cys Ala
            420                 425                 430

Gly Ser Leu Gln Ala Leu Leu Thr Ala Ser Ile Gly Ile Gly Arg Met
435                 440                 445

Val Gln Glu Phe Glu Trp Lys Leu Lys Asp Met Thr Gln Glu Glu Val
        450                 455                 460

Asn Thr Ile Gly Leu Thr Thr Gln Met Leu Arg Pro Leu Arg Ala Ile
465                 470                 475                 480

Ile Lys Pro Arg Ile
                485                 490                 495

500

<210> SEQ ID NO 39
<211> LENGTH: 1503
<212> TYPE: DNA
<213> ORGANISM: Stevia rebaudiana

<400> SEQUENCE: 39
atggctctgt tattagcagt ttttgccgtc gctctggcgg tagcactgat cttctggtat     60
ctgaaatctt acactagcgc gcgccgctct cagtccaacc acctgccgcg tgtgccggaa    120
gttccgggtg tgccactgct gggcaacctg ctgcaactga agaaaagaa accgtacatg     180
acctttaccc gctgggcagc gacttatggt cctatctaca gcattaaaac cggcgctacg    240
tctatggttg tggttcttc aacgaaatc gcgaaagaag ccctggtgac tcgtttccag     300
tccattagca cccgcaacct gtccaaagcg ctgaaggttc tgacggctga caagactatg    360
gtggctatga gcgactatga tgactaccac aaaaccgtta acgtcacat cctgaccgca    420
gtactgggtc cgaacgcaca gaaaaaacat cgcatccacc gcacattat gatggataac    480
atctccacgc agctgcatga gttcgttaag aacaatccag aacaggaaga ggtagatctg    540
cgtaaaattt ttcagtccga actgttcggt ctggctatgc gtcaggcgct gggcaaagac    600
gttgaaagcc tgtatgtcga agacctgaaa attaccatga ccgtgatga gatcttccag    660
gttctggttg tagatccgat gatgggcgcc atcgacgtgg attggcgtga cttctttccg    720
tacctgaaat gggtcccgaa caagaagttc gaaaacacca tccagcaaat gtacatccgt    780
cgtgaagcgg tgatgaaaag cctgatcaaa gaacacaaaa agcgtattgc ttctggtgag    840
aaactgaact cctacatcga ttatctgctg tccgaagcgc agaccctgac cgaccaacag    900
ctgctgatgt ctctggtggga accgattatc gaaagcagcg acaccactat ggtcactacc    960
gaatgggcaa tgtatgagct ggccaaaaac ccgaaactgc aggatcgtct gtaccgtgac   1020

```
atcaaaagcg tttgcggctc cgagaaaatc actgaagaac acctgtctca gctgccgtac    1080
atcactgcta ttttccacga aaccctgcgt cgccattctc cggttccgat cattccgctg    1140
cgtcacgttc acgaagatac tgtgctgggt ggttaccatg taccggcagg cactgaactg    1200
gctgtcaaca tctacggctg taacatggat aaaaacgttt gggagaatcc tgaagaatgg    1260
aacccggaac gcttcatgaa agagaacgaa accatcgact tccagaaaac gatggctttc    1320
ggcggtggta acgtgtgtg cgcaggttct ctgcaggcgc tgctgacggc gtccattggt    1380
atcggtcgca tggtacagga atttgaatgg aagctgaaag acatgaccca agaagaggtg    1440
aataccattg gtctgactac ccagatgctg cgtccactgc gtgcaatcat caaacctcgt    1500
att                                                                  1503
```

```
<210> SEQ ID NO 40
<211> LENGTH: 546
<212> TYPE: PRT
<213> ORGANISM: Physcomitrella patens

<400> SEQUENCE: 40
```

Met Ala Lys His Leu Ala Thr Gln Leu Leu Gln Gln Trp Asn Glu Ala
1               5                   10                  15

Leu Lys Thr Met Pro Pro Gly Phe Arg Thr Ala Gly Lys Ile Leu Val
            20                  25                  30

Trp Glu Glu Leu Ala Ser Asn Lys Val Leu Ile Thr Ile Ala Leu Ala
        35                  40                  45

Trp Val Leu Leu Phe Val Ala Arg Thr Cys Leu Arg Asn Lys Lys Arg
50                  55                  60

Leu Pro Pro Ala Ile Pro Gly Gly Leu Pro Val Leu Gly Asn Leu Leu
65                  70                  75                  80

Gln Leu Thr Glu Lys Lys Pro His Arg Thr Phe Thr Ala Trp Ser Lys
                85                  90                  95

Glu His Gly Pro Ile Phe Thr Ile Lys Val Gly Ser Val Pro Gln Ala
            100                 105                 110

Val Val Asn Asn Ser Glu Ile Ala Lys Glu Val Leu Val Thr Lys Phe
        115                 120                 125

Ala Ser Ile Ser Lys Arg Gln Met Pro Met Ala Leu Arg Val Leu Thr
130                 135                 140

Arg Asp Lys Thr Met Val Ala Met Ser Asp Tyr Gly Glu Glu His Arg
145                 150                 155                 160

Met Leu Lys Lys Leu Val Met Thr Asn Leu Leu Gly Pro Thr Thr Gln
                165                 170                 175

Asn Lys Asn Arg Ser Leu Arg Asp Asp Ala Leu Ile Gly Met Ile Glu
            180                 185                 190

Gly Val Leu Ala Glu Leu Lys Ala Ser Pro Thr Ser Pro Lys Val Val
        195                 200                 205

Asn Val Arg Asp Tyr Val Gln Arg Ser Leu Phe Pro Phe Ala Leu Gln
    210                 215                 220

Gln Val Phe Gly Tyr Ile Pro Asp Gln Val Glu Val Leu Glu Leu Gly
225                 230                 235                 240

Thr Cys Val Ser Thr Trp Asp Met Phe Asp Ala Leu Val Val Ala Pro
                245                 250                 255

Leu Ser Ala Val Ile Asn Val Asp Trp Arg Asp Phe Phe Pro Ala Leu
            260                 265                 270

Arg Trp Ile Pro Asn Arg Ser Val Glu Asp Leu Val Arg Thr Val Asp

```
                    275                 280                 285
    Phe Lys Arg Asn Ser Ile Met Lys Ala Leu Ile Arg Ala Gln Arg Met
    290                 295                 300

Arg Leu Ala Asn Leu Lys Glu Pro Pro Arg Cys Tyr Ala Asp Ile Ala
305                 310                 315                 320

Leu Thr Glu Ala Thr His Leu Thr Glu Lys Gln Leu Glu Met Ser Leu
                    325                 330                 335

Trp Glu Pro Ile Ile Glu Ser Ala Asp Thr Thr Leu Val Thr Ser Glu
                340                 345                 350

Trp Ala Met Tyr Glu Ile Ala Lys Asn Pro Asp Cys Gln Asp Arg Leu
                355                 360                 365

Tyr Arg Glu Ile Val Ser Val Ala Gly Thr Glu Arg Met Val Thr Glu
                370                 375                 380

Asp Asp Leu Pro Asn Met Pro Tyr Leu Gly Ala Ile Ile Lys Glu Thr
385                 390                 395                 400

Leu Arg Lys Tyr Thr Pro Val Pro Leu Ile Pro Ser Arg Phe Val Glu
                    405                 410                 415

Glu Asp Ile Thr Leu Gly Gly Tyr Asp Ile Pro Lys Gly Tyr Gln Ile
                    420                 425                 430

Leu Val Asn Leu Phe Ala Ile Ala Asn Asp Pro Ala Val Trp Ser Asn
                435                 440                 445

Pro Glu Lys Trp Asp Pro Glu Arg Met Leu Ala Asn Lys Lys Val Asp
                450                 455                 460

Met Gly Phe Arg Asp Phe Ser Leu Met Pro Phe Gly Ala Gly Lys Arg
465                 470                 475                 480

Met Cys Ala Gly Ile Thr Gln Ala Met Phe Ile Ile Pro Met Asn Val
                    485                 490                 495

Ala Ala Leu Val Gln His Cys Glu Trp Arg Leu Ser Pro Gln Glu Ile
                    500                 505                 510

Ser Asn Ile Asn Asn Lys Ile Glu Asp Val Val Tyr Leu Thr Thr His
                515                 520                 525

Lys Leu Ser Pro Leu Ser Cys Glu Ala Thr Pro Arg Ile Ser His Arg
                530                 535                 540

Leu Pro
    545

<210> SEQ ID NO 41
<211> LENGTH: 548
<212> TYPE: PRT
<213> ORGANISM: Physcomitrella patens

<400> SEQUENCE: 41

Met Ala Leu Leu Leu Ala Val Phe Thr Gln Leu Leu Gln Gln Trp Asn
    1               5                   10                  15

Glu Ala Leu Lys Thr Met Pro Pro Gly Phe Arg Thr Ala Gly Lys Ile
                    20                  25                  30

Leu Val Trp Glu Glu Leu Ala Ser Asn Lys Val Leu Ile Thr Ile Ala
                35                  40                  45

Leu Ala Trp Val Leu Leu Phe Val Ala Arg Thr Cys Leu Arg Asn Lys
                50                  55                  60

Lys Arg Leu Pro Pro Ala Ile Pro Gly Gly Leu Pro Val Leu Gly Asn
65                  70                  75                  80

Leu Leu Gln Leu Thr Glu Lys Lys Pro His Arg Thr Phe Thr Ala Trp
                    85                  90                  95
```

-continued

```
Ser Lys Glu His Gly Pro Ile Phe Thr Ile Lys Val Gly Ser Val Pro
            100                 105                 110

Gln Ala Val Val Asn Asn Ser Glu Ile Ala Lys Glu Val Leu Val Thr
        115                 120                 125

Lys Phe Ala Ser Ile Ser Lys Arg Gln Met Pro Met Ala Leu Arg Val
    130                 135                 140

Leu Thr Arg Asp Lys Thr Met Val Ala Met Ser Asp Tyr Gly Glu Glu
145                 150                 155                 160

His Arg Met Leu Lys Lys Leu Val Met Thr Asn Leu Leu Gly Pro Thr
                165                 170                 175

Thr Gln Asn Lys Asn Arg Ser Leu Arg Asp Asp Ala Leu Ile Gly Met
            180                 185                 190

Ile Glu Gly Val Leu Ala Glu Leu Lys Ala Ser Pro Thr Ser Pro Lys
        195                 200                 205

Val Val Asn Val Arg Asp Tyr Val Gln Arg Ser Leu Phe Pro Phe Ala
    210                 215                 220

Leu Gln Gln Val Phe Gly Tyr Ile Pro Asp Gln Val Glu Val Leu Glu
225                 230                 235                 240

Leu Gly Thr Cys Val Ser Thr Trp Asp Met Phe Asp Ala Leu Val Val
                245                 250                 255

Ala Pro Leu Ser Ala Val Ile Asn Val Asp Trp Arg Asp Phe Phe Pro
            260                 265                 270

Ala Leu Arg Trp Ile Pro Asn Arg Ser Val Glu Asp Leu Val Arg Thr
        275                 280                 285

Val Asp Phe Lys Arg Asn Ser Ile Met Lys Ala Leu Ile Arg Ala Gln
    290                 295                 300

Arg Met Arg Leu Ala Asn Leu Lys Glu Pro Pro Arg Cys Tyr Ala Asp
305                 310                 315                 320

Ile Ala Leu Thr Glu Ala Thr His Leu Thr Glu Lys Gln Leu Glu Met
                325                 330                 335

Ser Leu Trp Glu Pro Ile Ile Glu Ser Ala Asp Thr Thr Leu Val Thr
            340                 345                 350

Ser Glu Trp Ala Met Tyr Glu Ile Ala Lys Asn Pro Asp Cys Gln Asp
        355                 360                 365

Arg Leu Tyr Arg Glu Ile Val Ser Val Ala Gly Thr Glu Arg Met Val
    370                 375                 380

Thr Glu Asp Asp Leu Pro Asn Met Pro Tyr Leu Gly Ala Ile Ile Lys
385                 390                 395                 400

Glu Thr Leu Arg Lys Tyr Thr Pro Val Pro Leu Ile Pro Ser Arg Phe
                405                 410                 415

Val Glu Glu Asp Ile Thr Leu Gly Gly Tyr Asp Ile Pro Lys Gly Tyr
            420                 425                 430

Gln Ile Leu Val Asn Leu Phe Ala Ile Ala Asn Asp Pro Ala Val Trp
        435                 440                 445

Ser Asn Pro Glu Lys Trp Asp Pro Glu Arg Met Leu Ala Asn Lys Lys
    450                 455                 460

Val Asp Met Gly Phe Arg Asp Phe Ser Leu Met Pro Phe Gly Ala Gly
465                 470                 475                 480

Lys Arg Met Cys Ala Gly Ile Thr Gln Ala Met Phe Ile Ile Pro Met
                485                 490                 495

Asn Val Ala Ala Leu Val Gln His Cys Glu Trp Arg Leu Ser Pro Gln
            500                 505                 510

Glu Ile Ser Asn Ile Asn Asn Lys Ile Glu Asp Val Val Tyr Leu Thr
```

515                 520                 525
Thr His Lys Leu Ser Pro Leu Ser Cys Glu Ala Thr Pro Arg Ile Ser
            530                 535                 540

His Arg Leu Pro
545

<210> SEQ ID NO 42
<211> LENGTH: 1644
<212> TYPE: DNA
<213> ORGANISM: Physcomitrella patens

<400> SEQUENCE: 42

| | | | | | |
|---|---|---|---|---|---|
| atggctctgt | tattagcagt | ttttacgcaa | ctgctgcaac | aatggaatga | agctctgaag | 60 |
| acgatgccgc | cgggttttcg | caccgctggc | aaaattctgg | tgtgggaaga | actggcaagc | 120 |
| aataaagttc | tgattacgat | cgcactggct | tgggtcctgc | tgtttgtggc | tcgtacctgc | 180 |
| ctgcgcaata | aaaagcgtct | gccgccggca | atcccgggcg | gtctgccggt | gctgggcaac | 240 |
| ctgctgcagc | tgacggaaaa | gaaaccgcat | cgtaccttta | cggcgtggag | caaggaacac | 300 |
| ggcccgattt | tcaccatcaa | agtcggttcg | gtgccgcagg | ctgtggttaa | caatagcgaa | 360 |
| attgcgaaag | aagtcctggt | gaccaagttc | gccagcatct | ctaaacgtca | aatgccgatg | 420 |
| gcactgcgcg | tcctgacgcg | tgataaaacg | atggtggcta | tgtctgacta | tggcgaagaa | 480 |
| catcgcatgc | tgaaaaagct | ggtgatgacg | aatctgctgg | gtccgaccac | gcagaacaaa | 540 |
| aatcgtagtc | tgcgcgatga | cgcactgatt | ggcatgatcg | aaggtgttct | ggcggaactg | 600 |
| aaggccagtc | cgacctcccc | gaaagtcgtg | aacgttcgcg | attatgtcca | gcgttctctg | 660 |
| tttccgttcg | cgctgcagca | agtgtttggc | tacattccgg | atcaagttga | agtcctggaa | 720 |
| ctgggcacgt | gtgtttctac | ctgggatatg | ttcgacgcac | tggttgtcgc | tccgctgagt | 780 |
| gcggttatta | acgtcgattg | gcgtgacttt | ttccggccc | tgcgctggat | tccgaatcgt | 840 |
| tccgtggaag | atctggtgcg | caccgttgac | tttaagcgta | actcaattat | gaaagccctg | 900 |
| atccgtgcac | agcgtatgcg | cctggctaac | ctgaaggaac | cgccgcgctg | ctacgcagat | 960 |
| attgctctga | ccgaagcgac | gcacctgacc | gaaaaacaac | tggaaatgag | tctgtgggaa | 1020 |
| ccgattatcg | aatccgccga | taccacgctg | gtgacctcag | aatgggctat | gtatgaaatt | 1080 |
| gcgaaaaatc | cggattgtca | ggaccgtctg | taccgcgaaa | tcgtgtccgt | gccggcacg | 1140 |
| gaacgcatgg | ttaccgaaga | tgacctgccg | aacatgccgt | atctgggtgc | aattatcaaa | 1200 |
| gaaacgctgc | gcaagtacac | cccggttccg | ctgattccga | gtcgttttgt | cgaagaagat | 1260 |
| atcaccctgg | gcggttatga | cattccgaaa | ggttaccaga | tcctggtcaa | cctgttcgcg | 1320 |
| attgccaatg | atccggccgt | ttggtcgaac | ccggaaaaat | gggacccgga | acgcatgctg | 1380 |
| gcaaataaaa | aggtggatat | gggctttcgt | gacttcagcc | tgatgccgtt | tggcgccggt | 1440 |
| aaacgcatgt | gcgccggtat | cacccaagca | atgttcatta | tcccgatgaa | tgtggcggcc | 1500 |
| ctggttcagc | attgtgaatg | gcgcctgagc | cgcaagaaa | tctctaacat | caacaacaag | 1560 |
| atcgaagatg | tggtttacct | gaccacgcat | aaactgtcac | cgctgtcgtg | cgaagcaacc | 1620 |
| ccgcgtatca | gccaccgtct | gccg | | | | 1644 |

<210> SEQ ID NO 43
<211> LENGTH: 1049
<212> TYPE: PRT
<213> ORGANISM: Bacillus megaterium

<400> SEQUENCE: 43

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
            35                  40                  45

Val Thr Arg Tyr Leu Ser Ser Gln Arg Leu Ile Lys Glu Ala Cys Asp
        50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415
```

```
Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
```

```
                835                840                845
Val Val Ser Gly Glu Ala Trp Ser Gly Tyr Gly Glu Tyr Lys Gly Ile
            850                855                860
Ala Ser Asn Tyr Leu Ala Glu Leu Gln Glu Gly Asp Thr Ile Thr Cys
865                870                875                880
Phe Ile Ser Thr Pro Gln Ser Glu Phe Thr Leu Pro Lys Asp Pro Glu
                885                890                895
Thr Pro Leu Ile Met Val Gly Pro Gly Thr Gly Val Ala Pro Phe Arg
            900                905                910
Gly Phe Val Gln Ala Arg Lys Gln Leu Lys Glu Gln Gly Gln Ser Leu
                915                920                925
Gly Glu Ala His Leu Tyr Phe Gly Cys Arg Ser Pro His Glu Asp Tyr
            930                935                940
Leu Tyr Gln Glu Glu Leu Glu Asn Ala Gln Ser Glu Gly Ile Ile Thr
945                950                955                960
Leu His Thr Ala Phe Ser Arg Met Pro Asn Gln Pro Lys Thr Tyr Val
                965                970                975
Gln His Val Met Glu Gln Asp Gly Lys Lys Leu Ile Glu Leu Leu Asp
            980                985                990
Gln Gly Ala His Phe Tyr Ile Cys  Gly Asp Gly Ser Gln  Met Ala Pro
                995                1000               1005
Ala Val  Glu Ala Thr Leu Met  Lys Ser Tyr Ala Asp  Val His Gln
     1010                1015                1020
Val Ser  Glu Ala Asp Ala Arg  Leu Trp Leu Gln Gln  Leu Glu Glu
     1025                1030                1035
Lys Gly  Arg Tyr Ala Lys Asp  Val Trp Ala Gly
     1040                1045

<210> SEQ ID NO 44
<211> LENGTH: 3150
<212> TYPE: DNA
<213> ORGANISM: Bacillus megaterium

<400> SEQUENCE: 44
atgacgatta aagaaatgcc gcaaccgaag acgtttggcg aactgaagaa cctgccgctg      60
ctgaacacgg ataagccggt gcaagccctg atgaagattg ctgatgaact gggcgaaatc     120
tttaaattcg aagcgccggg tcgtgtgacc cgttatctga gcagccagcg tctgattaaa     180
gaagcctgcg atgaatcgcg cttttgacaag aacctgagcc aggcactgaa atttgttcgt     240
gatttcgcag tgacggtct ggccaccagc tggacgcatg aaaagaactg aaaaaggcc      300 cacaatattc tgctgccgtc gttcagccag caagcaatga aaggctacca tgctatgatg     360
gtcgatatcg cggttcagct ggtccaaaaa tgggaacgtc tgaatgcgga cgaacacatt     420
gaagtgccgg aagatatgac ccgcctgacg ctggacacca tcggtctgtg tggctttaac     480
tatcgtttta attcgttcta ccgcgatcag ccgcatccgt tcattaccag catggtgcgt     540
gcgctggacg aagccatgaa caaactgcag cgtgcaaacc cggatgaccc ggcgtatgat     600
gaaaacaagc gtcagtttca agaagacatc aaagtgatga atgatctggt tgacaagatt     660
atcgcagatc gcaaagcgag cggcgaacag tcagatgacc tgctgacgca catgctgaac     720
ggcaaagacc cggaaaccgg tgaaccgctg gatgacgaaa acatccgtta tcagatcatc     780
acctttctga tcgcaggcca tgaaaccaca tcggtctgc tgagctttgc gctgtacttc     840
ctggtcaaga acccgcacgt gctgcagaaa gcggccgaag aagcagctcg tgtgctggtt     900
```

```
gatccggttc cgtcgtataa acaggtcaag caactgaaat acgtgggtat ggttctgaat     960
gaagcgctgc gcctgtggcc gacgattccg gcatttagcc tgtatgctaa ggaagatacc    1020
gttctgggcg gtgaatacccc gctggaaaaa ggcgatgaac tgatggtcct gattccgcag   1080
ctgcatcgcg acaaaaccat ctggggtgat gacgtggaag aatttcgccc ggaacgcttc    1140
gaaaacccga gcgcgattcc gcagcatgcc tttaaaccgt tcggcaatgg tcaacgtgcg    1200
tgcatcggcc agcaatttgc gctgcacgaa gccacgctgg ttctgggtat gatgctgaaa    1260
cattttgatt tcgaagacca caccaactat gaactggata ttaaggaaac cctgacgctg    1320
aaaccggaag gcttcgtggt taaagcgaag tctaaaaaga ttccgctggg cggtatcccg    1380
tctccgagta cggaacagag tgccaaaaag gtccgtaaaa aggcggaaaa cgcccataat    1440
accccgctgc tggtgctgta tggttctaac atgggcacgg cagaaggcac cgctcgcgat    1500
ctggcagaca ttgctatgtc taaaggtttt gcgccgcagg tggccacgct ggatagtcat    1560
gcaggcaatc tgccgcgtga aggtgctgtc ctgatcgtga ccgcaagcta caacggtcac    1620
ccgccggata atgcgaagca gttcgttgat tggctggacc aagcgtcggc cgatgaagtt    1680
aaaggtgtcc gctatagcgt gtttggctgt ggtgacaaga actgggctac cacgtaccag    1740
aaagttccgg cgttcattga tgaaacgctg gcggccaaag gcgcagaaaa tatcgctgat    1800
cgtggtgaag cagacgcttc cgatgacttt gaaggcacct atgaagaatg gcgcgaacac    1860
atgtggtcgg atgtggcagc ttacttcaac ctggatattg aaaacagcga agacaataaa    1920
tccaccctgt cactgcagtt tgttgatagt gcggccgaca tgccgctggc aaagatgcac    1980
ggcgcttttct ccacgaatgt cgtggcttca aaagaactgc agcaaccggg ttcggcacgt   2040
agcacccgcc atctggaaat tgaactgccg aaagaagcca gctatcagga aggcgatcac    2100
ctgggtgtga ttccgcgtaa ctacgaaggc atcgtgaatc gtgttacggc ccgctttggt    2160
ctggatgcat cccagcaaat ccgcctggaa gcggaagaag aaaagctggc gcatctgccg    2220
ctggccaaaa ccgtctcagt ggaagaactg ctgcagtatg tggaactgca agatccggtt    2280
acccgtacgc agctgcgtgc gatggcggct aagaccgtct gcccgccgca caaagtggaa    2340
ctggaagctc tgctggaaaa gcaggcgtat aaagaacaag tgctggcgaa acgcctgacc    2400
atgctggaac tgctggaaaa gtacccggcc tgtgaaatga agttctctga atttatcgca    2460
ctgctgccgt ctatccgtcc gcgttattac agtattagtt cctcaccgcg tgtggatgaa    2520
aaacaggcca gtatcaccgt ttctgttgtc agtggcgaag catggtctgg ctatggtgaa    2580
tacaagggta tcgcaagtaa ctacctggct gaactgcagg aaggcgatac cattacgtgc    2640
tttatctcta cgccgcaaag tgaatttacc ctgccgaaag accggaaaac gccgctgatc    2700
atggttggcc cgggcaccgg tgtcgcaccg tttcgtggtt tcgtgcaggc acgcaagcaa    2760
ctgaaagaac agggccaatc cctgggtgaa gcgcatctgt attttggctg tcgctcaccg    2820
cacgaagatt atctgtacca ggaagaactg gaaaacgcgc aatccgaagg tattatcacg    2880
ctgcataccg ccttctcacg tatgccgaat cagccgaaaa cctacgtcca gcacgtgatg    2940
gaacaagatg gcaaaaagct gattgaactg ctggaccagg gtgcgcattt ttatatctgc    3000
ggtgatggca gccaaatggc accggcagtg gaagcaaccc tgatgaaatc ctacgcagat    3060
gttcaccagg tctcagaagc agacgctcgt ctgtggctgc agcaactgga agaaaagggc    3120
cgctatgcga aagatgtttg ggccggttaa                                      3150

<210> SEQ ID NO 45
<211> LENGTH: 396
```

```
<212> TYPE: PRT
<213> ORGANISM: Pleurotus sapidus

<400> SEQUENCE: 45
```

| | | | | | | | | | | | | | | |
|---|---|---|---|---|---|---|---|---|---|---|---|---|---|---|
|Met|Arg|Tyr|Gly|Cys|Ala|Ala|Val|Ala|Leu|Phe|Tyr|Leu|Thr|Ala|Met|
|1| | | |5| | | | |10| | | | |15|

Met Arg Tyr Gly Cys Ala Ala Val Ala Leu Phe Tyr Leu Thr Ala Met
1               5                   10                  15

Gly Lys Leu His Pro Leu Ala Ile Ile Pro Asp Tyr Lys Gly Ser Met
                20                  25                  30

Ala Ala Ser Val Thr Ile Phe Asn Lys Arg Thr Asn Pro Leu Asp Ile
            35                  40                  45

Ser Val Asn Gln Ala Asn Asp Trp Pro Trp Arg Tyr Ala Lys Thr Cys
50                  55                  60

Val Leu Ser Ser Asp Trp Ala Leu His Glu Met Ile Ile His Leu Asn
65                  70                  75                  80

Asn Thr His Leu Val Glu Glu Ala Val Ile Val Ala Ala Gln Arg Lys
                85                  90                  95

Leu Ser Pro Ser His Ile Val Phe Arg Leu Leu Glu Pro His Trp Val
            100                 105                 110

Val Thr Leu Ser Leu Asn Ala Leu Ala Arg Ser Val Leu Ile Pro Glu
            115                 120                 125

Val Ile Val Pro Ile Ala Gly Phe Ser Ala Pro His Ile Phe Gln Phe
            130                 135                 140

Ile Arg Glu Ser Phe Thr Asn Phe Asp Trp Lys Ser Leu Tyr Val Pro
145                 150                 155                 160

Ala Asp Leu Glu Ser Arg Gly Phe Pro Val Asp Gln Leu Asn Ser Pro
                165                 170                 175

Lys Phe His Asn Tyr Ala Tyr Ala Arg Asp Ile Asn Asp Met Trp Thr
            180                 185                 190

Thr Leu Lys Lys Phe Val Ser Ser Val Leu Gln Asp Ala Gln Tyr Tyr
            195                 200                 205

Pro Asp Asp Ala Ser Val Ala Gly Asp Thr Gln Ile Gln Ala Trp Cys
            210                 215                 220

Asp Glu Met Arg Ser Gly Met Gly Ala Gly Met Thr Asn Phe Pro Glu
225                 230                 235                 240

Ser Ile Thr Thr Val Asp Asp Leu Val Asn Met Val Thr Met Cys Ile
                245                 250                 255

His Ile Ala Ala Pro Gln His Thr Ala Val Asn Tyr Leu Gln Gln Tyr
            260                 265                 270

Tyr Gln Thr Phe Val Ser Asn Lys Pro Ser Ala Leu Phe Ser Pro Leu
            275                 280                 285

Pro Thr Ser Ile Ala Gln Leu Gln Lys Tyr Thr Glu Ser Asp Leu Met
290                 295                 300

Ala Ala Leu Pro Leu Asn Ala Lys Arg Gln Trp Leu Leu Met Ala Gln
305                 310                 315                 320

Ile Pro Tyr Leu Leu Ser Met Gln Val Gln Glu Asp Glu Asn Ile Val
                325                 330                 335

Thr Tyr Ala Ala Asn Ala Ser Thr Asp Lys Asp Pro Ile Ile Ala Ser
            340                 345                 350

Ala Gly Arg Gln Leu Ala Asp Leu Lys Lys Leu Ala Ala Val Phe
            355                 360                 365

Leu Val Asn Ser Ala Gln Leu Asp Asp Gln Asn Thr Pro Tyr Asp Val
            370                 375                 380

Leu Ala Pro Glu Gln Leu Ala Asn Ala Ile Val Ile
385                 390                 395

<210> SEQ ID NO 46
<211> LENGTH: 1191
<212> TYPE: DNA
<213> ORGANISM: Pleurotus sapidus

<400> SEQUENCE: 46

```
atgcgttatg ctgtgctgc tgtggctctg ttctatctga ccgctatggg caaactgcac      60
ccgctggcta ttatcccgga ctacaagggt agcatggcgg cctctgtcac cattttaaac     120
aaacgtacga atccgctgga tatcagcgtt aaccaggcaa atgactggcc gtggcgctat     180
gctaagacgt gcgtgctgag cagcgattgg gcgctgcatg aaatgattat ccacctgaac     240
aatacccatc tggtggaaga agccgtcatt gtggcagctc agcgtaaact gtcaccgtcg     300
cacatcgttt tcgcctgct ggaaccgcat gggtggtta ccctgtcgct gaacgcactg      360
gctcgtagcg tgctgatccc ggaagttatt gtcccgatcg cgggtttctc tgccccgcac     420
attttcagt tcatccgcga atcttttacc aatttcgatt ggaaaagtct gtacgtcccg      480
gcggacctgg aatcgcgtgg ctttccggtg atcagctga acagcccgaa gttccataat      540
tatgcgtacg cccgcgatat caacgacatg tggaccacgc tgaaaaagtt tgtgagttcc     600
gttctgcagg atgcccaata ttacccggat gacgcaagtg tggctggtga tacgcagatt     660
caagcatggt gcgacgaaat gcgttccggc atgggtgcgg gcatgaccaa cttcccggaa     720
tcaatcacca cggttgatga cctggtcaat atggtgacca tgtgtattca catcgcggcc     780
ccgcagcata cggcggttaa ctatctgcag caatactacc aaaccttcgt cagtaacaag     840
ccgtccgcac tgttctcacc gctgccgacc tctattgctc agctgcaaaa atacacggaa     900
agtgatctga tggcagctct gccgctgaac gcgaagcgtc agtggctgct gatggcccaa     960
attccgtatc tgctgtcgat gcaggtgcaa gaagatgaaa acatcgttac ctacgcggcc    1020
aatgcgtcca cggataaaga cccgattatc gcatcagctg ccgccagct ggcagctgac    1080
ctgaaaaagc tggcggccgt ttttctggtc aactcagccc agctggatga ccaaaatacc    1140
ccgtatgatg tgctggcacc ggaacagctg gcgaatgcca ttgttatcta a             1191
```

<210> SEQ ID NO 47
<211> LENGTH: 640
<212> TYPE: PRT
<213> ORGANISM: Pleurotus ostreatus

<400> SEQUENCE: 47

Met Ala Pro Thr Met Ser Leu Ser Arg Ser Ala Leu Lys Asn Val His
1               5                   10                  15

Leu Pro Tyr Met Val Gln His Pro Glu Pro Thr Asp Cys Ser Thr Ala
            20                  25                  30

Met Lys His Ala Ala Glu Gly Tyr Asp Arg Ala Arg Gln Met Ile Ala
        35                  40                  45

Phe Leu Phe Asp Ile Leu Asp Tyr Glu Ser Ser Val Pro Gln Lys Phe
    50                  55                  60

Thr Pro Glu Glu Lys Lys Glu Lys Tyr Thr Trp Ser His Ser Asp Lys
65                  70                  75                  80

Phe Pro Pro His Leu Ala Ile Ile Pro Glu Asp Ile Asp Val Pro Ala
                85                  90                  95

Tyr Ile Ile Phe Ser Ile Val Arg Leu Val Gln Thr Leu Ser Ile Met
            100                 105                 110

Ser Gly Ile Gln Cys Asn Glu Arg Leu Ala Pro Gly Pro Glu Gln Asn

-continued

```
            115                 120                 125
Thr Met Glu Lys Leu Thr Lys Trp Asn Ala Glu Arg His Lys Asn Gln
    130                 135                 140
Gly Trp Val Lys Asp Met Phe Asn Glu Pro Asn Ile Gly Leu Arg Asn
145                 150                 155                 160
Asp Trp Tyr Thr Asp Ala Val Phe Ala Gln Gln Phe Phe Thr Gly Pro
                165                 170                 175
Asn Pro Thr Thr Ile Thr Leu Ala Ser Asp Thr Trp Met Lys Ala Phe
            180                 185                 190
Thr Glu Glu Ala Ala Ser Gln Gly Lys Arg Asp Leu Ile Ser Leu Phe
        195                 200                 205
Arg Ser Ala Pro Pro Asn Ser Phe Tyr Val Gln Asp Phe Ser Asp Phe
    210                 215                 220
Arg Ala Arg Met Gly Ala Lys Pro Asp Glu Leu Cys Ala Thr Ser
225                 230                 235                 240
Asp Gly Gly Val Thr Arg Tyr Gly Cys Ala Ala Val Ala Leu Phe Tyr
                245                 250                 255
Leu Pro Pro Thr Gly Glu Leu His Pro Leu Ala Ile Val Pro Asp Tyr
            260                 265                 270
Lys Gly Ser Met Ala Ala Ser Ile Thr Leu Phe Asn Lys Arg Val Asp
        275                 280                 285
Pro Ser Asp Ala Ser Val Asp Gln Ala Asn Asp Trp Pro Trp Arg Tyr
    290                 295                 300
Ala Lys Thr Cys Val Leu Ser Ala Asp Trp Val Leu His Glu Met Ile
305                 310                 315                 320
Ile His Leu Asn Asn Thr His Leu Val Gln Glu Ala Val Ile Val Ala
                325                 330                 335
Val Gln Arg Thr Leu Pro Asp Ser His Ile Val Phe Arg Leu Leu Lys
            340                 345                 350
Pro His Trp Val Val Thr Leu Ser Leu Asn Ala Gln Ala Arg Ser Val
        355                 360                 365
Leu Ile Pro Glu Val Ile Val Pro Ile Ala Gly Phe Ser Glu Leu Arg
    370                 375                 380
Ile Phe Gln Phe Val Gly His Ala Phe Thr Asn Phe Asp Trp Lys Ala
385                 390                 395                 400
Leu Tyr Val Pro Thr Asp Leu Glu Phe Arg Gly Phe Pro Leu Asp Arg
                405                 410                 415
Leu Asp Asp Asp Lys Phe His Asn Tyr Ala Tyr Ala Lys Asp Ile Lys
            420                 425                 430
Asp Met Trp Met Ala Leu Arg Lys Phe Val Ser Ser Val Leu Lys Asp
        435                 440                 445
Gly Lys Tyr Tyr Pro Asp Asp Ser Ala Val Ala Ala Asp Ala Gln Ile
    450                 455                 460
Gln Asp Trp Cys Asp Glu Met Arg Ser Glu Lys Gly Ala Gly Met Lys
465                 470                 475                 480
Lys Phe Pro Glu Ser Ile Ser Thr Leu Asp Asp Leu Ile Asp Met Val
                485                 490                 495
Thr Met Cys Ile His Ile Ala Ala Pro Gln His Thr Ala Val Asn Tyr
            500                 505                 510
Leu Gln Gln Tyr Tyr Gln Thr Phe Val Pro Asn Lys Pro Ser Ala Leu
        515                 520                 525
Phe Ser Pro Leu Pro Thr Leu Leu Ser Gln Leu Glu Ser Tyr Thr Glu
    530                 535                 540
```

| Ser | Asp | Leu | Met | Ala | Ala | Leu | Pro | Leu | Gly | Ala | Lys | Gln | Glu | Trp | Leu |
| 545 | | | | | 550 | | | | | 555 | | | | | 560 |

| Leu | Met | Ala | Gln | Val | Pro | Tyr | Leu | Leu | Ser | Lys | Glu | Val | Glu | Gln | Asp |
| | | | | 565 | | | | | 570 | | | | | 575 | |

| Gly | Asn | Ile | Val | Thr | Tyr | Ala | Gly | Thr | Ala | Ser | Asn | Asn | Glu | Asp | Pro |
| | | | 580 | | | | | 585 | | | | | 590 | | |

| Ile | Ile | Ala | Ala | Ala | Gly | Lys | Glu | Leu | Ser | Ala | Asp | Leu | Val | Ile | Leu |
| | | | 595 | | | | | 600 | | | | | 605 | | |

| Ala | Gly | Val | Phe | Leu | Lys | Asn | Ser | Glu | Lys | Leu | Asp | Asp | Gln | Asn | Thr |
| | 610 | | | | | 615 | | | | | 620 | | | | |

| Ala | Tyr | Asn | Val | Leu | Ala | Pro | Asp | Gln | Leu | Ala | Asn | Ala | Ile | Val | Ile |
| 625 | | | | | 630 | | | | | 635 | | | | | 640 |

<210> SEQ ID NO 48
<211> LENGTH: 1923
<212> TYPE: DNA
<213> ORGANISM: Pleurotus ostreatus

<400> SEQUENCE: 48

| atggccccga cgatgtcact gtctcgctcc gcactgaaga atgtccacct gccgtatatg | 60 |
| gtccaacacc cggaaccgac cgattgcagc accgcgatga acacgcggc cgaaggttat | 120 |
| gatcgtgctc gccagatgat tgcgtttctg ttcgacatcc tggattacga aagctctgtt | 180 |
| ccgcaaaaat ttaccccgga agaaaagaaa gaaaaatata cgtggtcaca ctcggataag | 240 |
| ttcccgccgc atctggccat tatcccgaaa gacattgatg tgccggcata cattatcttt | 300 |
| agcatcgttc gtctggtcca gaccctgagt attatgtccg gcatccaatg caacgaacgt | 360 |
| ctggcaccgg ggccggaaca gaatacgatg gaaaaactga cgaagtggaa cgcggaacgt | 420 |
| cataaaaatc aaggctgggt caaggatatg tttaacgaac gaatattgg tctgcgcaac | 480 |
| gactggtata ccgatgctgt gttcgcgcag caatttttca cgggtccgaa tccgaccacg | 540 |
| attaccctgg cctctgatac gtggatgaaa gcatttaccg aagaagcagc tagtcagggc | 600 |
| aagcgtgacc tgatcagcct gtttcgctct gccccgccga actccttcta cgttcaggac | 660 |
| ttttcagatt tccgtgctcg catgggcgcg aaaccggacg aagaactgtg cgcgacctct | 720 |
| gatggcggtg ttacccgtta tggctgtgca gcagtcgcac tgttttacct gccgccgacc | 780 |
| ggtgaactgc atccgctggc cattgtgccg gattataaag gcagtatggc agcttccatc | 840 |
| acgctgttca caagcgtgt ggacccgtca gatgcctcgg ttgaccaggc aaatgattgg | 900 |
| ccgtggcgct acgctaaaac ctgtgttctg tccgcggatt gggtcctgca tgaaatgatt | 960 |
| atccacctga caatacccca tctggtgcag gaagccgtca ttgtggcagt caacgtacg | 1020 |
| ctgccggatt cacacatcgt ttttcgcctg ctgaaaccgc attgggtggt tacccgtcg | 1080 |
| ctgaatgccc aggcacgtag cgttctgatc ccggaagtca ttgtgccgat cgcgggcttc | 1140 |
| agtgaactgc gcatctttca gttcgttggt cacgccttta ccaacttcga ctggaaagca | 1200 |
| ctgtatgtcc cgacggatct ggaatttcgt ggtttcccgc tggaccgcct ggatgacgat | 1260 |
| aagttccata actatgctta cgcgaaggac attaaggata tgtggatggc cctgcgtaag | 1320 |
| ttcgtgagtt ccgttctgaa agatggcaag tattacccgg acgattcggc tgttgcagca | 1380 |
| gacgcgcaga ttcaagactg gtgcgatgaa atgcgcagcg aaaaaggcgc gggtatgaaa | 1440 |
| aagttcccgg aaagcatttc taccctggac gatctgatcg atatggtgac gatgtgtatt | 1500 |
| cacatcgcag ctccgcagca taccgccgtg aactatctgc agcaatatta ccaaacgttt | 1560 |

-continued

```
gttccgaata aaccgtcagc actgttctcg ccgctgccga ccctgctgag ccagctggaa     1620
tcttacacgg aaagtgatct gatggcggcc ctgccgctgg gtgctaaaca ggaatggctg     1680
ctgatggcgc aagtgccgta tctgctgtct aaggaagtcg aacaggatgg caacattgtg     1740
acctacgccg gtacggcaag taacaatgaa gatccgatta tcgcagctgc gggcaaagaa     1800
ctgtccgctg acctggtcat cctggcgggt gtgtttctga aaaactcaga aaagctggac     1860
gatcagaaca ccgcctataa tgtcctggca ccggatcaac tggccaatgc aattgtgatc     1920
taa                                                                  1923
```

<210> SEQ ID NO 49
<211> LENGTH: 495
<212> TYPE: PRT
<213> ORGANISM: Cichorium intybus

<400> SEQUENCE: 49

```
Met Glu Ile Ser Ile Pro Thr Thr Leu Gly Leu Ala Val Ile Ile Phe
1               5                   10                  15

Ile Ile Phe Lys Leu Leu Thr Arg Thr Thr Ser Lys Lys Asn Leu Leu
            20                  25                  30

Pro Glu Pro Trp Arg Leu Pro Ile Ile Gly His Met His His Leu Ile
        35                  40                  45

Gly Thr Met Pro His Arg Gly Val Met Glu Leu Ala Arg Lys His Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Asn Lys Lys Val Lys Ser Phe
    130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
    210                 215                 220

His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
                245                 250                 255

Ser Ser Ser Gln Glu Thr Leu Leu Asp Val Leu Leu Arg Leu Lys Glu
            260                 265                 270

Ser Ala Glu Phe Pro Leu Thr Ala Asp Asn Val Lys Ala Val Ile Leu
        275                 280                 285

Asp Met Phe Gly Ala Gly Thr Asp Thr Ser Ser Ala Thr Ile Glu Trp
    290                 295                 300
```

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
            325                 330                 335

Asp Leu Gln Glu Leu Asn Tyr Leu Lys Leu Val Ile Lys Glu Thr Leu
            340                 345                 350

Arg Leu His Pro Pro Leu Pro Leu Val Met Pro Arg Glu Cys Arg Glu
            355                 360                 365

Pro Cys Val Leu Gly Gly Tyr Asp Ile Pro Ser Lys Thr Lys Leu Ile
        370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Thr Val Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
            435                 440                 445

Ile Leu Tyr Phe Asn Trp Lys Leu Pro Asn Gly Lys Thr Phe Glu Asp
450                 455                 460

Leu Asp Met Thr Glu Ser Phe Gly Ala Thr Val Gln Arg Lys Thr Glu
465                 470                 475                 480

Leu Leu Leu Val Pro Thr Asp Phe Gln Thr Leu Thr Ala Ser Thr
                485                 490                 495

<210> SEQ ID NO 50
<211> LENGTH: 493
<212> TYPE: PRT
<213> ORGANISM: Cichorium intybus

<400> SEQUENCE: 50

Met Ala Leu Leu Leu Ala Val Phe Leu Ala Val Ile Ile Phe Ile Ile
1               5                   10                  15

Phe Lys Leu Leu Thr Arg Thr Thr Ser Lys Lys Asn Leu Leu Pro Glu
            20                  25                  30

Pro Trp Arg Leu Pro Ile Ile Gly His Met His His Leu Ile Gly Thr
        35                  40                  45

Met Pro His Arg Gly Val Met Glu Leu Ala Arg Lys His Gly Ser Leu
    50                  55                  60

Met His Leu Gln Leu Gly Glu Val Ser Thr Ile Val Val Ser Ser Pro
65                  70                  75                  80

Arg Trp Ala Lys Glu Val Leu Thr Thr Tyr Asp Ile Thr Phe Ala Asn
                85                  90                  95

Arg Pro Glu Thr Leu Thr Gly Glu Ile Val Ala Tyr His Asn Thr Asp
            100                 105                 110

Ile Val Leu Ala Pro Tyr Gly Glu Tyr Trp Arg Gln Leu Arg Lys Leu
        115                 120                 125

Cys Thr Leu Glu Leu Leu Ser Asn Lys Lys Val Lys Ser Phe Gln Ser
    130                 135                 140

Leu Arg Glu Glu Glu Cys Trp Asn Leu Val Lys Asp Ile Arg Ser Thr
145                 150                 155                 160

Gly Gln Gly Ser Pro Ile Asn Leu Ser Glu Asn Ile Phe Lys Met Ile
                165                 170                 175

Ala Thr Ile Leu Ser Arg Ala Ala Phe Gly Lys Gly Ile Lys Asp Gln
            180                 185                 190

```
Met Lys Phe Thr Glu Leu Val Lys Glu Ile Leu Arg Leu Thr Gly Gly
            195                 200                 205

Phe Asp Val Ala Asp Ile Phe Pro Ser Lys Lys Leu Leu His His Leu
    210                 215                 220

Ser Gly Lys Arg Ala Lys Leu Thr Asn Ile His Asn Lys Leu Asp Asn
225                 230                 235                 240

Leu Ile Asn Asn Ile Ile Ala Glu His Pro Gly Asn Arg Thr Ser Ser
                245                 250                 255

Ser Gln Glu Thr Leu Leu Asp Val Leu Leu Arg Leu Lys Glu Ser Ala
            260                 265                 270

Glu Phe Pro Leu Thr Ala Asp Asn Val Lys Ala Val Ile Leu Asp Met
            275                 280                 285

Phe Gly Ala Gly Thr Asp Thr Ser Ser Ala Thr Ile Glu Trp Ala Ile
    290                 295                 300

Ser Glu Leu Ile Arg Cys Pro Arg Ala Met Glu Lys Val Gln Thr Glu
305                 310                 315                 320

Leu Arg Gln Ala Leu Asn Gly Lys Glu Arg Ile Gln Glu Glu Asp Leu
                325                 330                 335

Gln Glu Leu Asn Tyr Leu Lys Leu Val Ile Lys Glu Thr Leu Arg Leu
            340                 345                 350

His Pro Pro Leu Pro Leu Val Met Pro Arg Glu Cys Arg Glu Pro Cys
            355                 360                 365

Val Leu Gly Gly Tyr Asp Ile Pro Ser Lys Thr Lys Leu Ile Val Asn
    370                 375                 380

Val Phe Ala Ile Asn Arg Asp Pro Glu Tyr Trp Lys Asp Ala Glu Thr
385                 390                 395                 400

Phe Met Pro Glu Arg Phe Glu Asn Ser Pro Ile Thr Val Met Gly Ser
                405                 410                 415

Glu Tyr Glu Tyr Leu Pro Phe Gly Ala Gly Arg Arg Met Cys Pro Gly
            420                 425                 430

Ala Ala Leu Gly Leu Ala Asn Val Glu Leu Pro Leu Ala His Ile Leu
            435                 440                 445

Tyr Phe Asn Trp Lys Leu Pro Asn Gly Lys Thr Phe Glu Asp Leu Asp
    450                 455                 460

Met Thr Glu Ser Phe Gly Ala Thr Val Gln Arg Lys Thr Glu Leu Leu
465                 470                 475                 480

Leu Val Pro Thr Asp Phe Gln Thr Leu Thr Ala Ser Thr
                485                 490

<210> SEQ ID NO 51
<211> LENGTH: 1482
<212> TYPE: DNA
<213> ORGANISM: Cichorium intybus

<400> SEQUENCE: 51
atggctctgt tattagcagt ttttctggct gtcattatct ttatcatctt caaactgctg      60
acccgcacca cctcgaagaa aaacctgctg ccggaaccgt ggcgtctgcc gattatcggc     120
cacatgcatc acctgattgg caccatgccg caccgtggtg tgatggaact ggcgcgcaaa     180
catggctcac tgatgcacct gcagctgggt gaagtgagca ccatcgtggt tagctctccg     240
cgttgggcga agaagttcct gaccacgtat gatattacct ttgccaaccg cccggaaacc     300
ctgacgggcg aaatcgtggc ataccataat acggacattg ttctggctcc gtatggtgaa     360
tactggcgtc agctgcgcaa actgtgcacc ctggaactgc tgagtaacaa aaaagtcaaa     420
```

```
tcttttcaaa gtctgcgtga agaagaatgt tggaatctgg tgaaagatat ccgctccacc    480
ggccagggtt caccgatcaa cctgtcggaa acatcttca aaatgatcgc gacgatcctg    540
tctcgtgcgg cctttggcaa aggtattaaa gaccaaatga aattcaccga actggttaaa    600
gaaatcctgc gcctgacggg cggttttgat gtcgcagaca ttttcccgag taaaaaactg    660
ctgcatcacc tgtccggcaa acgtgctaaa ctgaccaaca tccataacaa actggataac    720
ctgatcaaca acattatcgc cgaacacccg ggtaatcgta ccagttcctc acaggaaacg    780
ctgctggatg ttctgctgcg cctgaaagaa agcgcagaat tccgctgacc gcggacaat     840 gttaaagccg tcattctgga tatgttcggt gcaggcaccg acacgtcgag cgcaaccatt    900
gaatgggcta tctctgaact gattcgttgc ccgcgcgcga tggaaaaagt gcagacggaa    960
ctgcgtcaag ccctgaacgg caagaacgc atccaggaag aagatctgca agaactgaac    1020
tacctgaaac tggttatcaa agaaaccctg cgcctgcatc cgccgctgcc gctggtcatg    1080
ccgcgtgaat gccgcgaacc gtgtgtgctg ggcggttatg atatcccgag caaaaccaaa    1140
ctgatcgtca acgtgtttgc aattaatcgt gacccggaat actggaaaga cgctgaaacc    1200
tttatgccgg aacgcttcga aaacagcccg attacggtta tgggttctga atatgaatac    1260
ctgccgtttg gtgcaggtcg tcgcatgtgt ccgggtgcag ctctgggtct ggcgaatgtc    1320
gaactgccgc tggcccacat cctgtattac ttcaactgga aactgccgaa tggcaaaacc    1380
tttgaagatc tggacatgac cgaatccttc ggtgcaacgg tgcaacgcaa aaccgaactg    1440
ctgctggtgc cgacggattt ccaaacgctg accgcatcaa cg                       1482
```

<210> SEQ ID NO 52
<211> LENGTH: 488
<212> TYPE: PRT
<213> ORGANISM: Helianthus annuus

<400> SEQUENCE: 52

```
Met Glu Val Ser Leu Thr Thr Ser Ile Ala Leu Ala Thr Ile Val Phe
1               5                   10                  15

Phe Leu Tyr Lys Leu Leu Thr Arg Pro Thr Ser Ser Lys Asn Arg Leu
            20                  25                  30

Pro Glu Pro Trp Arg Leu Pro Ile Ile Gly His Met His His Leu Ile
        35                  40                  45

Gly Thr Met Pro His Arg Gly Val Met Asp Leu Ala Arg Lys Tyr Gly
    50                  55                  60

Ser Leu Met His Leu Gln Leu Gly Glu Val Ser Ala Ile Val Val Ser
65                  70                  75                  80

Ser Pro Lys Trp Ala Lys Glu Ile Leu Thr Thr Tyr Asp Ile Pro Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Val Lys Ser Phe
    130                 135                 140

Gln Ser Leu Arg Glu Glu Glu Cys Trp Asn Leu Val Gln Glu Ile Lys
145                 150                 155                 160

Ala Ser Gly Ser Gly Thr Pro Phe Asn Leu Ser Glu Gly Ile Phe Lys
                165                 170                 175

Val Ile Ala Thr Val Leu Ser Arg Ala Ala Phe Gly Lys Gly Ile Lys
```

```
                    180                 185                 190
Asp Gln Lys Gln Phe Thr Glu Ile Val Lys Glu Ile Leu Arg Glu Thr
                195                 200                 205

Gly Gly Phe Asp Val Ala Asp Ile Phe Pro Ser Lys Lys Phe Leu His
            210                 215                 220

His Leu Ser Gly Lys Arg Gly Arg Leu Thr Ser Ile His Asn Lys Leu
225                 230                 235                 240

Asp Ser Leu Ile Asn Asn Leu Val Ala Glu His Thr Val Ser Lys Ser
                245                 250                 255

Ser Lys Val Asn Glu Thr Leu Leu Asp Val Leu Arg Leu Lys Asn
            260                 265                 270

Ser Glu Glu Phe Pro Leu Thr Ala Asp Asn Val Lys Ala Ile Ile Leu
                275                 280                 285

Asp Met Phe Gly Ala Gly Thr Asp Thr Ser Ser Ala Thr Val Glu Trp
290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Arg Ile Lys Glu Glu
                325                 330                 335

Glu Ile Gln Asp Leu Pro Tyr Leu Asn Leu Val Ile Arg Glu Thr Leu
                340                 345                 350

Arg Leu His Pro Pro Leu Pro Leu Val Met Pro Arg Glu Cys Arg Gln
            355                 360                 365

Ala Met Asn Leu Ala Gly Tyr Asp Val Ala Asn Lys Thr Lys Leu Ile
            370                 375                 380

Val Asn Val Phe Ala Ile Asn Arg Asp Pro Glu Tyr Trp Lys Asp Ala
385                 390                 395                 400

Glu Ser Phe Asn Pro Glu Arg Phe Glu Asn Ser Asn Thr Thr Ile Met
                405                 410                 415

Gly Ala Asp Tyr Glu Tyr Leu Pro Phe Gly Ala Gly Arg Arg Met Cys
            420                 425                 430

Pro Gly Ser Ala Leu Gly Leu Ala Asn Val Gln Leu Pro Leu Ala Asn
            435                 440                 445

Ile Leu Tyr Tyr Phe Lys Trp Lys Leu Pro Asn Gly Ala Ser His Asp
            450                 455                 460

Gln Leu Asp Met Thr Glu Ser Phe Gly Ala Thr Val Gln Arg Lys Thr
465                 470                 475                 480

Glu Leu Met Leu Val Pro Ser Phe
                485

<210> SEQ ID NO 53
<211> LENGTH: 488
<212> TYPE: PRT
<213> ORGANISM: Helianthus annuus

<400> SEQUENCE: 53

Met Ala Leu Leu Leu Ala Val Phe Ile Ala Leu Ala Thr Ile Val Phe
1               5                   10                  15

Phe Leu Tyr Lys Leu Leu Thr Arg Pro Thr Ser Ser Lys Asn Arg Leu
                20                  25                  30

Pro Glu Pro Trp Arg Leu Pro Ile Ile Gly His Met His His Leu Ile
            35                  40                  45

Gly Thr Met Pro His Arg Gly Val Met Asp Leu Ala Arg Lys Tyr Gly
        50                  55                  60
```

```
Ser Leu Met His Leu Gln Leu Gly Glu Val Ser Ala Ile Val Val Ser
 65                  70                  75                  80

Ser Pro Lys Trp Ala Lys Glu Ile Leu Thr Thr Tyr Asp Ile Pro Phe
                 85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Val Lys Ser Phe
130                 135                 140

Gln Ser Leu Arg Glu Glu Cys Trp Asn Leu Val Gln Glu Ile Lys
145                 150                 155                 160

Ala Ser Gly Ser Gly Thr Pro Phe Asn Leu Ser Glu Gly Ile Phe Lys
                165                 170                 175

Val Ile Ala Thr Val Leu Ser Arg Ala Ala Phe Gly Lys Gly Ile Lys
            180                 185                 190

Asp Gln Lys Gln Phe Thr Glu Ile Val Lys Glu Ile Leu Arg Glu Thr
        195                 200                 205

Gly Gly Phe Asp Val Ala Asp Ile Phe Pro Ser Lys Lys Phe Leu His
210                 215                 220

His Leu Ser Gly Lys Arg Gly Arg Leu Thr Ser Ile His Asn Lys Leu
225                 230                 235                 240

Asp Ser Leu Ile Asn Asn Leu Val Ala Glu His Thr Val Ser Lys Ser
                245                 250                 255

Ser Lys Val Asn Glu Thr Leu Leu Asp Val Leu Leu Arg Leu Lys Asn
            260                 265                 270

Ser Glu Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Arg Ile Lys Glu Glu
                325                 330                 335

Glu Ile Gln Asp Leu Pro Tyr Leu Asn Leu Val Ile Arg Glu Thr Leu
            340                 345                 350

Arg Leu His Pro Pro Leu Pro Leu Val Met Pro Arg Glu Cys Arg Gln
        355                 360                 365

Ala Met Asn Leu Ala Gly Tyr Asp Val Ala Asn Lys Thr Lys Leu Ile
370                 375                 380

Val Asn Val Phe Ala Ile Asn Arg Asp Pro Glu Tyr Trp Lys Asp Ala
385                 390                 395                 400

Glu Ser Phe Asn Pro Glu Arg Phe Glu Asn Ser Asn Thr Thr Ile Met
                405                 410                 415

Gly Ala Asp Tyr Glu Tyr Leu Pro Phe Gly Ala Gly Arg Arg Met Cys
            420                 425                 430

Pro Gly Ser Ala Leu Gly Leu Ala Asn Val Gln Leu Pro Leu Ala Asn
        435                 440                 445

Ile Leu Tyr Tyr Phe Lys Trp Lys Leu Pro Asn Gly Ala Ser His Asp
450                 455                 460

Gln Leu Asp Met Thr Glu Ser Phe Gly Ala Thr Val Gln Arg Lys Thr
465                 470                 475                 480

Glu Leu Met Leu Val Pro Ser Phe
```

<210> SEQ ID NO 54
<211> LENGTH: 1464
<212> TYPE: DNA
<213> ORGANISM: Helianthus annuus

<400> SEQUENCE: 54

```
atggctctgt tattagcagt tttcatcgcc ctggcaacca ttgtcttttt cctgtataaa      60
ctgctgaccc gtccgacctc atctaaaaac cgtctgccgg aaccgtggcg cctgccgatt     120
atcggccaca tgcatcacct gattggcacc atgccgcacc gtggtgtcat ggatctggca     180
cgcaaatatg gcagcctgat gcatctgcaa ctgggtgaag tttctgcgat gtgttagc      240
tctccgaaat gggccaaaga attctgacc acctatgata ttccgtttgc gaaccgcccg      300
gaaaccctga cgggcgaaat tatcgcatac acaataccg acattgtgct ggctccgtat      360
ggtgaatact ggcgtcaact gcgtaaactg tgcacgctgg aactgctgag tgttaaaaaa      420
gtcaaaagtt ccagagcct gcgtgaagaa gaatgttgga acctggttca agaaattaaa      480
gcgagcggca gcggcacccc gtttaatctg agtgaaggta ttttcaaagt gattgcgacc      540
gtgctgagcc gtgcggcatt tggtaaaggt atcaaagatc agaaacaatt caccgaaatt      600
gtcaaagaaa tcctgcgcga acgggcggt tttgatgtgg cggacatctt tccgagcaaa      660
aaattcctgc atcacctgtc tggcaaacgt ggtcgcctga cctcaattca taacaaactg      720
gattcgctga tcaacaatct ggtcgccgaa cataccgtga gcaaaagcag caaagtgaat      780
gaaacgctgc tggatgtcct gctgcgtctg aaaaaactcgg aagaatttcc gctgaccgca      840
gacaatgtga agctattat cctggatatg ttcggtgcag caccgatac cagcagcgca      900
acggtggaat gggccattag cgaactgatc cgttgcccgc gcgcaatgga aaaagttcag      960
gcagaactgc gtcaagctct gaacggcaaa gaacgcatta agaagaaga atccaggat     1020
ctgccgtatc tgaatctggt tattcgtgaa accctgcgtc tgcatccgcc gctgccgctg     1080
gtcatgccgc gtgaatgtcg ccaagcaatg aacctggctg ctatgacgt ggcaaataaa     1140
accaaactga tcgtcaatgt gtttgcgatt aaccgtgacc cggaatactg gaaagacgcg     1200
gaaagttta acccggaacg ctttgaaaac agcaacacca cgattatggg tgcggattat     1260
gaatacctgc cgtttggcgc cggtcgtcgc atgtgtccgg cagcgcgct gggtctggcc     1320
aacgttcaac tgccgctggc caatatcctg tattacttca atggaaaact gccgaatggc     1380
gcctcacacg atcaactgga catgaccgaa tcgtttggtg caaccgtgca acgcaaaacg     1440
gaactgatgc tggttccgtc tttc                                            1464
```

<210> SEQ ID NO 55
<211> LENGTH: 504
<212> TYPE: PRT
<213> ORGANISM: Artificial Sequence
<220> FEATURE:
<223> OTHER INFORMATION: Synthetic - Engineered valencene oxidase

<400> SEQUENCE: 55

```
Met Ala Trp Glu Tyr Ala Leu Ile Gly Leu Val Val Gly Ile Ile Ile
1               5                   10                  15

Gly Ala Val Ala Ala Trp Tyr Leu Lys Ser Tyr Thr Ser Ala Arg Arg
            20                  25                  30

Ser Gln Ser Asn His Leu Pro Arg Val Pro Glu Val Pro Gly Val Pro
        35                  40                  45
```

```
Leu Leu Gly Asn Leu Leu Gln Leu Lys Glu Lys Lys Pro Tyr Met Thr
 50                  55                  60

Phe Thr Arg Trp Ala Ala Thr Tyr Gly Pro Ile Tyr Ser Ile Lys Thr
 65                  70                  75                  80

Gly Ala Thr Ser Met Val Val Ser Ser Asn Glu Ile Ala Lys Glu
                 85                  90                  95

Ala Leu Val Thr Arg Phe Gln Ser Ile Ser Thr Arg Asn Leu Ser Lys
                100                 105                 110

Ala Leu Lys Val Leu Thr Ala Asp Lys Thr Met Val Ala Met Ser Asp
                115                 120                 125

Tyr Asp Asp Tyr His Lys Thr Val Lys Arg His Ile Leu Thr Ala Val
130                 135                 140

Leu Gly Pro Asn Ala Gln Lys Lys His Arg Ile His Arg Asp Ile Met
145                 150                 155                 160

Met Asp Asn Ile Ser Thr Gln Leu His Glu Phe Val Lys Asn Asn Pro
                165                 170                 175

Glu Gln Glu Glu Val Asp Leu Arg Lys Ile Phe Gln Ser Glu Leu Phe
                180                 185                 190

Gly Leu Ala Met Arg Gln Ala Leu Gly Lys Asp Val Glu Ser Leu Tyr
                195                 200                 205

Val Glu Asp Leu Lys Ile Thr Met Asn Arg Asp Glu Ile Phe Gln Val
210                 215                 220

Leu Val Val Asp Pro Met Met Gly Ala Ile Asp Val Asp Trp Arg Asp
225                 230                 235                 240

Phe Phe Pro Tyr Leu Lys Trp Val Pro Asn Lys Lys Phe Glu Asn Thr
                245                 250                 255

Ile Gln Gln Met Tyr Ile Arg Arg Glu Ala Val Met Lys Ser Leu Ile
                260                 265                 270

Lys Glu His Lys Lys Arg Ile Ala Ser Gly Glu Lys Leu Asn Ser Tyr
                275                 280                 285

Ile Asp Tyr Leu Leu Ser Glu Ala Gln Thr Leu Thr Asp Gln Gln Leu
                290                 295                 300

Leu Met Ser Leu Trp Glu Pro Ile Ile Glu Ser Ser Asp Thr Thr Met
305                 310                 315                 320

Val Thr Thr Glu Trp Ala Met Tyr Glu Leu Ala Lys Asn Pro Lys Leu
                325                 330                 335

Gln Asp Arg Leu Tyr Arg Asp Ile Lys Ser Val Cys Gly Ser Glu Lys
                340                 345                 350

Ile Thr Glu Glu His Leu Ser Gln Leu Pro Tyr Ile Thr Ala Ile Phe
                355                 360                 365

His Glu Thr Leu Arg Arg His Ser Pro Val Pro Ile Ile Pro Leu Arg
370                 375                 380

His Val His Glu Asp Thr Val Leu Gly Gly Tyr His Val Pro Ala Gly
385                 390                 395                 400

Thr Glu Leu Ala Val Asn Ile Tyr Gly Cys Asn Met Asp Lys Asn Val
                405                 410                 415

Trp Glu Asn Pro Glu Glu Trp Asn Pro Glu Arg Phe Met Lys Glu Asn
                420                 425                 430

Glu Thr Ile Asp Phe Gln Lys Thr Met Ala Phe Gly Gly Gly Lys Arg
                435                 440                 445

Val Cys Ala Gly Ser Leu Gln Ala Leu Leu Thr Ala Ser Ile Gly Ile
                450                 455                 460

Gly Arg Met Val Gln Glu Phe Glu Trp Lys Leu Lys Asp Met Thr Gln
```

```
                      465                 470                 475                 480
Glu Glu Val Asn Thr Ile Gly Leu Thr Thr Gln Met Leu Arg Pro Leu
                        485                 490                 495
Arg Ala Ile Ile Lys Pro Arg Ile
                500

<210> SEQ ID NO 56
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 56

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
                20                  25                  30

Arg Ser Gln Ser Asn His Leu Pro Arg Val Pro Glu Val Pro Gly Val
            35                  40                  45

Pro Leu Leu Gly Asn Leu Leu Gln Leu Lys Glu Lys Lys Pro Tyr Met
        50                  55                  60

Thr Phe Thr Arg Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Met Val Thr Arg Phe Gln Ser Ile Ser Thr Arg Asn Leu Ser
                100                 105                 110

Lys Ala Leu Lys Val Leu Thr Ala Asp Lys Thr Met Val Ala Met Ser
            115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
                180                 185                 190

Phe Gly Leu Ala Met Arg Gln Ala Leu Gly Lys Asp Val Glu Ser Leu
            195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
                260                 265                 270

Ile Lys Glu His Lys Lys Arg Ile Ala Ser Gly Glu Lys Leu Asn Ser
            275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
```

```
              325                 330                 335
Leu Gln Asp Arg Leu Tyr Arg Asp Ile Lys Ser Val Cys Gly Ser Glu
            340                 345                 350
Lys Ile Thr Glu Glu His Leu Ser Gln Leu Pro Tyr Ile Thr Ala Ile
        355                 360                 365
Phe His Glu Thr Leu Arg Lys His Ser Pro Val Pro Ile Leu Pro Leu
    370                 375                 380
Arg His Val His Glu Asp Thr Val Leu Gly Gly Tyr His Val Pro Ala
385                 390                 395                 400
Gly Thr Glu Leu Ala Val Asn Ile Tyr Gly Cys Asn Met Asp Lys Asn
                405                 410                 415
Val Trp Glu Asn Pro Glu Glu Trp Asn Pro Glu Arg Phe Met Lys Glu
            420                 425                 430
Asn Glu Thr Ile Asp Phe Gln Lys Thr Met Ala Phe Gly Gly Gly Lys
        435                 440                 445
Arg Val Cys Ala Gly Ser Leu Gln Ala Leu Leu Ile Ala Ser Ile Gly
    450                 455                 460
Ile Gly Arg Met Val Gln Glu Phe Glu Trp Lys Leu Lys Asp Met Thr
465                 470                 475                 480
Gln Glu Glu Val Asn Thr Ile Gly Leu Thr Asn Gln Met Leu Arg Pro
                485                 490                 495
Leu Arg Ala Ile Ile Lys Pro Arg Ile
            500                 505

<210> SEQ ID NO 57
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 57

Met Ala Trp Glu Tyr Ala Leu Ile Gly Leu Val Val Gly Ile Ile Ile
1               5                   10                  15
Gly Ala Val Ala Met Arg Trp Tyr Leu Lys Ser Tyr Thr Ser Ala Arg
            20                  25                  30
Arg Ser Gln Ser Asn His Leu Pro Arg Val Pro Glu Val Pro Gly Val
        35                  40                  45
Pro Leu Leu Gly Asn Leu Leu Gln Leu Lys Glu Lys Lys Pro Tyr Met
    50                  55                  60
Thr Phe Thr Lys Trp Ala Ala Thr Tyr Gly Pro Ile Tyr Ser Ile Lys
65                  70                  75                  80
Thr Gly Ala Thr Ser Met Val Val Ser Ser Asn Glu Ile Ala Lys
                85                  90                  95
Glu Ala Met Val Thr Arg Phe Gln Ser Ile Ser Thr Arg Asn Leu Ser
            100                 105                 110
Lys Ala Leu Lys Val Leu Thr Ala Asp Lys Gln Met Val Ala Met Ser
        115                 120                 125
Asp Tyr Asp Asp Tyr His Lys Thr Val Lys Arg His Ile Leu Thr Ala
    130                 135                 140
Val Leu Gly Pro Asn Ala Gln Lys Lys His Arg Ile His Arg Asp Ile
145                 150                 155                 160
Met Met Asp Asn Ile Ser Thr Gln Leu His Glu Phe Val Lys Asn Asn
                165                 170                 175
Pro Glu Gln Glu Glu Val Asp Leu Arg Lys Ile Phe Gln Ser Glu Leu
```

```
            180                 185                 190
Phe Gly Leu Ala Met Arg Gln Ala Leu Gly Lys Asp Val Glu Ser Leu
            195                 200                 205

Tyr Val Glu Asp Leu Lys Ile Thr Met Asn Arg Asp Glu Ile Leu Gln
        210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 58
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 58

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
```

```
           35                  40                  45
Pro Leu Leu Gly Asn Leu Leu Gln Leu Lys Glu Lys Pro Tyr Met
 50                  55                  60

Thr Phe Thr Arg Trp Ala Ala Thr Tyr Gly Pro Ile Tyr Ser Ile Lys
 65                  70                  75                  80

Thr Gly Ala Thr Ser Val Val Val Ser Asn Glu Ile Ala Lys
                 85                  90                  95

Glu Ala Met Val Thr Arg Phe Gln Ser Ile Ser Thr Arg Asn Leu Ser
                100                 105                 110

Lys Ala Leu Lys Val Leu Thr Ala Asp Lys Gln Met Val Ala Met Ser
                115                 120                 125

Asp Tyr Asp Asp Tyr His Lys Thr Val Lys Arg His Ile Leu Thr Ala
            130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
                180                 185                 190

Phe Gly Leu Ala Met Arg Gln Ala Leu Gly Lys Asp Val Glu Ser Leu
            195                 200                 205

Tyr Val Glu Asp Leu Lys Ile Thr Met Asn Arg Asp Glu Ile Leu Gln
210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
                260                 265                 270

Ile Lys Glu His Lys Lys Arg Ile Ala Ser Gly Glu Lys Leu Asn Ser
            275                 280                 285

Tyr Ile Asp Tyr Leu Leu Ser Glu Ala Gln Thr Leu Thr Asp Gln Gln
290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
                340                 345                 350

Lys Ile Thr Glu Glu His Leu Ser Gln Leu Pro Tyr Ile Thr Ala Ile
            355                 360                 365

Phe His Glu Thr Leu Arg Lys His Ser Pro Val Pro Ile Leu Pro Leu
370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
                420                 425                 430

Asn Glu Thr Ile Asp Phe Gln Lys Thr Met Ala Phe Gly Gly Gly Lys
            435                 440                 445

Arg Val Cys Ala Gly Ser Leu Gln Ala Leu Leu Ile Ala Ser Ile Gly
450                 455                 460
```

-continued

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
            485                 490                 495

Leu Arg Ala Ile Ile Lys Pro Arg Ile
            500                 505

<210> SEQ ID NO 59
<211> LENGTH: 504
<212> TYPE: PRT
<213> ORGANISM: Artificial Sequence
<220> FEATURE:
<223> OTHER INFORMATION: Synthetic - Engineered valencene oxidase

<400> SEQUENCE: 59

Met Ala Trp Glu Tyr Ala Leu Ile Gly Leu Val Val Gly Ile Ile Ile
1               5                   10                  15

Gly Ala Val Ala Ala Trp Tyr Leu Lys Ser Tyr Thr Ser Ala Arg Arg
            20                  25                  30

Ser Gln Ser Asn His Leu Pro Arg Val Pro Glu Val Pro Gly Val Pro
        35                  40                  45

Leu Leu Gly Asn Leu Leu Gln Leu Lys Glu Lys Pro Tyr Met Thr
    50                  55                  60

Phe Thr Lys Trp Ala Ala Thr Tyr Gly Pro Ile Tyr Ser Ile Lys Thr
65                  70                  75                  80

Gly Ala Thr Ser Met Val Val Ser Ser Asn Glu Ile Ala Lys Glu
            85                  90                  95

Ala Met Val Thr Arg Phe Gln Ser Ile Ser Thr Arg Asn Leu Ser Lys
            100                 105                 110

Ala Leu Lys Val Leu Thr Ala Asp Lys Gln Met Val Ala Met Ser Asp
            115                 120                 125

Tyr Asp Asp Tyr His Lys Thr Val Lys Arg His Ile Leu Thr Ala Val
        130                 135                 140

Leu Gly Pro Asn Ala Gln Lys Lys His Arg Ile His Arg Asp Ile Met
145                 150                 155                 160

Met Asp Asn Ile Ser Thr Gln Leu His Glu Phe Val Lys Asn Asn Pro
            165                 170                 175

Glu Gln Glu Glu Val Asp Leu Arg Lys Ile Phe Gln Ser Glu Leu Phe
            180                 185                 190

Gly Leu Ala Met Arg Gln Ala Leu Gly Lys Asp Val Glu Ser Leu Tyr
        195                 200                 205

Val Glu Asp Leu Lys Ile Thr Met Asn Arg Asp Glu Ile Leu Gln Val
    210                 215                 220

Leu Val Val Asp Pro Met Met Gly Ala Ile Asp Val Asp Trp Arg Asp
225                 230                 235                 240

Phe Phe Pro Tyr Leu Lys Trp Val Pro Asn Lys Lys Phe Glu Asn Thr
            245                 250                 255

Ile Gln Gln Met Tyr Ile Arg Arg Glu Ala Val Met Lys Ser Leu Ile
            260                 265                 270

Lys Glu His Lys Lys Arg Ile Ala Ser Gly Glu Lys Leu Asn Ser Tyr
        275                 280                 285

Ile Asp Tyr Leu Leu Ser Glu Ala Gln Thr Leu Thr Asp Gln Gln Leu
    290                 295                 300

Leu Met Ser Leu Trp Glu Pro Ile Ile Glu Ser Ser Asp Thr Thr Met
305                 310                 315                 320

```
Val Thr Thr Glu Trp Ala Met Tyr Glu Leu Ala Lys Asn Pro Lys Leu
            325                 330                 335

Gln Asp Arg Leu Tyr Arg Asp Ile Lys Ser Val Cys Gly Ser Glu Lys
            340                 345                 350

Ile Thr Glu Glu His Leu Ser Gln Leu Pro Tyr Ile Thr Ala Ile Phe
            355                 360                 365

His Glu Thr Leu Arg Lys His Ser Pro Val Pro Ile Leu Pro Leu Arg
            370                 375                 380

His Val His Glu Asp Thr Val Leu Gly Gly Tyr His Val Pro Ala Gly
385                 390                 395                 400

Thr Glu Leu Ala Val Asn Ile Tyr Gly Cys Asn Met Asp Lys Asn Val
                405                 410                 415

Trp Glu Asn Pro Glu Glu Trp Asn Pro Glu Arg Phe Met Lys Glu Asn
            420                 425                 430

Glu Thr Ile Asp Phe Gln Lys Thr Met Ala Phe Gly Gly Gly Lys Arg
            435                 440                 445

Val Cys Ala Gly Ser Leu Gln Ala Leu Leu Ile Ala Ser Ile Gly Ile
        450                 455                 460

Gly Arg Met Val Gln Glu Phe Glu Trp Lys Leu Lys Asp Met Thr Gln
465                 470                 475                 480

Glu Glu Val Asn Thr Ile Gly Leu Thr Asn Gln Met Leu Arg Pro Leu
            485                 490                 495

Arg Ala Ile Ile Lys Pro Arg Ile
            500

<210> SEQ ID NO 60
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 60

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Met Val Thr Arg Phe Gln Ser Ile Ser Thr Arg Asn Leu Ser
            100                 105                 110

Lys Ala Leu Lys Val Leu Thr Ala Asp Lys Thr Met Val Ala Met Ser
            115                 120                 125

Asp Tyr Asp Asp Tyr His Lys Thr Val Lys Arg His Ile Leu Thr Ala
            130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175
```

```
Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
            195                 200                 205

Tyr Val Glu Asp Leu Lys Ile Thr Met Asn Arg Asp Glu Ile Leu Gln
210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
            275                 280                 285

Tyr Ile Asp Tyr Leu Leu Ser Glu Ala Gln Thr Leu Thr Asp Gln Gln
            290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
            355                 360                 365

Phe His Glu Thr Leu Arg Lys His Ser Pro Val Pro Ile Ile Pro Leu
            370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
            435                 440                 445

Arg Val Cys Ala Gly Ser Leu Gln Ala Leu Leu Ile Ala Ser Ile Gly
450                 455                 460

Ile Gly Arg Met Val Gln Glu Phe Gly Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 61
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 61

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30
```

```
Arg Ser Gln Ser Asn His Leu Pro Arg Val Pro Glu Val Pro Gly Val
         35                  40                  45

Pro Leu Leu Gly Asn Leu Leu Gln Leu Lys Glu Lys Lys Pro Tyr Met
 50                  55                  60

Thr Phe Thr Lys Trp Ala Ala Thr Tyr Gly Pro Ile Tyr Ser Ile Lys
 65                  70                  75                  80

Thr Gly Ala Thr Ser Val Val Val Ser Ser Asn Glu Ile Ala Lys
             85                  90                  95

Glu Ala Leu Val Thr Arg Phe Gln Ser Ile Ser Thr Arg Asn Leu Ser
             100                 105                 110

Lys Ala Leu Lys Val Leu Thr Ala Asp Lys Gln Met Val Ala Met Ser
             115                 120                 125

Asp Tyr Asp Asp Tyr His Lys Thr Val Lys Arg His Ile Leu Thr Ala
     130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
             165                 170                 175

Pro Glu Gln Glu Glu Val Asp Leu Arg Lys Ile Phe Gln Ser Glu Leu
             180                 185                 190

Phe Gly Leu Ala Met Arg Gln Ala Leu Gly Lys Asp Val Glu Ser Leu
     195                 200                 205

Tyr Val Glu Asp Leu Lys Ile Thr Met Asn Arg Asp Glu Ile Leu Gln
     210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
             245                 250                 255

Thr Ile Gln Gln Met Tyr Ile Arg Arg Glu Ala Val Met Lys Ser Leu
             260                 265                 270

Ile Lys Glu Gln Lys Lys Arg Ile Ala Ser Gly Glu Lys Leu Asn Ser
     275                 280                 285

Tyr Ile Asp Tyr Leu Leu Ser Glu Ala Gln Thr Leu Thr Asp Gln Gln
     290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
             325                 330                 335

Leu Gln Asp Arg Leu Tyr Arg Asp Ile Lys Ser Val Cys Gly Ser Glu
             340                 345                 350

Lys Ile Thr Glu Glu His Leu Ser Gln Leu Pro Tyr Ile Thr Ala Ile
     355                 360                 365

Phe His Glu Thr Leu Arg Lys His Ser Pro Val Pro Ile Leu Pro Leu
     370                 375                 380

Arg His Val His Glu Asp Thr Val Leu Gly Tyr His Val Pro Ala
385                 390                 395                 400

Gly Thr Glu Leu Ala Val Asn Ile Tyr Gly Cys Asn Met Asp Lys Asn
             405                 410                 415

Val Trp Glu Asn Pro Glu Glu Trp Asn Pro Glu Arg Phe Met Lys Glu
             420                 425                 430

Asn Glu Thr Ile Asp Phe Gln Lys Thr Met Ala Phe Gly Gly Gly Lys
             435                 440                 445
```

```
Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
                500                 505

<210> SEQ ID NO 62
<211> LENGTH: 710
<212> TYPE: PRT
<213> ORGANISM: Stevia rebaudiana

<400> SEQUENCE: 62

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
                20                  25                  30

Asp Pro Thr Thr Leu Pro Ala Leu Lys Met Leu Val Glu Asn Arg Glu
            35                  40                  45

Leu Leu Thr Leu Phe Thr Thr Ser Phe Ala Val Leu Ile Gly Cys Leu
50                  55                  60

Val Phe Leu Met Trp Arg Arg Ser Ser Lys Lys Leu Val Gln Asp
65                  70                  75                  80

Pro Val Pro Gln Val Ile Val Lys Lys Glu Lys Glu Ser Glu
                85                  90                  95

Val Asp Asp Gly Lys Lys Val Ser Ile Phe Tyr Gly Thr Gln Thr
                100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
        130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Thr Ser Val Thr Thr Pro
            260                 265                 270

Tyr Thr Ala Ala Val Leu Glu Tyr Arg Val Val Tyr His Asp Lys Pro
        275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320
```

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
        355                 360                 365

Gly Leu Ser Pro Asp Thr Tyr Phe Ser Val His Ala Asp Lys Glu Asp
    370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710

<210> SEQ ID NO 63
<211> LENGTH: 2133

<212> TYPE: DNA
<213> ORGANISM: Stevia rebaudiana

<400> SEQUENCE: 63

```
atgcagagcg attctgttaa agtatccccg ttcgacctgg tctctgcggc tatgaacggc      60
aaagcaatgg agaaactgaa cgcgagcgaa tctgaagatc caaccaccct gccggcactg     120
aaaatgctgg tagaaaaccg tgaactgctg actctgttca ccacctcctt cgccgttctg     180
attggttgcc tggtcttcct gatgtggcgc cgttcctctt ccaagaagct ggtacaggac     240
ccggttcctc aggtgatcgt cgttaaaaag aaagagaagg aaagcgaagt cgatgacggc     300
aaaaagaagg tttccatttt ctacggtact cagaccggca ccgctgaggg ttttgccaaa     360
gcactggttg aagaggcaaa agtgcgttac gaaaaaactt ccttcaaagt gattgacctg     420
gacgactatg ctgcggatga tgatgaatac gaggaaaaac tgaaaaaaga aagcctggcc     480
ttcttcttcc tggcaaccta tggcgatggt gaaccgaccg acaacgcggc gaacttctac     540
aaatggttta ccgaaggcga cgacaaaggt gaatggctga gaaaactgca gtatggtgtt     600
ttcggtctgg gcaatcgcca gtacgaacat tttaacaaaa tcgcaatcgt tgttgatgac     660
aaactgactg aaatgggtgc gaaacgtctg gtgccggttg gctgggtga cgatgatcaa     720
tgcatcgaag atgacttcac cgcatggaaa gaactggttt ggccggaact ggatcagctg     780
ctgcgcgacg aagacgacac ttccgtgacc accccgtata ccgctgcagt gctggagtac     840
cgtgttgttt accacgataa accggcggac tcttacgccg aagatcagac tcacactaac     900
ggtcacgtcg tacatgacgc acagcacccg tctcgtagca atgttgcgtt taagaaagag     960
ctgcacacga gccagtccga ccgctcttgt acgcacctgg agttcgatat ctcccacacc    1020
ggtctgtcct atgaaaccgg tgaccatgtt ggcgtttaca cgcgaaaacct gagcgaggta    1080
gttgatgaag cgctgaaact gctgggcctg tctccagaca cctactttag cgtgcatgct    1140
gacaaggaag atggtactcc gattggcggc gcttccctgc cgccaccgtt tccaccttgc    1200
actctgcgtg atgctctgac tcgttacgct gatgttctgt ctagcccgaa aaaggttgcg    1260
ctgctggcgc tggccgcaca tgcttctgac ccgtctgaag ctgaccgtct gaaattcctg    1320
gcgtctccgg ccggcaaaga cgaatacgcg cagtggattg tcgctaacca gcgctctctg    1380
ctggaagtga tgcagtcctt cccgtctgcc aaaccgccac tgggcgtgtt tttcgcagct    1440
gtggctccgc gcctgcagcc gcgctactat tctatctcta gctccccgaa aatgagcccg    1500
aaccgcatcc acgttacttg tgctctggtt tacgaaacca cccctgcggg ccgtatccac    1560
cgtggtctgt gctctacgtg gatgaaaaat gccgtgccgc tgaccgaatc ccggactgc    1620
tctcaggcgt ccatcttcgt gcgtacctct aacttccgtc tgccggtgga cccgaaagtt    1680
cctgttatca tgatcggtcc tggcacgggt ctggcccgt tcgtggtttt tctgcaggag    1740
cgtctggctc tgaaagaatc cggtactgag ctgggctctt ccatcttttt cttcggttgt    1800
cgtaaccgca aagtcgattt catctatgaa gacgaactga caacttcgt agagactggt    1860
gcactgtccg aactgattgt ggcattctct cgtgaaggca cggcgaaaga atacgttcaa    1920
cacaaaatgt ctcagaaagc gagcgatatc tggaaactgc tgtccgaggg tgcgtatctg    1980
tatgtttgtg gcgacgcgaa aggcatggct aaagatgtac accgcaccct gcacaccatt    2040
gtacaagaac aaggctctct ggatagctcc aaggcagaac tgtacgtgaa aaacctgcag    2100
atgtctggcc gttacctgcg tgatgtatgg taa                                 2133
```

<210> SEQ ID NO 64

<211> LENGTH: 692
<212> TYPE: PRT
<213> ORGANISM: Arabidopsis thaliana

<400> SEQUENCE: 64

```
Met Thr Ser Ala Leu Tyr Ala Ser Asp Leu Phe Lys Gln Leu Lys Ser
1               5                   10                  15

Ile Met Gly Thr Asp Ser Leu Ser Asp Val Val Leu Val Ile Ala
            20                  25                  30

Thr Thr Ser Leu Ala Leu Val Ala Gly Phe Val Val Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Phe Pro Gly Pro Cys Thr Leu
    370                 375                 380

Gly Thr Gly Leu Ala Arg Tyr Ala Asp Leu Leu Asn Pro Pro Arg Lys
```

```
            385                 390                 395                 400
Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
690

<210> SEQ ID NO 65
<211> LENGTH: 2079
<212> TYPE: DNA
<213> ORGANISM: Arabidopsis thaliana

<400> SEQUENCE: 65
atgaccagcg cactgtacgc aagcgacctg tttaagcaac tgaagagcat tatgggcacc      60
gatagcctga gcgatgatgt tgtcctggtc attgcgacca cgagcctggc actggtggct     120
ggttttgtgg ttctgctgtg gaaaaagacc acggccgatc gttctggcga actgaaaccg     180
ctgatgattc cgaaaagtct gatggcaaag gacgaagatg acgatctgga tctgggctcc     240
ggtaaaaccc gtgtgtcaat cttttttcggt acccagacgg gcaccgcaga aggtttcgca     300
aaagctctgt ctgaagaaat taggcgcgc tatgaaaaag cggccgttaa ggtcatcgat     360
```

```
ctggacgatt atgcagctga cgatgaccag tacgaagaaa aactgaaaaa ggaaaccctg      420
gcgttttcct gcgttgccac ctacggcgac ggtgaaccga cggataacgc ggcccgtttt      480
agtaaatggt tcaccgaaga aaatgaacgc gacattaagc tgcagcaact ggcgtatggc      540
gtgtttgctc tgggtaaccg tcagtacgaa catttcaaca agatcggtat cgtcctggat      600
gaagaactgt gtaaaaaggg cgcgaagcgc ctgattgaag tgggcctggg tgatgacgat      660
caatccatcg aagacgattt taacgcctgg aaagaatctc tgtggagtga actggacaaa      720
ctgctgaagg atgaagacga taagagcgtg gcgacgccgt ataccgccgt tattccggaa      780
taccgtgtcg tgacccatga tccgcgcttc accacgcaga aaagcatgga atcaaatgtt      840
gcgaacggta ataccacgat tgacatccat caccccgtgcc gtgtggatgt tgccgtccaa      900
aaagaactgc ataccacga tcggaccgt agctgtatcc acctggaatt tgatattagc      960
cgcacgggca tcacctatga acgggcgac catgtgggtg tttacgcaga aaaccacgtg     1020
gaaattgttg aagaagctgg caaactgctg ggtcattcgc tggatctggt ttttagcatc     1080
cacgcggaca aggaagatgg ttcgccgctg aaagcgcag tgccgccgcc gttcccgggt     1140
ccgtgcaccc tgggtacggg tctggcacgt tatgcagatc tgctgaatcc gccgcgcaaa     1200
tccgcactgg tggctctggc agcttacgca accgaaccgt cagaagctga aaaactgaag     1260
catctgacgt cgccggacgg taaagatgaa tatagccagt ggattgttgc gtctcaacgc     1320
agtctgctga agtcatggc agcatttccg tcggcaaaac cgccgctggg cgtgttttc     1380 gcagctattg caccgcgtct gcagccgcgc tattacagca tcagctcttg tcaagattgg     1440
gcgccgtctc gtgtccatgt gaccagtgca ctggtgtatg tccgacgcc gaccggtcgc     1500 attcacaaag gcgtgtgctc tacctggatg aaaaacgcgg ttccggccga aaagtctcac     1560
gaatgtagtg gtgcgccgat tttatccgt gccagtaact tcaaactgcc gtccaatccg     1620
tcaaccccga tcgttatggt cggtccgggt acgggtctgg caccgtttcg tggtttcctg     1680
caggaacgca tggctctgaa agaagatggc gaagaactgg gtagttccct gctgtttttc     1740
ggctgccgta atcgccagat ggacttcatc tacgaagatg aactgaacaa cttcgtcgat     1800
caaggtgtga tttccgaact gatcatggca ttttcacgcg aaggcgctca gaaagaatac     1860
gtccaacata aaatgatgga aaaggcggcc caagtgtggg atctgatcaa agaagaaggc     1920
tatctgtacg tttgtggcga cgcaaagggt atggctcgtg atgtccatcg caccctgcac     1980
acgattgttc aggaacaaga aggtgtctca tcgagcgaag cggaagccat cgtgaaaaag     2040
ctgcagaccg aaggccgtta tctgcgcgat gtttggtaa                            2079
```

<210> SEQ ID NO 66
<211> LENGTH: 717
<212> TYPE: PRT
<213> ORGANISM: Taxus cuspidata

<400> SEQUENCE: 66

```
Met Gln Ala Asn Ser Asn Thr Val Glu Gly Ala Ser Gln Gly Lys Ser
1               5                   10                  15

Leu Leu Asp Ile Ser Arg Leu Asp His Ile Phe Ala Leu Leu Leu Asn
            20                  25                  30

Gly Lys Gly Gly Asp Leu Gly Ala Met Thr Gly Ser Ala Leu Ile Leu
        35                  40                  45

Thr Glu Asn Ser Gln Asn Leu Met Ile Leu Thr Thr Ala Leu Ala Val
    50                  55                  60

Leu Val Ala Cys Val Phe Phe Phe Val Trp Arg Arg Gly Gly Ser Asp
```

```
                65                  70                  75                  80
Thr Gln Lys Pro Ala Val Arg Pro Thr Pro Leu Val Lys Glu Glu Asp
                    85                  90                  95
Glu Glu Glu Glu Asp Asp Ser Ala Lys Lys Lys Val Thr Ile Phe Phe
                    100                 105                 110
Gly Thr Gln Thr Gly Thr Ala Glu Gly Phe Ala Lys Ala Leu Ala Glu
                    115                 120                 125
Glu Ala Lys Ala Arg Tyr Glu Lys Ala Val Phe Lys Val Val Asp Leu
                    130                 135                 140
Asp Asn Tyr Ala Ala Asp Asp Glu Gln Tyr Glu Glu Lys Leu Lys Lys
145                 150                 155                 160
Glu Lys Leu Ala Phe Phe Met Leu Ala Thr Tyr Gly Asp Gly Glu Pro
                    165                 170                 175
Thr Asp Asn Ala Ala Arg Phe Tyr Lys Trp Phe Leu Glu Gly Lys Glu
                    180                 185                 190
Arg Glu Pro Trp Leu Ser Asp Leu Thr Tyr Gly Val Phe Gly Leu Gly
                    195                 200                 205
Asn Arg Gln Tyr Glu His Phe Asn Lys Val Ala Lys Ala Val Asp Glu
                    210                 215                 220
Val Leu Ile Glu Gln Gly Ala Lys Arg Leu Val Pro Val Gly Leu Gly
225                 230                 235                 240
Asp Asp Asp Gln Cys Ile Glu Asp Phe Thr Ala Trp Arg Glu Gln
                    245                 250                 255
Val Trp Pro Glu Leu Asp Gln Leu Leu Arg Asp Glu Asp Asp Glu Pro
                    260                 265                 270
Thr Ser Ala Thr Pro Tyr Thr Ala Ala Ile Pro Glu Tyr Arg Val Glu
                    275                 280                 285
Ile Tyr Asp Ser Val Val Ser Val Tyr Glu Glu Thr His Ala Leu Lys
                    290                 295                 300
Gln Asn Gly Gln Ala Val Tyr Asp Ile His His Pro Cys Arg Ser Asn
305                 310                 315                 320
Val Ala Val Arg Arg Glu Leu His Thr Pro Leu Ser Asp Arg Ser Cys
                    325                 330                 335
Ile His Leu Glu Phe Asp Ile Ser Asp Thr Gly Leu Ile Tyr Glu Thr
                    340                 345                 350
Gly Asp His Val Gly Val His Thr Glu Asn Ser Ile Glu Thr Val Glu
                    355                 360                 365
Glu Ala Ala Lys Leu Leu Gly Tyr Gln Leu Asp Thr Ile Phe Ser Val
                    370                 375                 380
His Gly Asp Lys Glu Asp Gly Thr Pro Leu Gly Gly Ser Ser Leu Pro
385                 390                 395                 400
Pro Pro Phe Pro Gly Pro Cys Thr Leu Arg Thr Ala Leu Ala Arg Tyr
                    405                 410                 415
Ala Asp Leu Leu Asn Pro Pro Arg Lys Ala Ala Phe Leu Ala Leu Ala
                    420                 425                 430
Ala His Ala Ser Asp Pro Ala Glu Ala Glu Arg Leu Lys Phe Leu Ser
                    435                 440                 445
Ser Pro Ala Gly Lys Asp Glu Tyr Ser Gln Trp Val Thr Ala Ser Gln
                    450                 455                 460
Arg Ser Leu Leu Glu Ile Met Ala Glu Phe Pro Ser Ala Lys Pro Pro
465                 470                 475                 480
Leu Gly Val Phe Phe Ala Ala Ile Ala Pro Arg Leu Gln Pro Arg Tyr
                    485                 490                 495
```

| Tyr | Ser | Ile | Ser | Ser | Pro | Arg | Phe | Ala | Pro | Ser | Arg | Ile | His | Val |
| | | | 500 | | | 505 | | | | 510 | | | | |

Thr Cys Ala Leu Val Tyr Gly Pro Ser Pro Thr Gly Arg Ile His Lys
            515                 520                 525

Gly Val Cys Ser Asn Trp Met Lys Asn Ser Leu Pro Ser Glu Glu Thr
530                     535                 540

His Asp Cys Ser Trp Ala Pro Val Phe Val Arg Gln Ser Asn Phe Lys
545                 550                 555                 560

Leu Pro Ala Asp Ser Thr Thr Pro Ile Val Met Val Gly Pro Gly Thr
                565                 570                 575

Gly Phe Ala Pro Phe Arg Gly Phe Leu Gln Glu Arg Ala Lys Leu Gln
            580                 585                 590

Glu Ala Gly Glu Lys Leu Gly Pro Ala Val Leu Phe Phe Gly Cys Arg
        595                 600                 605

Asn Arg Gln Met Asp Tyr Ile Tyr Glu Asp Glu Leu Lys Gly Tyr Val
    610                 615                 620

Glu Lys Gly Ile Leu Thr Asn Leu Ile Val Ala Phe Ser Arg Glu Gly
625                 630                 635                 640

Ala Thr Lys Glu Tyr Val Gln His Lys Met Leu Glu Lys Ala Ser Asp
            645                 650                 655

Thr Trp Ser Leu Ile Ala Gln Gly Gly Tyr Leu Tyr Val Cys Gly Asp
        660                 665                 670

Ala Lys Gly Met Ala Arg Asp Val His Arg Thr Leu His Thr Ile Val
            675                 680                 685

Gln Glu Gln Glu Ser Val Asp Ser Ser Lys Ala Glu Phe Leu Val Lys
        690                 695                 700

Lys Leu Gln Met Asp Gly Arg Tyr Leu Arg Asp Ile Trp
705                 710                 715

<210> SEQ ID NO 67
<211> LENGTH: 2154
<212> TYPE: DNA
<213> ORGANISM: Taxus cuspidata

<400> SEQUENCE: 67

| atgcaggcta | attccaacac | ggtggaaggt | gcctcccagg | ggaagagcct | gctggacata | 60 |
| tctcggctgg | accatatttt | tgcgctgctg | ttgaacggca | aggaggagaa | tctgggagcc | 120 |
| atgaccggct | cggctttgat | tttgacagag | aattcgcaga | atttgatgat | tttgaccacg | 180 |
| gctttggctg | ttttggtcgc | gtgtgttttc | ttcttcgttt | ggaggagggg | aggatcggat | 240 |
| acgcagaagc | cggcggtgag | accgacgcct | ctggtgaagg | aggaagatga | ggaggaagaa | 300 |
| gacgattctg | caaagaagaa | agtcacgatt | tcctttggga | cacagactgg | gacggccgag | 360 |
| ggatttgcca | aggctctagc | agaagaggca | aaggcaagat | atgagaaagc | tgtgtttaaa | 420 |
| gtcgtagatt | tggacaacta | tgcagcagat | gatgagcagt | atgaagaaaa | attgaaaaag | 480 |
| gaaaaattag | catttttat | gctagcaacg | tatggagatg | gggagcccac | tgacaatgca | 540 |
| gcaagatttt | ataagtggtt | tcttgagggc | aaggagaggg | agccatggct | ttctgatctc | 600 |
| acttatgggg | tgtttggatt | aggcaacaga | caatatgaac | attttaataa | ggtggctaaa | 660 |
| gcagtagatg | aagtcttaat | tgaacaaggt | gcaaagcgac | ttgttccagt | gggccttggt | 720 |
| gatgatgacc | aatgcattga | agatgacttt | actgcttggc | gagagcaggt | ttggcctgaa | 780 |
| ctggatcagt | tactccggga | tgaagatgat | gagcccacaa | gtgctacacc | ttatacagct | 840 |

```
gccatacctg agtatagggt tgaaatttat gattccgtgg tttcagtgta cgaggaaact    900
catgctctca agcaaaatgg ccaagctgtt tatgatatcc atcacccctg cagatctaat    960
gtggcagtga aagagagct tcatacacct ttgtctgacc gctcttgcat ccatttggaa    1020
tttgatatat cagacactgg ccttatatat gagacaggag atcatgttgg tgtccataca    1080
gaaaacagca ttgaaactgt ggaggaagca gcaaagctac taggctacca attggacact    1140
atattctcag tccacggtga caaagaagat ggcacgccac ttggagggtc ttctttgcca    1200
ccacctttcc ctggtccatg caccctacga actgctcttg ctcgttatgc tgatttgctg    1260
aatcctcctc ggaaggccgc ctttcttgca ttggcagctc atgcatctga tccagcagag    1320
gcagagcggt tgaagttcct ctcatcacca gctggaaagg atgaatattc tcaatgggtc    1380
actgcaagtc agagaagtct tttagaaata atggcagaat tccatcagc aaaaccaccc    1440 cttggtgttt tctttgcagc aatagcccct cgtctgcaac cccgatatta ttctatttct    1500
tcctctccca ggtttgcacc ctcaagaata catgtgacat gtgctcttgt ttacgggccc    1560
agtccaaccg gtagaattca caaaggtgtt tgttctaact ggatgaagaa ttcgctaccc    1620
tcagaagaaa cccatgactg tagctgggct ccagtctttg tcaggcaatc aaattttaaa    1680
ttgccagcag attctactac tcctattgtc atggtgggtc ctggaactgg ttttgcacct    1740
tttagaggtt ttttgcagga aagagcaaaa cttcaagaag ctggtgagaa gctcggtccg    1800
gctgttttat tttttgggtg caggaatcgc caaatggact acatttatga agatgagctg    1860
aagggctatg tggagaaagg aatactgacc aatctcattg ttgctttctc tcgtgaagga    1920
gcaaccaaag agtatgtcca gcacaagatg ctggaaaagg catccgatac ctggagtctc    1980
attgctcagg gtgggtatct ttatgtatgt ggtgatgcca agggtatggc tagggatgta    2040
cacaggacac tgcacactat tgtccaagag caggaatctg tggatagcag caaagcagag    2100
tttctagtga agaaattaca gatggatgga agatacttac gagatatatg gtga          2154
```

<210> SEQ ID NO 68
<211> LENGTH: 705
<212> TYPE: PRT
<213> ORGANISM: Artemisia annua

<400> SEQUENCE: 68

```
Met Ala Gln Ser Thr Thr Ser Val Lys Leu Ser Pro Phe Asp Leu Met
1               5                   10                  15

Thr Ala Leu Leu Asn Gly Lys Val Ser Phe Asp Thr Ser Asn Thr Ser
            20                  25                  30

Asp Thr Asn Ile Pro Leu Ala Val Phe Met Glu Asn Arg Glu Leu Leu
        35                  40                  45

Met Ile Leu Thr Thr Ser Val Ala Val Leu Ile Gly Cys Val Val Val
    50                  55                  60

Leu Val Trp Arg Arg Ser Ser Ser Ala Ala Lys Lys Ala Ala Glu Ser
65                  70                  75                  80

Pro Val Ile Val Val Pro Lys Lys Val Thr Glu Asp Glu Val Asp Asp
                85                  90                  95

Gly Arg Lys Lys Val Thr Val Phe Phe Gly Thr Gln Thr Gly Thr Ala
            100                 105                 110

Glu Gly Phe Ala Lys Ala Leu Val Glu Glu Ala Lys Ala Arg Tyr Glu
        115                 120                 125

Lys Ala Val Phe Lys Val Ile Asp Leu Asp Asp Tyr Ala Ala Glu Asp
    130                 135                 140
```

```
Asp Glu Tyr Glu Glu Lys Leu Lys Lys Glu Ser Leu Ala Phe Phe Phe
145                 150                 155                 160

Leu Ala Thr Tyr Gly Asp Gly Glu Pro Thr Asp Asn Ala Ala Arg Phe
                165                 170                 175

Tyr Lys Trp Phe Thr Glu Gly Glu Lys Gly Glu Trp Leu Asp Lys
                180                 185                 190

Leu Gln Tyr Ala Val Phe Gly Leu Gly Asn Arg Gln Tyr Glu His Phe
        195                 200                 205

Asn Lys Ile Ala Lys Val Val Asp Glu Lys Leu Val Glu Gln Gly Ala
        210                 215                 220

Lys Arg Leu Val Pro Val Gly Met Gly Asp Asp Gln Cys Ile Glu
225                 230                 235                 240

Asp Asp Phe Thr Ala Trp Lys Glu Leu Val Trp Pro Glu Leu Asp Gln
                245                 250                 255

Leu Leu Arg Asp Glu Asp Asp Thr Ser Val Ala Thr Pro Tyr Thr Ala
                260                 265                 270

Ala Val Ala Glu Tyr Arg Val Val Phe His Asp Lys Pro Glu Thr Tyr
            275                 280                 285

Asp Gln Asp Gln Leu Thr Asn Gly His Ala Val His Asp Ala Gln His
290                 295                 300

Pro Cys Arg Ser Asn Val Ala Val Lys Lys Glu Leu His Ser Pro Leu
305                 310                 315                 320

Ser Asp Arg Ser Cys Thr His Leu Glu Phe Asp Ile Ser Asn Thr Gly
                325                 330                 335

Leu Ser Tyr Glu Thr Gly Asp His Val Gly Val Tyr Val Glu Asn Leu
                340                 345                 350

Ser Glu Val Val Asp Glu Ala Glu Lys Leu Ile Gly Leu Pro Pro His
            355                 360                 365

Thr Tyr Phe Ser Val His Ala Asp Asn Glu Asp Gly Thr Pro Leu Gly
        370                 375                 380

Gly Ala Ser Leu Pro Pro Pro Phe Pro Pro Cys Thr Leu Arg Lys Ala
385                 390                 395                 400

Leu Ala Ser Tyr Ala Asp Val Leu Ser Ser Pro Lys Lys Ser Ala Leu
                405                 410                 415

Leu Ala Leu Ala Ala His Ala Thr Asp Ser Thr Glu Ala Asp Arg Leu
                420                 425                 430

Lys Phe Leu Ala Ser Pro Ala Gly Lys Asp Glu Tyr Ala Gln Trp Ile
            435                 440                 445

Val Ala Ser His Arg Ser Leu Leu Glu Val Met Glu Ala Phe Pro Ser
450                 455                 460

Ala Lys Pro Pro Leu Gly Val Phe Phe Ala Ser Val Ala Pro Arg Leu
465                 470                 475                 480

Gln Pro Arg Tyr Tyr Ser Ile Ser Ser Ser Pro Arg Phe Ala Pro Asn
                485                 490                 495

Arg Ile His Val Thr Cys Ala Leu Val Tyr Glu Gln Thr Pro Ser Gly
                500                 505                 510

Arg Val His Lys Gly Val Cys Ser Thr Trp Met Lys Asn Ala Val Pro
            515                 520                 525

Met Thr Glu Ser Gln Asp Cys Ser Trp Ala Pro Ile Tyr Val Arg Thr
        530                 535                 540

Ser Asn Phe Arg Leu Pro Ser Asp Pro Lys Val Pro Val Ile Met Ile
545                 550                 555                 560

Gly Pro Gly Thr Gly Leu Ala Pro Phe Arg Gly Phe Leu Gln Glu Arg
```

```
                        565                 570                 575
Leu Ala Gln Lys Glu Ala Gly Thr Glu Leu Gly Thr Ala Ile Leu Phe
                580                 585                 590

Phe Gly Cys Arg Asn Arg Lys Val Asp Phe Ile Tyr Glu Asp Glu Leu
            595                 600                 605

Asn Asn Phe Val Glu Thr Gly Ala Leu Ser Glu Leu Val Thr Ala Phe
        610                 615                 620

Ser Arg Glu Gly Ala Thr Lys Glu Tyr Val Gln His Lys Met Thr Gln
625                 630                 635                 640

Lys Ala Ser Asp Ile Trp Asn Leu Leu Ser Glu Gly Ala Tyr Leu Tyr
                645                 650                 655

Val Cys Gly Asp Ala Lys Gly Met Ala Lys Asp Val His Arg Thr Leu
            660                 665                 670

His Thr Ile Val Gln Glu Gln Gly Ser Leu Asp Ser Ser Lys Ala Glu
        675                 680                 685

Leu Tyr Val Lys Asn Leu Gln Met Ala Gly Arg Tyr Leu Arg Asp Val
    690                 695                 700

Trp
705

<210> SEQ ID NO 69
<211> LENGTH: 2118
<212> TYPE: DNA
<213> ORGANISM: Artemisia annua

<400> SEQUENCE: 69
atggcgcagt ctaccaccag cgtgaaattg tcccctttg atctcatgac cgctctgctg     60
aatgggaaag tctcattcga tacaagcaac acaagtgata ccaacatccc tttggcggtt    120
tttatggaga atagagagtt actcatgatt ttaacgactt ccgtggccgt gctcattggg    180
tgcgtcgtcg tacttgtctg cgccggtca agtagcgcag caagaaggc ggcggagtcc      240 ccggttatcg tcgtcccaaa gaaggttaca gaggacgagg tggacgacgg acgcaaaaaa    300
gtgacggtat tctttggtac acagaccgga accgcggaag gatttgctaa agcgctggtg    360
gaagaagcta aagcccgtta cgaaaaagcg gtattcaaag tgatagacct ggatgactat    420
gcggcagagg acgacgagta cgaggaaaaa ttgaaaaaag aatctcttgc gttctttttt    480
ctcgccactt acggcgatgg agaacctact gataatgcgg ctcggttta aagtggttc     540 actgagggtg aagaaaaagg tgaatggctg acaaattgc agtacgcagt atttggactc    600
gggaatcgtc aatatgaaca ttttaacaaa attgctaagg tcgtcgatga aaactggtt    660 gagcagggtg cgaaacgtct ggtcccggtt ggaatgggcg atgacgacca gtgcattgaa    720 gacgactta cagcatggaa ggaactggtg tggccggaac tggaccaact tttgcgtgac    780
gaggatgaca catctgtagc tacgccgtac actgctgcgg tagccgagta tagggtcgtt    840
tttcacgata aaccgaaaac ctacgaccaa gaccagctca caaatggtca tgcagtacat    900
gatgcgcaac atccttgcag gtcaaatgtg gcggtgaaga aagagctgca cagtcctctg    960
tcagatcgtt cttgcaccca cctggaattt gacatatcca atacgggcct ttcgtatgaa   1020
accggagatc acgttggtgt ctatgttgaa atctgtcgg aagtggttga tgaggcggaa   1080
aaacttatcg gtctgccgcc tcatacgtac ttttcagtcc acgctgataa tgaagacgga   1140
accccgctgg gtgcgcatc gttaccccca ccctttccac catgcactct gcgtaaggcg   1200
cttgccagtt atgctgatgt ttgtctagt cccaaaaaga gtgcacttct cgcactggcg   1260
```

```
gcccatgcca ctgatagtac agaggccgac aggctgaaat ttctggcgtc accagcggga    1320
aaagacgaat acgcccaatg gatcgttgcc agtcatcggt ctttactgga agtgatggaa    1380
gcgttcccct ccgctaagcc acctctgggg gtcttttcg ctagtgtggc accccgtcta     1440
cagccccggt attactcaat atctagctca cccagatttg ctccgaatag aatacacgta    1500
acatgcgcgc tggtctatga gcagacccca agtggacggg tgcataaagg gtttgttct    1560 acctggatga agaacgccgt cccaatgacc gagtctcagg attgttcctg ggcacctata    1620
tatgttagaa catcaaactt tcgactgcca agtgacccga aagttccggt aattatgata    1680
ggtccaggaa cagggctggc tccctttcgc gggttcctcc aggaacgtct ggcgcagaag    1740
gaggcgggaa ctgaactggg gacggcgatt ttatttttcg ggtgtagaaa tcgtaaagtc    1800
gattttatat atgaagatga gttgaacaat ttcgtggaaa ccggggcatt atcggaatta    1860
gttacggctt ttagcaggga gggggcgact aaagagtatg tccagcacaa gatgactcag    1920
aaagcctcag atatatggaa cctgctgtcg gagggagcct atctttatgt ttgcggtgat    1980
gcaaaaggaa tggccaaaga tgtccaccgg accctccaca ctattgtgca ggaacagggt    2040
tcattagact caagtaaagc cgaactttac gtaaaaaatc tacagatggc gggccgttac    2100
ctccgtgacg tttggtaa                                                  2118
```

<210> SEQ ID NO 70
<211> LENGTH: 693
<212> TYPE: PRT
<213> ORGANISM: Arabidopsis thaliana

<400> SEQUENCE: 70

```
Met Ala Thr Ser Ala Leu Tyr Ala Ser Asp Leu Phe Lys Gln Leu Lys
1               5                   10                  15

Ser Ile Met Gly Thr Asp Ser Leu Ser Asp Asp Val Val Leu Val Ile
            20                  25                  30

Ala Thr Thr Ser Leu Ala Leu Val Ala Gly Phe Val Val Leu Leu Trp
        35                  40                  45

Lys Lys Thr Thr Ala Asp Arg Ser Gly Glu Leu Lys Pro Leu Met Ile
    50                  55                  60

Pro Lys Ser Leu Met Ala Lys Asp Glu Asp Asp Leu Asp Leu Gly
65                  70                  75                  80

Ser Gly Lys Thr Arg Val Ser Ile Phe Phe Gly Thr Gln Thr Gly Thr
                85                  90                  95

Ala Glu Gly Phe Ala Lys Ala Leu Ser Glu Glu Ile Lys Ala Arg Tyr
            100                 105                 110

Glu Lys Ala Ala Val Lys Val Ile Asp Leu Asp Asp Tyr Ala Ala Asp
        115                 120                 125

Asp Asp Gln Tyr Glu Glu Lys Leu Lys Lys Glu Thr Leu Ala Phe Phe
    130                 135                 140

Cys Val Ala Thr Tyr Gly Asp Gly Glu Pro Thr Asp Asn Ala Ala Arg
145                 150                 155                 160

Phe Tyr Lys Trp Phe Thr Glu Glu Asn Glu Arg Asp Ile Lys Leu Gln
                165                 170                 175

Gln Leu Ala Tyr Gly Val Phe Ala Leu Gly Asn Arg Gln Tyr Glu His
            180                 185                 190

Phe Asn Lys Ile Gly Ile Val Leu Asp Glu Glu Leu Cys Lys Lys Gly
        195                 200                 205

Ala Lys Arg Leu Ile Glu Val Gly Leu Gly Asp Asp Asp Gln Ser Ile
    210                 215                 220
```

```
Glu Asp Asp Phe Asn Ala Trp Lys Glu Ser Leu Trp Ser Glu Leu Asp
225                 230                 235                 240

Lys Leu Leu Lys Asp Glu Asp Lys Ser Val Ala Thr Pro Tyr Thr
            245                 250                 255

Ala Val Ile Pro Glu Tyr Arg Val Val Thr His Asp Pro Arg Phe Thr
            260                 265                 270

Thr Gln Lys Ser Met Glu Ser Asn Val Ala Asn Gly Asn Thr Thr Ile
        275                 280                 285

Asp Ile His His Pro Cys Arg Val Asp Val Ala Val Gln Lys Glu Leu
        290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335

Ala Glu Asn His Val Glu Ile Val Glu Glu Ala Gly Lys Leu Leu Gly
            340                 345                 350

His Ser Leu Asp Leu Val Phe Ser Ile His Ala Asp Lys Glu Asp Gly
        355                 360                 365

Ser Pro Leu Glu Ser Ala Val Pro Pro Pro Phe Pro Gly Pro Cys Thr
        370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
            405                 410                 415

Ala Glu Lys Leu Lys His Leu Thr Ser Pro Asp Gly Lys Asp Glu Tyr
            420                 425                 430

Ser Gln Trp Ile Val Ala Ser Gln Arg Ser Leu Leu Glu Val Met Ala
        435                 440                 445

Ala Phe Pro Ser Ala Lys Pro Pro Leu Gly Val Phe Phe Ala Ala Ile
    450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
                485                 490                 495

Thr Pro Thr Gly Arg Ile His Lys Gly Val Cys Ser Thr Trp Met Lys
            500                 505                 510

Asn Ala Val Pro Ala Glu Lys Ser His Glu Cys Ser Gly Ala Pro Ile
        515                 520                 525

Phe Ile Arg Ala Ser Asn Phe Lys Leu Pro Ser Asn Pro Ser Thr Pro
    530                 535                 540

Ile Val Met Val Gly Pro Gly Thr Gly Leu Ala Pro Phe Arg Gly Phe
545                 550                 555                 560

Leu Gln Glu Arg Met Ala Leu Lys Glu Asp Gly Glu Glu Leu Gly Ser
            565                 570                 575

Ser Leu Leu Phe Phe Gly Cys Arg Asn Arg Gln Met Asp Phe Ile Tyr
        580                 585                 590

Glu Asp Glu Leu Asn Asn Phe Val Asp Gln Gly Val Ile Ser Glu Leu
        595                 600                 605

Ile Met Ala Phe Ser Arg Glu Gly Ala Gln Lys Glu Tyr Val Gln His
        610                 615                 620

Lys Met Met Glu Lys Ala Ala Gln Val Trp Asp Leu Ile Lys Glu Glu
625                 630                 635                 640
```

Gly Tyr Leu Tyr Val Cys Gly Asp Ala Lys Gly Met Ala Arg Asp Val
                645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
        675                 680                 685

Leu Arg Asp Val Trp
        690

<210> SEQ ID NO 71
<211> LENGTH: 2082
<212> TYPE: DNA
<213> ORGANISM: Arabidopsis thaliana

<400> SEQUENCE: 71

```
atggcgacca gcgctctgta tgctagtgac cttttaaac agctcaaaag catcatgggc      60
actgatagcc tgtccgacga tgttgtcctg gtaatcgcaa ccacttccct tgcgcttgtt    120
gcgggctttg tggtgttact gtggaagaag actaccgcga taggagtgg tgaattgaaa    180
ccgctgatga tcccaaaaag tctgatggcc aaagatgagg atgatgatct ggatcttgga    240
tcagggaaga cgcgagtcag tatttttttc gggacccaga cgggcaccgc ggagggcttc    300
gccaaagctc tgtccgagga aataaaggcc agatacgaga agccgccgt aaaggttata    360
gacctagatg attacgccgc tgatgacgat cagtatgagg agaaacttaa aaaggagact    420
ctggcgtttt tttgcgtggc aacttacgga gacggcgagc ccaccgataa tgcagctagg    480
ttttacaagt ggtttaccga ggagaacgaa cgagatataa agttacagca gttggcctat    540
ggcgtgtttg ccctgggtaa tcggcaatat gagcatttca acaaaattgg catcgttctg    600
gatgaggaat tgtgcaaaaa gggtgcaaaa cggctgatag aggtgggtct aggtgacgat    660
gatcaatcta tagaagacga ttttaatgcg tggaaagaga gcttatggag tgaactggat    720
aagctcttga agatgaaga cgacaagtca gtggcgaccc cttataccgc ggtaatcccg    780
gaataccgcg tcgtgacaca cgatccgagg tttacaaccc aaaaatctat ggagtctaat    840
gtcgccaatg caacacaac gattgatatt caccacccct gtcgtgttga cgtggctgtt    900
caaaaagaac ttcatacaca cgaaagtgac cgaagttgca tacacttgga atttgacatt    960
agtcgcaccg gaattacgta tgaaactggt gatcacgtgg gtgtatacgc agaaaatcat   1020
gtcgaaatag tagaagaagc tggcaaactg ctgggacatt cactcgatct agtgtttagt   1080
atacatgccg ataaagagga tggcagccca ttggaaagtg ccgtccctcc gccgtttcct   1140
ggaccgtgta ctctggggac gggactcgcc cgctatgctg acctgttaaa ccccctcgt    1200
aaaagcgccc ttgtggccct gcggcatac gcaactgaac cgagcgaagc ggagaagctg   1260
aaacatctga catcaccgga tggcaaagac gagtatagtc agtggatagt agcctctcag   1320
cgctctctgc tggaagtgat ggccgcattt ccgtccgcca aaccaccttt gggagtattt   1380
ttcgctgcta tcgcacctcg gctccagccg cgctattaca gcatatcttc aagtccccgc   1440
ttagcaccgt ctcgtgtcca tgtcacttct gcgttggttt atggtccgac tccaacaggt   1500
cgcatccaca aagtgtctg ttcaacctgg atgaaaaacg cggtgcccgc ggagaaatct   1560
catgagtgca gtggtgcacc tatttttatc cgcgcaagta acttcaaact cccttctaat   1620
ccgagcacgc ccattgtgat ggttggccca ggcactggcc ttgctccgtt tcgcggtttt   1680
ctacaggagc ggatggccct taagaagat ggggaagaat tgggatcatc gttgctcttt   1740
tttggctgcc gaaatcgcca gatggatttt atctacgaag acgagttgaa taactttgtc   1800
```

```
gatcaaggag taatttcgga gttgattatg gcattttcac gcgaaggggc tcagaaagag    1860
tatgtccaac acaagatgat ggaaaaagcg gcacaagtgt gggatcttat aaagaagaa     1920 ggctatcttt atgtatgtgg ggatgcgaaa ggtatggccc gtgatgtcca tcgcaccctg    1980
cacacgattg tacaggaaca ggaaggtgtg tcctcgtccg aagcagaagc aatcgttaaa    2040
aaactgcaaa cagagggtcg ttaccttcgc gacgtgtggt aa                      2082
```

<210> SEQ ID NO 72
<211> LENGTH: 712
<212> TYPE: PRT
<213> ORGANISM: Arabidopsis thaliana

<400> SEQUENCE: 72

```
Met Ala Ser Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
            20                  25                  30

Ala Ser Ala Tyr Glu Ser Val Ala Ala Glu Leu Ser Ser Met Leu Ile
        35                  40                  45

Glu Asn Arg Gln Phe Ala Met Ile Val Thr Thr Ser Ile Ala Val Leu
    50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
        115                 120                 125

Lys Ala Arg Tyr Glu Lys Thr Arg Phe Lys Ile Val Asp Leu Asp Asp
    130                 135                 140

Tyr Ala Ala Asp Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
        195                 200                 205

Gln Tyr Glu His Phe Asn Lys Val Ala Lys Val Val Asp Ile Leu
    210                 215                 220

Val Glu Gln Gly Ala Gln Arg Leu Val Gln Val Gly Leu Gly Asp Asp
225                 230                 235                 240

Asp Gln Cys Ile Glu Asp Asp Phe Thr Ala Trp Arg Glu Ala Leu Trp
                245                 250                 255

Pro Glu Leu Asp Thr Ile Leu Arg Glu Gly Asp Thr Ala Val Ala
            260                 265                 270

Thr Pro Tyr Thr Ala Ala Val Leu Glu Tyr Arg Val Ser Ile His Asp
        275                 280                 285

Ser Glu Asp Ala Lys Phe Asn Asp Ile Asn Met Ala Asn Gly Asn Gly
    290                 295                 300

Tyr Thr Val Phe Asp Ala Gln His Pro Tyr Lys Ala Asn Val Ala Val
305                 310                 315                 320
```

```
Lys Arg Glu Leu His Thr Pro Glu Ser Asp Arg Ser Cys Ile His Leu
                325                 330                 335

Glu Phe Asp Ile Ala Gly Ser Gly Leu Thr Tyr Glu Thr Gly Asp His
            340                 345                 350

Val Gly Val Leu Cys Asp Asn Leu Ser Glu Thr Val Asp Glu Ala Leu
        355                 360                 365

Arg Leu Leu Asp Met Ser Pro Asp Thr Tyr Phe Ser Leu His Ala Glu
    370                 375                 380

Lys Glu Asp Gly Thr Pro Ile Ser Ser Ser Leu Pro Pro Phe Pro
385                 390                 395                 400

Pro Cys Asn Leu Arg Thr Ala Leu Thr Arg Tyr Ala Cys Leu Leu Ser
                405                 410                 415

Ser Pro Lys Lys Ser Ala Leu Val Ala Leu Ala Ala His Ala Ser Asp
            420                 425                 430

Pro Thr Glu Ala Glu Arg Leu Lys His Leu Ala Ser Pro Ala Gly Lys
        435                 440                 445

Asp Glu Tyr Ser Lys Trp Val Val Glu Ser Gln Arg Ser Leu Leu Glu
    450                 455                 460

Val Met Ala Glu Phe Pro Ser Ala Lys Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
        515                 520                 525

Trp Met Lys Asn Ala Val Pro Tyr Glu Lys Ser Glu Asn Cys Ser Ser
    530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Met Asp
    595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710

<210> SEQ ID NO 73
<211> LENGTH: 2139
<212> TYPE: DNA
```

<213> ORGANISM: Arabidopsis thaliana

<400> SEQUENCE: 73

```
atggcgtcca gcagttcatc gagttctaca agcatgatcg atctgatggc cgctattatc      60
aaagggaac ccgtaattgt ctctgatcca gcaaatgcct cggcatacga gtcggtggct     120
gccgaattat catctatgtt aattgaaaat agacaatttg ccatgattgt gacaacttct     180
attgctgtgc tgataggttg catcgtcatg ctcgtgtggc gccgtagcgg atcaggcaac     240
tcaaagcgcg tcgagccttt gaaacccctg gttatcaaac cgcgagagga ggaaatcgat     300
gatggcagaa aaaggttac tatctttttt ggcacacaga cggggacagc ggaaggtttc     360
gcgaaagcac tcggagagga agcgaaagcc cgatacgaga aaacacggtt caaaattgtg     420
gatctggatg actatgcggc tgatgatgat gagtatgaag aaaaactgaa aaagaagat      480
gtggcgtttt tttttcttgc cacttatggc gacggagagc ccaccgataa tgcagcgcgg     540
ttttacaagt ggttcaccga aggaaatgat cggggagaat ggttaaaaaa tctgaaatac     600
ggtgtgttcg gtcttggcaa tgccaatat gagcatttta ataaagtcgc gaaagtggtc     660
gatgatatat tggtagaaca gggcgctcag cgcctcgtcc aggtggggct tggcgacgat     720
gatcagtgca tagaagatga ttttactgca tggcgtgaag cgctgtggcc ggagctggac     780
accattttac gtgaagaggg cgatacagca gtggcaaccc cgtacacggc tgccgtctta     840
gagtatcgtg tgtccattca tgatagcgag atgccaaat tcaatgacat caatatggcg      900
aatggaaatg ggtacaccgt gtttgacgcg cagcacccgt ataaggcaaa cgttgcagtc     960
aagagggaac tgcatactcc tgaaagtgat cgcagttgca tccacctgga gttcgatatt    1020
gcgggatcag gtttaacgta cgaaacgggc gaccacgtag gtgtgctgtg cgacaatctt    1080
tcagagacag tggacgaagc tctgcgcctg ctggatatga gcccggatac ctatttagc     1140
ttgcacgctg agaagaaga tgggactcca attagcagta gcttacctcc accctttccg     1200
ccgtgtaatt tgcgtaccgc ccttacgcgc tatgcgtgtc tgctgagttc gccaaagaag    1260
tcggcccttg tggcactggc ggcacatgca agtgacccga ccgaggcgga gaggctgaaa    1320
catctggctt ctccagcggg caaagatgaa tacagcaaat gggtggtaga atcacagcgt    1380
tccctactag aagtaatggc cgaattcccc tcagctaaac caccgctggg agtgttcttt    1440
gcgggcgttg ctccccgctt gcaaccacgc ttttattcaa ttagctcaag tcctaagata    1500
gcggaaacac ggatacatgt aacttgcgca ttggtttatg aaaaaatgcc aaccgggagg    1560
atacataaag gcgtatgttc aacctggatg aaaaatgctg tgccatacga aaagtcggag    1620
aattgctcct ctgccccaat tttcgtgcgt caaagcaact ttaaactgcc gagtgattca    1680
aaggtgccta ttattatgat aggccctggt acaggactcg ccccgtttcg tggttttctt    1740
caagaaagac tggctctggt cgaatcaggc gtggaattag accctccgt gttattttt     1800
ggctgccgca accgtcgaat ggacttcatc tatgaagaag aattgcaacg ttttgtggag    1860
tcaggcgctc tggcggaact atccgtcgcc tttagtagag aaggcccaac caaagaatac    1920
gtacagcata gatgatgga taaagcgagc gacatttgga atatgatctc acaaggggcg    1980
tacctgtacg tatgtggaga tgccaaagga atggcacgag acgtacatag atcgttgcat    2040
actattgctc aagaacaggg aagcatggat tcgactaaag cagaaggctt tgttaaaaat    2100
ctacagacat ctggtcgcta tctgcgtgac gtgtggtaa                          2139
```

<210> SEQ ID NO 74
<211> LENGTH: 713

<212> TYPE: PRT
<213> ORGANISM: Arabidopsis thaliana

<400> SEQUENCE: 74

```
Met Ala Ser Ser Ser Ser Ser Thr Ser Met Ile Asp Leu Met
1               5                   10                  15

Ala Ala Ile Ile Lys Gly Glu Pro Val Ile Ser Asp Pro Ala Asn
            20                  25                  30

Ala Ser Ala Tyr Glu Ser Val Ala Ala Glu Leu Ser Ser Met Leu Ile
        35                  40                  45

Glu Asn Arg Gln Phe Ala Met Ile Val Thr Thr Ser Ile Ala Val Leu
    50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
        115                 120                 125

Lys Ala Arg Tyr Glu Lys Thr Arg Phe Lys Ile Val Asp Leu Asp Asp
    130                 135                 140

Tyr Ala Ala Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
        195                 200                 205

Gln Tyr Glu His Phe Asn Lys Val Ala Lys Val Val Asp Asp Ile Leu
    210                 215                 220

Val Glu Gln Gly Ala Gln Arg Leu Val Gln Val Gly Leu Gly Asp Asp
225                 230                 235                 240

Asp Gln Cys Ile Glu Asp Phe Thr Ala Trp Arg Glu Ala Leu Trp
                245                 250                 255

Pro Glu Leu Asp Thr Ile Leu Arg Glu Glu Gly Asp Thr Ala Val Ala
            260                 265                 270

Thr Pro Tyr Thr Ala Ala Val Leu Glu Tyr Arg Val Ser Ile His Asp
        275                 280                 285

Ser Glu Asp Ala Lys Phe Asn Asp Ile Thr Leu Ala Asn Gly Asn Gly
    290                 295                 300

Tyr Thr Val Phe Asp Ala Gln His Pro Tyr Lys Ala Asn Val Ala Val
305                 310                 315                 320

Lys Arg Glu Leu His Thr Pro Glu Ser Asp Arg Ser Cys Ile His Leu
                325                 330                 335

Glu Phe Asp Ile Ala Gly Ser Gly Leu Thr Met Lys Leu Gly Asp His
            340                 345                 350

Val Gly Val Leu Cys Asp Asn Leu Ser Glu Thr Val Asp Glu Ala Leu
        355                 360                 365

Arg Leu Leu Asp Met Ser Pro Asp Thr Tyr Phe Ser Leu His Ala Glu
    370                 375                 380

Lys Glu Asp Gly Thr Pro Ile Ser Ser Ser Leu Pro Pro Pro Phe Pro
385                 390                 395                 400
```

Pro Cys Asn Leu Arg Thr Ala Leu Thr Arg Tyr Ala Cys Leu Leu Ser
            405                 410                 415

Ser Pro Lys Lys Ser Ala Leu Val Ala Leu Ala Ala His Ala Ser Asp
        420                 425                 430

Pro Thr Glu Ala Glu Arg Leu Lys His Leu Ala Ser Pro Ala Gly Lys
    435                 440                 445

Asp Glu Tyr Ser Lys Trp Val Val Glu Ser Gln Arg Ser Leu Leu Glu
450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
        515                 520                 525

Trp Met Lys Asn Ala Val Pro Tyr Glu Lys Ser Glu Lys Leu Phe Leu
    530                 535                 540

Gly Arg Pro Ile Phe Val Arg Gln Ser Asn Phe Lys Leu Pro Ser Asp
545                 550                 555                 560

Ser Lys Val Pro Ile Ile Met Ile Gly Pro Gly Thr Gly Leu Ala Pro
                565                 570                 575

Phe Arg Gly Phe Leu Gln Glu Arg Leu Ala Leu Val Glu Ser Gly Val
            580                 585                 590

Glu Leu Gly Pro Ser Val Leu Phe Phe Gly Cys Arg Asn Arg Arg Met
        595                 600                 605

Asp Phe Ile Tyr Glu Glu Leu Gln Arg Phe Val Glu Ser Gly Ala
    610                 615                 620

Leu Ala Glu Leu Ser Val Ala Phe Ser Arg Glu Gly Pro Thr Lys Glu
625                 630                 635                 640

Tyr Val Gln His Lys Met Met Asp Lys Ala Ser Asp Ile Trp Asn Met
                645                 650                 655

Ile Ser Gln Gly Ala Tyr Leu Tyr Val Cys Gly Asp Ala Lys Gly Met
            660                 665                 670

Ala Arg Asp Val His Arg Ser Leu His Thr Ile Ala Gln Glu Gln Gly
        675                 680                 685

Ser Met Asp Ser Thr Lys Ala Glu Gly Phe Val Lys Asn Leu Gln Thr
    690                 695                 700

Ser Gly Arg Tyr Leu Arg Asp Val Trp
705                 710

<210> SEQ ID NO 75
<211> LENGTH: 2142
<212> TYPE: DNA
<213> ORGANISM: Arabidopsis thaliana

<400> SEQUENCE: 75
atggcgagca gttcgtcctc ctcttctacc agtatgatcg atctgatggc cgctattata      60
aaaggagaac cagtcattgt gtctgatcct gcaaacgcat cagcctacga atctgtggct     120
gctgaactgt cctcgatgct gatcgaaaat cgccaatttg caatgattgt tacaaccagc     180
atcgctgttc ttatcgggtg tattgtcatg ctggtttggc ggcggagtgg cagcggcaat     240
tctaaaagag tggagccact gaagcctctg gtaatcaaac cccgcgaaga agaaatcgat     300

```
gatggacgta agaaagttac aattttttt ggtacacaga caggtacagc agagggcttt      360
gccaaagctc ttggagaaga agcaaaagct cgatatgaga aaacacgctt caagatcgtc      420
gatctggatg actacgcggc agacgacgat gagtacgaag aaaaactcaa aaagaggat       480
gtggcttttt ttttcctggc aacttatggg gacggcgagc ctaccgacaa tgcagcgcgg      540
ttttacaaat ggtttaccga aggcaatgat agaggggagt ggctcaaaaa tctcaaatac      600
ggagttttcg gattggggaa tagacaatac gaacactta taaggttgc gaaagtggta       660
gatgatattc tggtcgagca gggcgcgcaa cgtttagtac aggtcggcct gggtgatgac      720
gaccagtgca tcgaagatga ctttacggcc tggcgagaag cgctctggcc ggaattagat      780
acaatccttc gggaagaggg ggacactgct gtcgctaccc cgtacactgc cgcagtgctg      840
gaatatcgtg tttcaataca tgattcggaa gatgccaagt taatgacat cacctggca      900
aacggcaacg gataccgt atttgacgct caacatccgt ataaggccaa tgtagcagta       960
aagcgggaac tccatactcc cgaaagtgac agaagttgca tccatctgga gttcgatata     1020
gcgggaagcg gactgactat gaactgggga gatcatgtag gggtcctgtg cgataatttg     1080
agcgaaaccg ttgacgaagc gctccggctt ttagatatgt cccctgatac ttatttctct     1140
ttgcacgccg agaaggaaga tggtacacct atatcctcct cgctgccgcc gccttttcca     1200
ccatgtaatc tgcgtacggc cttgactagg tatgcatgtc ttcttagctc cccgaaaaag     1260
tccgcactgg tagcgttggc agctcatgcc agcgatccca cggaggcaga gcgtttaaaa     1320
cacctggcga gtcctgctgg caaagatgaa tacagcaaat gggtggttga gtcgcagagg     1380
tccctgctgg aagtcatggc tgaatttccg tctgcgaaac cgcctctggg agttttcttc     1440
gcaggagtag ccccacgttt acaaccgcgt ttctattcta ttcttcctc ccccaagatc      1500
gcggaaactc gaatacacgt aacgtgcgca ttggtgtatg aaaagatgcc aactggtcgt     1560
atccacaagg gagtgtgctc aacctggatg aaaaacgccg ttccgtatga aaaatcggaa     1620
aaattgtttt tgggtagacc catattcgtt cggcagtcaa actttaaact accttctgat     1680
agcaaggttc cgattattat gattggaccg ggtactggcc tggcgccgtt ccgtggtttc     1740
ctgcaagaac ggttggcgct ggtggaatcc ggcgtggaac ttgggccatc ggttttgttt     1800
ttcgggtgcc gcaatcgtcg catggacttc atctacgagg aagaactcca gcgttttgtc     1860
gaaagcggtg cccttgctga attgtccgtt gcattcagcc gcgaaggtcc aactaaggag     1920
tatgtgcagc acaaaatgat ggacaaagcg agcgatattt ggaatatgat tagccagggc     1980
gcataccttt atgtgtgcgg tgatgctaag ggaatggcgc gcgatgtcca tagatcttta    2040
cataccattg cacaggagca gggctctatg gattcaacaa aagctgaagg ttttgtgaaa     2100
aaccttcaga ccagcgggcg gtatcttcgc gatgtttggt aa                       2142
```

<210> SEQ ID NO 76
<211> LENGTH: 711
<212> TYPE: PRT
<213> ORGANISM: Stevia rebaudiana

<400> SEQUENCE: 76

Met Ala Gln Ser Asp Ser Val Lys Val Ser Pro Phe Asp Leu Val Ser
1               5                   10                  15

Ala Ala Met Asn Gly Lys Ala Met Glu Lys Leu Asn Ala Ser Glu Ser
            20                  25                  30

Glu Asp Pro Thr Thr Leu Pro Ala Leu Lys Met Leu Val Glu Asn Arg
        35                  40                  45

```
Glu Leu Leu Thr Leu Phe Thr Thr Ser Phe Ala Val Leu Ile Gly Cys
 50                  55                  60

Leu Val Phe Leu Met Trp Arg Arg Ser Ser Lys Lys Leu Val Gln
 65                  70                  75                  80

Asp Pro Val Pro Gln Val Ile Val Val Lys Lys Glu Lys Glu Ser
                 85                  90                  95

Glu Val Asp Asp Gly Lys Lys Val Ser Ile Phe Tyr Gly Thr Gln
                100                 105                 110

Thr Gly Thr Ala Glu Gly Phe Ala Lys Ala Leu Val Glu Glu Ala Lys
             115                 120                 125

Val Arg Tyr Glu Lys Thr Ser Phe Lys Val Ile Asp Leu Asp Asp Tyr
130                 135                 140

Ala Ala Asp Asp Glu Tyr Glu Glu Lys Leu Lys Lys Glu Ser Leu
145                 150                 155                 160

Ala Phe Phe Phe Leu Ala Thr Tyr Gly Asp Gly Glu Pro Thr Asp Asn
                165                 170                 175

Ala Ala Asn Phe Tyr Lys Trp Phe Thr Glu Gly Asp Asp Lys Gly Glu
            180                 185                 190

Leu Leu Lys Lys Leu Gln Tyr Gly Val Phe Gly Leu Gly Asn Arg Gln
            195                 200                 205

Tyr Glu His Phe Asn Lys Ile Ala Ile Val Val Asp Asp Lys Leu Thr
210                 215                 220

Glu Met Gly Ala Lys Arg Leu Val Pro Val Gly Leu Gly Asp Asp Asp
225                 230                 235                 240

Gln Cys Ile Glu Asp Asp Phe Thr Ala Trp Lys Glu Leu Val Trp Pro
                245                 250                 255

Glu Leu Asp Gln Leu Leu Arg Asp Glu Asp Thr Ser Val Thr Thr
            260                 265                 270

Pro Tyr Thr Ala Ala Val Leu Glu Tyr Arg Val Val Tyr His Asp Lys
    275                 280                 285

Pro Ala Asp Ser Tyr Ala Glu Asp Gln Thr His Thr Asn Gly His Val
    290                 295                 300

Val His Asp Ala Gln His Pro Ser Arg Ser Asn Val Ala Phe Lys Lys
305                 310                 315                 320

Glu Leu His Thr Ser Gln Ser Asp Arg Ser Cys Thr His Leu Glu Phe
                325                 330                 335

Asp Ile Ser His Thr Gly Leu Ser Tyr Glu Thr Gly Asp His Val Gly
            340                 345                 350

Val Tyr Ser Glu Asn Leu Ser Glu Val Val Asp Glu Ala Leu Lys Leu
            355                 360                 365

Leu Gly Leu Ser Pro Asp Thr Tyr Phe Ser Val His Ala Asp Lys Glu
    370                 375                 380

Asp Gly Thr Pro Ile Gly Gly Ala Ser Leu Pro Pro Phe Pro Pro
385                 390                 395                 400

Cys Thr Leu Arg Asp Ala Leu Thr Arg Tyr Ala Asp Val Leu Ser Ser
                405                 410                 415

Pro Lys Lys Val Ala Leu Leu Ala Leu Ala Ala His Ala Ser Asp Pro
            420                 425                 430

Ser Glu Ala Asp Arg Leu Lys Phe Leu Ala Ser Pro Ala Gly Lys Asp
            435                 440                 445

Glu Tyr Ala Gln Trp Ile Val Ala Asn Gln Arg Ser Leu Leu Glu Val
    450                 455                 460

Met Gln Ser Phe Pro Ser Ala Lys Pro Pro Leu Gly Val Phe Phe Ala
```

```
                465                 470                 475                 480
        Ala Val Ala Pro Arg Leu Gln Pro Arg Tyr Tyr Ser Ile Ser Ser Ser
                        485                 490                 495

Pro Lys Met Ser Pro Asn Arg Ile His Val Thr Cys Ala Leu Val Tyr
                        500                 505                 510

Glu Thr Thr Pro Ala Gly Arg Ile His Arg Gly Leu Cys Ser Thr Trp
                        515                 520                 525

Met Lys Asn Ala Val Pro Leu Thr Glu Ser Pro Asp Cys Ser Gln Ala
                        530                 535                 540

Ser Ile Phe Val Arg Thr Ser Asn Phe Arg Leu Pro Val Asp Pro Lys
        545                 550                 555                 560

Val Pro Val Ile Met Ile Gly Pro Gly Thr Gly Leu Ala Pro Phe Arg
                        565                 570                 575

Gly Phe Leu Gln Glu Arg Leu Ala Leu Lys Glu Ser Gly Thr Glu Leu
                        580                 585                 590

Gly Ser Ser Ile Phe Phe Phe Gly Cys Arg Asn Arg Lys Val Asp Phe
                        595                 600                 605

Ile Tyr Glu Asp Glu Leu Asn Asn Phe Val Glu Thr Gly Ala Leu Ser
                        610                 615                 620

Glu Leu Ile Val Ala Phe Ser Arg Glu Gly Thr Ala Lys Glu Tyr Val
        625                 630                 635                 640

Gln His Lys Met Ser Gln Lys Ala Ser Asp Ile Trp Lys Leu Leu Ser
                        645                 650                 655

Glu Gly Ala Tyr Leu Tyr Val Cys Gly Asp Ala Lys Gly Met Ala Lys
                        660                 665                 670

Asp Val His Arg Thr Leu His Thr Ile Val Gln Glu Gln Gly Ser Leu
                        675                 680                 685

Asp Ser Ser Lys Ala Glu Leu Tyr Val Lys Asn Leu Gln Met Ser Gly
                        690                 695                 700

Arg Tyr Leu Arg Asp Val Trp
        705                 710

<210> SEQ ID NO 77
<211> LENGTH: 2136
<212> TYPE: DNA
<213> ORGANISM: Stevia rebaudiana

<400> SEQUENCE: 77
atggctcaga gcgattctgt taaagtatcc ccgttcgacc tggtctctgc ggctatgaac     60
ggcaaagcaa tggagaaact gaacgcgagc gaatctgaag atccaaccac cctgccggca    120
ctgaaaatgc tggtagaaaa ccgtgaactg ctgactctgt tcaccacctc cttcgccgtt    180
ctgattggtt gcctggtctt cctgatgtgg cgccgttcct cttccaagaa gctggtacag    240
gacccggttc tcaggtgat cgtcgttaaa aagaaagaga aggaaagcga agtcgatgac    300
ggcaaaaaga aggtttccat tttctacggt actcagaccg gcaccgctga gggttttgcc    360
aaagcactgg ttgaagaggc aaaagtgcgt tacgaaaaaa cttccttcaa agtgattgac    420
ctggacgact atgctgcgga tgatgatgaa tacgaggaaa aactgaaaaa agaaagcctg    480
gccttcttct tcctggcaac ctatggcgat ggtgaaccga ccgacaacgc ggcgaacttc    540
tacaaatggt ttaccgaagg cgacgacaaa ggtgaattgc tgaagaaact gcagtatggt    600
gttttcggtc tgggcaatcg ccagtacgaa catttaaca aaatcgcaat cgttgttgat    660
gacaaactga ctgaaatggg tgcgaaacgt ctggtgccgg ttggcctggg tgacgatgat    720
```

```
caatgcatcg aagatgactt caccgcatgg aaagaactgg tttggccgga actggatcag    780
ctgctgcgcg acgaagacga cacttccgtg accaccccgt ataccgctgc agtgctggag    840
taccgtgttg tttaccacga taaaccggcg gactcttacg ccgaagatca gactcacact    900
aacggtcacg tcgtacatga cgcacagcac ccgtctcgta gcaatgttgc gtttaagaaa    960
gagctgcaca cgagccagtc cgaccgctct tgtacgcacc tggagttcga tatctcccac   1020
accggtctgt cctatgaaac cggtgaccat gttggcgttt acagcgaaaa cctgagcgag   1080
gtagttgatg aagcgctgaa actgctgggc ctgtctccag acacctactt tagcgtgcat   1140
gctgacaagg aagatggtac tccgattggc ggcgcttccc tgccgccacc gtttccacct   1200
tgcactctgc gtgatgctct gactcgttac gctgatgttc tgtctagccc gaaaaaggtt   1260
gcgctgctgg cgctggccgc acatgcttct gacccgtctg aagctgaccg tctgaaattc   1320
ctggcgtctc cggccggcaa agacgaatac gcgcagtgga ttgtcgctaa ccagcgctct   1380
ctgctggaag tgatgcagtc cttcccgtct gccaaaccgc cactgggcgt gttttcgca   1440
gctgtggctc cgcgcctgca gccgcgctac tattctatct ctagctcccc gaaaatgagc   1500
ccgaaccgca tccacgttac ttgtgctctg gtttacgaaa ccaccccctgc gggccgtatc   1560
caccgtggtc tgtgctctac gtggatgaaa aatgccgtgc cgctgaccga atccccggac   1620
tgctctcagg cgtccatctt cgtgcgtacc tctaacttcc gtctgccggt ggacccgaaa   1680
gttcctgtta tcatgatcgg tcctggcacg gtctggccc cgtttcgtgg ttttctgcag   1740
gagcgtctgg ctctgaaaga atccggtact gagctgggct cttccatctt tttcttcggt   1800
tgtcgtaacc gcaaagtcga tttcatctat gaagacgaac tgaacaactt cgtagagact   1860
ggtgcactgt ccgaactgat tgtggcattc tctcgtgaag gcacggcgaa agaatacgtt   1920
caacacaaaa tgtctcagaa agcgagcgat atctggaaac tgctgtccga gggtgcgtat   1980
ctgtatgttt gtggcgacgc gaaaggcatg gctaaagatg tacaccgcac cctgcacacc   2040
attgtacaag aacaaggctc tctggatagc tccaaggcag aactgtacgt gaaaaacctg   2100
cagatgtctg gccgttacct gcgtgatgta tggtaa                             2136
```

<210> SEQ ID NO 78
<211> LENGTH: 710
<212> TYPE: PRT
<213> ORGANISM: Stevia rebaudiana

<400> SEQUENCE: 78

```
Met Ala Gln Ser Glu Ser Val Glu Ala Ser Thr Ile Asp Leu Met Thr
1               5                   10                  15

Ala Val Leu Lys Asp Thr Val Ile Asp Thr Ala Asn Ala Ser Asp Asn
            20                  25                  30

Gly Asp Ser Lys Met Pro Pro Ala Leu Ala Met Met Phe Glu Ile Arg
        35                  40                  45

Asp Leu Leu Leu Ile Leu Thr Thr Ser Val Ala Leu Val Gly Cys
    50                  55                  60

Phe Val Val Leu Val Trp Lys Arg Ser Ser Gly Lys Lys Ser Gly Lys
65                  70                  75                  80

Glu Leu Glu Pro Pro Lys Ile Val Val Pro Lys Arg Arg Leu Glu Gln
                85                  90                  95

Glu Val Asp Asp Gly Lys Lys Lys Val Thr Ile Phe Phe Gly Thr Gln
            100                 105                 110

Thr Gly Thr Ala Glu Gly Phe Ala Lys Ala Leu Phe Glu Glu Ala Lys
        115                 120                 125
```

```
Ala Arg Tyr Glu Lys Ala Ala Phe Lys Val Ile Asp Leu Asp Asp Tyr
    130                 135                 140
Ala Ala Asp Leu Asp Glu Tyr Ala Glu Lys Leu Lys Lys Glu Thr Tyr
145                 150                 155                 160
Ala Phe Phe Leu Ala Thr Tyr Gly Asp Gly Glu Pro Thr Asp Asn
                165                 170                 175
Ala Ala Lys Phe Tyr Lys Trp Phe Thr Glu Gly Asp Glu Lys Gly Val
            180                 185                 190
Trp Leu Gln Lys Leu Gln Tyr Gly Val Phe Gly Leu Gly Asn Arg Gln
        195                 200                 205
Tyr Glu His Phe Asn Lys Ile Gly Ile Val Val Asp Asp Gly Leu Thr
    210                 215                 220
Glu Gln Gly Ala Lys Arg Ile Val Pro Val Gly Leu Gly Asp Asp Asp
225                 230                 235                 240
Gln Ser Ile Glu Asp Asp Phe Ser Ala Trp Lys Glu Leu Val Trp Pro
                245                 250                 255
Glu Leu Asp Leu Leu Arg Asp Glu Asp Asp Lys Ala Ala Ala Thr
                260                 265                 270
Pro Tyr Thr Ala Ala Ile Pro Glu Tyr Arg Val Val Phe His Asp Lys
        275                 280                 285
Pro Asp Ala Phe Ser Asp Asp His Thr Gln Thr Asn Gly His Ala Val
    290                 295                 300
His Asp Ala Gln His Pro Cys Arg Ser Asn Val Ala Val Lys Lys Glu
305                 310                 315                 320
Leu His Thr Pro Glu Ser Asp Arg Ser Cys Thr His Leu Glu Phe Asp
                325                 330                 335
Ile Ser His Thr Gly Leu Ser Tyr Glu Thr Gly Asp His Val Gly Val
            340                 345                 350
Tyr Cys Glu Asn Leu Ile Glu Val Val Glu Glu Ala Gly Lys Leu Leu
        355                 360                 365
Gly Leu Ser Thr Asp Thr Tyr Phe Ser Leu His Ile Asp Asn Glu Asp
    370                 375                 380
Gly Ser Pro Leu Gly Gly Pro Ser Leu Gln Pro Pro Phe Pro Pro Cys
385                 390                 395                 400
Thr Leu Arg Lys Ala Leu Thr Asn Tyr Ala Asp Leu Leu Ser Ser Pro
                405                 410                 415
Lys Lys Ser Thr Leu Leu Ala Leu Ala Ala His Ala Ser Asp Pro Thr
            420                 425                 430
Glu Ala Asp Arg Leu Arg Phe Leu Ala Ser Arg Glu Gly Lys Asp Glu
        435                 440                 445
Tyr Ala Glu Trp Val Val Ala Asn Gln Arg Ser Leu Leu Glu Val Met
    450                 455                 460
Glu Ala Phe Pro Ser Ala Arg Pro Pro Leu Gly Val Phe Phe Ala Ala
465                 470                 475                 480
Val Ala Pro Arg Leu Gln Pro Arg Tyr Tyr Ser Ile Ser Ser Ser Pro
                485                 490                 495
Lys Met Glu Pro Asn Arg Ile His Val Thr Cys Ala Leu Val Tyr Glu
            500                 505                 510
Lys Thr Pro Ala Gly Arg Ile His Lys Gly Ile Cys Ser Thr Trp Met
        515                 520                 525
Lys Asn Ala Val Pro Leu Thr Glu Ser Gln Asp Cys Ser Trp Ala Pro
    530                 535                 540
```

```
Ile Phe Val Arg Thr Ser Asn Phe Arg Leu Pro Ile Asp Pro Lys Val
545                 550                 555                 560

Pro Val Ile Met Ile Gly Pro Gly Thr Gly Leu Ala Pro Phe Arg Gly
            565                 570                 575

Phe Leu Gln Glu Arg Leu Ala Leu Lys Glu Ser Gly Thr Glu Leu Gly
        580                 585                 590

Ser Ser Ile Leu Phe Phe Gly Cys Arg Asn Arg Lys Val Asp Tyr Ile
    595                 600                 605

Tyr Glu Asn Glu Leu Asn Asn Phe Val Glu Asn Gly Ala Leu Ser Glu
    610                 615                 620

Leu Asp Val Ala Phe Ser Arg Asp Gly Pro Thr Lys Glu Tyr Val Gln
625                 630                 635                 640

His Lys Met Thr Gln Lys Ala Ser Glu Ile Trp Asn Met Leu Ser Glu
            645                 650                 655

Gly Ala Tyr Leu Tyr Val Cys Gly Asp Ala Lys Gly Met Ala Lys Asp
        660                 665                 670

Val His Arg Thr Leu His Thr Ile Val Gln Gln Gly Ser Leu Asp
    675                 680                 685

Ser Ser Lys Ala Glu Leu Tyr Val Lys Asn Leu Gln Met Ser Gly Arg
    690                 695                 700

Tyr Leu Arg Asp Val Trp
705             710

<210> SEQ ID NO 79
<211> LENGTH: 2133
<212> TYPE: DNA
<213> ORGANISM: Stevia rebaudiana

<400> SEQUENCE: 79
atggcgcaat ctgaaagtgt tgaggccagt accatcgacc ttatgacggc agtgttgaag      60
gatacagtta ttgacactgc aaatgcttca gataacggcg attctaaaat gcctcctgcg     120
cttgcgatga tgttcgagat ccgcgatctt ctgctgatcc ttaccacatc agtagcggtg     180
ctggtgggat gctttgtggt actcgtgtgg aaacgttcgt cgggcaaaaa atcaggtaag     240
gagctggaac cgcctaagat tgtcgtaccg aaacgccgac tggaacaaga agttgatgat     300
ggcaaaaaaa aagtgactat atttttttggg acacagacag gcacagcgga gggatttgcg     360
aaagccttat tcgaggaggc gaaggcacgt tacgagaaag cagcttttaa agtcattgat     420
ctggatgact atgcagcaga cctagatgaa tacgcagaga aactgaaaaa agaaacttat     480
gcgtttttct tcctggccac atacggagac ggtgaaccga cggacaatgc cgccaagttt     540
tataagtggt tcactgaagg ggatgagaaa ggtgtatggc ttcagaaatt gcaatacgga     600
gtgttcggac taggaaatcg gcaatatgag cactttaata aaataggcat agtagtagac     660
gatgggctaa ccgagcaggg ggccaaacgg attgtacccg tgggcctggg ggacgatgat     720
cagtctattg aggatgattt tagtgcttgg aaagagcttg tttggcctga actggactta     780
ctcctgcgtg atgaagacga taaagcggca gcgactccat acacggcagc aatccccgag     840
tatagagtcg tattccatga taaaccggat gctttctctg atgaccatac ccaaactaat     900
ggtcatgcgc tccatgatgc acaacatccc tgccgcagca atgtagcggt gaaaaggag     960 ctgcatacgc tgaaagtga tcgctcatgt acgcatctgg agtttgatat ttcacacaca    1020
ggtcttagct acgagactgg agatcacgtc ggagtctatt gcgaaaatct gatcgaagtg    1080
gttgaagagg ccgggaaact gttgggacta agtacagata cttattttc tttacatata    1140
```

```
gataacgagg atggttcccc acttggcggt ccatctcttc agcctccatt cccaccatgt    1200
accttacgca aagcgctgac taactacgca gatctgctgt ctagcccaaa gaaatcaacg    1260
cttctggcgt tggctgctca tgcctcagat ccgaccgaag ctgatcgcct tcgtttttctg   1320 gcatcccgag aaggtaaaga tgaatatgca gaatgggtgg tagcgaatca gcgttctttg    1380
ctggaagtca tggaggcatt ccccagcgcg cgccctccgc tgggtgtttt cttcgcagcg    1440
gtggccccgc ggctccagcc gcgttattat tcaattagca gttctcctaa gatgaacct     1500 aatcgaatcc atgtaacatg tgcattggtc tatgagaaaa cgccggctgg ccgcatccat    1560
aaaggtatat gtagcacatg gatgaaaaat gcagtacccc tcacggagtc ccaggattgt    1620
agttgggcgc cgatatttgt tcggacgagc aatttttagac ttcctataga cccaaaggtt   1680
ccagttatta tgattggtcc tggcaccgga cttgcgccat tccgggggtt tctgcaagaa    1740
agactggctc tgaaagaaag cggtacagaa ctcggctcca gtatattgtt tttcggctgt    1800
cgcaaccgga aagtagatta tatatatgaa aacgagctga ataacttcgt tgaaaatggt    1860
gccctgtctg aactcgatgt cgcttttttcg cgagatggcc cgacaaaaga atacgtgcag   1920
cataaaatga cccagaaagc aagtgaaatc tggaatatgc tgtcagaagg ggcatatctg    1980
tatgtgtgcg gagatgcaaa gggcatggcc aaagacgttc acagaacctt gcataccata    2040
gtacaagagc agggctctct ggatagctca aaagccgagc tgtacgtgaa aaatctccag    2100
atgagtggac gctacctgag ggatgtttgg taa                                 2133
```

<210> SEQ ID NO 80
<211> LENGTH: 708
<212> TYPE: PRT
<213> ORGANISM: Stevia rebaudiana

<400> SEQUENCE: 80

```
Met Ala Gln Ser Asn Ser Val Lys Ile Ser Pro Leu Asp Leu Val Thr
1               5                   10                  15

Ala Leu Phe Ser Gly Lys Val Leu Asp Thr Ser Asn Ala Ser Glu Ser
            20                  25                  30

Gly Glu Ser Ala Met Leu Pro Thr Ile Ala Met Ile Met Glu Asn Arg
        35                  40                  45

Glu Leu Leu Met Ile Leu Thr Thr Ser Val Ala Val Leu Ile Gly Cys
    50                  55                  60

Val Val Val Leu Val Trp Arg Arg Ser Ser Thr Lys Lys Ser Ala Leu
65                  70                  75                  80

Glu Pro Pro Val Ile Val Pro Lys Arg Val Gln Glu Glu Val
                85                  90                  95

Asp Asp Gly Lys Lys Lys Val Thr Val Phe Phe Gly Thr Gln Thr Gly
            100                 105                 110

Thr Ala Glu Gly Phe Ala Lys Ala Leu Val Glu Glu Ala Lys Ala Arg
        115                 120                 125

Tyr Glu Lys Ala Val Phe Lys Val Ile Asp Leu Asp Asp Tyr Ala Ala
    130                 135                 140

Asp Asp Asp Glu Tyr Glu Glu Lys Leu Lys Lys Glu Ser Leu Ala Phe
145                 150                 155                 160

Phe Phe Leu Ala Thr Tyr Gly Asp Gly Glu Pro Thr Asp Asn Ala Ala
                165                 170                 175

Arg Phe Tyr Lys Trp Phe Thr Glu Gly Asp Ala Lys Gly Glu Trp Leu
            180                 185                 190

Asn Lys Leu Gln Tyr Gly Val Phe Gly Leu Gly Asn Arg Gln Tyr Glu
```

```
                195                 200                 205
His Phe Asn Lys Ile Ala Lys Val Val Asp Asp Gly Leu Val Glu Gln
210                 215                 220

Gly Ala Lys Arg Leu Val Pro Val Gly Leu Gly Asp Asp Gln Cys
225                 230                 235                 240

Ile Glu Asp Asp Phe Thr Ala Trp Lys Glu Leu Val Trp Pro Glu Leu
                245                 250                 255

Asp Gln Leu Leu Arg Asp Glu Asp Thr Thr Val Ala Thr Pro Tyr
        260                 265                 270

Thr Ala Ala Val Ala Glu Tyr Arg Val Val Phe His Glu Lys Pro Asp
        275                 280                 285

Ala Leu Ser Glu Asp Tyr Ser Tyr Thr Asn Gly His Ala Val His Asp
        290                 295                 300

Ala Gln His Pro Cys Arg Ser Asn Val Ala Val Lys Lys Glu Leu His
305                 310                 315                 320

Ser Pro Glu Ser Asp Arg Ser Cys Thr His Leu Glu Phe Asp Ile Ser
                325                 330                 335

Asn Thr Gly Leu Ser Tyr Glu Thr Gly Asp His Val Gly Val Tyr Cys
        340                 345                 350

Glu Asn Leu Ser Glu Val Val Asn Asp Ala Glu Arg Leu Val Gly Leu
        355                 360                 365

Pro Pro Asp Thr Tyr Phe Ser Ile His Thr Asp Ser Glu Asp Gly Ser
370                 375                 380

Pro Leu Gly Gly Ala Ser Leu Pro Pro Phe Pro Pro Cys Thr Leu
385                 390                 395                 400

Arg Lys Ala Leu Thr Cys Tyr Ala Asp Val Leu Ser Ser Pro Lys Lys
                405                 410                 415

Ser Ala Leu Leu Ala Leu Ala Ala His Ala Thr Asp Pro Ser Glu Ala
        420                 425                 430

Asp Arg Leu Lys Phe Leu Ala Ser Pro Ala Gly Lys Asp Glu Tyr Ser
        435                 440                 445

Gln Trp Ile Val Ala Ser Gln Arg Ser Leu Leu Glu Val Met Glu Ala
        450                 455                 460

Phe Pro Ser Ala Lys Pro Ser Leu Gly Val Phe Ala Ser Val Ala
465                 470                 475                 480

Pro Arg Leu Gln Pro Arg Tyr Tyr Ser Ile Ser Ser Ser Pro Lys Met
                485                 490                 495

Ala Pro Asp Arg Ile His Val Thr Cys Ala Leu Val Tyr Glu Lys Thr
        500                 505                 510

Pro Ala Gly Arg Ile His Lys Gly Val Cys Ser Thr Trp Met Lys Asn
        515                 520                 525

Ala Val Pro Met Thr Glu Ser Gln Asp Cys Ser Trp Ala Pro Ile Tyr
        530                 535                 540

Val Arg Thr Ser Asn Phe Arg Leu Pro Ser Asp Pro Lys Val Pro Val
545                 550                 555                 560

Ile Met Ile Gly Pro Gly Thr Gly Leu Ala Pro Phe Arg Gly Phe Leu
                565                 570                 575

Gln Glu Arg Leu Ala Leu Lys Glu Ala Gly Thr Asp Leu Gly Leu Ser
        580                 585                 590

Ile Leu Phe Phe Gly Cys Arg Asn Arg Lys Val Asp Phe Ile Tyr Glu
        595                 600                 605

Asn Glu Leu Asn Asn Phe Val Glu Thr Gly Ala Leu Ser Glu Leu Ile
        610                 615                 620
```

| | | | | | | | | | | | |
|---|---|---|---|---|---|---|---|---|---|---|---|
|Val|Ala|Phe|Ser|Arg|Glu|Gly|Pro|Thr|Lys|Glu|Tyr|Val|Gln|His|Lys|
|625| | | | |630| | | | |635| | | | |640|

| | | | | | | | | | | | |
|---|---|---|---|---|---|---|---|---|---|---|---|
|Met|Ser|Glu|Lys|Ala|Ser|Asp|Ile|Trp|Asn|Leu|Leu|Ser|Glu|Gly|Ala|
| | | | |645| | | | |650| | | | |655| |

| | | | | | | | | | | | |
|---|---|---|---|---|---|---|---|---|---|---|---|
|Tyr|Leu|Tyr|Val|Cys|Gly|Asp|Ala|Lys|Gly|Met|Ala|Lys|Asp|Val|His|
| | | |660| | | | |665| | | | |670| | |

| | | | | | | | | | | | |
|---|---|---|---|---|---|---|---|---|---|---|---|
|Arg|Thr|Leu|His|Thr|Ile|Val|Gln|Glu|Gln|Gly|Ser|Leu|Asp|Ser|Ser|
| | |675| | | | |680| | | | |685| | | |

| | | | | | | | | | | | |
|---|---|---|---|---|---|---|---|---|---|---|---|
|Lys|Ala|Glu|Leu|Tyr|Val|Lys|Asn|Leu|Gln|Met|Ser|Gly|Arg|Tyr|Leu|
| |690| | | | |695| | | | |700| | | | |

Arg Asp Val Trp
705

<210> SEQ ID NO 81
<211> LENGTH: 2127
<212> TYPE: DNA
<213> ORGANISM: Stevia rebaudiana

<400> SEQUENCE: 81

```
atggcgcaat ctaattctgt gaaaatctct ccattggatc tggttacagc actctttagc      60
gggaaggtac tggatacaag taacgccagt gaaagcgggg aatccgcgat gctgccaaca     120
atcgcgatga tcatggaaaa tcgggaactg ctaatgattc tgacaacgtc tgtagcagtt     180
ttaatcggtt gcgttgtggt tctggtgtgg cgtcgatcat ccacgaaaaa gagcgcatta     240
gaaccgcctg ttatcgtagt accaaaaaga gttcaggagg aagaggtgga tgatgggaaa     300
aaaaagtca  ccgttttctt cgggacccaa actggtacgg cagaaggttt tgcgaaagca     360
ctggtcgaag aggcgaaagc ccgctatgag aaggcggttt taaggttat tgaccttgat      420
gactatgcgg cggacgatga tgaatacgaa gaaaattaa agaaagaatc acttgccttt      480
ttttttttgg caacatacgg tgatggcgag ccgactgata acgcggcacg gttttacaaa     540
tggtttaccg aaggcgacgc gaaggggag tggttgaaca agttacagta cggtgtgttc      600
ggcttgggga accgccagta cgagcacttt aacaagatag ctaaagttgt cgatgatggt     660
ctggtagaac agggagcgaa gcgtctcgtg ccagtagggc tgggcgatga tgatcagtgt     720
atagaagatg attttacggc ttggaaggag ttagtttggc cggaactgga ccaactgctg     780
cgcgatgagg atgatacaac tgtcgctacc ccgtatacag cagcggtagc tgaatacagg     840
gtggttttc  acgagaaacc tgatgcgctg agtgaggact attcgtatac aacggccat      900
gccgttcacg atgcacagca cccgtgccgt tctaatgtcg ccgtaaaaaa ggaactgcat     960
agcccggagt cggaccgcag ttgtacccat ctggagtttg atatttcaaa taccgggctg    1020
agttacgaaa cggcgatca cgttggcgtg tactgtgaga atctaagcga ggttgttaac    1080
gatgcagaac gactggtcgg tttgcctcca gatacttatt tctcgatcca cactgatagc    1140
gaagatggct ctccactcgg gggggcgagt ctgccgcccc cgtttccccc gtgtacgctg    1200
agaaaggccc ttacatgtta tgcagatgta ctctcttccc ccaaaaaaag tgccttgctc    1260
gcattagcag cccacgctac cgatccctcg gaagcagatc gtctgaaatt cttggcatcg    1320
ccggcgggca aagatgaata cagccaatgg atagttgcaa gtcagcgcag tctcttagaa    1380
gtgatggaag cgtttccgtc cgcaaagccg tccttaggtg tgttttcgc gtccgtggca    1440
ccgcgtcttc agcctagata ttacagcatt agttcctctc caaaaatggc cccggaccgt    1500
attcacgtga cttgtgctct tgtatatgag aaaaccccgg caggtcgtat tcacaaaggc    1560
```

-continued

```
gtgtgcagca cctggatgaa gaatgcagtg ccgatgaccg aaagccagga ttgttcatgg    1620
gcgccaatct atgtcaggac aagtaatttc agacttccgt ctgatcctaa agttccagtc    1680
ataatgattg gccccggcac gggactggct ccttttcgtg gtttcctgca agagcgcttg    1740
gcactgaaag aagcaggcac tgacctggga ctgtccatcc tgttctttgg gtgccgtaat    1800
cgtaaggtcg attttatata tgaaaatgaa ttgaacaact ttgtagaaac aggcgcatta    1860
tccgaactga tcgtagcttt tagtagagag gggccgacga agaatatgt acaacacaag     1920 atgtctgaga aggcttcgga tatatggaac ctgctctctg agggtgccta tctgtacgtt    1980
tgcggtgatg ccaaaggaat ggccaaagat gtgcaccgca ctttacatac aatcgtccaa    2040
gagcagggta gcttggactc atctaaagct gaactgtatg tgaagaactt acagatgagc    2100
gggcgctatt tgcgagatgt ttggtaa                                        2127
```

```
<210> SEQ ID NO 82
<211> LENGTH: 706
<212> TYPE: PRT
<213> ORGANISM: Pelargonium graveolens

<400> SEQUENCE: 82
```

```
Met Ala Gln Ser Ser Gly Ser Met Ser Pro Phe Asp Phe Met Thr
1               5                   10                  15

Ala Ile Ile Lys Gly Lys Met Glu Pro Ser Asn Ala Ser Leu Gly Ala
            20                  25                  30

Ala Gly Glu Val Thr Ala Met Ile Leu Asp Asn Arg Glu Leu Val Met
        35                  40                  45

Ile Leu Thr Thr Ser Ile Ala Val Leu Ile Gly Cys Val Val Val Phe
    50                  55                  60

Ile Trp Arg Arg Ser Ser Ser Gln Thr Pro Thr Ala Val Gln Pro Leu
65                  70                  75                  80

Lys Pro Leu Leu Ala Lys Glu Thr Gly Ser Glu Val Asp Asp Gly Lys
                85                  90                  95

Gln Lys Val Thr Ile Phe Phe Gly Thr Gln Thr Gly Thr Ala Glu Gly
            100                 105                 110

Phe Ala Lys Ala Leu Ala Asp Glu Ala Lys Ala Arg Tyr Asp Lys Val
        115                 120                 125

Thr Phe Lys Val Val Asp Leu Asp Asp Tyr Ala Ala Asp Asp Glu Glu
    130                 135                 140

Tyr Glu Glu Lys Leu Lys Lys Glu Thr Leu Ala Phe Phe Phe Leu Ala
145                 150                 155                 160

Thr Tyr Gly Asp Gly Glu Pro Thr Asp Asn Ala Ala Arg Phe Tyr Lys
                165                 170                 175

Trp Phe Leu Glu Gly Lys Glu Arg Gly Glu Trp Leu Gln Asn Leu Lys
            180                 185                 190

Phe Gly Val Phe Gly Leu Gly Asn Arg Gln Tyr Glu His Phe Asn Lys
        195                 200                 205

Ile Ala Ile Val Val Asp Glu Ile Leu Ala Glu Gln Gly Gly Lys Arg
    210                 215                 220

Leu Ile Ser Val Gly Leu Gly Asp Asp Gln Cys Ile Glu Asp Asp
225                 230                 235                 240

Phe Thr Ala Trp Arg Glu Ser Leu Trp Pro Glu Leu Asp Gln Leu Leu
                245                 250                 255

Arg Asp Glu Asp Asp Thr Thr Val Ser Thr Pro Tyr Thr Ala Ala Val
            260                 265                 270
```

```
Leu Glu Tyr Arg Val Val Phe His Asp Pro Ala Asp Pro Thr Leu
            275                 280                 285
Glu Lys Ser Tyr Ser Asn Ala Asn Gly His Ser Val Val Asp Ala Gln
            290                 295                 300
His Pro Leu Arg Ala Asn Val Ala Val Arg Arg Glu Leu His Thr Pro
305                 310                 315                 320
Ala Ser Asp Arg Ser Cys Thr His Leu Glu Phe Asp Ile Ser Gly Thr
                    325                 330                 335
Gly Ile Ala Tyr Glu Thr Gly Asp His Val Gly Val Tyr Cys Glu Asn
            340                 345                 350
Leu Ala Glu Thr Val Glu Glu Ala Leu Glu Leu Leu Gly Leu Ser Pro
            355                 360                 365
Asp Thr Tyr Phe Ser Val His Ala Asp Lys Glu Asp Gly Thr Pro Leu
            370                 375                 380
Ser Gly Ser Ser Leu Pro Pro Pro Phe Pro Pro Cys Thr Leu Arg Thr
385                 390                 395                 400
Ala Leu Thr Leu His Ala Asp Leu Leu Ser Ser Pro Lys Lys Ser Ala
                    405                 410                 415
Leu Leu Ala Leu Ala Ala His Ala Ser Asp Pro Thr Glu Ala Asp Arg
            420                 425                 430
Leu Arg His Leu Ala Ser Pro Ala Gly Lys Asp Glu Tyr Ala Gln Trp
            435                 440                 445
Ile Val Ala Ser Gln Arg Ser Leu Leu Glu Val Met Ala Glu Phe Pro
            450                 455                 460
Ser Ala Lys Pro Pro Leu Gly Val Phe Phe Ala Ser Val Ala Pro Arg
465                 470                 475                 480
Leu Gln Pro Arg Tyr Tyr Ser Ile Ser Ser Ser Pro Arg Ile Ala Pro
                    485                 490                 495
Ser Arg Ile His Val Thr Cys Ala Leu Val Tyr Glu Lys Thr Pro Thr
                    500                 505                 510
Gly Arg Val His Lys Gly Val Cys Ser Thr Trp Met Lys Asn Ser Val
            515                 520                 525
Pro Ser Glu Lys Ser Asp Glu Cys Ser Trp Ala Pro Ile Phe Val Arg
530                 535                 540
Gln Ser Asn Phe Lys Leu Pro Ala Asp Ala Lys Val Pro Ile Ile Met
545                 550                 555                 560
Ile Gly Pro Gly Thr Gly Leu Ala Pro Phe Arg Gly Phe Leu Gln Glu
                    565                 570                 575
Arg Leu Ala Leu Lys Glu Ala Gly Thr Glu Leu Gly Pro Ser Ile Leu
            580                 585                 590
Phe Phe Gly Cys Arg Asn Ser Lys Met Asp Tyr Ile Tyr Glu Asp Glu
            595                 600                 605
Leu Asp Asn Phe Val Gln Asn Gly Ala Leu Ser Glu Leu Val Leu Ala
            610                 615                 620
Phe Ser Arg Glu Gly Pro Thr Lys Glu Tyr Val Gln His Lys Met Met
625                 630                 635                 640
Glu Lys Ala Ser Asp Ile Trp Asn Leu Ile Ser Gln Gly Ala Tyr Leu
                    645                 650                 655
Tyr Val Cys Gly Asp Ala Lys Gly Met Ala Arg Asp Val His Arg Thr
            660                 665                 670
Leu His Thr Ile Ala Gln Glu Gln Gly Ser Leu Asp Ser Ser Lys Ala
            675                 680                 685
Glu Ser Met Val Lys Asn Leu Gln Met Ser Gly Arg Tyr Leu Arg Asp
```

Val Trp
705

<210> SEQ ID NO 83
<211> LENGTH: 2121
<212> TYPE: DNA
<213> ORGANISM: Pelargonium graveolens

<400> SEQUENCE: 83

| | | | | | |
|---|---|---|---|---|---|
| atggcgcagt | caagcagtgg | atcaatgagc | cctttcgatt | ttatgaccgc | tataataaaa | 60 |
| ggtaaaatgg | agccaagtaa | tgcgtcttta | ggagcggcag | gtgaagtcac | agcaatgata | 120 |
| cttgataata | gggagctggt | tatgattctg | acgaccagca | ttgcagtgct | gatcggttgc | 180 |
| gttgtagtgt | tcatttggcg | tcgttcatca | tcccagaccc | ctaccgcggt | gcagccatta | 240 |
| aaaccacttt | tagcgaagga | aacagagagc | gaagtagacg | atggcaaaca | gaaagtaact | 300 |
| atcttttttg | gtactcaaac | tggaaccgct | gaaggtttcg | cgaaagcgct | cgcagacgag | 360 |
| gccaaagcac | ggtatgataa | agtcactttt | aaagtggttg | atctggacga | ttatgccgca | 420 |
| gatgacgaag | aatatgaaga | aaagctgaag | aaggaaacgt | tagcattctt | ttttcttgcg | 480 |
| acgtatggag | atggtgaacc | tactgacaat | gctgcaaggt | tttataagtg | gtttctggaa | 540 |
| ggtaaagaac | gcggagaatg | gcttcagaat | ctaaaatttg | gtgtgtttgg | tttaggcaac | 600 |
| cgtcagtatg | agcatttcaa | taaaattgcc | attgtggttg | atgaaatcct | gcagaacaa | 660 |
| ggtggtaagc | gtctcatttc | agttggcctg | ggcgatgatg | atcagtgtat | tgaggatgac | 720 |
| tttactgcct | ggagggaatc | gctgtggccg | gagctagatc | agttattacg | cgatgaggat | 780 |
| gatactacgg | tttctacgcc | gtataccgcc | gcggtgctgg | aatacagagt | cgtttttcat | 840 |
| gatccggcag | atgccccaac | tctcgaaaaa | agctacagca | acgctaacgg | gcatagcgtg | 900 |
| gttgatgcgc | aacatccgtt | acgggcaaat | gttgccgtca | gacgggagtt | gcatactcct | 960 |
| gcgtctgacc | gctcatgtac | ccatctggaa | tttgatatat | ctggtactgg | catcgcatac | 1020 |
| gagacgggtg | atcatgttgg | cgtgtattgc | gagaatcttg | cagagacggt | agaagaagcg | 1080 |
| ttggaacttt | taggtctttc | cccggataca | tacttctccg | tacacgcaga | taaagaggac | 1140 |
| ggtacgcctc | tctcaggctc | atctctcccg | ccgccatttc | caccgtgcac | tttacgtaca | 1200 |
| gccctgacgt | tacatgctga | cttactgtct | tccccaaaga | aatctgcatt | gctcgcgctt | 1260 |
| gcagctcatg | catcagaccc | cactgaagct | gatcgattgc | ggcacctagc | aagccctgcg | 1320 |
| ggcaaggacg | aatacgctca | gtggatagtt | gctagtcagc | gttccttgct | ggaagtgatg | 1380 |
| gcggagttcc | ccagtgccaa | gccccgctg | ggagtattct | tcgcatcggt | tgctccaaga | 1440 |
| ttgcagcccc | ggtactactc | tatttcttct | tccccaagaa | tagcgccgtc | tcgcatacac | 1500 |
| gtgacctgcg | cgttagttta | cgagaaaaca | cctacgggca | gagtacacaa | aggagtttgc | 1560 |
| tccacttgga | tgaaaaactc | agtgccctct | gaaaagagtg | atgaatgttc | atggcaccca | 1620 |
| attttcgtac | gacagagcaa | ctttaaactg | cccgccgatg | cgaaagtacc | cataattatg | 1680 |
| attggtccag | gaacgggtct | ggcaccattt | cgcggcttcc | tccaggagcg | gcttgcattg | 1740 |
| aaagaagcag | ggacagaact | gggaccttcc | atattatttt | ttgggtgccg | caacagcaaa | 1800 |
| atggactata | tatacgagga | tgaactggat | aattttgtac | agaatggggc | actctctgaa | 1860 |
| ctcgtgttgg | cgttctcacg | tgaaggtcct | accaaagagt | atgtgcaaca | taagatgatg | 1920 |
| gagaaagcct | cagatatatg | gaaccttatt | tcacagggag | cttatttgta | tgtgtgcggg | 1980 |

```
                                              -continued
gacgcaaaag gcatggcgcg tgatgtgcac cgcacgttac ataccatcgc tcaggagcag         2040
gggtcattag atagctcaaa agcagagagt atggtgaaga atcttcagat gtcaggcaga         2100
tacctgcgcg atgtctggta a                                                   2121

<210> SEQ ID NO 84
<211> LENGTH: 277
<212> TYPE: PRT
<213> ORGANISM: Rhodococcus erythropolis

<400> SEQUENCE: 84

Met Ala Arg Val Glu Gly Gln Val Ala Leu Ile Thr Gly Ala Ala Arg
1               5                   10                  15

Gly Gln Gly Arg Ser His Ala Ile Lys Leu Ala Glu Glu Gly Ala Asp
            20                  25                  30

Val Ile Leu Val Asp Val Pro Asn Asp Val Val Asp Ile Gly Tyr Pro
        35                  40                  45

Leu Gly Thr Ala Asp Glu Leu Asp Gln Thr Ala Lys Asp Val Glu Asn
    50                  55                  60

Leu Gly Arg Lys Ala Ile Val Ile His Ala Asp Val Arg Asp Leu Glu
65                  70                  75                  80

Ser Leu Thr Ala Glu Val Asp Arg Ala Val Ser Thr Leu Gly Arg Leu
                85                  90                  95

Asp Ile Val Ser Ala Asn Ala Gly Ile Ala Ser Val Pro Phe Leu Ser
            100                 105                 110

His Asp Ile Pro Asp Asn Thr Trp Arg Gln Met Ile Asp Ile Asn Leu
        115                 120                 125

Thr Gly Val Trp His Thr Ala Lys Val Ala Val Pro His Ile Leu Ala
    130                 135                 140

Gly Glu Arg Gly Gly Ser Ile Val Leu Thr Ser Ser Ala Ala Gly Leu
145                 150                 155                 160

Lys Gly Tyr Ala Gln Ile Ser His Tyr Ser Ala Ala Lys His Gly Val
                165                 170                 175

Val Gly Leu Met Arg Ser Leu Ala Leu Glu Leu Ala Pro His Arg Val
            180                 185                 190

Arg Val Asn Ser Leu His Pro Thr Gln Val Asn Thr Pro Met Ile Gln
        195                 200                 205

Asn Glu Gly Thr Tyr Arg Ile Phe Ser Pro Asp Leu Glu Asn Pro Thr
    210                 215                 220

Arg Glu Asp Phe Glu Ile Ala Ser Thr Thr Asn Ala Leu Pro Ile
225                 230                 235                 240

Pro Trp Val Glu Ser Val Asp Val Ser Asn Ala Leu Leu Phe Leu Val
                245                 250                 255

Ser Glu Asp Ala Arg Tyr Ile Thr Gly Ala Ala Ile Pro Val Asp Ala
            260                 265                 270

Gly Thr Thr Leu Lys
        275

<210> SEQ ID NO 85
<211> LENGTH: 834
<212> TYPE: DNA
<213> ORGANISM: Rhodococcus erythropolis

<400> SEQUENCE: 85
atggcccgtg tggaaggtca agtggctctg attaccggcg ctgctcgtgg tcaaggtcgt         60
agtcatgcga ttaaactggc ggaagaaggc gcggatgtga ttctggttga cgtcccgaat        120
```

```
gatgtggttg acatcggcta tccgctgggt acggcagatg aactggacca gaccgctaaa      180
gatgttgaaa acctgggtcg taaggcgatt gtcatccatg ccgatgtgcg cgacctggaa      240
tcactgacgg cagaagtgga tcgtgctgtt agtaccctgg ccgcctggga cattgtttcc      300
gcaaatgctg gtatcgccag cgtcccgttt ctgtctcacg atattccgga caacacctgg      360
cgtcagatga ttgatatcaa tctgacgggc gtctggcata ccgcgaaagt ggccgttccg      420
cacattctgg ccggtgaacg cggcggttcc atcgttctga ccagctctgc ggccggcctg      480
aaaggttatg cacaaattag tcattactcc gcagctaagc acggcgtcgt gggtctgatg      540
cgttcactgg cactggaact ggctccgcat cgtgtccgcg tgaactcgct gcacccgacg      600
caggtgaaca ccccgatgat tcaaaatgaa ggcacgtatc gtatctttag cccggatctg      660
gaaaacccga cccgcgaaga cttcgaaatt gcgtctacca cgaccaatgc cctgccgatc      720
ccgtgggtgg aatcagttga tgtctcgaac gcactgctgt tcctggttag cgaagacgca      780
cgttacatta ccggtgcagc aatcccggtg gatgccggta cgaccctgaa gtaa           834
```

<210> SEQ ID NO 86  
<211> LENGTH: 280  
<212> TYPE: PRT  
<213> ORGANISM: Citrus sinensis

<400> SEQUENCE: 86

```
Met Ala Thr Pro Pro Ile Ser Ser Leu Ile Ser Gln Arg Leu Leu Gly
1               5                   10                  15

Lys Val Ala Leu Val Thr Gly Gly Ala Ser Gly Ile Gly Glu Gly Ile
            20                  25                  30

Val Arg Leu Phe His Arg His Gly Ala Lys Val Cys Phe Val Asp Val
        35                  40                  45

Gln Asp Glu Leu Gly Tyr Arg Leu Gln Glu Ser Leu Val Gly Asp Lys
    50                  55                  60

Asp Ser Asn Ile Phe Tyr Ser His Cys Asp Val Thr Val Glu Asp Asp
65                  70                  75                  80

Val Arg Arg Ala Val Asp Leu Thr Val Thr Lys Phe Gly Thr Leu Asp
                85                  90                  95

Ile Met Val Asn Asn Ala Gly Ile Ser Gly Thr Pro Ser Ser Asp Ile
            100                 105                 110

Arg Asn Val Asp Val Ser Glu Phe Glu Lys Val Phe Asp Ile Asn Val
        115                 120                 125

Lys Gly Val Phe Met Gly Met Lys Tyr Ala Ala Ser Val Met Ile Pro
    130                 135                 140

Arg Lys Gln Gly Ser Ile Ile Ser Leu Gly Ser Val Gly Ser Val Ile
145                 150                 155                 160

Gly Gly Ile Gly Pro His His Tyr Ile Ser Ser Lys His Ala Val Val
                165                 170                 175

Gly Leu Thr Arg Ser Ile Ala Ala Glu Leu Gly Gln His Gly Ile Arg
            180                 185                 190

Val Asn Cys Val Ser Pro Tyr Ala Val Pro Thr Asn Leu Ala Val Ala
        195                 200                 205

His Leu Pro Glu Asp Glu Arg Thr Glu Asp Met Phe Thr Gly Phe Arg
    210                 215                 220

Glu Phe Ala Lys Lys Asn Ala Asn Leu Gln Gly Val Glu Leu Thr Val
225                 230                 235                 240

Glu Asp Val Ala Asn Ala Val Leu Phe Leu Ala Ser Glu Asp Ala Arg
```

```
                    245                 250                 255
Tyr Ile Ser Gly Asp Asn Leu Ile Val Asp Gly Gly Phe Thr Arg Val
            260                 265                 270

Asn His Ser Phe Arg Val Phe Arg
            275                 280

<210> SEQ ID NO 87
<211> LENGTH: 843
<212> TYPE: DNA
<213> ORGANISM: Citrus sinensis

<400> SEQUENCE: 87
atggcaacgc cgccgatttc atccctgatt tcacaacgcc tgctgggtaa agtcgccctg    60
gtcacgggtg gtgcttctgg tattggtgaa ggcatcgtgc gtctgtttca ccgtcatggc   120
gcgaaagtgt gctttgttga tgtgcaggat gaactgggct accgtctgca agaatctctg   180
gtgggcgaca aagattcaaa catcttttat agccactgtg atgtcaccgt ggaagacgat   240
gtgcgccgcg ctgtggatct gaccgtgacg aaattcggta cgctggatat tatggtcaat   300
aacgcgggta ttagtggcac cccgtccagc gatattcgta atgttgatgt gagcgaattt   360
gaaaaagtgt ttgatattaa cgtcaaaggc gtgtttatgg catgaaaata tgccgcgagc   420
gtgatgatcc cgcgcaaaca gggtagcatc atctccctgg ttctgttgg cagcgtgatc    480 ggtggcattg cccgcacca ttatatcagc tcgaaacatg cggttgtggg cctgaccccgc   540 agcattgcag cggaactggg tcagcatggc attcgtgtga actgtgtgtc tccgtatgcg   600
gttccgacca atctggcggt tgcacacctg ccggaagatg aacgtaccga agatatgttt   660
acgggcttcc gtgaatttgc gaaaaagaat gccaacctgc aaggtgttga actgaccgtc   720
gaagatgtgg ccaatgcggt gctgtttctg gccagcgaag atgcacgcta cattagcggt   780
gataatctga tcgttgatgg cggctttacc cgtgtgaacc actcatttcg tgttttccgt   840
taa                                                                 843

<210> SEQ ID NO 88
<211> LENGTH: 262
<212> TYPE: PRT
<213> ORGANISM: Citrus sinensis

<400> SEQUENCE: 88

Met Ser Lys Pro Arg Leu Gln Gly Lys Val Ala Ile Ile Met Gly Ala
1               5                   10                  15

Ala Ser Gly Ile Gly Glu Ala Thr Ala Lys Leu Phe Ala Glu His Gly
            20                  25                  30

Ala Phe Val Ile Ile Ala Asp Ile Gln Asp Glu Leu Gly Asn Gln Val
        35                  40                  45

Val Ser Ser Ile Gly Pro Glu Lys Ala Ser Tyr Arg His Cys Asp Val
    50                  55                  60

Arg Asp Glu Lys Gln Val Glu Glu Thr Val Ala Tyr Ala Ile Glu Lys
65                  70                  75                  80

Tyr Gly Ser Leu Asp Ile Met Tyr Ser Asn Ala Gly Val Ala Gly Pro
                85                  90                  95

Val Gly Thr Ile Leu Asp Leu Asp Met Ala Gln Phe Asp Arg Thr Ile
            100                 105                 110

Ala Thr Asn Leu Ala Gly Ser Val Met Ala Val Lys Tyr Ala Ala Arg
        115                 120                 125

Val Met Val Ala Asn Lys Ile Arg Gly Ser Ile Ile Cys Thr Thr Ser
```

```
                130             135              140
Thr Ala Ser Thr Val Gly Gly Ser Gly Pro His Ala Tyr Thr Ile Ser
145                 150                 155                 160

Lys His Gly Leu Leu Gly Leu Val Arg Ser Ala Ala Ser Glu Leu Gly
                165                 170                 175

Lys His Gly Ile Arg Val Asn Cys Val Ser Pro Phe Gly Val Ala Thr
                180                 185                 190

Pro Phe Ser Ala Gly Thr Ile Asn Asp Val Glu Gly Phe Val Cys Lys
            195                 200                 205

Val Ala Asn Leu Lys Gly Ile Val Leu Lys Ala Lys His Val Ala Glu
            210                 215                 220

Ala Ala Leu Phe Leu Ala Ser Asp Glu Ser Ala Tyr Val Ser Gly His
225                 230                 235                 240

Asp Leu Val Val Asp Gly Gly Phe Thr Ala Val Thr Asn Val Met Ser
                245                 250                 255

Met Leu Glu Gly His Gly
            260

<210> SEQ ID NO 89
<211> LENGTH: 789
<212> TYPE: DNA
<213> ORGANISM: Citrus sinensis

<400> SEQUENCE: 89
atgtcaaaac cgcgtctgca aggcaaagtg gctattatta tgggtgctgc gtctggcatc      60
ggtgaagcta cggctaaact gttcgctgaa catggcgcat ttgtgattat cgctgatatt     120
caggacgaac tgggcaacca ggtggttagc tctatcggcc cggaaaaagc gtcttatcgt     180
cactgcgatg tgcgtgatga aaaacaggtt gaagaaaccg tcgcgtatgc gattgaaaaa     240
tacggcagcc tggatattat gtactccaat gcgggcgtgg ccggtccggt tggcacgatt     300
ctggatctgg acatggccca attcgaccgt accatcgcaa cgaacctggc tggtagtgtt     360
atggcagtca atatgcggc ccgtgtcatg gtggcgaata aaattcgcgg tagcattatc     420
tgtaccacga gtaccgcctc cacggtgggc ggcagcggcc gcacgcccta ccattagc       480
aaacacggtc tgctgggcct ggttcgttca gcagcttcgg aactgggtaa acatggcatc    540
cgcgtgaact gcgttagccc gtttggtgtt gcgaccccgt tctctgccgg tacgattaac    600
gatgtcgaag ctttgtctg taaagtggcg aatctgaaag catcgtcct gaaagcgaag      660
catgtggccg aagcggccct gttcctggca agcgatgaat ctgcttatgt gagcggtcac    720
gacctggtgg tggatggtgg ctttacggca gttacgaatg tcatgtcaat gctggaaggt    780
cacggctaa                                                            789

<210> SEQ ID NO 90
<211> LENGTH: 263
<212> TYPE: PRT
<213> ORGANISM: Citrus sinensis

<400> SEQUENCE: 90

Met Ser Asn Pro Arg Met Glu Gly Lys Val Ala Leu Ile Thr Gly Ala
1               5                   10                  15

Ala Ser Gly Ile Gly Glu Ala Ala Val Arg Leu Phe Ala Glu His Gly
                20                  25                  30

Ala Phe Val Val Ala Ala Asp Val Gln Asp Glu Leu Gly His Gln Val
            35                  40                  45
```

Ala Ala Ser Val Gly Thr Asp Gln Val Cys Tyr His His Cys Asp Val
 50                  55                  60

Arg Asp Glu Lys Gln Val Glu Glu Thr Val Arg Tyr Thr Leu Glu Lys
 65                  70                  75                  80

Tyr Gly Lys Leu Asp Val Leu Phe Ser Asn Ala Gly Ile Met Gly Pro
                 85                  90                  95

Leu Thr Gly Ile Leu Glu Leu Asp Leu Thr Gly Phe Gly Asn Thr Met
            100                 105                 110

Ala Thr Asn Val Cys Gly Val Ala Thr Ile Lys His Ala Ala Arg
            115                 120                 125

Ala Met Val Asp Lys Asn Ile Arg Gly Ser Ile Cys Thr Thr Ser
130                 135                 140

Val Ala Ser Ser Leu Gly Gly Thr Ala Pro His Ala Tyr Thr Thr Ser
145                 150                 155                 160

Lys His Ala Leu Val Gly Leu Val Arg Thr Ala Cys Ser Glu Leu Gly
                165                 170                 175

Ala Tyr Gly Ile Arg Val Asn Cys Ile Ser Pro Phe Gly Val Ala Thr
            180                 185                 190

Pro Leu Ser Cys Thr Ala Tyr Asn Leu Arg Pro Asp Glu Val Glu Ala
            195                 200                 205

Asn Ser Cys Ala Leu Ala Asn Leu Lys Gly Ile Val Leu Lys Ala Lys
210                 215                 220

His Ile Ala Glu Ala Ala Leu Phe Leu Ala Ser Asp Glu Ser Ala Tyr
225                 230                 235                 240

Ile Ser Gly His Asn Leu Ala Val Asp Gly Gly Phe Thr Val Val Asn
                245                 250                 255

His Ser Ser Ser Ser Ala Thr
            260

<210> SEQ ID NO 91
<211> LENGTH: 792
<212> TYPE: DNA
<213> ORGANISM: Citrus sinensis

<400> SEQUENCE: 91
atgtcaaacc cgcgtatgga aggcaaagtc gcactgatta cgggcgcagc atctggtatc      60
ggtgaagcag cagtccgtct gttcgctgaa catggtgcgt ttgtcgtggc ggcagatgtg     120
caagacgaac tgggtcatca ggtggcggca tctgtgggta cggaccaggt gtgctaccat     180
cactgcgatg tgcgcgatga aaacaagtg gaagaaaccg tgcgttatac cctggaaaaa     240
tacggcaaac tggatgtcct gttttcaaac gcgggcatca tgggtccgct gaccggcatt     300
ctggaactgg atctgaccgg cttcggtaac acgatggcaa ccaatgtgtg cggtgttgcc     360
gcgaccatta acacgcggc acgcgcaatg gtggacaaaa acattcgcgg tagcattatc     420
tgcaccacca cgtggcttc atcgctgggt ggcaccgcgc cgcacgcata caccacgagc     480
aaacacgcac tggtgggcct ggttcgtacg gcatgttcgg aactgggtgc gtatggcatt     540
cgtgtgaact gtatcagccc gtttggtgtt gcaacgccgc tgtcttgcac ggcctataac     600
ctgcgcccgg atgaagtgga agcaaactca tgcgcactgg cgaacctgaa aggtattgtg     660
ctgaaagcga aacacattgc ggaagcagcg ctgttcctgg cgagcgatga aagcgcgtat     720
attagcggtc ataatctggc ggtggatggt ggtttcacgg tggttaatca ttcaagttcg     780
tcggcgacgt aa                                                         792

<210> SEQ ID NO 92
<211> LENGTH: 278
<212> TYPE: PRT
<213> ORGANISM: Citrus sinensis

<400> SEQUENCE: 92

```
Met Thr Thr Ala Gly Ser Arg Asp Ser Pro Leu Val Ala Gln Arg Leu
1               5                   10                  15

Leu Gly Lys Val Ala Leu Val Thr Gly Gly Ala Thr Gly Ile Gly Glu
            20                  25                  30

Ser Ile Val Arg Leu Phe His Lys His Gly Ala Lys Val Cys Val Val
        35                  40                  45

Asp Ile Asn Asp Asp Leu Gly Gln His Leu Cys Gln Thr Leu Gly Pro
    50                  55                  60

Thr Thr Arg Phe Ile His Gly Asp Val Ala Ile Glu Asp Asp Val Ser
65                  70                  75                  80

Arg Ala Val Asp Phe Thr Val Ala Asn Phe Gly Thr Leu Asp Ile Met
                85                  90                  95

Val Asn Asn Ala Gly Met Gly Gly Pro Pro Cys Pro Asp Ile Arg Glu
            100                 105                 110

Phe Pro Ile Ser Thr Phe Glu Lys Val Phe Asp Ile Asn Thr Lys Gly
        115                 120                 125

Thr Phe Ile Gly Met Lys His Ala Ala Arg Val Met Ile Pro Ser Lys
    130                 135                 140

Lys Gly Ser Ile Val Ser Ile Ser Ser Val Thr Ser Ala Ile Gly Gly
145                 150                 155                 160

Ala Gly Pro His Ala Tyr Thr Ala Ser Lys His Ala Val Leu Gly Leu
                165                 170                 175

Thr Lys Ser Val Ala Ala Glu Leu Gly Gln His Gly Ile Arg Val Asn
            180                 185                 190

Cys Val Ser Pro Tyr Ala Ile Leu Thr Asn Leu Ala Leu Ala His Leu
        195                 200                 205

His Glu Asp Glu Arg Thr Asp Asp Ala Arg Ala Gly Phe Arg Ala Phe
    210                 215                 220

Ile Gly Lys Asn Ala Asn Leu Gln Gly Val Asp Leu Val Glu Asp Asp
225                 230                 235                 240

Val Ala Asn Ala Val Leu Phe Leu Ala Ser Asp Ala Arg Tyr Ile
                245                 250                 255

Ser Gly Asp Asn Leu Phe Val Asp Gly Gly Phe Thr Cys Thr Asn His
            260                 265                 270

Ser Leu Arg Val Phe Arg
        275
```

<210> SEQ ID NO 93
<211> LENGTH: 837
<212> TYPE: DNA
<213> ORGANISM: Citrus sinensis

<400> SEQUENCE: 93

```
atgacgacgg ctggttcgcg tgacagtccg ctggtcgctc aacgcctgct gggcaaagtg    60
gccctggtta cgggtggtgc taccggcatt ggtgaaagta tcgtgcgtct gtttcataaa   120
cacggcgcga agtttgcgt ggttgatatt aacgatgacc tgggccagca tctgtgtcaa   180
accctgggtc cgaccacccg tttcattcac ggcgatgttg caatcgaaga tgatgtgagc   240
cgtgcggttg attttaccgt cgccaacttc ggtacgctgg acattatggt gaacaatgcc   300
```

-continued

```
ggtatgggcg gtccgccgtg cccggatatt cgtgaatttc cgatctcgac ctttgaaaaa    360
gtcttcgaca ttaacaccaa aggcacgttc atcggtatga acatgcggc cgcgtgatg      420 attccgagta aaaaggtag tatttgtcagc attagcagcg tgaccagcgc gattggcggc    480
gcgggtccgc acgcctatac cgcgagcaaa catgcggtgc tgggcctgac gaaatctgtc    540
gcggcggaac tgggccagca cggtattcgt gtcaactgtg tgtctccgta cgccatcctg    600
accaatctgg cgctggccca tctgcacgaa gatgaacgta cggatgacgc gcgtgcgggt    660
tttcgtgcat tcattggtaa aaacgctaat ctgcaaggtg ttgatctggt cgaagatgac    720
gtggcgaatg ccgttctgtt tctggcatca gatgacgctc gctatatctc gggcgataac    780
ctgttcgtgg atggcggctt cacctgtacc aatcactccc tgcgtgtgtt ccgttaa       837
```

<210> SEQ ID NO 94
<211> LENGTH: 280
<212> TYPE: PRT
<213> ORGANISM: Vitis vinifera

<400> SEQUENCE: 94

```
Met Ala Ala Thr Ser Ile Asp Asn Ser Pro Leu Pro Ser Gln Arg Leu
1               5                   10                  15

Leu Gly Lys Val Ala Leu Val Thr Gly Gly Ala Thr Gly Ile Gly Glu
            20                  25                  30

Ser Ile Val Arg Leu Phe Leu Lys Gln Gly Ala Lys Val Cys Ile Val
        35                  40                  45

Asp Val Gln Asp Leu Gly Gln Lys Leu Cys Asp Thr Leu Gly Gly
    50                  55                  60

Asp Pro Asn Val Ser Phe Phe His Cys Asp Val Thr Ile Glu Asp Asp
65                  70                  75                  80

Val Cys His Ala Val Asp Phe Thr Val Thr Lys Phe Gly Thr Leu Asp
                85                  90                  95

Ile Met Val Asn Asn Ala Gly Met Ala Gly Pro Pro Cys Ser Asp Ile
            100                 105                 110

Arg Asn Val Glu Val Ser Met Phe Glu Lys Val Phe Asp Val Asn Val
        115                 120                 125

Lys Gly Val Phe Leu Gly Met Lys His Ala Ala Arg Ile Met Ile Pro
    130                 135                 140

Leu Lys Lys Gly Thr Ile Ile Ser Leu Cys Ser Val Ser Ser Ala Ile
145                 150                 155                 160

Ala Gly Val Gly Pro His Ala Tyr Thr Gly Ser Lys Cys Ala Val Ala
                165                 170                 175

Gly Leu Thr Gln Ser Val Ala Ala Glu Met Gly Gly His Gly Ile Arg
            180                 185                 190

Val Asn Cys Ile Ser Pro Tyr Ala Ile Ala Thr Gly Leu Ala Leu Ala
        195                 200                 205

His Leu Pro Glu Asp Glu Arg Thr Glu Asp Ala Met Ala Gly Phe Arg
    210                 215                 220

Ala Phe Val Gly Lys Asn Ala Asn Leu Gln Gly Val Glu Leu Thr Val
225                 230                 235                 240

Asp Asp Val Ala His Ala Ala Val Phe Leu Ala Ser Asp Glu Ala Arg
                245                 250                 255

Tyr Ile Ser Gly Leu Asn Leu Met Leu Asp Gly Gly Phe Ser Cys Thr
            260                 265                 270

Asn His Ser Leu Arg Val Phe Arg
        275                 280
```

<210> SEQ ID NO 95
<211> LENGTH: 843
<212> TYPE: DNA
<213> ORGANISM: Vitis vinifera

<400> SEQUENCE: 95

```
atggccgcaa cgagcattga taattctccg ctgccgagtc aacgtctgct gggtaaagtc    60
gcactggtca cgggtggcgc tacgggtatt ggcgaaagca tcgtgcgtct gtttctgaaa   120
cagggtgcta agtgtgcat tgtggacgtg caagatgacc tgggccagaa actgtgcgat   180
accctgggtg cgatccgaa cgttagcttt ttccattgcg atgtgaccat cgaagatgat   240
gtgtgccatg cagttgattt taccgtcacg aaattcggca ccctggatat tatggtgaac   300
aatgcgggta tggcaggtcc gccgtgctcg gacatccgca acgtggaagt cagcatgttt   360
gaaaaagtgt ttgatgtgaa tgtgaaaggt gttttcctgg gcatgaaaca tgcagcccgc   420
attatgattc cgctgaaaaa aggcaccatt atcagcctgt gttcagtttc cagcgctatc   480
gcgggcgttg gtccgcacgc atatacgggt agcaaatgcg cagtggcggg tctgacgcaa   540
tcggtcgcag cagaaatggg tggtcatggc attcgcgtga actgtatcag cccgtatgca   600
atcgcaacgg tctggcgct ggcacatctg ccggaagatg aacgcacgga agatgcaatg   660
gcgggttttcc gtgcgtttgt gggtaaaaat gcgaatctgc aaggtgttga actgaccgtg   720
gatgatgtgg cgcacgcagc ggtgtttctg caagcgatg aagcacgtta catctctggt   780
ctgaatctga tgctggacgg cggcttttcg tgtaccaacc actcgctgcg tgtctttcgc   840
taa                                                                  843
```

<210> SEQ ID NO 96
<211> LENGTH: 279
<212> TYPE: PRT
<213> ORGANISM: Vitis vinifera

<400> SEQUENCE: 96

```
Met Ser Thr Ala Ser Ser Gly Asp Val Ser Leu Leu Ser Gln Arg Leu
1               5                   10                  15

Val Gly Lys Val Ala Leu Ile Thr Gly Gly Ala Thr Gly Ile Gly Glu
            20                  25                  30

Ser Ile Ala Arg Leu Phe Tyr Arg His Gly Ala Lys Val Cys Ile Val
        35                  40                  45

Asp Ile Gln Asp Asn Pro Gly Gln Asn Leu Cys Arg Glu Leu Gly Thr
    50                  55                  60

Asp Asp Ala Cys Phe Phe His Cys Asp Val Ser Ile Glu Ile Asp Val
65                  70                  75                  80

Ile Arg Ala Val Asp Phe Val Val Asn Arg Phe Gly Lys Leu Asp Ile
                85                  90                  95

Met Val Asn Asn Ala Gly Ile Ala Asp Pro Pro Cys Pro Asp Ile Arg
            100                 105                 110

Asn Thr Asp Leu Ser Ile Phe Glu Lys Val Phe Asp Val Asn Val Lys
        115                 120                 125

Gly Thr Phe Gln Cys Met Lys His Ala Ala Arg Val Met Val Pro Gln
    130                 135                 140

Lys Lys Gly Ser Ile Ile Ser Leu Thr Ser Val Ala Ser Val Ile Gly
145                 150                 155                 160

Gly Ala Gly Pro His Ala Tyr Thr Gly Ser Lys His Ala Val Leu Gly
                165                 170                 175
```

Leu Thr Lys Ser Val Ala Ala Glu Leu Gly Leu His Gly Ile Arg Val
            180                 185                 190

Asn Cys Val Ser Pro Tyr Ala Val Pro Thr Gly Met Pro Leu Ala His
        195                 200                 205

Leu Pro Glu Ser Glu Lys Thr Glu Asp Ala Met Met Gly Met Arg Ala
    210                 215                 220

Phe Val Gly Arg Asn Ala Asn Leu Gln Gly Ile Glu Leu Thr Val Asp
225                 230                 235                 240

Asp Val Ala Asn Ser Val Val Phe Leu Ala Ser Asp Glu Ala Arg Tyr
                245                 250                 255

Val Ser Gly Leu Asn Leu Met Leu Asp Gly Gly Phe Ser Cys Val Asn
            260                 265                 270

His Ser Leu Arg Val Phe Arg
        275

<210> SEQ ID NO 97
<211> LENGTH: 840
<212> TYPE: DNA
<213> ORGANISM: Vitis vinifera

<400> SEQUENCE: 97
atgtcaacgg cttcctcggg tgatgtgtcg ctgctgtcgc aacgcctggt cggtaaagtc      60
gctctgatta cgggtggtgc aacgggcatt ggtgaatcga ttgcgcgtct gttttaccgt     120
catggtgcga aagtgtgcat cgttgacatt caggataatc cgggtcaaaa cctgtgccgt     180
gaactgggca ccgacgatgc gtgcttcttt cactgcgatg tgagcattga aatcgatgtg     240
attcgtgctg ttgactttgt ggttaaccgc tttggtaaac tggacattat ggttaataac     300
gcgggcatcg cagatccgcc gtgcccggat attcgcaaca ccgatctgag catttttgaa     360
aaagtgttcg atgtgaacgt gaaaggcacc tttcagtgta tgaaacacgc agcgcgcgtt     420
atggtgccgc agaaaaaagg tagcattatc agcctgacct cggtggcgag cgtgattggt     480
ggcgcgggtc cgcacgccta cgggtagc aaacacgcgg ttctgggtct gacgaaaagc     540
gttgcggcag aactgggtct gcatggtatt cgcgtgaact gtgtgagtcc gtatgcagtt     600
ccgacgggta tgccgctggc acatctgccg gaatcggaaa aaaccgaaga tgcgatgatg     660
ggtatgcgtg catttgtggg tcgtaatgcc aacctgcaag gtattgaact gaccgtggac     720
gatgtcgcaa atagcgtcgt gtttctggcg tcggatgaag cgcgttatgt tagcggtctg     780
aacctgatgc tggacggcgg cttctcgtgt gtcaaccact cgctgcgtgt gtttcgctaa     840

<210> SEQ ID NO 98
<211> LENGTH: 280
<212> TYPE: PRT
<213> ORGANISM: Citrus sinensis

<400> SEQUENCE: 98

Met Ser Asn Ser Asn Ser Thr Asp Ser Ser Pro Ala Val Gln Arg Leu
1               5                   10                  15

Val Gly Arg Val Ala Leu Ile Thr Gly Gly Ala Thr Gly Ile Gly Glu
            20                  25                  30

Ser Thr Val Arg Leu Phe His Lys His Gly Ala Lys Val Cys Ile Ala
        35                  40                  45

Asp Val Gln Asp Asn Leu Gly Gln Gln Val Cys Gln Ser Leu Gly Gly
    50                  55                  60

Glu Pro Asp Thr Phe Phe Cys His Cys Asp Val Thr Lys Glu Glu Asp

```
                65                  70                  75                  80
Val Cys Ser Ala Val Asp Leu Thr Val Glu Lys Phe Gly Thr Leu Asp
                    85                  90                  95
Ile Met Val Asn Asn Ala Gly Ile Ser Gly Ala Pro Cys Pro Asp Ile
                100                 105                 110
Arg Glu Ala Asp Leu Ser Glu Phe Glu Lys Val Phe Asp Ile Asn Val
                115                 120                 125
Lys Gly Val Phe His Gly Met Lys His Ala Ala Arg Ile Met Ile Pro
            130                 135                 140
Gln Thr Lys Gly Thr Ile Ile Ser Ile Cys Ser Val Ala Gly Ala Ile
145                 150                 155                 160
Gly Gly Leu Gly Pro His Ala Tyr Thr Gly Ser Lys His Ala Val Leu
                165                 170                 175
Gly Leu Asn Lys Asn Val Ala Ala Glu Leu Gly Lys Tyr Gly Ile Arg
            180                 185                 190
Val Asn Cys Val Ser Pro Tyr Ala Val Ala Thr Gly Leu Ala Leu Ala
                195                 200                 205
His Leu Pro Glu Glu Glu Arg Thr Glu Asp Ala Met Val Gly Phe Arg
        210                 215                 220
Asn Phe Val Ala Arg Asn Ala Asn Met Gln Gly Thr Glu Leu Thr Ala
225                 230                 235                 240
Asn Asp Val Ala Asn Ala Val Leu Phe Leu Ala Ser Asp Glu Ala Arg
                245                 250                 255
Tyr Ile Ser Gly Thr Asn Leu Met Val Asp Gly Gly Phe Thr Ser Val
            260                 265                 270
Asn His Ser Leu Arg Val Phe Arg
        275                 280

<210> SEQ ID NO 99
<211> LENGTH: 843
<212> TYPE: DNA
<213> ORGANISM: Citrus sinensis

<400> SEQUENCE: 99
atgtccaata gcaactctac ggattcgtcg ccggcagtcc aacgcctggt cggtcgtgtc      60
gccctgatta cgggtggtgc aacgggtatt ggcgaaagca cggtgcgcct gtttcataaa     120
catggcgcga aagtgtgtat tgccgacgtt caggataacc tgggtcagca agtgtgtcag     180
agtctgggtg cgaaccgga taccttttc tgccattgtg atgtgacgaa agaagaagat      240
gtgtgtagcg cagttgatct gaccgtggaa aaatttggca ccctggacat tatggtgaac     300
aatgcgggta ttagcggcgc accgtgcccg gacattcgtg aagccgatct gagcgaattt     360
gaaaaagttt tcgacatcaa cgtgaaaggc gtgtttcacg gcatgaaaca tgcagcgcgt     420
attatgatcc cgcaaaccaa aggcaccatt atcagcattt gctccgtggc tggtgcgatt     480
ggtggcctgg gtccgcacgc atataccggc tccaaacatg cagtcctggg cctgaacaaa     540
aacgtggccg cggaactggg caaatacggt atccgtgtga attgcgtcag cccgtatgct     600
gttgccaccg gctggctct ggcacacctg ccggaagaag aacgtaccga agatgcaatg     660
gtgggctttc gtaattttgt ggcacgcaac gcgaatatgc aaggcaccga actgacggcg     720
aatgatgtgg caaacgcggt cctgtttctg gcctctgatg aagcccgtta tatcagcggc     780
acgaatctga tggtggatgg cggttttacc tcggtcaatc actcgctgcg tgtcttccgt     840
taa                                                                  843
```

<210> SEQ ID NO 100
<211> LENGTH: 282
<212> TYPE: PRT
<213> ORGANISM: Brachypodium distachyon

<400> SEQUENCE: 100

Met Ser Ala Ala Ala Val Ser Ser Ser Ser Pro Arg Leu Glu
1               5                   10                  15

Gly Lys Val Ala Leu Val Thr Gly Gly Ala Ser Gly Ile Gly Glu Ala
            20                  25                  30

Ile Val Arg Leu Phe Arg Gln His Gly Ala Lys Val Cys Ile Ala Asp
        35                  40                  45

Val Gln Asp Glu Ala Gly Gln Gln Val Arg Asp Ser Leu Gly Asp Asp
    50                  55                  60

Ala Gly Thr Asp Val Leu Phe Val His Cys Asp Val Thr Val Glu Glu
65                  70                  75                  80

Asp Val Ser Arg Ala Val Asp Ala Ala Ala Glu Lys Phe Gly Thr Leu
                85                  90                  95

Asp Ile Met Val Asn Asn Ala Gly Ile Thr Gly Asp Lys Val Thr Asp
            100                 105                 110

Ile Arg Asn Leu Asp Phe Ala Glu Val Arg Lys Val Phe Asp Ile Asn
        115                 120                 125

Val His Gly Met Leu Leu Gly Met Lys His Ala Ala Arg Val Met Ile
    130                 135                 140

Pro Gly Lys Lys Gly Ser Ile Val Ser Leu Ala Ser Val Ala Ser Val
145                 150                 155                 160

Met Gly Gly Met Gly Pro His Ala Tyr Thr Ala Ser Lys His Ala Val
                165                 170                 175

Val Gly Leu Thr Lys Ser Val Ala Leu Glu Leu Gly Lys His Gly Ile
            180                 185                 190

Arg Val Asn Cys Val Ser Pro Tyr Ala Val Pro Thr Ala Leu Ser Met
        195                 200                 205

Pro His Leu Pro Gln Gly Glu His Lys Gly Asp Ala Val Arg Asp Phe
    210                 215                 220

Leu Ala Phe Val Gly Gly Glu Ala Asn Leu Lys Gly Val Asp Leu Leu
225                 230                 235                 240

Pro Lys Asp Val Ala Gln Ala Val Leu Tyr Leu Ala Ser Asp Glu Ala
                245                 250                 255

Arg Tyr Ile Ser Ala Leu Asn Leu Val Val Asp Gly Gly Phe Thr Ser
            260                 265                 270

Val Asn Pro Asn Leu Lys Ala Phe Glu Asp
        275                 280

<210> SEQ ID NO 101
<211> LENGTH: 849
<212> TYPE: DNA
<213> ORGANISM: Brachypodium distachyon

<400> SEQUENCE: 101
atgtccgctg ctgccgccgt gtcctcctca tcgtcgccgc gtctggaagg caaagtcgct      60
ctggttacgg gtggtgcgtc aggtatcggc gaagccattg tgcgcctgtt ccgtcaacat     120
ggtgccaaag tgtgtatcgc ggatgtccaa gacgaagcgg ccaacaggt ccgtgatagc      180 ctgggtgacg atgccggtac ggatgtgctg tttgtgcatt gcgacgttac cgtggaagaa     240
gatgtgtcac gcgcggtgga tgccgctgcg gaaaaattcg gcaccctgga cattatggtg     300

```
aacaacgcag gtattacggg cgacaaagtg acggacattc gcaacctgga tttcgctgaa   360
gtccgtaaag tgttcgacat caatgtgcac ggtatgctgc tgggcatgaa acatgcggcc   420
cgcgtgatga ttccgggtaa aaaaggctcg attgtgagcc tggcatcggt cgcaagcgtt   480
atgggtggta tgggtccgca cgcatatacc gcaagcaaac acgcggttgt gggtctgacg   540
aaaagcgttg cactggaact gggcaaacat ggtattcgtg tcaactgtgt gagcccgtat   600
gcagttccga ccgcactgtc aatgccgcac ctgccgcagg gcaacataa aggtgatgcg   660
gtgcgtgatt tcctggcgtt tgttggcggt gaagcgaatc tgaaaggtgt cgatctgctg   720
ccgaaagatg ttgcacaggc ggttctgtat ctggcaagcg acgaagcgcg ctatatttct   780
gcgctgaatc tggtggttga tggcggtttt acgagcgtga atccgaatct gaaagcattt   840
gaagactaa                                                           849
```

<210> SEQ ID NO 102
<211> LENGTH: 267
<212> TYPE: PRT
<213> ORGANISM: Zingiber zerumbet
<400> SEQUENCE: 102

```
Met Arg Leu Glu Gly Lys Val Ala Leu Val Thr Gly Gly Ala Ser Gly
1               5                   10                  15
Ile Gly Glu Ser Ile Ala Arg Leu Phe Ile Glu His Gly Ala Lys Ile
            20                  25                  30
Cys Ile Val Asp Val Gln Asp Glu Leu Gly Gln Gln Val Ser Gln Arg
        35                  40                  45
Leu Gly Gly Asp Pro His Ala Cys Tyr Phe His Cys Asp Val Thr Val
    50                  55                  60
Glu Asp Asp Val Arg Arg Ala Val Asp Phe Thr Ala Glu Lys Tyr Gly
65                  70                  75                  80
Thr Ile Asp Ile Met Val Asn Asn Ala Gly Ile Thr Gly Asp Lys Val
                85                  90                  95
Ile Asp Ile Arg Asp Ala Asp Phe Asn Glu Phe Lys Lys Val Phe Asp
            100                 105                 110
Ile Asn Val Asn Gly Val Phe Leu Gly Met Lys His Ala Ala Arg Ile
        115                 120                 125
Met Ile Pro Lys Met Lys Gly Ser Ile Val Ser Leu Ala Ser Val Ser
    130                 135                 140
Ser Val Ile Ala Gly Ala Gly Pro His Gly Tyr Thr Gly Ala Lys His
145                 150                 155                 160
Ala Val Val Gly Leu Thr Lys Ser Val Ala Ala Glu Leu Gly Arg His
                165                 170                 175
Gly Ile Arg Val Asn Cys Val Ser Pro Tyr Ala Val Pro Thr Arg Leu
            180                 185                 190
Ser Met Pro Tyr Leu Pro Glu Ser Glu Met Gln Glu Asp Ala Leu Arg
        195                 200                 205
Gly Phe Leu Thr Phe Val Arg Ser Asn Ala Asn Leu Lys Gly Val Asp
    210                 215                 220
Leu Met Pro Asn Asp Val Ala Glu Ala Val Leu Tyr Leu Ala Thr Glu
225                 230                 235                 240
Glu Ser Lys Tyr Val Ser Gly Leu Asn Leu Val Ile Asp Gly Gly Phe
                245                 250                 255
Ser Ile Ala Asn His Thr Leu Gln Val Phe Glu
            260                 265
```

<210> SEQ ID NO 103
<211> LENGTH: 804
<212> TYPE: DNA
<213> ORGANISM: Zingiber zerumbet

<400> SEQUENCE: 103

```
atgcgtctgg aaggcaaagt ggctctggtc acgggcggtg cgtcgggtat tggcgaatct      60
attgctcgtc tgtttattga acacggtgca aaaatttgca tcgtggatgt ccaggatgaa     120
ctgggtcaac aggtctctca gcgtctgggt ggcgatccgc acgcctgtta tttccactgt     180
gatgtgaccg tggaagatga cgttcgtcgc gcggtggatt ttacggcgga aaaatatggc     240
accattgaca ttatggttaa caatgcgggc attacgggcg ataaagtgat cgatattcgt     300
gatgcggatt tcaacgaatt taaaaaagtg ttcgacatta cgtgaatgg tgtctttctg      360
ggcatgaaac acgcagcgcg tattatgatc ccgaaaatga aggctccat cgtttcgctg      420
gcgtccgtta gctcggtgat tgctggtgca ggtccgcatg ctataccgg cgcaaaacat      480
gcggttgtgg gtctgaccaa aagcgttgca gccgaactgg tcgtcatgg tattcgcgtg      540
aactgcgttt cgccgtatgc ggtgccgacg cgcctgtcaa tgccgtatct gccggaatcg      600
gaaatgcagg aagatgcact gcgcggcttt ctgacctttg tgcgtagcaa tgcgaacctg      660
aaaggcgttg atctgatgcc gaatgatgtg cggaagctg ttctgtatct ggcgaccgaa      720
gaaagcaaat atgtttcagg tctgaatctg gttattgacg gcggcttctc catcgctaat      780
catacccctgc aagtgtttga ataa                                            804
```

<210> SEQ ID NO 104
<211> LENGTH: 505
<212> TYPE: PRT
<213> ORGANISM: Artificial Sequence
<220> FEATURE:
<223> OTHER INFORMATION: Synthetic - Engineered valencene oxidase variant

<400> SEQUENCE: 104

```
Met Ala Trp Glu Tyr Ala Leu Ile Gly Leu Val Val Gly Ile Ile
1               5                   10                  15

Gly Ala Val Ala Met Arg Trp Tyr Leu Lys Ser Tyr Thr Ser Ala Arg
                20                  25                  30

Arg Ser Gln Ser Asn Arg Leu Pro Arg Val Pro Glu Val Pro Gly Val
            35                  40                  45

Pro Leu Leu Gly Asn Leu Leu Gln Leu Lys Glu Lys Lys Pro Tyr Met
        50                  55                  60

Thr Phe Thr Arg Trp Ala Ala Thr Tyr Gly Pro Ile Tyr Ser Ile Lys
65                  70                  75                  80

Thr Gly Ala Thr Ser Met Val Val Ser Ser Asn Glu Ile Ala Lys
                85                  90                  95

Glu Ala Leu Val Thr Arg Phe Gln Ser Ile Ser Thr Arg Asn Leu Ser
            100                 105                 110

Lys Ala Leu Lys Val Leu Thr Ala Asp Lys Thr Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
```

```
                165                 170                 175
Pro Glu Gln Glu Glu Val Asp Leu Arg Lys Ile Phe Gln Ser Glu Leu
                180                 185                 190

Phe Gly Leu Ala Met Arg Gln Ala Leu Gly Lys Asp Val Glu Ser Leu
            195                 200                 205

Tyr Val Glu Asp Leu Lys Ile Thr Met Asn Arg Asp Glu Ile Leu Gln
210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu Gln Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Ile Pro Leu
370                 375                 380

Arg His Val His Glu Asp Thr Gln Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ala Asp Phe Gln Lys Thr Met Ala Phe Gly Gly Gly Lys
        435                 440                 445

Arg Val Cys Ala Gly Ser Leu Gln Ala Leu Leu Thr Ala Ser Ile Gly
450                 455                 460

Ile Gly Arg Met Val Gln Glu Phe Glu Trp Lys Leu Lys Asp Met Asp
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 105
<211> LENGTH: 505
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 105

Met Ala Trp Glu Tyr Ala Leu Ile Gly Leu Val Val Gly Ile Ile Ile
1               5                   10                  15
```

```
Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Leu Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu Gln Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
```

```
                435                 440                 445
Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                    485                 490                 495

Leu Arg Ala Ile Ile Lys Pro Arg Ile
            500                 505

<210> SEQ ID NO 106
<211> LENGTH: 501
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 106

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
        35                  40                  45

Asn Leu Leu Gln Leu Lys Glu Lys Lys Pro Tyr Met Thr Phe Thr Arg
    50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
        115                 120                 125

Tyr His Lys Thr Val Lys Arg His Ile Leu Thr Ala Val Leu Gly Pro
    130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
        195                 200                 205

Leu Lys Ile Thr Met Asn Arg Asp Glu Ile Phe Gln Val Leu Val Val
    210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
        275                 280                 285
```

Leu Leu Ser Glu Ala Gln Thr Leu Thr Asp Gln Gln Leu Leu Met Ser
      290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
              325                 330                 335

Leu Tyr Arg Asp Ile Lys Ser Val Cys Gly Ser Lys Ile Thr Glu
              340                 345                 350

Glu His Leu Ser Gln Leu Pro Tyr Ile Thr Ala Ile Phe His Glu Thr
              355                 360                 365

Leu Arg Arg His Ser Pro Val Pro Ile Ile Pro Leu Arg His Val His
370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
              405                 410                 415

Pro Glu Glu Trp Asn Pro Glu Arg Phe Met Lys Glu Asn Glu Thr Ile
              420                 425                 430

Asp Phe Gln Lys Thr Met Ala Phe Gly Gly Gly Lys Arg Val Cys Ala
              435                 440                 445

Gly Ser Leu Gln Ala Leu Leu Thr Ala Ser Ile Gly Ile Gly Arg Met
450                 455                 460

Val Gln Glu Phe Glu Trp Lys Leu Lys Asp Met Thr Gln Glu Glu Val
465                 470                 475                 480

Asn Thr Ile Gly Leu Thr Thr Gln Met Leu Arg Pro Leu Arg Ala Ile
              485                 490                 495

Ile Lys Pro Arg Ile
              500

<210> SEQ ID NO 107
<211> LENGTH: 501
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 107

Met Ala Leu Leu Leu Ala Val Phe Ala Val Leu Ala Val Ala Leu
1               5                   10                  15

Ile Phe Trp Tyr Leu Lys Ser Tyr Thr Ser Ala Arg Arg Ser Gln Ser
              20                  25                  30

Asn His Leu Pro Arg Val Pro Glu Val Pro Gly Val Pro Leu Leu Gly
           35                  40                  45

Asn Leu Leu Gln Leu Lys Glu Lys Lys Pro Tyr Met Thr Phe Thr Arg
  50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
              100                 105                 110

Val Leu Thr Ala Asp Lys Thr Met Val Ala Met Ser Asp Tyr Asp Asp
           115                 120                 125

Tyr His Lys Thr Val Lys Arg His Ile Leu Thr Ala Val Leu Gly Pro
   130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
            165                 170                 175

Glu Val Asp Leu Arg Lys Ile Phe Gln Ser Glu Leu Phe Gly Leu Ala
        180                 185                 190

Met Arg Gln Ala Leu Gly Lys Asp Val Glu Ser Leu Tyr Val Glu Asp
    195                 200                 205

Leu Lys Ile Thr Met Asn Arg Asp Glu Ile Phe Gln Val Leu Val Val
210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
            245                 250                 255

Met Tyr Ile Arg Arg Glu Ala Val Met Lys Ser Leu Ile Lys Glu His
        260                 265                 270

Lys Lys Arg Ile Ala Ser Gly Glu Lys Leu Asn Ser Tyr Ile Asp Tyr
    275                 280                 285

Leu Leu Ser Glu Ala Gln Thr Leu Thr Asp Gln Gln Leu Leu Met Ser
290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
            325                 330                 335

Leu Tyr Arg Asp Ile Lys Ser Val Cys Gly Ser Glu Lys Ile Thr Glu
        340                 345                 350

Glu His Leu Ser Gln Leu Pro Tyr Ile Thr Ala Ile Phe His Glu Thr
    355                 360                 365

Leu Arg Arg His Ser Pro Val Pro Ile Ile Pro Leu Arg His Val His
370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
            405                 410                 415

Pro Glu Glu Trp Asn Pro Glu Arg Phe Met Lys Glu Asn Glu Thr Ile
        420                 425                 430

Asp Phe Gln Lys Thr Met Ala Phe Gly Gly Gly Lys Arg Val Cys Ala
    435                 440                 445

Gly Ser Leu Gln Ala Leu Leu Thr Ala Ser Ile Gly Ile Gly Arg Met
450                 455                 460

Val Gln Glu Phe Glu Trp Lys Leu Lys Asp Met Thr Gln Glu Glu Val
465                 470                 475                 480

Asn Thr Ile Gly Leu Thr Asn Gln Met Leu Arg Pro Leu Arg Ala Ile
            485                 490                 495

Ile Lys Pro Arg Ile
            500

<210> SEQ ID NO 108
<211> LENGTH: 513
<212> TYPE: PRT
<213> ORGANISM: Artificial Sequence
<220> FEATURE:
<223> OTHER INFORMATION: Synthetic - Engineered valencene oxidase variant

<400> SEQUENCE: 108

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415
```

```
Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
            435                 440                 445

Thr Met Ala Phe Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
            485                 490                 495

Leu Thr Thr Gln Met Leu Arg Pro Leu Arg Ala Ile Ile Lys Pro Arg
            500                 505                 510

Ile

<210> SEQ ID NO 109
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 109

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
            85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
            165                 170                 175

Leu His Glu Phe Val Lys Asn Asn Pro Glu Gln Glu Glu Val Asp Leu
        180                 185                 190

Arg Lys Ile Phe Gln Ser Glu Leu Phe Gly Leu Ala Met Arg Gln Ala
    195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
            245                 250                 255
```

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Asn Gln Met Leu Arg Pro Leu Arg Ala Ile Ile Lys Pro Arg
            500                 505                 510

Ile

<210> SEQ ID NO 110
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 110

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn Arg Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

-continued

```
Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
            115                 120                 125

Asp Lys Thr Met Val Ala Met Ser Asp Tyr Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Val Asp Leu
            180                 185                 190

Arg Lys Ile Phe Gln Ser Glu Leu Phe Gly Leu Ala Met Arg Gln Ala
            195                 200                 205

Leu Gly Lys Asp Val Glu Ser Leu Tyr Val Glu Asp Leu Lys Ile Thr
    210                 215                 220

Met Asn Arg Asp Glu Ile Leu Gln Val Leu Val Asp Pro Met Met
225                 230                 235                 240

Gly Ala Ile Asp Val Asp Trp Arg Asp Phe Phe Pro Tyr Leu Lys Trp
            245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu Gln Lys Lys Arg Ile
            275                 280                 285

Ala Ser Gly Glu Lys Leu Asn Ser Tyr Ile Asp Tyr Leu Leu Ser Glu
            290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
            355                 360                 365

Gln Leu Pro Tyr Ile Thr Ala Ile Phe His Glu Thr Leu Arg Lys His
    370                 375                 380

Ser Pro Val Pro Ile Ile Pro Leu Arg His Val His Glu Asp Thr Gln
385                 390                 395                 400

Leu Gly Gly Tyr His Val Pro Ala Gly Thr Glu Leu Ala Val Asn Ile
            405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ala Asp Phe Gln Lys
            435                 440                 445

Thr Met Ala Phe Gly Gly Gly Lys Arg Val Cys Ala Gly Ser Leu Gln
            450                 455                 460

Ala Leu Leu Thr Ala Ser Ile Gly Ile Gly Arg Met Val Gln Glu Phe
465                 470                 475                 480

Glu Trp Lys Leu Lys Asp Met Asp Gln Glu Glu Val Asn Thr Ile Gly
            485                 490                 495

Leu Thr Asn Gln Met Leu Arg Pro Leu Arg Ala Ile Ile Lys Pro Arg
            500                 505                 510
```

Ile

<210> SEQ ID NO 111
<211> LENGTH: 513
<212> TYPE: PRT
<213> ORGANISM: Artificial Sequence
<220> FEATURE:
<223> OTHER INFORMATION: Synthetic - Engineered valencene oxidase variant

<400> SEQUENCE: 111

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Lys Trp Ala Ala Thr
65                  70                  75                  80

Tyr Gly Pro Ile Tyr Ser Ile Lys Thr Gly Ala Thr Ser Val Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Gln Met Val Ala Met Ser Asp Tyr Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Leu Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu Gln Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350
```

-continued

```
Ile Lys Ser Val Cys Gly Ser Glu Lys Ile Thr Glu His Leu Ser
            355                 360                 365
Gln Leu Pro Tyr Ile Thr Ala Ile Phe His Glu Thr Leu Arg Lys His
    370                 375                 380
Ser Pro Val Pro Ile Leu Pro Leu Arg His Val His Glu Asp Thr Val
385                 390                 395                 400
Leu Gly Gly Tyr His Val Pro Ala Gly Thr Glu Leu Ala Val Asn Ile
                405                 410                 415
Tyr Gly Cys Asn Met Asp Lys Asn Val Trp Glu Asn Pro Glu Glu Trp
            420                 425                 430
Asn Pro Glu Arg Phe Met Lys Gly Asn Glu Thr Ile Asp Phe Gln Lys
    435                 440                 445
Thr Met Ala Phe Gly Gly Gly Lys Arg Val Cys Ala Gly Ser Leu Gln
450                 455                 460
Ala Leu Leu Ile Ala Ser Ile Gly Ile Gly Arg Met Val Gln Glu Phe
465                 470                 475                 480
Glu Trp Lys Leu Lys Asp Met Thr Gln Glu Val Asn Thr Ile Gly
                485                 490                 495
Leu Thr Asn Gln Met Leu Arg Pro Leu Arg Ala Ile Ile Lys Pro Arg
                500                 505                 510
Ile

<210> SEQ ID NO 112
<211> LENGTH: 8
<212> TYPE: PRT
<213> ORGANISM: Artificial Sequence
<220> FEATURE:
<223> OTHER INFORMATION: Synthetic - Leader sequence

<400> SEQUENCE: 112

Met Ala Leu Leu Leu Ala Val Phe
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic - Linker sequence

<400> SEQUENCE: 113

Gly Ser Gly Gly Gly Gly Ser
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic - Linker sequence

<400> SEQUENCE: 114

Gly Ser Gly Glu Ala Ala Ala Lys
1               5

<210> SEQ ID NO 115
<211> LENGTH: 13
<212> TYPE: PRT
<213> ORGANISM: Artificial Sequence
<220> FEATURE:
<223> OTHER INFORMATION: Synthetic - Linker sequence
```

<400> SEQUENCE: 115

Gly Ser Gly Glu Ala Ala Ala Lys Glu Ala Ala Ala Lys
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Synthetic - Linker sequence

<400> SEQUENCE: 116

Gly Ser Gly Met Gly Ser Ser Ser Asn
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic - Linker sequence

<400> SEQUENCE: 117

Gly Ser Thr Gly Ser
1               5

<210> SEQ ID NO 118
<211> LENGTH: 20
<212> TYPE: PRT
<213> ORGANISM: Artificial Sequence
<220> FEATURE:
<223> OTHER INFORMATION: Synthetic - N-terminal fragment of yhcB

<400> SEQUENCE: 118

Met Ala Trp Glu Tyr Ala Leu Ile Gly Leu Val Val Gly Ile Ile Ile
1               5                   10                  15

Gly Ala Val Ala
            20

<210> SEQ ID NO 119
<211> LENGTH: 1647
<212> TYPE: DNA
<213> ORGANISM: Citrus sinensis

<400> SEQUENCE: 119
atggcctccg gcgaaacctt ccgtccgacc gcagacttcc atccgtcact gtggcgtaat      60
cacttcctga aggcgcaag cgacttcaaa acggtggatc tacggcaac ccaggaacgt       120 cacgaagctc tgaaggaaga agtccgtcgc atgattaccg atgccgaaga caaaccggtg     180
cagaagctgc gtctgatcga tgaagttcaa cgcctgggcg tcgcgtatca ttttgaaaaa    240
gaaattggtg acgccatcca gaagctgtgc ccgatttaca tcgatagcaa ccgcgcagac    300
ctgcataccg tgtctctgca ctttcgtctg ctgcgccagc aaggcatcaa gatcagctgt    360
gatgttttcg aaaagttcaa ggatgacgaa ggccgtttca aaagctctct gattaatgat    420
gttcagggta tgctgtctct gtatgaagcg gcctacatgg cggtccgcgg tgaacatatt    480
ctggatgaag cgatcgcctt taccacgacc catctgaaaa gcctggtggc ccaggaccac    540
gttacgccga agctggcgga acaaattaac cacgccctgt atcgtccgct gcgcaaaacc    600
ctgccgcgtc tggaagcacg ctacttcatg agcatgatta atagtacgtc cgatcatctg    660
tgcaacaaaa ccctgctgaa ttttgctaag ctggacttca acatcctgct ggaactgcac    720

```
aaagaagaac tgaatgaact gaccaaatgg tggaaggatc tggactttac gaccaaactg      780
ccgtatgcac gtgatcgcct ggttgaactg tacttctggg acctgggcac gtattttgaa      840
ccgcagtacg ctttcggtcg taaaattatg acccaactga actatatcct gtcaattatc      900
gatgacacgt atgatgcgta cggcaccctg aagaactgt cgctgtttac ggaagcggtg       960
cagcgttgga atattgaagc cgttgatatg ctgccggaat atgaaact gatttaccgc       1020 accctgctgg atgcattcaa cgaaatcgaa gaagacatgg ctaaacaagg tcgtagtcat     1080
tgcgtgcgct atgcgaaaga agaaaatcag aaggttattg gcgcgtactc agtccaagcc     1140
aaatggtttt cggaaggtta tgttccgacg attgaagaat acatgccgat cgcactgacc     1200
tcatgtgctt atacgtttgt gatcaccaac tcgttcctgg gcatgggtga ttttgccacc     1260
aaagaagttt tcgaatggat tagcaacaat ccgaaagtgg ttaaggcagc ttctgtcatc     1320
tgccgtctga tggatgacat gcagggccat gaatttgaac aaaaacgcgg tcacgttgca     1380
agtgctattg aatgttatac caagcagcac ggcgtctcca agaagaagc aattaagatg      1440 ttcgaagaag aagtggcgaa cgcctggaaa gatatcaatg aagaactgat gatgaagccg     1500
acggtcgtgg cacgtccgct gctgggcacc atcctgaatc tggcacgcgc tatcgatttc     1560
atctacaaag aagatgacgg ctacacccat agttacctga ttaaggatca gatcgcctcc     1620
gtcctgggtg accacgtgcc gttctaa                                         1647
```

<210> SEQ ID NO 120
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 120

```
atggcaaccc aggtgagcgc cagtagcctg gcacaaatcc gcagcctaa aaaccgccct       60 gttgccaatt ccatccgaa catctgggc gaccactta tcacctacac cccggaagac       120
aaagtgaccc gcgccaaaaa agaagagagg attgaagatc tgaaggaaga agtgaaacgc     180
aaactgaccg cagccgccgt ggccaatccg agtcaactgc tgaacttcat tgatgcagtt     240
cagcgcctgg gcgttgccta tcactttgag caggagatcg aggaggcatt acagcatatt     300
tgtaatagct ttcacgactg caatgatatg gatggcgacc tgtataatat cgccctgcta     360
tttcgtctgc tgcgccaaca gggttacaca atcagttgcg acatctttaa caagttcacc     420
gatgaagagg gccgctttaa agaagccctg attagcgacg tgcgcggtat gttaggcctg     480
tatgaagcag cccacctgcg cgttcacggc gaagacatcc tggcagaggc actggccttt     540
acaaccaccc acctgaaagc aatggttgaa tcgctgggct accatctggc cgagcaagtg     600
aggcacgcct taaaccgtcc gatccgtaaa ggcatggaac gtctggaagc acgttggtac     660
atcagcatat accaggatga ggccttcat gacaaaaccc tgctggagct ggccaaactg      720
gacttcaacc tggtgcagag cctgcacaaa gaagagctga gcaatctggc acgctggtgg     780
aaggagctgg atttgccac caaactgcct tttgcccgcg accgtttagt tgaaggctac      840
ttttggatga tgggtgtgta ttttgagccg cagtatctgc gtggccgtcg catcctgaca     900
aaggtgatcg ccctgaccag catcattgac acatccacg atgcctatgg caccccggag      960
gaactgaaac tgtttatcga ggccatcgaa aatgggacg agagcagcat caaccaactg     1020
cctgagtaca tgaagctgtg ctatgtggcc ctgctggaca tgtataatga atcgaagag     1080 gagatggaaa aggagggcaa ccaataccgt atccactacc tgaaggaggt tatgaaaaac    1140
```
caggtgcgtg cctactttgc agaggcaaaa tggctgcacg atgagcatgt gccggccttt 1200
gaagaataca tgcgcgttgc cctggccagc agtggttatt gtctgctggc cgttacaagt 1260
tttgtgggca tgggcgagat cgtgacaaag gaagcctttg actgggttac aagcgacccg 1320
cgcatcataa gcagcagcaa cacaattaca cgcctgatgg acgacattaa agccataaa 1380
tttgaacaga aacgcggtca tgtgaccagc gccgtggaat gctacatgaa acagtacgcc 1440
gtgaccgaag agcaggttta cgaggaattt aaaaaacaga ttgaaaacgc atggctggac 1500
attaatcagg agtgtctgaa gccgaccgca gtgccgatgc cgctgttagc acgcctgctg 1560
aatttcaccc gcacaatgga tgtgatttat aaagaagaag acagctatac ccatgtgggc 1620
aagaccatgc gcgacaacat cgccagcgtg tttatcaacc ctgtgatcta a 1671

<210> SEQ ID NO 121
<211> LENGTH: 1515
<212> TYPE: DNA
<213> ORGANISM: Artificial Sequence
<220> FEATURE:
<223> OTHER INFORMATION: Synthetic - Engineered valencene oxidase

<400> SEQUENCE: 121
atggcttggg aatatgcgct aattgggtta gtcgtcggca tcattattgg tgctgtggcc 60
ttctggtatc tgaaatctta cactagcgcg cgccgctctc agtccaacca cctgccgcgt 120
gtgccggaag ttccgggtgt gccactgctg ggcaacctgc tgcaactgaa agaaaagaaa 180
ccgtacatga cctttacccg ctgggcagcg acttatggtc ctatctacag cattaaaacc 240
ggcgctacgt ctatggttgt ggtttcttcc aacgaaatcg cgaaagaagc cctggtgact 300
cgtttccagt ccattagcac ccgcaacctg tccaaagcgc tgaaggttct gacggctgac 360
aagactatgg tggctatgag cgactatgat gactaccaca aaaccgttaa acgtcacatc 420
ctgaccgcag tactgggtcc gaacgcacag aaaaaacatc gcatccaccg cgacattatg 480
atggataaca tctccacgca gctgcatgag ttcgttaaga acaatccaga acaggaagag 540
gtagatctgc gtaaaatttt tcagtccgaa ctgttcggtc tggctatgcg tcaggcgctg 600
ggcaaagacg ttgaaagcct gtatgtcgaa gacctgaaaa ttaccatgaa ccgtgatgag 660
atcttccagg ttctggttgt agatccgatg atgggcgcca tcgacgtgga ttggcgtgac 720
ttctttccgt acctgaaatg ggtcccgaac aagaagttcg aaaacaccat ccagcaaatg 780
tacatccgtc gtgaagcggt gatgaaaagc ctgatcaaag aacacaaaaa gcgtattgct 840
tctggtgaga aactgaactc ctacatcgat tatctgctgt ccgaagcgca gaccctgacc 900
gaccaacagc tgctgatgtc tctgtgggaa ccgattatcg aaagcagcga caccactatg 960
gtcactaccg aatgggcaat gtatgagctg gccaaaaacc cgaaactgca ggatcgtctg 1020
taccgtgaca tcaaaagcgt ttgcggctcc gagaaaatca ctgaagaaca cctgtctcag 1080
ctgccgtaca tcactgctat tttccacgaa accctgcgtc gccattctcc ggttccgatc 1140
attccgctgc gtcacgttca cgaagatact gtgctgggtg gttaccatgt accggcaggc 1200
actgaactgg ctgtcaacat ctacggctgt aacatggata aaaacgtttg ggagaatcct 1260
gaagaatgga acccggaacg cttcatgaaa gagaacgaaa ccatcgactt ccagaaaacg 1320
atggctttcg gcgtggtaa acgtgtgtgc gcaggttctc tgcaggcgct gctgacggcg 1380
tccattggta tcgtcgcat ggtacaggaa tttgaatgga agctgaaaga catgacccaa 1440
gaagaggtga ataccattgg tctgactacc cagatgctgc gtccactgcg tgcaatcatc 1500
aaacctcgta tttaa                                                         1515

<210> SEQ ID NO 122
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 122

| | | | | | |
|---|---|---|---|---|---|
| atggcttggg | aatatgcgct | aattgggtta | gtcgtcggca | tcattattgg | tgctgtggcc | 60 |
| atgcgttggt | atctgaaatc | ttacactagc | gcgcgccgct | ctcagtccaa | ccacctgccg | 120 |
| cgtgtgccgg | aagttccggg | tgtgccactg | ctgggcaacc | tgctgcaact | gaaagaaaag | 180 |
| aaaccgtaca | tgacctttac | ccgctgggca | gcgacttatg | gtcctatcta | cagcattaaa | 240 |
| accggcgcta | cgtctgtggt | tgtggtttct | tccaacgaaa | tcgcgaaaga | agccctggtg | 300 |
| actcgtttcc | agtccattag | cacccgcaac | ctgtccaaag | cgctgaaggt | tctgacggct | 360 |
| gacaagacta | tggtggctat | gagcgactat | gatgactacc | acaaaaccgt | taaacgtcac | 420 |
| atcctgaccg | cattactggg | tccgaacgca | cagaaaaaac | atcgcatcca | ccgcgacatt | 480 |
| atgatggata | acatctccac | gcagctgcat | gagttcgtta | agaacaatcc | agaacaggaa | 540 |
| gaggtagatc | tgcgtaaaat | ttttcagtcc | gaactgttcg | gtctggctat | gcgtcaggcg | 600 |
| ctgggcaaag | acgttgaaag | cctgtatgtc | gaagacctga | aaattaccat | gaaccgtgat | 660 |
| gagatcctac | aggttctggt | tgtagatccg | atgatgggcg | ccatcgacgt | ggattggcgt | 720 |
| gacttctttc | gtacctgaa | atgggtcccg | aacaagaagt | tcgaaaacac | catccagcaa | 780 |
| atgtacatcc | gtcgtgaagc | ggtgatgaaa | agcctgatca | agaacaaaa | aaagcgtatt | 840 |
| gcttctggtg | agaaactgaa | ctcctacatc | gattatctgc | tgtccgaagc | gcagaccctg | 900 |
| accgaccaac | agctgctgat | gtctctgtgg | gaaccgatta | tcgaaagcag | cgacaccact | 960 |
| atggtcacta | ccgaatgggc | aatgtatgag | ctggccaaaa | acccgaaact | gcaggatcgt | 1020 |
| ctgtaccgtg | acatcaaaag | cgtttgcggc | tccgagaaaa | tcactgaaga | cacctgtct | 1080 |
| cagctgccgt | acatcactgc | tattttccac | gaaaccctgc | gtaagcattc | tccggttccg | 1140 |
| atcctgccgc | tgcgtcacgt | tcacgaagat | actgtgctgg | gtggttacca | tgtaccggca | 1200 |
| ggcactgaac | tggctgtcaa | catctacggc | tgtaacatgg | ataaaaacgt | ttgggagaat | 1260 |
| cctgaagaat | ggaacccgga | acgcttcatg | aaagagaacg | aaaccatcga | cttccagaaa | 1320 |
| acgatggctt | tcggcggtgg | taaacgtgtg | tgcgcaggtt | ctctgcaggc | gctgctgatt | 1380 |
| gcgtccattg | gtatcggtcg | catggtacag | gaatttgaat | ggaagctgaa | agacatgacc | 1440 |
| caagaagagg | tgaataccat | tggtctgact | aatcagatgc | tgcgtccact | gcgtgcaatc | 1500 |
| atcaaacctc | gtatttaa | | | | | 1518 |

<210> SEQ ID NO 123
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 123

| | | | | | |
|---|---|---|---|---|---|
| atggcttggg | aatatgcgct | aattgggtta | gtcgtcggca | tcattattgg | tgctgtggcc | 60 |
| atgcgttggt | atctgaaatc | ttacactagc | gcgcgccgct | ctcagtccaa | ccacctgccg | 120 |
| cgtgtgccgg | aagttccggg | tgtgccactg | ctgggcaacc | tgctgcaact | gaaagaaaag | 180 |

```
aaaccgtaca tgacctttac caaatgggca gcgacttatg gtcctatcta cagcattaaa    240
accggcgcta cgtctatggt tgtggtttct tccaacgaaa tcgcgaaaga agccctggtg    300
actcgtttcc agtccattag cacccgcaac ctgtccaaag cgctgaaggt tctgacggct    360
gacaagcaga tggtggctat gagcgactat gatgactacc acaaaaccgt taaacgtcac    420
atcctgaccg cagtactggg tccgaacgca cagaaaaaac atcgcatcca ccgcgacatt    480
atgatggata acatctccac gcagctgcat gagttcgtta agaacaatcc agaacaggaa    540
gaggtagatc tgcgtaaaat ttttcagtcc gaactgttcg gtctggctat gcgtcaggcg    600
ctgggcaaag acgttgaaag cctgtatgtc gaagacctga aaattaccat gaaccgtgat    660
gagatcctac aggttctggt tgtagatccg atgatgggcg ccatcgacgt ggattggcgt    720
gacttctttc cgtacctgaa atgggtcccg aacaagaagt cgaaaacac catccagcaa    780 atgtacatcc gtcgtgaagc ggtgatgaaa agcctgatca agaacaaaa aaagcgtatt    840 gcttctggtg agaaactgaa ctcctacatc gattatctgc tgtccgaagc gcagaccctg    900
accgaccaac agctgctgat gtctctgtgg gaaccgatta tcgaaagcag cgacaccact    960
atggtcacta ccgaatgggc aatgtatgag ctggccaaaa acccgaaact gcaggatcgt   1020
ctgtaccgtg acatcaaaag cgtttgcggc tccgagaaaa tcactgaaga acacctgtct   1080
cagctgccgt acatcactgc tattttccac gaaaccctgc gtaagcattc tccggttccg   1140
atcctgccgc tgcgtcacgt tcacgaagat actgtgctgg gtggttacca tgtaccggca   1200
ggcactgaac tggctgtcaa catctacggc tgtaacatgg ataaaaacgt ttgggagaat   1260
cctgaagaat ggaacccgga acgcttcatg aaagagaacg aaaccatcga cttccagaaa   1320
acgatggctt tcggcggtgg taaacgtgtg tgcgcaggtt ctctgcaggc gctgctgatt   1380
gcgtccattg gtatcggtcg catggtacag gaatttgaat ggaagctgaa agacatgacc   1440
caagaagagg tgaataccat tggtctgact aatcagatgc tgcgtccact gcgtgcaatc   1500
atcaaacctc gtatttaa                                                 1518
```

<210> SEQ ID NO 124
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 124

```
atggcttggg aatatgcgct aattgggtta gtcgtcggca tcattattgg tgctgtggcc     60
atgcgttggt atctgaaatc ttacactagc gcgcgccgct ctcagtccaa ccatctgccg    120
cgtgtgccgg aagttccggg tgtgccactg ctgggcaacc tgctgcaact gaaagaaaag    180
aaaccgtaca tgacctttac ccgctgggca gcgacttatg gtcctatcta cagcattaaa    240
accggcgcta cgtctgtggt tgtggtttct tccaacgaaa tcgcgaaaga agccctggtg    300
actcgtttcc agtccattag cacccgcaac ctgtccaaag cgctgaaggt tctgacggct    360
gacaagcaga tggtggctat gagcgactat gatgactacc acaaaaccgt taaacgtcac    420
atcctgaccg cagtactggg tccgaacgca cagaaaaaac atcgcatcca ccgcgacatt    480
atgatggata acatctccac gcagctgcat gagttcgtta agaacaatcc agaacaggaa    540
gaggtagatc tgcgtaaaat ttttcagtcc gaactgttcg gtctggctat gcgtcaggcg    600
ctgggcaaag acgttgaaag cctgtatgtc gaagacctga aaattaccat gaaccgtgat    660
```

| | |
|---|---|
| gagatcctac aggttctggt tgtagatccg atgatgggcg ccatcgacgt ggattggcgt | 720 |
| gacttctttc cgtacctgaa atgggtcccg aacaagaagt tcgaaaacac catccagcaa | 780 |
| atgtacatcc gtcgtgaagc ggtgatgaaa agcctgatca agaacaaaa aaagcgtatt | 840 |
| gcttctggtg agaaactgaa ctcctacatc gattatctgc tgtccgaagc gcagaccctg | 900 |
| accgaccaac agctgctgat gtctctgtgg gaaccgatta tcgaaagcag cgacaccact | 960 |
| atggtcacta ccgaatgggc aatgtatgag ctggccaaaa acccgaaact gcaggatcgt | 1020 |
| ctgtaccgtg acatcaaaag cgtttgcggc tccgagaaaa tcactgaaga cacctgtct | 1080 |
| cagctgccgt acatcactgc tattttccac gaaaccctgc gtaagcattc tccggttccg | 1140 |
| atcctgccgc tgcgtcacgt tcacgaagat actgtgctgg gtggttacca tgtaccggca | 1200 |
| ggcactgaac tggctgtcaa catctacggc tgtaacatgg ataaaaacgt ttgggagaat | 1260 |
| cctgaagaat ggaacccgga acgcttcatg aaagagaacg aaaccatcga cttccagaaa | 1320 |
| acgatggctt tcggcggtgg taaacgtgtg tgcgcaggtt ctctgcaggc gctgctgatt | 1380 |
| gcgtccattg gtatcggtcg catggtacag gaatttgaat ggaagctgaa agacatgacc | 1440 |
| caagaagagg tgaataccat tggtctgact aatcagatgc tgcgtccact gcgtgcaatc | 1500 |
| atcaaacctc gtatttaa | 1518 |

<210> SEQ ID NO 125
<211> LENGTH: 1515
<212> TYPE: DNA
<213> ORGANISM: Artificial Sequence
<220> FEATURE:
<223> OTHER INFORMATION: Synthetic - Engineered valencene oxidase

<400> SEQUENCE: 125

| | |
|---|---|
| atggcttggg aatatgcgct aattgggtta gtcgtcggca tcattattgg tgctgtggcc | 60 |
| gcttggtatc tgaaatctta cactagcgcg cgccgctctc agtccaacca tctgccgcgt | 120 |
| gtgccggaag ttccgggtgt gccactgctg gcaacctgc tgcaactgaa agaaaagaaa | 180 |
| ccgtacatga cctttaccaa atgggcagcg acttatggtc ctatctacag cattaaaacc | 240 |
| ggcgctacgt ctatggttgt ggtttcttcc aacgaaatcg cgaaagaagc cctggtgact | 300 |
| cgtttccagt ccattagcac ccgcaacctg tccaaagcgc tgaaggttct gacggctgac | 360 |
| aagcagatgg tggctatgag cgactatgat gactaccaca aaaccgttaa acgtcacatc | 420 |
| ctgaccgcag tactgggtcc gaacgcacag aaaaaacatc gcatccaccg cgacattatg | 480 |
| atggataaca tctccacgca gctgcatgag ttcgttaaga caatccaga acaggaagag | 540 |
| gtagatctgc gtaaaatttt tcagtccgaa ctgttcggtc tggctatgcg tcaggcgctg | 600 |
| ggcaaagacg ttgaaagcct gtatgtcgaa gacctgaaaa ttaccatgaa ccgtgatgag | 660 |
| atcctacagg ttctggttgt agatccgatg atgggcgcca tcgacgtgga ttggcgtgac | 720 |
| ttctttccgt acctgaaatg ggtcccgaac aagaagttcg aaaacaccat ccagcaaatg | 780 |
| tacatccgtc gtgaagcggt gatgaaagc ctgatcaaag aacaaaaaa gcgtattgct | 840 |
| tctggtgaga aactgaactc ctacatcgat tatctgctgt ccgaagcgca gaccctgacc | 900 |
| gaccaacagc tgctgatgtc tctgtgggaa ccgattatcg aaagcagcga caccactatg | 960 |
| gtcactaccg aatgggcaat gtatgagctg gccaaaaacc cgaaactgca ggatcgtctg | 1020 |
| taccgtgaca tcaaaagcgt tgcggctcc gagaaaatca ctgaagaaca cctgtctcag | 1080 |
| ctgccgtaca tcactgctat tttccacgaa accctgcgta agcattctcc ggttccgatc | 1140 |
| ctgccgctgc gtcacgttca cgaagatact gtgctgggtg gttaccatgt accggcaggc | 1200 |

```
actgaactgg ctgtcaacat ctacggctgt aacatggata aaaacgtttg ggagaatcct    1260
gaagaatgga acccggaacg cttcatgaaa gagaacgaaa ccatcgactt ccagaaaacg    1320
atggctttcg gcggtggtaa acgtgtgtgc gcaggttctc tgcaggcgct gctgattgcg    1380
tccattggta tcggtcgcat ggtacaggaa tttgaatgga agctgaaaga catgacccaa    1440
gaagaggtga ataccattgg tctgactaat cagatgctgc gtccactgcg tgcaatcatc    1500
aaacctcgta tttaa                                                     1515
```

<210> SEQ ID NO 126
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 126

```
atggcttggg aatatgcgct aattgggtta gtcgtcggca tcattattgg tgctgtggcc      60
atgcgttggt atctgaaatc ttacactagc gcgcgccgct ctcagtccaa ccacctgccg     120
cgtgtgccgg aagttccggg tgtgccactg ctgggcaacc tgctgcaact gaaagaaaag     180
aaaccgtaca tgacctttac caaatgggca gcgacttatg gtcctatcta cagcattaaa     240
accggcgcta cgtctgtggt tgtggtttct tccaacgaaa tcgcgaaaga gccctggtg      300 actcgtttcc agtccattag cacccgcaac ctgtccaaag cgctgaaggt tctgacggct     360
gacaagcaga tggtggctat gagcgactat gatgactacc acaaaaccgt taaacgtcac     420
atcctgaccg cagtactggg tccgaacgca cagaaaaaac atcgcatcca ccgcgacatt     480
atgatggata acatctccac gcagctgcat gagttcgtta gaacaatcc agaacaggaa      540 gaggtagatc tgcgtaaaat tttttcagtcc gaactgttcg gtctggctat gcgtcaggcg     600
ctgggcaaag acgttgaaag cctgtatgtc gaagacctga aaattaccat gaaccgtgat     660
gagatcctac aggttctggt tgtagatccg atgatgggcg ccatcgacgt ggattggcgt     720
gacttctttc cgtacctgaa atgggtcccg aacaagaagt tcgaaaacac catccagcaa     780
atgtacatcc gtcgtgaagc ggtgatgaaa agcctgatca agaacaaaa aaagcgtatt      840 gcttctggtg agaaactgaa ctcctacatc gattatctgc tgtccgaagc gcagaccctg     900
accgaccaac agctgctgat gtctctgtgg gaaccgatta tcgaaagcag cgacaccact     960
atggtcacta ccgaatgggc aatgtatgag ctggccaaaa acccgaaact gcaggatcgt    1020
ctgtaccgtg acatcaaaag cgtttgcggc tccgagaaaa tcactgaaga cacctgtct     1080 cagctgccgt acatcactgc tattttccac gaaaccctgc gtaagcattc tccggttccg    1140
atcctgccgc tgcgtcacgt tcacgaagat actgtgctgg tggttacca tgtaccggca     1200 ggcactgaac tggctgtcaa catctacggc tgtaacatgg ataaaaacgt tgggagaat    1260 cctgaagaat ggaacccgga acgcttcatg aaagagaacg aaaccatcga cttccagaaa   1320
acgatggctt tcggcggtgg taaacgtgtg tgcgcaggtt ctctgcaggc gctgctgatt   1380
gcgtccattg gtatcggtcg catggtacag gaatttgaat ggaagctgaa agacatgacc   1440
caagaagagg tgaataccat tggtctgact aatcagatgc tgcgtccact gcgtgcaatc   1500
atcaaacctc gtatttaa                                                  1518
```

<210> SEQ ID NO 127
<211> LENGTH: 1518
<212> TYPE: DNA

<213> ORGANISM: Artificial Sequence
<220> FEATURE:
<223> OTHER INFORMATION: Synthetic - Engineered valencene oxidase

<400> SEQUENCE: 127

```
atggcttggg aatatgcgct aattgggtta gtcgtcggca tcattattgg tgctgtggcc      60
atgcgttggt atctgaaatc ttacactagc gcgcgccgct ctcagtccaa ccacctgccg     120
cgtgtgccgg aagttccggg tgtgccactg ctgggcaacc tgctgcaact gaaagaaaag     180
aaaccgtaca tgacctttac caaatgggca gcgacttatg gtcctatcta cagcattaaa     240
accggcgcta cgtctgtggt tgtggttttct tccaacgaaa tcgcgaaaga agccctggtg    300
actcgtttcc agtccattag cacccgcaac ctgtccaaag cgctgaaggt tctgacggct     360
gacaagacta tggtggctat gagcgactat gatgactacc acaaaaccgt taaacgtcac     420
atcctgaccg cagtactggg tccgaacgca cagaaaaaac atcgcatcca ccgcgacatt     480
atgatggata acatctccac gcagctgcat gagttcgtta agaacaatcc agaacaggaa     540
gaggtagatc tgcgtaaaat ttttcagtcc gaactgttcg gtctggctat gcgtcaggcg     600
ctgggcaaag acgttgaaag cctgtatgtc gaagacctga aaattaccat gaaccgtgat     660
gagatcctac aggttctggt tgtagatccg atgatgggcg ccatcgacgt ggattggcgt     720
gacttctttc cgtacctgaa atgggtcccg aacaagaagt tcgaaaacac catccagcaa     780
atgtacatcc gtcgtgaagc ggtgatgaaa gccctgatca agaacaaaaa aaagcgtatt     840
gcttctggtg agaaactgaa ctcctacatc gattatctgc tgtccgaagc gcagaccctg     900
accgaccaac agctgctgat gtctctgtgg gaaccgatta tcgaaagcag cgacaccact     960
atggtcacta ccgaatgggc aatgtatgag ctggccaaaa acccgaaact gcaggatcgt    1020
ctgtaccgtg acatcaaaag cgtttgcggc tccgagaaaa tcactgaaga cacctgtct    1080
cagctgccgt acatcactgc tattttccac gaaaccctgc gtaagcattc tccggttccg    1140
atcattccgc tgcgtcacgt tcacgaagat actgtgctgg tggttacca tgtaccggca    1200
ggcactgaac tggctgtcaa catctacggc tgtaacatgg ataaaaacgt ttgggagaat    1260
cctgaagaat ggaacccgga acgcttcatg aaagagaacg aaaccatcga cttccagaaa    1320
acgatggctt tcggcggtgg taaacgtgtg tgcgcaggtt ctctgcaggc gctgctgatt    1380
gcgtccattg gtatcggtcg catggtacag gaatttgaat ggaagctgaa agacatgacc    1440
caagaagagg tgaataccat tggtctgact aatcagatgc tgcgtccact gcgtgcaatc    1500
atcaaacctc gtatttaa                                                 1518
```

<210> SEQ ID NO 128
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 128

```
atggcaaccc aggtgagcgc cagtagcctg gcacaaatcc gcagcctaa aaaccgccct       60
gttgccaatt tccataaaaa catctggggc gaccacttta tcacctacac cccggaagac    120
aaagtgaccc gcgccaaaaa agaagagagg attgaagatc tgaaggaaga agtgaaacgc    180
aaactgaccg cagccgccgt ggccaatccg agtcaactgc tgaacttcat tgatgcagtt    240
cagcgcctgg gcgttgccta tcactttgag caggagatca ggaggcatt acagcatatt    300
tgtaatagct ttcacgactg caatgatatg gatggcgacc tgtataatat cgccctgcta    360
```

-continued

```
tttcgtctgc tgcgccaaca gggttacaca atcagttgcg acatctttaa caagttcacc      420
gatgaagagg gccgctttaa agaagccctg attagcgacg tgcgcggtat gttaggcctg      480
tatgaagcag cctacctgcg cgttcacggc gaagacatcc tggcagaggc actggccttt      540
acaaccaccc acctgaaagc aatggttgaa tcgctgggct accatctggc cgagcaagtg      600
aggcacgcct taaaccgtcc gatccgtaaa ggcatggaac gtctggaagc acgttggtac      660
atcagcatat accaggatga ggcctttcat gacaaaaccc tgctggagct ggccaaactg      720
gacttcaacc tggtgcagag cctgcacaaa gaagagctga gcaatctggc acgctggtgg      780
aaggagctgg attttgccac caaactgcct tttgcccgcg accgtttagt tgaaggctac      840
ttttggatga tgggtgtgta ttttgagccg cagtatctgc gtggccgtcg catcctgaca      900
aaggtgatcg ccctgaccag catcattgac gacatccacg atgcctatgg cacccccgga      960
gaactgaaac tgtttatcga ggccatcgaa aaatgggacg agagcagcat caaccaactg     1020
cctgagtaca tgaagctgtg ctataatgcc ctgctggacg tgtataatga aatcgaagag     1080
gagatggaaa aggagggcaa ccaataccgt atccactacc tgaaggaggt tatgaaaaac     1140
caggtgcgtg cctactttgc agaggcaaaa tggctgcacg atgagcatgt gccggccttt     1200
gaagaataca tgcgcgttgc cctggccagc agtggttatt gtctgctggc cgttacaagt     1260
tttgtgggca tgggcgagat cgtgacaaag gaagcctttg actgggttac aagcgacccg     1320
cgcatcataa gcagcagcaa cacaattaca cgcctgatgg acgacattaa agccataaaa     1380
tttgaacaga aacgcggtca tgtgtgggagc gccgtggaat gctacatgaa acagtacgcc     1440
gtgaccgaag agcaggttta cgaggaattt aaaaaacaga ttgaaaacgc atggctggac     1500
attaatcagg agtgtctgaa gccgaccgca gtgccgatgc cgctgttagc acgcctgctg     1560
aatttcaccc gcacaatgga tgtgatttat aaagaagaag acagctatac ccatgtgggc     1620
aagaccatgc gcgacaacat cgccagcgtg tttatcaacc ctgtgatcta a              1671
```

<210> SEQ ID NO 129
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 129

```
Met Ala Thr Gln Val Ser Ala Ser Ser Leu Ala Gln Ile Pro Gln Pro
1               5                   10                  15

Lys Asn Arg Pro Val Ala Asn Phe His Lys Asn Ile Trp Gly Asp His
            20                  25                  30

Phe Ile Thr Tyr Thr Pro Glu Asp Lys Val Thr Arg Ala Lys Lys Glu
        35                  40                  45

Glu Arg Ile Glu Asp Leu Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Leu Phe Arg Leu Leu Arg Gln Gln Gly
        115                 120                 125
```

```
Tyr Thr Ile Ser Cys Asp Ile Phe Asn Lys Phe Thr Asp Glu Glu Gly
    130                 135                 140

Arg Phe Lys Glu Ala Leu Ile Ser Asp Val Arg Gly Met Leu Gly Leu
145                 150                 155                 160

Tyr Glu Ala Ala Tyr Leu Arg Val His Gly Glu Asp Ile Leu Ala Glu
                165                 170                 175

Ala Leu Ala Phe Thr Thr His Leu Lys Ala Met Val Glu Ser Leu
            180                 185                 190

Gly Tyr His Leu Ala Glu Gln Val Arg His Ala Leu Asn Arg Pro Ile
        195                 200                 205

Arg Lys Gly Met Glu Arg Leu Glu Ala Arg Trp Tyr Ile Ser Ile Tyr
210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
    275                 280                 285

Glu Pro Gln Tyr Leu Arg Gly Arg Ile Leu Thr Lys Val Ile Ala
    290                 295                 300

Leu Thr Ser Ile Ile Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Asn Ala Leu Leu
            340                 345                 350

Asp Val Tyr Asn Glu Ile Glu Glu Met Glu Lys Glu Gly Asn Gln
    355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Ile Ser Ser Ser Asn Thr
            435                 440                 445

Ile Thr Arg Leu Met Asp Asp Ile Lys Ser His Lys Phe Glu Gln Lys
    450                 455                 460

Arg Gly His Val Trp Ser Ala Val Glu Cys Tyr Met Lys Gln Tyr Ala
465                 470                 475                 480

Val Thr Glu Glu Gln Val Tyr Glu Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
            515                 520                 525

Ile Tyr Lys Glu Glu Asp Ser Tyr Thr His Val Gly Lys Thr Met Arg
    530                 535                 540

Asp Asn Ile Ala Ser Val Phe Ile Asn Pro Val Ile
```

<210> SEQ ID NO 130
<211> LENGTH: 132
<212> TYPE: PRT
<213> ORGANISM: Escherichia coli

<400> SEQUENCE: 130

```
Met Thr Trp Glu Tyr Ala Leu Ile Gly Leu Val Val Gly Ile Ile Ile
1               5                   10                  15

Gly Ala Val Ala Met Arg Phe Gly Asn Arg Lys Leu Arg Gln Gln Gln
            20                  25                  30

Ala Leu Gln Tyr Glu Leu Glu Lys Asn Lys Ala Glu Leu Asp Glu Tyr
        35                  40                  45

Arg Glu Glu Leu Val Ser His Phe Ala Arg Ser Ala Glu Leu Leu Asp
    50                  55                  60

Thr Met Ala His Asp Tyr Arg Gln Leu Tyr Gln His Met Ala Lys Ser
65                  70                  75                  80

Ser Ser Ser Leu Leu Pro Glu Leu Ser Ala Glu Ala Asn Pro Phe Arg
                85                  90                  95

Asn Arg Leu Ala Glu Ser Glu Ala Ser Asn Asp Gln Ala Pro Val Gln
            100                 105                 110

Met Pro Arg Asp Tyr Ser Glu Gly Ala Ser Gly Leu Leu Arg Thr Gly
        115                 120                 125

Ala Lys Arg Asp
    130
```

<210> SEQ ID NO 131
<211> LENGTH: 1542
<212> TYPE: DNA
<213> ORGANISM: Stevia rebaudiana

<400> SEQUENCE: 131

| | |
|---|---:|
| atggatgccg tcaccggttt gctgacagtt ccggcaaccg caataaccat cggcggtacg | 60 |
| gccgtcgcac tcgccgtcgc tctgatattc tggtacctca aaagctacac atctgcacgc | 120 |
| aggagccaat caaccatctc ccctcgggtt cccgaggtac ctggtgtgcc attattgggg | 180 |
| aatttattgc agttgaagga gaagaaacct tacatgactt ttacaagatg ggcggcaact | 240 |
| tatggtccga tttattcgat taaaaccgga gcaacttcta tggtggtcgt cagttcaaat | 300 |
| gaaattgcaa ggaggcattg gttaccagat ttcaatctat ctcaaccaga aacctatca | 360 |
| aaggcattaa aggttctcac agcagataaa accatggtgg cgatgagtga ttatgatgat | 420 |
| tatcataaga ctgtcaaacg ccatatactg accgctgttt gggaccaaa tgctcagaag | 480 |
| aaacaccgca tccataggga catcatgatg ataatatat caacccaact tcatgaattt | 540 |
| gttaaaaata tcctgaaca agaggaagtg atctaagga aaatattcca atccgaactt | 600 |
| tttggattag ctatgagaca agcattggga aaggatgtgg agagcttata tgttgaggat | 660 |
| cttaaaatca ccatgaaccg agacgagata tttcaggtat tggttgttga cccgatgatg | 720 |
| ggtgcaattg acgtcgactg gagagatttc ttcccgtatc taaagtgggt cccgaataaa | 780 |
| aagtttgaaa acacgatcca acaaatgtat atccggagag aagctgtgat gaagtctctt | 840 |
| attaaagaac ataaaaaacg tattgcatcc ggagagaaat taaacagcta cattgattac | 900 |
| ttgctatcgg aagcacaaac gttaaccgat caacaactac ttatgtctct atgggaacct | 960 |
| attattgaat catcagacac cactatggtt acaactgaat gggctatgta tgaacttgca | 1020 |

| | |
|---|---|
| aaaaacccca aacttcagga tcgtttgtat cgggatatca aaagtgtttg cgggtcagag | 1080 |
| aagattacag aagaacactt gtctcaactg ccatacataa ctgccatttt tcatgaaacc | 1140 |
| ttgagaaggc atagtccagt tcctataatt ccattaagac acgtgcatga agacacagtg | 1200 |
| ttaggagggt accatgtgcc agctggaacc gagctagcgg taaacattta tggatgtaac | 1260 |
| atggataaga atgtgtggga gaatcctgaa gaatggaatc cagagagatt catgaaggaa | 1320 |
| aatgaaacga tagatttcca gaaaacaatg gcgtttggag gtggaaagcg cgtatgtgct | 1380 |
| ggttcgcttc aagcattgtt gactgcttcc attggaattg gaagaatggt gcaagagttt | 1440 |
| gagtggaaac tgaaagatat gacccaagaa gaagttaata cgattgggct tacgacccag | 1500 |
| atgcttcgtc cactgcgggc cataataaag cccaggatat ga | 1542 |

<210> SEQ ID NO 132
<211> LENGTH: 1518
<212> TYPE: DNA
<213> ORGANISM: Artificial Sequence
<220> FEATURE:
<223> OTHER INFORMATION: Synthetic - Engineered valencene oxidase variant

<400> SEQUENCE: 132

| | |
|---|---|
| atggcttggg aatatgcgct aattgggtta gtcgtcggca tcattattgg tgctgtggcc | 60 |
| atgcgttggt atctgaaatc ttacactagc gcgcgccgct ctcagtccaa ccacctgccg | 120 |
| cgtgtgccgg aagttccggg tgtgccactg ctgggcaacc tgctgcaact gaaagaaaag | 180 |
| aaaccgtaca tgacctttac caaatgggca gcgacttatg gtcctatcta cagcattaaa | 240 |
| accggcgcta cgtctgtggt tgtggttct tccaacgaaa tcgcgaaaga agccctggtg | 300 |
| actcgttccc agtccattag cacccgcaac ctgtccaaag cgctgaaggt tctgacggct | 360 |
| gacaagcaga tggtggctat gagcgactat gatgactacc acaaaaccgt taaacgtcac | 420 |
| atcctgaccg cagtactggg tccgaacgca cagaaaaaac atcgcatcca ccgcgacatt | 480 |
| atgatggata acatctccac gcagctgcat gagttcgtta agaacaatcc agaacaggaa | 540 |
| gaggtagatc tgcgtaaaat tttttcagtcc gaactgttcg gtctggctat gcgtcaggcg | 600 |
| ctgggcaaag acgttgaaag cctgtatgtc gaagacctga aaattaccat gaaccgtgat | 660 |
| gagatcctac aggttctggt tgtagatccg atgatgggcg ccatcgacgt ggattggcgt | 720 |
| gacttctttc cgtacctgaa atgggtcccg aacaagaagt tcgaaaacac catccagcaa | 780 |
| atgtacatcc gtcgtgaagc ggtgatgaaa agcctgatca agaacaaaaa aaagcgtatt | 840 |
| gcttctggtg agaaactgaa ctcctacatc gattatctgc tgtccgaagc gcagaccctg | 900 |
| accgaccaac agctgctgat gtctctgtgg gaaccgatta tcgaaagcag cgacaccact | 960 |
| atggtcacta ccgaatgggc aatgtatgag ctggccaaaa acccgaaact gcaggatcgt | 1020 |
| ctgtaccgtg acatcaaaag cgtttgcggc tccgagaaaa tcactgaaga cacctgtct | 1080 |
| cagctgccgt acatcactgc tattttccac gaaaccctgc gtaagcattc tccggttccg | 1140 |
| atcctgccgc tgcgtcacgt tcacgaagat actgtgctgg tggttaccag tgtaccggca | 1200 |
| ggcactgaac tggctgtcaa catctacggc tgtaacatga taaaaacgt ttgggagaat | 1260 |
| cctgaagaat ggaacccgga acgcttcatg aaagagaacg aaaccatcga cttccagaaa | 1320 |

```
acgatggctt tcggcggtgg taaacgtgtg tgcgcaggtt ctctgcaggc gctgctgatt  1380
gcgtccattg gtatcggtcg catggtacag gaatttgaat ggaagctgaa agacatgacc  1440
caagaagagg tgaataccat tggtctgact aatcagatgc tgcgtccact gcgtgcaatc  1500
atcaaacctc gtatttaa                                                1518
```

METHODS FOR PRODUCTION OF OXYGENATED TERPENES

CROSS-REFERENCE TO RELATED APPLICATIONS

This application is a continuation of U.S. patent application Ser. No. 16/669,051, filed on Oct. 30, 2019, which is a divisional of U.S. patent application Ser. No. 15/505,022, filed Feb. 17, 2017, which is a United States National Stage Application of International Application No. PCT/US2015/046421, filed Aug. 21, 2015, which claims the benefit of, and priority to, U.S. Provisional Application No. 62/040,284, filed Aug. 21, 2014, each of which is incorporated herein by reference in its entirety.

FIELD OF THE INVENTION

The present disclosure relates to oxygenated sesquiterpenes (e.g., nootkatone and/or nootkatol) and methods for their production and use. The disclosure also provides enzymes for the production of oxygenated sesquiterpenes (e.g., nootkatone and/or nootkatol) and methods for identifying, selecting, making and using these enzymes.

BACKGROUND OF THE INVENTION

The food and beverage industries as well as other industries such as the perfume, cosmetic and health care industries routinely use terpenes and/or terpenoid products as flavours and fragrances. By way of example, many sesquiterpene compounds are used in perfumery (e.g., patchoulol) and in the flavour industry (e.g., nootkatone) and many are extracted from plants. However, factors such as: (i) the availability and high price of the plant raw material; (ii) the relatively low terpene content in plant; and (iii) the tedious and inefficient extraction processes to produce sufficient quantities of terpene products on an industrial scale all have stimulated research on the biosynthesis of terpenes using plant-independent systems. Consequently, effort has been expended in developing technologies to engineer microorganisms for converting renewable resources such as glucose into terpenoid products. By comparison with traditional methods, microorganisms have the advantage of fast growth without the need for land to sustain development.

Many microorganisms use either the methylerythritol 4-phosphate (MEP) pathway or the melavonate (MVA) pathway to supply intermediates necessary to produce terpenoid products. These MEP or MVA pathways can include an endogenous or an engineered MEP or MVA pathway or both. A detailed understanding of isoprenoid pathway engineering and optimization is disclosed in WO 2011/060057, US 2011/0189717, US 2012/107893, U.S. Pat. No. 8,512,988 and Ajikumar et al (2010) Science 330 70-74, which discloses the production of various terpenoid compounds including sesquiterpene compounds such as nootkatone, which is an oxidised sesquiterpene produced from a valencene sesquiterpene substrate.

Nootkatone (4,4a,5,6,7,8-hexahydro-6-isopropenyl-4,4a-dimethyl-2(3II)-naphtalenone) is an important flavour constituent of grapefruit and is used commercially to flavour soft drinks and other beverages, as well as being used in perfumery. The conventional method for nootkatone preparation is by oxidation of valencene (see, e.g., U.S. Pat. Nos. 6,200,786 and 8,097,442). The starting material valencene is expensive and thus methods that consume valencene are less commercially acceptable. Because of these drawbacks, there is a need for commercially feasible and sustainable methods to prepare nootkatone and associated products.

SUMMARY OF THE INVENTION

An object of the present disclosure is to provide sustainable production of oxygenated sesquiterpene products. Specifically, the present disclosure provides enzyme catalysts for the ex vivo or in vivo production of certain oxygenated sesquiterpenes. In some embodiments, the disclosure provides host cells engineered for the biosynthesis of the oxygenated sesquiterpenes. Another object of the present disclosure is to provide engineered cytochrome P450 (CYP450) enzymes for synthesis of oxygenated sesquiterpenes, including in some embodiments functional expression alongside a reductase counterpart in E. coli, yeast, or other host cell. The disclosure thereby harnesses the unique capability of this class of enzymes to conduct oxidative chemistry.

In one aspect, the disclosure provides a method for making an oxygenated product of a sesquiterpene. The method comprises contacting the sesquiterpene with Stevia rebaudiana Kaurene Oxidase (SrKO) or a derivative thereof having sesquiterpene oxidizing activity. Surprisingly, the wild type SrKO enzyme was shown to have activity on a sesquiterpene substrate even though its natural activity is understood to act on a diterpene substrate. Further, SrKO enzyme showed unique activities, including oxygenation, by creating different stereoisomers of the hydroxylated product (alpha and beta nootkatol and further oxidizing to ketone, nootkatone), and produced different oxygenated terpene products including hydroxygermacra-1(10)5-diene, and murolan-3,9(11) diene-10-peroxy. This activity is distinct from other P450 enzymes tested, which produced only one of the stereoisomers of the hydroxylated product (e.g., β-nootkatol), as the major product and produced only minor amounts of nootkatone. This activity of SrKO provides a unique sesquiterpene oil for flavoring applications.

In some embodiments, the method takes place in an ex vivo (e.g., cell free) system. In other embodiments, the sesquiterpene substrate and the SrKO or derivative thereof are contacted in a cell expressing the SrKO, such as a bacterium (e.g., E. coli). The oxygenated product of a sesquiterpene may be recovered, or may be the substrate for further chemical transformation. Functional expression of wild type cytochrome P450 in E. coli has inherent limitations attributable to the bacterial platforms (such as the absence of electron transfer machinery and cytochrome P450 reductases, and translational incompatibility of the membrane signal modules of P450 enzymes due to the lack of an endoplasmic reticulum). Thus, in some embodiments the SrKO enzyme is modified for functional expression in an E. coli host cell, for example, by replacing a portion of the SrKO N-terminal transmembrane region with a short peptide sequence that stabilizes interactions with the E. coli inner membrane and/or reduces cell stress.

In some embodiments, the SrKO derivative has at least one mutation with respect to the wild type SrKO that increases valencene oxidase activity, or increases production of nootkatone, α-nootkatol, and/or β-nootkatol. For example, the SrKO may have from 1 to 50 mutations independently selected from substitutions, deletions, or insertions relative to wild type SrKO (SEQ ID NOS: 37 and 108) or an SrKO modified for expression and activity in E. coli (e.g., SEQ ID NOS: 38 and 106). For example, the SrKO derivative may have from 1 to 40 mutations, from 1 to 30 mutations, from 1 to 20 mutations, or from 1 to 10 mutations relative to SrKO (SEQ ID NOS: 37 or 38). In these or other embodiments, the SrKO derivative may comprise an amino acid sequence having at least 50% sequence identity, or at least 60% sequence identity, or at least 70% sequence identity, or at least 80% sequence identity, or at least 90% sequence identity to SrKO (SEQ ID NOS: 37 or 38), and has valencene oxidase activity. The SrKO in various embodiments maintains valencene oxidase activity, or has increased valencene oxidase activity as compared to the wild type enzyme in an ex vivo or bacterial system (e.g., E coli). Various mutations of SrKO which maintain or enhance valencene oxidase activity are listed in Tables 2.1, 2.2, 2.3 and 6. Thus, in various embodiments, the SrKO may have at least 2, at least 3, at least 4, at least 5, at least 6, at least 7, at least 8, at least 9, or at least 10 mutations selected from Tables 2.1, 2.2, 2.3 and/or 6. Exemplary derivatives of SrKO, also referred to herein as "valencene oxidase" or "VO" are represented by, for example, SEQ ID NOS: 104 and 105, which may further be derivatized for improvements in desired activity. Mutations may be selected empirically for increases in oxygenated sesquiterpene titer, or selected by in silico evaluation, or both.

In accordance with aspects of the disclosure, oxygenated sesquiterpene products are obtainable by contacting a sesquiterpene substrate with *Stevia rebaudiana* Kaurene Oxidase (SrKO) or derivative thereof having valencene oxidizing activity. Unlike other CYP450 enzymes, when a SrKO enzyme is used with valencene sesquiterpene substrate, it produces a different oxygenated terpene product profile that can include hydroxygermacra-1(10)5-diene, murolan-3,9(11) diene-10-peroxy, alpha-nootkatol, beta-nootkatol, and nootkatone. By comparison, other CYP450's having the activity of hydroxylating valencene only produced one of the stereoisomers (beta nootkatol) and did not produce significant amounts of the ketone (nootkatone), which requires two oxygenation cycles. See Table 4 and FIG. 7.

In various embodiments, the sesquiterpene substrate is (or the predominant sesquiterpene substrate is) valencene, germacrene (A, B, C, D, or E), farnesene, farnesol, nootkatol, patchoulol, cadinene, cedrol, humulene, longifolene, and/or bergamotene, β-ylangene, β-santalol, β-santalene, α-santalene, α-santalol, β-vetivone, α-vetivone, khusimol, bisabolene, β-aryophyllene, longifolene; α-sinensal; α-bisabolol, (–)-β-copaene, (–)-α-copaene, 4(Z),7(Z)-ecadienal, cedrol, cedrene, cedrol, guaiol, (–)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol, which in some embodiments comprises both α and β nootkatol.

The disclosure, when applied in vivo, is applicable to a wide array of host cells. In some embodiments, the host cell is a microbial host, such as a bacterium selected from *E. coli, Bacillus subtillus*, or *Pseudomonas putida*; or a yeast, such as a species of *Saccharomyces, Pichia*, or *Yarrowia*, including *Saccharomyces cerevisiae, Pichia pastoris*, and *Yarrowia lipolytica*.

In some embodiments, the host cell produces isopentyl pyrophosphate (IPP), which acts as a substrate for the synthesis of the sesquiterpene. In some embodiments, the IPP is produced by metabolic flux through an endogenous or heterologous methylerythritol phosphate (MEP) or mevalonic acid (MVA) pathway. In some embodiments, the sesquiterpene is produced at least in part by metabolic flux through an MEP pathway, and wherein the host cell has at least one additional copy of a dxs, ispD, ispF, and/or idi gene.

In some embodiments, the host cell expresses a farnesyl pyrophosphate synthase (FPPS), which produces farnesyl pyrophosphate (FPP) from IPP or DMAPP. The host cell may further express a heterologous sesquiterpene synthase to produce the desired sesquiterpene scaffold. For example, in some embodiments the cell expresses a valencene synthase. Several valencene synthase enzymes are known including *Vitis vinifera* valencene synthase (VvVS) (SEQ ID NO: 1) or *Citrus sinensis* valencene synthase (CsVS) (SEQ ID NO: 12), which may be employed with the present disclosure, or alternatively a derivative of the VvVS or CsVS. Exemplary derivative VvVS enzymes are disclosed herein. In certain embodiments, the sesquiterpene synthase is a valencene synthase selected from Vv1M1 (SEQ ID NO: 3), Vv2M1 (SEQ ID NO: 5), Vv1M5 (SEQ ID NO: 7), Vv2M5 (SEQ ID NO: 9), VS2 (SEQ ID NO: 11), and VS3 (SEQ ID NO: 129), as disclosed herein.

The SrKO or derivative thereof acts on the sesquiterpene (e.g., valencene) to produce the oxygenated terpene product. In some embodiments the SrKO is a fusion protein with a cytochrome P450 reductase partner (e.g., SrCPR), allowing the cofactor to be efficiently regenerated. In other embodiments, a P450 reductase is provided (e.g., to in vitro system) or expressed in the host cell separately, and may be expressed in the same operon as the SrKO in some embodiments. In some embodiments, the CPR enzyme is expressed separately, and the gene may be integrated into the host cell genome in some embodiments. Various exemplary CPR enzymes are disclosed herein, and which may be derivatized to improve oxygenated sesquiterpenoid titer and/or to improve P450 efficiency.

In some embodiments, the host cell expresses one or more enzymes that further direct oxygenated product to nootkatone, such as the expression of one or more alcohol dehydrogenase (ADH) enzymes. Exemplary ADH enzymes are disclosed herein.

In other aspects, the disclosure provides a method for making a product containing an oxygenated sesquiterpene, which comprises incorporating the oxygenated sesquiterpene prepared and recovered according to the methods described herein into a consumer or industrial product. For example, the product may be a flavor product, a fragrance product, a cosmetic, a cleaning product, a detergent or soap, or a pest control product. In some embodiments, the oxygenated product recovered comprises nootkatol (e.g., α and/or β nootkatol) and/or nootkatone, and the product is a flavor product selected from a beverage, a chewing gum, a candy, or a flavor additive.

In other aspects, the disclosure provides engineered SrKO enzymes having enhanced valencene oxidase activity as compared to wild type, as well as host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell, and which may be enhanced through expression of heterologous enzymes or duplication of certain enzymes in the pathway. Host cells include various bacteria and yeast as described herein. The oxygenated sesquiterpene (e.g., nootkatone and/or nootkatol) may be recovered from the culture, and/or optionally may act as the substrate for further chemical transformation in the cell or ex vivo system.

In another aspect, the disclosure provides sesquiterpene-containing oil produced by the methods and host cells described herein. In some embodiments, the oil comprises hydroxygermacra-1(10)5-diene, murolan-3,9(11) diene-10-peroxy, alpha-nootkatol, beta-nootkatol, and nootkatone. In some embodiments, the predominant oxygenated products of valencene is nootkatone and nootkatol, and the oxygenated sesquiterpene product comprises both alpha and beta nootkatol.

In another aspect, there is provided an SrKO crystal model structure (CMS) based on the structural coordinates of P45017A1 (which catalyzes the biosynthesis of androgens). The CMS, including the terpene binding pocket domain (TBD) that comprises a terpene binding pocket (TBP) and a terpene (e.g., valencene) bound to the TBD, is illustrated in FIGS. 8A and 8B. This SrKO crystal model structure (CMS) facilitates in-silico testing of SrKO derivatives. In part aided by this homology model, the present disclosure illustrates the use of several mutational strategies to identify increases or improvements in sesquiterpene oxygenation activity, including back-to-consensus mutagenesis, site-saturation mutagenesis, and recombination library screening.

Additional aspects and embodiments of the invention will be apparent from the following detailed description.

DESCRIPTION OF THE DRAWINGS

FIG. 2 shows the number of VvVS mutants (y-axis) exhibiting certain levels of productivity (x-axis) versus the wild type.

FIG. 3 (A and B) provides the amino acid and nucleotide sequences of valencene synthases. FIG. 3A shows amino acid and nucleotide sequences from *Vitis vinfera* wild-type (WT) (VvVS) (SEQ ID NOS: 1 and 2) and derivatives Vv1M1 (SEQ ID NOS: 3 and 4), Vv2M1 (SEQ ID NOS: 5 and 6), Vv1M5 (SEQ ID NOS: 7 and 8), Vv2M5 (SEQ ID NOS: 9 and 10), and VS2 (SEQ ID NOS: 11 and 120); as well as amino acid sequence for *Citrus sinensis* wild-type (CsVS) (SEQ ID NOS: 12 and 119). FIG. 3B shows an alignment of wild-type VvVS and CsVS sequences, and the engineered Vv2M5 and VS2 sequences.

FIG. 4 (A and B) provides the amino acid and nucleotide sequences of various CYP450 (Cytochrome P450) enzymes having activity on sesquiterpene scaffolds. FIG. 4A shows sequences of wild type amino acid sequences and amino acid and nucleotide sequences engineered for bacterial expression: ZzHO (SEQ ID NO: 13, 14, and 15 respectively), BsGAO (SEQ ID NO: 16, 17, and 18, respectively), HmPO (SEQ ID NO: 19, 20, and 21 respectively), LsGAO (SEQ ID NO: 22, 23, and 24, respectively), NtEAO (SEQ ID NO: 25, 26, and 27, respectively), CpVO (SEQ ID NO: 28, 29, and 30, respectively), AaAO (SEQ ID NO: 31, 32, and 33, respectively), AtKO (SEQ ID NO: 34, 35, and 36 respectively), SrKO (SEQ ID NO: 37, 38, and 39 respectively), PpKO (SEQ ID NO: 40, 41, and 42, respectively), BmVO (SEQ ID NO: 43 and SEQ ID NO: 44, respectively), PsVO (SEQ ID NO: 45 and SEQ ID NO: 46, respectively), PoLO (SEQ ID NO: 47 and SEQ ID NO: 48, respectively), CiVO (SEQ ID NO: 49, 50, and 51 respectively), HaGAO (SEQ ID NO: 52, 53, and 54, respectively). FIG. 4B shows amino acid sequences of engineered Valencene Oxidase enzymes based on the SrKO scaffold (SEQ ID NOS: 55-61).

FIGS. 5A and 5B depict construct designs for expression of MEP, terpene and terpenoid synthases, and P450 enzymes in *E. coli*. FIG. 5A shows strain configuration of upstream MEP pathway genes and the two plasmids harboring downstream pathway genes. FIG. 5B shows construction of P450 fusions, whereby N-terminal regions of both the P450 and CPR (Cytochrome P450 reductase) are truncated and an exemplary leader sequence (MALLLAVF—SEQ ID NO:112) (8RP) is added while the two are fused with a short linker peptide.

FIG. 6 (A-D) provides the amino acid and nucleotide sequences of various CPR (Cytochrome P450 reductase) enzymes with sequence alignments. In FIG. 6A: *Stevia rebaudiana* (Sr)CPR (SEQ ID NOS: 62 and 63, *Stevia rebaudiana* (Sr)CPR1 SEQ ID NOS: 76 and 77), *Arabidopsis thaliana* (At) CPR (SEQ ID NOS: 64 and 65), *Taxus cuspidata* (Tc) CPR (SEQ ID NOS: 66 and 67), *Artemisia annua* (Aa)CPR) SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). FIG. 6B shows an alignment of amino acid sequences for *Arabidopsis thaliana* and *Artemisia annua* CPR sequences (SEQ ID NOS:72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NO: 74, 72, 82, 68, 80, 62, 78, and 76).

FIG. 8B depicts a structural model of SrKO active site with valencene docked in its α-binding mode. Secondary structure motifs (B-C Loop and I-Helix) and amino acids targeted for mutagenesis are shown.

FIG. 22 (A and B) depicts alcohol dehydrogenase enzymes. FIG. 22A shows amino acid and nucleotide sequences including those for *Rhodococcus erythropolis* (Re)CDH (SEQ ID NOS: 84 and 85), *Citrus sinensis* (Cs) DH (SEQ ID NOS: 86 and 87), *Citrus sinensis* (Cs)DH1 (SEQ ID NOS: 88 and 89), *Citrus sinensis* (Cs)DH2 (SEQ ID NOS: 90 and 91), *Citrus sinensis* (Cs)DH3 (SEQ ID NOS: 92 and 93), *Vitis vinifera* (Vv)DH (SEQ ID NOS: 94 and 95), *Vitis vinifera* (Vv)DH1 (SEQ ID NOS: 96 and 97), *Citrus sinensis* (Cs)ABA2 (SEQ ID NOS: 98 and 99), *Brachypodium distachyon* (Bd)DH (SEQ ID NO: 100 and 101), *Zingiber zerumbet* (Zz)SDR (SEQ ID NOS: 102 and 103). FIG. 22B shows an alignment of the amino acid sequences.

FIG. 23 (A and B) shows alignments of several engineered valencene oxidase (VO) variants. In FIG. 23A: 8rp-t20SrKO (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO: 104) has a 30-amino acid truncation of the SrKO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30VO2 (SEQ ID NO: 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 23B, point mutations in VO0 (SEQ ID NO: 109), VO1 (SEQ ID NO: 110), and VO2 (SEQ ID NO: 111) are shown against wild-type SrKO (SEQ ID NO: 108) (all shown with the wild-type SrKO N-terminus for convenience).

DETAILED DESCRIPTION OF THE INVENTION

Figure 1:
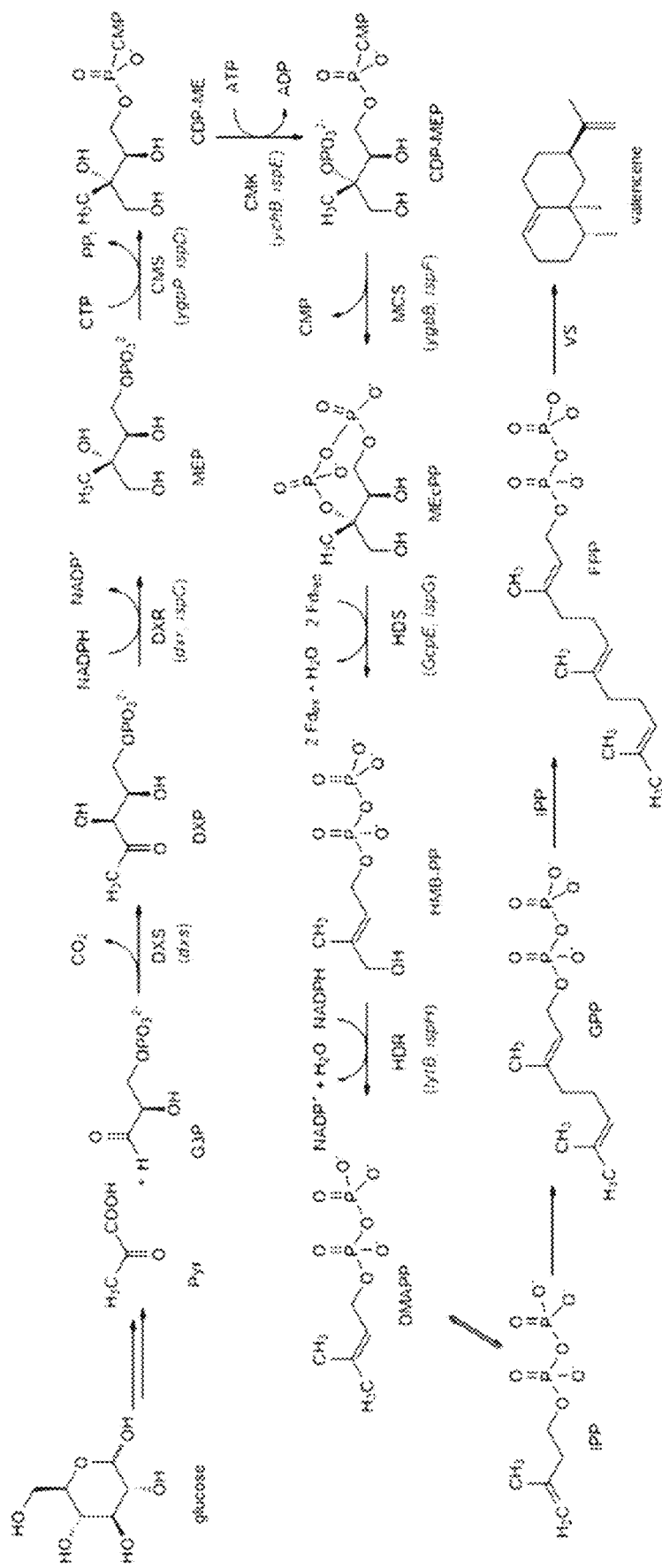
FIG. 1 shows a scheme for biosynthesis of valencene, which is a substrate for SrKO in accordance with the present disclosure.

The present disclosure in various aspects provides methods for making oxygenated terpenes or terpenoids in ex vivo or in cell systems. The disclosure further provides engineered or modified enzymes, polynucleotides, and host cells for use in such methods. The disclosure in various embodiments is directed to a method to produce nootkatone and/or nootkatol using an SrKO enzyme. Surprisingly, it was found that the SrKO enzyme can be used to catalyze sesquiterpene oxidation (e.g., valencene oxidation to nootkatol and nootkatone).

As used herein, SrKO refers to ent-kaurene oxidase CYP701A5 [*Stevia rebaudiana*] with Accession No AAQ63464.1 (SEQ ID NO: 37). SrKO and its activity on diterpenes (and kaurene in particular) are known and are described in, for example, US 2012/0164678, which is hereby incorporated by reference in its entirety. It is a member of the CYP70 family of cytochrome p450 enzymes (CYP450). An exemplary SrKO sequence modified for expression in *E. coli* is shown as SEQ ID NO: 38. As shown herein, SrKO is active on sesquiterpene substrates (e.g., valencene), producing nootkatol (both α and β) and nootkatone, which are valuable terpenoid compounds. Further, SrKO provides a unique product profile with unique sensory characteristics that is based on the oxygenation of valencene. These activities and product profiles can be further refined by mutagenesis of the SrKO using processes (and aided by in silico models) described in detail herein.

As used herein, the term "SrKO derivative," "modified SrKO polypeptide," "engineered SrKO," "SrKO variant," "engineered valencene oxidase," or "valencene oxidase variant" refers to an amino acid sequence that has substantial structural and/or sequence identity with SrKO, and catalyzes oxygenation of a sesquiterpene scaffold, such as valencene. SrKO enzymes engineered for the oxygenation of valencene are also referred to herein as "valencene oxidase" or "VO" enzymes. Generally, derivatives comprise mutated forms of SrKO having at least one mutation that increases the activity of the enzyme for the valencene substrate or for the production of nootkatone, nootkatol, and/or other products. Some SrKO mutations are provided in Tables 2.1, 2.2, and 2.3. Some such additional SrKO mutations are provided in Table 6.

The term "contacting" means that the components are physically brought together, whether in vivo through co-expression of relevant protein products (e.g., sesquiterpene synthase and CYP450) in a host cell, or by adding or feeding a substrate of interest to a host cell expressing an SrKO or derivative thereof, or in vitro (or "ex vivo") by adding sesquiterpene substrate to purified P450 enzyme or cellular extract or partially purified extract containing the same. The terms in vitro and ex vivo refer to a cell free system, and may be performed in a reaction tube or well.

As used herein, "terpenes" are a large and varied class of hydrocarbons that have a simple unifying feature, despite their structural diversity. According to the "isoprene rule", all terpenes consist of isoprene (C5) units. This fact is used for a rational classification depending on the number of such units. Monoterpenes comprise 2 isoprene units and are classified as (C10) terpenes, sesquiterpenes comprise 3 isoprene units and are classified as (C15) terpenes, diterpenes comprise 4 isoprene units and are classified as (C20) terpenes, sesterterpenes (C25), triterpenes (C30) and rubber (C5)n. They occur as acyclic or mono- to pentacyclic derivatives with alcohol, ether, ester, aldehyde, or ketone groups (the so called "terpenoids"), everywhere in organisms, particularly in higher plants, and are characteristic of the individual type of plants. Terpenes such as Monoterpenes (C10), Sesquiterpenes (C15) and Diterpenes (C20) are derived from the prenyl diphosphate substrates, geranyl diphosphate (GPP), farnesyl diphosphate (FPP) and geranylgeranyl diphosphate (GGPP) respectively through the action of a very large group of enzymes called the terpene (terpenoid) synthases. These enzymes are often referred to as terpene cyclases since the product of the reactions are cyclised to various monoterpene, sesquiterpene and diterpene carbon skeleton products. Many of the resulting carbon skeletons undergo subsequence oxygenation by cytochrome p450 hydrolysase enzymes to give rise to large families of derivatives. The technical syntheses of top-selling flavours and fragrances can start from terpenes which can also serve as excellent solvents or diluting agents for dyes and varnishes. Natural or synthetic resins of terpenes are used and also many pharmaceutical syntheses of vitamins and insecticides start from terpenes. As used herein, the term "terpene" or "sesquiterpene" (for example) includes corresponding terpenoid or sesquiterpenoid compounds.

As used herein, the term "oxygenated sesquiterpene" refers to a sesquiterpene scaffold having one or more oxygenation events, producing a corresponding alcohol, aldehyde, carboxylic acid and/or ketone. One or more oxygenated sesquiterpenes may be referred to herein as an "oxygenated product."

As used herein, the term "unoxygenated sesquiterpene" refers to a sesquiterpene scaffold that has not undergone any oxygenation events. An unoxygenated sesquiterpene may also be referred to herein as an "unoxygenated product."

As used herein, the term "oxygenated product titer" or "oxygenated titer" refers to the sum of titers of α-nootkatol, β-nootkatol, and (+)-nootkatone.

As used herein, the term "MEP pathway" refers to the (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway. In the MEP pathway, pyruvate and D-glyceraldehyde-3-phosphate are converted via a series of reactions to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA.

As used herein, the "MVA pathway" refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

As used herein, the term "cytochrome P450 reductase partner" or "CPR partner" refers to a cytochrome P450 reductase capable of regenerating the cofactor component of the cytochrome P450 oxidase of interest (e.g., SrKO) for oxidative chemistry. For example, SrCPR is a natural CPR partner for SrKO. In some embodiments, the CPR partner is not the natural CPR partner for SrKO. In some embodiments employing in vivo production of oxygenated sesquiterpene, the SrKO and SrCPR are co-expressed as separate proteins, or in some embodiments are expressed as a fusion protein.

As used herein, the term "natural product" refers to a product obtained, at least in part, from plant and/or animal material or obtained from microbial enzymatic biotransformations/bioconversions/biocatalysis and/or biosynthesis.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The similarity of nucleotide and amino acid sequences, i.e., the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package, hmmer.wustl.edu/) or with the CLUSTAL algorithm (Thompson, J. D., Higgins, D. G. & Gibson, T. J. (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:
(1) hydrophobic: Met, Ala, Val, Leu, He;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and He; (ii) Ser and Thr; (ii) Asn and Gin; (iv) Lys and Arg; and (v) Tyr and Phe.

As used herein, "non-conservative substitutions" or "non-conservative amino acid exchanges" are defined as exchanges of an amino acid by another amino acid listed in a different group of the six standard amino acid groups (1) to (6) shown above.

In one aspect, the disclosure provides a method for making an oxygenated product of a sesquiterpene. In various embodiments, the sesquiterpene substrate is (or the predominant sesquiterpene substrate is) valencene, germacrene (A, B, C, D, or E), farnesene, farnesol, nootkatol, patchoulol, cadinene, cedrol, humulene, longifolene, and/or bergamotene, β-ylangene, β-santalol, β-santalene, α-santalene, α-santalol, β-vetivone, α-vetivone, khusimol, bisabolene, β-aryophyllene, Longifolene; α-sinensal; α-bisabolol, (-)-β-copaene, (-)-α-copaene, 4(Z),7(Z)-ecadienal, cedrol, cedrene, cedrol, guaiol, (-)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol, which in some embodiments comprises both α and β nootkatol. In this context, the term "predominant" means that the particular sesquiterpene is present at a level higher than all other terpene or terpenoid species individually. In some embodiments, the predominant sesquiterpene (either the substrate or the oxygenated product after the reaction) makes up at least 25%, at least 40%, at least 50%, or at least 75% of the terpene or terpenoid component of the composition. In various embodiments involving in vivo production of oxygenated sesquiterpenes, the oxygenated product is recovered from the culture media, and can be fractionated to isolate or enrich for various components of the product, such as nootkatone, nootkatol, and/or other components.

In various embodiments, the disclosure comprises contacting a sesquiterpene with a terpene oxidizing P450 enzyme, or a derivative thereof. The contacting may take place in a host cell or in a cell free system. The substrate for oxidation (e.g., the sesquiterpene), may be produced by the cells (e.g., through metabolic flux through the MEP or MVA pathways), or alternatively fed to the host cells expressing the P450 enzyme. The oxygenated product may be recovered, or be the substrate for further chemical transformation either in the cellular system or cell free system. Table 1 below provides a list of exemplary P450 enzymes. While in certain embodiments the disclosure involves the use of the following P450 enzymes (optionally engineered to increase the oxygenation of valencene to nootkatone and/or nootkatol), a preferred enzyme in accordance with this disclosure is SrKO. Exemplary oxygenated sesquiterpene products obtained by these reactions in accordance with the disclosure are shown in Table 4.

TABLE 1

| # | Species | Name | Native Substrate | Native Reaction Product |
|---|---|---|---|---|
| 1 | Zingiber zerumbet | zzHO | α-humulene | 8-hydroxy-α-humulene |
| 2 | Barnadesia spinosa | BsGAO | germacrene A | germacra-1(10), 4,11(13)-trien-12-ol |
| 3 | Hyoscyamus muticus | HmPO | premnaspirodiene | solavetivol |
| 4 | Latuca spicata | LsGAO | germacrene A | germacra-1(10), 4,11(13)-trien-12-ol |
| 5 | Nicotiana tabacum | NtEAO | 5-epi-aristolochene | capsidiol |
| 6 | Citrus x paradisi | CpVO | valencene | nootkatol |
| 7 | Artemesia annua | AaAO | amorphadiene | artemisinic acid |
| 8 | Arabidopsis thaliana | AtKO | kaurene | kaurenoic acid |
| 9 | Stevia rebaudiana | SrKO | kaurene | kaurenoic acid |
| 10 | Pseudomonas putida | PpKO | kaurene | kaurenoic acid |
| 11 | Bacillus megaterium | BmVO | fatty acids | hydroxylated FAs |
| 12 | Pleurotus sapidus | PsVO | valencene | nootkatone |

TABLE 1-continued

| # | Species | Name | Native Substrate | Native Reaction Product |
|---|---|---|---|---|
| 13 | *Pleurotus ostreatus* | PoLO | unknown | unknown |
| 14 | *Cichorium intybus* | CiVO | valencene | nootkatone |
| 15 | *Helianthus annuus* | HaGAO | germacrene A | germacrene A acid |

In various embodiments, the method comprises contacting the sesquiterpene with a protein comprising *Stevia rebaudiana* Kaurene Oxidase (SrKO) or derivative thereof. In some embodiments the SrKO is expressed in a host cell as described below, or is provided in a cell free system. For example, certain in vitro and in vivo systems for oxidizing terpenes with P450 enzymes are disclosed in U.S. Pat. No. 7,211,420, which are hereby incorporated by reference. McDougle D R, Palaria A, Magnetta E, Meling D D, Das A. *Functional Studies of N-terminally modified CYP2J2 epoxygenase in Model Lipid Bilayers*, Protein Sci. 2013 22:964-79; Luthra, A., Gregory, M., Grinkova, Y. V., Denisov, I. G., Sligar, S. G. (2013) "Nanodiscs in the studies of membrane-bound cytochrome P450 enzymes." Methods Mol. Biol., 987, 115-127).

In some embodiments, the SrKO derivative comprises an amino acid sequence that has from about 1 to about 50 mutations independently selected from substitutions, deletions, or insertions relative to SrKO (SEQ ID NO: 37 or 38), or relative to an SrKO enzyme modified at its N-terminus for functional expression in *E. coli* (SEQ ID NO: 38 or 55). In various embodiments, the mutation or combination of mutations enhances the activity of the enzyme for oxygenation of valencene, such as the production of nootkatone and/or nootkatol. Protein modeling as described herein may be used to guide such substitutions, deletions, or insertions in the SrKO sequence. For example, a structural model of the SrKO amino acid sequence may be created using the coordinates for P45017A1. As demonstrated herein, such a homology model is useful for directing improvement of SrKO for valencene oxygenation. Thus, in various embodiments, the SrKO derivative may have from about 1 to about 45 mutations, about 1 to about 40 mutations, about 1 to about 35 mutations, from about 1 to about 30 mutations, about 1 to about 25 mutations, from about 1 to about 20 mutations, about 1 to about 15 mutations, about 1 to about 10 mutations, or from about 1 to about 5 mutations relative to SrKO (SEQ ID NO: 37, 38, or 55). In various embodiments, the SrKO comprises a sequence having at least 5 or at least 10 mutations with respect to SEQ ID NO: 37, 38, or 55, but not more than about 20 or 30 mutations. In various embodiments, the SrKO derivative may have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, or about 50 mutations relative to SrKO (SEQ ID NO: 37, 38, or 55). SEQ ID NO: 37, and other WT enzymes disclosed herein, can optionally contain an Ala inserted at position 2 where not present in the wild-type.

In these or other embodiments, the SrKO derivative may comprise an amino acid sequence having at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, to SrKO (SEQ ID NO: 37, 38, or 55). In various embodiments, the SrKO derivative has higher activity for the oxygenation of valencene than the wild type enzyme, such as a higher production of oxygenated oil upon contact with valencene substrate than the wild type enzyme (SEQ ID NO: 37) or the wild type enzyme as modified for functional expression in *E. coli* (e.g., SEQ ID NO: 38). For example, the SrKO derivative may comprise an amino acid sequence having at least: about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, about 90% identity, about 91% sequence identity, about 92% sequence identity, about 93% sequence identity, about 94% sequence identity, about 95% sequence identity, about 96% sequence identity, about 97% sequence identity, about 98% sequence identity, or about 99% sequence identity to SrKO (SEQ ID NO: 37, 38, or 55).

In some embodiments, mutants are selected for an increase in production of oxygenated valencene, such as nootkatone, α-nootkatol, and/or β-nootkatol. For example, the SrKO derivative may have one or more mutations at positions selected from 46, 76, 94, 131, 231, 284, 383, 390, 400, 444, 468, 488 and 499, numbered according to SEQ ID NO: 37. For example, in some embodiments, the SrKO is a derivative comprising an amino acid sequence having one or more (or all) of the mutations selected from H46R, R76K, M94V, T131Q, F231L, H284Q, R383K, I390L, V400Q, I444A, T468I, T488D, and T499N, numbered according to SEQ ID NO: 37. In certain embodiments, the SrKO is a derivative comprising an amino acid sequence having one or more (or all) of the mutations selected from R76K, M94V, T131Q, F231L, H284Q, R383K, I390L, T468I, and T499N, numbered according to SEQ ID NO: 37. In some embodiments, the SrKO derivative comprises an amino acid sequence selected from SEQ ID NOS: 55-61, which were engineered according to this disclosure to improve activity for oxygenation of valencene (e.g., production of nootkatone). In some embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488, and 499 (numbered according to SEQ ID NO: 37), or the proviso that the SrKO derivative comprises an amino acid sequence having one or more (or all) of the mutations selected from H46R, R76K, M94V, T131Q, F231L, H284Q, R383K, I390L, V400Q, I444A, T468I, T488D, and T499N (numbered according to SEQ ID NO: 37). In certain embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488, and 499 (numbered according to SEQ ID NO: 37), or the proviso that the SrKO derivative comprises an amino acid sequence having one or more (or all) of the mutations selected from R76K, M94V, T131Q, F231L, H284Q, R383K, I390L, T468I, and T499N (numbered according to SEQ ID NO: 37).

In some embodiments, the disclosure provides a recombinant polynucleotide encoding the SrKO derivative described above, which may be inserted into expression vectors for expression and optional purification. In some embodiments, the polynucleotide is incorporated into the genome of valencene-producing cells, such as valencene-producing E. coli cells.

The SrKO or derivative in various embodiments has valencene oxidase activity. Assays for determining and quantifying valencene oxidase activity are described herein and are known in the art. Assays include expressing the SrKO (or derivative) in valencene-producing cells (e.g., E. coli expressing FPPS and valencene synthase), and extracting the oxygenated oil from the aqueous reaction media. The profile of terpenoid product can be determined quantitatively by GC/MS. Various mutations of SrKO tested for effect on valencene oxidase activity are listed in Tables 2.1, 2.2, 2.3 and/or 6. Thus, in various embodiments, the SrKO may have at least about 1, at least about 2, at least about 3, at least about 4, at least about 5, at least about 6, at least about 7, at least about 8, at least about 9, or at least about 10 mutations selected from Tables 2.1, 2.2, 2.3 and/or 6. In some embodiments, the SrKO derivative is a modified SrKO polypeptide comprising an amino acid sequence which has up to 25 mutations compared to the wild type protein according to SEQ ID NO: 37 (or its counterpart that is modified for expression in E. coli), and comprises at least the substitutions I310V, V375I or T487N in combination with at least any one or more of V375F, V375A, V375M, M120L, M120I, M120V, F129L, F129I, L114V, L114F and V121A (numbered according to SEQ ID NO: 38) (see Table 6), and optionally comprises a leader sequence (as shown in SEQ ID NO: 38) supporting functional expression in E. coli.

TABLE 2.1

Summary of some Stevia rebaudiana kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 1 | L | 59/47 | 51 | I |
| 2 | Y | 71/59 | 63 | H |

TABLE 2.1-continued

Summary of some Stevia rebaudiana kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 3 | M | 72/60 | 64 | K |
| 4 | T | 75/63 | 67 | A |
| 5 | A | 79/67 | 71 | E |
| 6 | K | 88/76 | 80 | R |
| 7 | T | 92/80 | 84 | C |
| 8 | M | 94/82 | 86 | V |
| 9 | V | 97/85 | 89 | L |
| 10 | V | 97/85 | 89 | I |
| 11 | S | 98/86 | 90 | N |
| 12 | Q | 112/100 | 104 | S |
| 13 | N | 118/106 | 110 | K |
| 14 | K | 124/112 | 116 | T |
| 15 | A | 128/116 | 120 | R |
| 16 | T | 131/119 | 123 | S |
| 17 | M | 135/123 | 127 | T |
| 18 | M | 135/123 | 127 | Q |
| 19 | M | 135/123 | 127 | F |
| 20 | M | 135/123 | 127 | T |
| 21 | D | 139/127 | 131 | G |
| 22 | Y | 141/129 | 133 | F |
| 23 | A | 152/140 | 144 | R |
| 24 | K | 161/149 | 153 | R |
| 25 | H | 162/150 | 154 | F |
| 26 | N | 183/171 | 175 | D |
| 27 | L | 192/180 | 184 | F |
| 28 | I | 195/183 | 187 | V |
| 29 | D | 220/208 | 212 | E |
| 30 | D | 244/232 | 236 | E |
| 31 | S | 279/267 | 271 | A |
| 32 | H | 284/272 | 276 | Q |
| 33 | S | 296/284 | 288 | C |
| 34 | I | 298/286 | 290 | L |
| 35 | Q | 306/294 | 298 | K |
| 36 | Q | 311/299 | 303 | E |
| 37 | I | 322/310 | 314 | T |
| 38 | I | 322/310 | 314 | V |
| 39 | R | 383/371 | 375 | K |
| 40 | R | 383/371 | 375 | I |
| 41 | V | 387/375 | 379 | T |
| 42 | V | 387/375 | 379 | I |
| 43 | V | 387/375 | 379 | L |
| 44 | I | 390/378 | 382 | V |
| 45 | H | 394/382 | 386 | Y |
| 46 | V | 400/388 | 392 | Q |
| 47 | V | 400/388 | 392 | M |
| 48 | H | 405/393 | 397 | D |
| 49 | L | 412/400 | 404 | I |
| 50 | V | 425/413 | 417 | D |
| 51 | V | 425/413 | 417 | K |
| 52 | F | 446/434 | 438 | L |
| 53 | G | 454/442 | 446 | A |
| 54 | S | 462/450 | 454 | A |
| 55 | L | 466/454 | 458 | M |
| 56 | G | 472/460 | 464 | A |
| 57 | M | 476/464 | 468 | L |
| 58 | M | 487/475 | 479 | G |
| 59 | T | 499/487 | 491 | N |
| 60 | P | 504/492 | 496 | K |
| 61 | I | 509/497 | 501 | L |
|  | T | 499/487 | 491 | S |
| 62 | M | 135/123 | 127 | Q |
|  | T | 499/487 | 491 | V |
| 63 | M | 135/123 | 127 | F |
|  | T | 499/487 | 491 | V |
| 64 | M | 135/123 | 127 | F |
|  | T | 499/487 | 491 | F |

TABLE 2.1-continued

Summary of some *Stevia rebaudiana* kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 65 | M | 135/123 | 127 | F |
|  | T | 499/487 | 491 | M |
| 66 | M | 135/123 | 127 | F |
|  | T | 499/487 | 491 | G |

TABLE 2.2

The following mutants were evaluated in the VO1 background (n22-yhcB-t30-VO1, SEQ ID NO: 110) according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| No. | WT | Position SEQ ID NO: 37 (SEQ ID NO: 108)/SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 1 | A | 2 |  | T |
| 2 | H | 46/34 | 38 | R |
| 3 | E | 52/40 | 44 | A |
| 4 | R | 76/64 | 68 | K |
| 5 | M | 94/82 | 86 | V |
| 6 | T | 131/119 | 123 | K |
| 7 | T | 131/119 | 123 | Q |
| 8 | L | 150/138 | 142 | M |
| 9 | D | 191/179 | 183 | N |
| 10 | L | 231/219 | 223 | M |
| 11 | Q | 268/256 | 260 | T |
| 12 | E | 323/311 | 315 | L |
| 13 | K | 344/332 | 336 | D |
| 14 | R | 351/339 | 343 | Q |
| 15 | I | 389/377 | 381 | L |
| 16 | I | 389/377 | 381 | V |
| 17 | I | 389/377 | 381 | A |
| 18 | I | 390/378 | 382 | L |
| 19 | I | 390/378 | 382 | M |
| 20 | V | 400/388 | 392 | Q |
| 21 | I | 444/432 | 436 | A |
| 22 | T | 468/456 | 460 | I |
| 23 | T | 488/476 | 480 | D |
| 24 | E | 491/479 | 483 | K |
| 25 | I | 495/483 | 487 | V |

TABLE 2.3

Summary of mutations of several engineered SrKO derivatives based on alignments relative to wild type SrKO (SEQ ID NOS: 37 and 108). The point mutations for each of the SrKO derivatives (SEQ ID NOS: 38, 61, 104, 105, 106, and 107) are identified based on the shift value for each sequence relative to wild type SrKO. 8rp-t20SrKO (SEQ ID NOS: 38 and 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 487. n22yhcB-t30VO1 (SEQ ID NO: 104) has a 30-amino acid truncation of the SrKO N-terminus, a membrane anchor based on 22 amino acids from *E. coli* yhcB, and eight point mutations at positions 38, 223, 276, 375, 392, 436, 480, and 491, and a n22t30-yhcB mutation. n22yhcB-t30VO2 (SEQ ID NOS: 61 and 105) has a 30-amino acid truncation of the SrKO N-terminus, a membrane anchor based on 22 amino acids from *E. coli* yhcB, and nine point mutations at positions 68, 86, 123, 223, 276, 375, 382, 460, and 491, and a n22t30-yhcB mutation.

| Wild Type SrKO (SEQ ID NOS: 37 and 108) (Shift Value: 0) | 8rp-t20SrKO (SEQ ID NOS: 38 and 106) (Shift Value: −12) | 8rp-t20VO0 (SEQ ID NO: 107) (Shift Value: −12) | n22yhcB-t30VO1 (SEQ ID NO: 104) (Shift Value: −8) | n22yhcB-t30VO2 (SEQ ID NOS: 61 and 105) (Shift Value: −8) |
|---|---|---|---|---|
| H46 | H34 |  | H38R |  |
| R76 | R64 |  |  | R68K |
| M94 | M82 |  |  | M86V |
| T131 | T119 |  |  | T123Q |
| F231 | F219 |  | F223L | F223L |
| H284 | H272 |  | H276Q | H276Q |
| R383 | R371 |  | R375K | R375K |
| I390 | I378 |  |  | I382L |
| V400 | V388 |  | V392Q |  |
| I444 | I432 |  | I436A |  |
| T468 | T456 |  |  | T460I |
| T488 | T476 |  | T480D |  |
| T499 | T487 | T487N | T491N | T491N |

The SrKO may be expressed in a variety of host cells, either for recombinant protein production, or for sesquiterpene (e.g., valencene) oxidation. For example, the host cells include those described in U.S. Pat. No. 8,512,988, which is hereby incorporated by reference in its entirety. The host cell may be a prokaryotic or eukaryotic cell. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., Comamonas spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, such as, for example, *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. In an embodiment, the host cell is a bacterium selected from *E. coli*, *Bacillus subtillus*, or *Pseudomonas putida*. In an embodiment, the host cell is a yeast, and may be a species of *Saccharomyces*, *Pichia*, or *Yarrowia*, including *Saccharomyces cerevisiae*, *Pichia pastoris*, and *Yarrowia lipolytica*.

In some embodiments, the host cell produces isopentyl pyrophosphate (IPP), which acts as a substrate for the synthesis of the sesquiterpene. In some embodiments, the IPP is produced by metabolic flux (e.g., starting with a carbon source supplied to the cell) through an endogenous or heterologous methylerythritol phosphate (MEP) or mevalonic acid (MVA) pathway. In certain embodiments, the MEP or MVA pathway may be enhanced through expression of heterologous enzymes or duplication of certain enzymes in the pathway.

The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA. In some embodiments, the sesquiterpene is produced at least in part by metabolic flux through an MEP pathway, and wherein the host cell has at least one additional copy of a dxs, ispD, ispF, and/or idi gene (e.g., dxs and idi; or dxs, ispD, ispF, and/or idi).

The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

In some embodiments, the host cell expresses a farnesyl pyrophosphate synthase (FPPS), which produces farnesyl pyrophosphate from IPP or DMAPP. As shown in FIG. 1, farnesyl pyrophosphate is an intermediate for production of valencene. An exemplary farnesyl pyrophosphate synthase is ERG20 of *Saccharomyces cerevisiae* (NCBI accession P08524) and *E. coli* ispA. Various other prokaryotic, yeast, plant, and mammalian FPPS enzymes are known, and may be used in accordance with this aspect.

The host cell may further express a heterologous sesquiterpene synthase to produce the desired sesquiterpene, such as a valencene synthase. Several valencene synthase enzymes are known including valencene synthase from *Citrusxparadisi* or from *Citrus sinensis*. *Citrus sinensis* VS (e.g., AAQ04608.1) as well as various derivatives thereof are described in US 2012/0246767, which is hereby incorporated by reference. For example, the disclosure may employ an amino acid sequence of *Citrus sinensis* valencene synthase (CsVS) (SEQ ID NO: 12), or a derivative, having from 1 to 30 mutations or from 1 to 20 or from 1 to 10 mutations with respect to the wild type amino acid sequence (SEQ ID NO: 12). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with the wild type sequence (SEQ ID NO: 12). Further, valencene synthase from *Vitis vinifera* (VvVS) (SEQ ID NO: 1) has been described by Licker et al. (*Phytochemistry* (2004) 65: 2649-2659). In an embodiment, a valencene synthase comprising the amino acid sequence of VvVS (SEQ ID NO: 1) or an engineered derivative thereof may be employed with the present disclosure. Various sesquiterpene synthase enzymes such as valencene synthase are known and are described in, for example, US 2012/0107893, US 2012/0246767, and U.S. Pat. No. 7,273,735, which are hereby incorporated by reference in their entireties.

For example, in some embodiments, the valencene synthase is a VvVS derivative that comprises an amino acid sequence having from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to VvVS (SEQ ID NO: 1). For example, the VvVS derivative may comprise an amino acid sequence having at least about 5 or at least about 10, but less than about 30 or about 20 mutations with respect to SEQ ID NO: 1. In various embodiments, the VvVS derivative comprises an amino acid sequence that has about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations relative to VvVS (SEQ ID NO: 1). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with SEQ ID NO:1. Exemplary mutations of VvVS are shown in Table 3. Mutations can be guided by a homology model of *Vitis vinifera* valencene synthase (VvVS) based on the 5-epi-aristolochene synthase crystal structure as a template (PDB: 5EAT).

TABLE 3.1

Summary of *Vitis vinifera* valencene synthase mutations with respect to wild type (SEQ ID NO: 1)

| No. | WT | Position | Mutation |
|---|---|---|---|
| 1 | N | 23 | D |
| 2 | T | 37 | R |
| 3 | P | 38 | S |
| 4 | V | 42 | R |
| 5 | A | 45 | E |
| 6 | C | 46 | K |
| 7 | Q | 50 | R |
| 8 | K | 56 | E |
| 9 | K | 59 | R |
| 10 | R | 60 | K |
| 11 | K | 61 | M |
| 12 | T | 63 | R |
| 13 | T | 63 | K |
| 14 | N | 69 | Q |
| 15 | N | 69 | K |
| 16 | S | 71 | I |
| 17 | Q | 72 | R |
| 18 | L | 73 | K |
| 19 | N | 75 | E |
| 20 | F | 76 | M |
| 21 | F | 76 | L |
| 22 | V | 80 | M |
| 23 | V | 80 | L |
| 24 | V | 85 | I |
| 25 | A | 86 | S |
| 26 | Q | 91 | D |
| 27 | A | 96 | I |
| 28 | Q | 98 | E |
| 29 | Q | 98 | D |
| 30 | C | 101 | Y |
| 31 | N | 102 | H |
| 32 | S | 103 | D |
| 33 | F | 104 | D |
| 34 | F | 104 | N |
| 35 | D | 111 | E |
| 36 | N | 116 | T |
| 37 | I | 117 | S |
| 38 | I | 117 | V |
| 39 | I | 117 | T |
| 40 | G | 120 | R |
| 41 | Q | 127 | H |

TABLE 3.1-continued

Summary of *Vitis vinifera* valencene synthase mutations with respect to wild type (SEQ ID NO: 1)

| No. | WT | Position | Mutation |
|---|---|---|---|
| 42 | T | 130 | N |
| 43 | I | 131 | V |
| 44 | I | 135 | V |
| 45 | T | 140 | K |
| 46 | E | 142 | K |
| 47 | E | 148 | D |
| 48 | A | 149 | S |
| 49 | A | 149 | D |
| 50 | I | 151 | S |
| 51 | R | 155 | K |
| 52 | M | 157 | L |
| 53 | G | 159 | S |
| 54 | G | 159 | N |
| 55 | E | 162 | Q |
| 56 | E | 162 | K |
| 57 | A | 164 | S |
| 58 | V | 168 | T |
| 59 | G | 170 | D |
| 60 | L | 174 | M |
| 61 | A | 175 | E |
| 62 | A | 175 | D |
| 63 | K | 176 | E |
| 64 | T | 183 | K |
| 65 | A | 187 | S |
| 66 | M | 188 | L |
| 67 | E | 190 | N |
| 68 | G | 193 | K |
| 69 | A | 201 | S |
| 70 | N | 205 | E |
| 71 | R | 206 | Q |
| 72 | I | 208 | L |
| 73 | R | 209 | H |
| 74 | G | 211 | R |
| 75 | L | 212 | M |
| 76 | E | 213 | P |
| 77 | I | 221 | L |
| 78 | V | 223 | R |
| 79 | Q | 225 | D |
| 80 | Q | 225 | E |
| 81 | D | 226 | K |
| 82 | D | 226 | E |
| 83 | A | 228 | E |
| 84 | F | 229 | I |
| 85 | H | 230 | V |
| 86 | D | 231 | N |
| 87 | K | 232 | E |
| 88 | T | 233 | A |
| 89 | T | 233 | V |
| 90 | S | 247 | D |
| 91 | L | 248 | M |
| 92 | L | 248 | K |
| 93 | K | 250 | Q |
| 94 | E | 251 | K |
| 95 | S | 254 | K |
| 96 | N | 255 | E |
| 97 | A | 257 | S |
| 98 | K | 261 | A |
| 99 | E | 262 | D |
| 100 | D | 264 | G |
| 101 | Y | 280 | F |
| 102 | M | 283 | I |
| 103 | H | 284 | M |
| 104 | H | 284 | A |
| 105 | G | 285 | A |
| 106 | Y | 287 | F |
| 107 | Q | 291 | N |
| 108 | R | 294 | L |
| 109 | R | 297 | I |
| 110 | L | 299 | M |
| 111 | M | 305 | A |
| 112 | M | 305 | L |
| 113 | I | 308 | M |
| 114 | T | 318 | S |
| 115 | P | 319 | L |
| 116 | P | 319 | I |

TABLE 3.1-continued

Summary of *Vitis vinifera* valencene synthase mutations with respect to wild type (SEQ ID NO: 1)

| No. | WT | Position | Mutation |
|---|---|---|---|
| 117 | K | 323 | Q |
| 118 | R | 331 | K |
| 119 | D | 333 | E |
| 120 | I | 334 | E |
| 121 | I | 334 | V |
| 122 | N | 335 | K |
| 123 | N | 335 | Q |
| 124 | N | 335 | S |
| 125 | S | 336 | A |
| 126 | Y | 343 | W |
| 127 | Y | 348 | F |
| 128 | V | 349 | L |
| 129 | L | 352 | I |
| 130 | D | 353 | E |
| 131 | D | 353 | N |
| 132 | V | 354 | T |
| 133 | Y | 355 | F |
| 134 | K | 356 | E |
| 135 | K | 356 | N |
| 136 | I | 358 | V |
| 137 | E | 359 | D |
| 138 | E | 360 | Y |
| 139 | E | 363 | K |
| 140 | E | 363 | L |
| 141 | G | 366 | A |
| 142 | Y | 369 | N |
| 143 | R | 370 | V |
| 144 | V | 371 | I |
| 145 | H | 372 | E |
| 146 | H | 372 | P |
| 147 | A | 374 | G |
| 148 | A | 374 | L |
| 149 | E | 376 | D |
| 150 | M | 378 | I |
| 151 | N | 380 | I |
| 152 | N | 380 | K |
| 153 | R | 383 | Q |
| 154 | E | 394 | Q |
| 155 | E | 394 | D |
| 156 | E | 395 | N |
| 157 | E | 395 | G |
| 158 | H | 396 | Y |
| 159 | H | 396 | Q |
| 160 | E | 402 | D |
| 161 | R | 405 | E |
| 162 | C | 414 | R |
| 163 | L | 415 | M |
| 164 | A | 417 | L |
| 165 | T | 418 | V |
| 166 | T | 419 | H |
| 167 | V | 422 | L |
| 168 | M | 424 | V |
| 169 | A | 428 | V |
| 170 | T | 429 | S |
| 171 | T | 437 | F |
| 172 | S | 438 | G |
| 173 | D | 439 | Y |
| 174 | K | 441 | R |
| 175 | I | 442 | M |
| 176 | I | 442 | L |
| 177 | M | 443 | V |
| 178 | S | 444 | R |
| 179 | N | 447 | S |
| 180 | F | 448 | T |
| 181 | M | 453 | A |
| 182 | G | 466 | E |
| 183 | T | 469 | A |
| 184 | Q | 478 | E |
| 185 | Y | 479 | F |
| 186 | G | 480 | A |
| 187 | V | 481 | A |
| 188 | S | 482 | T |
| 189 | Y | 487 | C |
| 190 | S | 488 | E |
| 191 | E | 489 | H |
| 192 | F | 490 | I |
| 193 | F | 490 | L |
| 194 | Q | 491 | K |
| 195 | Q | 491 | N |
| 196 | Q | 493 | L |
| 197 | I | 494 | M |
| 198 | N | 496 | D |
| 199 | D | 500 | E |
| 200 | L | 506 | M |
| 201 | T | 509 | S |
| 202 | V | 511 | M |
| 203 | S | 512 | P |
| 204 | S | 512 | T |
| 205 | M | 513 | K |
| 206 | P | 514 | D |
| 207 | L | 519 | A |
| 208 | D | 527 | E |
| 209 | V | 528 | F |
| 210 | E | 532 | D |
| 211 | Q | 533 | E |
| 212 | Q | 533 | G |
| 213 | S | 535 | G |
| 214 | V | 539 | S |
| 215 | V | 542 | L |
| 216 | V | 542 | T |
| 217 | M | 543 | I |
| 218 | N | 546 | H |
| 219 | V | 550 | L |
| 220 | F | 551 | L |
| 221 | I | 552 | V |
| 222 | N | 553 | D |
| 223 | N | 553 | E |
| 224 | A | 554 | P |
| 225 | V | 555 | I |

TABLE 3.2

Summary of mutations evaluated in the Vv2M5 background (SEQ ID NO: 9).

| No. | WT | Position | Mutation |
|---|---|---|---|
| 226 | N | 18 | V |
| 227 | V | 21 | S |
| 228 | N | 23 | D |
| 229 | N | 27 | S |
| 230 | Q | 32 | H |
| 231 | I | 34 | L |
| 232 | T | 35 | S |
| 233 | T | 37 | S |
| 234 | K | 41 | S |
| 235 | V | 42 | E |
| 236 | A | 45 | E |
| 237 | K | 46 | C |
| 238 | K | 47 | M |
| 239 | Q | 50 | R |
| 240 | I | 51 | V |
| 241 | D | 53 | E |
| 242 | K | 56 | E |
| 243 | V | 67 | A |
| 244 | A | 68 | N |
| 245 | N | 69 | D |
| 246 | N | 69 | Q |
| 247 | S | 71 | L |
| 248 | Q | 72 | R |
| 249 | V | 80 | I |
| 250 | A | 86 | S |
| 251 | Q | 91 | K |
| 252 | C | 101 | Y |
| 253 | N | 102 | D |
| 254 | N | 102 | H |
| 255 | M | 110 | D |

TABLE 3.2-continued

Summary of mutations evaluated in the Vv2M5 background (SEQ ID NO: 9).

| No. | WT | Position | Mutation |
|---|---|---|---|
| 256 | D | 111 | E |
| 257 | G | 112 | D |
| 258 | I | 117 | S |
| 259 | T | 130 | N |
| 260 | R | 143 | E |
| 261 | R | 145 | N |
| 262 | A | 149 | S |
| 263 | S | 152 | N |
| 264 | G | 159 | N |
| 265 | G | 159 | S |
| 266 | V | 168 | T |
| 267 | K | 176 | E |
| 268 | K | 186 | E |
| 269 | A | 187 | S |
| 270 | S | 191 | H |
| 271 | Y | 194 | P |
| 272 | H | 195 | P |
| 273 | N | 205 | E |
| 274 | L | 212 | M |
| 275 | E | 213 | P |
| 276 | W | 219 | H |
| 277 | V | 223 | I |
| 278 | D | 226 | E |
| 279 | A | 228 | E |
| 280 | F | 229 | S |
| 281 | T | 233 | V |
| 282 | V | 245 | L |
| 283 | L | 248 | M |
| 284 | L | 256 | I |
| 285 | K | 261 | A |
| 286 | E | 262 | D |
| 287 | C | 347 | F |
| 288 | E | 363 | A |
| 289 | H | 372 | E |
| 290 | V | 377 | A |
| 291 | E | 395 | G |
| 292 | E | 395 | N |
| 293 | H | 396 | Y |
| 294 | A | 399 | T |
| 295 | C | 414 | R |
| 296 | E | 426 | D |
| 297 | S | 438 | G |
| 298 | M | 443 | I |
| 299 | T | 469 | A |
| 300 | S | 488 | E |
| 301 | K | 491 | R |
| 302 | M | 513 | K |
| 303 | A | 517 | E |
| 304 | L | 519 | V |
| 305 | E | 532 | D |
| 306 | V | 550 | L |
| 307 | N | 553 | D |

TABLE 3.3

Summary of mutations evaluated in VS2 background (SEQ ID NO: 11).

| No. | WT | Position | Mutation |
|---|---|---|---|
| 308 | P | 20 | R |
| 309 | N | 23 | D |
| 310 | I | 28 | F |
| 311 | K | 41 | P |
| 312 | K | 41 | S |
| 313 | V | 42 | D |
| 314 | R | 44 | H |
| 315 | Q | 50 | D |
| 316 | Q | 50 | R |
| 317 | E | 52 | R |
| 318 | K | 61 | M |
| 319 | N | 69 | Q |

TABLE 3.3-continued

Summary of mutations evaluated in VS2 background (SEQ ID NO: 11).

| No. | WT | Position | Mutation |
|---|---|---|---|
| 320 | Q | 72 | R |
| 321 | L | 73 | K |
| 322 | A | 79 | I |
| 323 | A | 86 | S |
| 324 | H | 88 | L |
| 325 | Q | 91 | H |
| 326 | A | 96 | I |
| 327 | Q | 98 | R |
| 328 | C | 101 | Y |
| 329 | N | 102 | H |
| 330 | C | 107 | F |
| 331 | I | 117 | S |
| 332 | G | 120 | L |
| 333 | T | 140 | K |
| 334 | R | 145 | N |
| 335 | S | 152 | V |
| 336 | V | 154 | I |
| 337 | V | 154 | P |
| 338 | R | 155 | K |
| 339 | M | 157 | L |
| 340 | G | 159 | M |
| 341 | A | 175 | D |
| 342 | K | 176 | E |
| 343 | A | 177 | P |
| 344 | L | 178 | I |
| 345 | H | 184 | Y |
| 346 | H | 184 | Q |
| 347 | A | 187 | S |
| 348 | S | 191 | H |
| 349 | H | 195 | N |
| 350 | L | 196 | P |
| 351 | A | 201 | R |
| 352 | L | 212 | M |
| 353 | E | 213 | P |
| 354 | A | 217 | Q |
| 355 | A | 228 | E |
| 356 | D | 231 | N |
| 357 | K | 232 | P |
| 358 | T | 233 | V |
| 359 | E | 236 | D |
| 360 | D | 241 | E |
| 361 | N | 255 | D |
| 362 | A | 257 | M |
| 363 | L | 276 | P |
| 364 | Y | 280 | F |
| 365 | M | 283 | I |
| 366 | V | 286 | A |
| 367 | T | 300 | M |
| 368 | T | 300 | I |
| 369 | T | 306 | L |
| 370 | T | 306 | I |
| 371 | L | 309 | I |
| 372 | A | 315 | V |
| 373 | E | 320 | D |
| 374 | K | 323 | R |
| 375 | S | 336 | T |
| 376 | E | 342 | D |
| 377 | C | 347 | L |
| 378 | A | 350 | I |
| 379 | N | 356 | H |
| 380 | E | 363 | G |
| 381 | Q | 368 | P |
| 382 | N | 380 | D |
| 383 | Q | 381 | L |
| 384 | E | 395 | G |
| 385 | A | 407 | G |
| 386 | A | 407 | S |
| 387 | C | 414 | P |
| 388 | A | 417 | I |
| 389 | A | 432 | I |
| 390 | V | 436 | L |
| 391 | I | 442 | P |
| 392 | I | 442 | L |
| 393 | S | 445 | R |
| 394 | S | 446 | M |

TABLE 3.3-continued

Summary of mutations evaluated
in VS2 background (SEQ ID NO: 11).

| No. | WT | Position | Mutation |
|---|---|---|---|
| 395 | T | 450 | C |
| 396 | S | 458 | T |
| 397 | H | 459 | Y |
| 398 | H | 459 | M |
| 399 | H | 467 | Q |
| 400 | T | 469 | A |
| 401 | E | 484 | P |
| 402 | Q | 485 | H |
| 403 | Q | 485 | E |
| 404 | V | 486 | A |
| 405 | Y | 487 | L |
| 406 | S | 488 | E |
| 407 | I | 494 | V |
| 408 | N | 496 | D |
| 409 | N | 496 | K |
| 410 | M | 513 | T |
| 411 | T | 523 | I |
| 412 | D | 527 | L |
| 413 | I | 529 | L |
| 414 | I | 529 | M |
| 415 | E | 532 | H |
| 416 | E | 532 | Y |
| 417 | S | 535 | A |
| 418 | R | 544 | H |
| 419 | N | 546 | Y |
| 420 | N | 546 | F |
| 421 | A | 548 | I |
| 422 | V | 550 | L |
| 423 | V | 555 | I |

Thus, in various embodiments, the engineered VvVS may have at least about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations selected from Table 3. Exemplary recombinant valencene synthases Vv1M1 (SEQ ID NO: 3), Vv2M1 (SEQ ID NO: 5), Vv1M5 (SEQ ID NO: 7), Vv2M5 (SEQ ID NO: 9), and VS2 (SEQ ID NO: 11) are further depicted in FIG. 3, including an alignment in FIG. 3B. A further exemplary recombinant valencene synthase VS3 (SEQ ID NO: 129) is also depicted herein.

In certain aspects, the disclosure provides polynucleotides comprising a nucleotide sequence encoding a valencene synthase modified for increased expression of valencene as described above. Such polynucleotides may be expressed in host cells, either on extrachromosomal elements such as plasmids, or may be chromosomally integrated.

In various embodiments, the SrKO is expressed alongside a P450 reductase to regenerate the enzyme, or alternatively, the SrKO or derivative is expressed with the P450 reductase as a chimeric P450 enzyme. Functional expression of cytochrome P450 has been considered challenging due to the inherent limitations of bacterial platforms, such as the absence of electron transfer machinery and cytochrome P450 reductases, and translational incompatibility of the membrane signal modules of P450 enzymes due to the lack of an endoplasmic reticulum.

Accordingly, in some embodiments the SrKO is expressed as a fusion protein with a cytochrome P450 reductase partner. Cytochrome P450 reductase is a membrane protein found in the endoplasmic reticulum. It catalyzes pyridine nucleotide dehydration and electron transfer to membrane bound cytochrome P450s. Isozymes of similar structure are found in humans, plants, other mammals, and insects. Exemplary P450 reductase partners include, for example, *Stevia rebaudiana* (Sr)CPR (SEQ ID NOS: 62 and 63), *Stevia rebaudiana* (Sr)CPR1 (SEQ ID NOS: 76 and 77), *Arabidopsis thaliana* (At)CPR (SEQ ID NOS: 64 and 65), *Taxus cuspidata* (Tc) CPR (SEQ ID NOS: 66 and 67), *Artemisia annua* (Aa)CPR (SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). Any of these P450s can be derivatized in some embodiments, for example, to introduce from 1 to about 20 mutations, or from about 1 to about 10 mutations. FIG. 6B shows an alignment of amino acid sequences for *Arabidopsis thaliana* and *Artemisia annua* CPR sequences (SEQ ID NOS: 72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NOS: 74, 72, 82, 68, 80, 62, 78, and 76).

Engineering of P450 fusion proteins is disclosed, for example, in US 2012/0107893 and US 2012/0164678, both of which are hereby incorporated by reference in their entireties. In certain embodiments, the SrKO is fused to the cytochrome P450 reductase partner through a linker. Exemplary linker sequences, which are predominantly serine, glycine, and/or alanine, and optionally from one to five charged amino acids such as lysine or arginine, include, for example, GSG, GSGGGGS (SEQ ID NO: 113), GSGEAAAK (SEQ ID NO: 114), GSGEAAAKEAAAK (SEQ ID NO: 115), GSGMGSSSN (SEQ ID NO: 116), and GSTGS (SEQ ID NO: 117). The linker is generally flexible, and contains no more than one, two, or three hydrophobic residues, and is generally from three to fifty amino acids in length, such as from three to twenty amino acids in length. In other embodiments, a P450 reductase is expressed in the host cell separately, and may be expressed in the same operon as the SrKO in some embodiments. In some embodiments, the P450 reductase enzyme is expressed separately in the host cell, and the gene is optionally integrated into the genome or expressed from a plasmid.

In certain embodiments the N-terminus of the P450 enzymes may be engineered to increase their functional expression. The N-terminus of membrane-bound P450 plays important roles in enzyme expression, membrane association and substrate access. It has been reported that the use of rare codons in the N-terminus of P450 significantly improved the expression level of P450. Further, since most plant P450 enzymes are membrane-bound and hydrophobic substrates are thought to enter the enzymes through channels dynamically established between the P450 and membrane, N-terminal engineering can affect the association of the membrane and P450 and therefore the access of substrate to the enzyme. Accordingly, in an embodiment, N-terminal engineering of SrKO generates an SrKO derivative that either maintains or shows enhanced valencene oxidase activity in a host system such as *E. coli* or yeast. An exemplary N-terminal sequence is 8rp or MALLLAVF (SEQ ID NO:

112), and other exemplary sequences include sequences of from four to twenty amino acids (such as from four to fifteen amino acids, or from four to ten amino acids, or about eight amino acids) that are predominately hydrophobic, for example, constructed predominately of (at least 50%, or at least 75%) amino acids selected from leucine, valine, alanine, isoleucine, and phenylalanine.

In some embodiments, the SrKO is a derivative having a deletion of at least a portion of its N-terminal transmembrane region, and the addition of an inner membrane transmembrane domain from *E. coli* yhcB or derivative thereof. In these embodiments, the P450 enzyme has a more stable and/or productive association with the *E. coli* inner membrane, which reduces cell stress otherwise induced by the expression of a membrane-associated P450 enzyme. In some embodiments, the SrKO is a derivative having a deletion of from 15 to 35 amino acids of its N-terminal transmembrane domain, and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIIIGAVA (SEQ ID NO: 118), or an amino acid sequence having from 1 to 10 or from 1 to 5 amino acid mutations with respect to SEQ ID NO: 118.

In some embodiments, the host cell further expresses one or more enzymes, such as an alcohol dehydrogenase (ADH). In certain embodiments, the host cell may express an ADH enzyme producing nootkatone from nootkatol, examples of which include *Rhodococcus erythropolis* CDH (SEQ ID NO: 84), *Citrus sinensis* DH (SEQ ID NO: 86), *Citrus sinensis* DH1 (SEQ ID NO: 88), *Citrus sinensis* DH2 (SEQ ID NO: 90), *Citrus sinensis* DH3 (SEQ ID NO: 92), *Vitis vinifera* DH (SEQ ID NO: 94), *Vitis vinifera* DH1 (SEQ ID NO: 96), *Citrus sinensis* ABA2 (SEQ ID NO: 98), *Brachypodium distachyon* DH (SEQ ID NO: 100), and *Zingiber zerumbet* SDR (SEQ ID NO: 102). The ADH may comprise an amino acid sequence having at least 70%, at least 80%, or at least 90% sequence identity to one or more of the enzymes described in this paragraph, and with the activity of converting nootkatol to nootkatone.

Sesquiterpenes (e.g., valencene and its oxygenated products) can be produced as biosynthetic products of the non-mevalonate pathway in *E. coli* comprising two modules: the native upstream pathway forming Isopentenyl Pyrophosphate (IPP) and a heterologous downstream terpenoid-forming pathway. A multivariate-modular approach to metabolic pathway engineering can be employed to optimize the production of sesquiterpenes in an engineered *E. coli*. The multivariate-modular pathway engineering approach is based on a systematic multivariate search to identify conditions that optimally balance the two pathway modules to minimize accumulation of inhibitory intermediates and flux diversion to side products.

WO 2011/060057, US 2011/0189717, US 2012/107893, and U.S. Pat. No. 8,512,988 (each of which are hereby incorporated by reference) describe methods and compositions for optimizing production of terpenoids in cells by controlling expression of genes or proteins participating in an upstream pathway and a downstream pathway. This can be achieved by grouping the enzyme pathways into two modules: an upstream (MEP) pathway module (e.g., containing one or more genes of the MEP pathway) and a downstream, heterologous pathway to sesquiterpene production. Using this basic configuration, parameters such as the effect of plasmid copy number on cell physiology, gene order and promoter strength in an expression cassette, and chromosomal integration are evaluated with respect to their effect on terpene and terpenoid (e.g., sesquiterpene) production. Expression of genes within the MEP pathway can thus be regulated in a modular method. As used herein, regulation by a modular method refers to regulation of multiple genes together. By way of example, multiple genes within the MEP pathway can be recombinantly expressed on a contiguous region of DNA, such as an operon. It should be appreciated that modules of genes within the MEP pathway, consistent with aspects of the disclosure, can contain any of the genes within the MEP pathway, in any order. In some embodiments, a gene within the MEP pathway is one of the following: dxs, ispC, ispD, ispE, ispF, ispG, ispH, idi, ispA or ispB. A non-limiting example of a module of genes within the MEP pathway is a module containing the genes dxs, idi, ispD and ispF, and referred to as dxs-idi-ispDF.

The manipulation of the expression of genes and/or proteins, including modules such as the dxs-idi-ispDF operon, and a FPPS-VS operon, can be achieved through methods known to one of ordinary skill in the art. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell.

The expression of one or more genes and/or proteins within the MEP pathway can be upregulated and/or downregulated. In certain embodiments, upregulation of one or more genes and/or proteins within the MEP pathway can be combined with downregulation of one or more genes and/or proteins within the MEP pathway. By way of example, in some embodiments, a cell that overexpresses one or more components of the non-mevalonate (MEP) pathway is used, at least in part, to amplify isopentyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. In this regards, copy numbers of components at rate-limiting steps in the MEP pathway such as (dxs, ispD, ispF, idi) can be amplified, such as by additional episomal expression.

In some embodiments, the production of indole is used as a surrogate marker for sesquiterpene production, and/or the accumulation of indole in the culture is controlled to increase sesquiterpene production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing protein expression and activity using the multivariate modular approach described above, and/or is controlled by chemical means.

In other aspects, the disclosure provides a method for making a product containing an oxygenated sesquiterpene (as described), which comprises incorporating the oxygenated sesquiterpene prepared and recovered according to the method described above into a consumer or industrial product. For example, the product may be a flavor product, a fragrance product, a cosmetic, a cleaning product, a detergent or soap, or a pest control product (e.g., an insect repellant). In some embodiments, the oxygenated product recovered and optionally enriched by fractionation is nootkatol (e.g., a and R nootkatol) and/or nootkatone, and the product is a flavor product selected from a beverage, a chewing gum, a candy, or a flavor additive, or is a pest control product (e.g., an insect repellant).

The oxygenated product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, oxygenated oil is extracted from aqueous reaction medium, which may be done by using an organic solvent, such as an alkane such as heptane, followed by fractional distillation. Sesquiterpene and sesquiterpenoid components of fractions may be measured quantitatively by GC/MS, followed by blending of the fractions to generate a desired nootkatone-containing ingredient for flavour (or other) applications.

In other aspects, the disclosure provides polynucleotides comprising a nucleotide sequence encoding a P450 derivative described herein. The polynucleotide may be codon optimized for expression in *E. coli* or yeast in some embodiments. In another example, the polynucleotide may comprise a nucleotide sequence encoding a SrKO fusion protein, optionally with a P450 reductase partner as described herein. In other embodiments, the disclosure provides polynucleotides comprising a nucleotide sequence encoding a sesquiterpene synthase variant described herein, which may likewise be codon optimized for expression in *E. coli* or yeast. Such polynucleotides may further comprise, in addition to sequences encoding the P450 or sesquiterpene synthase, one or more expression control elements. For example, the polynucleotide may comprise one or more promoters or transcriptional enhancers, ribosomal binding sites, transcription termination signals, and polyadenylation signals, as expression control elements. The polynucleotide may be inserted within any suitable vector, including an expression vector, and which may be contained within any suitable host cell for expression. The polynucleotide may be designed for introduction and/or protein expression in any suitable host cell, including bacterial cells and yeast cells, and may be expressed from a plasmid, or may be chromosomally integrated. In some embodiments, the recombinant nucleic acid molecule encodes an SrKO derivative with a higher activity for oxidation of valencene than the wild type enzyme (SEQ ID NO: 37), and having a leader sequence as described, such as the leader sequence MALLLAVF (SEQ ID NO: 112) or leader sequence derived from *E. coli* yhcB. In certain embodiments, the recombinant nucleic acid molecules further encodes either as an operon or as a fusion in frame with the SrKO derivative, an SrCPR or derivative thereof capable of regenerating the SrKO enzyme. When present as a fusion protein, the SrKO derivative and the SrCPR may be connected by a linking sequence of from 3 to 10 amino acids (e.g., 5 amino acids). In some embodiments, the linking sequence is predominately glycine, serine, and/or alanine and may comprise the sequence GSTGS.

In other aspects, the disclosure provides host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell or modified through expression of heterologous enzymes or duplication of certain enzymes in the pathway. Host cells include various bacteria and yeast as described herein.

In still other aspects, the disclosure provides sesquiterpene products produced by the methods and host cells described herein. As disclosed herein, SrKO enzyme showed unique activities by creating different stereoisomers of the hydroxylated product (alpha and beta nootkatol and further oxidizing to ketone, nootkatone), and produced different oxygenated terpene products including hydroxygermacra-1 (10)5-diene, and murolan-3,9(11) diene-10-peroxy. This activity provides for the incorporation of a unique valencene oxidation profile into an oil suitable for flavouring applications.

In certain embodiments, the processes and methods disclosed herein provide compositions and formulations comprising an oxygenated product. In some embodiments, said compositions and formulations may further comprise an unoxygenated product, a sesquiterpene, valencene, a non-sesquiterpene component, and/or one or more additional ingredients. In particular embodiments, the compositions and formulations disclosed herein comprise at least one of valencene, hydroxygermacra-1(10)5-diene, murolan-3,9(11) diene-10-peroxy, α-nootkatol, β-nootkatol, and nootkatone. In certain embodiments of the compositions and formulations disclosed herein, the compositions and formulations comprise at least one of nootkatone, α-nootkatol, β-nootkatol, and valencene. For example, in certain such embodiments, the nootkatone content may be selected from about 50% to about 65% (w/w), about 52.5% to about 62.5% (w/w), and about 55% to about 60% (w/w); the α-nootkatol content may be selected from about 15% to about 30% (w/w), about 17.5% to about 27.5% (w/w), and about 20% to about 25% (w/w); the β-nootkatol content may be selected from about 1% to about 15% (w/w), about 3% to about 12% (w/w), and about 5% to about 10% (w/w); and the valencene content may be selected from about 1% to about 15% (w/w), about 3% to about 12% (w/w), and about 5% to about 10% (w/w).

In specific embodiments of the compositions and formulations disclosed herein, the compositions and formulations comprise at least one of nootkatone, α-nootkatol, and β-nootkatol. For example, in certain such embodiments, the nootkatone content may be selected from about 50% to about 65% (w/w), about 52.5% to about 62.5% (w/w), and about 55% to about 60% (w/w); the α-nootkatol content may be selected from about 15% to about 30% (w/w), about 17.5% to about 27.5% (w/w), and about 20% to about 25% (w/w); and the 3-nootkatol content may be selected from about 1% to about 15% (w/w), about 3% to about 12% (w/w), and about 5% to about 10% (w/w).

In one embodiment, the composition or formulation comprise nootkatone, α-nootkatol, and β-nootkatol, wherein the nootkatone is present in an amount ranging from about 55% to about 60% (w/w), the α-nootkatol is present in an amount ranging from about 20% to about 25% (w/w), and the β-nootkatol is present in an amount ranging from about 5% to about 10% (w/w).

In another embodiment, the composition or formulation comprise valencene, nootkatone, α-nootkatol, and β-nootkatol, wherein the valencene is present in an amount ranging from about 5% to about 10% (w/w), the nootkatone is present in an amount ranging from about 55% to about 60% (w/w), the α-nootkatol is present in an amount ranging from about 20% to about 25% (w/w), and the β-nootkatol is present in an amount ranging from about 5% to about 10% (w/w).

Figure 7:
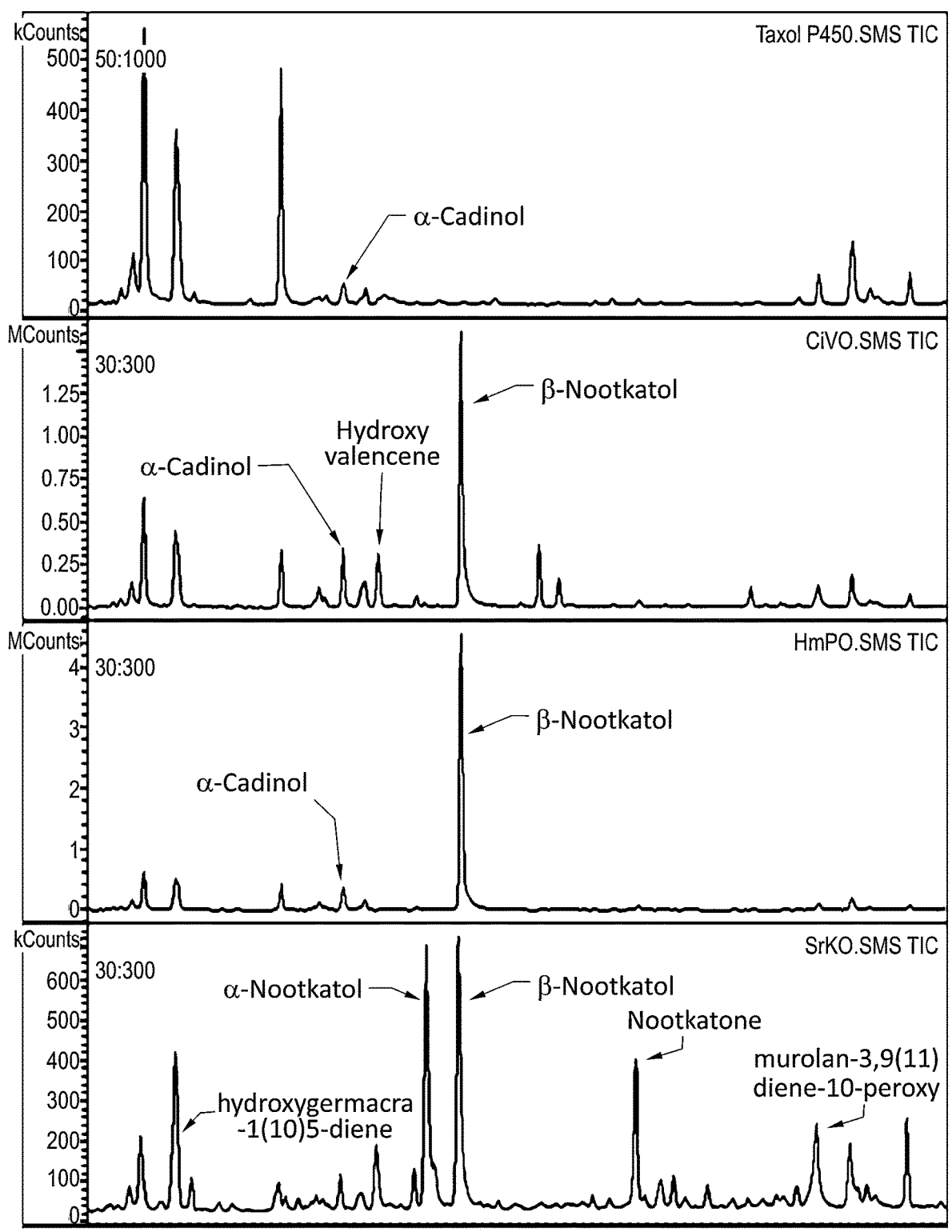
FIG. 7 provides GC-chromatographs which show the different activities of various CYP450 enzymes, as expressed in valencene-producing *E. coli* along with CPR partners as described in Example 2. Strains were cultured for four days and extracted with Methyl Tert-Butyl Ether (MTBE). 1 μl of MTBE was injected through GC-MS and the product profiles were monitored by comparing with a MS library. From top to bottom: Taxus 5-alpha hydroxylase, *Cichorium intybus* (CiVO) P450 (SEQ ID NO:50), *Hyoscyamus muticus* (HmPO) P450 (SEQ ID NO:20), and SrKO (SEQ ID NO:38).

Further, other P450 enzymes tested, including previously known sesquiterpene CYP450's or P450's having hydroxylating activity on the valencene substrate produced one of the stereoisomers (beta nootkatol) and only minor amounts of the ketone (nootkatone). Specifically, the other sesquiterpene CYP450 enzymes produced beta-nootkatol and hydroxyl valencene as major products, while Taxol CYP450 enzyme did not produce any oxygenated valencene (Table 4 and FIG. 7). The different blend of sesquiterpene products produced by SrKO provides a unique profile with a unique sensory/taste profile.

In certain aspects, the disclosure relates to SrKO derivative enzymes. In certain embodiments, the SrKO derivative polypeptide comprises an amino acid sequence that has up to 25 mutations compared to the wild type protein according to SEQ ID NO: 37. For example, the SrKO derivative may comprise an amino acid sequence that has one or more mutations at positions selected from 46, 76, 94, 131, 231, 284, 383, 390, 400, 444, 468, 488 and 499, numbered according to SEQ ID NO: 37. For example, in some embodiments, the SrKO is a derivative comprising an amino acid sequence having one or more (or all) of the mutations selected from H46R, R76K, M94V, T131Q, F231L, H284Q, R383K, I390L, V400Q, I444A, T468I, T488D, and T499N, numbered according to SEQ ID NO:37. In certain embodiments, the SrKO is a derivative comprising an amino acid sequence having one or more (or all) of the mutations selected from R76K, M94V, T131Q, F231L, H284Q, R383K, I390L, T468I, and T499N, numbered according to SEQ ID NO: 37. In some embodiments, the SrKO derivative comprises an amino acid sequence selected from SEQ ID NOS: 55-61, which were engineered according to this disclosure to improve activity for oxygenation of valencene (e.g., production of nootkatone and/or nootkatol). In some embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488 and 499 (numbered according to SEQ ID NO: 37), or the proviso that the SrKO derivative comprises an amino acid sequence having one or more (or all) of the mutations selected from H46R, R76K, M94V, T131Q, F231L, H284Q, R383K, I390L, V400Q, I444A, T468I, T488D, and T499N (numbered according to SEQ ID NO: 37). In certain embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488 and 499 (numbered according to SEQ ID NO: 37), or the proviso that the SrKO derivative comprises an amino acid sequence having one or more (or all) of the mutations selected from R76K, M94V, T131Q, F231L, H284Q, R383K, I390L, T468I, and T499N (numbered according to SEQ ID NO: 37). As shown herein, these mutations increase the level of SrKOs valencene oxidation activity.

In these or other embodiments, the SrKO is a derivative having a deletion of at least a portion of its N-terminal transmembrane region, and the addition of an inner membrane transmembrane domain from E. coli yhcB or derivative thereof. In some embodiments, the SrKO is a derivative having a deletion of from 15 to 35 amino acids of its N-terminal transmembrane domain, and the addition of from 15 to 25 amino acids of the transmembrane domain from E. coli yhcB or derivative thereof. In some embodiments, the N-terminal transmembrane domain of the derivative comprises the amino acid sequence MAWEYALIGLVVGIII-GAVA (SEQ ID NO:118), or an amino acid sequence having from 1 to 10 or from 1 to 5 amino acid mutations with respect to SEQ ID NO:118.

In still other aspects, the disclosure provides a method of preparing the modified SrKO polypeptide, wherein the method comprises the steps of: (i) culturing a host cell expressing the modified polypeptide under conditions which permit expression of the polypeptide; and (ii) optionally recovering the polypeptide.

In still other aspects, the disclosure provides a method of producing an oxygenated sesquiterpene comprising the steps of: (i) providing the modified SrKO polypeptide, (ii) contacting a sesquiterpene with the modified SrKO polypeptide, and (iii) recovering the produced oxygenated sesquiterpene. The method may further comprise providing a CPR enzyme for regenerating the SrKO cofactor (e.g., SrCPR). In some embodiments, the oxygenated sesquiterpene is recovered as an oil. In some embodiments, the sesquiterpene is valencene. In some embodiments, the oxygenated sesquiterpene comprises hydroxygermacra-1(10)5-diene, murolan-3,9(11) diene-10-peroxy, alpha-nootkatol, beta-nootkatol, and nootkatone. In some embodiments, the predominant oxygenated product is nootkatone and/or nootkatol. In some embodiments, the oxygenated product comprises both alpha and beta nootkatol.

Figure 8A:
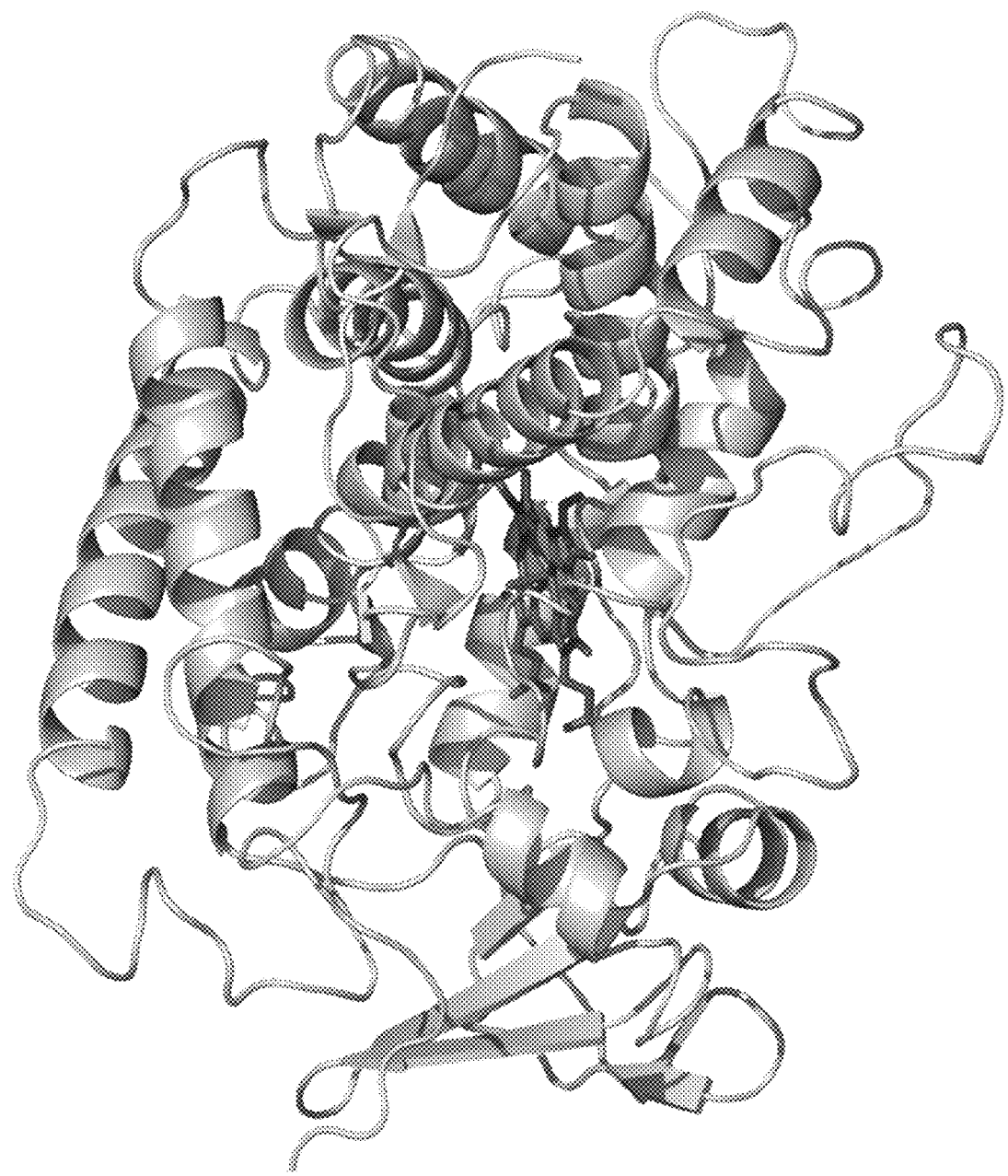
FIGS. 8A and 8B illustrate a homology model of SrKO and its active site. The SrKO homology model is based on the known mutant P45017A1 (the crystal structure of membrane-bound cytochrome P450 17 A1 as disclosed in DeVore N M and Scott E E (*Nature*, 482, 116-119, 2012), which catalyzes the biosynthesis of androgens in human. The position of the heme is shown as sticks.
Figure 8B:
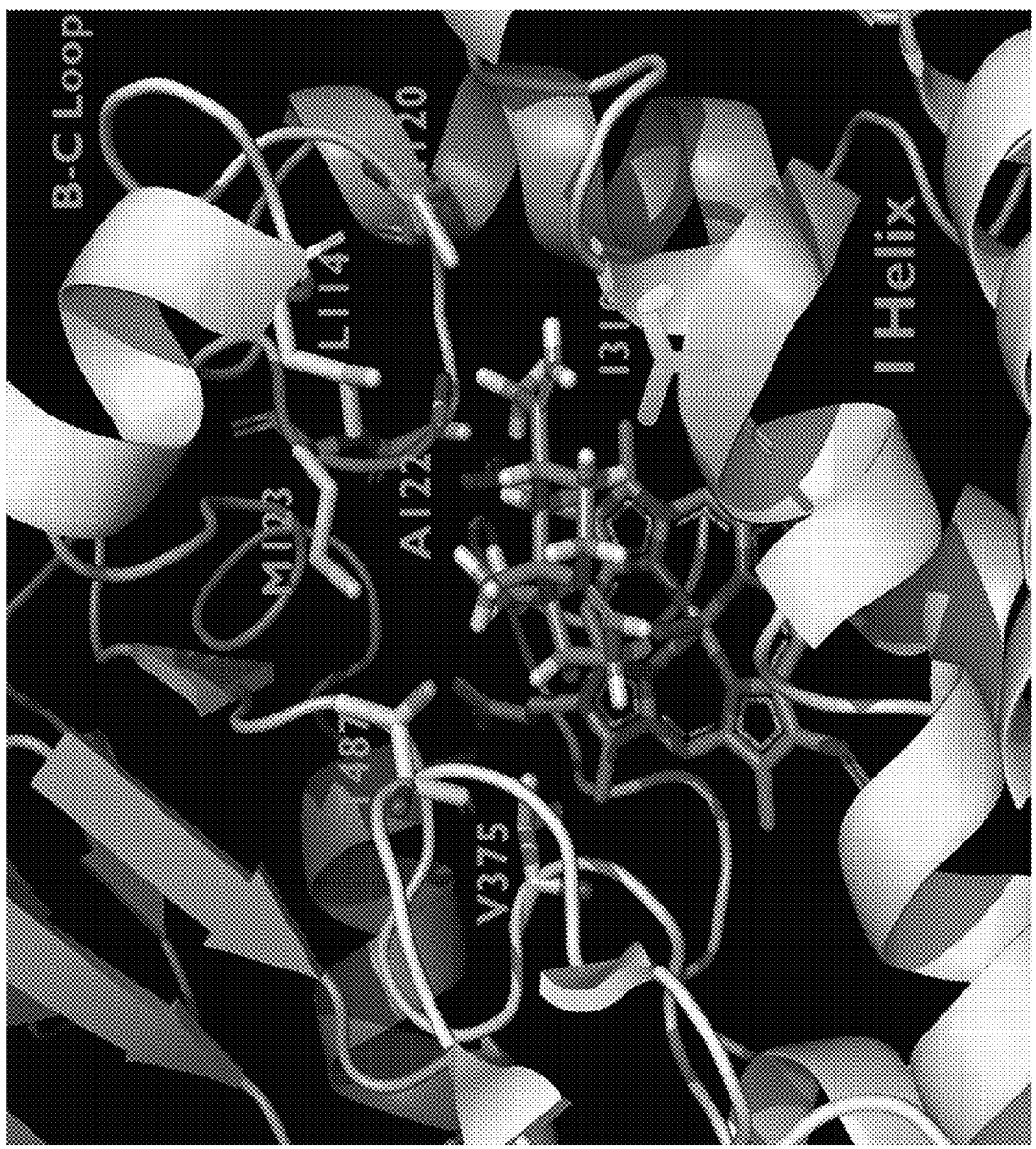

In another aspect, there is provided an SrKO crystal model structure (CMS) based on the structural coordinates of P45017A1, with an amino acid sequence of SrKO or derivative described herein. The CMS comprises a terpene binding pocket domain (TBD) that comprises a terpene binding pocket (TBP) and a terpene (e.g., valencene) bound to the TBD. FIGS. 8A and 8B. This SrKO crystal model structure (CMS) facilitates in-silico testing of SrKO derivatives.

Thus, in still other embodiments, the disclosure provides a method of screening for a terpene capable of binding to a TBD wherein the method comprises the use of the SrKO CMS. In another aspect, the disclosure provides a method for screening for a terpene capable of binding to the TBP, and the method comprises contacting the TBP with a test compound, and determining if said test compound binds to said TBP. In some embodiments, the method is to screen for a test compound (e.g., terpenes) useful in modulating the activity of a SrKO enzyme.

In another aspect, the disclosure provides a method for predicting, simulating or modelling the molecular characteristics and/or molecular interactions of a terpene binding domain (TBD) comprising the use of a computer model, said computer model comprising, using or depicting the structural coordinates of a terpene binding domain as defined above to provide an image of said ligand binding domain and to optionally display said image.

EXAMPLES

Example 1: Construction of Sesquiterpene Precursor (Valencene) Producing E. coli Strain E. coli overexpressing upstream MEP pathway genes dxs, ispD, ispF, and idi was created, which facilitates flux to the isoprenoid precursor isopentyl-pyrophosphate (IPP) supporting more than 1 g/L titers of a heterologous diterpenoid product (3). Strains were constructed producing a variety of terpenoids including mono- and sesquiterpenes by replacing the geranylgeranyl pyrophosphate synthase (GGPS) and diterpene synthase with a farnesyl pyrophosphate synthase (FPPS) and sesquiterpene synthase or a geranyl pyrophosphate synthase (GPPS) and monoterpene synthase. For developing a sesquiterpene producing strain to test the CYP450s for novel oxygenated terpenes, a valencene synthase enzyme was cloned and expressed in the MEP pathway overexpressed *E. coli* strain. The high substrate flux helps identify the activity of the CYP450. Previously, research on an oxygenated taxadiene producing strain showed a significant drop in the productivity upon transferring the CYP450 pathway to the taxadiene producing strain (300 mg/L to ~10 mg/L).

Further, multivariate modular metabolic engineering (MMME) was applied for balancing the pathway for high level production of valencene. Naturally occurring valencene synthases, such as that from *Vitis vinifera*, often perform sub-optimally (~5 mg/L) even after MMME optimization, compared to previous results obtaining 100's of mg/L diterpenoids. Enzymes involved in the sesquiterpene biosynthesis can be difficult to express in *E. coli*, and also are deficient in kinetics relative to those involved in primary metabolism (17).

A homology model for the *Vitis vinifera* valencene synthase (VvVS) was constructed using the BioLuminate® software package (Schrodinger, Inc.) with the 5-epi-aristolochene synthase crystal structure as a template (PDB: 5EAT). Further, to identify the natural mutational landscape of terpene synthases, an extensive multiple sequence alignment incorporating hundreds of related terpene synthase sequences was created. Using this information, mutations were designed using a combination of back-to-consensus, in silico energetics, and structural analysis. Back-to-consensus mutations have been shown to be an important tool for improving stability (19,20) and expression (21). Energetics calculations based on atomic force-field models in BioLuminate were used to assess the ΔΔG of folding for individual mutations predicted for positions with low solvent-accessible surface area, which were predicted to affect folding and stability.

By applying the MMME approach, a balanced upstream and downstream valencene production strain was identified incorporating a codon-optimized version of VvVS on a plasmid with a p15A origin of replication and a T7 promoter. This strain background was then used to screen designed synthase enzyme mutations. Using the aforementioned protein engineering tools we designed over 200 unique point mutations (Table 3) which were then constructed in the p15A-T7 screening plasmid using site-directed mutagenesis. Mutated enzyme variants were transformed into the screening strain, triplicate colonies were cultured in selective LB cell culture medium overnight, and then inoculated into a minimal R-medium and cultured for four days at 22° C. Cultures were extracted using methyl tert-butyl ether (MTBE) and analyzed by combined gas chromatography/mass spectrometry for productivity of valencene.

Figure 2:
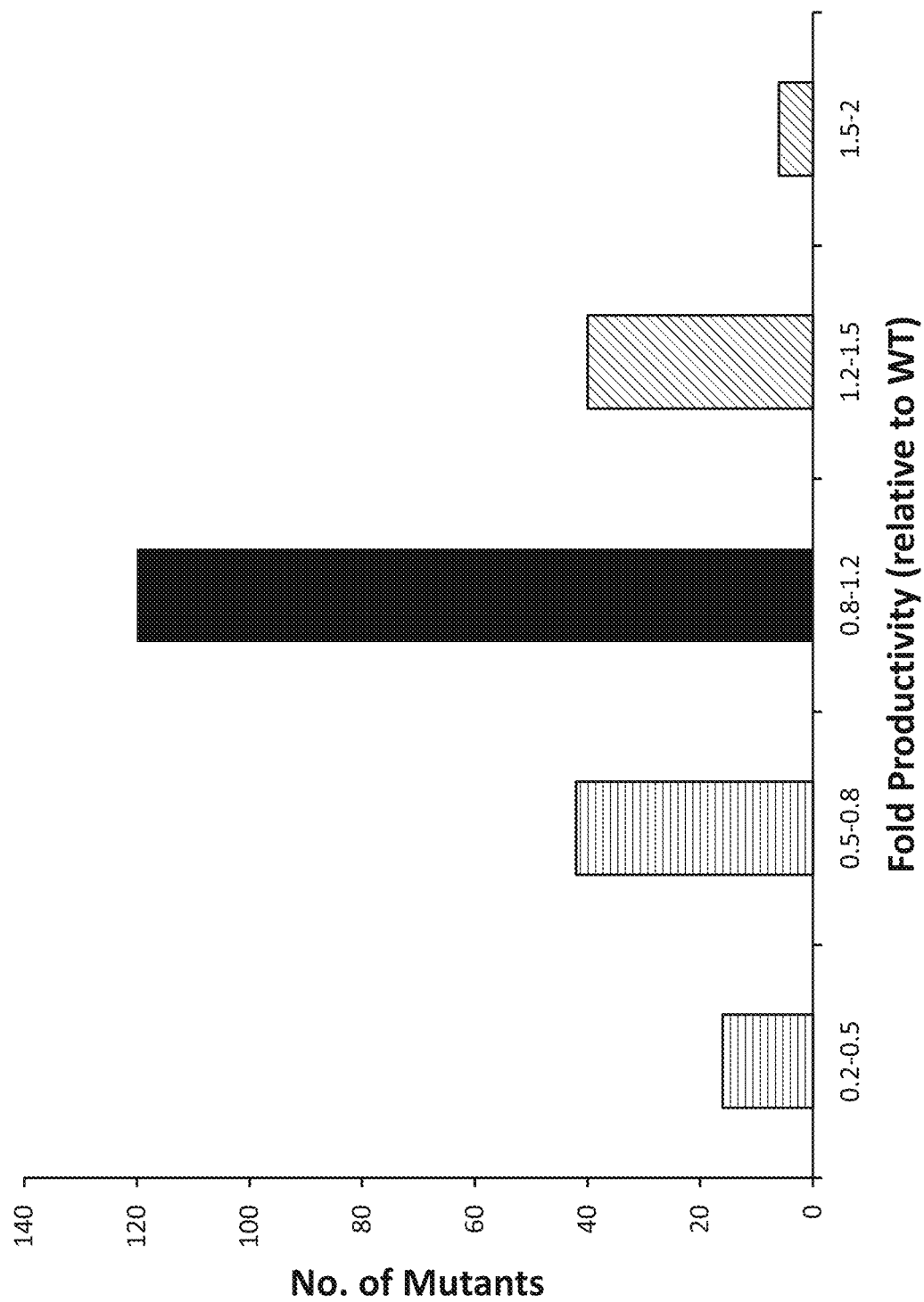
FIG. 2 depicts the fold productivities for site-directed mutants made to VvVS. 46 of the 225 point mutations convey an average improvement in productivity of valencene of at least 20% compared to the wild-type WT VvVS.

Approximately one-fifth of the designed point mutations increased valencene productivity in our screening strain by at least 20% (FIG. 2). Beneficial point mutations were then strategically combined to confer increasingly advantageous phenotypes. Recombined valencene synthase sequences are provided as Vv1M1 (Mutations—R331K, I334E, N335S, V371I, A374L, T418V, S482T, S512P, K356N, Q491K, E394D, A428V, Y348F, T318S, L352I, I442L, A554P), Vv2M1 (Mutations—R331K, I334E, N335S, V371I, A374L, T418V, S482T, S512P, K356N, Q491K, E394D, A428V, V542T, G480A, M305L, K441R, A554P), Vv1M5 (Mutations—R331K, I334E, N335S, V371I, A374L, T418V, S482T, S512P, K356N, Q491K, E394D, A428V, Y348F, T318S, L352I, I442L, A554P, H284M, C46K, F448T, Q533E), and Vv2M5 (Mutations—R331K, I334E, N335S, V371I, A374L, T418V, S482T, S512P, K356N, Q491K, E394D, A428V, V542T, G480A, M305L, K441R, A554P, H284M, C46K, F448T, Q533E) (FIG. 3). When either of these enzymes was overexpressed in our MEP pathway strain with dxs-idi-ispDF overexpressed, and balanced using MMME, the titers of valencene obtained were sufficient to motivate incorporation of P450 enzymes to test their ability to catalyze the formation of oxygenated valencene. Titers of valencene before P450 incorporation were about 30 mg/L.

Example 2: Functional Activity of CYP450 Library on Valencene Scaffold

Valencene was used as a model system to validate the power of CYP450-based oxygenation chemistry for production terpene chemicals.

Figure 5A:
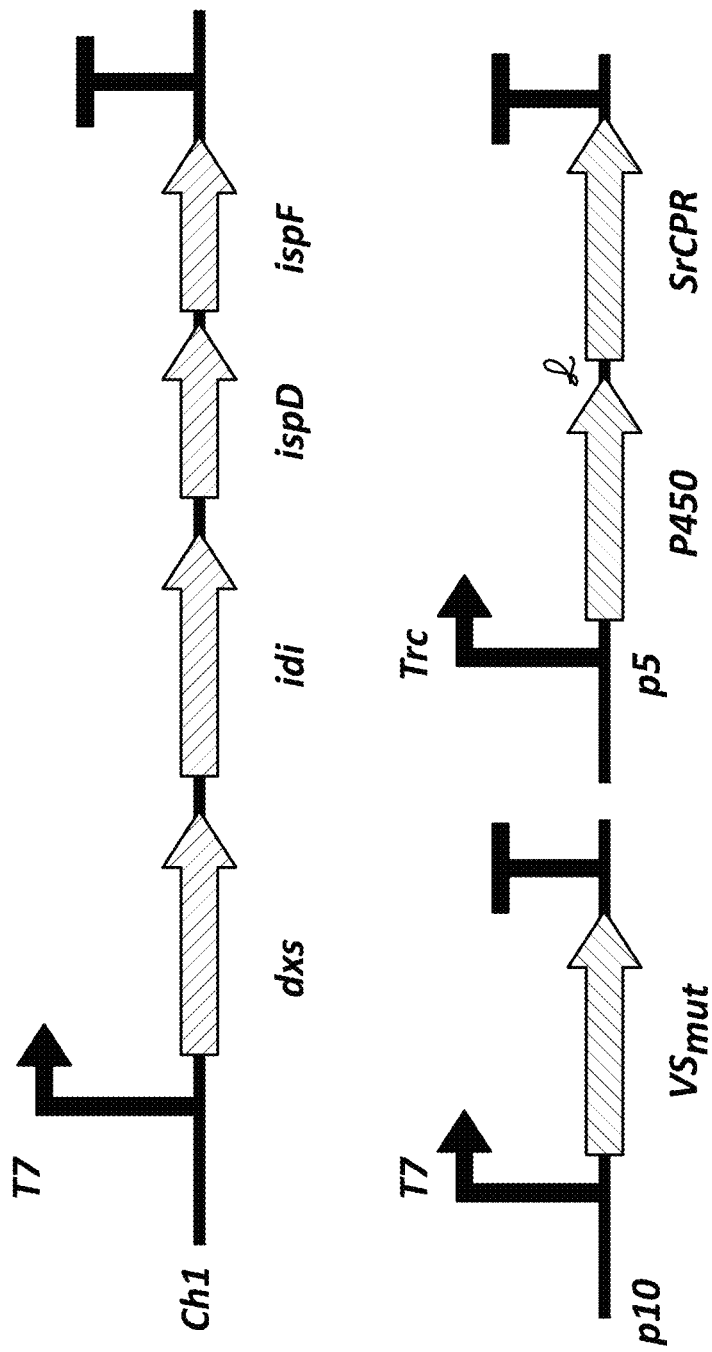

The CYPP450 candidate screening was conducted using the valencene producing *E. coli* strains as host background. For constructing the CYP450 for functional expression, a proprietary plasmid system, p5Trc (plasmid derived from pSC101) was used to construct a plasmid containing the candidate P450 fused to an N-terminal truncated *Stevia rebaudiana* cytochrome P450 reductase (SrCPR) through a flexible 5-amino acid linker (GSTGS, SEQ ID NO: 117). The sequences of the various candidate P450s are shown in FIG. 4. The candidate CYP450's were analyzed for N-terminal membrane associating regions which were truncated and a 8-amino acid leader sequence (MALLLAVF, SEQ ID NO: 112) was added to the fusion (FIGS. 5A and 5B). CPR red/ox partners from *Arabidopsis thaliana* and *Taxus cuspidata* were also prepared in similar genetic constructions. Since the native SrCPR was effective, the level of activity of these constructs was not determined. The sequences of the various CPR red/ox partners are shown in FIG. 6. Following transformation of p5Trc-CYP450-L-SrCPR to valencene producing strain, the strains were cultured overnight at 30° C. in antibiotic selective LB media. These cultures were then used to inoculate 2 mL antibiotic selective R-media cultures in hungate tubes with 15 g/L glycerol and 0.1 mM IPTG which were subsequently cultured for 4-days at 22° C. before being extracted with methyl tert-butyl ether (MTBE).

A set of CYP450 enzymes, from those listed in Table 4, was selected and classified for both sesqui- and diterpene oxygenation in this *E. coli* system. Among the various CYP450 enzymes tested for oxygenation on valencene, kaurene oxidase from *Stevia rebaudiana* (SrKO) (16) was discovered to have a unique oxygenation chemistry on the valencene scaffold. SrKO natively oxidizes the diterpene (−)-kaurene at the C19 position to (−)-kaurenoic acid. SrKO enzyme showed unique activities in the present studies by creating different stereoisomers of the hydroxylated product (alpha and beta nootkatol and further oxidizing to the ketone, nootkatone), and produced different oxygenated terpene products including hydroxygermacra-1(10)5-diene, murolan-3,9(11) diene-10-peroxy, in addition to the alpha-nootkatol, beta-nootkatol, and nootkatone. Other P450's, including the previously known sesquiterpene CYP45's for hydroxylating valencene produced only one of the isomers (beta nootkatol) and only detectable amounts of ketone (nootkatone). Specifically, the other sesquiterpene CYP450 enzymes produced beta-nootkatol and hydroxyl valencene as major products, while another diterpene CYP45 enzymes (e.g., Taxus 5-alpha hydroxylase) produced nootkatol as only a minor (detectable) product (Table 4 and FIG. 7).

TABLE 4

Major Products Formed From Valencene by Select P450 Enzymes in *E. coli*

| SPECIES | NAME | MAJOR PRODUCTS |
|---|---|---|
| *Cichorium intybus* | CiVO | β-nootkatol, α-cadinol, hydroxyl valencene. |
| *Hyoscyamus muticus* | HmPO | β-nootkatol, α-cadinol, hydroxyl valencene, nootkatone |
| *Latuca spicata* | LsGAO | β-nootkatol, α-cadinol, isovalencenol, nootkat-11-en-10-ol. |
| *Barnadesia spinosa* | BsGAO | β-nootkatol, α-cadinol, isovalencenol. |
| *Nicotiana tabacum* | NtEAO | α-cadinol, nootkat-11-en-10-ol. |
| *Stevia rebaudiana* | SrKO | α-nootkatol, hydroxygermacra-1(10)5-diene, β-nootkatol, nootkatone, murolan-3,9(11) diene-10-peroxy |
| *Zingiber zerumbet* | ZzHO | α-cadinol, nootkat-11-en-10-ol. |
| *Citrus x paradisi* | CpVO | α-cadinol, nootkat-11-en-10-ol. |
| *Mentha spicata* | MSL6OH | α-cadinol. |
| *Nicotiana tabacum* | NtVO | α-cadinol, nootkat-11-en-10-ol. |
| *Solanum tuberosum* | StVO | α-cadinol, β-nootkatol, globulol. |
| *Arabidopsis thaliana* | AtKO | α-cadinol, nootkat-11-en-10-ol. |
| *Cichorium intybus* | Ci2VO | β-nootkatol, a-cadinol, isovalencenol. |
| *Artemesia annua* | AaAO | α-cadinol, murolol, nootkat-11-en-10-ol. |
| Taxus 5-alpha hydroxylase P450 | | α-cadinol |

Example 3: Structural and Mutational Studies of SrKO

Once the unique activities of SrKO were identified, experiments were conducted to improve its ability to conduct its diverse oxidation of valencene. The crystal structure for SrKO has not been described. Blast search of SrKO against RCSB Protein Data Bank shows the sequence identity of SrKO to P450 enzymes with crystal structures are low (~20%). Given the conservative folding structures of P450s regardless of its low sequence identity, state-of-the-art protein modeling tools were used to build on SrKO. The crystal structure of membrane-bound cytochrome P450 17 A1 (see DeVore N. M., Scott E. E., *Nature*, 482, 116-119, 2012) which catalyses the biosynthesis of androgens in human was selected as the template for model development. Using BioLuminate protein modeling software, a homology model was developed (FIG. 8A) such that the positioning of key residues and characteristic motifs (see Gotoh O., *J. Biol Chem*, 267, 83-90, 1992) aligned well with the template. Furthermore, a homology model for SrKO which included the prosthetic heme-iron complex was also constructed. AutoDock VINA was then used to create an ensemble of possible binding modes for valencene in the SrKO active site (FIG. 8B) (29).

In addition, a Blast search of SrKO against NCBI non-redundant protein sequence library returned no orthologs with sequence identity greater than 80% (except the SrKO itself). The top hits are listed in the Table 5.

TABLE 5

BLAST search with SrKO in preparation of Homology Model

| kaurene oxidase | *Stevia rebaudiana* | 99% | AAQ63464.1 |
|---|---|---|---|
| ent-kaurene oxidase 2 | *Lactuca sativa* | 79% | BAG71198.1 |
| ent-kaurene oxidase 1 | *Lactuca sativa* | 71% | BAG71197.1 |
| ent-kaurene oxidase | *Ricinus communis* | 63% | XP_002510288.1 |

Once the unique activities of SrKO were identified, experiments were conducted to improve its ability to conduct its diverse oxidation of valencene. Using the back-to-consensus mutagenesis strategy, a multiple sequence alignment of P450 enzymes was constructed including sequences (after clustering and elimination of sequences with greater than 90% identity) from a BLAST search of the Uniref100 database using 4 seed kaurene oxidase genes, from a BLAST search of the bacterial proteome using $P450_{BM3}$, $P45_{CAM}$, and $P40_{eryF}$ as seed genes, and the most closely related SrKO homologs. Based on the homology model, the multiple sequence alignment, and the literature, various point mutations and double mutations were designed and tested. These cytochrome P450 derivatives were assessed for improvements in total oxygenated terpene productivity (e.g., total of the major peaks observed by GUMS) in the in vivo testing system described above. Mutagenesis on active site positions guided by the model revealed several variants with significantly improved oxygenated products (Table 6 and Table 7 below).

TABLE 6

Binding pocket mutations and their fold productivity of total oxygenated oil according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| Mutant # (Table 2.1) | Mutants (numbered according to SEQ ID NO: 38) (SEQ ID NO: 106) | Mutants (numbered according to SEQ ID NO: 37) (SEQ ID NO: 108) (Shift value relative to SEQ ID NO: 38: +12) | Mutants (numbered according to SEQ ID NO: 104/ SEQ ID NO: 105 (SEQ ID NO: 61)) (Shift value relative to SEQ ID NO.: 38: +4) | Fold productivity (as measured in mg/L) |
|---|---|---|---|---|
| 38 | I310V | I322V | I314V | 1.5 |
| 37 | I310T | I322T | I314T | 0.0 |
| 42 | V375I | V387I | V379I | 1.4 |
| 41 | V375T | V387T | V379T | 0.0 |
| 19 | M123F | M135F | M127F | 0.0 |

TABLE 6-continued

Binding pocket mutations and their fold productivity of total oxygenated oil according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| Mutant # (Table 2.1) | Mutants (numbered according to SEQ ID NO: 38) (SEQ ID NO: 106) | Mutants (numbered according to SEQ ID NO: 37) (SEQ ID NO: 108) (Shift value relative to SEQ ID NO: 38: +12) | Mutants (numbered according to SEQ ID NO: 104/ SEQ ID NO: 105 (SEQ ID NO: 61)) (Shift value relative to SEQ ID NO.: 38: +4) | Fold productivity (as measured in mg/L) |
|---|---|---|---|---|
| 20 | M123T | M135T | M127T | 0.3 |
| 18 | M123Q | M135Q | M127Q | 0.0 |
| 59 | T487N | T499N | T491N | 2.5 |
| 66 | M123F_T487G | M135F_T499G | M127F_T491G | 0.0 |
| 63 | M123F_T487V | M13SF_T499V | M127F_T491V | 0.0 |
| 62 | M123Q_T487V | M135Q_T499V | M127Q_T491V | 0.0 |
| 59 | T487N_V375F | T499N_V387F | T491N_V379F | 2.2 |
| 59 | T487N_V375A | T499N_V387A | T491N_V379F | 1.8 |
| 59 | T487N_V121A | T499N_V133A | T491N_V125A | 2.0 |
| 59 | T487N_V375M | T499N_V387M | T491N_V379M | 1.9 |
| 59 | T487N_M120L | T499N_M132L | T491N_M124L | 1.8 |
| 59 | T487N_M120I | T499N_M132I | T491N_M124I | 1.8 |
| 59 | T487N_L114V | T499N_L126V | T491N_L118V | 1.4 |
| 59 | T487N_F219L | T499N_F231L | T491N_F223L | 3.5 |
| 59 | T487N_M120V | T499N_M132V | T491N_M124V | 1.1 |
| 59 | T487N_F219I | T499N_F231I | T49IN_F223I | 3.3 |
| 59 | T487N_L114F | T499N_L126F | T491N_L118F | 1.2 |

TABLE 7

Non-binding pocket point mutations and productivity of total oxygenated oil compared to the wild type SrKO (SEQ ID NOS: 38 and 106).

| Mutant # (Table 2.1) | Mutants (numbered according to SEQ ID NOS: 38 and 106) | Mutants (numbered according to SEQ ID NO: 37) (SEQ ID NO: 108) (Shift value relative to SEQ ID NO:38: +12) | Mutants (numbered according to SEQ ID NO: 104/ SEQ ID NO: 105 (SEQ ID NO: 61)) (Shift value relative to SEQ ID NO: 38: +4) | Fold productivity (as measured in mg/L) |
|---|---|---|---|---|
| 53 | G442A | G454A | G446A | 0.849153 |
| 55 | L454M | L466M | L458M | 0.717318 |
| 44 | I378V | I390V | I382V | 0.349005 |
| 47 | V388M | V400M | V392M | 0.792428 |
| 9 | V85I | V97I | V89I | 0.795913 |
| 51 | V413K | V425K | V417K | 0.902039 |
| 60 | P492K | P504K | P496K | 0.131657 |
| 40 | R371I | R383I | R375I | 0.657808 |
| 7 | T80C | T92C | T84C | 0.342501 |
| 23 | A140R | A152R | A144R | 0.014872 |
| 2 | Y59H | Y71H | Y63H | 0.406787 |
| 5 | A67E | A78E | A71E | 0.937429 |
| 8 | M82V | M94V | M86V | 1.585588 |
| 11 | S86N | S98N | S90N | 0.977752 |
| 22 | Y129F | Y141F | Y133F | 0.686276 |
| 24 | K149R | K161R | K153R | 0.990776 |
| 29 | D208E | D220E | D212E | 0.853446 |
| 31 | S267A | S279A | S271A | 0.79152 |
| 32 | H272Q | H284Q | H276Q | 0.958227 |
| 33 | S284C | S296C | S288C | 0.652348 |
| 39 | R371K | R383K | R375K | 1.443497 |
| 45 | H382Y | H394Y | H386Y | 0.609951 |
| 46 | V388Q | V400Q | V392Q | 0.924043 |
| 49 | L400I | L412I | K404I | 0.682775 |
| 50 | V413D | V425D | V417D | 0.039261 |
| 52 | F434L | F446L | F438L | 0.793926 |
| 57 | M464L | M476L | M468L | 0.689696 |
| 58 | M475G | M487G | M479G | 0.573906 |
| 61 | I497L | I509L | I501L | 0.679949 |
| 15 | A116R | A128R | A120R | 0.216353 |
| 1 | L47I | L59I | L51I | 0.88992 |
| 25 | H150F | H162F | H154F | 0.666723 |

Example 4: Isolation and Evaluation of Oxygenated Product

The product derived from oxidation of valencene by the cytochrome P450 enzyme SrKO (SEQ ID NO: 38) was analysed by GC/MS (Agilent 6800; Column: Rtx-5, 0.32 mm×60 m×1.0 μm film thickness; GC Temp. Program: 40° C. for 5 min, increased at 4° C./min to 300° C. and held for 30 min.) resulting in the data provided in Table 8A and 8B.

TABLE 8A

SrKO oxidation of valencene

| Ret.Time | Compound Name | CAS # | GC-FID Area % |
|---|---|---|---|
| 33.762 | dodecane | 112-40-3 | 6.70 |
| 35.440 | glyceryl diacetate I | | 5.26 |
| 38.767 | triacetin | 102-76-1 | 4.48 |
| 39.518 | unknown | | 10.17 |
| 40.176 | unknown | | 7.52 |
| 42.012 | unknown | | 2.53 |
| 44.437 | unknown | | 20.25 |
| 44.816 | valencene | 4630-07-3 | 1.97 |
| 45.546 | nootkatene | 5090-61-9 | 1.09 |
| 46.260 | unknown | | 2.14 |
| 46.395 | unknown | | 6.77 |
| 46.869 | unknown | | 4.01 |
| 47.394 | germacrene D-4-ol | 74841-87-5 | 1.23 |
| 48.273 | unknown | | 1.86 |
| 49.659 | T-muurolol | 19912-62-0 | 0.69 |
| 49.753 | an unknown sesquiterpene | | 0.56 |
| 50.336 | an unknown sesquiterpene | | 0.58 |
| 51.025 | epinootkatol (or alpha nootkatol) | 50763-66-1 | 1.96 |
| 51.430 | Nootkatol (or beta nootkatol) | 50763-67-2 | 3.54 |
| 54.138 | nootkatone | 4674-50-4 | 15.87 |
| 54.501 | 6-isopropenyl-4,8a-dimethyl-4a,5,6,7,8,8a-hexahydro-2(1H)-naphthalenone | 76784-84-4 | 0.84 |
| | TOTAL | | 100.00 |

TABLE 8B

SrKO oxidation of valencene

| Ret.Time | Compound Name | CAS # | GC-FID Area % |
|---|---|---|---|
| 33.763 | dodecane | 112-40-3 | 7.26 |
| 35.470 | glyceryl diacetate I | | 7.07 |
| 38.773 | triacetin | 102-76-1 | 6.19 |
| 39.526 | unknown | | 11.56 |
| 40.179 | unknown | | 8.10 |
| 44.440 | unknown | | 23.95 |
| 44.821 | valencene | 4630-07-3 | 6.88 |
| 45.545 | nootkatene | 5090-61-9 | 2.22 |
| 46.404 | unknown | | 5.08 |
| 46.879 | unknown | | 3.66 |
| 47.399 | germacrene D-4-ol | 74841-87-5 | 2.89 |
| 48.279 | unknown | | 2.27 |
| 49.665 | T-muurolol | 19912-62-0 | 0.94 |
| 50.342 | an unknown sesquiterpene | | 1.71 |
| 51.027 | epinootkatol | 50763-66-1 | 2.48 |
| 51.444 | nootkatol | 50763-67-2 | 5.24 |
| 54.152 | nootkatone | 4674-50-4 | 2.49 |
| | TOTAL | | 100.00 |

Similar analysis was conducted on the product produced by SrKO derivatives. It was confirmed that product profiles are comparable, and that the major products of nootkatone, α-nootkatol, and β-nootkatol can be produced at higher levels based on mutagenesis of SrKO.

The oxygenated oil product can then be extracted from the aqueous reaction medium using an appropriate solvent (e.g., heptane) followed by fractional distillation. The chemical composition of each fraction can be measured quantitatively by GC/MS. Fractions can be blended to generate the desired alpha/beta nootkatol and/or nootkatone ingredients for use in flavour or other applications.

Verification of acceptability can be carried out by direct comparison to a reference nootkatone flavouring product (for example, an existing natural flavouring commercial product obtained from Frutarom) with analysis provided in Table 9.

TABLE 9

Analysis of commercially available natural flavouring nootkatone from Frutarom

| Ret.Time | Compound Name | CAS # | GC-FID Area % |
|---|---|---|---|
| 42.307 | limonene glycol | 1946-00-5 | 0.201 |
| 42.792 | decanoic acid | 334-48-5 | 0.115 |
| 49.405 | valencene | 4630-07-3 | 0.039 |
| 50.362 | delta-cadinene | 483-76-1 | 0.268 |
| 52.757 | alpha-elemol | 639-99-6 | 2.178 |
| 53.11 | spathulenol | 6750-60-3 | 0.264 |
| 53.423 | caryophyllene oxide | 1139-30-6 | 0.394 |
| 53.748 | viridiflorol | 552-02-3 | 0.061 |
| 54.225 | unknown sesquiterpenoid (MW = 220, tent) | | 0.113 |
| 54.853 | unknown | | 2.985 |
| 55.386 | unknown | | 2.251 |
| 55.97 | T-muurolol | 19912-62-0 | 0.399 |
| 56.192 | bulnesol | 22451-73-6 | 0.722 |
| 56.523 | 7(11), 4b-selinenol; tentative | | 1.425 |
| 56.65 | unknown (MW = 232, tent) | | 0.663 |
| 56.937 | beta-sinensal | 3779-62-2 | 0.914 |
| 57.449 | unknown | | 0.285 |
| 57.589 | cedrenal; tentative | | 0.438 |
| 58.189 | unknown sesquiterpenoid(s) | | 1.077 |
| 58.73 | unknown sesquiterpenoids (MW = 220, 222, tent) | | 0.537 |
| 59.102 | beta,gamma-nootkatone | 35936-67-5 | 1.805 |
| 59.32 | myristic acid | 544-63-8 | 0.058 |
| 59.537 | 1,10-dihydronootkatone | 20489-53-6 | 0.582 |
| 59.75 | a nootkatone isomer | | 0.442 |
| 60.507 | nootkatone isomers (2); tentative | | 0.812 |
| 60.782 | unknowns (2) | | 0.605 |
| 61.034 | hexadecanal | 629-80-1 | 0.302 |
| 62.93 | nootkatone | 4674-50-4 | 74.287 |
| 63.057 | 3,11-eudesmadiene-2-one (5S,7R,10R) | 86917-81-9 | 1.909 |
| 63.14 | unknown (MW = 234, tent) | | 0.18 |
| 63.26 | unknown (MW = 232, tent) | | 0.105 |
| 64.112 | heptadecanal | 629-90-3 | 0.344 |
| 64.403 | unknown sesquiterpenoid | | 0.446 |
| 65.16 | unknown sesquiterpenoid | | 0.147 |
| 65.384 | palmitic acid | 57-10-3 | 0.154 |
| 65.599 | alpha-camphorene | 532-87-6 | 0.249 |
| 65.75 | unknown(s) | | 0.054 |
| 65.878 | dehydro-alpha-vetivenone; tentative | | 0.115 |
| 66.056 | nootkatone, 9-oxo | 86925-44-2 | 0.172 |
| 66.371 | ethyl palmitate | 628-97-7 | 0.185 |
| 66.856 | cis-9-octadecenal | 2423-10-1 | 0.239 |
| 66.986 | unknown sesquiterpenoids | | 0.114 |
| 67.556 | octadecanal | 638-66-4 | 0.096 |
| 74.551 | osthol | 484-12-8 | 0.367 |
| 80.543 | isomerazin | 1088-17-1 | 0.112 |
| 84.671 | unknown (MW = 298) | | 0.07 |
| | TOTAL | | 99.28 |

Two exemplary methods of verification are: 1) Duo-Trio Test, 2) Forced-Choice Preference Test. In one method, the SrKO derived product can be compared to the reference product (for example a commercial Frutarom sourced nootkatone ingredient) in a duo-trio test to determine if the ingredients can be distinguished with statistical significance.

This test will determine if the two nootkatone containing ingredients at least match one another based on perception of overall taste and aroma profiles. In the second test, assuming the two products are determined to be distinguishable in a duo trio test, one could determine if the SrKO derived nootkatone is preferred by conducting a forced-choice preference test. More details on these tests are provided as follows.

Duo-Trio Test:

A Duo-Trio Test can be conducted to determine if the blended fractions obtained from the SrKO derived nootkatone flavouring can be distinguished with statistical significance from a reference nootkatone product (for example, a commercially available nootkatone flavouring sourced from Frutarom). The test will determine if the nootkatone flavouring ingredients at least match in terms of overall taste and aroma profile typically conducted in a sugar/acid solution but could also be evaluated in water or sugar water.

TABLE 10

| Name | Finished Beverage |
|---|---|
| Spring Water | 1000 g |
| Citric Acid | 0.1% |
| Sucrose | 8% |
| Nootkatone flavouring | 2.5 ppm |

Methodology: One ounce of the reference sample, labelled "REF" is presented first followed by a one ounce sample of the reference and a one ounce sample of the test sample presented blindly in random order to a minimum of 15 discriminator panellists. The panellists are asked which blind sample is the same as the reference sample. The data are subjected to a statistical analysis to determine the degree of difference between the test sample and the reference control.

Forced-Choice Preference Test:

Assuming a difference is observed between nootkatone flavouring derived from SrKO oxidation and the reference nootkatone product (for example, a Frutarom nootkatone flavouring), a Forced-Choice Preference Test can be conducted to determine if one sample is preferred over the other as a nootkatone flavouring ingredient. The test can be conducted in sugar/acid solution, sugar water or water.

TABLE 11

| Name | Finished Beverage |
|---|---|
| Spring Water | 1000 g |
| Citric Acid | 0.1% |
| Sucrose | 8% |
| Nootkatone flavouring | 2.5 ppm |

Methodology: One ounce of each test sample is presented blindly in random order to a minimum of 40 discriminator panellists. The panellists are asked which blind sample is preferred based on aroma and taste when consumed orally and are forced to make a decision. The data are subjected to a statistical analysis to determine the degree of preference for one sample over the other.

Example 5: N-Terminal Anchor Engineering

Figure 9:
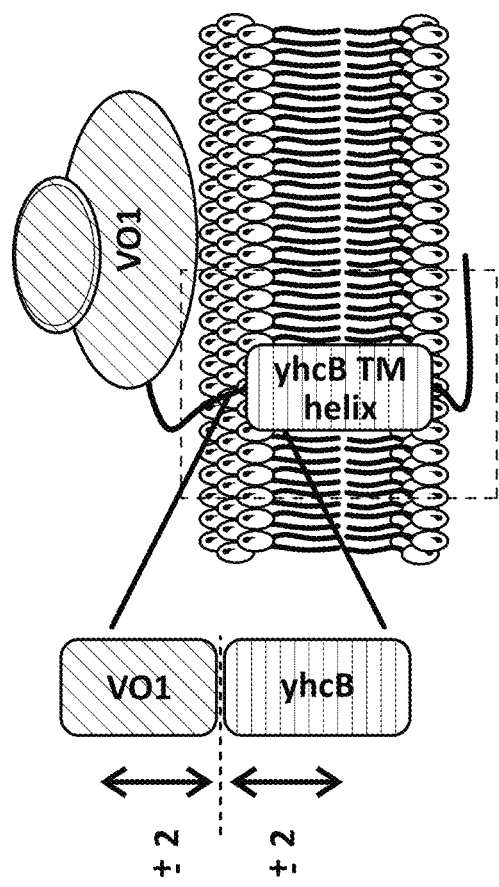
FIG. 9 shows optimizing the valencene oxidase (VO) N-terminal membrane anchor. The N-terminus of *E. coli* yhcB was selected as a membrane anchor sequence, which provides a single-pass transmembrane helix. The length of the anchor (from 20 to 24 amino acids) and the VO N-terminal truncation length (from 28 to 32 amino acids) were screened for improvements in oxygenation titer.

To optimize membrane interaction of the initial SrKO variants (referred to in these examples as Valencene Oxidase 1, or VO1), E. coli proteins anchored in the inner membrane with a cytoplasmic C-terminus were identified. An N-terminal sequence of E. coli yhcB was selected, which provides a single-pass transmembrane domain. 20-24 amino acids from the N-terminus of yhcB was exchanged for the original membrane anchor sequence MALLLAVF (SEQ ID NO:112), and the size of the SrKO N-terminal truncation was varied from 28 to 32. See FIG. 9. VO1 was expressed under control of a T7 promoter on a p5 plasmid. SrCPR was expressed independently from the chromosome. Strains were cultured in 96 deepwell plates at 30° C. for 48 hours, in R-medium plus glycerol and dodecane overlay as already described.

Figure 10:
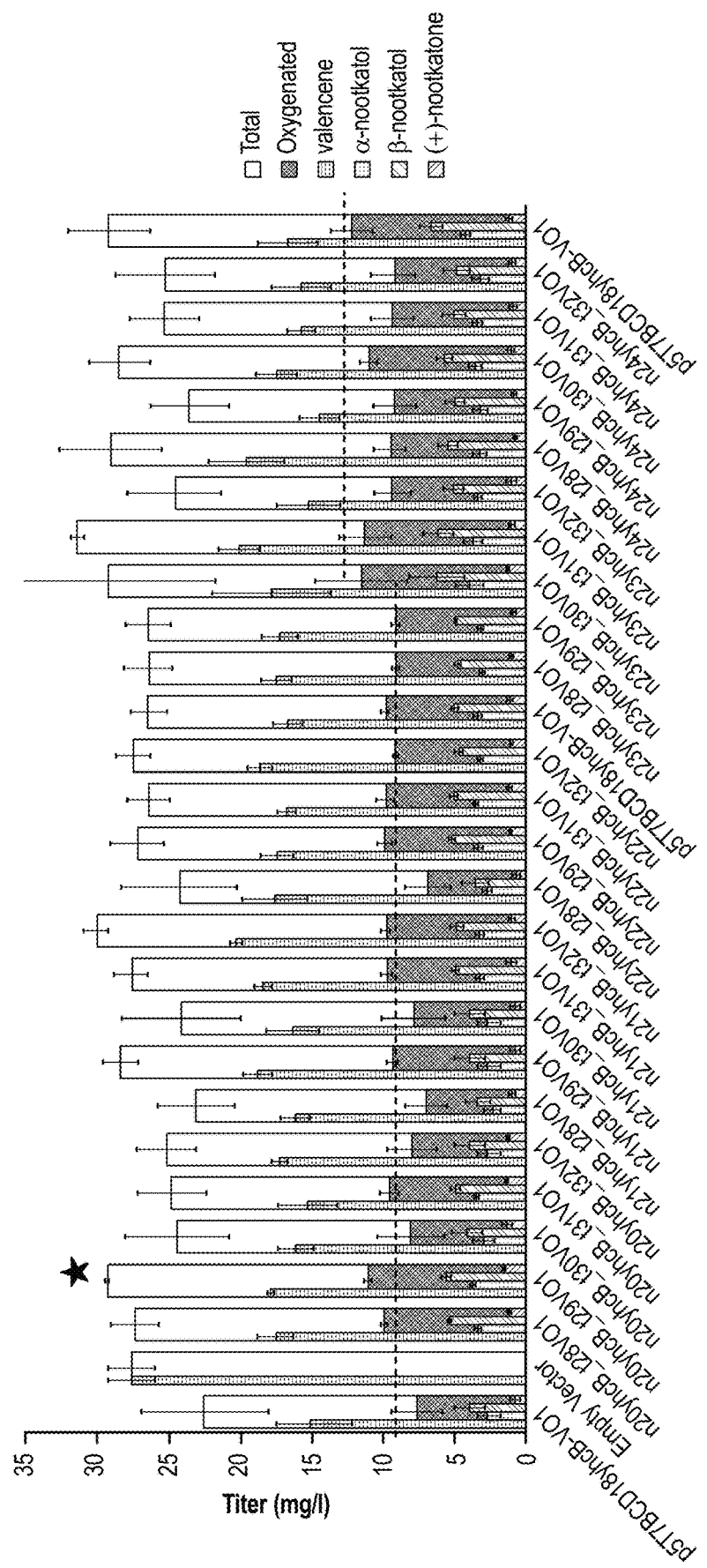
FIG. 10 shows that a truncation length of 29, and a 20 amino acid N-terminal anchor based on *E. coli* yhcB, led to a 1.2-fold increase in total oxygenated titer compared to the average of controls.
Figure 11:
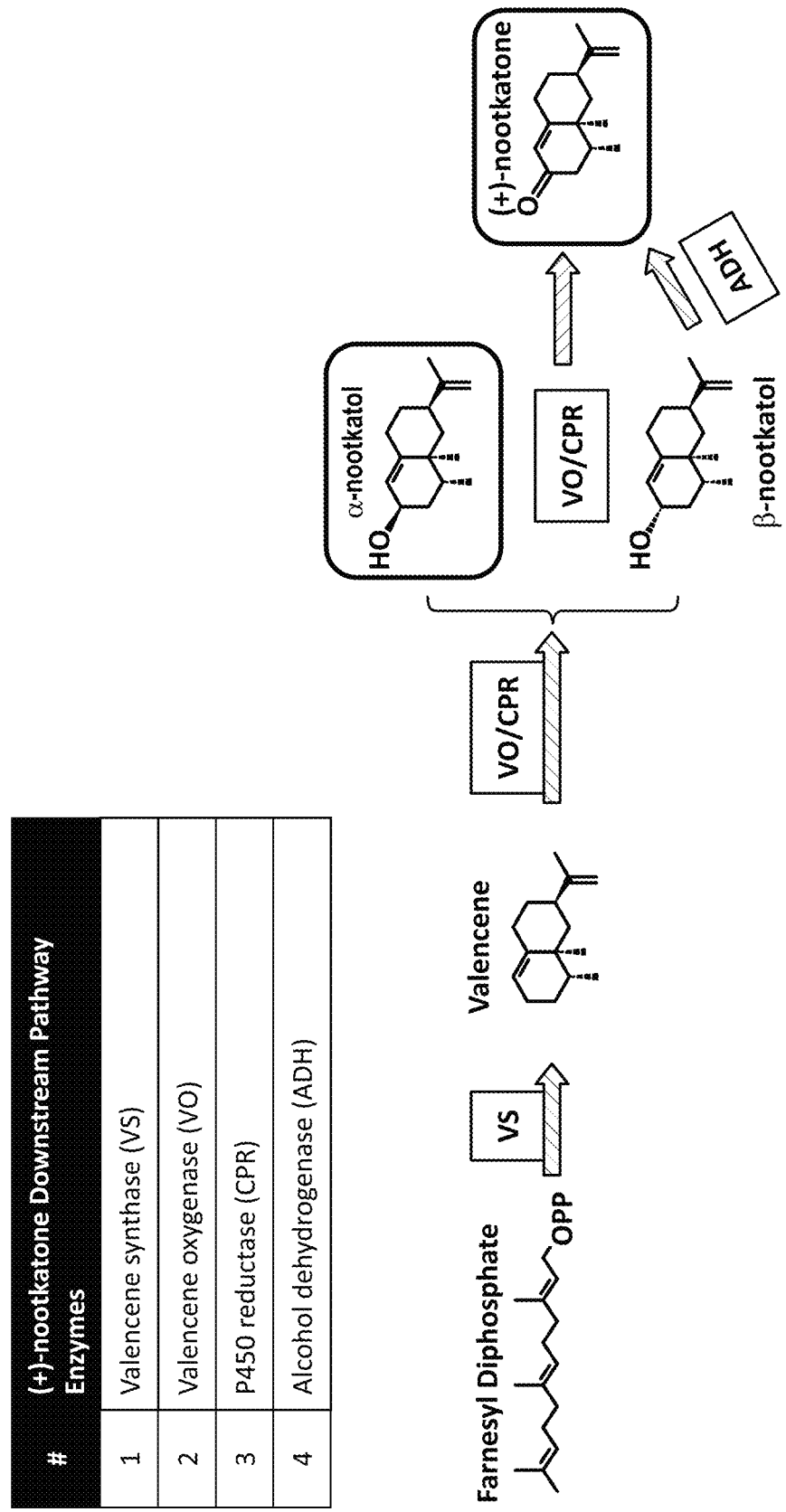
FIG. 11 illustrates an exemplary downstream pathway for expression in the host cell, for conversion of farnesyl diphosphate to nootkatone. Farnesyl diphosphate (produced from IPP/DMAPP by an expressed Farnesyl Pyrophosphate Synthase) is converted to valencene by the action of a Valencene Synthase (VS), which is oxidized by a Valencene Oxidase (VO), such as SrKO or an SrKO derivative described herein. The VO cofactor is regenerated by a cytochrome P450 reductase (CPR). The products of oxidation by VO can include nootkatol (α and β) and nookatone, which can be further directed to nootkatone by the action of an Alcohol Dehydrogenase (ADH).
Figure 12B:
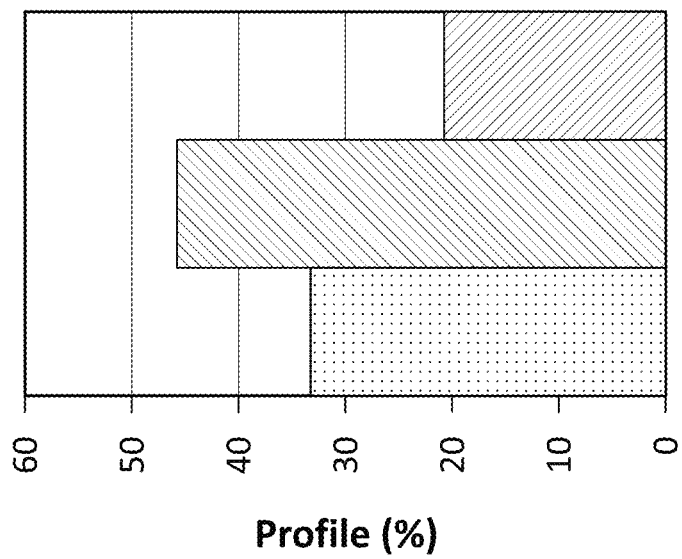
FIG. 12 (A and B) shows the oxygenation profile for a strain expressing VO1-L-SrCPR. The oxygenation profile includes the single oxygenation products of β-nootkatol and α-nootkatol along with the two-step oxygenation product, nootkatone. Panel (A) shows the profile in mg/L. Panel (B) shows the profile by percent of total oxygenated product (the legend for panels (A) and (B) are the same).
Figure 12A:
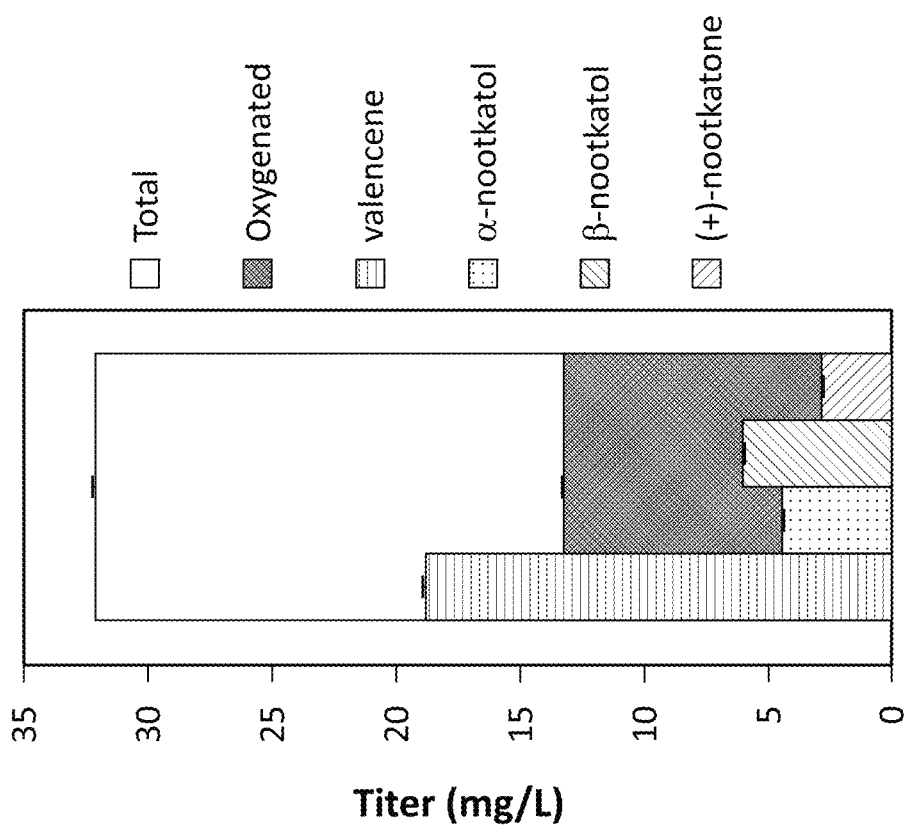

As shown in FIG. 10, n20yhcB_t29VO1 exhibited 1.2-fold productivity in total oxygenated titer compared to the average of controls. N20yhcB_t29VO1 exhibited a total oxygenated titer approximately 1.8 fold of the original 8RP anchor (not shown).

Example 6: Mutational Analysis of VO1

Mutational analysis of VO1 was conducted in an effort to increase oxygenated titers, as well as to produce altered product profiles. Strain MB2509 (MP6-MEP MP1-ScFPPS Fab46-VS2 MP6-ScCPR) was used as the background, which when transformed with a p5-T7-yhcB-VO1 plasmid produces about 18% nootkatone, about 35% α-nootkatol, and about 47% β-nootkatol, with a complete conversion of valencene. Strains were evaluated for higher production of nootkatone and α-nootkatol.

Guided by the homology model based on P450 17A1 (Example 3) site-saturation mutagenesis of the VO active site was conducted at 18 positions, and 5 paired position libraries were constructed. First shell residues were identified through substrate docking, and non-conserved first shell residues were selected based on relative proximity and position for altering the binding pocket geometry. Paired position libraries were constructed by overlap extension PCR and Gibson assembly.

TABLE 12

Paired Position Libraries
(numbered according to SEQ ID NOS: 37 and 108)

| Library | Pos. 1 | Allowed AA | Pos. 2 | Allowed AA |
|---|---|---|---|---|
| 1 | V387 | F, L, I, S, P, T, A, M | P388 | S, T, A |
| 2 | M132 | F, L, I, V, S, P, T, A | V133 | F, L, I, S, P, T, A, M |
| 3 | L123 | F, I, V, S, T, A, P, M | L126 | F, I, V, S, T, A, P, M |
| 4 | V387 | F, L, I, S, P, T, A, M | I322 | F, L, V, S, P, A, M, T |
| 5 | I322 | F, L, V, S, P, A, M, T | V133 | F, L, I, S, P, T, A, M |

Strains were evaluated as in Example 4 for total oxygenation of valencene, and ratio of α- to β-nootkatol. Strains were evaluated at 30° C. and 22° C.

Primary screening of paired position libraries revealed that many of the variants lost activity. Library 3 contained variants with improved activity at 22° C. but not 30° C. Thus, introducing two or more mutations simultaneously in the first shell residues can be determimental to activity.

TABLE 13

The following single position SSM was conducted
(numbered according to SEQ ID NOS: 37 and 108)

| Residue | Location |
|---|---|
| I390 | Channel |
| L392 | Channel |

TABLE 13-continued

The following single position SSM was conducted
(numbered according to SEQ ID NOS: 37 and 108)

| Residue | Location | |
|---|---|---|
| V387 | 1st Shell | |
| E323 | 1st Shell | I helix |
| I322 | 1st Shell | I helix |
| T499 | 1st Shell | |
| Q500 | 1st Shell | |
| L231 | 1st Shell | F helix |
| L123 | 1st Shell | B-C loop |
| L126 | 1st Shell | B-C loop |
| V125 | 1st Shell | B-C loop |
| V133 | 1st Shell | F87 on BM3 |
| T131 | Channel | |
| M135 | 1st Shell | |
| L234 | 1st Shell | F helix |
| P238 | 1st Shell | F-G loop |
| M132 | 1st Shell | B-C loop |
| P388 | 1st Shell | |

Several variants improved oxygenated titers up to 1.7-fold or improved α/β-LGN ratios up to 3.8-fold. Mutations at positions E323, I390, and Q500 showed several hits with improved oxygenation titer and/or improved α/β profile, and these positions were selected for secondary screening.

Figure 13A:
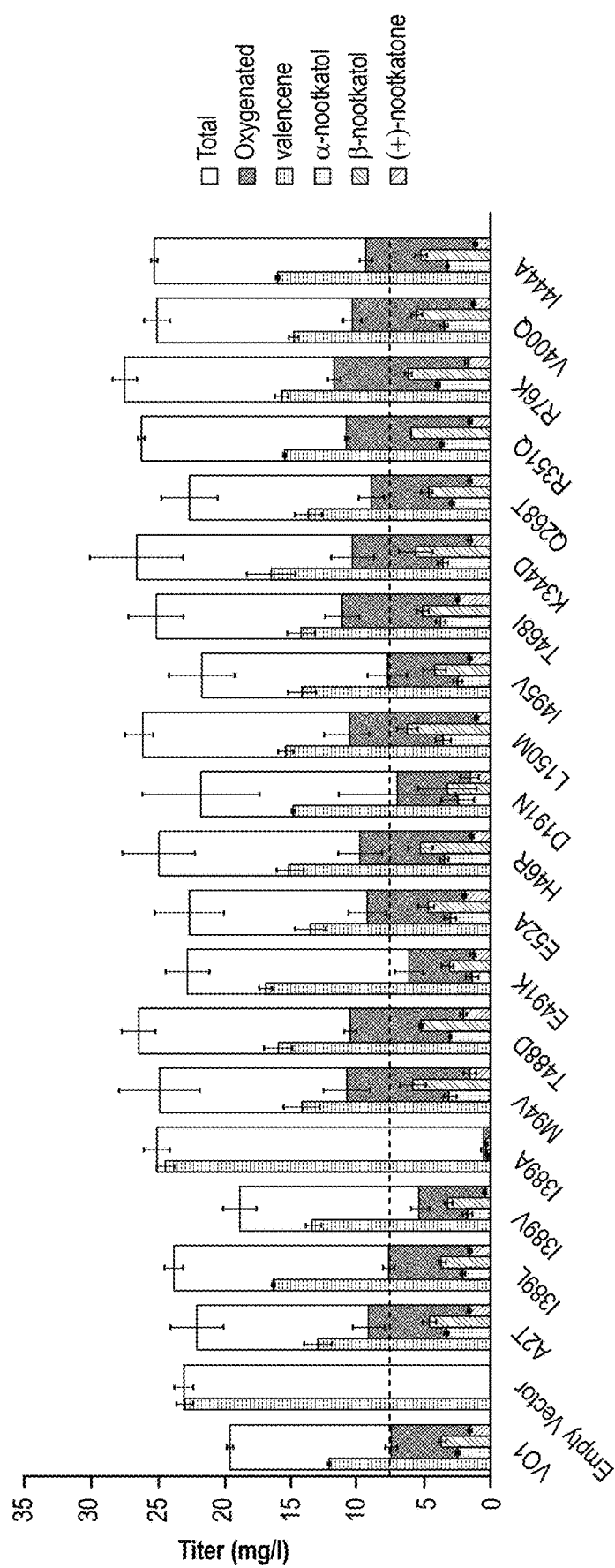
FIG. 13 (A and B) shows evaluation of mutations identified using a back-to-consensus strategy in wild-type SrKO, translated into an engineered valencene oxidase background (n22yhcB_t30VO1 (SEQ ID NO: 104)). More than 50% of the mutations resulted in a 1.2 to 1.45 fold improvement in total oxygenated titers. Panel (A) shows titer in mg/L. Panel (B) shows fold change in oxygenated titer and ratio of a/P nootkatol.
Figure 13B:
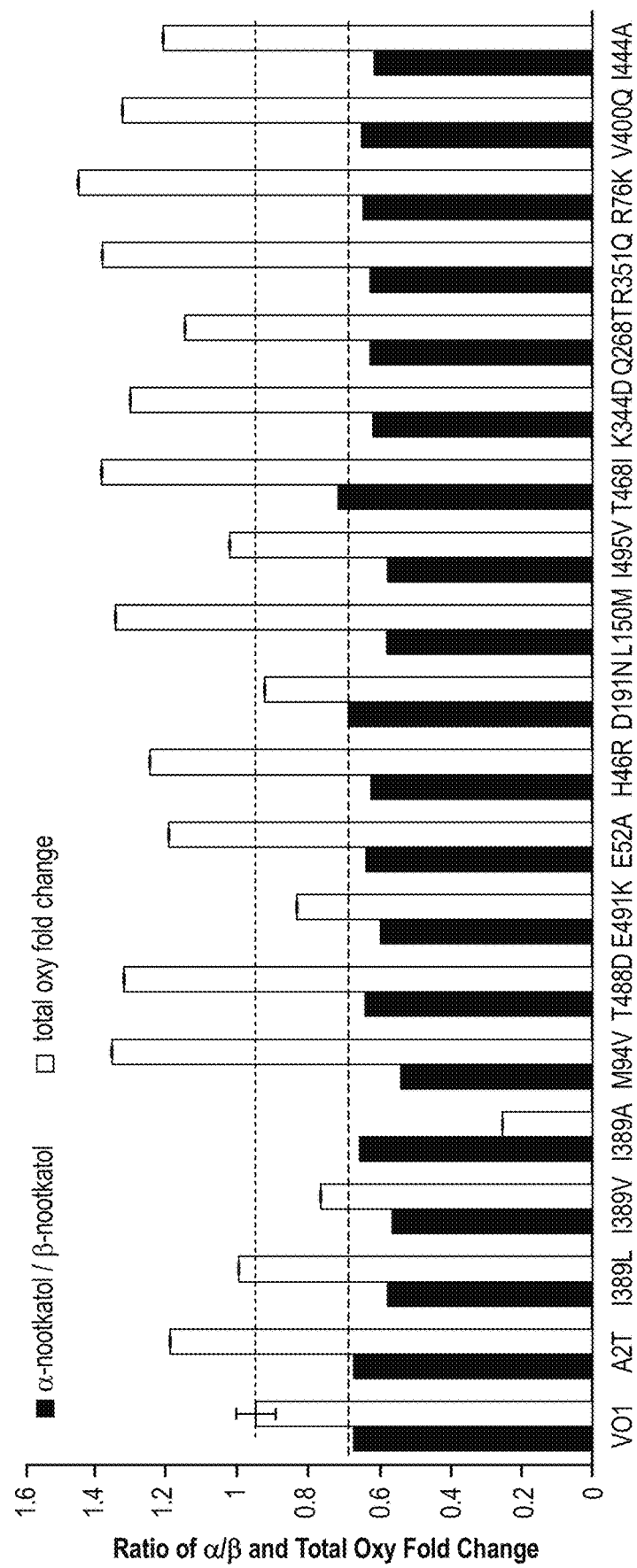

Next, back-to-consensusmutations (19 mutants) were screened in the VO1 background. Using the screening process described in Example 3, the following mutations were screened: A2T, I389L, I389V, I389A, M94V, T488D, E491K, E52A, H46R, D191N, L150M, I495V, T468I, K344D, Q268T, R351Q, R76K, V400Q, and I444A (numbered according to SEQ ID NO: 37). As shown in FIG. 13A, more than 50% of the mutations resulted in 1.2 to 1.45 times oxygenated titers (shown as mg/L), without dramatic shifts in product profile. Improvements were seen with A2T, M94V, T488D, E52A, H46R, L150M, T468I, K344D, Q268T, R351Q, R76K, V400Q, and I444A, which were selected for secondary screening. FIG. 13B shows the same screen plotted versus fold total oxygenated product change and α-/β-nootkatol ratio.

Figure 14:
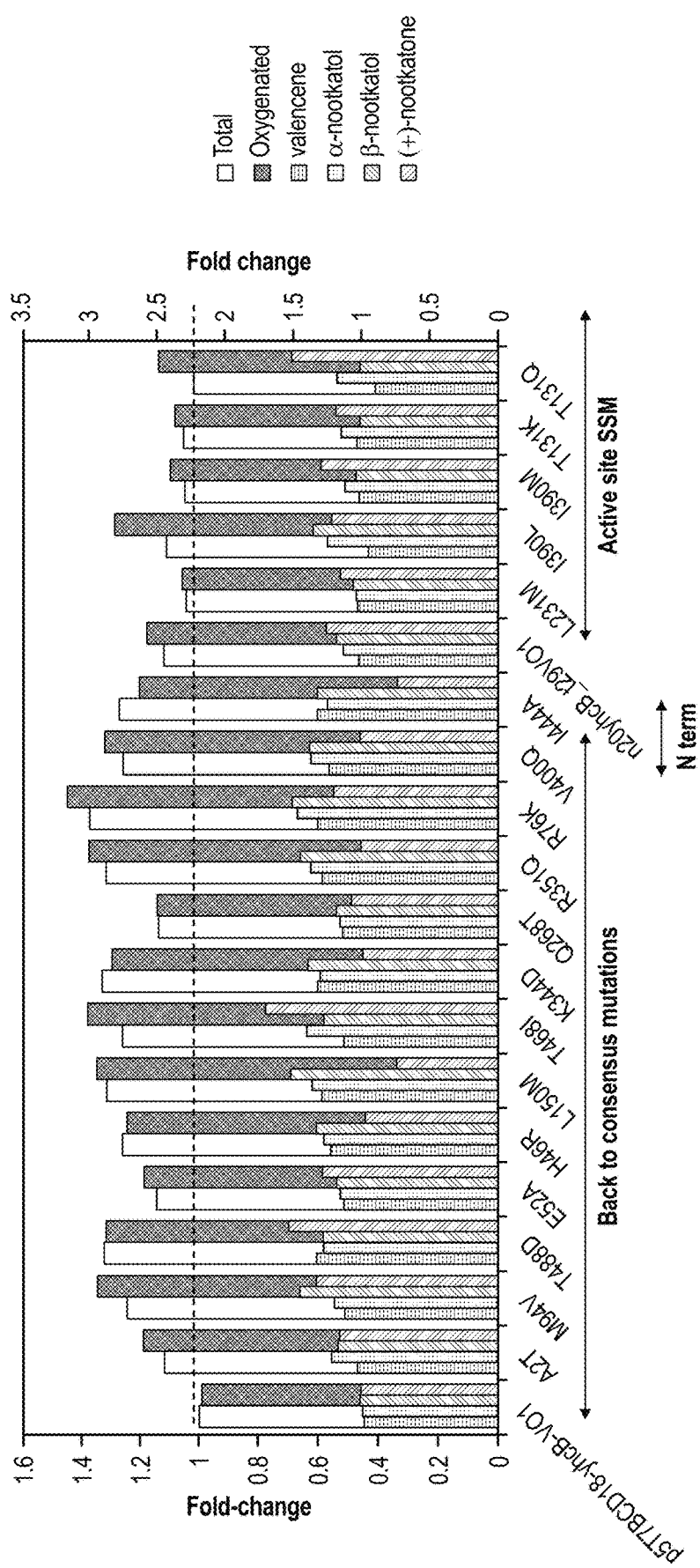
FIG. 14 shows results of secondary screening of back-to-consensus mutations, N-terminal anchor optimization, and site-saturation mutagenesis (SSM). Several mutations were identified that show a 1.1 to 1.4-fold improvement in oxygenated titers.
Figure 15:
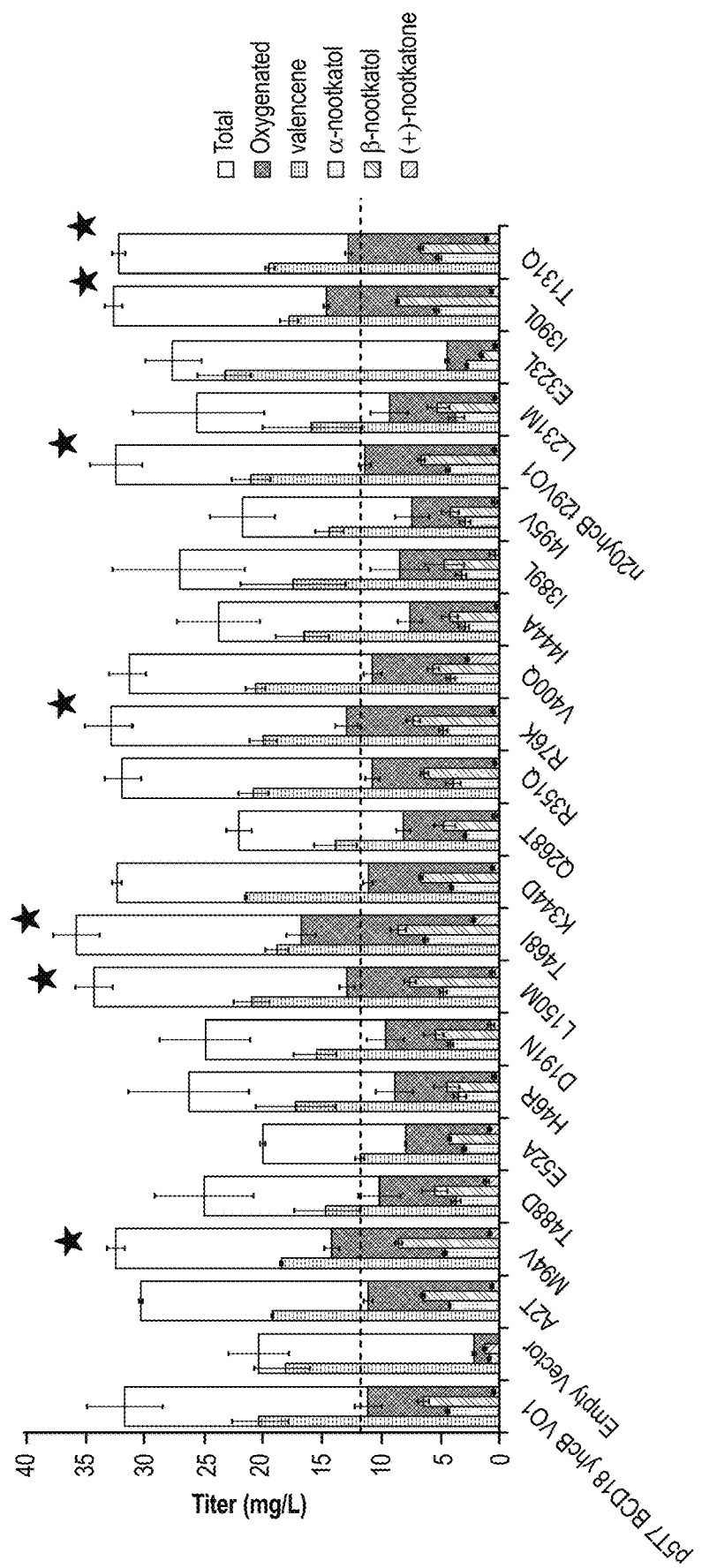
FIG. 15 shows performance of select VO1 variants at 33° C. Six mutations were identified that maintained improved productivities at 33° C.

Lead variants from active site SSM (L231M, I390L, I390M, T131K, and T131Q), the N-terminal anchor variant n20yhcB_t29VO1, and back-to-consensus mutagenesis were selected, and re-screened. The results of this secondary screen are shown in FIG. 14. Several mutations showed a 1.1-1.4-fold improvement in oxygenated titers. To narrow the list of mutations for recombination, the same mutations were screened at 33° C. to differentiate stabilizing mutations which could enable a process shift to higher temperature. As shown in FIG. 15, six mutations (M94V, L150M, T468I, R76K, I390L, and T131Q) maintained improved productivities at 33° C. These six mutations, in addition to the lead N-terminal anchor, were selected for recombination.

Example 7: SrKO Recombination Library Screening

The seven mutations selected after secondary screening (Example 6) were randomly incorporated into a VO recombination library by allowing either the variant or wild type at each site. The background strain was MB2509 (EGV G2 MP6-CPR)+pBAC-T7-BCD7-yhcB-VO.

Figure 16A:
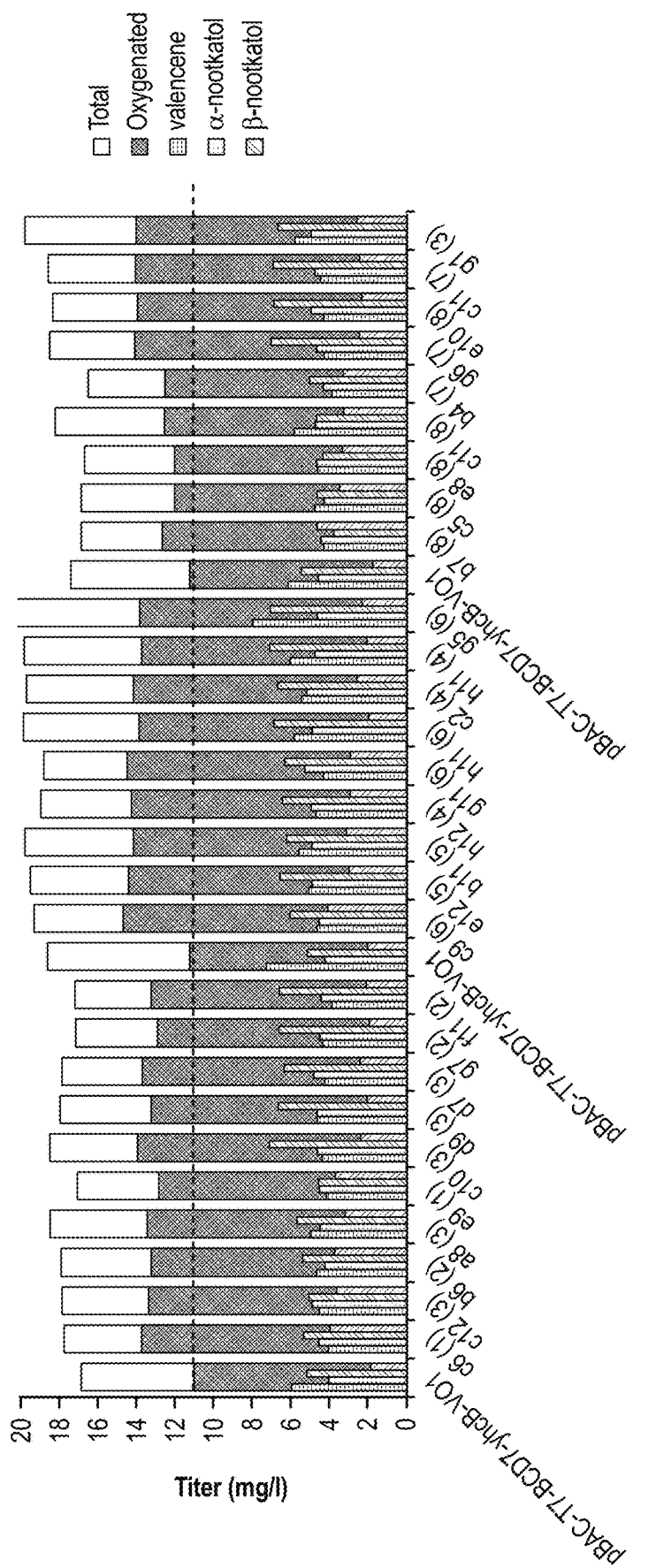
FIG. 16 (A and B) shows results from primary screening of the recombination library. Several variants (shown) exhibited up to 1.35-fold improvement in oxygenated product titer. There was a shift in profile to more (+)-nootkatone and higher oxygenation capacity for select variants. Panel (A) shows oxygenated product in mg/L. Panel (B) plots the fold change in oxygenation capacity (nootkatols require only one oxygenation cycle from valencene, while nootkatone requires two oxygenation cycles).
Figure 16B:
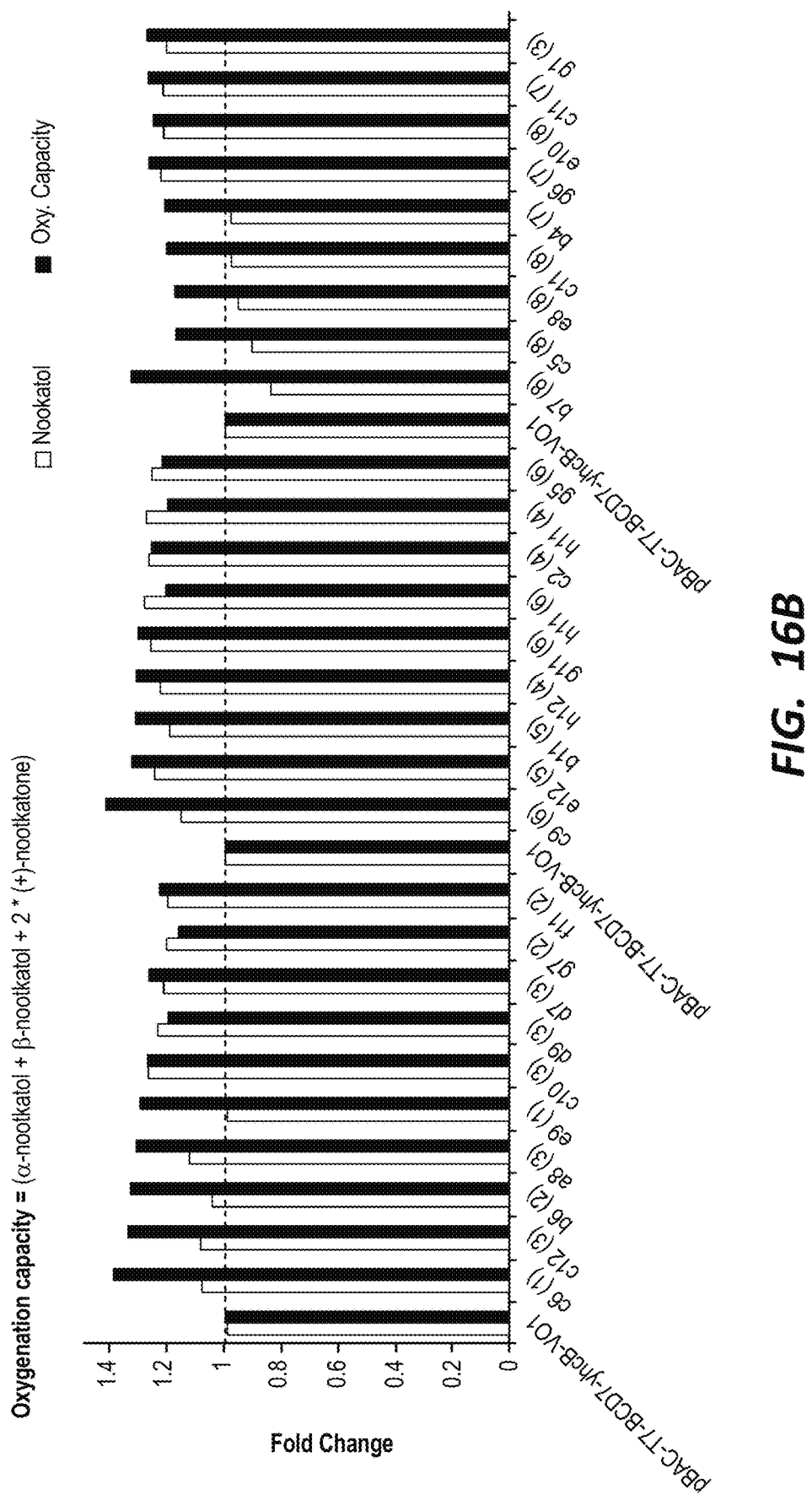

Primary screening at 30° C. (using the same process described in Example 5) identified several variants with up to 1.35-fold improvement in oxygenated product titers, compared to VOL. Further, select variants showed a shift in production to nootkatone, suggesting higher P450 activity (since production of nootkatone requires two oxygenation cycles). Results of primary screening are shown in FIG. 16A (strain versus titer in mg/L). FIG. 16B presents the same screen shown based on oxygenation capacity (total of nootkatone, α-nootkatol, and β-nootkatol).

Figure 17:
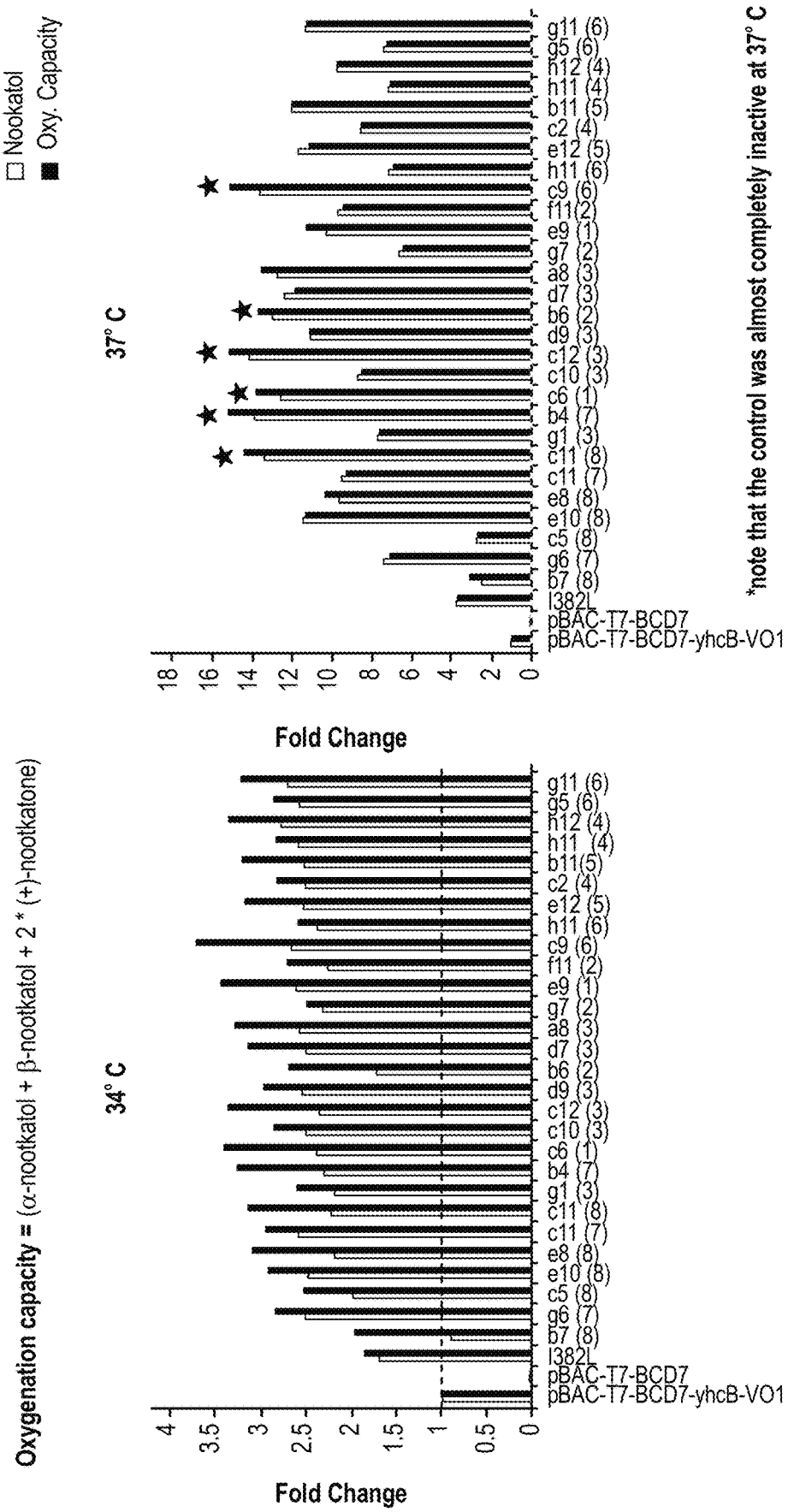
FIG. 17 shows oxygenation capacity at 34° C. and 37° C. for select VO recombination library variants.
Figure 18:
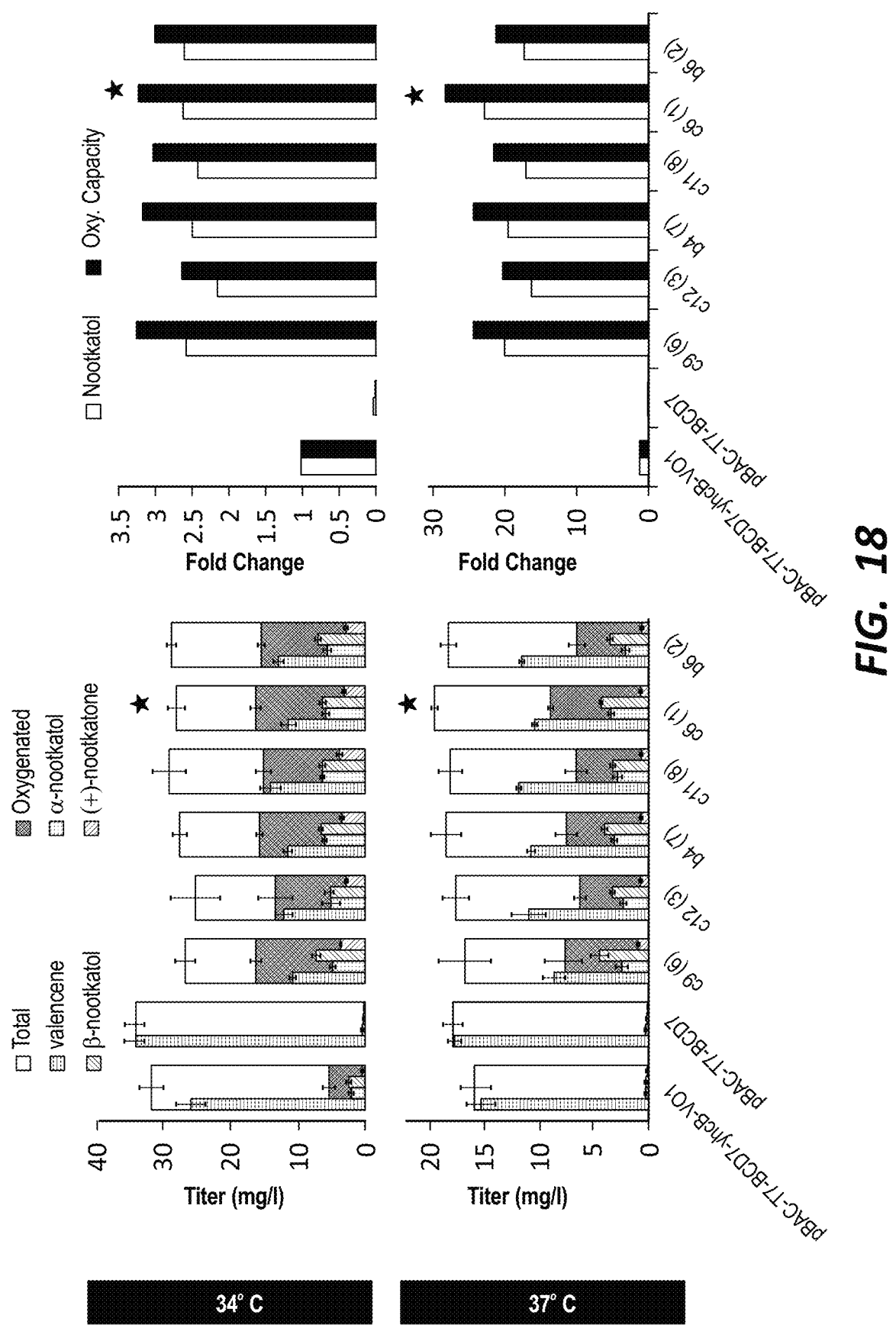
FIG. 18 shows oxygenation titer at 34° C. and 37° C. after re-screen of lead VO variants. C6(1) (R76K, M94V, T131Q, I390L, T468I) had the highest oxygenation capacity at 37° C., and was designated VO2 (SEQ ID NO: 111).
Figure 19:
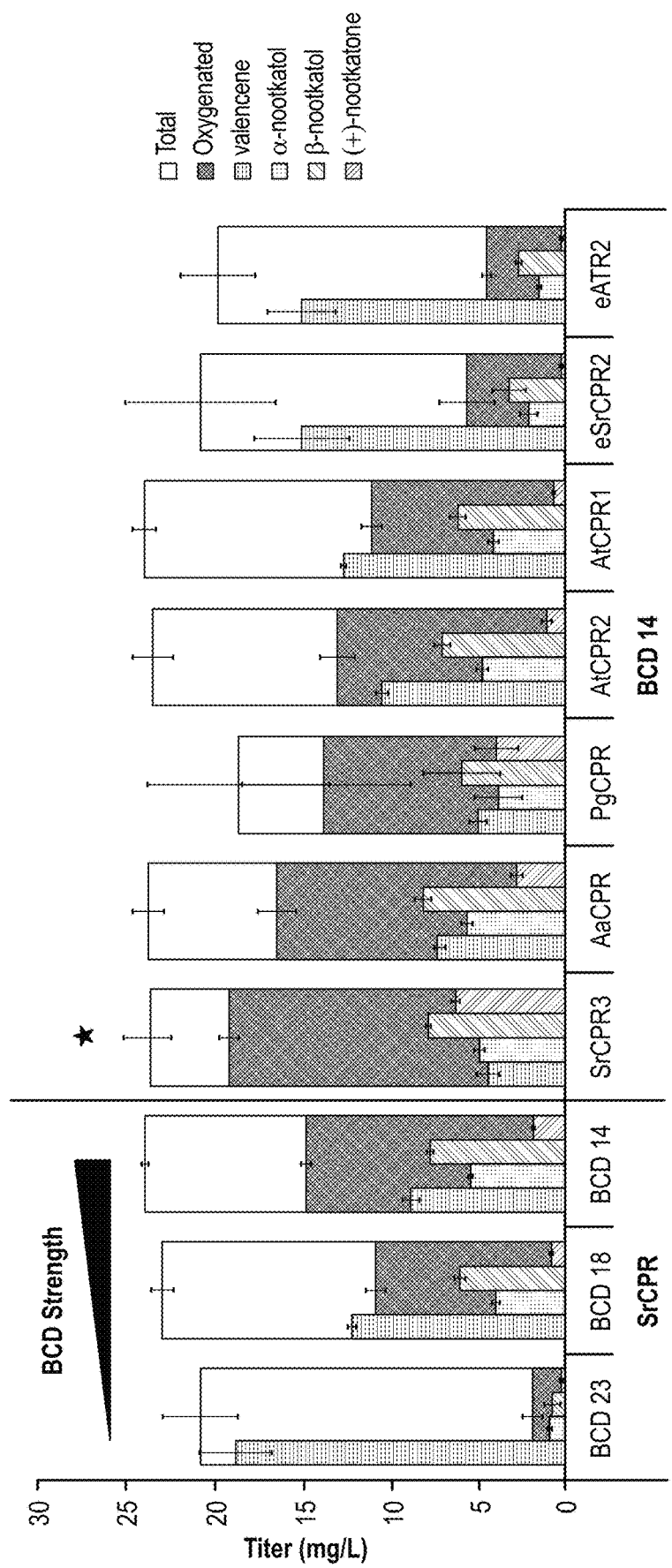
FIG. 19 shows screening of cytochrome P450 reductase (CPR) orthologs for enhanced valencene oxidase activity (30° C.). SrCPR3 shows increased oxygenation titer and higher production of Nootkatone.

The recombination variants were then screened at 34° C. and 37° C. to select leads with improved activity and stability at higher temperature. The results of the secondary screen are shown in FIG. 17. While the control was almost completely inactive at 37° C., six leads showed promising activity at the higher temperatures, and were selected for further screening (c11(8), b4(7), c6(1), c12(3), b6(2), and c9(6)). Based on this further screening (FIG. 18) c6(1) was selected as the best variant based on oxygenation capacity. Variant c6(1) was further modified to generate V02 (SEQ ID NO: 111). The six leads contain the following sets of mutations.

TABLE 14

Sets of mutations in lead variants from recombination library (shown relative to SEQ ID NOS: 37 and 108).

| | N20_t29yhcB | R76K | M94V | T131Q | L150M | I390L | T468I | A39H | Others |
|---|---|---|---|---|---|---|---|---|---|
| c9(6) | | | X | | | X | X | | V146L |
| c12(3) | | X | | X | | X | X | | |
| b4(7) | | | X | X | | X | X | X | |
| c11(8) | X | X | | X | | X | X | X | |
| c6(1) | | X | X | X | | X | X | | |
| b6(2) | | X | X | | | | X | | |

FIG. 23 (A and B) shows alignments of several engineered valencene oxidase (VO) variants as described herein, and highlights select mutations evaluated in the screening process. In FIG. 23A: 8rp-t20SrKO (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO: 104) has a 30-amino acid truncation of the SrKO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30VO2 (SEQ ID NOS: 61 and 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 23B, point mutations in VO0 (SEQ ID NO: 109), VO1 (SEQ ID NO: 110), and VO2

(SEQ ID NO: 111) are shown against wild-type SrKO (SEQ ID NO: 108) (all shown with the wild-type SrKO N-terminus for convenience).

Example 8: Cytochrome P450 Reductase Screening

A set of cytochrome P450 reductases were screened for improved activity with VO1. This example was done using the strain MB2459 as the background, with pBAC-T7-BCD7-VO1(I382L)-T7BCDx-CPRx. BCD stands for BiCistronic Design, and is described in Mutalik et. al. Nature Methods 2013(10)4:354. Lower BCD numbers refer to higher translation rate. CPRs included SrCPR (SEQ ID NO: 62), SrCPR3 (SEQ ID NO: 80), AaCPR (SEQ ID NO: 68), PgCPR (SEQ ID NO: 82), AtCPR2 (SEQ ID NO: 72), AtCPR1 (SEQ ID NO: 70), eSrCPR1 (SEQ ID NO: 76), and eATR2 (SEQ ID NO: 74). Strains were tested as in Example 5, at 30° C.

Figure 20:
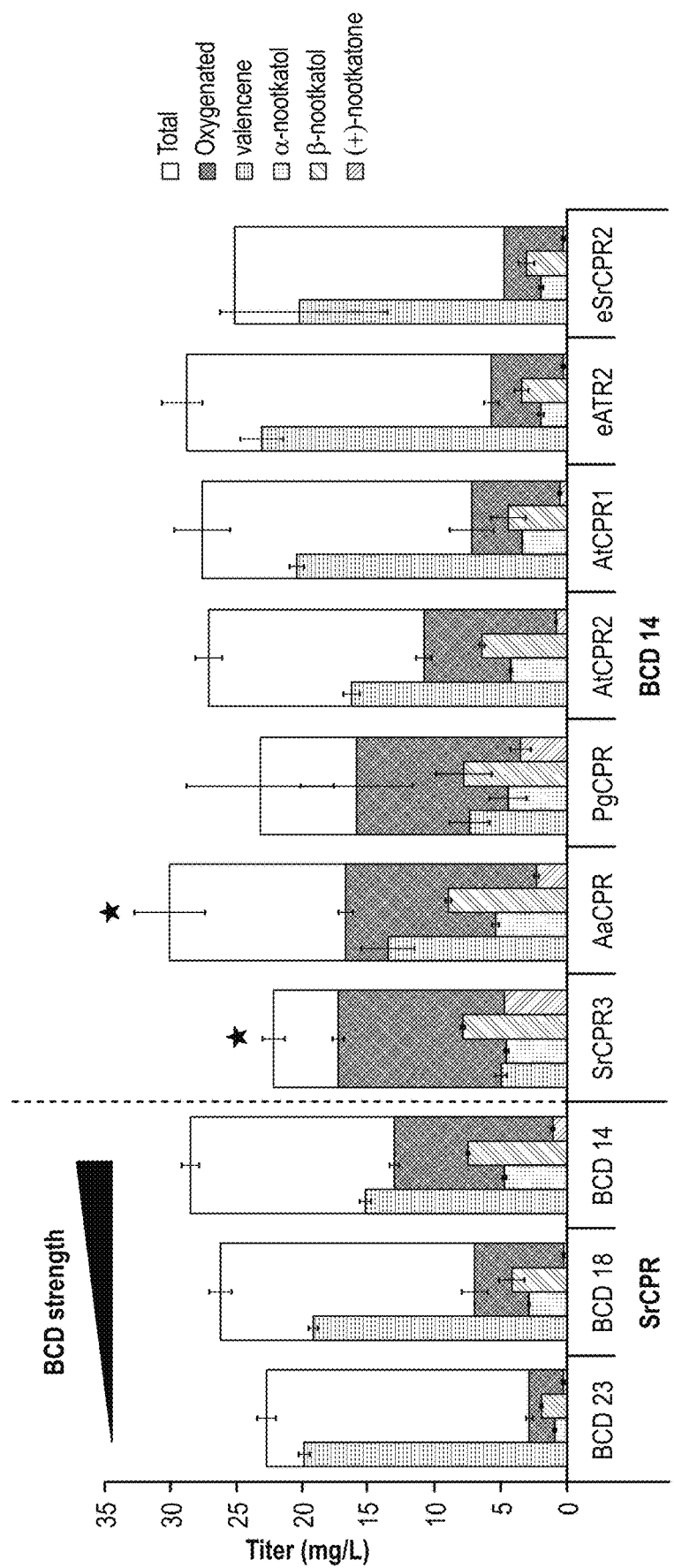
FIG. 20 shows screening of CPR orthologs at 34° C. SrCPR3 and AaCPR exhibit ~1.3-fold improvement in oxygenated titer, even at the higher temperature.

As shown in FIG. 20, SrCPR3, which was obtained through RNA sequencing studies, exhibited a 1.3-fold improvement in oxygenated titer.

The CPR orthologs were retested at 34° C. The results are shown in FIG. 20. Both SrCPR3 (SEQ ID NO: 80) and AaCPR (SEQ ID NO: 68) exhibited a 1.3-fold improvement in oxygenated titer, even at the higher temperature. Oxygenated titers are comparable to those obtained at 30° C.

Example 9: Alcohol Dehydrogenase Enzymes to Alter Product Profile

The ability of alcohol dehydrogenases to convert nootkatols to nootkatone was evaluated. The following ADH enzymes were evaluated:

TABLE 15

| \multicolumn{3}{c}{CPR enzymes} | | |
| --- | --- | --- |
| Gene | UniProtID | Organism |
| reCDH | Q9RA05 | *Rhodococcus erythropolis* |
| csDH1 | A0A067H4B8 | *Citrus sinensis* |
| csDH2 | A0A067H4S0 | *Citrus sinensis* |
| csDH3 | | *Citrus sinensis* |
| vvDH | F6GX78 | *Vitis vinifera* |
| voDH1 | | |
| csABA2 | A0A067DRA0 | *Citrus sinensis* |
| csDH | A0A0AOKNF1 | *Cucumis sativus* |
| bdDH | I1GLS4 | *Brachypodium distachyon* |
| zzSDR | F1SWA0 | *Zingiber zerumbet* |

Strains were evaluated as in Example 5, using MB2490 as the background strain (MP6-MEP FAB46-ScFPPS-L-VS1 MP6-VO1-o-SrCPR+p5-T7-BCD14-ADH). Briefly, MP6, Fab46 and T7 refer to the promoter for the attached gene or operon. Here MEP is an operon overexpressing *E. coli* dxs, idi, and ispDF genes. The L between ScFPPS and VS1 refers to a short polypeptide linker encoding (GSTGS) while -o-between VO1 and SrCPR refers to an operonic construction in which an RBS sequence is inserted between the two genes. The plus denotes a plasmid following which is described as a p5 (five copy) plasmid with a promoter, BCD (described above) and the ADH in question.

Figure 21:
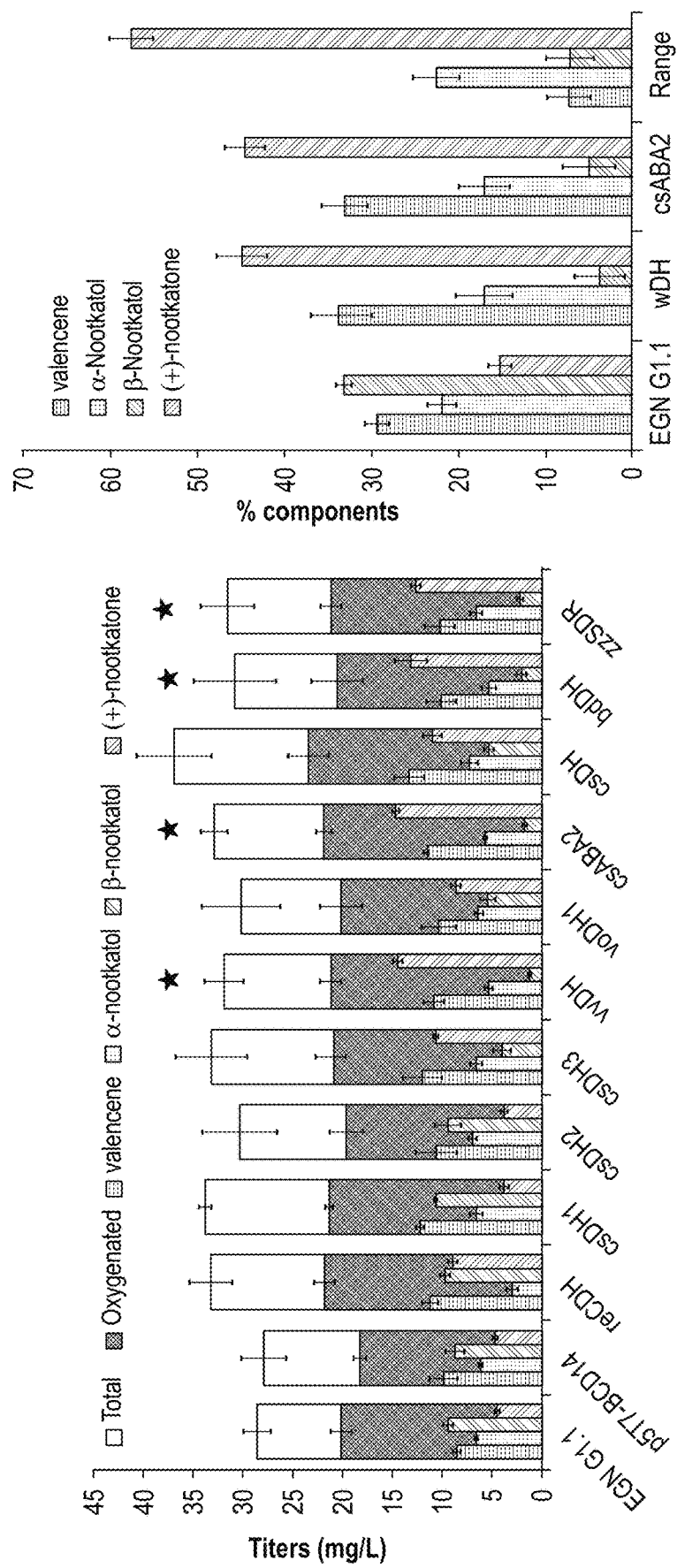
FIG. 21 shows conversion of nootkatols to nootkatone with an alcohol dehydrogenase (ADH). Four ADH orthologs (vvDH, csABA2, bdDH, and zzSDR) were identified that convert β-nootkatol to (+)-nootkatone, resulting in a 3-fold increase in (+)-nootkatone titers and an increase in proportion of α-nootkatol.

Four orthologs were identified (vvDH, csABA2, bdDH, and zzSDR) that convert (3-nootkatol to nootkatone, resulting in more than a 3-fold increase in nootkatone titers. FIG. 21.

REFERENCES

1. Qualley A, Dudareva N. Plant Volatiles. Encycl. Life Sci. 2010; 1-9.
2. Ajikumar P, Tyo K, Carlsen S. Terpenoids: opportunities for biosynthesis of natural product drugs using engineered microorganisms. Mol. Pharm. [Internet]. 2008 [cited 2013 May 16]; 5(2):167-90.
3. Ajikumar P K, Xiao W-H, Tyo K E J, Wang Y, Simeon F, Leonard E, et al. Isoprenoid pathway optimization for Taxol precursor overproduction in *Escherichia coli*. Science [Internet]. 2010 Oct. 1 [cited 2013 May 22]; 330 (6000):70-4.
4. Ro D-K, Paradise E M, Ouellet M, Fisher K J, Newman K L, Ndungu J M, et al. Production of the antimalarial drug precursor artemisinic acid in engineered yeast. Nature [Internet]. 2006 Apr. 13 [cited 2013 Mar. 1]; 440(7086):940-3.
5. Sevrioukova I F, Li H, Zhang H, Peterson J a, Poulos T L. Structure of a cytochrome P450-redox partner electron-transfer complex. Proc. Natl. Acad. Sci. U.S.A [Internet]. 1999 Mar. 2; 96(5):1863-8.
6. Sevrioukova I F, Poulos T L. Structural biology of redox partner interactions in P450cam monooxygenase: a fresh look at an old system. Arch. Biochem. Biophys. [Internet]. Elsevier Inc.; 2011 Mar. 1 [cited 2013 Mar. 26]; 507(1):66-74.
7. Ekroos M, Sjögren T. Structural basis for ligand promiscuity in cytochrome P450 3A4. Proc. Natl. Acad. Sci. U.S.A [Internet]. 2006 Sep. 12; 103(37):13682-7.
8. Takahashi S, Yeo Y-S, Zhao Y, O'Maille P E, Greenhagen B T, Noel J P, et al. Functional characterization of premnaspirodiene oxygenase, a cytochrome P450 catalyzing regio- and stereo-specific hydroxylations of diverse sesquiterpene substrates. J. Biol. Chem. [Internet]. 2007 Oct. 26 [cited 2013 Mar. 10]; 282(43):31744-54.
9. Morrone D, Chen X, Coates R M, Peters R J. Characterization of the kaurene oxidase CYP701A3, a multifunctional cytochrome P450 from gibberellin biosynthesis. Biochem. J. [Internet]. 2010 Nov. 1 [cited 2013 Feb. 6]; 431(3):337-44.
10. Zhang Z, Sibbesen O. The substrate specificity of cytochrome P450 cam. Bioorganic Med. . . . [Internet]. 1998 [cited 2013 Sep. 24]; 6:1501-8.
11. Stjernschantz E, van Vugt-Lussenburg B M a, Bonifacio A, de Beer S B a, van der Zwan G, Gooijer C, et al. Structural rationalization of novel drug metabolizing mutants of cytochrome P450 BM3. Proteins [Internet]. 2008 April [cited 2013 May 16]; 71(1):336-52.
12. Chen M M Y, Snow C D, Vizcarra C L, Mayo S L, Arnold F H. Comparison of random mutagenesis and semi-rational designed libraries for improved cytochrome P450 BM3-catalyzed hydroxylation of small alkanes. Protein Eng. Des. Sel. [Internet]. 2012 April [cited 2013 Mar. 11]; 25(4):171-8.
13. Harford-Cross C F, Carmichael a B, Allan F K, England P a, Rouch D a, Wong L L.
    Protein engineering of cytochrome p450(cam) (CYP101) for the oxidation of polycyclic aromatic hydrocarbons. Protein Eng. [Internet]. 2000 February; 13(2):121-8.
14. Bell S G, Chen X, Sowden R J, Xu F, Williams J N, Wong L, et al. Molecular Recognition in (+)-r-Pinene Oxidation by Cytochrome P450cam. J. Am. Chem. Soc. 2003; 125:705-14.
15. Sowden R, Yasmin S, Rees N, Bell S G, Wong L-L. Biotransformation of the sesquiterpene (+)-valencene by cytochrome P450cam and P450BM-3. Org. Biomol. Chem. [Internet]. 2005 [cited 2013 May 16]; 3:57-64.
16. Brandle J E, Richman A, Swanson A K, Chapman B P. Leaf Ests from *Stevia rebaudiana*: a resource for gene 17. Bar-even A, Noor E, Savir Y, Liebermeister W, Davidi D, Tawfik D S, et al. The Moderately Efficient Enzyme: Evolutionary and Physicochemical Trends Shaping Enzyme Parameters. Biochemistry. 2011;
18. Pleiss J. Protein design in metabolic engineering and synthetic biology. Curr. Opin. Biotechnol. [Internet]. 2011 October [cited 2013 Mar. 5]; 22(5):611-7.
19. Lehmann M, Pasamontes L, Lassen S F, Wyss M. The consensus concept for thermostability engineering of proteins. Biochim. Biophys. Acta [Internet]. 2000 Dec. 29 [cited 2013 Oct. 17]; 1543(2):408-15.
20. Vazquez-Figueroa E, Yeh V, Broering J M, Chaparro-Riggers J F, Bommarius A S. Thermostable variants constructed via the structure-guided consensus method also show increased stability in salts solutions and homogeneous aqueous-organic media. Protein Eng. Des. Sel. [Internet]. 2008 November [cited 2013 Oct. 17]; 21(11): 673-80.
21. Dai M, Fisher H E, Temirov J, Kiss C, Phipps M E, Pavlik P, et al. The creation of a novel fluorescent protein by guided consensus engineering. Protein Eng. Des. Sel. [Internet]. 2007 February [cited 2013 Sep. 19]; 20(2):69-79.
22. Fraatz M a., Riemer S J L, Stöber R, Kaspera R, Nimtz M, Berger R G, et al. A novel oxygenase from *Pleurotus sapidus* transforms valencene to nootkatone. J. Mol. Catal. B Enzym. [Internet]. 2009 December [cited 2013 Apr. 17]; 61(3-4):202-7.
23. Krugener S, Krings U, Zorn H, Berger R G. A dioxygenase of *Pleurotus sapidus* transforms (+)-valencene regio-specifically to (+)-nootkatone via a stereo-specific allylic hydroperoxidation. Bioresour. Technol. [Internet]. Elsevier Ltd; 2010 January [cited 2013 Apr. 12]; 101(2): 457-62.
24. Zorn H, Fraatz M A, Riemer S J L, Takenberg M. Enzymatic synthesis of nootkatone. GERMANY; 2010.
25. Kaspera R, Krings U, Nanzad T, Berger R G. Bioconversion of (+)-valencene in submerged cultures of the ascomycete Chaetomium globosum. Appl. Microbiol. Biotechnol. [Internet]. 2005 June [cited 2013 May 16]; 67(4):477-83.
26. Cankar K, van Houwelingen A, Bosch D, Sonke T, Bouwmeester H, Beekwilder J. A chicory cytochrome P450 mono-oxygenase CYP71AV8 for the oxidation of (+)-valencene. FEBS Lett. [Internet]. Federation of European Biochemical Societies; 2011 Jan. 3 [cited 2013 Mar. 6]; 585(1):178-82.
27. Girhard M, Machida K, Itoh M, Schmid R D, Arisawa A, Urlacher V B. Regioselective biooxidation of (+)-valencene by recombinant *E. coli* expressing CYP109B1 from *Bacillus subtilis* in a two-liquid-phase system. Microb. Cell Fact. [Internet]. 2009 January [cited 2013 May 16]; 8(4):36.
28. Bm-P, Sowden R J, Yasmin S, Rees N H, Bell S G, Wong L. Biotransformation of the sesquiterpene (+)-valencene by cytochrome P450. 2005; 57-64.
29. Trott O, Olson A. AutoDock Vina: improving the speed and accuracy of docking with a new scoring function, efficient optimization, and multithreading. J. Comput. Chem. [Internet]. 2010 [cited 2013 Jul. 26]; 31(2):455-61.1

---

The invention claimed is:

1. A product comprising:
an oxygenated terpene formulation comprising:
nootkatone in an amount ranging from about 55% to about 60% (w/w);
α-nootkatol in an amount ranging from about 20% to about 25% (w/w); and
β-nootkatol in an amount ranging from about 5% to about 10% (w/w),
wherein the product is a flavor product, a natural flavor product, a fragrance product, a cosmetic product, a cleaning product, a detergent product, a soap product, or a pest control product.

2. The product of claim 1, wherein the flavor product is a natural flavor, beverage, a chewing gum, a candy, an artificial flavor, or a flavor additive.

3. The product of claim 1, wherein the formulation further comprises valencene.

4. The product of claim 3, wherein the valencene is present in the oxygenated terpene formulation in an amount ranging from about 5% to about 10% (w/w).

5. The product of claim 1, wherein at least one of the nootkatone, the α-nootkatol, and the β-nootkatol, is produced using a biosynthetic process.

6. The product of claim 1, wherein the nootkatone, the α-nootkatol, and the β-nootkatol, are produced using at least one biosynthetic process.

7. A method of making a product for providing oxygenated terpenes, comprising:
obtaining a formulation, said formulation comprising:
nootkatone in an amount ranging from about 55% to about 60% (w/w);
α-nootkatol in an amount ranging from about 20% to about 25% (w/w); and
β-nootkatol in an amount ranging from about 5% to about 10% (w/w), and incorporating the formulation into a consumer product, an industrial product, a flavor product, a fragrance product, a cosmetic product, a cleaning product, a detergent product, a soap product, or a pest control product.

8. The method of claim 7, wherein the flavor product is a beverage, a chewing gum, a candy, a natural flavor, an artificial flavor, or a flavor additive.

9. The method of claim 7, wherein obtaining the formulation comprises contacting valencene with *Stevia rebaudiana* Kaurene Oxidase (SrKO) or an SrKO derivative comprising a sequence having at least 70% sequence identity to SEQ ID NO: 37, SEQ ID NO: 38, or SEQ ID NO: 55, and having valencene oxidizing activity in an in vivo or in vitro system to yield an oxygenated product.

10. The method of claim 7, further comprising processing the oxygenated product by fractional distillation to yield two or more fractions of the oxygenated product.

11. The method of claim 10, further comprising blending the two or more fractions of the oxygenated product.

12. The method of claim 7, further comprising adding an unoxygenated product to the oxygenated product, one or more fractions of the oxygenated product, or the formulation.

13. The method of claim 12, wherein the unoxygenated product comprises valencene.

14. The method of claim 13, wherein the valencene is present in the formulation in an amount ranging from about 5% to about 10% (w/w).

15. The method of claim 7, wherein the formulation further comprises one or more non-sesquiterpene components or sesquiterpene components.

16. The method of claim 15, wherein the one or more non-sesquiterpene components or sesquiterpene components is selected from Table 8A, Table 8B, and Table 9.

* * * * *